(12) United States Patent
Doench et al.

(10) Patent No.: US 12,264,323 B2
(45) Date of Patent: Apr. 1, 2025

(54) CRISPR CPF1 DIRECT REPEAT VARIANTS

(71) Applicant: THE BROAD INSTITUTE, INC., Cambridge, MA (US)

(72) Inventors: John G. Doench, Cambridge, MA (US); Ruth Hanna, Cambridge, MA (US)

(73) Assignee: THE BROAD INSTITUTE, INC., Cambridge, MA (US)

( * ) Notice: Subject to any disclaimer, the term of this patent is extended or adjusted under 35 U.S.C. 154(b) by 923 days.

(21) Appl. No.: 16/718,155

(22) Filed: Dec. 17, 2019

(65) Prior Publication Data

US 2020/0255861 A1   Aug. 13, 2020

Related U.S. Application Data

(60) Provisional application No. 62/780,748, filed on Dec. 17, 2018, provisional application No. 62/884,101, filed on Aug. 7, 2019.

(51) Int. Cl.
| | |
|---|---|
| *C12N 15/86* | (2006.01) |
| *C12N 9/22* | (2006.01) |
| *C12N 9/96* | (2006.01) |

(52) U.S. Cl.
CPC .............. *C12N 15/86* (2013.01); *C12N 9/22* (2013.01); *C12N 9/96* (2013.01); *C12N 2310/20* (2017.05); *C12N 2750/14143* (2013.01)

(58) Field of Classification Search
CPC .......... C12N 15/86; C12N 2750/14143; C12N 2740/16043; C12N 2310/20; C12N 9/22; C12N 15/90; C12N 9/96
See application file for complete search history.

(56) References Cited

U.S. PATENT DOCUMENTS

| | | |
|---|---|---|
| 6,603,061 B1 | 8/2003 | Armstrong et al. |
| 7,868,149 B2 | 1/2011 | Boukharov et al. |
| 8,889,418 B2 | 11/2014 | Zhang et al. |
| 8,895,308 B1 | 11/2014 | Zhang et al. |
| 8,945,839 B2 | 2/2015 | Zhang |
| 10,648,020 B2 * | 5/2020 | Zhang ................ C12N 9/22 |
| 11,414,657 B2 * | 8/2022 | Rahdar ................ C12N 9/96 |
| 2009/0100536 A1 | 4/2009 | Adams et al. |
| 2011/0059502 A1 | 3/2011 | Chalasani |
| 2012/0164118 A1 | 6/2012 | Trobridge et al. |
| 2013/0202678 A1 | 8/2013 | Yu et al. |
| 2014/0186919 A1 | 7/2014 | Zhang et al. |
| 2014/0242700 A1 | 8/2014 | Zhang et al. |
| 2014/0273234 A1 | 9/2014 | Zhang et al. |
| 2014/0335620 A1 | 11/2014 | Zhang et al. |
| 2015/0232881 A1 | 8/2015 | Glucksmann et al. |
| 2016/0208243 A1 | 7/2016 | Zhang et al. |

FOREIGN PATENT DOCUMENTS

| | | |
|---|---|---|
| EP | 3009511 A2 | 4/2016 |
| WO | 2011141027 A1 | 11/2011 |
| WO | 2013126794 A1 | 8/2013 |
| WO | 2013130824 A1 | 9/2013 |
| WO | 2014018423 A2 | 1/2014 |
| WO | 2014066505 A1 | 5/2014 |
| WO | 2014093595 A1 | 6/2014 |
| WO | 2014093622 A2 | 6/2014 |
| WO | 2014093635 A1 | 6/2014 |
| WO | 2014093655 A2 | 6/2014 |
| WO | 2014093661 A2 | 6/2014 |
| WO | 2014093694 A1 | 6/2014 |
| WO | 2014093701 A1 | 6/2014 |
| WO | 2014093705 A1 | 6/2014 |
| WO | 2014093709 A1 | 6/2014 |
| WO | 2014093712 A1 | 6/2014 |
| WO | 2014093718 A1 | 6/2014 |
| WO | 2015048577 A2 | 4/2015 |
| WO | 2015070083 A1 | 5/2015 |
| WO | 2015086795 A1 | 6/2015 |
| WO | 2015089351 A1 | 6/2015 |
| WO | 2015089354 A1 | 6/2015 |
| WO | 2015089419 A2 | 6/2015 |
| WO | 2015089427 A1 | 6/2015 |
| WO | 2015089465 A1 | 6/2015 |
| WO | 2015089486 A2 | 6/2015 |
| WO | 2015105928 A1 | 7/2015 |

(Continued)

OTHER PUBLICATIONS

Chen et al., CRISPR-Cas12a target binding unleashes single-stranded DNase activity. bioRxiv, Nov. 29, 2017, pp. 1-29. (Year: 2017).*
Fonfara et al., The CRISPR-associated DNA-cleaving enzyme Cpf1 also processes precursor CRISPR RNA. Nature, 2016, vol. 532: 517-521. (Year: 2016).*
Stella et al., Conformational Activation Promotes CRISPRCas12a Catalysis and Resetting of the Endonuclease Activity. Cell, 2018, vol. 175: 1856-1871. (Year: 2018).*
Sundaresan et al., RNA-Independent DNA cleavage activities of Cas9 and Cas12a. Cell Reports, 2017, vol. 21: 3728-3739. (Year: 2017).*
Swarts et al., Structural basis for guide RNA processing and seed-dependent DNA targeting by CRISPR-Cas12a. Mol. Cell, 2017 vol. 66: 221-233. (Year: 2017).*

(Continued)

*Primary Examiner* — Ganapathirama Raghu
(74) *Attorney, Agent, or Firm* — Johnson, Marcou, Issacs & Nix, LLC; F. Brent Nix, Esq.

(57) ABSTRACT

The present invention generally relates to systems, methods and compositions related to Clustered Regularly Interspaced Short Palindromic Repeats (CRISPR) and components thereof. Provided herein are engineered Cpf1 polynucleotides that can direct the activity of a CRISPR protein to multiple targets using a single crRNA. The guide sequences can target a sequence in a eukaryotic cell, for example, an animal or a plant cell. The animal cell can be a human or a nonhuman cell. Additionally, the present invention relates to methods for developing or designing CRISPR-Cas system-based therapy or therapeutics.

33 Claims, 62 Drawing Sheets
Specification includes a Sequence Listing.

(56) References Cited

FOREIGN PATENT DOCUMENTS

| WO | 2015109752 A1 | 7/2015 |
|---|---|---|
| WO | 2015134812 A1 | 9/2015 |
| WO | 2015138855 A1 | 9/2015 |
| WO | 2015148670 A1 | 10/2015 |
| WO | 2015148860 A1 | 10/2015 |
| WO | 2015148863 A2 | 10/2015 |
| WO | 2015153780 A1 | 10/2015 |
| WO | 2015153789 A1 | 10/2015 |
| WO | 2015153791 A1 | 10/2015 |
| WO | 2015161276 A2 | 10/2015 |
| WO | 2016011210 A2 | 1/2016 |
| WO | 2016025131 A1 | 2/2016 |
| WO | 2016073433 A1 | 5/2016 |
| WO | 2016094867 A1 | 6/2016 |
| WO | 2016094874 A1 | 6/2016 |
| WO | 2016099887 A1 | 6/2016 |
| WO | 2016100272 A1 | 6/2016 |
| WO | 2016100562 A1 | 6/2016 |
| WO | 2016100568 A1 | 6/2016 |
| WO | 2016100571 A1 | 6/2016 |
| WO | 2016106244 A1 | 6/2016 |
| WO | 2016161516 A1 | 10/2016 |
| WO | 2017011804 A1 | 1/2017 |
| WO | 2017019867 A1 | 2/2017 |
| WO | 2017066175 A1 | 4/2017 |
| WO | 2017100158 A1 | 6/2017 |
| WO | 2017105991 A1 | 6/2017 |
| WO | 2017106414 A1 | 6/2017 |
| WO | 2017218979 A1 | 6/2017 |

OTHER PUBLICATIONS

Chen JS., Mechanisms and applications of DNA-targeting CRISPR interference proteins. PhD Thesis, Univ of California, Berkeley., Summer 2018, pp. 1-130. (Year: 2018).*
Cornu et al., Refining strategies to translate genome editing to the clinic. Nat. Med., 2017, vol. 23(4); 415-423. (Year: 2017).*
Cox et al., Therapeutic genome editing: prospects and challenges. Nat. Med., 2015, vol. 21(2); 121-131. (Year: 2015).*
Nishimasu et al., Structural Basis for the Altered PAM Recognition by Engineered CRISPR-Cpf1. Mol. Cell., 2017, vol. 67: 139-147. (Year: 2017).*
Zetshe et al., Multiplex gene editing by CRISPR-Cpf1 using a single crRNA array. Nat. Biotechnol., 2017, vol. 35(1); 31-34. (Year: 2017).*
Kleinstiver et al., Engineered CRISPR-Cas12a variants with increased activities and improved targeting ranges for gene, epigenetic and base editing. Nat. Biotechnol., 2019, vol. 37: 276-282. (Year: 2019).*
Adamson, et al., "A Multiplexed Single-Cell CRISPR Screening Platform Enables Systematic Dissection of the Unfolded Protein Response", Cell, vol. 167, No. 7, Dec. 15, 2016, 49 pages.
Aguirre, et al., "Genomic Copy Number Dictates a Gene-Independent Cell Response to CRISPR/Cas9 Targeting", Cancer Discovery, vol. 6, No. 8, Jun. 3, 2016, 914-929.
Anton, et al., "Visualization of Specific DNA Sequences in Living Mouse Embryonic Stem Cells With a Programmable Fluorescent CRISPR/Cas System", Nucleus, vol. 5, No. 2, Mar./Apr. 2014, 163-172.
Bakondi, et al., "In Vivo CRISPR/Cas9 Gene Editing Corrects Retinal Dystrophy in the S334ter-3 Rat Model of Autosomal Dominant Retinitis Pigmentosa", Molecular Therapy, vol. 24, No. 3, Mar. 2016, 556-563.
Belhaj, et al., "Plant Genome Editing Made EasyTargeted Mutagenesis in Model and Crop Plants using The CRISPR/CAS System", Plant Methods, vol. 9, No. 39, 2013, 10 pages.
Bikard, et al., "Exploiting CRISPR-Cas Nucleases to Produce Sequence-Specific Antimicrobials", Nature Biotechnology, vol. 32, No. 11, Nov. 2014, 1146-1150.

Brooks, et al., "Efficient Gene Editing in Tomato in the First Generation Using the Clustered Regularly Interspaced Short Palindromic Repeats/CRISPR-Associated9 System", Plant Physiology, vol. 166, Nov. 2014, 1292-1297.
Caliando, et al., "Targeted DNA Degradation using a CRISPR Device Stably Carried in the Host Genome", Nature Communications, vol. 6, No. 6989, May 19, 2015, 10 pages.
Cameron, et al., "Mapping the Genomic Landscape of CRISPR-Cas9 Cleavage", Nature Methods, vol. 14, No. 6, Jun. 2017, 10 pages.
Campa, et al., "Multiplexed Genome Engineering by Cas12A and CRISPR Arrays Encoded on Single Transcripts", Nature Methods, vol. 16, 2019, 887-893.
Canela, et al., "DNA Breaks and End Resection Measured Genome-wide by End Sequencing", Molecular Cell, vol. 63, No. 5, Sep. 1, 2016, 898-911.
Carr, et al., "Genome Engineering", Nature Biotechnology, vol. 27, No. 12, Dec. 9, 2009, 1151-1162.
Chan, et al., "Deadman and Passcode Microbial Kill Switches for Bacterial Containment", Nature Chemical Biology, vol. 12, No. 2, Feb. 2016, 19 pages.
Chen, et al., "Dynamic Imaging of Genomic Loci in Living Human Cells by an Optimized CRISPR/Cas System", Cell, vol. 155, Issue 7, Dec. 19, 2013, 1479-1491.
Chen, et al., "Predicting Peptide-Mediated Interactions on a Genome-Wide Scale", PLOS Computational Biology, vol. 11, No. 5, May 4, 2015, 13 pages.
Chu, et al., "Efficient Generation of Rosa26 Knock-in Mice using Crispr/cas9 in C57bl/6 Zygotes", BMC Biotechnology, vol. 16, No. 4, Jan. 16, 2016, 15 pages.
Chung, et al., "Tunable and Reversible Drug Control of Protein Production Via a Self-excising Degron", Nature Chemical Biology, vol. 11, No. 9, Sep. 2015, 26 pages.
Cong, et al., "Multiplex Genome Engineering Using CRISPR/Cas Systems", Science, vol. 339, No. 6121, Feb. 15, 2013, 6 pages.
Crosetto, et al., "Nucleotide-resolution DNA Double-strand Break Mapping by Next-generation Sequencing", Nature Methods, vol. 10, No. 4, Apr. 2013, 17 pages.
Dahlman, et al., "Orthogonal Gene Knockout and Activation with a Catalytically Active Cas9 Nuclease", Nature Biotechnology, vol. 34, No. 4, Oct. 5, 2015, 4 pages.
Dey, et al., "Toward a "Structural Blast": Using Structural Relationships to Infer Function", Protein Science, vol. 22, No. 4, Apr. 2013, 359-366.
Ding, et al., "Permanent Alteration of PCSK9 With In Vivo CRISPR-Cas9 Genome Editing", Circulation Research, Aug. 15, 2014, 488-492.
Doench, et al., "Optimized sgRNA Design to Maximize Activity and Minimize Off-Target Effects of CRISPR-Cas9", Nature Biotechnology, vol. 34, No. 2, Feb. 2016, 35 pages.
Doench, et al., "Rational Design of Highly Active SgRNAs for CRISPR-Cas9-Mediated Gene Inactivation", Nature Biotechnology, vol. 32, No. 12, Dec. 2014, 17 pages.
Dong, et al., "Targeting Hepatitis B virus cccDNA by CRISPR/Cas9 Nuclease Efficiently Inhibits Viral Replication", Antiviral Research, vol. 118, Apr. 3, 2015, 110-117.
Ebina, et al., "Harnessing the CRISPR/Cas9 system to Disrupt latent HIV-1 Provirus", Scientific Reports, vol. 3, No. 2510, 2013, 7 pages.
Ehrke-Schulz, et al., "CRISPR/Cas9 Delivery with One Single Adenoviral Vector Devoid of All Viral Genes", Scientific Reports, vol. 7, No. 1, Dec. 7, 2017, 11 pages.
Esvelt, et al., "Concerning RNA-guided Gene Drives for the Alteration of Wild Populations", eLIFE, vol. 3, e03401, 2014, 21 pages.
Eyquem, et al., "Targeting a CAR to the TRAC Locus with CRISPR/Cas9 Enhances Tumour Rejection", Nature, vol. 543, No. 7643, Mar. 2, 2017, 113-117.
Feng, et al., "Efficient Genome Editing in Plants using a CRISPR/Cas System", Cell Research, vol. 23, Issue 10, Oct. 2013, 1229-1232.
Ferry, et al., "Rational Design of Inducible CRISPR Guide RNAs for De Novo Assembly of Transcriptional Programs", Nature Communications, vol. 8, No. 14633, Mar. 3, 2017, 10 pages.

(56) References Cited

OTHER PUBLICATIONS

Fine, et al., "Trans-Spliced Cas9 Allows Cleavage of HBB and CCR5 Genes in Human Cells Using Compact Expression Cassettes", Scientific Reports, vol. 5, No. 10777, Jul. 1, 2015, 9 pages.

Frock, et al., "Genome-wide Detection of DNA Double-stranded Breaks Induced by Engineered Nucleases", Nature Biotechnology, vol. 33, No. 2, Feb. 2015, 179-186.

Gantz, et al., "Highly Efficient Cas9-Mediated Gene Drive for Population Modification of the Malaria Vector Mosquito Anopheles Stephensi", Proceedings of the National Academy of Sciences, Nov. 23, 2015, E6736-E6743.

Gao, et al., "Engineered Cpf1 Enzymes with Altered PAM Specificities", Nature Biotechnology, vol. 35, No. 8, Dec. 4, 2016, 17 pages.

Ghorbal, et al., "Genome Editing in The Human Malaria Parasite Plasmodium Falciparum using The Crispr-cas9 System", Nature Biotechnology, vol. 32, No. 8, Aug. 2014, 819-821.

Groenen, et al., "Nature of DNA Polymorphism in the Direct Repeat Cluster of Mycobacterium Tuberculosis; Application for Strain Differentiation by a Novel Typing Method", Molecular Microbiology, vol. 10, No. 5, Jan. 1994, 10 pages.

Gruber, et al., "The Vienna RNA Websuite", Nucleic Acids Research, vol. 36, Apr. 19, 2008, W70-W74.

Han, et al., "Synergistic Drug Combinations for Cancer Identified in a Crispr Screen for Pairwise Genetic Interactions", Nature Biotechnology, vol. 35, No. 5, May 2017, 463-474.

Hanna, et al., "A Case of Mistaken Identity", Nature Biotechnology, vol. 36, No. 9, Sep. 2018, 802-804.

Hart, et al., "Measuring Error Rates in Genomic Perturbation Screens: Gold Standards for Human Functional Genomics", Molecular Systems Biology, vol. 10, No. 7, 2014, 16 pages.

Hendel, et al., "Chemically Modified Guide RNAs Enhance CRISPR-cas Genome Editing in Human Primary Cells", Nature Biotechnology, vol. 33, No. 9, Sep. 2015, 14 pages.

Cekaite, Lina et al., "Gene Expression Analysis in Blood Cells in Response to Unmodified and 2'-Modified siRNAs Reveals TLR-dependent and Independent Effects", Journal of Molecular Biology, vol. 365, No. 1, 90-108, Jan. 5, 2007.

Heo, et al., "CRISPR/Cas9 Nuclease-Mediated Gene Knock-In in Bovine-Induced Pluripotent Cells", Stem Cells Development, vol. 24, No. 3, Feb. 2015, 10 pages.

Hicke, et al., "Escort Aptamers: A Delivery Service for Diagnosis and Therapy", The Journal of Clinical Investigation, vol. 106, No. 8, Oct. 2000, 923-928.

Hill, et al., "On the design of CRISPR-based Single-Cell Molecular Screens", Nature Methods, vol. 15, No. 4, Apr. 2018, 22 pages.

Hoe, et al., "Rapid Molecular Genetic Subtyping of Serotype M1 Group A *Streptococcus* Strains", Emerging Infectious Diseases, vol. 5, No. 2, Mar.-Apr. 1999, 254-263.

Horlbeck, et al., "Nucleosomes Impede Cas9 Access to DNA in Vivo and in Vitro", Retrieved as on Oct. 14, 2020:—"DOI: 10.7554/eLife.12677", 2016, 21 pages.

Hsu, et al., "DNA Targeting Specificity of RNA-Guided Cas9 Nucleases", Nature Biotechnology, vol. 31, No. 9, Sep. 2013, 17 pages.

Iacovoni, et al., "High-resolution Profiling of Gammah2Ax Around DNA Double Strand Breaks in the Mammalian Genome", The EMBO Journal, vol. 29, No. 8, 2010, 1446-1457.

Moore, Richard, et al., "CRISPR-based self-cleaving mechanism for controllable gene delivery in human cells," Nucleic Acids Research, pp. 1-7, Accepted: Dec. 7, 2014.

Inoue, et al., "An Inducible Translocation Strategy to Rapidly Activate and Inhibit Small GTPase Signaling Pathways", Nature Methods, vol. 2, No. 6, May 20, 2005, 7 pages.

Isaac, et al., "Nucleosome Breathing and Remodeling Constrain CRISPR-Cas9 Function", Retrieved as on Oct. 14, 2020:—"DOI: 10.7554/eLife.13450", 2016, 14 pages.

Ishino, et al., "Nucleotide Sequence of the iap Gene, Responsible for Alkaline Phosphatase Isozyme Conversion in *Escherichia coli*, and Identification of the Gene Product", Journal of Bacteriology, vol. 169, No. 12, Dec. 1987, 5429-5433.

Jakočiūnas, et al., "Multiplex Metabolic Pathway Engineering Using CRISPR/Cas9 in *Saccharomyces cerevisiae*", Metabolic Engineering, vol. 28, Mar. 2015, 213-222.

Jansen, et al., "Identification of a Novel Family of Sequence Repeats among Prokaryotes", OMICS: A Journal of Integrative Biology, vol. 6, No. 1, Feb. 2002, 23-33.

Jansen, et al., "Identification of Genes that are Associated with DNA Repeats in Prokaryotes", Molecular Microbiology, vol. 43, Issue 6, Apr. 25, 2002, 1565-1575.

Jiang, et al., "RNA-Guided Editing of Bacterial Genomes Using CRISPR-Cas Systems", Nature Biotechnology, vol. 31, No. 3, Mar. 2013, 233-239.

Judge, et al., "Design of Noninflammatory Synthetic Sirna Mediating Potent Gene Silencing In Vivo", Molecular Therapy, vol. 13, No. 3, Mar. 2006, 494-505.

Kabadi, et al., "Multiplex CRISPR/Cas9-Based Genome Engineering from a Single Lentiviral Vector", Nucleic Acids Research, vol. 42, No. 19, Aug. 13, 2014, 11 pages.

Karimi-Ashtiyani, et al., "Point Mutation Impairs Centromeric CENH3 Loading and Induces Haploid Plants", Proceedings of the National Academy of Sciences, vol. 112, No. 36, Sep. 8, 2015, 11211-11216.

Karimova, et al., "CRISPR/Cas9 Nickase-Mediated Disruption of Hepatitis B Virus Open Reading Frame S and X", Scientific Reports, vol. 5, Sep. 3, 2015, 20 pages.

Katrekar, et al., "Oligonucleotide Conjugated Multi-functional Adeno-associated Viruses", Scientific Reports, vol. 8, No. 3589, Feb. 26, 2018, 8 pages.

Keefe, et al., "Aptamers as Therapeutics", Nature Reviews Drug Discovery, vol. 9, No. 7, Jul. 2010, 537-550.

Kim, et al., "Deep Learning Improves Prediction of Crispr-Cpf1 Guide RNA Activity", Nature Biotechnology, vol. 36, Mar. 2018, 8 pages.

Kim, et al., "Genome-Wide Analysis Reveals Specificities of Cpf1 Endonucleases in Human Cells", Nature Biotechnology, vol. 34, No. 8, Aug. 2016, 863-888.

Kim, et al., "Highly Efficient Rna-guided Genome Editing in Human Cells via Delivery of Purified Cas9 Ribonucleoproteins", Genome Research, vol. 24, No. 6, Jun. 24, 2014, 1012-1019.

Kleinstiver, et al., "Engineered CRISPR-Cas12A Variants with Increased Activities and Improved Targeting Ranges for Gene, Epigenetic and Base Editing", Nature Biotechnology, vol. 37, Mar. 2019, 13 pages.

Kleinstiver, et al., "Genome-wide Specificities of CRISPR-Cas Cpf1 Nucleases in Human Cells", Nature Biotechnology, vol. 34, No. 8, Aug. 2016, 869-874.

Kleinstiver, et al., "High-Fidelity CRISPR-Cas9 Nucleases with No. Detectable Genome-Wide Off-Target Effects", Nature, vol. 529, No. 7587, Jan. 2016, 17 pages.

Konermann, et al., "Genome-Scale Transcriptional Activation by an Engineered CRISPR-Cas9 Complex", Nature, vol. 517, No. 7536, Jan. 29, 2015, 583-588.

Koo, et al., "Representation Learning of Genomic Sequence Motifs with Convolutional Neural Networks", bioRxiv, Retrieved as on Oct. 20, 2020:—https://doi.org/10.1101/362756, Apr. 11, 2019, 13 pages.

Kudla, et al., "High Guanine and Cytosine Content Increases mRNA Levels in Mammalian Cells", PLoS Biology, vol. 4, Issue 6, May 23, 2006, 0933-0942.

Kunze, et al., "Synthetic AAV/CRISPR Vectors for Blocking Hiv-1 Expression in Persistently Infected Astrocytes", Glia, vol. 66, No. 2, Feb. 2018, 15 pages.

Lek, et al., "Analysis of Protein-Coding Genetic Variation in 60,706 Humans", Nature, vol. 536, No. 7616, Aug. 18, 2016, 33 pages.

Lensing, et al., "DSBcapture: In Situ Capture And Sequencing of DNA Breaks", Nature Methods, vol. 13, No. 10, Oct. 2016, 17 pages.

Levy-Nissenbaum, et al., "Nanotechnology and Aptamers: Applications in Drug Delivery", Trends Biotech., vol. 26, No. 8, Aug. 26, 2008, 442-449.

(56) References Cited

OTHER PUBLICATIONS

Li, et al., "Inhibition of HIV-1 Infection of Primary CD4+ T-Cells by Gene Editing Of CCR5 Using Adenovirus-Delivered CRISPR/Cas", Journal of General Virology, vol. 96, No. 8, Aug. 2015, 2381-2393.

Li, et al., "Targeted Plant Genome Editing via the CRISPR/Cas9 Technology", Plant Functional Genomics: Methods and Protocols, vol. 1284, Feb. 2015, 239-255.

Liang, et al., "Crispr/cas9-Mediated Gene Editing in Human Tripronuclear Zygotes", Protein Cell, vol. 6, No. 5, 2015, 363-372.

Liang, et al., "Engineering the ABA Plant Stress Pathway for Regulation of Induced Proximity", Science signaling, vol. 4, Issue 164, Jun. 7, 2011, 18 pages.

Lin, et al., "The CRISPR/Cas9 System Facilitates Clearance of the Intrahepatic HBV Templates in Vivo", Molecular Therapy—Nucleic Acids, vol. 3, e186, Aug. 19, 2014, 7 pages.

Liu, et al., "CRISPR-Cas9-mediated Multiplex Gene Editing in CAR-T Cells", Cell Research, vol. 27, No. 1, 2017, 154-157.

Liu, et al., "Engineering Cell Signaling Using Tunable CRISPR-Cpf1-based Transcription Factors", Nature Communications, vol. 8, No. 2095, Dec. 13, 2017, 8 pages.

Liu, et al., "Enhanced Cas12A editing in Mammalian Cells and Zebrafish", Nucleic Acids Research, vol. 47, No. 8, Mar. 20, 2019, 4169-4180.

Liu, et al., "Inhibition of Hepatitis B Virus by the CRISPR/Cas9 System via Targeting the Conserved Regions of the Viral Genome", Journal of General Virology, vol. 96, No. 8, Aug. 2015, 2252-2261.

Long, et al., "Postnatal Genome Editing Partially Restores Dystrophin Expression in a Mouse Model of Muscular Dystrophy", Science, vol. 351, No. 6271, Jan. 22, 2016, 10 pages.

Lowder, et al., "A CRISPR/Cas9 Toolbox for Multiplexed Plant Genome Editing and Transcriptional Regulation", Plant Physiology, vol. 169, No. 2, Oct. 2015, 15 pages.

Ma, et al., "A Robust CRISPR/Cas9 System for Convenient, High-Efficiency Multiplex Genome Editing in Monocot and Dicot Plants", Molecular Plant, vol. 8, No. 8, Aug. 3, 2015, 1274-1284.

Maji, et al., "Multidimensional Chemical Control of CRISPR-Cas9", Nature Chemical Biology, vol. 13, No. 1, Jan. 2017, 11 pages.

Makarova, et al., "Annotation and Classification of CRISPR-Cas Systems", Methods in Molecular Biology, vol. 1311, 2015, 27 pages.

Mali, et al., "RNA-Guided Human Genome Engineering via Cas9", Science, vol. 339, No. 6121, Feb. 15, 2013, 8 pages.

Malina, et al., "Repurposing CRISPR/Cas9 for in Situ Functional Assays", Genes & Development, vol. 27, No. 23, Oct. 25, 2013, 2602-2614.

Mandal, et al., "Efficient Ablation of Genes in Human Hematopoietic Stem and Effector Cells Using CRISPR/Cas9", Cell Stem Cell, vol. 15, No. 5, Nov. 6, 2014, 15 pages.

Masepohl, et al., "Long Tandemly Repeated Repetitive (LTRR) Sequences in the Filamentous *Cyanobacterium anabaena* sp. PCC 7120", Biochimica et Biophysica Acta (BBA)—Gene Structure and Expression, vol. 1307, No. 1, Jun. 3, 1996, 26-30.

Matsuda, et al., "Controlled Expression of Transgenes Introduced by in vivo Electroporation", Proceedings of the National Academy of Sciences of the United States of America, vol. 104, No. 3, Jan. 16, 2007, 1027-1032.

Miyamoto, et al., "Rapid and Orthogonal Logic Gating with a Gibberellin-induced Dimerization System", Nature chemical biology, vol. 8, Issue 5, Mar. 25, 2012, 14 pages.

Miyazaki, et al., "Destabilizing Domains Derived from the Human Estrogen Receptor", Journal of the American Chemical Society, vol. 134, No. 9, Mar. 7, 2012, 3942-3945.

Mojica, et al., "Intervening Sequences of Regularly Spaced Prokaryotic Repeats Derive from Foreign Genetic Elements", Journal of Molecular Evolution, vol. 60, No. 2, Mar. 2005, 174-182.

Mojica, et al., "Long Stretches of Short Tandem Repeats Are Present in the Largest Replicons of the Archaea Haloferax Mediterranei and Haloferax Volcanii and Could Be Involved in Replicon Partitioning", Molecular Microbiology, vol. 17, No. 1, Jul. 1995, 85-93.

Mojica, et al., "MicroCorrespondence: Biological significance of a family of regularly spaced repeats in the genomes of Archaea, Bacteria and mitochondria", Molecular Microbiology, vol. 36, No. 1, Apr. 2000, 244-246.

Moreno, et al., "In Situ Gene Therapy via AAV-CRISPR-Cas9-Mediated Targeted Gene Regulation", Molecular Therapy, vol. 26, Issue 7, Jul. 2018, 1818-1827.

Morrell, et al., "Crop Genomics: Advances and Applications", Nature Reviews Genetics, vol. 13, No. 2, Feb. 2012, 85-96.

Morrissey, et al., "Potent and Persistent In vivo Anti-HBV Activity of Chemically Modified siRNAs", Nature Biotechnology, vol. 23, No. 8, Aug. 2005, 6 pages.

Munoz, et al., "CRISPR Screens Provide a Comprehensive Assessment of Cancer Vulnerabilities but Generate False-Positive Hits for Highly Amplified Genomic Regions", Cancer Discovery, vol. 6, No. 8, 2016, 14 pages.

Najm, et al., "Orthologous CRISPR-Cas9 Enzymes for Combinatorial Genetic Screens", Nature Biotechnology, vol. 36, No. 2, Nov. 18, 2017, 30 pages.

Nakata, et al., "Unusual Nucleotide Arrangement with Repeated Sequences in the *Escherichia coli* K-12 Chromosome", Journal of Bacteriology, vol. 171, No. 6, Jun. 1989, 3553-3556.

Nelson, et al., "In Vivo Genome Editing Improves Muscle Function In A Mouse Model Of Duchenne Muscular Dystrophy", Science, vol. 351, Issue 6271, Jan. 22, 2016, 403-407.

Nihongaki, et al., "Photoactivatable CRISPR-cas9 for Optogenetic Genome Editing", Nature Biology, vol. 33, 2015, 755-760.

Paige, et al., "RNA Mimics of Green Fluorescent Protein", Science, vol. 333, No. 6042, Jul. 29, 2011, 14 pages.

Paix, et al., "High Efficiency, Homology-Directed Genome Editing in Caenorhabditis Elegans using CRISPR-Cas9 Ribonucleoprotein Complexes", Genetics, vol. 201, No. 1, Sep. 2015, 47-54.

Pattanayak, et al., "High-Throughput Profiling of Off-Target DNA Cleavage Reveals RNA-Programmed Cas9 Nuclease Specificity", Nature biotechnology, vol. 31, No. 9, Sep. 2013, 16 pages.

Pawluk, et al., "Naturally Occurring Off-Switches for CRISPR-Cas9", Cell, vol. 167, No. 7, Dec. 15, 2016, 19 pages.

Perez, et al., "GuideScan Software for Improved Single and Paired CRISPR Guide RNA Design", Nature Biotechnology, vol. 35, No. 4, Apr. 2017, 10 pages.

Prather, et al., "Knockout Of Maternal Cd163 Protects Fetuses From Infection With Porcine Reproductive And Respiratory Syndrome Virus (Prrsv)", Scientific Reports, vol. 7, No. 13371, 2015, 5 pages.

Price, et al., "Cas9-Mediated Targeting of Viral RNA in Eukaryotic Cells", Proceedings of the National Academy of Sciences, vol. 112, No. 19, May 12, 2015, 6164-6169.

Ramakrishna, et al., "Gene Disruption by Cell-Penetrating Peptide-Mediated Delivery of Cas9 Protein and Guide RNA", Genome Research, vol. 24, No. 6, Jun. 2014, 1020-1027.

Ramanan, et al., "CRISPR/Cas9 Cleavage of Viral DNA Efficiently Suppresses Hepatitis B Virus", Scientific Reports, vol. 5, No. 10833, Jun. 2, 2015, 9 pages.

Ran, et al., "In Vivo Genome Editing using *Staphylococcus aureus* Cas9", Nature, vol. 520, No. 7546, Apr. 1, 2015, 30 pages.

Rauch, et al., "Inhibition of CRISPR-Cas9 with Bacteriophage Proteins", Cell, vol. 168, No. (1-2), Jan. 12, 2017, 26 pages.

Rohs, et al., "The Role of DNA Shape in Protein-DNA Recognition", Nature, vol. 461, No. 7268, Oct. 29, 2009, 18 pages.

Rupp, et al., "CRISPR/Cas9-mediated PD-1 Disruption Enhances Anti-tumor Efficacy of Human Chimeric Antigen Receptor T Cells", Scientific Reports, vol. 7, No. 737, Apr. 7, 2017, 10 pages.

Rusk, "Nanopores Read Long Genomic DNA", Nature Methods, vol. 11, No. 9, Sep. 2014, 1 page.

Sanson, et al., "Optimization of Ascas12A for Combinatorial Genetic Screens in Human Cells", Nature Biotechnology, Retrieved as on Oct. 2020:—doi: 10.1038/s41587-020-0600-6, Aug. 28, 2019, 29 pages.

Sapranauskas, et al., "The *Streptococcus thermophilus* CRISPR/Cas System Provides Immunity in *Escherichia coli*", Nucleic Acids Research, vol. 39, No. 21, Aug. 2011, 9275-9282.

(56) References Cited

OTHER PUBLICATIONS

Schaeffer, et al., "CRISPR/Cas9-mediated Genome Editing and Gene Replacement in Plants: Transitioning From Lab to Field", Plant Science, vol. 240, 2015, 57 pages.

Schiwon, et al., "One-Vector System for Multiplexed CRISPR/Cas9 against Hepatitis B Virus cccDNA Utilizing High-Capacity Adenoviral Vectors", Molecular Therapy—Nucleic Acids, vol. 12, Sep. 2018, 242-253.

Schwank, et al., "Functional Repair of CFTR by CRISPR/Cas9 in Intestinal Stem Cell Organoids of Cystic Fibrosis Patients", Cell Stem Cell, vol. 13, No. 6, Dec. 5, 2013, 653-658.

Shan, et al., "Targeted Genome Modification of Crop Plants Using a CRISPR-Cas System", Nature biotechnology, vol. 31, No. 8, Aug. 2013, 686-688.

Shen, et al., "Combinatorial CRISPR-Cas9 Screens for De Novo Mapping of Genetic Interactions", Nature Methods, vol. 14, No. 6, Jun. 2017, 19 pages.

Shen, et al., "Efficient Gene Disruption in Diverse Strains of Toxoplasma Gondii Using CRISPR/Cas9", Mbio, vol. 5, Issue 3, May 2014, 11 pages.

Shin, et al., "Disabling Cas9 by an Anti-CRISPR DNA Mimic", Science Advances, vol. 3, No. 7, Jul. 12, 2017, 9 pages.

Shmakov, et al., "Discovery and Functional Characterization of Diverse Class 2 CRISPR-Cas Systems", Molecular Cell, vol. 60, No. 3, Nov. 5, 2015, 385-397.

Sidik, et al., "Efficient Genome Engineering of Toxoplasma gondii Using CRISPR/Cas9", PLOS one, vol. 9, Issue 6, Jun. 27, 2014, 8 pages.

Slaymaker, et al., "Rationally Engineered Cas9 Nucleases with Improved Specificity", Science, vol. 351, No. 6268, Jan. 1, 2016, 84-88.

Song, et al., "Improved Hematopoietic Differentiation Efficiency of Gene-Corrected Beta-Thalassemia Induced Pluripotent Stem Cells by CRISPR/Cas9 System", Stem Cells and Development, vol. 24, No. 9, May 2015, 1053-1065.

Stanley, et al., "Radio-Wave Heating of Iron Oxide Nanoparticles Can Regulate Plasma Glucose in Mice", Science, vol. 336, Issue 6081, May 4, 2012, 604-608.

Stovicek, et al., "CRISPR-Cas System Enables Fast and Simple Genome Editing of Industrial *Saccharomyces cerevisiae* Strains", Metabolic Engineering Communications, vol. 2, Dec. 2015, 13-22.

Sugano, et al., "CRISPR/Cas9-Mediated Targeted Mutagenesis in the Liverwort Marchantia polymorpha L.", Plant and Cell Physiology, vol. 55, No. 3, Mar. 2014, 475-481.

Suzuki, et al., "In Vivo Genome Editing Via CRISPR/Cas9 Mediated Homology-Independent Targeted Integration", Nature, vol. 540, Dec. 2016, 24 pages.

Szilard, et al., "Systematic Identification of Fragile Sites Via Genome-wide Location Analysis of y-h2Ax", Nature Structural & Molecular Biology, vol. 17, No. 3, Mar. 2010, 21 pages.

Tabebordbar, et al., "In Vivo Gene Editing In Dystrophic Mouse Muscle And Muscle Stem Cells", Science, vol. 351, Issue 6271, Jan. 22, 2016, 407-411.

Tan, et al., "Efficient Nonmeiotic Allele Introgression in Livestock Using Custom Endonucleases", Proceedings of the National Academy of Sciences, vol. 110, No. 41, Oct. 2013, 16526-16531.

Tebas, et al., "Gene Editing of CCR5 in Autologous CD4 T Cells of Persons Infected with HIV", The New England journal of medicine, vol. 370, No. 10, Mar. 6, 2014, 901-910.

Teng, et al., "Enhanced Mammalian Genome Editing by New Cas12A Orthologs with Optimized CrRNA Scaffolds", Genome Biology, vol. 20, No. 15, 2019, 6 pages.

Tsai, et al., "CIRCLE-Seq: A Highly Sensitive In Vitro Screen for Genome-wide CRISPR-Cas9 Nuclease Off-targets", Nature Methods, vol. 14, No. 6, Jun. 2017, 19 pages.

Tsai, et al., "Dimeric CRISPR RNA-Guided FokI Nucleases for Highly Specific Genome Editing", Nature Biotechnology, vol. 32, No. 6, Jun. 2014, 569-576.

Tsai, et al., "Guide-seq Enables Genome-wide Profiling of Off-target Cleavage by Crispr-cas Nucleases", Nature Biotechnology, vol. 33, No. 2, Feb. 2015, 187-197.

Tsherniak, et al., "Defining a Cancer Dependency Map", Cell, vol. 170, Issue 3, Jul. 27, 2017, 30 pages.

Tuerk, et al., "Systematic Evolution of Ligands by Exponential Enrichment: RNA Ligands to Bacteriophage T4 DNA Polymerase", Science, vol. 249, No. 4968, Aug. 1990, 505-510.

Tycko, et al., "Identification and Mitigation of Pervasive Off-target Activity in Crispr-cas9 Screens for Essential Non-coding Elements", Retrieved as on Oct. 20, 2020:—doi: https://doi.org/10.1101/520569., Jan. 18, 2019, 60 pages.

Van Delft, et al., "The BH3 Mimetic ABT-737 Targets Selective Bcl-2 Proteins and Efficiently Induces Apoptosis Via Bak/Bax if Mcl-1 is Neutralized", Cancer Cell, vol. 10, Nov. 2006, 389-399.

Van Embden, et al., "Genetic Variation and Evolutionary Origin of the Direct Repeat Locus of *Mycobacterium tuberculosis* Complex Bacteria", Journal of Bacteriology, vol. 182, No. 9, May 2000, 2393-2401.

Vyas, et al., "A Candida Albicans CRISPR System Permits Genetic Engineering of Essential Genes and Gene Families", Science Advances, vol. 1, e1500248, Apr. 3, 2015, 6 pages.

Waldrip, et al., "A CRISPR-based Approach for Proteomic Analysis of a Single Genomic Locus", Epigenetics, vol. 9, No. 9, Sep. 2014, 1207-1211.

Wang, et al., "CCR5 Gene Disruption via Lentiviral Vectors Expressing Cas9 and Single Guided RNA Renders Cells Resistant to HIV-1 Infection", PLoS One, vol. 9, No. 12, e115987, Dec. 26, 2014, 26 pages.

Wang, et al., "Dual gRNAs Guided CRISPR/Cas9 System Inhibits Hepatitis B Virus Replication", World Journal on Gastroenterology, vol. 21, Issue 32, Aug. 28, 2015, 9554-9565.

Wang, et al., "One-Step Generation of Mice Carrying Mutations in Multiple Genes by CRISPR/Cas-Mediated Genome Engineering", Cell, vol. 153, No. 4, May 9, 2013, 13 pages.

Wang, et al., "Optimizing Multiplex CRISPR/Cas9-Based Genome Editing for Wheat", Retrived as on Oct. 18, 2020:—doi: http://dx.doi.org/10.1101/051342, May 12, 2016, 34 pages.

Woo, et al., "DNA-Free Genome Editing in Plants with Preassembled CRISPR-Cas9 Ribonucleoproteins", Nature Biotechnology, vol. 33, No. 11, Nov. 2015, 1162-1164.

Wu, et al., "Correction of a Genetic Disease in Mouse via Use of CRISPR-Cas9", Cell Stem Cell, vol. 13, Dec. 5, 2013, 659-662.

Xie, et al., "RNA-guided Genome Editing in Plants Using a Crispr-cas System", Molecular Plant, vol. 6, No. 6, Nov. 2013, 1975-1983.

Xie, et al., "Seamless Gene Correction of B-Thalassemia Mutations in Patient-Specific Ipscs Using CRISPR/Cas9 and Piggybac", Genome Research, vol. 24, No. 9, 2014, 1526-1533.

Xing, et al., "A CRISPR/Cas9 Toolkit for Multiplex Genome Editing in Plants", BMC Plant Biology, vol. 14, No. 327, 2014, 1-12.

Xu, et al., "Both TALENs and CRISPR/Cas9 Directly Target the HBB IVS2-654 (C > T) Mutation In β-Thalassemia-Derived iPSCs", Scientific Reports, vol. 5, No. 12065, Jul. 9, 2015, 12 pages.

Xu, et al., "Gene Targeting using the Agrobacterium Tumefaciens-Mediated CRISPR-Cas System in Rice", Rice, vol. 7, No. 1, May 2, 2014, 4 pages.

Yan, et al., "BLISS: Quantitative And Versatile Genome-wide Profiling of DNA Breaks In Situ", Retrieved as on Oct. 15, 2020:—"doi: https://doi.org/10.1101/091629", Dec. 4, 2016, 23 pages.

Yang, et al., "Genome-Wide Inactivation of Porcine Endogenous Retroviruses (PERVs)", Science, vol. 350, No. 6264, Nov. 27, 2015, 1101-1104.

Yin, et al., "A Geminivirus-Based Guide RNA Delivery System for CRISPR/Cas9 Mediated Plant Genome Editing", Scientific Reports, vol. 5, Article No. 14926, Oct. 9, 2015, 10 pages.

Yin, et al., "Genome Editing with Cas9 in Adult Mice Corrects a Disease Mutation and Phenotype", Nature Biotechnology, vol. 32, No. 6, Jun. 2014, 9 pages.

(56) References Cited

OTHER PUBLICATIONS

Yin, et al., "Therapeutic Genome Editing by Combined Viral and Non-Viral Delivery of CRISPR System Components in Vivo", Nature Biotechnology, vol. 34, No. 3, Mar. 3, 2016, 328-333.

Yosef, et al., "Temperate and Lytic Bacteriophages Programmed to Sensitize and Kill Antibiotic-Resistant Bacteria", Proceedings of the National Academy of Sciences, vol. 112, No. 23, Jun. 9, 2015, 7267-7272.

Yu, et al., "Small Molecules Enhance CRISPR Genome Editing in Pluripotent Stem Cells", Cell Stem Cell, vol. 16, No. 2, Feb. 5, 2015, 142-147.

Zetsche, et al., "A Split-Cas9 Architecture for Inducible Genome Editing and Transcription Modulation", Nature Biotechnology, vol. 33, No. 2, Feb. 2015, 139-142.

Zetsche, et al., "Multiplex Gene Editing by CRISPR-Cpf1 using a Single crRNA Array", National Biotechnology, vol. 35, No. 1, Jan. 2017, 6 pages.

Zhang, et al., "Efficient Editing of Malaria Parasite Genome Using the CRISPR/Cas9 System", MBio, vol. 5, No. 4, Jul. 1, 2014, 9 pages.

Zhang, et al., "Structure-Based Prediction of Protein-Protein Interactions on a Genome-Wide Scale", Nature, vol. 490, Oct. 25, 2012, 556-560.

Zhong, et al., "CPF1 Proteins Excise CRISPR RNAs from mRNA Transcripts in Mammalian Cells", Nature Chemical Biology, vol. 13, No. 8, Aug. 2017, 11 pages.

Zhou, et al., "Aptamer-Targeted Cell-Specific RNA Interference", Silence, vol. 1, No. 4, 2010, 1-10.

Zhou, et al., "Exploiting SNPs for Biallelic CRISPR Mutations in The Outcrossing Woody Perennial Populus Reveals 4-coumarate:CoA Ligase Specificity and Redundancy", New Phytologist, vol. 208, No. 2, 2015, 298-301.

Zou, et al., "Generation of Gene-Target Dogs Using CRISPR/Cas9 System", Journal of Molecular Cell Biology, vol. 7, Issue 6, Oct. 12, 2015, 580-583.

Zuker, et al., "Optimal Computer Folding of Large RNA Sequences Using Thermodynamics and Auxiliary Information", Nucleic Acids Research, vol. 9, No. 1, 1981, 133-148.

Zuris, et al., "Efficient Delivery of Genome-Editing Proteins In Vitro and In Vivo", Nature Biotechnology, vol. 33, No. 1, Jan. 2015, 26 pages.

Yang, Yang, et al., "Crispr/Cas9-Mediated In Vivo Gene Targeting Corrects Haemostasis in Newborn and Adult FIX-KO Mice", Blood, American Society of Hematology, vol. 128, Issue 22, pp. 1-3, Dec. 2, 2016.

Tak, Ester, et al., "Inducible and multiplex gene regulation using CRISPR-Cpf1-based transcription factors", Nature Methods, vol. 14, No. 12, pp. 1163-1166, Dec. 2017.

Kim, et al., "Digenome-seq: genome-wide profiling of CRISPR-Cas9 off-target effects in human cells", Nature Methods, vol. 12, No. 3, pp. 1-8, Mar. 2015.

Kim, et al., "In vivo high-throughput profiling of CRISPR-Cpf1 activity", Nature Methods, vol. 14, No. 2, pp. 1-10, Published online: Dec. 19, 2016.

Li, et al., "Base editing with a Cpf1-cytidine deaminase fusion", Nature Biotechnology, vol. 36, No. 4, pp. 1-8, Published online: Mar. 19, 2018.

Schmelas, et al., "Split Cas9, Not Hairs—Advancing the Therapeutic Index of CRISPR Technology", Special Issue: Advances in CRISPR Technologies for Microbial Engineering, vol. 13, No. 9, pp. 1-27, Accepted: Dec. 29, 2017.

Yang, Yang, et al., "CRISPR/Cas9-mediated in vivo gene targeting corrects hemostasis in newborn and adult factor IX-knockout mice", Blood, American Society of Hematology, vol. 133, Issue 26, pp. 2745-2752, Jun. 27, 2019.

* cited by examiner

FIG. 6

| Construct IDs | SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | TYPE | Total Number of Mismatches |
|---|---|---|---|---|---|---|---|---|---|---|---|---|---|---|---|---|---|---|---|---|---|---|---|
| TAATTCTACTGTCGTAGAT | 1 | T | A | A | T | T | T | C | T | A | C | T | G | T | C | G | T | A | G | A | T | test | 2 |
| TAATTCTACTATCGTAGAT | 2 | T | A | A | T | T | T | C | T | A | C | T | A | T | C | G | T | A | G | A | T | test | 2 |
| AAATTCTACTCTAGTAGAT | 3 | A | A | A | T | T | T | C | T | A | C | T | C | T | A | G | T | A | G | A | T | test | 2 |
| TAATTCTACTATTGTAGAT | 4 | T | A | A | T | T | T | C | T | A | C | T | A | T | T | G | T | A | G | A | T | test | 1 |
| TAATTCTACTATAGTAGAT | 5 | T | A | A | T | T | T | C | T | A | C | T | A | T | A | G | T | A | G | A | T | test | 2 |
| AAATTCTCCTCTGGAGAT | 6 | A | A | A | T | T | T | C | T | C | C | T | C | T | G | G | G | A | G | A | T | test | 4 |
| TAATTCTCCTATTGGAGAT | 7 | T | A | A | T | T | T | C | T | C | C | T | A | T | T | G | G | A | G | A | T | test | 3 |
| TAATTCTCCTCTAGGAGAT | 8 | T | A | A | T | T | T | C | T | C | C | T | C | T | A | G | G | A | G | A | T | test | 3 |
| AAATTCTCCTCCTTGGAGAT | 9 | A | A | A | T | T | T | C | T | C | C | T | C | T | T | G | G | A | G | A | T | test | 3 |
| TAATTCTACTTCGTAGAT | 10 | T | A | A | T | T | T | C | T | A | C | T | T | T | C | G | T | A | G | A | T | test | 2 |
| AAATTCTACTATTGTAGAT | 11 | A | A | A | T | T | T | C | T | A | C | T | A | T | A | G | T | A | G | A | T | test | 2 |
| TAATTCTACTATGGTAGAT | 12 | T | A | A | T | T | T | C | T | A | C | T | A | T | G | G | T | A | G | A | T | test | 2 |
| GAATTCTCCTCTCGGAGAT | 13 | G | A | A | T | T | T | C | T | C | C | T | C | T | C | G | G | A | G | A | T | test | 4 |
| GAATTCCTACTATTGTAGGT | 14 | G | A | A | T | T | C | C | T | A | C | T | A | T | T | G | T | A | G | G | T | test | 4 |
| TAATTCCTACTCTAGTAGGT | 15 | T | A | A | T | T | C | C | T | A | C | T | C | T | A | G | T | A | G | G | T | test | 3 |
| GAATTCTACTCTCGTAGAT | 16 | G | A | A | T | T | T | C | T | A | C | T | C | T | C | G | T | A | G | A | T | test | 2 |
| TAATTCTACTCTTGTAGGT | 17 | T | A | A | T | T | T | C | T | A | C | T | C | T | T | G | T | A | G | G | T | test | 2 |
| AAATTCTCCCTCTAGGAGAT | 18 | A | A | A | T | T | T | C | T | C | C | T | C | T | A | G | G | A | G | A | T | test | 4 |
| AAATTCCTACTCTCGTAGGT | 19 | A | A | A | T | T | C | C | T | A | C | T | C | T | C | G | T | A | G | G | T | test | 4 |
| TAATTCTACTGTTGTAGAT | 20 | T | A | A | T | T | T | C | T | A | C | T | G | T | T | G | T | A | G | A | T | test | 1 |
| GAATTCTACTCTAGTAGAT | 21 | G | A | A | T | T | T | C | T | A | C | T | C | T | A | G | T | A | G | A | T | test | 2 |
| TAATTCTCCTCTTGGAGAT | 22 | T | A | A | T | T | T | C | T | C | C | T | C | T | T | G | G | A | G | A | T | test | 2 |
| GAATTCTACTCTCGGAGAT | 23 | G | A | A | T | T | T | C | T | A | C | T | C | T | C | G | G | A | G | A | T | test | 2 |
| TAATTTCTACTTTAGTAGAT | 24 | T | A | A | T | T | T | C | T | A | C | T | T | T | A | G | T | A | G | A | T | test | 2 |
| TAATTTCTACTCTTGTAGAT | 25 | T | A | A | T | T | T | C | T | A | C | T | C | T | T | G | T | A | G | A | T | widtype | 0 |

| Construct IDs | SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | TYPE | Total Number of Mismatches |
|---|---|---|---|---|---|---|---|---|---|---|---|---|---|---|---|---|---|---|---|---|---|---|---|
| TAATTCTACTGTCGTAGAT | 1 | T | A | A | T | T | T | C | T | A | C | T | G | T | C | G | T | A | G | A | T | test | 2 |
| TAATTCTACTATCGTAGAT | 2 | T | A | A | T | T | T | C | T | A | C | T | A | T | C | G | T | A | G | A | T | test | 2 |
| AAATTCTACTCAGTAGAT | 3 | A | A | A | T | T | T | C | T | A | C | T | C | T | A | G | T | A | G | A | T | test | 2 |
| TAATTCTACTATTGTAGAT | 4 | T | A | A | T | T | T | C | T | A | C | T | A | T | T | G | T | A | G | A | T | test | 1 |
| TAATTCTACTATAGTAGAT | 5 | T | A | A | T | T | T | C | T | A | C | T | A | T | A | G | T | A | G | A | T | test | 2 |
| AAATTCTCCTCGGAGAT | 6 | A | A | A | T | T | T | C | T | C | C | T | C | T | C | G | G | A | G | A | T | test | 4 |
| TAATTCTCCTATTGGAGAT | 7 | T | A | A | T | T | T | C | T | C | C | T | A | T | T | G | G | A | G | A | T | test | 3 |
| TAATTCTCCTCTAGGAGAT | 8 | T | A | A | T | T | T | C | T | C | C | T | C | T | A | G | G | A | G | A | T | test | 3 |
| AAATTCTCCTCTCGGAGAT | 9 | A | A | A | T | T | T | C | T | C | C | T | C | T | C | G | G | A | G | A | T | test | 3 |
| TAATTCTACTTTCGTAGAT | 10 | T | A | A | T | T | T | C | T | A | C | T | T | T | C | G | T | A | G | A | T | test | 2 |
| AAATTCTACTATTGTAGAT | 11 | A | A | A | T | T | T | C | T | A | C | T | A | T | T | G | T | A | G | A | T | test | 2 |
| TAATTCTACTATGGGAGAT | 12 | T | A | A | T | T | T | C | T | A | C | T | A | T | G | G | G | A | G | A | T | test | 2 |
| GAATTCTCCTCTCGGAGAT | 13 | G | A | A | T | T | T | C | T | C | C | T | C | T | C | G | G | A | G | A | T | test | 4 |
| GAATTCCTACTATTGTAGGT | 14 | G | A | A | T | T | C | C | T | A | C | T | A | T | T | G | T | A | G | G | T | test | 4 |
| TAATTCCTACTCTAGTAGGT | 15 | T | A | A | T | T | C | C | T | A | C | T | C | T | A | G | T | A | G | G | T | test | 3 |
| GAATTCTACTCTCGTAGGT | 16 | G | A | A | T | T | T | C | T | A | C | T | C | T | C | G | T | A | G | G | T | test | 2 |
| TAATTCTACTCTCTTGGT | 17 | T | A | A | T | T | T | C | T | A | C | T | C | T | C | T | T | A | G | G | T | test | 2 |
| AAATTCTCCCTCTAGGAGAT | 18 | A | A | A | T | T | T | C | T | C | C | C | T | C | T | A | G | G | A | G | A | T | test | 4 |
| AAATTCCTACTCTCGGAGT | 19 | A | A | A | T | T | C | C | T | A | C | T | C | T | C | G | G | A | G | G | T | test | 4 |
| TAATTCTACTGTTGTAGAT | 20 | T | A | A | T | T | T | C | T | A | C | T | G | T | T | G | T | A | G | A | T | test | 1 |
| GAATTCTACTCTAGTAGAT | 21 | G | A | A | T | T | T | C | T | A | C | T | C | T | A | G | T | A | G | A | T | test | 2 |
| TAATTCTCCTCTTGGAGAT | 22 | T | A | A | T | T | T | C | T | C | C | T | C | T | T | G | G | A | G | A | T | test | 2 |
| GAATTCTACTCTGGAGAT | 23 | G | A | A | T | T | T | C | T | A | C | T | C | T | G | G | G | A | G | A | T | test | 2 |
| TAATTCTACTTAGTAGAT | 24 | T | A | A | T | T | T | C | T | A | C | T | T | T | A | G | T | A | G | A | T | test | 2 |
| TAATTCTACTCTTGTAGAT | 25 | T | A | A | T | T | T | C | T | A | C | T | C | T | T | G | T | A | G | A | T | wildtype | 0 |

FIG. 7

| Construct IDs | SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | TYPE | Total Number of Mismatches |
|---|---|---|---|---|---|---|---|---|---|---|---|---|---|---|---|---|---|---|---|---|---|---|---|
| TAATTTCTACTGTCGTAGAT | 1 | T | A | A | T | T | T | C | T | A | C | T | G | T | C | G | T | A | G | A | T | test | 2 |
| TAATTTCTACTATCGTAGAT | 2 | T | A | A | T | T | T | C | T | A | C | T | A | T | C | G | T | A | G | A | T | test | 2 |
| AAATTTCTACTCAGTAGAT | 3 | A | A | A | T | T | T | C | T | A | C | T | C | T | A | G | T | A | G | A | T | test | 2 |
| TAATTTCTACTATTGTAGAT | 4 | T | A | A | T | T | T | C | T | A | C | T | A | T | T | G | T | A | G | A | T | test | 1 |
| TAATTTCTACTATAGTAGAT | 5 | T | A | A | T | T | T | C | T | A | C | T | A | T | A | G | T | A | G | A | T | test | 2 |
| AAATTTCTCCCTCGGAGAT | 6 | A | A | A | T | T | T | C | T | C | C | C | T | C | G | G | A | G | A | T |  | test | 4 |
| TAATTTCTCCTATTGGAGAT | 7 | T | A | A | T | T | T | C | T | C | C | T | A | T | T | G | G | A | G | A | T | test | 3 |
| TAATTTCTCCCTCTAGGAGAT | 8 | T | A | A | T | T | T | C | T | C | C | C | T | C | T | A | G | G | A | G | A | test | 3 |
| AAATTTCTCCCTTGGAGAT | 9 | A | A | A | T | T | T | C | T | C | C | C | T | T | G | G | A | G | A | T |  | test | 3 |
| TAATTTCTACTTCGTAGAT | 10 | T | A | A | T | T | T | C | T | A | C | T | T | T | C | G | T | A | G | A | T | test | 2 |
| AAATTTCTACTATTGTAGAT | 11 | A | A | A | T | T | T | C | T | A | C | T | A | T | T | G | T | A | G | A | T | test | 2 |
| TAATTTCTACTATGGTAGAT | 12 | T | A | A | T | T | T | C | T | A | C | T | A | T | G | G | T | A | G | A | T | test | 2 |
| GAATTCTCCTCGGAGAT | 13 | G | A | A | T | T | C | T | C | C | T | C | G | G | A | G | A | T |  |  |  | test | 4 |
| GAATTCCTACTATTGTAGGT | 14 | G | A | A | T | T | C | C | T | A | C | T | A | T | T | G | T | A | G | G | T | test | 4 |
| TAATTTCCTACTCTAGTAGGT | 15 | T | A | A | T | T | T | C | C | T | A | C | T | C | T | A | G | T | A | G | G | test | 3 |
| GAATTCTACTCGTAGGT | 16 | G | A | A | T | T | C | T | A | C | T | C | G | T | A | G | G | T |  |  |  | test | 2 |
| TAATTTCCTACTCTTGTAGGT | 17 | T | A | A | T | T | T | C | C | T | A | C | T | C | T | T | G | T | A | G | G | test | 2 |
| AAATTTCTCCCTAGGAGAT | 18 | A | A | A | T | T | T | C | T | C | C | C | T | A | G | G | A | G | A | T |  | test | 4 |
| AAATTTCCTACTCTCGTAGGT | 19 | A | A | A | T | T | T | C | C | T | A | C | T | C | T | C | G | T | A | G | G | test | 4 |
| TAATTTCTACTGTTGTAGAT | 20 | T | A | A | T | T | T | C | T | A | C | T | G | T | T | G | T | A | G | A | T | test | 1 |
| GAATTTCTACTCTAGTAGAT | 21 | G | A | A | T | T | T | C | T | A | C | T | C | T | A | G | T | A | G | A | T | test | 2 |
| TAATTTCTCCCTTGGAGAT | 22 | T | A | A | T | T | T | C | T | C | C | C | T | T | G | G | A | G | A | T |  | test | 2 |
| GAATTTCTACTCTGGTAGAT | 23 | G | A | A | T | T | T | C | T | A | C | T | C | T | G | G | T | A | G | A | T | test | 2 |
| TAATTTCACTTTAGTAGAT | 24 | T | A | A | T | T | T | C | A | C | T | T | T | A | G | T | A | G | A | T |  | test | 2 |
| TAATTTCTACTCTTGTAGAT | 25 | T | A | A | T | T | T | C | T | A | C | T | C | T | T | G | T | A | G | A | T | wildtype | 0 |

| Construct IDs | SEQ ID NO: | 1 | 2 | 3 | 4 | 5 | 6 | 7 | 8 | 9 | 10 | 11 | 12 | 13 | 14 | 15 | 16 | 17 | 18 | 19 | 20 | TYPE | Total Number of Mismatches |
|---|---|---|---|---|---|---|---|---|---|---|---|---|---|---|---|---|---|---|---|---|---|---|---|
| TAATTTCTACTGTCGTAGAT | 1 | T | A | A | T | T | T | C | T | A | C | T | G | T | C | G | T | A | G | A | T | test | 2 |
| TAATTTCTACTATCGTAGAT | 2 | T | A | A | T | T | T | C | T | A | C | T | A | T | C | G | T | A | G | A | T | test | 2 |
| AAATTTCTACTCTAGTAGAT | 3 | A | A | A | T | T | T | C | T | A | C | T | C | T | A | G | T | A | G | A | T | test | 2 |
| TAATTTCTACTATTGTAGAT | 4 | T | A | A | T | T | T | C | T | A | C | T | A | T | T | G | T | A | G | A | T | test | 1 |
| TAATTTCTACTATAGTAGAT | 5 | T | A | A | T | T | T | C | T | A | C | T | A | T | A | G | T | A | G | A | T | test | 2 |
| AAATTTCTCCTCGGAGAT | 6 | A | A | A | T | T | T | C | T | C | C | T | C | T | C | G | G | A | G | A | T | test | 4 |
| TAATTTCTCCTATTGGAGAT | 7 | T | A | A | T | T | T | C | T | C | C | T | A | T | T | G | G | A | G | A | T | test | 3 |
| TAATTTCTCCTCTAGGAGAT | 8 | T | A | A | T | T | T | C | T | C | C | T | C | T | A | G | G | A | G | A | T | test | 3 |
| AAATTTCTCCTCTTGGAGAT | 9 | A | A | A | T | T | T | C | T | C | C | T | C | T | T | G | G | A | G | A | T | test | 3 |
| TAATTTCTACTTCGTAGAT | 10 | T | A | A | T | T | T | C | T | A | C | T | T | T | C | G | T | A | G | A | T | test | 2 |
| AAATTTCTACTATTGTAGAT | 11 | A | A | A | T | T | T | C | T | A | C | T | A | T | T | G | T | A | G | A | T | test | 2 |
| TAATTTCTACTATGGTAGAT | 12 | T | A | A | T | T | T | C | T | A | C | T | A | T | G | G | T | A | G | A | T | test | 2 |
| GAATTCTCCTCGGAGAT | 13 | G | A | A | T | T | C | T | C | C | T | C | T | C | G | G | A | G | A | T |  | test | 4 |
| GAATTCCTACTATTGTAGGT | 14 | G | A | A | T | T | C | C | T | A | C | T | A | T | T | G | T | A | G | G | T | test | 4 |
| TAATTCCTACTCTAGTAGGT | 15 | T | A | A | T | T | C | C | T | A | C | T | C | T | A | G | T | A | G | G | T | test | 3 |
| GAATTCTACTCTCGTAGAT | 16 | G | A | A | T | T | C | T | A | C | T | C | T | C | G | T | A | G | A | T |  | test | 2 |
| TAATTCTCCTTGTAGGT | 17 | T | A | A | T | T | C | T | C | C | T | T | G | T | A | G | G | T |  |  |  | test | 2 |
| AAATTCTCCTAGGAGAT | 18 | A | A | A | T | T | C | T | C | C | T | A | G | G | A | G | A | T |  |  |  | test | 4 |
| AAATTCTACTCTCGTAGGT | 19 | A | A | A | T | T | C | T | A | C | T | C | T | C | G | T | A | G | G | T |  | test | 4 |
| TAATTCTACTGTTGTAGAT | 20 | T | A | A | T | T | C | T | A | C | T | G | T | T | G | T | A | G | A | T |  | test | 1 |
| GAATTTCTACTCTAGTAGAT | 21 | G | A | A | T | T | T | C | T | A | C | T | C | T | A | G | T | A | G | A | T | test | 2 |
| TAATTTCTCCTCTTGGAGAT | 22 | T | A | A | T | T | T | C | T | C | C | T | C | T | T | G | G | A | G | A | T | test | 2 |
| GAATTTCTACTCTGGTAGAT | 23 | G | A | A | T | T | T | C | T | A | C | T | C | T | G | G | T | A | G | A | T | test | 2 |
| TAATTTCTACTTTAGTAGAT | 24 | T | A | A | T | T | T | C | T | A | C | T | T | T | A | G | T | A | G | A | T | test | 2 |
| TAATTTCTACTCTTGTAGAT | 25 | T | A | A | T | T | T | C | T | A | C | T | C | T | T | G | T | A | G | A | T | wildtype | 0 |

FIG. 12

Amino acid sequence of human codon optimized Cpf1 orthologs

In certain of the following, Cpf1 amino acids are followed by *nuclear localization signals (NLS)* (italics), a glycine-serine (GS) linker, and 3x HA tag.

SEQ ID NO: 28: Franscisella tularensis subsp. novicida U112 (FnCpf1).

MSIYQEFVNKYSLSKTLRFELIPQGKTLENIKARGLILDDEKRAKDYKKAKQIIDKYHQFFIEEILSSVCISED
LLQNYSDVYFKLKKSDDDNLQKDFKSAKDTIKKQISEYIKDSEKFKNLFNQNLIDAKKGQESDLILWLKQS
KDNGIELFKANSDITDIDEALEIIKSFKGWTTYFKGFHENRKNVYSSNDIPTSIIYRIVDDNLPKFLENKAKYE
SLKDKAPEAINYEQIKKDLAEELTFDIDYKTSEVNQRVFSLDEVFEIANFNNYLNQSGITKFNTIIGGKFVNG
ENTRKGINEYINLYSQQINDKTLKKYKMSVLFKQILSDTESKSFVIDKLEDDSDVVTTMQSFYEQIAAFKT
VEEKSIKETLSLLFDDLKAQKLDLSKIYFKNDKSLTDLSQQVFDDYSVIGTAVLEYITQQIAPKNLDNPSKKE
QELIAKKTEKAKYLSLETIKLALEEFNKHRDIDKQCRFEEILANFAAIPMIFDEIAQNKDNLAQISIKYQNQG
KKDLLQASAEDDVKAIKDLLDQTNNLLHKLKIFHISQSEDKANILDKDEHFYLVFEECYFELANIVPLYNKI
RNYITQKPYSDEKFKLNFENSTLANGWDKNKEPDNTAILFIKDDKYYLGVMNKKNNKIFDDKAIKENKGE
GYKKIVYKLLPGANKMLPKVFFSAKSIKFYNPSEDILRIRNHSTHTKNGSPQKGYEKFEFNIEDCRKFIDFYK
QSISKHPEWKDFGFRFSDTQRYNSIDEFYREVENQGYKLTFENISESYIDSVVNQGKLYLFQIYNKDFSAYSK
GRPNLHTLYWKALFDERNLQDVVYKLNGEAELFYRKQSIPKKITHPAKEAIANKNKDNPKKESVFEYDLIK
DKRFTEDKFFFHCPITINFKSSGANKFNDEINLLLKEKANDVHILSIDRGERHLAYYTLVDGKGNIIKQDTFNI
IGNDRMKTNYHDKLAAIEKDRDSARKDWKKINNIKEMKEGYLSQVVHEIAKLVIEYNAIVVFEDLNFGFK
RGRFKVEKQVYQKLEKMLIEKLNYLVFKDNEFDKTGGVLRAYQLTAPFETFKKMGKQTGIIYYVPAGFTS
KICPVTGFVNQLYPKYESVSKSQEFFSKFDKICYNLDKGYFEFSFDYKNFGDKAAKGKWTIASFGSRLINFR
NSDKNHNWDTREVYPTKELEKLLKDYSIEYGHGECIKAAICGESDKKFFAKLTSVLNTILQMRNSKTGTEL
DYLISPVADVNGNFFDSRQAPKNMPQDADANGAYHIGLKGLMLLGRIKNNQEGKKLNLVIKNEEYFEFVQ
NRNN*KRPAATKKAGQAKKKK*<u>GS</u>YPYDVPDYAYPYDVPDYAYPYDVPDYA

SEQ ID NO: 29 Lachnospiraceae bacterium MC2017 (Lb3Cpf1)

MDYGNGQFERRAPLTKTITLRLKPIGETRETIREQKLLEQDAAFRKLVETVTPIVDDCIRKIADNALCHFGTE
YDFSCLGNAISKNDSKAIKKETEKVEKLLAKVLTENLPDGLRKVNDINSAAFIQDTLTSFVQDDADKRVLIQ
ELKGKTVLMQRFLTTRITALTVWLPDRVFENFNIFIENAEKMRILLDSPLNEKIMKFDPDAEQYASLEFYGQ
CLSQKDIDSYNLIISGIYADDEVKNPGINEIVKEYNQQIRGDKDESPLPKLKKLHKQILMPVEKAFFVRVLSN
DSDARSILEKILKDTEMLPSKIIEAMKEADAGDIAVYGSRLHELSHVIYGDHGKLSQIIYDKESKRISELMETL
SPKERKESKKRLEGLEEHIRKSTYTFDELNRYAEKNVMAAYIAAVEESCAEIMRKEKDLRTLLSKEDVKIR
GNRHNTLIVKNYFNAWTVFRNLIRILRRKSEAEIDSDFYDVLDDSVEVLSLTYKGENLCRSYITKKIGSDLKP
EIATYGSALRPNSRWWSPGEKFNVKFHTIVRRDGRLYYFILPKGAKPVELEDMDGDIECLQMRKIPNPTIFL
PKLVFKDPEAFFRDNPEADEFVFLSGMKAPVTITRETYEAYRYKLYTVGKLRDGEVSEEEYKRALLQVLTA
YKEFLENRMIYADLNFGFKDLEEYKDSSEFIKQVETHNTFMCWAKVSSSQLDDLVKSGNGLLFEIWSERLE
SYYKYGNEKVLRGYEGVLLSILKDENLVSMRTLLNSRPMLVYRPKESSKPMVVHRDGSRVVDRFDKDGK
YIPPEVHDELYRFFNNLLIKEKLGEKARKILDNKKVKVKVLESERVKWSKFYDEQFAVTFSVKKNADCLDT
TKDLNAEVMEQYSESNRLILIRNTTDILYYLVLDKNGKVLKQRSLNIINDGARDVDWKERFRQVTKDRNEG
YNEWDYSRTSNDLKEVYLNYALKEIAEAVIEYNAILIIEKMSNAFKDKYSFLDDVTFKGFETKLLAKLSDLH
FRGIKDGEPCSFTNPLQLCQNDSNKILQDGVIFMVPNSMTRSLDPDTGFIFAINDHNIRTKKAKLNFLSKFDQ
LKVSSEGCLIMKYSGDSLPTHNTDNRVWNCCCNHPITNYDRETKKVEFIEEPVEELSRVLEENGIETDTELN
KLNERENVPGKVVDAIYSLVLNYLRGTVSGVAGQRAVYYSPVTGKKYDISFIQAMNLNRKCDYYRIGSKE
RGEWTDFVAQLIN*KRPAATKKAGQAKKKK*<u>GS</u>YPYDVPDYAYPYDVPDYAYPYDVPDYA

FIG. 13

SEQ ID NO: 30 Butyrivibrio proteoclasticus (BpCpf1)

MLLYENYTKRNQITKSLRLELRPQGKTLRNIKELNLLEQDKAIYALLERLKPVIDEGIKDIARDTLKNCELSF
EKLYEHFLSGDKKAYAKESERLKKEIVKTLIKNLPEGIGKISEINSAKYLNGVLYDFIDKTHKDSEEKQNILS
DILETKGYLALFSKFLTSRITTLEQSMPKRVIENFEIYAANIPKMQDALERGAVSFAIEYESICSVDYYNQILS
QEDIDSYNRLISGIMDEDGAKEKGINQTISEKNIKIKSEHLEEKPFRILKQLHKQILEEREKAFTIDHIDSDEEV
VQVTKEAFEQTKEQWENIKKINGFYAKDPGDITLFIVVGPNQTHVLSQLIYGEHDRIRLLLEEYEKNTLEVL
PRRTKSEKARYDKFVNAVPKKVAKESHTFDGLQKMTGDDRLFILYRDELARNYMRIKEAYGTFERDILKS
RRGIKGNRDVQESLVSFYDELTKFRSALRIINSGNDEKADPIFYNTFDGIFEKANRTYKAENLCRNYVTKSP
ADDARIMASCLGTPARLRTHWWNGEENFAINDVAMIRRGDEYYYFVLTPDVKPVDLKTKDETDAQIFVQR
KGAKSFLGLPKALFKCILEPYFESPEHKNDKNCVIEEYVSKPLTIDRRAYDIFKNGTFKKTNIGIDGLTEEKF
KDDCRYLIDVYKEFIAVYTRYSCFNMSGLKRADEYNDIGEFFSDVDTRLCTMEWIPVSFERINDMVDKKEG
LLFLVRSMFLYNRPRKPYERTFIQLFSDSNMEHTSMLLNSRAMIQYRAASLPRRVTHKKGSILVALRDSNGE
HIPMHIREAIYKMKNNFDISSEDFIMAKAYLAEHDVAIKKANEDIIRNRRYTEDKFFLSLSYTKNADISARTL
DYINDKVEEDTQDSRMAVIVTRNLKDLTYVAVVDEKNNVLEEKSLNEIDGVNYRELLKERTKIKYHDKTR
LWQYDVSSKGLKEAYVELAVTQISKLATKYNAVVVESMSSTFKDKFSFLDEQIFKAFEARLCARMSDLSF
NTIKEGEAGSISNPIQVSNNNGNSYQDGVIYFLNNAYTRTLCPDTGFVDVFDKTRLITMQSKRQFFAKMKDI
RIDDGEMLFTFNLEEYPTKRLLDRKEWTVKIAGDGSYFDKDKGEYVYVNDIVREQIIPALLEDKAVFDGNM
AEKFLDKTAISGKSVELIYKWFANALYGIITKKDGEKIYRSPITGTEIDVSKNTTYNFGKKFMFKQEYRGDG
DFLDAFLNYMQAQDIA*KRPAATKKAGQAKKKK*<u>GS</u>YPYDVPDYAYPYDVPDYAYPYDVPDYA

SEQ ID NO: 31 Peregrinibacteria bacterium GW2011_GWA_33_10 (PeCpf1)

MSNFFKNFTNLYELSKTLRFELKPVGDTLTNMKDHLEYDEKLQTFLKDQNIDDAYQALKPQFDEIHEEFIT
DSLESKKAKEIDFSEYLDLFQEKKELNDSEKKLRNKIGETFNKAGEKWKKEKYPQYEWKKGSKIANGADIL
SCQDMLQFIKYKNPEDEKIKNYIDDTLKGFFTYFGGFNQNRANYYETKKEASTAVATRIVHENLPKFCDNV
IQFKHIIKRKKDGTVEKTERKTEYLNAYQYLKNNNKITQIKDAETEKMIESTPIAEKIFDVYYFSSCLSQKQIE
EYNRIIGHYNLLINLYNQAKRSEGKHLSANEKKYKDLPKFKTLYKQIGCGKKKDLFYTIKCDTEEEANKSR
NEGKESHSVEEIINKAQEAINKYFKSNNDCENINTVPDFINYILTKENYEGVYWSKAAMNTISDKYFANYHD
LQDRLKEAKVFQKADKKSEDDIKIPEAIELSGLFGVLDSLADWQTTLFKSSILSNEDKLKIITDSQTPSEALLK
MIFNDIEKNMESFLKETNDIITLKKYKGNKEGTEKIKQWFDYTLAINRMLKYFLVKENKIKGNSLDTNISEA
LKTLIYSDDAEWFKWYDALRNYLTQKPQDEAKENKLKLNFDNPSLAGGWDVNKECSNFCVILKDKNEKK
YLAIMKKGENTLFQKEWTEGRGKNLTKKSNPLFEINNCEILSKMEYDFWADVSKMIPKCSTQLKAVVNHF
KQSDNEFIFPIGYKVTSGEKFREECKISKQDFELNNKVFNKNELSVTAMRYDLSSTQEKQYIKAFQKEYWEL
LFKQEKRDTKLTNNEIFNEWINFCNKKYSELLSWERKYKDALTNWINFCKYFLSKYPKTTLFNYSFKESEN
YNSLDEFYRDVDICSYKLNINTTINKSILDRLVEEGKLYLFEIKNQDSNDGKSIGHKNNLHTIYWNAIFENFD
NRPKLNGEAEIFYRKAISKDKLGIVKGKKTKNGTEIIKNYRFSKEKFILHVPITLNFCSNNEYVNDIVNTKFY
NFSNLHFLGIDRGEKHLAYYSLVNKNGEIVDQGTLNLPFTDKDGNQRSIKKEKYFYNKQEDKWEAKEVDC
WNYNDLLDAMASNRDMARKNWQRIGTIKEAKNGYVSLVIRKIADLAVNNERPAFIVLEDLNTGFKRSRQK
IDKSVYQKFELALAKKLNFLVDKNAKRDEIGSPTKALQLTPPVNNYGDIENKKQAGIMLYTRANYTSQTDP
ATGWRKTIYLKAGPEETTYKKDGKIKNKSVKDQIIETFTDIGFDGKDYYFEYDKGEFVDEKTGEIKPKKWR
LYSGENGKSLDRFRGEREKDKYEWKIDKIDIVKILDDLFVNFDKNISLLKQLKEGVELTRNNEHGTGESLRF
AINLIQQIRNTGNNERDNDFILSPVRDENGKHFDSREYWDKETKGEKISMPSSGDANGAFNIARKGIIMNAH
ILANSDSKDLSLFVSDEEWDLHLNNKTEWKKQLNIFSSRKAMA*KRKKKRPAATKKAGQAKKKK*<u>GS</u>**YPYDVP
DYAYPYDVPDYAYPYDVPDYA**

SEQ ID NO: 32 Parcubacteria bacterium GWC2011_GWC2_44_17 (PbCpf1)

MENIFDQFIGKYSLSKTLRFELKPVGKTEDFLKINKVFEKDQTIDDSYNQAKFYFDSLHQKFIDAALASDKT
SELSFQNFADVLEKQNKIILDKKREMGALRKRDKNAVGIDRLQKEINDAEDIIQKEKEKIYKDVRTLFDNEA
ESWKTYYQEREVDGKKITFSKADLKQKGADFLTAAGILKVLKYEFPEEKEKEFQAKNQPSLFVEEKENPGQ
KRYIFDSFDKFAGYLTKFQQTKKNLYAADGTSTAVATRIADNFIIFHQNTKVFRDKYKNNHTDLGFDEENIF
EIERYKNCLLQREIEHIKNENSYNKIIGRINKKIKEYRDQKAKDTKLTKSDFPFFKNLDKQILGEVEKEKQLIE
KTREKTEEDVLIERFKEFIENNEERFTAAKKLMNAFCNGEFESEYEGIYLKNKAINTISRRWFVSDRDFELKL
PQQKSKNKSEKNEPKVKKFISIAEIKNAVEELDGDIFKAVFYDKKIIAQGGSKLEQFLVIWKYEFEYLFRDIE
RENGEKLLGYDSCLKIAKQLGIFPQEKEAREKATAVIKNYADAGLGIFQMMKYFSLDDKDRKNTPGQLST
NFYAEYDGYYKDFEFIKYYNEFRNFITKKPFDEDKIKLNFENGALLKGWDENKEYDFMGVILKKEGRLYL
GIMHKNHRKLFQSMGNAKGDNANRYQKMIYKQIADASKDVPRLLLTSKKAMEKFKPSQEILRIKKEKTFK
RESKNFSLRDLHALIEYYRNCIPQYSNWSFYDFQFQDTGKYQNIKEFTDDVQKYGYKISFRDIDDEYINQAL
NEGKMYLFEVVNKDIYNTKNGSKNLHTLYFEHILSAENLNDPVFKLSGMAEIFQRQPSVNEREKITTQKNQ
CILDKGDRAYKYRRYTEKKIMFHMSLVLNTGKGEIKQVQFNKIINQRISSSDNEMRVNVIGIDRGEKNLLYY
SVVKQNGEIIEQASLNEINGVNYRDKLIEREKERLKNRQSWKPVVKIKDLKKGYISHVIHKICQLIEKYSAIV
VLEDLNMRFKQIRGGIERSVYQQFEKALIDKLGYLVFKDNRDLRAPGGVLNGYQLSAPFVSFEKMRKQTGI
LFYTQAEYTSKTDPITGFRKNVYISNSASLDKIKEAVKKFDAIGWDGKEQSYFFKYNPYNLADEKYKNSTV
SKEWAIFASAPRIRRQKGEDGYWKYDRVKVNEEFEKLLKVWNFVNPKATDIKQEIIKKEKAGDLQGEKEL
DGRLRNFWHSFIYLFNLVLELRNSFSLQIKIKAGEVIAVDEGVDFIASPVKPFFTTPNPYIPSNLCWLAVENA
DANGAYNIARKGVMILKKIREHAKKDPEFKKLPNLFISNAEWDEAARDWGKYAGTTALNLDH*KRPAATKK
AGQAKKKKG*SYPYDVPDYAYPYDVPDYAYPYDVPDYA

SEQ ID NO: 33 Smithella sp. SC_K08D17 (SsCpf1)

MQTLFENFTNQYPVSKTLRFELIPQGKTKDFIEQKGLLKKDEDRAEKYKKVKNIIDEYHKDFIEKSLNGLKL
DGLEKYKTLYLKQEKDDKDKKAFDKEKENLRKQIANAFRNNEKFKTLFAKELIKNDLMSFACEEDKKNV
KEFEAFTTYFTGFHQNRANMYVADEKRTAIASRLIHENLPKFIDNIKIFEKMKKEAPELLSPFNQTLKDMKD
VIKGTTLEEIFSLDYFNKTLTQSGIDIYNSVIGGRTPEEGKTKIKGLNEYINTDFNQKQTDKKKRQPKFKQLY
KQILSDRQSLSFIAEAFKNDTEILEAIEKFYVNELLHFSNEGKSTNVLDAIKNAVSNLESFNLTKMYFRSGAS
LTDVSRKVFGEWSIINRALDNYYATTYPIKPREKSEKYEERKEKWLKQDFNVSLIQTAIDEYDNETVKGKN
SGKVIADYFAKFCDDKETDLIQKVNEGYIAVKDLLNTPCPENEKLGSNKDQVKQIKAFMDSIMDIMHFVRP
LSLKDTDKEKDETFYSLFTPLYDHLTQTIALYNKVRNYLTQKPYSTEKIKLNFENSTLLGGWDLNKETDNT
AIILRKDNLYYLGIMDKRHNRIFRNVPKADKKDFCYEKMVYKLLPGANKMLPKVFFSQSRIQEFTPSAKLL
ENYANETHKKGDNFNLNHCHKLIDFFKDSINKHEDWKNFDFRFSATSTYADLSGFYHEVEHQGYKISFQSV
ADSFIDDLVNEGKLYLFQIYNKDFSPFSKGKPNLHTLYWKMLFDENNLKDVVYKLNGEAEVFYRKKSIAE
KNTTIHKANESIINKNPDNPKATSTFNYDIVKDKRYTIDKFQFHIPITMNFKAEGIFNMNQRVNQFLKANPDI
NIIGIDRGERHLLYYALINQKGKILKQDTLNVIANEKQKVDYHNLLDKKEGDRATARQEWGVIETIKELKE
GYLSQVIHKLTDLMIENNAIIVMEDLNFGFKRGRQKVEKQVYQKFEKMLIDKLNYLVDKNKKANELGGLL
NAFQLANKFESFQKMGKQNGFIFYVPAWNTSKTDPATGFIDFLKPRYENLNQAKDFFEKFDSIRLNSKADY
FEFAFDFKNFTEKADGGRTKWTVCTTNEDRYAWNRALNNNRGSQEKYDITAELKSLFDGKVDYKSGKDL
KQQIASQESADFFKALMKNLSITLSLRHNNGEKGDNEQDYILSPVADSKGRFFDSRKADDDMPKNADANG
AYHIALKGLWCLEQISKTDDLKKVKLAISNKEWLEFVQTLKG*KRPAATKKAGQAKKKKG*S**YPYDVPDYAY
PYDVPDYAYPYDVPDYA**

FIG. 13 cntd.

SEQ ID NO: 34 Acidaminococcus sp. BV3L6 (AsCpf1)

MTQFEGFTNLYQVSKTLRFELIPQGKTLKHIQEQGFIEEDKARNDHYKELKPIIDRIYKTYADQCLQLVQLD
WENLSAAIDSYRKEKTEETRNALIEEQATYRNAIHDYFIGRTDNLTDAINKRHAEIYKGLFKAELFNGKVLK
QLGTVTTTEHENALLRSFDKFTTYFSGFYENRKNVFSAEDISTAIPHRIVQDNFPKFKENCHIFTRLITAVPSL
REHFENVKKAIGIFVSTSIEEVFSFPFYNQLLTQTQIDLYNQLLGGISREAGTEKIKGLNEVLNLAIQKNDETA
HIIASLPHRFIPLFKQILSDRNTLSFILEEFKSDEEVIQSFCKYKTLLRNENVLETAEALFNELNSIDLTHIFISHK
KLETISSALCDHWDTLRNALYERRISELTGKITKSAKEKVQRSLKHEDINLQEIISAAGKELSEAFKQKTSEIL
SHAHAALDQPLPTTLKKQEEKEILKSQLDSLLGLYHLLDWFAVDESNEVDPEFSARLTGIKLEMEPSLSFYN
KARNYATKKPYSVEKFKLNFQMPTLASGWDVNKEKNNGAILFVKNGLYYLGIMPKQKGRYKALSFEPTE
KTSEGFDKMYYDYFPDAAKMIPKCSTQLKAVTAHFQTHTTPILLSNNFIEPLEITKEIYDLNNPEKEPKKFQT
AYAKKTGDQKGYREALCKWIDFTRDFLSKYTKTTSIDLSSLRPSSQYKDLGEYYAELNPLLYHISFQRIAEK
EIMDAVETGKLYLFQIYNKDFAKGHHGKPNLHTLYWTGLFSPENLAKTSIKLNGQAELFYRPKSRMKRMA
HRLGEKMLNKKLKDQKTPIPDTLYQELYDYVNHRLSHDLSDEARALLPNVITKEVSHEIIKDRRFTSDKFFF
HVPITLNYQAANSPSKFNQRVNAYLKEHPETPIIGIDRGERNLIYITVIDSTGKILEQRSLNTIQQFDYQKKLD
NREKERVAARQAWSVVGTIKDLKQGYLSQVIHEIVDLMIHYQAVVVLENLNFGFKSKRTGIAEKAVYQQF
EKMLIDKLNCLVLKDYPAEKVGGVLNPYQLTDQFTSFAKMGTQSGFLFYVPAPYTSKIDPLTGFVDPFVW
KTIKNHESRKHFLEGFDFLHYDVKTGDFILHFKMNRNLSFQRGLPGFMPAWDIVFEKNETQFDAKGTPFIA
GKRIVPVIENHRFTGRYRDLYPANELIALLEEKGIVFRDGSNILPKLLENDDSHAIDTMVALIRSVLQMRNSN
AATGEDYINSPVRDLNGVCFDSRFQNPEWPMDADANGAYHIALKGQLLLNHLKESKDLKLQNGISNQDW
LAYIQELRN*KRPAATKKAGQAKKKK*GSYPYDVPDYAYPYDVPDYAYPYDVPDYA)

SEQ ID NO: 35 Lachnospiraceae bacterium MA2020 (Lb2Cpf1)

MYYESLTKQYPVSKTIRNELIPIGKTLDNIRQNNILESDVKRKQNYEHVKGILDEYHKQLINEALDNCTLPSL
KIAAEIYLKNQKEVSDREDFNKTQDLLRKEVVEKLKAHENFTKIGKKDILDLLEKLPSISEDDYNALESFRN
FYTYFTSYNKVRENLYSDKEKSSTVAYRLINENFPKFLDNVKSYRFVKTAGILADGLGEEEQDSLFIVETFN
KTLTQDGIDTYNSQVGKINSSINLYNQKNQKANGFRKIPKMKMLYKQILSDREESFIDEFQSDEVLIDNVES
YGSVLIESLKSSKVSAFFDALRESKGKNVYVKNDLAKTAMSNIVFENWRTFDDLLNQEYDLANENKKKDD
KYFEKRQKELKKNKSYSLEHLCNLSEDSCNLIENYIHQISDDIENIIINNETFLRIVINEHDRSRKLAKNRKAV
KAIKDFLDSIKVLERELKLINSSGQELEKDLIVYSAHEELLVELKQVDSLYNMTRNYLTKKPFSTEKVKLNF
NRSTLLNGWDRNKETDNLGVLLLKDGKYYLGIMNTSANKAFVNPPVAKTEKVFKKVDYKLLPVPNQMLP
KVFFAKSNIDFYNPSSEIYSNYKKGTHKKGNMFSLEDCHNLIDFFKESISKHEDWSKFGKFSDTASYNDISE
FYREVEKQGYKLTYTDIDETYINDLIERNELYLFQIYNKDFSMYSKGKLNLHTLYFMMLFDQRNIDDVVYK
LNGEAEVFYRPASISEDELIIHKAGEEIKNKNPNRARTKETSTFSYDIVKDKRYSKDKFTLHIPITMNFGVDE
VKRFNDAVNSAIRIDENVNVIGIDRGERNLLYVVVIDSKGNILEQISLNSIINKEYDIETDYHALLDEREGGR
DKARKDWNTVENIRDLKAGYLSQVVNVVAKLVLKYNAIICLEDLNFGFKRGRQKVEKQVYQKFEKMLID
KLNYLVIDKSREQTSPKELGGALNALQLTSKFKSFKELGKQSGVIYYVPAYLTSKIDPTTGFANLFYMKCEN
VEKSKRFFDGFDFIRFNALENVFEFGFDYRSFTQRACGINSKWTVCTNGERIIKYRNPDKNNMFDEKVVVV
TDEMKNLFEQYKIPYEDGRNVKDMIISNEEAEFYRRLYRLLQQTLQMRNSTSDGTRDYIISPVKNKREAYF
NSELSDGSVPKDADANGAYNIARKGLWVLEQIRQKSEGEKINLAMTNAEWLEYAQTHLL*KRPAATKKAGQ
AKKKK*GSYPYDVPDYAYPYDVPDYAYPYDVPDYA

FIG. 13 cntd.

SEQ ID NO: 36 Candidatus Methanoplasma termitum (CMtCpf1)

MNNYDEFTKLYPIQKTIRFELKPQGRTMEHLETFNFFEEDRDRAEKYKILKEAIDEYHKKFIDEHLTNMSLD
WNSLKQISEKYYKSREEKDKKVFLSEQKRMRQEIVSEFKKDDRFKDLFSKKLFSELLKEEIYKKGNHQEID
ALKSFDKFSGYFIGLHENRKNMYSDGDEITAISNRIVNENFPKFLDNLQKYQEARKKYPEWIIKAESALVAH
NIKMDEVFSLEYFNKVLNQEGIQRYNLALGGYVTKSGEKMMGLNDALNLAHQSEKSSKGRIHMTPLFKQI
LSEKESFSYIPDVFTEDSQLLPSIGGFFAQIENDKDGNIFDRALELISSYAEYDTERIYIRQADINRVSNVIFGE
WGTLGGLMREYKADSINDINLERTCKKVDKWLDSKEFALSDVLEAIKRTGNNDAFNEYISKMRTAREKID
AARKEMKFISEKISGDEESIHIIKTLLDSVQQFLHFFNLFKARQDIPLDGAFYAEFDEVHSKLFAIVPLYNKVR
NYLTKNNLNTKKIKLNFKNPTLANGWDQNKVYDYASLIFLRDGNYYLGIINPKRKKNIKFEQGSGNGPFYR
KMVYKQIPGPNKNLPRVFLTSTKGKKEYKPSKEIIEGYEADKHIRGDKFDLDFCHKLIDFFKESIEKHKDWS
KFNFYFSPTESYGDISEFYLDVEKQGYRMHFENISAETIDEYVEKGDLFLFQIYNKDFVKAATGKKDMHTIY
WNAAFSPENLQDVVVKLNGEAELFYRDKSDIKEIVHREGEILVNRTYNGRTPVPDKIHKKLTDYHNGRTK
DLGEAKEYLDKVRYFKAHYDITKDRRYLNDKIYFHVPLTLNFKANGKKNLNKMVIEKFLSDEKAHIIGIDR
GERNLLYYSIIDRSGKIIDQQSLNVIDGFDYREKLNQREIEMKDARQSWNAIGKIKDLKEGYLSKAVHEITK
MAIQYNAIVVMEELNYGFKRGRFKVEKQIYQKFENMLIDKMNYLVFKDAPDESPGGVLNAYQLTNPLESF
AKLGKQTGILFYVPAAYTSKIDPTTGFVNLFNTSSKTNAQERKEFLQKFESISYSAKDGGIFAFAFDYRKFGT
SKTDHKNVWTAYTNGERMRYIKEKKRNELFDPSKEIKEALTSSGIKYDGGQNILPDILRSNNNGLIYTMYSS
FIAAIQMRVYDGKEDYIISPIKNSKGEFFRTDPKRRELPIDADANGAYNIALRGELTMRAIAEKFDPDSEKMA
KLELKHKDWFEFMQTRGD*KRPAATKKAGQAKKKK*GSYPYDVPDYAYPYDVPDYAYPYDVPDYA

SEQ ID NO: 37 Eubacterium eligens (EeCpf1)

MNGNRSIVYREFVGVIPVAKTLRNELRPVGHTQEHIIQNGLIQEDELRQEKSTELKNIMDDYYREYIDKSLS
GVTDLDFTLLFELMNLVQSSPSKDNKKALEKEQSKMREQICTHLQSDSNYKNIFNAKLLKEILPDFIKNYNQ
YDVKDKAGKLETLALFNGFSTYFTDFFEKRKNVFTKEAVSTSIAYRIVHENSLIFLANMTSYKKISEKALDEI
EVIEKNNQDKMGDWELNQIFNPDFYNMVLIQSGIDFYNEICGVVNAHMNLYCQQTKNNYNLFKMRKLHK
QILAYTSTSFEVPKMFEDDMSVYNAVNAFIDETEKGNIIGKLKDIVNKYDELDEKRIYISKDFYETLSCFMSG
NWNLITGCVENFYDENIHAKGKSKEEKVKKAVKEDKYKSINDVNDLVEKYIDEKERNEFKNSNAKQYIREI
SNIITDTETAHLEYDDHISLIESEEKADEMKKRLDMYMNMYHWAKAFIVDEVLDRDEMFYSDIDDIYNILE
NIVPLYNRVRNYVTQKPYNSKKIKLNFQSPTLANGWSQSKEFDNNAIILIRDNKYYLAIFNAKNKPDKKIIQ
GNSDKKNDNDYKKMVYNLLPGANKMLPKVFLSKKGIETFKPSDYIISGYNAHKHIKTSENFDISFCRDLIDY
FKNSIEKHAEWRKYEFKFSATDSYSDISEFYREVEMQGYRIDWTYISEADINKLDEEGKIYLFQIYNKDFAE
NSTGKENLHTMYFKNIFSEENLKDIIIKLNGQAELFYRRASVKNPVKHKKDSVLVNKTYKNQLDNGDVVRI
PIPDDIYNEIYKMYNGYIKESDLSEAAKEYLDKVEVRTAQKDIVKDYRYTVDKYFIHTPITINYKVTARNNV
NDMVVKYIAQNDDIHVIGIDRGERNLIYISVIDSHGNIVKQKSYNILNNYDYKKKLVEKEKTREYARKNWK
SIGNIKELKEGYISGVVHEIAMLIVEYNAIIAMEDLNYGFKRGRFKVERQVYQKFESMLINKLNYFASKEKS
VDEPGGLLKGYQLTYVPDNIKNLGKQCGVIFYVPAAFTSKIDPSTGFISAFNFKSISTNASRKQFFMQFDEIR
YCAEKDMFSFGFDYNNFDTYNITMGKTQWTVYTNGERLQSEFNNARRTGKTKSINLTETIKLLLEDNEINY
ADGHDIRIDMEKMDEDKKSEFFAQLLSLYKLTVQMRNSYTEAEEQENGISYDKIISPVINDEGEFFDSDNYK
ESDDKECKMPKDADANGAYCIALKGLYEVLKIKSEWTEDGFDRNCLKLPHAEWLDFIQNKRYE*KRPAATK
KAGQAKKKK*GSYPYDVPDYAYPYDVPDYAYPYDVPDYA

FIG. 13 cntd.

SEQ ID NO: 38 Moraxella bovoculi 237 (MbCpf1)

MLFQDFTHLYPLSKTVRFELKPIDRTLEHIHAKNFLSQDETMADMHQKVKVILDDYHRDFIADMMGEVKL
TKLAEFYDVYLKFRKNPKDDELQKQLKDLQAVLRKEIVKPIGNGGKYKAGYDRLFGAKLFKDGKELGDL
AKFVIAQEGESSPKLAHLAHFEKFSTYFTGFHDNRKNMYSDEDKHTAIAYRLIHENLPRFIDNLQILTTIKQK
HSALYDQIINELTASGLDVSLASHLDGYHKLLTQEGITAYNTLLGGISGEAGSPKIQGINELINSHHNQHCHK
SERIAKLRPLHKQILSDGMSVSFLPSKFADDSEMCQAVNEFYRHYADVFAKVQSLFDGFDDHQKDGIYVEH
KNLNELSKQAFGDFALLGRVLDGYYVDVVNPEFNERFAKAKTDNAKAKLTKEKDKFIKGVHSLASLEQAI
EHYTARHDDESVQAGKLGQYFKHGLAGVDNPIQKIHNNHSTIKGFLERERPAGERALPKIKSGKNPEMTQL
RQLKELLDNALNVAHFAKLLTTKTTLDNQDGNFYGEFGVLYDELAKIPTLYNKVRDYLSQKPFSTEKYKL
NFGNPTLLNGWDLNKEKDNFGVILQKDGCYYLALLDKAHKKVFDNAPNTGKSIYQKMIYKYLEVRKQFP
KVFFSKEAIAINYHPSKELVEIKDKGRQRSDDERLKLYRFILECLKIHPKYDKKFEGAIGDIQLFKKDKKGRE
VPISEKDLFDKINGIFSSKPKLEMEDFFIGEFKRYNPSQDLVDQYNIYKKIDSNDNRKKENFYNNHPKFKKDL
VRYYYESMCKHEEWEESFEFSKKLQDIGCYVDVNELFTEIETRRLNYKISFCNINADYIDELVEQGQLYLFQ
IYNKDFSPKAHGKPNLHTLYFKALFSEDNLADPIYKLNGEAQIFYRKASLDMNETTIHRAGEVLENKNPDN
PKKRQFVYDIIKDKRYTQDKFMLHVPITMNFGVQGMTIKEFNKKVNQSIQQYDEVNVIGIDRGERHLLYLT
VINSKGEILEQCSLNDITTASANGTQMTTPYHKILDKREIERLNARVGWGEIETIKELKSGYLSHVVHQISQL
MLKYNAIVVLEDLNFGFKRGRFKVEKQIYQNFENALIKKLNHLVLKDKADDEIGSYKNALQLTNNFTDLK
SIGKQTGFLFYVPAWNTSKIDPETGFVDLLKPRYENIAQSQAFFGKFDKICYNADKDYFEFHIDYAKFTDKA
KNSRQIWTICSHGDKRYVYDKTANQNKGAAKGINVNDELKSLFARHHINEKQPNLVMDICQNNDKEFHKS
LMYLLKTLLALRYSNASSDEDFILSPVANDEGVFFNSALADDTQPQNADANGAYHIALKGLWLLNELKNS
DDLNKVKLAIDNQTWLNFAQNR*KRPAATKKAGQAKKKK*GSYPYDVPDYAYPYDVPDYAYPYDVPDYA

SEQ ID NO: 39 Leptospira inadai (LiCpf1)

MEDYSGFVNIYSIQKTLRFELKPVGKTLEHIEKKGFLKKDKIRAEDYKAVKKIIDKYHRAYIEEVFDSVLHQ
KKKKDKTRFSTQFIKEIKEFSELYYKTEKNIPDKERLEALSEKLRKMLVGAFKGEFSEEVAEKYKNLFSKELI
RNEIEKFCETDEERKQVSNFKSFTTYFTGFHSNRQNIYSDEKKSTAIGYRIIHQNLPKFLDNLKIIESIQRRFKD
FPWSDLKKNLKKIDKNIKLTEYFSIDGFVNVLNQKGIDAYNTILGGKSEESGEKIQGLNEYINLYRQKNNID
RKNLPNVKILFKQILGDRETKSFIPEAFPDDQSVLNSITEFAKYLKLDKKKKSIIAELKKFLSSFNRYELDGIY
LANDNSLASISTFLFDDWSFIKKSVSFKYDESVGDPKKKIKSPLKYEKEKEKWLKQKYYTISFLNDAIESYSK
SQDEKRVKIRLEAYFAEFKSKDDAKKQFDLLERIEEAYAIVEPLLGAEYPRDRNLKADKKEVGKIKDFLDSI
KSLQFFLKPLLSAEIFDEKDLGFYNQLEGYYEEIDSIGHLYNKVRNYLTGKIYSKEKFKLNFENSTLLKGWD
ENREVANLCVIFREDQKYYLGVMDKENNTILSDIPKVKPNELFYEKMVYKLIPTPHMQLPRIIFSSDNLSIYN
PSKSILKIREAKSFKEGKNFKLKDCHKFIDFYKESISKNEDWSRFDFKFSKTSSYENISEFYREVERQGYNLDF
KKVSKFYIDSLVEDGKLYLFQIYNKDFSIFSKGKPNLHTIYFRSLFSKENLKDVCLKLNGEAEMFFRKKSINY
DEKKKREGHHPELFEKLKYPILKDKRYSEDKFQFHLPISLNFKSKERLNFNLKVNEFLKRNKDINIIGIDRGE
RNLLYLVMINQKGEILKQTLLDSMQSGKGRPEINYKEKLQEKEIERDKARKSWGTVENIKELKEGYLSIVIH
QISKLMVENNAIVVLEDLNIGFKRGRQKVERQVYQKFEKMLIDKLNFLVFKENKPTEPGGVLKAYQLTDEF
QSFEKLSKQTGFLFYVPSWNTSKIDPRTGFIDFLHPAYENIEKAKQWINKFDSIRFNSKMDWFEFTADTRKFS
ENLMLGKNRVWVICTTNVERYFTSKTANSSIQYNSIQITEKLKELFVDIPFSNGQDLKPEILRKNDAVFFKSL
LFYIKTTLSLRQNNGKKGEEEKDFILSPVVDSKGRFFNSLEASDDEPKDADANGAYHIALKGLMNLLVLNE
TKEENLSRPKWKIKNKDWLEFVWERNR*KRPAATKKAGQAKKKK*GSYPYDVPDYAYPYDVPDYAYPYDVP
DYA

SEQ ID NO: 40 Lachnospiraceae bacterium ND2006 (LbCpf1)

MSKLEKFTNCYSLSKTLRFKAIPVGKTQENIDNKRLLVEDEKRAEDYKGVKKLLDRYYLSFINDVLHSIKL
KNLNNYISLFRKKTRTEKENKELENLEINLRKEIAKAFKGNEGYKSLFKKDIIETILPEFLDDKDEIALVNSFN
GFTTAFTGFFDNRENMFSEEAKSTSIAFRCINENLTRYISNMDIFEKVDAIFDKHEVQEIKEKILNSDYDVEDF
FEGEFFNFVLTQEGIDVYNAIIGGFVTESGEKIKGLNEYINLYNQKTKQKLPKFKPLYKQVLSDRESLSFYGE
GYTSDEEVLEVFRNTLNKNSEIFSSIKKLEKLFKNFDEYSSAGIFVKNGPAISTISKDIFGEWNVIRDKWNAE
YDDIHLKKKAVVTEKYEDDRRKSFKKIGSFSLEQLQEYADADLSVVEKLKEIIIQKVDEIYKVYGSSEKLFD
ADFVLEKSLKKNDAVVAIMKDLLDSVKSFENYIKAFFGEGKETNRDESFYGDFVLAYDILLKVDHIYDAIR
NYVTQKPYSKDKFKLYFQNPQFMGGWDKDKETDYRATILRYGSKYYLAIMDKKYAKCLQKIDKDDVNG
NYEKINYKLLPGPNKMLPKVFFSKKWMAYYNPSEDIQKIYKNGTFKKGDMFNLNDCHKLIDFFKDSISRYP
KWSNAYDFNFSETEKYKDIAGFYREVEEQGYKVSFESASKKEVDKLVEEGKLYMFQIYNKDFSDKSHGTP
NLHTMYFKLLFDENNHGQIRLSGGAELFMRRASLKKEELVVHPANSPIANKNPDNPKKTTTLSYDVYKDK
RFSEDQYELHIPIAINKCPKNIFKINTEVRVLLKHDDNPYVIGIDRGERNLLYIVVVDGKGNIVEQYSLNEIIN
NFNGIRIKTDYHSLLDKKEKERFEARQNWTSIENIKELKAGYISQVVHKICELVEKYDAVIALEDLNSGFKN
SRVKVEKQVYQKFEKMLIDKLNYMVDKKSNPCATGGALKGYQITNKFESFKSMSTQNGFIFYIPAWLTSKI
DPSTGFVNLLKTKYTSIADSKKFISSFDRIMYVPEEDLFEFALDYKNFSRTDADYIKKWKLYSYGNRIRIFRN
PKKNNVFDWEEVCLTSAYKELFNKYGINYQQGDIRALLCEQSDKAFYSSFMALMSLMLQMRNSITGRTDV
DFLISPVKNSDGIFYDSRNYEAQENAILPKNADANGAYNIARKVLWAIGQFKKAEDEKLDKVKIAISNKEW
LEYAQTSVKH*KRPAATKKAGQAKKKK*GSYPYDVPDYAYPYDVPDYAYPYDVPDYA

SEQ ID NO: 41 Porphyromonas crevioricanis (PcCpf1)

MDSLKDFTNLYPVSKTLRFELKPVGKTLENIEKAGILKEDEHRAESYRRVKKIIDTYHKVFIDSSLENMAKM
GIENEIKAMLQSFCELYKKDHRTEGEDKALDKIRAVLRGLIVGAFTGVCGRRENTVQNEKYESLFKEKLIKE
ILPDFVLSTEAESLPFSVEEATRSLKEFDSFTSYFAGFYENRKNIYSTKPQSTAIAYRLIHENLPKFIDNILVFQ
KIKEPIAKELEHIRADFSAGGYIKKDERLEDIFSLNYYIHVLSQAGIEKYNALIGKIVTEGDGEMKGLNEHINL
YNQQRGREDRLPLFRPLYKQILSDREQLSYLPESFEKDEELLRALKEFYDHIAEDILGRTQQLMTSISEYDLS
RIYVRNDSQLTDISKKMLGDWNAIYMARERAYDHEQAPKRITAKYERDRIKALKGEESISLANLNSCIAFLD
NVRDCRVDTYLSTLGQKEGPHGLSNLVENVFASYHEAEQLLSFPYPEENNLIQDKDNVVLIKNLLDNISDL
QRFLKPLWGMGDEPDKDERFYGEYNYIRGALDQVIPLYNKVRNYLTRKPYSTRKVKLNFGNSQLLSGWD
RNKEKDNSCVILRKGQNFYLAIMNNRHKRSFENKMLPEYKEGEPYFEKMDYKFLPDPNKMLPKVFLSKKG
IEIYKPSPKLLEQYGHGTHKKGDTFSMDDLHELIDFFKHSIEAHEDWKQFGFKFSDTATYENVSSFYREVED
QGYKLSFRKVSESYVYSLIDQGKLYLFQIYNKDFSPCSKGTPNLHTLYWRMLFDERNLADVIYKLDGKAEI
FFREKSLKNDHPTHPAGKPIKKKSRQKKGEESLFEYDLVKDRRYTMDKFQFHVPITMNFKCSAGSKVNDM
VNAHIREAKDMHVIGIDRGERNLLYICVIDSRGTILDQISLNTINDIDYHDLLESRDKDRQQEHRNWQTIEGI
KELKQGYLSQAVHRIAELMVAYKAVVALEDLNMGFKRGRQKVESSVYQQFEKQLIDKLNYLVDKKKRPE
DIGGLLRAYQFTAPFKSFKEMGKQNGFLFYIPAWNTSNIDPTTGFVNLFHVQYENVDKAKSFFQKFDSISYN
PKKDWFEFAFDYKNFTKKAEGSRSMWILCTHGSRIKNFRNSQKNGQWDSEEFALTEAFKSLFVRYEIDYTA
DLKTAIVDEKQKDFFVDLLKLFKLTVQMRNSWKEKDLDYLISPVAGADGRFFDTREGNKSLPKDADANGA
YNIALKGLWALRQIRQTSEGGKLKLAISNKEWLQFVQERSYEKD*KRPAATKKAGQAKKKK*GSYPYDVPDY
AYPYDVPDYAYPYDVPDYA

FIG. 13 cntd.

SEQ ID NO: 42 Prevotella disiens (PdCpf1)

MENYQEFTNLFQLNKTLRFELKPIGKTCELLEEGKIFASGSFLEKDKVRADNVSYVKKEIDKKHKIFIEETLS
SFSISNDLLKQYFDCYNELKAFKKDCKSDEEEVKKTALRNKCTSIQRAMREAISQAFLKSPQKKLLAIKNLI
ENVFKADENVQHFSEFTSYFSGFETNRENFYSDEEKSTSIAYRLVHDNLPIFIKNIYIFEKLKEQFDAKTLSEIF
ENYKLYVAGSSLDEVFSLEYFNNTLTQKGIDNYNAVIGKIVKEDKQEIQGLNEHINLYNQKHKDRRLPFFIS
LKKQILSDREALSWLPDMFKNDSEVIKALKGFYIEDGFENNVLTPLATLLSSLDKYNLNGIFIRNNEALSSLS
QNVYRNFSIDEAIDANAELQTFNNYELIANALRAKIKKETKQGRKSFEKYEEYIDKKVKAIDSLSIQEINELV
ENYVSEFNSNSGNMPRKVEDYFSLMRKGDFGSNDLIENIKTKLSAAEKLLGTKYQETAKDIFKKDENSKLI
KELLDATKQFQHFIKPLLGTGEEADRDLVFYGDFLPLYEKFEELTLLYNKVRNRLTQKPYSKDKIRLCFNKP
KLMTGWVDSKTEKSDNGTQYGGYLFRKKNEIGEYDYFLGISSKAQLFRKNEAVIGDYERLDYYQPKANTI
YGSAYEGENSYKEDKKRLNKVIIAYIEQIKQTNIKKSIIESISKYPNISDDDKVTPSSLLEKIKKVSIDSYNGILS
FKSFQSVNKEVIDNLLKTISPLKNKAEFLDLINKDYQIFTEVQAVIDEICKQKTFIYFPISNVELEKEMGDKDK
PLCLFQISNKDLSFAKTFSANLRKKRGAENLHTMLFKALMEGNQDNLDLGSGAIFYRAKSLDGNKPTHPAN
EAIKCRNVANKDKVSLFTYDIYKNRRYMENKFLFHLSIVQNYKAANDSAQLNSSATEYIRKADDLHIIGIDR
GERNLLYYSVIDMKGNIVEQDSLNIIRNNDLETDYHDLLDKREKERKANRQNWEAVEGIKDLKKGYLSQA
VHQIAQLMLKYNAIIALEDLGQMFVTRGQKIEKAVYQQFEKSLVDKLSYLVDKKRPYNELGGILKAYQLA
SSITKNNSDKQNGFLFYVPAWNTSKIDPVTGFTDLLRPKAMTIKEAQDFFGAFDNISYNDKGYFEFETNYDK
FKIRMKSAQTRWTICTFGNRIKRKKDKNYWNYEEVELTEEFKKLFKDSNIDYENCNLKEEIQNKDNRKFFD
DLIKLLQLTLQMRNSDDKGNDYIISPVANAEGQFFDSRNGDKKLPLDADANGAYNIARKGLWNIRQIKQTK
NDKKLNLSISSTEWLDFVREKPYLK*KRPAATKKAGQAKKKK*GSYPYDVPDYAYPYDVPDYAYPYDVPDYA

SEQ ID NO: 43 Porphyromonas macacae (PmCpf1)

MKTQHFFEDFTSLYSLSKTIRFELKPIGKTLENIKKNGLIRRDEQRLDDYEKLKKVIDEYHEDFIANILSSFSFS
EEILQSYIQNLSESEARAKIEKTMRDTLAKAFSEDERYKSIFKKELVKKDIPVWCPAYKSLCKKFDNFTTSLV
PFHENRKNLYTSNEITASIPYRIVHVNLPKFIQNIEALCELQKKMGADLYLEMMENLRNVWPSFVKTPDDLC
NLKTYNHLMVQSSISEYNRFVGGYSTEDGTKHQGINEWINIYRQRNKEMRLPGLVFLHKQILAKVDSSSFIS
DTLENDDQVFCVLRQFRKLFWNTVSSKEDDAASLKDLFCGLSGYDPEAIYVSDAHLATISKNIFDRWNYIS
DAIRRKTEVLMPRKKESVERYAEKISKQIKKRQSYSLAELDDLLAHYSEESLPAGFSLLSYFTSLGGQKYLV
SDGEVILYEEGSNIWDEVLIAFRDLQVILDKDFTEKKLGKDEEAVSVIKKALDSALRLRKFFDLLSGTGAEIR
RDSSFYALYTDRMDKLKGLLKMYDKVRNYLTKKPYSIEKFKLHFDNPSLLSGWDKNKELNNLSVIFRQNG
YYYLGIMTPKGKNLFKTLPKLGAEEMFYEKMEYKQIAEPMLMLPKVFFPKKTKPAFAPDQSVVDIYNKKT
FKTGQKGFNKKDLYRLIDFYKEALTVHEWKLFNFSFSPTEQYRNIGEFFDEVREQAYKVSMVNVPASYIDE
AVENGKLYLFQIYNKDFSPYSKGIPNLHTLYWKALFSEQNQSRVYKLCGGGELFYRKASLHMQDTTVHPK
GISIHKKNLNKKGETSLFNYDLVKDKRFTEDKFFFHVPISINYKNKKITNVNQMVRDYIAQNDDLQIIGIDRG
ERNLLYISRIDTRGNLLEQFSLNVIESDKGDLRTDYQKILGDREQERLRRRQEWKSIESIKDLKDGYMSQVV
HKICNMVVEHKAIVVLENLNLSFMKGRKKVEKSVYEKFERMLVDKLNYLVVDKKNLSNEPGGLYAAYQL
TNPLFSFEELHRYPQSGILFFVDPWNTSLTDPSTGFVNLLGRINYTNVGDARKFFDRFNAIRYDGKGNILFDL
DLSRFDVRVETQRKLWTLTTFGSRIAKSKKSGKWMVERIENLSLCFLELFEQFNIGYRVEKDLKKAILSQDR
KEFYVRLIYLFNLMMQIRNSDGEEDYILSPALNEKNLQFDSRLIEAKDLPVDADANGAYNVARKGLMVVQ
RIKRGDHESIHRIGRAQWLRYVQEGIVE*KRPAATKKAGQAKKKK*GSYPYDVPDYAYPYDVPDYAYPYDVP
DYA

FIG. 13 cntd.

SEQ ID NO: 44 Thiomicrospira sp. XS5 (TsCpf1)

MTKTFDSEFFNLYSLQKTVRFELKPVGETASFVEDFKNEGLKRVVSEDERRAVDYQKVKEIIDDYHRDFIEE
SLNYFPEQVSKDALEQAFHLYQKLKAAKVEEREKALKEWEALQKKLREKVVKCFSDSNKARFSRIDKKEL
IKEDLINWLVAQNREDDIPTVETFNNFTTYFTGFHENRKNIYSKDDHATAISFRLIHENLPKFFDNVISFNKL
KEGFPELKFDKVKEDLEVDYDLKHAFEIEYFVNFVTQAGIDQYNYLLGGKTLEDGTKKQGMNEQINLFKQ
QQTRDKARQIPKLIPLFKQILSERTESQSFIPKQFESDQELFDSLQKLHNNCQDKFTVLQQAILGLAEADLKK
VFIKTSDLNALSNTIFGNYSVFSDALNLYKESLKTKKAQEAFEKLPAHSIHDLIQYLEQFNSSLDAEKQQSTD
TVLNYFIKTDELYSRFIKSTSEAFTQVQPLFELEALSSKRRPPESEDEGAKGQEGFEQIKRIKAYLDTLMEAV
HFAKPLYLVKGRKMIEGLDKDQSFYEAFEMAYQELESLIIPIYNKARSYLSRKPFKADKFKINFDNNTLLSG
WDANKETANASILFKKDGLYYLGIMPKGKTFLFDYFVSSEDSEKLQRRQKTAEEALAQDGESYFEKIRYK
LLPGASKMLPKVFFSNKNIGFYNPSDDILRIRNTASHTKNGTPQKGHSKVEFNLNDCHKMIDFFKSSIQKHP
EWGSFGFTFSDTSDFEDMSAFYREVENQGYVISFDKIKETYIQSQVEQGNLYLFQIYNKDFSPYSKGKPNLH
TLYWKALFEEANLNNVVAKLNGEAEIFFRRHSIKASDKVVHPANQAIDNKNPHTEKTQSTFEYDLVKDKR
YTQDKFFFHVPISLNFKAQGVSKFNDKVNGFLKGNPDVNIIGIDRGERHLLYFTVVNQKGEILVQESLNTLM
SDKGHVNDYQQKLDKKEQERDAARKSWTTVENIKELKEGYLSHVVHKLAHLIIKYNAIVCLEDLNFGFKR
GRFKVEKQVYQKFEKALIDKLNYLVFKEKELGEVGHYLTAYQLTAPFESFKKLGKQSGILFYVPADYTSKI
DPTTGFVNFLDLRYQSVEKAKQLLSDFNAIRFNSVQNYFEFEIDYKKLTPKRKVGTQSKWVICTYGDVRYQ
NRRNQKGHWETEEVNVTEKLKALFASDSKTTTVIDYANDDNLIDVILEQDKASFFKELLWLLKLTMTLRH
SKIKSEDDFILSPVKNEQGEFYDSRKAGEVWPKDADANGAYHIALKGLWNLQQINQWEKGKTLNLAIKNQ
DWFSFIQEKPYQE*KRPAATKKAGQAKKKK*GSYPYDVPDYAYPYDVPDYAYPYDVPDYA

SEQ ID NO: 45 Moraxella bovoculi AAX08_00205 (Mb2Cpf1)

MLFQDFTHLYPLSKTVRFELKPIGRTLEHIHAKNFLSQDETMADMYQKVKVILDDYHRDFIADMMGEVKL
TKLAEFYDVYLKFRKNPKDDGLQKQLKDLQAVLRKESVKPIGSGGKYKTGYDRLFGAKLFKDGKELGDL
AKFVIAQEGESSPKLAHLAHFEKFSTYFTGFHDNRKNMYSDEDKHTAIAYRLIHENLPRFIDNLQILTTIKQK
HSALYDQIINELTASGLDVSLASHLDGYHKLLTQEGITAYNRIIGEVNGYTNKHNQICHKSERIAKLRPLHK
QILSDGMGVSFLPSKFADDSEMCQAVNEFYRHYTDVFAKVQSLFDGFDDHQKDGIYVEHKNLNELSKQAF
GDFALLGRVLDGYYVDVVNPEFNERFAKAKTDNAKAKLTKEKDKFIKGVHSLASLEQAIEHHTARHDDES
VQAGKLGQYFKHGLAGVDNPIQKIHNNHSTIKGFLERERPAGERALPKIKSGKNPEMTQLRQLKELLDNAL
NVAHFAKLLTTKTTLDNQDGNFYGEFGVLYDELAKIPTLYNKVRDYLSQKPFSTEKYKLNFGNPTLLNGW
DLNKEKDNFGVILQKDGCYYLALLDKAHKKVFDNAPNTGKNVYQKMVYKLLPGPNKMLPKVFFAKSNL
DYYNPSAELLDKYAKGTHKKGDNFNLKDCHALIDFFKAGINKHPEWQHFGFKFSPTSSYRDLSDFYREVEP
QGYQVKFVDINADYIDELVEQGKLYLFQIYNKDFSPKAHGKPNLHTLYFKALFSEDNLADPIYKLNGEAQIF
YRKASLDMNETTIHRAGEVLENKNPDNPKKRQFVYDIIKDKRYTQDKFMLHVPITMNFGVQGMTIKEFNK
KVNQSIQQYDEVNVIGIDRGERHLLYLTVINSKGEILEQRSLNDITTASANGTQVTTPYHKILDKREIERLNA
RVGWGEIETIKELKSGYLSHVVHQINQLMLKYNAIVVLEDLNFGFKRGRFKVEKQIYQNFENALIKKLNHL
VLKDKADDEIGSYKNALQLTNNFTDLKSIGKQTGFLFYVPAWNTSKIDPETGFVDLLKPRYENIAQSQAFFG
KFDKICYNTDKGYFEFHIDYAKFTDKAKNSRQKWAICSHGDKRYVYDKTANQNKGAAKGINVNDELKSL
FARYHINDKQPNLVMDICQNNDKEFHKSLMCLLKTLLALRYSNASSDEDFILSPVANDEGVFFNSALADDT
QPQNADANGAYHIALKGLWLLNELKNSDDLNKVKLAIDNQTWLNFAQNR*KRPAATKKAGQAKKKK*GSYP
YDVPDYAYPYDVPDYAYPYDVPDYA

FIG. 13 cntd.

SEQ ID NO: 46 Moraxella bovoculi AAX11_00205 (Mb3Cpf1)

MLFQDFTHLYPLSKTVRFELKPIGKTLEHIHAKNFLNQDETMADMYQKVKAILDDYHRDFIADMMGEVKL
TKLAEFYDVYLKFRKNPKDDGLQKQLKDLQAVLRKEIVKPIGNGGKYKAGYDRLFGAKLFKDGKELGDL
AKFVIAQEGESSPKLAHLAHFEKFSTYFTGFHDNRKNMYSDEDKHTAIAYRLIHENLPRFIDNLQILATIKQK
HSALYDQIINELTASGLDVSLASHLDGYHKLLTQEGITAYNTLLGGISGEAGSRKIQGINELINSHHNQHCHK
SERIAKLRPLHKQILSDGMGVSFLPSKFADDSEVCQAVNEFYRHYADVFAKVQSLFDGFDDYQKDGIYVEY
KNLNELSKQAFGDFALLGRVLDGYYVDVVNPEFNERFAKAKTDNAKAKLTKEKDKFIKGVHSLASLEQAI
EHYTARHDDESVQAGKLGQYFKHGLAGVDNPIQKIHNNHSTIKGFLERERPAGERALPKIKSDKSPEIRQLK
ELLDNALNVAHFAKLLTTKTTLHNQDGNFYGEFGALYDELAKIATLYNKVRDYLSQKPFSTEKYKLNFGN
PTLLNGWDLNKEKDNFGVILQKDGCYYLALLDKAHKKVFDNAPNTGKSVYQKMIYKLLPGPNKMLPKVF
FAKSNLDYYNPSAELLDKYAQGTHKKGDNFNLKDCHALIDFFKAGINKHPEWQHFGFKFSPTSSYQDLSDF
YREVEPQGYQVKFVDINADYINELVEQGQLYLFQIYNKDFSPKAHGKPNLHTLYFKALFSEDNLVNPIYKL
NGEAEIFYRKASLDMNETTIHRAGEVLENKNPDNPKKRQFVYDIIKDKRYTQDKFMLHVPITMNFGVQGM
TIKEFNKKVNQSIQQYDEVNVIGIDRGERHLLYLTVINSKGEILEQRSLNDITTASANGTQMTTPYHKILDKR
EIERLNARVGWGEIETIKELKSGYLSHVVHQISQLMLKYNAIVVLEDLNFGFKRGRFKVEKQIYQNFENALI
KKLNHLVLKDKADDEIGSYKNALQLTNNFTDLKSIGKQTGFLFYVPAWNTSKIDPETGFVDLLKPRYENIA
QSQAFFGKFDKICYNADRGYFEFHIDYAKFNDKAKNSRQIWKICSHGDKRYVYDKTANQNKGATIGVNVN
DELKSLFTRYHINDKQPNLVMDICQNNDKEFHKSLMYLLKTLLALRYSNASSDEDFILSPVANDEGVFFNS
ALADDTQPQNADANGAYHIALKGLWLLNELKNSDDLNKVKLAIDNQTWLNFAQNR*KRPAATKKAGQAKK*
*KKGS*YPYDVPDYAYPYDVPDYAYPYDVPDYA

SEQ ID NO: 47 Butyrivibrio sp. NC3005 (BsCpf1)

MYYQNLTKKYPVSKTIRNELIPIGKTLENIRKNNILESDVKRKQDYEHVKGIMDEYHKQLINEALDNYMLP
SLNQAAEIYLKKHVDVEDREEFKKTQDLLRREVTGRLKEHENYTKIGKKDILDLLEKLPSISEEDYNALESF
RNFYTYFTSYNKVRENLYSDEEKSSTVAYRLINENLPKFLDNIKSYAFVKAAGVLADCIEEEEQDALFMVE
TFNMTLTQEGIDMYNYQIGKVNSAINLYNQKNHKVEEFKKIPKMKVLYKQILSDREEVFIGEFKDDETLLSS
IGAYGNVLMTYLKSEKINIFFDALRESEGKNVYVKNDLSKTTMSNIVFGSWSAFDELLNQEYDLANENKKK
DDKYFEKRQKELKKNKSYTLEQMSNLSKEDISPIENYIERISEDIEKICIYNGEFEKIVVNEHDSSRKLSKNIK
AVKVIKDYLDSIKELEHDIKLINGSGQELEKNLVVYVGQEEALEQLRPVDSLYNLTRNYLTKKPFSTEKVKL
NFNKSTLLNGWDKNKETDNLGILFFKDGKYYLGIMNTTANKAFVNPPAAKTENVFKKVDYKLLPGSNKM
LPKVFFAKSNIGYYNPSTELYSNYKKGTHKKGPSFSIDDCHNLIDFFKESIKKHEDWSKFGFEFSDTADYRDI
SEFYREVEKQGYKLTFTDIDESYINDLIEKNELYLFQIYNKDFSEYSKGKLNLHTLYFMMLFDQRNLDNVV
YKLNGEAEVFYRPASIAENELVIHKAGEGIKNKNPNRAKVKETSTFSYDIVKDKRYSKYKFTLHIPITMNFG
VDEVRRFNDVINNALRTDDNVNVIGIDRGERNLLYVVVINSEGKILEQISLNSIINKEYDIETNYHALLDERE
DDRNKARKDWNTIENIKELKTGYLSQVVNVVAKLVLKYNAIICLEDLNFGFKRGRQKVEKQVYQKFEKM
LIEKLNYLVIDKSREQVSPEKMGGALNALQLTSKFKSFAELGKQSGIIYYVPAYLTSKIDPTTGFVNLFYIKY
ENIEKAKQFFDGFDFIRFNKKDDMFEFSFDYKSFTQKACGIRSKWIVYTNGERIIKYPNPEKNNLFDEKVINV
TDEIKGLFKQYRIPYENGEDIKEIIISKAEADFYKRLFRLLHQTLQMRNSTSDGTRDYIISPVKNDRGEFFCSE
FSEGTMPKDADANGAYNIARKGLWVLEQIRQKDEGEKVNLSMTNAEWLKYAQLHLL*KRPAATKKAGQAK*
*KKKGS*YPYDVPDYAYPYDVPDYAYPYDVPDYA

FIG. 13 cntd.

SEQ ID NO: 48 NCBI WP_055225123.1

MNNGTNNFQNFIGISSLQKTLRNALIPTETTQQFIVKNGIIKEDELRGENRQILKDIMDDYYRGFISETLSSID
DIDWTSLFEKMEIQLKNGDNKDTLIKEQTEYRKAIHKKFANDDRFKNMFSAKLISDILPEFVIHNNNYSASE
KEEKTQVIKLFSRFATSFKDYFKNRANCFSADDISSSSCHRIVNDNAEIFFSNALVYRRIVKSLSNDDINKISG
DMKDSLKEMSLEEIYSYEKYGEFITQEGISFYNDICGKVNSFMNLYCQKNKENKNLYKLQKLHKQILCIAD
TSYEVPYKFESDEEVYQSVNGFLDNISSKHIVERLRKIGDNYGYNLDKIYIVSKFYESVSQKTYRDWETIN
TALEIHYNNILPGNGKSKADKVKKAVKNDLQKSITEINELVSNYKLCSDDNIKAETYIHEISHILNNFEAQEL
KYNPEIHLVESELKASELKNVLDVIMNAFHWCSVFMTEELVDKDNNFYAELEEIYDEIYPVISLYNLVRNY
VTQKPYSTKKIKLNFGIPTLADGWSKSKEYSNNAIILMRDNLYYLGIFNAKNKPDKKIIEGNTSENKGDYKK
MIYNLLPGPNKMIPKVFLSSKTGVETYKPSAYILEGYKQNKHIKSSKDFDITFCHDLIDYFKNCIAIHPEWKN
FGFDFSDTSTYEDISGFYREVELQGYKIDWTYISEKDIDLLQEKGQLYLFQIYNKDFSKKSTGNDNLHTMYL
KNLFSEENLKDIVLKLNGEAEIFFRKSSIKNPIIHKKGSILVNRTYEAEEKDQFGNQIVRKNIPENIYQELYKY
FNDKSDKELSDEAAKLKNVVGHHEAATNIVKDYRYTYDKYFLHMPITINFKANKTGFINDRILQYIAKEKD
LHVIGIDRGERNLIYVSVIDTCGNIVEQKSFNIVNGYDYQIKLKQQEGARQIARKEWKEIGKIKEIKEGYLSL
VIHEISKMVIKYNAIIAMEDLSYGFKKGRFKVERQVYQKFETMLINKLNYLVFKDISITENGGLLKGYQLTYI
PDKLKNVGHQCGCIFYVPAAYTSKIDPTTGFVNIFKFKDLTVDAKREFIKKFDSIRYDSEKNLFCFTFDYNNF
ITQNTVMSKSSWSVYTYGVRIKRRFVNGRFSNESDTIDITKDMEKTLEMTDINWRDGHDLRQDIIDYEIVQH
IFEIFRLTVQMRNSLSELEDRDYDRLISPVLNENNIFYDSAKAGDALPKDADANGAYCIALKGLYEIKQITEN
WKEDGKFSRDKLKISNKDWFDFIQNKRYL

SEQ ID NO: 49 NCBI WP_055237260.1

MNNGTNNFQNFIGISSLQKTLRNALIPTETTQQFIVKNGIIKEDELRGENRQILKDIMDDYYRGFISETLSSID
DIDWTSLFEKMEIQLKNGDNKDTLIKEQAEKRKAIYKKFADDDRFKNMFSAKLISDILPEFVIHNNNYSASE
KEEKTQVIKLFSRFATSFKDYFKNRANCFSADDISSSSCHRIVNDNAEIFFSNALVYRRIVKNLSNDDINKISG
DMKDSLKEMSLDEIYSYEKYGEFITQEGISFYNDICGKVNSFMNLYCQKNKENKNLYKLRKLHKQILCIAD
TSYEVPYKFESDEEVYQSVNGFLDNISSKHIVERLRKIGDNYGYNLDKIYIVSRFYESVSQKTYRDWETIN
TALEIHYNNILPGNGKSKADKVKKAVKNDLQKSITEINELVSNYKLCPDDNIKAETYIHEISHILNNFEAQEL
KYNPEIHLVESELKASELKNVLDVIMNAFHWCSVFMTEELVDKDNNFYAELEEIYDEIYPVISLYNLVRNY
VTQKPYSTKKIKLNFGIPTLADGWSKSKEYSNNAIILMRDNLYYLGIFNAKNKPDKKIIEGNTSENKGDYKK
MIYNLLPGPNKMIPKVFLSSKTGVETYKPSAYILEGYKQNKHLKSSKDFDITFCRDLIDYFKNCIAIHPEWKN
FGFDFSDTSTYEDISGFYREVELQGYKIDWTYISEKDIDLLQEKGQLYLFQIYNKDFSKKSTGNDNLHTMYL
KNLFSEENLKDIVLKLNGEAEIFFRKSSIKNPIIHKKGSILVNRTYEAEEKDQFGNIQIVRKTIPENIYQELYKY
FNDKSDKELSDEAAKLKNVVGHHEAATNIVKDYRYTYDKYFLHMPITINFKANKTSFINDRILQYIAKEND
LHVIGIDRGERNLIYVSVIDTCGNIVEQKSFNIVNGYDYQIKLKQQEGARQIARKEWKEIGKIKEIKEGYLSL
VIHEISKMVIKYNAIIAMEDLSYGFKKGRFKVERQVYQKFETMLINKLNYLVFKDISITENGGLLKGYQLTYI
PEKLKNVGHQCGCIFYVPAAYTSKIDPTTGFANIFKFKDLTVDAKREFIKKFDSIRYDSEKNLFCFTFDYNNF
ITQNTVMSKSSWSVYTYGVRIKRRFVNGRFSNESDTIDITKDMEKTLEMTDINWRDGHDLRQDIIDYEIVQH
IFEIFKLTVQMRNSLSELEDRDYDRLISPVLNENNIFYDSAKAGDALPKDADANGAYCIALKGLYEIKQITEN
WKEDGKFSRDKLKISNKDWFDFIQNKRYL

FIG. 13 cntd.

SEQ ID NO: 50 NCBI WP_055272206.1

MNNGTNNFQNFIGISSLQKTLRNALTPTETTQQFIVKNGIIKEDELRGENRQILKDIMDDYYRGFISETLSSID
DIDWTSLFEKMEIQLKNGDNKDTLIKEQAEKRKAIYKKFADDDRFKNMFSAKLISDILPEFVIHNNNYSASE
KEEKTQVIKLFSRFATSFKDYFKNRANCFSADDISSSSCHRIVNDNAEIFFSNALVYRRIVKNLSNDDINKISG
DMKDSLKKMSLEKIYSYEKYGEFITQEGISFYNDICGKVNSFMNLYCQKNKENKNLYKLRKLHKQILCIAD
TSYEVPYKFESDEEVYQSVNGFLDNISSKHIVERLRKIGDNYGYNLDKIYIVSKFYESVSQKTYRDWETIN
TALEIHYNNILPGNGKSKADKVKKAVKNDLQKSITEINELVSNYKLCPDDNIKAETYIHEISHILNNFEAQEL
KYNPEIHLVESELKASELKNVLDVIMNAFHWCSVFMTEELVDKDNNFYAELEEIYDEIYPVISLYNLVRNY
VTQKPYSTKKIKLNFGIPTLADGWSKSKEYSNNAIILMRDNLYYLGIFNAKNKPEKKIIEGNTSENKGDYKK
MIYNLLPGPNKMIPKVFLSSKTGVETYKPSAYILEGYKQNKHLKSSKDFDITFCRDLIDYFKNCIAIHPEWKN
FGFDFSDTSTYEDISGFYREVELQGYKIDWTYISEKDIDLLQEKGQLYLFQIYNKDFSKKSTGNDNLHTMYL
KNLFSEENLKDVVLKLNGEAEIFFRKSSIKNPIIHKKGSILVNRTYEAEEKDQFGNIQIVRKTIPENIYQELYK
YFNDKSDKELSDEAAKLKNAVGHHEAATNIVKDYRYTYDKYFLHMPITINFKANKTSFINDRILQYIAKEK
DLHVIGIDRGERNLIYVSVIDTCGNIVEQKSFNIVNGYDYQIKLKQQEGARQIARKEWKEIGKIKEIKEGYLS
LVIHEISKMVIKYNAIIAMEDLSYGFKKGRFKVERQVYQKFETMLINKLNYLVFKDISITENGGLLKGYQLT
YIPEKLKNVGHQCGCIFYVPAAYTSKIDPTTGFVNIFKFKDLTVDAKREFIKKFDSIRYDSDKNLFCFTFDYN
NFITQNTVMSKSSWSVYTYGVRIKRRFVNGRFSNESDTIDITKDMEKTLEMTDINWRDGHDLRQDIIDYEIV
QHIFEIFKLTVQMRNSLSELEDRNYDRLISPVLNENNIFYDSAKAGDALPKDADANGAYCIALKGLYEIKQIT
ENWKEDGKFSRDKLKISNKDWFDFIQNKRYL

SEQ ID NO: 51 GenBank OLA16049.1

MNNGTNNFQNFIGISSLQKTLRNALIPTETTQQFIVKNGIIKEDELRGKNRQILKDIMDDYYRGFISETLSSID
DIDWTSLFEKMEIQLKNGDNKDTLIKEQAEKRKAIYKKFADDDRFKNMFSAKLISDILPEFVIHNNNYSASE
KKEKTQVIKLFSRFATSFKDYFKNRANCFSADDISSSSCHRIVNDNAEIFFSNALVYRRIVKNLSNDDINKISG
DMKDSLKEMSLEEIYSYEKYGEFITQEGISFYNDICGKVNSFMNLYCQKNKENKNLYKLRKLHKQILCIAD
TSYEVPYKFESDEEVYQSVNGFLDNISSKHIVERLRKIGDNYDYNLDKIYIVSKFYESVSQKTYRDWETIN
TALEIHYNNILPGNGKSKADKVKKAVKNDLQKSITEINELVSNYKLCSDDNIKAETYIHEISHILNNFEAHEL
KYNPEIHLVESELKASELKNVLDIIMNAFHWCSVFMTEELVDKDNNFYAELEEIYDEIYPVISLYNLVRNYV
TQKPYSTKKIKLNFGIPTLADGWSKSKEYSNNAIILMRDNLYYLGIFNAKNKPDKKIIEGNTSENKGDYKKM
IYNLLPGPNKMIPKVFLSSKTGVETYKPSAYILEGYKQNKHLKSSKDFDITFCHDLIDYFKNCIAIHPEWKNF
GFDFSDTSAYEDISGFYREVELQGYKIDWTYISEKDIDLLQEKGQLYLFQIYNKDFSKKSTGNDNLHTMYLK
NLFSEENLKDIVLKLNGEAEIFFRKSSIKNPIIHKKGSILVNRTYEAEEKDQFGNIQIVRKTIPENIYQELYKYF
NDKSDKELSDEAAKLKNVVGHHEAATNIVKDYRYTYDKYFLHMPITINFKANKTSFINDRILQYIAKEKDL
HVIGIDRGERNLIYVSVIDTCGNIVEQKSFNIVNGYDYQIKLKQQEGARQIARKEWKEIGKIKEIKEGYLSVI
HEISKMVIKYNAIIAMEDLSYGFKKGRFKVERQVYQKFETMLINKLNYLVFKDISITENGGLLKGYQLTYIP
DKLKNVGHQCGCIFYVPAAYTSKIDPTTGFVNIFKFKDLTVDAKREFIKKFDSIRYDSEKNLFCFTFDYNNFI
TQNTVMSKSSWSVYTYGVRIKRRFVNGRFSNESDTIDITKDMEKTLEMTDINWRDGHDLRQDIIDYEIVQHI
FEIFKLTVQMRNSLSELEDRDYDRLISPVLNENNIFYDSAKAGYALPKDADANGAYCIALKGLYEIKQITEN
WKEDGKFSRDKLKISNKDWFDFIQNKRYL

FIG. 13 cntd.

FIG. 18C
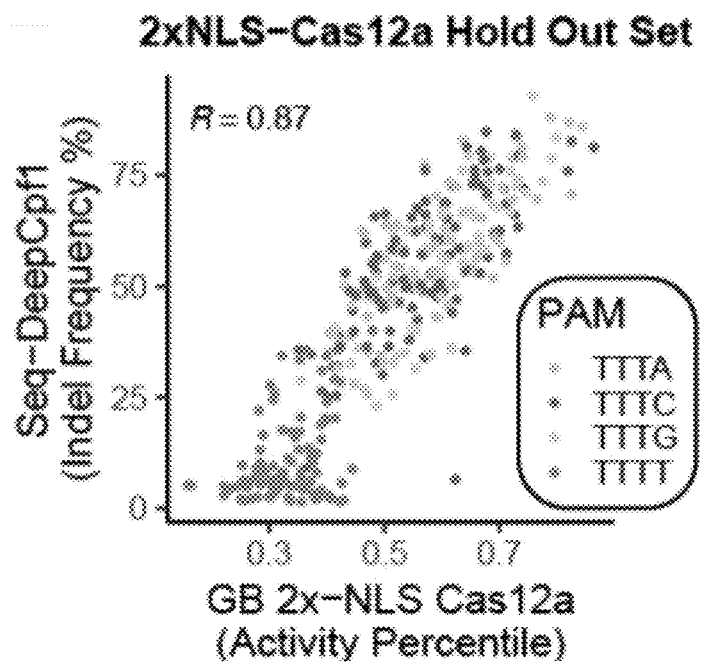
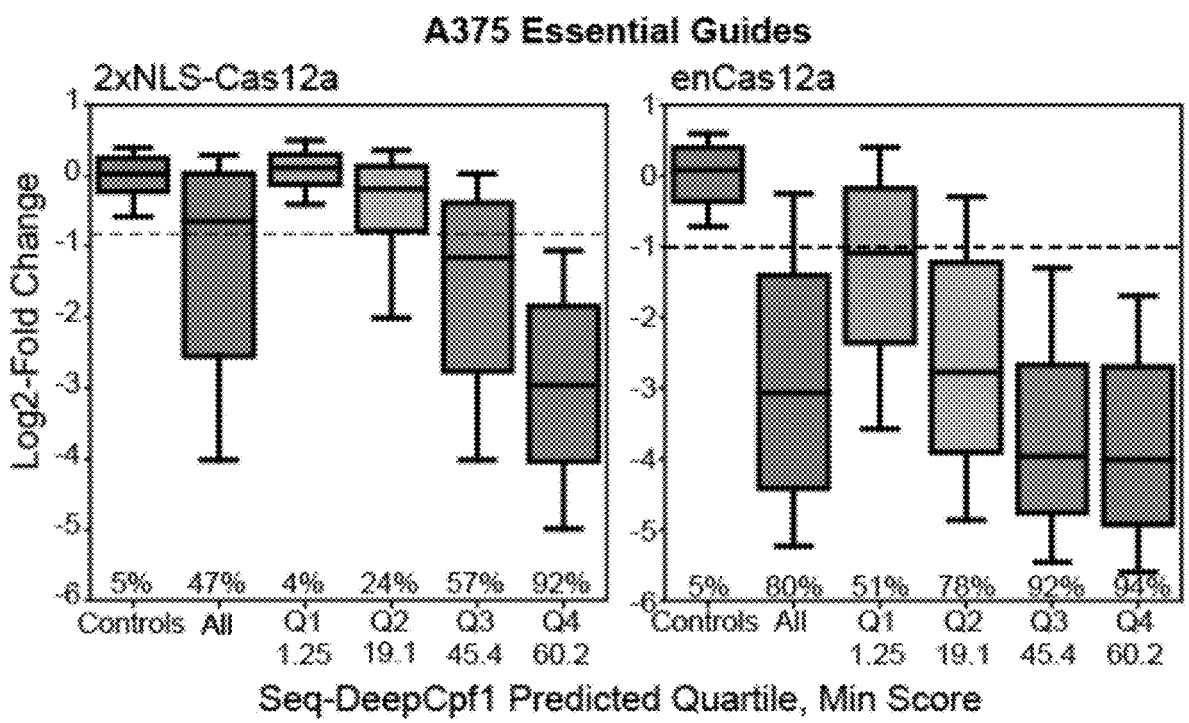
FIG. 18D

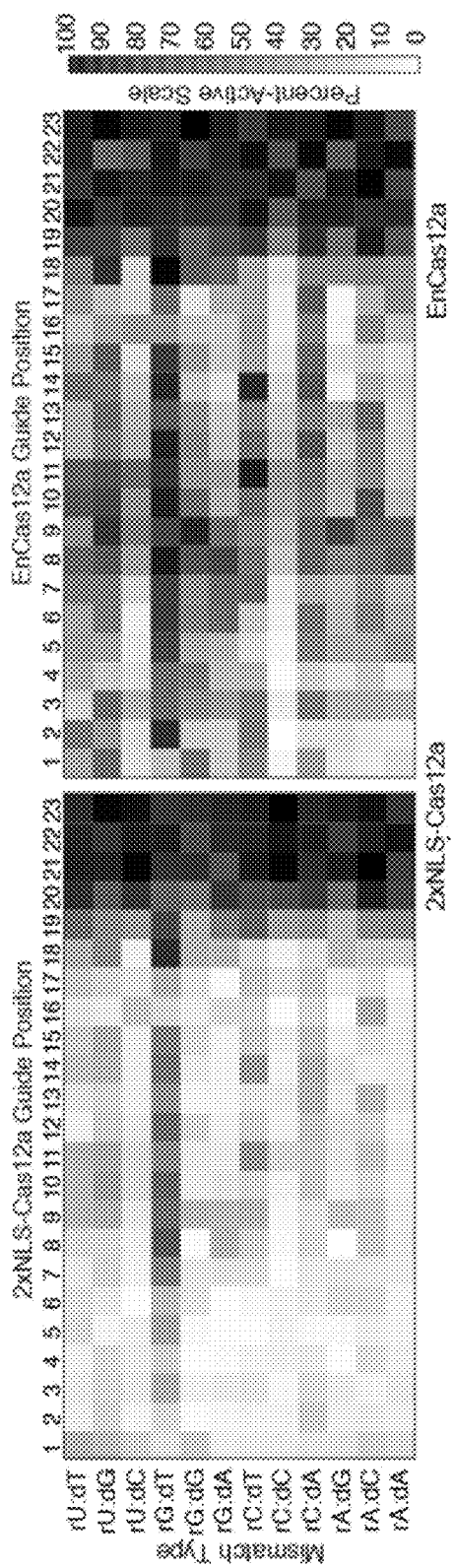
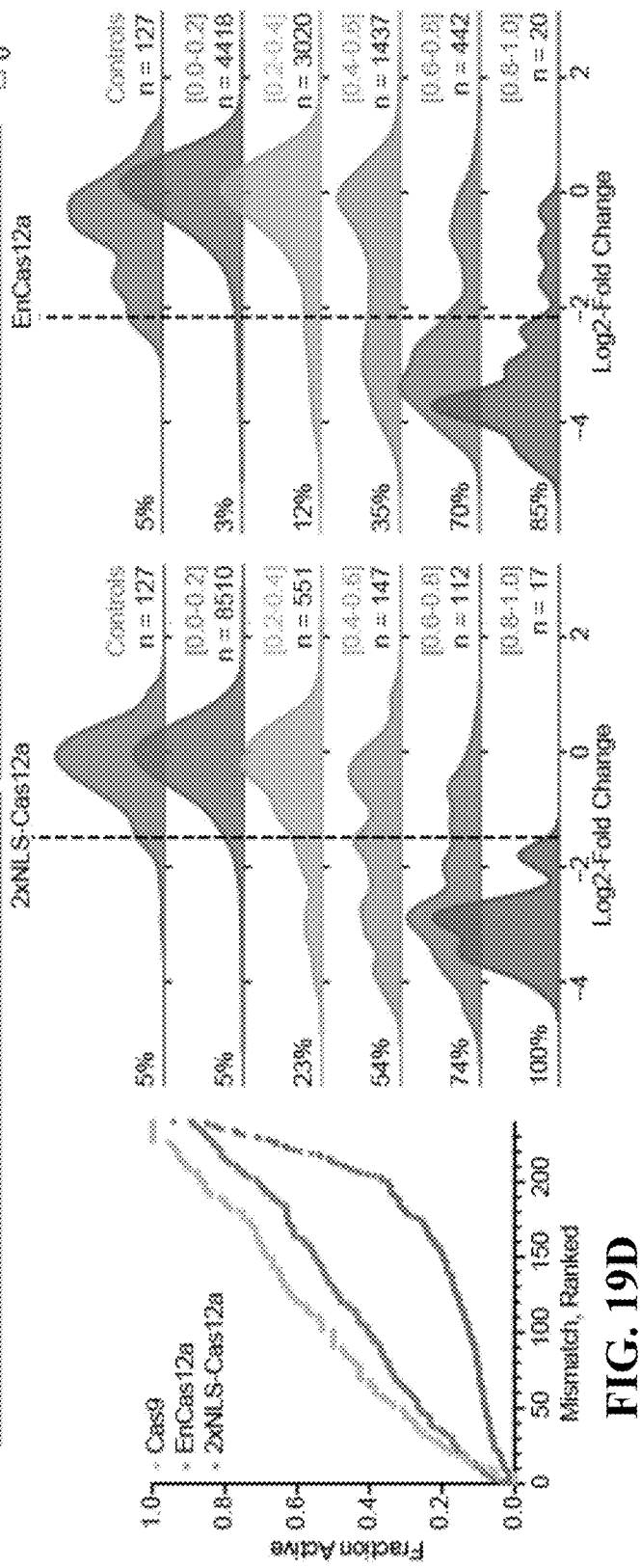
FIG. 19C
FIG. 19D
FIG. 19E

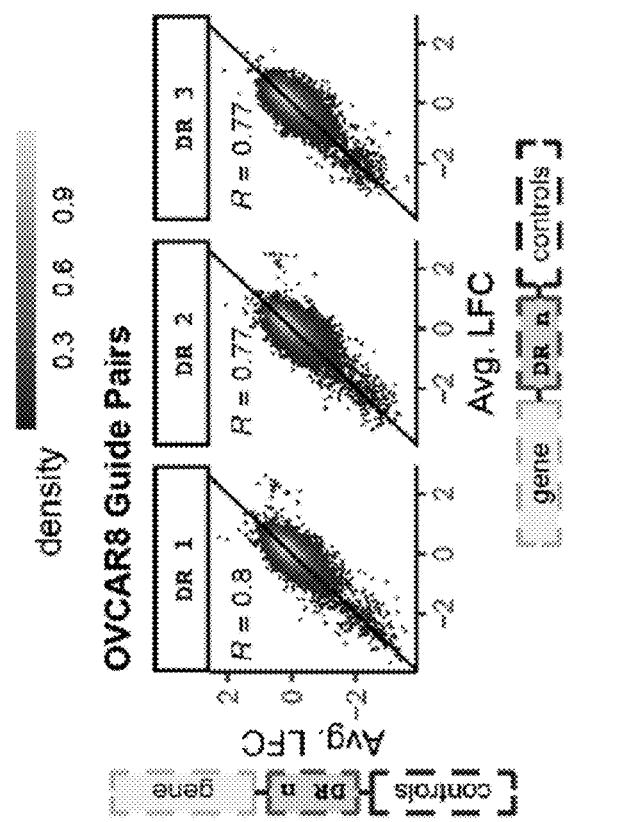
FIG. 20A
FIG. 20B
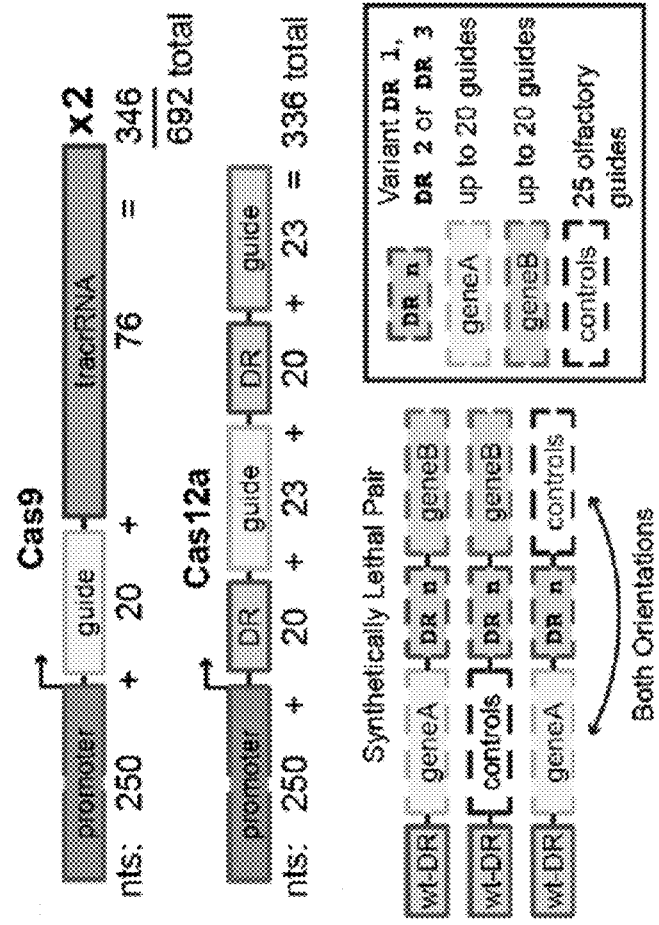
FIG. 20C

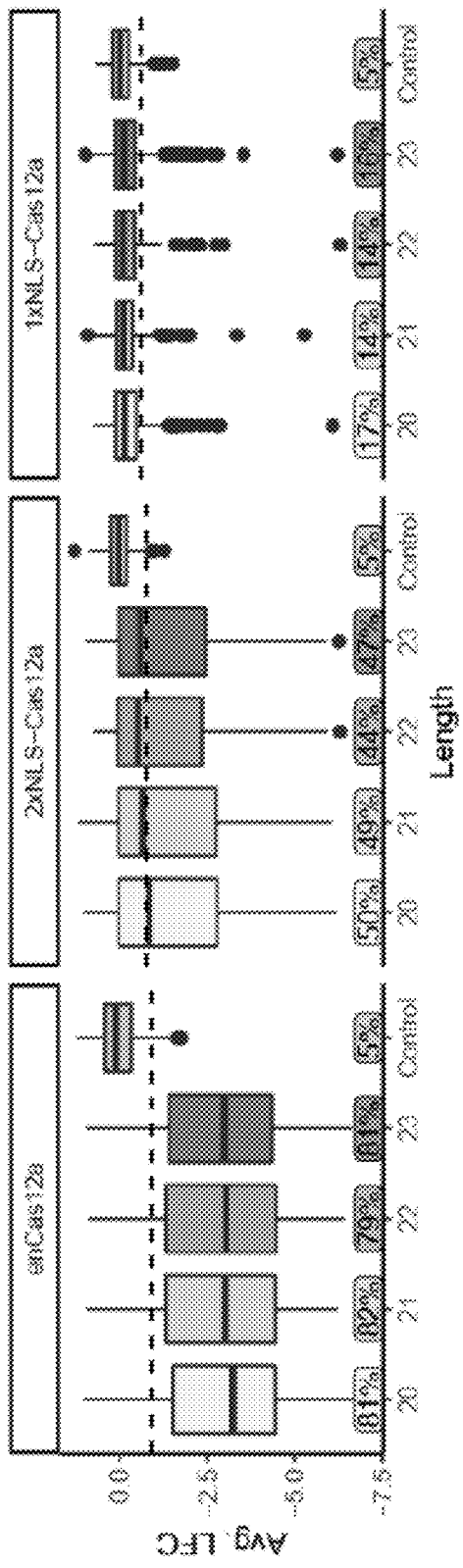
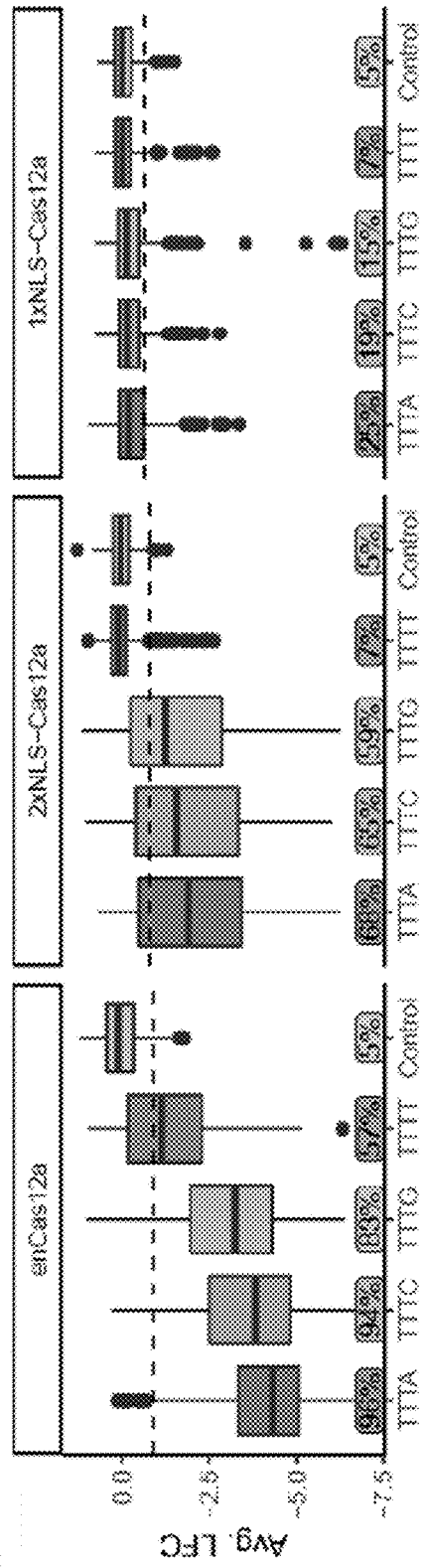
FIG. 22A
FIG. 22B

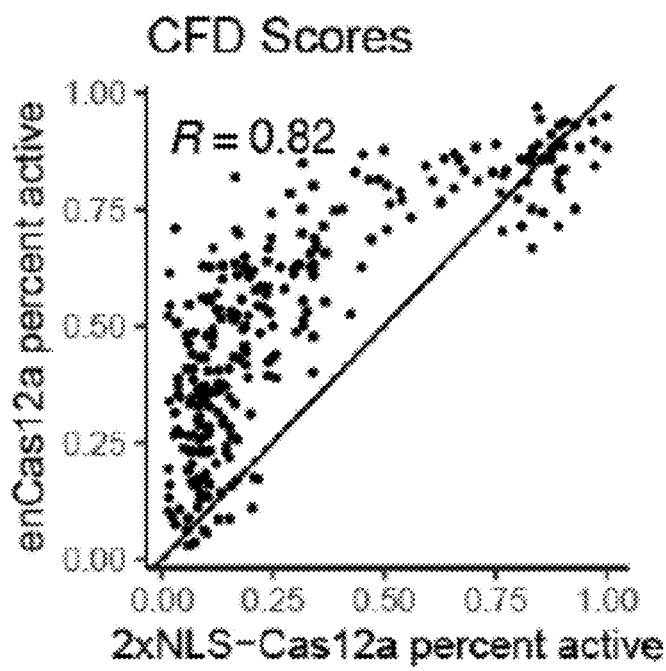
FIG. 26B
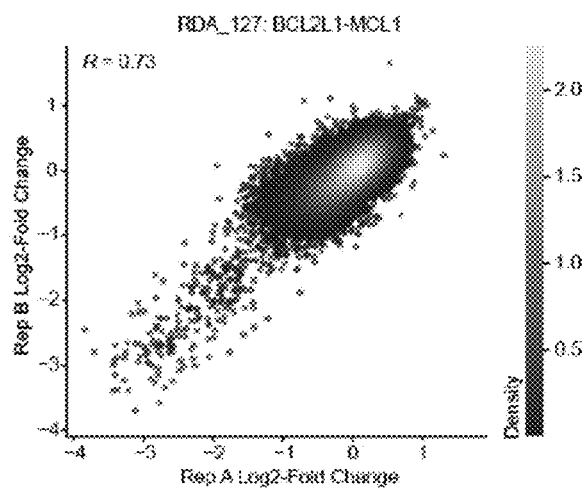 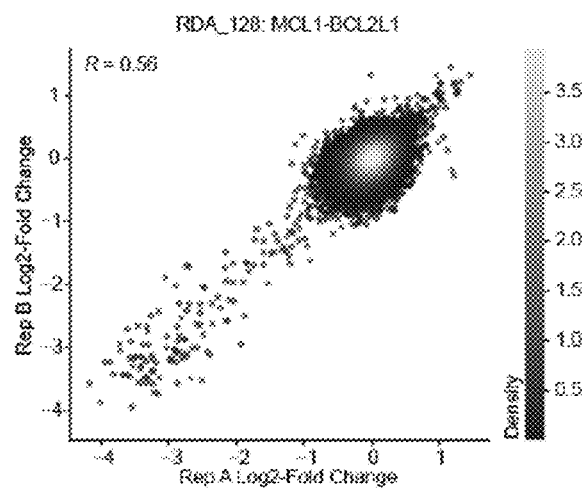
FIG. 27A  FIG. 27B

| Gene ID | # of Guides | Category |
|---|---|---|
| EEF2, HNRNPU, PELP1, TFRC, SF3B1, PSMA6, KPNB1, SNRPD1, RPS20, POLR1C | 1592 | Pan-lethal genes |
| MED12, NF1, NF2, CUL3 | 1640 | Vemurafenib resistance genes |
| HPRT1, NUDT5 | 113 | 6-thioguanine resistance genes |
| BRCA1, BRCA2 | 2628 | Olaparib / Talazoparib sensitive genes |
| BCL2L2, BCL2L1, MCL1, BAX, PMAIP1, BAK1 | 255 | Pro & Anti-apoptotic genes |
| CD81, CD33, FAS, ICAM1 | 231 | Cell surface control genes |
| HRAS, NRAS, PEX6, PEX10, SOX10 | 218 | MelJuSo sensitive genes |
| FBXO42, RNH1, ELOF1, YAP1 | 284 | OVCAR8 sensitive genes |
| TNFSF10, PAX8, STEAP3, SLC25A28, ARNT | 318 | 786O sensitive genes |
| FOXA2, ERBB2, NFE2L2, KRAS, PIK3CA | 941 | A549 sensitive genes |
| EEF2 – Any PAM | 4252 | Guides targeting EEF2 with any PAM |
| Total Guides: | 12472 | |

FIG. 34

| Condition | Cell Line | | | | |
|---|---|---|---|---|---|
| | A375 | Meljuso | OVCAR8 | 786O | A549 |
| Viability (no small molecule treatment) | Sp: 0.80<br>1x: 0.51<br>2x: 0.86<br>en: 0.80 | 2x: 0.79 | 2x: 0.81 | 2x: 0.42 | 2x: 0.64 |
| S63845 | 1x: 0.32<br>2x: 0.57 | 2x: 0.51 | | | |
| A-1331852 | 1x: 0.51<br>2x: 0.68 | 2x: 0.85 | | | |
| 6-thioguanine | 1x: 0.34<br>2x: 0.88<br>en: 0.90 | | | | |
| Talazoparib | | | 2x:<br>0.17 (250nM)<br>0.15 (7.81nM) | | |
| Olaparib | | | 2x:<br>0.23 (1mM)<br>0.16 (500nM) | | |
| Vemurafenib | 1x: 0.67<br>2x: 0.69<br>en: 0.55 | | | | |

FIG. 35

CRISPR CPF1 DIRECT REPEAT VARIANTS

CROSS-REFERENCE TO RELATED APPLICATIONS

This application claims the benefit of U.S. Provisional Application No. 62/780,748, filed Dec. 17, 2018. This application claims the benefit of U.S. Provisional Application No. 62/884,101, filed Aug. 7, 2019. The entire contents of the above-identified applications are hereby fully incorporated herein by reference.

STATEMENT REGARDING FEDERALLY SPONSORED RESEARCH

This invention was made with government support under Grant No. K99-CA218870 granted by The National Institutes of Health. The government has certain rights in the invention.

SEQUENCE LISTING

This application contains a sequence listing filed in electronic form as an ASCII.txt file entitled BROD-4530US_ST25.txt, created on Jan. 5, 2023 and having a size of 298,585 bytes. The content of the sequence listing is incorporated herein in its entirety.

TECHNICAL FIELD

The present invention generally relates to systems, methods and compositions related to Clustered Regularly Interspaced Short Palindromic Repeats (CRISPR) and components thereof. The present invention also generally relates to delivery of large payloads and includes novel delivery particles, particularly using lipid and viral particle, and also novel viral capsids, both suitable to deliver large payloads, such as Clustered Regularly Interspaced Short Palindromic Repeats (CRISPR), CRISPR protein (e.g., Cas, Cas9, Cpf1, Cas13a, Cas13b and the like), CRISPR-Cas or CRISPR system or CRISPR-Cas complex, components thereof, nucleic acid molecules, e.g., vectors, involving the same and uses of all of the foregoing, amongst other aspects. Additionally, the present invention relates to methods for developing or designing CRISPR-Cas system-based therapy or therapeutics.

BACKGROUND

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that employ novel strategies and molecular mechanisms and are affordable, easy to set up, scalable, and amenable to targeting multiple positions within the eukaryotic genome. This would provide a major resource for new applications in genome engineering and biotechnology.

The CRISPR-Cas systems of bacterial and archaeal adaptive immunity show extreme diversity of protein composition and genomic loci architecture. The CRISPR-Cas system loci has more than 50 gene families and there is no strictly universal genes indicating fast evolution and extreme diversity of loci architecture. So far, adopting a multi-pronged approach, there is comprehensive cas gene identification of about 395 profiles for 93 Cas proteins. Classification includes signature gene profiles plus signatures of locus architecture. A new classification of CRISPR-Cas systems is proposed in which these systems are broadly divided into two classes, Class 1 with multisubunit effector complexes and Class 2 with single-subunit effector modules exemplified by the Cas9 protein. Novel effector proteins associated with Class 2 CRISPR-Cas systems may be developed as powerful genome engineering tools and the prediction of putative novel effector proteins and their engineering and optimization is important.

The development of CRISPR-Cas RNA-guided endonucleases for eukaryotic genome editing has sparked intense interest in the use of this technology for therapeutic applications.

Extensive research has led to the identification of different technologies which can address the challenges of safety and efficacy. In order to allow the translation of this genome editing technologies to the clinic. There is a need for the development of an algorithm for developing a CRISPR-Cas based therapeutic, which takes into account the different variables which need to be considered.

In contrast to small molecule therapies, which target highly conserved protein active sites, treatment of disease at the genomic level must contend with significant levels of genetic variation in patient populations. Recently, large scale sequencing datasets from the Exome Aggregation Consortium (ExAC) and 1000 Genomes Project have provided an unprecedented view of the landscape of human genetic variation. This variation can affect both the efficacy of a CRISPR-based therapeutic, by disrupting the target site, and its safety, by generating off-target candidate sites.

Citation or identification of any document in this application is not an admission that such document is available as prior art to the present invention.

SUMMARY

The present invention will be further illustrated in the following Examples which are given for illustration purposes only and are not intended to limit the invention in any way.

Provided herein are engineered Cpf1 polynucleotides that can direct the activity of a CRISPR protein to multiple targets using a single crRNA. The engineered polynucleotides can include 5' DR-G 3' wherein DR is a direct repeat that comprises at least one mutation in comparison to the wildtype direct repeat and G is a guide, or a multiplexing polynucleotide, comprising: 5' DR1-G1-DR2-G2 3'wherein DR1 is a first direct repeat, G1 is a first guide, DR2 is a second direct repeat, G2 is a second guide, G1 can be the same or different than G2, DR1 and D2 are the same or different, wherein when different one of DR1 and DR2 is a wildtype direct repeat and the other comprises at least one mutation in comparison to the wildtype direct repeat, and when the same each of DR1 and DR2 comprises at least one mutation in comparison to the wildtype direct repeat, wherein said at least one mutation may be the same or different when D1 and D2 both comprise at least one mutation. The guide sequences can target a sequence in a eukaryotic cell, for example, an animal or a plant cell. The animal cell can be a human or a nonhuman cell.

In an embodiment, the engineered polynucleotide is a DNA molecule. In an embodiment, the engineered polynucleotide is an RNA molecule. Also provided are vectors comprising the engineered polynucleotide. The vector can be a viral vector or a plasmid. Also provided are cells comprising the engineered polynucleotide.

In one aspect, the invention can include kits and delivery systems for the engineered polynucleotide along with a Cpf1 or a Cas12a or polynucleotide(s).

Also provided are methods of modifying one or more targets in a cell. The methods can include introducing a Cpf1 system comprising the engineered polynucleotide and a Cpf1 or a Cas12a or polynucleotide(s) encoding the Cpf1 or the Cas12a into the cell. In an embodiment, the methods can include introducing a vector comprising the engineered polynucleotide into the cell.

Also provided herein are methods of combinational gene screening that can include modifying one or more targets in a cell. In some aspects modifying one or more targets in a cell can include introducing an engineered polynucleotide, Cpf1 system or polynucleotide(s) encoding the Cpf1 or the Cas12a, or a combination thereof into a cell. In some aspects, the method can include determining an effect of the modification(s). In some aspects, the effect can be determined by performing a functional assay. In some aspects, the cell can be exposed to a test molecule and/or abiotic condition before performing the functional assay.

In some exemplary embodiments, provided herein are engineered polynucleotides comprising a nucleotide sequence encoding two or more Cas12 guide sequences, each guide sequence having a direct repeat (DR) sequence 5' of the guide sequence, wherein each DR sequence is the same or different and wherein at least one DR has at least one mutation in the DR sequence relative to a wildtype Cas12 DR sequence.

In some exemplary embodiments, the two or more guide sequences are capable of hybridizing with different target sequences. In some exemplary embodiments, the two or more guide sequences target a sequence in a eukaryotic cell.

In some exemplary embodiments, the mutation is with reference to or in comparison with a wildtype direct repeat of AsCas12a or EnCas12a.

In some exemplary embodiments, the mutation is with reference to or in comparison with a wildtype direct repeat of AsCas12a having a sequence TAATTTCTCCTCTTGTAGAT (SEQ ID NO: 126).

In some exemplary embodiments, the at least one mutation comprises a mutation at position 1, 6, 9, 12, position 14, position 16, 19, of SEQ ID NO 126, or any combination thereof.

In some exemplary embodiments, the at least one mutation is in a loop of the direct repeat.

In some exemplary embodiments, the at least one mutation is in a stem loop of the direct repeat.

In some exemplary embodiments, the at least one mutation comprises
(i) A or G or T at position 12 with reference to or in comparison with a wildtype direct repeat of AsCas12a having a sequence TAATTTCTCCTCTTGTAGAT (SEQ ID NO: 126);
(ii) A or G at position 12 with reference to or in comparison with a wildtype direct repeat of AsCas12a having a sequence TAATTTCTCCTCTTGTAGAT (SEQ ID NO: 126);
(iii) A or G at position 1 with reference to or in comparison with a wildtype direct repeat of AsCas12a having a sequence TAATTTCTCCTCTTGTAGAT (SEQ ID NO: 126);
(iv) C at position 6 with reference to or in comparison with a wildtype direct repeat of AsCas12a having a sequence TAATTTCTCCTCTTGTAGAT (SEQ ID NO: 126);
(v) C at position 9 with reference to or in comparison with a wildtype direct repeat of AsCas12a having a sequence TAATTTCTCCTCTTGTAGAT (SEQ ID NO: 126);
(vi) C or A or G at position 14 with reference to or in comparison with a wildtype direct repeat of AsCas12a having a sequence TAATTTCTCCTCTTGTAGAT (SEQ ID NO: 126);
(vii) G at position 16 with reference to or in comparison with a wildtype direct repeat of AsCas12a having a sequence TAATTTCTCCTCTTGTAGAT (SEQ ID NO: 126);
(viii) G at position 19 with reference to or in comparison with a wildtype direct repeat of AsCas12a having a sequence TAATTTCTCCTCTTGTAGAT (SEQ ID NO: 126); or
(ix) any combination thereof.

In some exemplary embodiments, the at least one mutation comprises:
(i) G at position 12, C at position 14;
(ii) A at position 12, C at position 14;
(iii) A at position 1, A at position 14;
(iv) A at position 12, A at position 14;
(v) T at position 12, C at position 14;
(vi) A at position 1, A at position 12;
(vii) A at position 12, G at position 14;
(viii) G at position 1, C at position 14;
(ix) C at position 6, G at position 19;
(x) G at position 1, A at position 14;
(xi) C at position 9, G at position 16;
(xii) G at position 1, G at position 14;
(xiii) T at position 12, A at position 14;
(xiv) C at position 9, A at position 12, G at position 16;
(xv) C at position 9, A at position 14, G at position 16;
(xvii) A at position 1, C at position 9, G at position 16;
(xviii) C at position 6, A at position 14, G at position 19;
(xix) A at position 1, C at position 9, C at position 14, position G at position 16;
(xx) G at position 1, C at position 9, C at position 14, position G at position 16;
(xxi) G at position 1, C at position 6, A at position 12, position G at position 19;
(xxii) A at position 1, C at position 9, A at position 14, G at position 16; or
(xxiii) A at position 1, C at position 6, C at position 14, G at position 19,
with reference to or in comparison with a wildtype direct repeat of AsCas12a having a sequence TAATTTCTCCTCTTGTAGAT (SEQ ID NO: 126).

In some exemplary embodiments, the mutation comprises a chemical alteration of a nucleotide naturally occurring at the position.

In some exemplary embodiments, the engineered polynucleotide comprises DNA.

In some exemplary embodiments, the engineered polynucleotide comprises RNA.

In some exemplary embodiments, the engineered polynucleotide comprises a WtDR-MCL1guide-MutDR-BCL2L1-BCL2guide, MutDR-MCL1guide-WtDR-BCL2L1-BCL2guide, a WtDR-MARCH5guide-MutDR- WSB2guide, a MutDR-WSB2guide-WtDR-MARCH5guide, a WtDR-WSB2guide-MutDR-MARCH5guide, a MutDR-MARCH5guide-WtDR-WSB2guide, a WtDR-WSB2guide-MutDR-MCL1guide, a WtDR-MCL1-guide-MutDR-WSB2guide, a MutDR-MCL1guide-WtDR-WSB2guide, a MutDR-WSB2guide-WtDR-MCL1-guide, a WtDR-MARCH5guide-MutDR-BCL2L1guide, a MutDR-BCL2L1guide-WtDR-MARCH5guide, a WtDR-BCL2L1guide-MutDR-MARCH5guide, or a MutDR-MARCH5guide-WtDR-BCL2L1guide.

In some exemplary embodiments, provided herein are vector systems comprising: the engineered polynucleotide as described herein including, but not limited to, any of those above.

In some exemplary embodiments, vector system is or comprises a plasmid, an AAV vector, a lentiviral vector, or a combination thereof. In some exemplary embodiments, the AAV vector is or comprises an AAV vector having a serotype or pseudotype of AAV1, AAV2, AAV3, AAV4, AAV5, AAV6, AAV8 or AAV9 or any combination thereof.

In some exemplary embodiments, provided herein are cell comprising: the engineered polynucleotide as described herein including, but not limited to, any of those above. In some exemplary embodiments, the cell further comprises a vector system, wherein the engineered polynucleotide is contained in the vector system and wherein the vector system is optionally capable of expressing the engineered polynucleotide in the cell. In some exemplary embodiments, the cell further comprises a Cas12 or one or more polynucleotide(s) encoding the Cas12. In some exemplary embodiments, the cell is a eukaryotic cell. In some exemplary embodiments, the cell is as prokaryotic cell.

In some exemplary embodiments, provided herein are kits comprising the engineered polynucleotide as described herein including, but not limited to those described above, a vector system comprising said engineered polynucleotide, a cell comprising the engineered polynucleotide, or a combination thereof.

In some exemplary embodiments, provided herein are Cas12 systems comprising the engineered polynucleotide as described herein including, but not limited to those described above, and a Cas12 or polynucleotide(s) encoding the Cas12.

In some exemplary embodiments, provided herein are delivery systems comprising the engineered polynucleotide as described herein including, but not limited to those described above, and, optionally, a Cas12 or one or more polynucleotide(s) encoding the Cas12. In some exemplary embodiments, the delivery system comprises one or more vectors or one or more particles. In some exemplary embodiments, the vector is or comprises one or more plasmids, a lentiviral vector, an AAV vector, or a combination thereof. In some exemplary embodiments, the vector is or comprises an AAV and wherein the AAV vector optionally has a serotype or pseudotype is or comprises an AAV1, AAV2, AAV3, AAV4, AAV5, AAV6, AAV8 or AAV9 or any combination thereof. In some exemplary embodiments, the particle is lipid-based, comprises a lipid, or is or comprises a liposome. In some exemplary embodiments, Cas12, when optionally present, is encoded by a single vector or by at least two vectors. In some exemplary embodiments, the single vector or the at least two vectors are contained in a particle or at least two particles. In some exemplary embodiments, the Cas12, when optionally present, is contained in one particle or at least two particles.

In some exemplary embodiments, provided herein are methods of modifying one or more targets in a cell comprising: introducing into the cell an engineered polynucleotide as described herein including, but not limited to those described above or a vector system thereof, and optionally a Cas12, a Cas12 encoding polynucleotide, or a vector system thereof. In some exemplary embodiments, cell comprises a eukaryotic cell. In some exemplary embodiments, the cell is ex vivo or in vivo.

In some exemplary embodiments, provided herein is a gene therapy method comprising a method of modifying one or more targets in a cell comprising: introducing into the cell an engineered polynucleotide as described herein including, but not limited to those described above or a vector system thereof, and optionally a Cas12, a Cas12 encoding polynucleotide, or a vector system thereof. In some exemplary embodiments, cell comprises a eukaryotic cell. In some exemplary embodiments, the cell is ex vivo or in vivo. In some exemplary embodiments, the cell is ex vivo and the method includes expanding modified cells, introducing modified cells into a subject, or both. In some exemplary embodiments, the cell is in vivo and wherein introducing comprises administering the engineered polynucleotide or vector system thereof, and optionally a Cas12, a Cas12 encoding polynucleotide, or a vector system thereof to a subject.

In some exemplary embodiments, provided herein are methods of producing a modified non-human animal or plant comprising: a method of modifying one or more targets in a cell comprising: introducing into the cell an engineered polynucleotide as described herein including, but not limited to, those described above or a vector system thereof, and optionally a Cas12, a Cas12 encoding polynucleotide, or a vector system thereof. In some exemplary embodiments, cell comprises a eukaryotic cell. In some exemplary embodiments, the cell is ex vivo or in vivo. In some exemplary embodiments, the cell is ex vivo and the method includes expanding modified cells, introducing modified cells into a subject, or both. In some exemplary embodiments, the cell is in vivo and wherein introducing comprises administering the engineered polynucleotide or vector system thereof, and optionally a Cas12, a Cas12 encoding polynucleotide, or a vector system thereof to a subject.

In some exemplary embodiments, the method is a method of producing a modified plant comprising, after the introducing step, generating a plant from the cell or progeny thereof, wherein the plant has the modification(s) of the introducing step. In some exemplary embodiments, the method further comprises selfing the plant, crossing the plant, or both to obtain progeny having the modification(s) of the introducing step. In some exemplary embodiments, the modification(s) are demonstrated by a phenotype of the plant.

In some exemplary embodiments, the method comprises a method of producing a modified non-human animal, wherein the introducing comprises introducing to the animal or the method comprises, after the introducing step, generating the animal from the cell or progeny thereof.

In some exemplary embodiments, provided herein are methods comprising modifying a polynucleotide at one or more target regions by contacting the polynucleotide with an engineered polynucleotide as described herein including, but not limited to, those described above or a vector system thereof and a Cas12 polypeptide or a Cas12 encoding polynucleotide or a vector system thereof to form a modified polynucleotide; and performing a functional assay to determine an effect of the one or more modifications to the polynucleotide. In some exemplary embodiments, contacting occurs within a cell. In some exemplary embodiments, contacting occurs in vitro, in vivo, or ex vivo.

In some exemplary embodiments, the method further comprises delivering the engineered polynucleotide as described herein including, but not limited to those described above, and optionally a Cas 12 polypeptide or Cas12 encoding polynucleotide or a vector system thereof to the cell.

In some exemplary embodiments, the functional assay is a genotypic assay, a transcriptomic assay, a proteomic assay, epigenetic assay, phenotypic assay, or a combination thereof.

In some exemplary embodiments, the method further comprises, exposing the modified polynucleotide to a test molecule, abiotic condition, or both before performing the functional assay. In some exemplary embodiments, polynucleotide is DNA or RNA. In some exemplary embodiments, the method comprises modifying two or more target regions. In some exemplary embodiments, the two or more target regions are on the same gene.

In some exemplary embodiments, provided herein are methods comprising modifying a polynucleotide at one or more target regions by contacting the polynucleotide with an engineered polynucleotide as described herein including, but not limited to those described above or a vector system thereof and a Cas12 polypeptide or a Cas12 encoding polynucleotide or a vector system thereof to form a modified polynucleotide; and determining an effect of modifying one or more targets in the cell. In some exemplary embodiments, modifying occurs in vitro, in vivo, or ex vivo. In some exemplary embodiments, determining the effect of the one or more modification comprises performing a functional assay. In some exemplary embodiments, the functional assay is a genotypic assay, a transcriptomic assay, a proteomic assay, epigenetic assay, phenotypic assay, or a combination thereof. In some exemplary embodiments, the method further includes comprising exposing the cell to a test molecule, abiotic condition, or both before performing the functional assay.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 6—Shows a table comparing DR variant sequences from both pRDA 127 and pRDA 128 that performed better than wild type DR sequences. (SEQ ID NOs: 1-25)

FIG. 7—Shows a table comparing DR variant sequences from both pRDA 127 and pRDA 128 that performed better than wild type DR sequences. The stem loop portion of the DR sequence (positions 6-19) is indicated by shading at the bottom of the table. (SEQ ID NOs: 1-25)

FIG. 8—Shows a table comparing DR variant sequences from both pRDA 127 and pRDA 128 that performed better than wild type DR sequences. The loop portion of the DR sequence (positions 9-16) indicated by shading at the bottom of the table. (SEQ ID NOs: 1-25)

FIG. 9—Shows a table comparing DR variant sequences from both pRDA 127 and pRDA 128 that performed better than wild type DR sequences. Exemplary positions (outlined) in the loop that tolerated changes (positions 12 and 14) are compared with positions that did not tolerate change (positions 11 and 13). (SEQ ID NOs: 1-25)

FIG. 12—Shows the sequence of an exemplary DR variant expression cassette. (SEQ ID NOs: 26 and 27)

FIG. 13—Shows the sequence of exemplary codon optimized Cpf1 sequences. (SEQ ID NOs: 28-51)

FIG. 14B shows an exemplary screening timeline used to quantify the activity of exemplary direct repeats. FIG. 14C shows results of a functional analysis used to quantify multiplexing activity of the exemplary direct repeats. FIG. 14D shows the sequence of exemplary direct repeats and wild-type direct repeats. FIG. 14E shows an exemplary sequence of a stem loop structure. (SEQ ID NOs: 25 and 77)

FIG. 16—shows cell fraction data demonstrating knockouts with Cas12a.

FIGS. 17A-7C—Optimization of AsCas12a for use in pooled screening. (FIG. 17A) Vector maps for Cas12a constructs. Point mutations for enCas12a are indicated.

FIGS. 18A-8D—Evaluation of AsCas12a on-target predictions. (FIG. 18A) Summary of models under consideration. (FIG. 18C) Predictions of GB 2×NLS-Cas12a and Seq-DeepCpf1 on the 2×NLS-Cas12a hold out set. Spearman correlation is included. (FIG. 18D) Activity of essential guides in A375 cells binned by predicted quartile for 2×NLS-Cas12a and enCas12a (n=1589 essential guides, 231 control guides) Boxes represent the 25th, 50th and 75th percentiles, whiskers show 10th and 90th percentiles. Minimum score for each quartile is indicated.

FIGS. 19A-19E—Prediction of off-target activity for AsCas12a. (FIG. 19A) Schematic depicting off-target library construction and guide selection. (FIG. 19B) Density plot showing activity of guides in dropout screens targeting essential genes with zero, one and two mismatches. Line is displayed at the 5th percentile of guides targeting control genes, and used as a cutoff to determine the percent of guides active in each tier as reported. (FIG. 19C) Heat map displaying the fraction of guides active for each mismatch type at a given position in the guide. Guide position is numbered such that position 1 is PAM proximal. The fraction of active guides is reported from essential guides in dropout assays, vemurafenib resistance genes in vemurafenib assays, and HPRT1 guides in 6-thioguanine assays. Cutoff to determine active guides was determined by the 5th percentile of control genes in negative selection assays and the 95th percentile of control genes in positive selection assays. (FIG. 19D) Comparison of off-target activity of Cas9, 2×NLS-Cas12a, and enCas12a constructs. For each construct, the CFD scores of each position and nucleotide type were ranked, and the values plotted in ascending order. For Cas12a, only the first 20 nucleotides of the guide are used. Cas9 data are from Doench et al. Nat. Biotechnol. 34:184-191 (2016). (FIG. 19E) Histograms displaying measured activity of double mismatch guides targeting essential genes in dropout scores binned by a prediction of activity, the Cutting Frequency Determination (CFD) score. The fraction activity determined by the fraction of guides that fell below the 5% flow control genes cutoff is reported for each CFD bin as well as the number of guides that fall into each bin.

FIGS. 20A-20F—Validation of AsCas12a performance with synthetic lethal gene pairs. (FIG. 20A) Comparison of DNA cassettes necessary for dual knockout with Cas9 versus Cas12a. (FIG. 20B) Schematic of library design. Numbered direct repeats reference the same sequences as in FIGS. 14A-14E. (FIG. 20C) Correlation between the average log 2-fold change (LFC) of target guides in position 1 versus position 2 for all three DR variants screened in OVCAR8. (FIG. 20D) Average LFC for guide pairs versus the sum of each guide paired with controls in OVCAR8. Control points represent guide pairs with one control guide and one target guide. Regression line fit with control points only. Dashed line represents a residual two standard deviations below the mean residual for control points. (FIG. 20E) Density of residuals for synthetic lethal guide pairs in OVCAR8, filtered for guides with a Seq-DeepCpf1 score greater than 50. Dashed line represents two standard deviations below the mean residual of controls. Percent of pairs with a residual to the left of the dashed line is included. Labeled on the right is the number of unique constructs in the distribution. (FIG. 20F) Comparison of residuals for BCL2L1/MCL1 in OVCAR8 across Cas platforms. Libraries were filtered and residuals recalculated to account for differences in library design. Control constructs have one target guide (BCL2L1 or MCL1) and one control guide (n=180), whereas target constructs contain a synthetic lethal guide pair. P-values were calculated using a one-sided t-test with the alternative hypothesis that the mean of the target population was less than the mean of controls. Boxes represent the 25th, 50th and 75th percentiles, whiskers show 10th and 90th percentiles.

FIGS. 21A-21B—Robust triple knockout with AsCas12a. (FIG. 21A) Schematic of 6 multiplexed arrays with guides targeting CD47, B2M and CD63. (FIG. 21B) Fraction of cells with no, one, two, or three genes knocked out, assayed by flow cytometry; gates were set such that ~1% of cells score as knockout in the control condition.

FIGS. 22A-22C—Length and PAM preferences for AsCas12a. (FIG. 22A) Activity of guides targeting essential genes (n=1589) binned by guide length and compared with cell surface control guides (n=231). Dashed line represents the 5th percentile of control guides. The box represents the 25th, 50th and 75th percentiles, whiskers show 10th and 90th percentiles. (FIG. 22B) Same as (FIG. 22A) but binned by PAM. (FIG. 22C) Correlation between all essential guides tiled across cell lines with 2×NLS-Cas12a. Size and darkness of each circle corresponds to the indicated Pearson correlation coefficient. An example scatter plot comparing guide activity in A375 and A549 cells is shown to the right. Contours represent density of points.

FIGS. 23A-23D—Machine learning to determine on target preferences for AsCas12a. (FIG. 23A) Pipeline for gradient boosted models. Colors in the box labelled "split" represent different genes. (FIG. 23B) Nucleotide importances for 2×NLS-Cas12a GB from in-silico saliency analysis. All tested sequences had a TTTN PAM at positions 5-8. (FIG. 23C) Sams as (FIG. 23A) but for enCas12a GB. (FIG. 23D) Comparison of nucleotide importances between enCas12a GB and 2×NLS-Cas12a GB. Grey line represents best fit. Labelled points have the largest residual from this line. Spearman correlation is included.

FIGS. 25A-25E—On-target activity scores for non-canonical PAMs with enCas12a. FIG. 25A) Activity of EEF2 guides in A375. Guides are grouped by tier of PAM. Dashed line represents the 5th percentile of flow controls. Fraction of guides beneath this cutoff is included as well as the number of guides in each box. Boxes represent the 25th, 50th and 75th percentiles, whiskers show 10th and 90th percentiles. (FIG. 25B) (SEQ ID NOs: 79-82) Example of in-silico PAM modification. (FIG. 25C) Pearson correlation between Seq-DeepCpf1 score and measured log 2-fold-change for active PAM tiers in A375 cells. (FIG. 25D) Activity of guides in A375 cells binned by TTTC-modified predicted quartile for active PAM tiers. Boxes represent the 25th, 50th and 75th percentiles, whiskers show 10th and 90th percentiles. Minimum score for each quartile is indicated. (FIG. 25E) Same as (FIG. 25C), but for TTTT PAM sites.

FIGS. 26A-26B—Comparison of off-target profiles. (FIG. 26A) Heatmap of the fraction of active guides for each mismatch type and guide position for enCas12a and 2×NLS-Cas12a across three assays. Note that the 6-thioguanine (6TG) conditions has substantially fewer guides than the dropout or vemurafenib screens. Guide position is numbered from PAM proximal to PAM distal. (FIG. 26B) Comparison of fraction active for each mismatch/position between enCas12a and 2×NLS-Cas12a. Each point represents one square from the matrices in FIG. 19C. Spearman correlation is indicated.

FIGS. 27A-27D—Replicate correlation and control distributions for testing alternate direct repeats. (FIG. 27A) Correlation between replicate log 2-fold changes for RDA 127, which has the ordered elements: promoter, BCL2L1 guide, direct repeat library, MCL1 guide. Pearson correlation is indicated. (FIG. 27B) Same as (FIG. 27A) but for RDA 128 with the ordered elements: promoter, MCL1 guide, direct repeat library, BCL2L1 guide. (FIG. 27C) Distribution of log 2-fold changes for each type of direct repeat for RDA 127. The two control distributions are on top, whereas variant and wildtype are on bottom. (FIG. 27D) Same as (FIG. 27C) but for RDA 128.

(FIG. 28A) Correlation between replicate log 2-fold changes in A375 and OVCAR8 cells. Pearson correlation is indicated. (FIG. 28B) Average log 2-fold changes for control guides. Each point represents a single control paired with all other controls. Axes show each orientation of the guide. Labeled points were removed in downstream analyses. (FIG. 28C) Correlation between the average LFC of target guides in position 1 versus position 2 for all three DR variants in A375.

FIGS. 29A-29D—Evaluating synthetic lethal interactions with enCas12a. (FIG. 29A) Average $log_2$-fold change for guides paired with controls in A375 and OVCAR8. (FIG. 29B) Density of residuals for synthetic lethal guide pairs in A375, filtered for guides with a Seq-DeepCpf1 score greater than 50. Dashed line represents two standard deviations below the mean residual of controls. Percent of pairs with a residual to the left of the dashed line is included. Labeled on the right is the number of guide pairs in the distribution. (FIG. 29C) Comparison of synthetic lethality rates with filtered and unfiltered guides in OVCAR8. (FIG. 29D) Same as (FIG. 29B) but in A375.

(FIG. 30A) Residuals for individual synthetic lethal pairs by cell line. Libraries were filtered and residuals recalculated to account for differences in library design strategy. Control constructs have one target guide and one control guide (n=180), whereas target constructs contain a synthetic lethal guide pair. P-value was calculated using a one-sided t-test with the alternative hypothesis that the mean of the target population was less than the mean of controls. Boxes represent the 25th, 50th and 75th percentiles, whiskers show 10th and 90th percentiles. BCL2L1-MCL1 in OVCAR8 cells repeated from FIGS. 20A-20F for ease of comparison. (FIG. 30B) Comparison of the average residual for four synthetic lethal gene pairs using enCas12a or the Big Papi approach. Spearman correlation is included.

(FIG. 31A) The live cell population was first gated using forward and side scatter in unstained enCas12a-expressing cells infected with an empty vector control guide. (FIG. 31B) CD47 negative gates were set using compensated FL1-A vs side scatter in empty vector control cells stained with all 3 antibodies. (FIG. 31C) Same as FIG. 31B, but for CD63 using FL2-A. (FIG. 31D) Same as (FIG. 31B) but for B2M using FL4-A. (FIG. 31E) CD63 positive and negative populations of representative plot of a representative triple knockout construct (Array 3).

(FIG. 31A) Fraction of cells with no, one, two, or three genes knocked out, assayed by flow cytometry on day 18 (left) and 25 (right). (FIG. 31B) Fraction of cells with triple knockout over time (days 9, 18 and 25).

(FIG. 33C) Fraction of EnCas12a+ cells, normalized to the empty vector control.

FIG. 34—Shows a table demonstrating an AsCas12a On-target tiling library.

FIG. 35—Shows a table demonstrating an On-target screens with AsCas12a tiling library. 1x: screens with 1xNLS-Cas12a construct; 2x: 2x-NLS-Cas12a construct; en: enCas12a construct (see FIG. 17A). Sp: SpCas9 screen with an analogous library. Screens were performed in duplicate, and the Pearson correlation of the $log_2$-fold-change is indicated.

Figure 1:
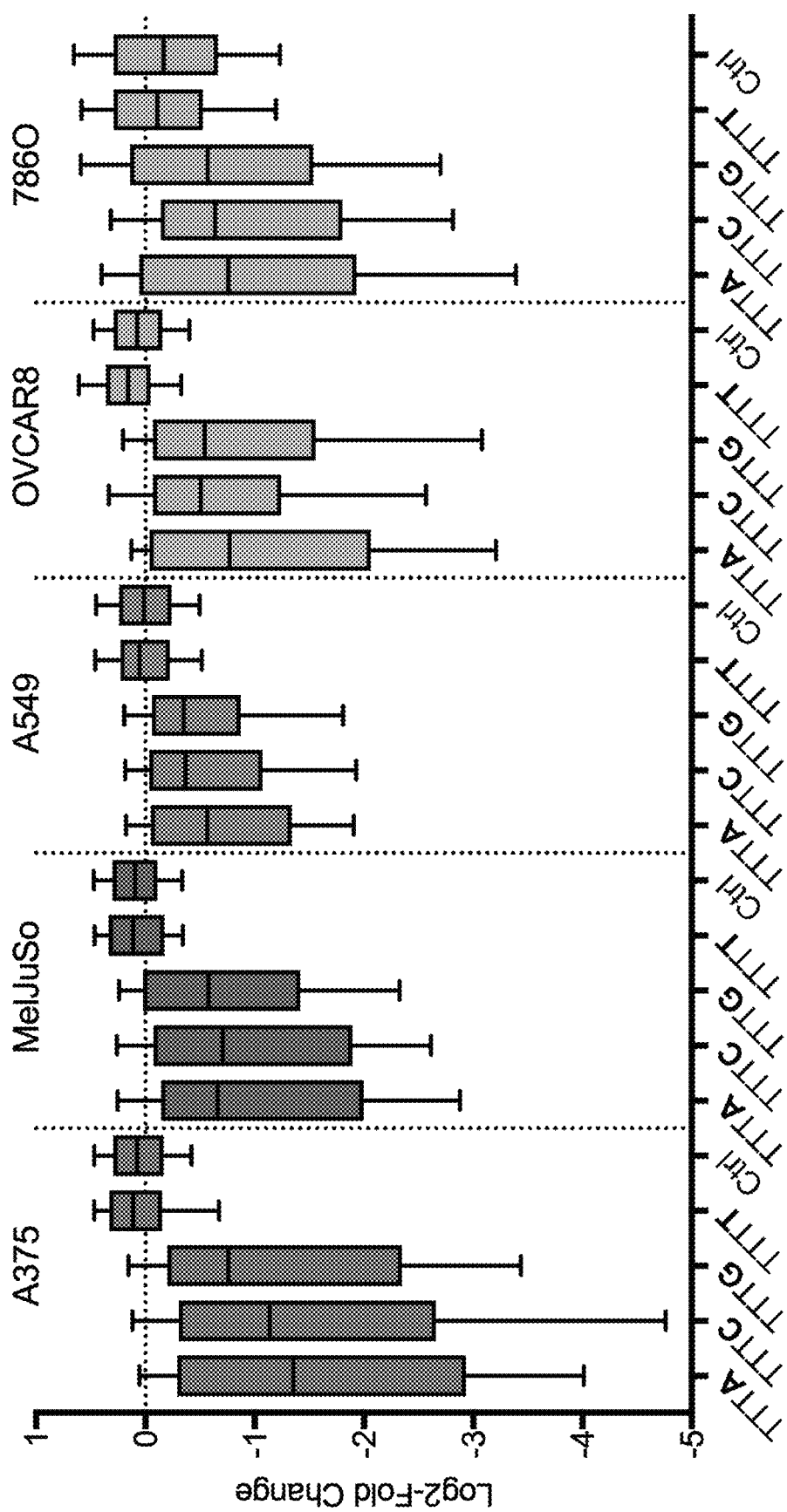
FIG. 1—Depicts identification of the protospacer adjacent motif (PAM) for AsCas12s by analysis of essential genes in a dropout screen using cell lines A375, MelJuSo, A549, OVCAR8, and 7860.

The figures herein are for illustrative purposes only and are not necessarily drawn to scale.

DETAILED DESCRIPTION OF THE EXAMPLE EMBODIMENTS

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R.I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a" "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

As used herein, a "biological sample" may contain whole cells and/or live cells and/or cell debris. The biological sample may contain (or be derived from) a "bodily fluid". The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

It will be appreciated that the terms Cas enzyme, CRISPR enzyme, CRISPR protein, Cas protein and CRISPR Cas are generally used interchangeably and at all points of reference herein refer by analogy to novel CRISPR effector proteins further described in this application, unless otherwise apparent, such as by specific reference to Cas9 or Cpf1. The CRISPR effector proteins described herein are preferably Cpf1 effector proteins.

All publications, published patent documents, and patent applications cited herein are hereby incorporated by reference to the same extent as though each individual publication, published patent document, or patent application was specifically and individually indicated as being incorporated by reference.

Overview

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008. The "tracrRNA" sequence or analogous terms includes any polynucleotide sequence that has sufficient complementarity with a crRNA sequence to hybridize. In embodiments of the present invention, the tracrRNA is not required for cleavage activity of Cpf1 effector protein complexes.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

Provided herein are engineered polynucleotide sequences that can direct the activity of a CRISPR protein to multiple targets using a single crRNA. The engineered polynucleotide sequences, also referred to as multiplexing polynucleotides, can include two or more direct repeats interspersed with two or more guide sequences. More specifically, the engineered polynucleotide sequences can include a direct repeat sequence having one or more mutations relative to the corresponding wild type direct repeat sequence. The engineered polynucleotide can be configured, for example, as: 5' DR1-G1-DR2-G2 3'. In some embodiments, the engineered polynucleotide can be configured to include three, four, five, or more additional direct repeat and guide sequences, for example: 5' DR1-G1-DR2-G2-DR3-G3 3', 5' DR1-G1-DR2-G2-DR3-G3-DR4-G4 3', or 5' DR1-G1-DR2-G2-DR3-G3-DR4-G4-DR5-G5 3'. Regardless of the number of direct repeat sequences, the direct repeat sequences differ from one another. Thus, DR1 can be a wild type sequence and DR2 can include one or more mutations relative to the wild type sequence. The guide sequences can also be the same or different. In some embodiments, the guide sequences can bind to different nucleic acid targets, for example, nucleic acids encoding different polypeptides.

The engineered polynucleotides are useful for designing CRISPR-Cas system-based therapy or therapeutics in which targeting multiple sequences may confer enhanced therapeutic benefit. The engineered polynucleotides are also effective reagents for generating multi-location genetic alterations in a variety of contexts, for example, in cellular assays, plant genetics, and animal models of human disease. The engineered polynucleotides disclosed herein are useful for efficient reprogramming differentiated cells into induced pluripotent stem cells, for example, by activation of Yamanaka factors (e.g., Oct3/4, Sox2, Klf4, c-Myc) which are highly expressed in embryonic stem cells.

The engineered polynucleotides can be delivered to a cell, for example, a human, animal, or plant cell in a variety of ways including, for example, contained within a vector, for example a viral vector or a plasmid, or as an RNA. The nucleic acid can be packaged in a nanoparticles or liposome depending upon the application. For example, in the case of primary T cells, which can be refractile to many standard methods of delivery of exogenous nucleic acids, delivery as an mRNA can be advantageous.

The inventors have shown that CRISPR enzymes as defined herein can employ more than one RNA guide without losing activity. This enables the use of the CRISPR enzymes, systems or complexes as defined herein for targeting multiple DNA targets, genes or gene loci, with a single enzyme, system or complex as defined herein. The guide RNAs may be tandemly arranged, optionally separated by a nucleotide sequence such as a direct repeat as defined herein. The position of the different guide RNAs is the tandem does not influence the activity.

Accordingly, the Cpf1 enzyme may form part of a CRISPR system or complex, which further comprises tandemly arranged guide RNAs (gRNAs) comprising a series of 2, 3, 4, 5, 6, 7, 8, 9, 10, 15, 25, 25, 30, or more than 30 guide sequences, each capable of specifically hybridizing to a target sequence in a genomic locus of interest in a cell. In some embodiments, the functional Cpf1 CRISPR system or complex binds to the multiple target sequences. In some embodiments, the functional CRISPR system or complex may edit the multiple target sequences, e.g., the target sequences may comprise a genomic locus, and in some embodiments, there may be an alteration of gene expression. In some embodiments, the functional CRISPR system or complex may comprise further functional domains. In some embodiments, the invention provides a method for altering or modifying expression of multiple gene products. The method may comprise introducing into a cell containing said target nucleic acids, e.g., DNA molecules, or containing and expressing target nucleic acid, e.g., DNA molecules; for instance, the target nucleic acids may encode gene products or provide for expression of gene products (e.g., regulatory sequences). In some general embodiments, the Cpf1 enzyme used for multiplex targeting is associated with one or more functional domains. In some more specific embodiments, the CRISPR enzyme used for multiplex targeting is a deadCpf1 as defined herein elsewhere. In some embodiments, each of the guide sequence is at least 16, 17, 18, 19, 20, 25 nucleotides, or between 16-30, or between 16-25, or between 16-20 nucleotides in length.

Examples of multiplex genome engineering using CRISPR effector proteins are provided in Cong et al. (Science February 15; 339(6121):819-23 (2013) and other publications cited herein. More specifically, multiplex gene editing using Cpf1 is described in Zetsche et al. 2016 (doi: http://dx.doi.org/10.1101/049122).

The application provides methods for developing the therapeutic use of a nucleic acid-targeting system. The nucleic acid-targeting complex an effective means for modifying a target DNA or RNA (single or double stranded, linear or super-coiled). The nucleic acid-targeting complex has a wide variety of utility including modifying (e.g., deleting, inserting, translocating, inactivating, activating) a target DNA or RNA in a multiplicity of cell types. As such the nucleic acid-targeting complex has a broad spectrum of applications in, e.g., gene therapy, drug screening, disease diagnosis, and prognosis. An exemplary nucleic acid-targeting complex comprises a DNA or RNA-targeting effector protein complexed with a guide RNA hybridized to a target sequence within the target locus of interest.

The invention involves developing a therapeutic based on the CRISPR system. In particular embodiments, the therapeutic comprises a DNA-targeting effector protein and/or a guide RNA capable of hybridizing to a target sequence of interest. In particular embodiments, the therapeutic is a vector system comprising one or more vectors, wherein the one or more vectors comprises: a) a first regulatory element operably linked to a nucleotide sequence encoding the Cpf1 effector protein; and b) a second regulatory element operably linked to one or more nucleotide sequences encoding one or more nucleic acid molecules comprising a guide RNA comprising a guide sequence, a direct repeat sequence; wherein components (a) and (b) are located on same or different vectors. In particular embodiments, the therapeutic is a composition comprising a delivery system operably configured to deliver CRISPR-Cpf1 complex components or one or more polynucleotide sequences comprising or encoding said components into a cell, and wherein said CRISPR-Cpf1 complex is operable in the cell; CRISPR-Cas complex components, the CRISPR-Cpf1 complex components, comprising (I) the Cpf1 effector protein as described herein; and guide RNA comprising the guide sequence, and a direct repeat sequence. In any such compositions, the delivery system may comprise a yeast system, a lipofection system, a microinjection system, a biolistic system, virosomes, liposomes, immunoliposomes, polycations, lipid:nucleic acid conjugates or artificial virions, or any other system as described herein. In particular embodiments, the delivery is via a particle, a nanoparticle, a lipid or a cell penetrating peptide (CPP).

In any such compositions, the composition may comprise more than one guide RNA, and each guide RNA has a different target whereby there is multiplexing. In any such systems comprising regulatory elements, at least one of said regulatory elements may comprise a tissue-specific promoter. The tissue-specific promoter may direct expression in a mammalian blood cell, in a mammalian liver cell or in a mammalian eye. In any of the above-described compositions or systems the direct repeat sequence, may comprise one or more protein-interacting RNA aptamers. The one or more aptamers may be located in the tetraloop. The one or more aptamers may be capable of binding MS2 bacteriophage coat protein.

In particular embodiments, the methods provided herein are methods of modifying a locus of interest in a cell comprising contacting the cell with any of the herein-described Cpf1 effector proteins. Any such method may be ex vivo or in vivo.

The invention thus provides a method of treating a disease, disorder or infection in an individual in need thereof comprising identifying suitable treatment conditions and administering an effective amount of the compositions, systems or CRISPR-Cpf1 complexes described herein. The disease, disorder or infection may comprise a viral infection. The viral infection may be HBV. The methods may also be methods for gene or genome editing.

Multiplexing Polynucleotides

In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

The engineered polynucleotide disclosed herein may comprise, consist essentially of, or consist of a two or more direct repeat (DR) sequences and two or more guide sequences. In certain embodiments, the direct repeat sequences are fused or linked to the guide sequences. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence. For example, the engineered polynucleotide can be configured as: 5' DR1-G1-DR2-G2 3'. In some embodiments, the engineered polynucleotide can be configured to include three, four, five, or more additional direct repeat and guide sequences, for example: 5' DR1-G1-DR2-G2-DR3-G3 3', 5' DR1-G1-DR2-G2-DR3-G3-DR4-G4 3', or 5' DR1-G1-DR2-G2-DR3-G3-DR4-G4-DR5-G5 3'.

The DR sequence can be a wild type DR sequence or a DR sequence having one or more mutations relative to the corresponding wild type sequence. The wild type DR and mutant DR sequences can be configured in any order. In some embodiments, one of the DR sequences in the engineered polynucleotide is a wild type DR sequence, that is, either DR1, DR2, DR3, DR4, or DR5 can be a wild type DR sequence. In an embodiment, DR1 is a wild type sequence, and DR2, and if present, DR3, DR4, and DR5 are mutant sequences. In an embodiment, DR2 is a wild type sequence, and DR1, and if present, DR3, DR4, and DR5 are mutant sequences. In an embodiment, DR3 is a wild type sequence, and DR1 and DR2, and if present, DR4, and DR5 are mutant sequences. In an embodiment, DR4 is a wild type sequence, and DR1, DR2, and DR3, and if present, DR5 is a mutant sequence. In an embodiment, DR5 is a wild type sequence, and DR1, DR2, and DR3, and DR4 are mutant sequences. Thus, the engineered polynucleotide can include one wild type DR sequence and 1, 2, 3 or more DR sequences having one or more mutations relative to the wild type sequence. The 1, 2, 3 or more mutant DR sequences are different from one another, that is, the position of the mutation (s) in each of the mutant sequences is different. In some embodiments, the engineered polynucleotide can exclude a wild type DR sequence so that all of the DR sequences have one or more mutations relative to the wild type sequence. In such embodiments, the mutant DR sequences are different from one another, that is, the position of the mutation (s) in each of the mutant sequences is different.

In some embodiments, such as in the context of a synthetic-lethal screening assay or other combinatorial assay, G1, G2, G3, G4, G5, and so on, can each be selected from a WSB2 guide, a MARCH5 guide, a MCL1 guide, a BCL2L1 guide. In some embodiments having two guides, G1 and G2 are each independently selected from WSB2 and MARCH5. In some embodiments having two guides, G1 and G2 are each independently selected from BCL2L1 and MARCH5. In some embodiments having two guides, G1 and G2 are each independently selected from WSB2 and MCL. Other suitable guides and combinations are discussed elsewhere herein. In some embodiments, the constructs, which can be polynucleotides or vectors, can contain 1, 2, 3, 4, or more guides per gene target. In some embodiments, constructs can be pooled such that the pool contains two or more (e.g. 2, 3, 4, etc.) guides per gene and the pool can be used to modify one or more target gene(s) as described in greater detail elsewhere herein. In some embodiments, each construct within a pool can contain a single 5' DR-guide sequence. In some embodiments, each construct within a pool can contain two or more serial 5' DR-guide sequences (e.g. DR-G1-DR-G2). In some embodiments, one or more constructs within a pool can contain a single 5' DR-guide sequence. In some embodiments, one or more constructs within a pool can contain two, three, four or more serial DR-guide sequences (e.g. DR-G1-DR-G2). In some embodiments, the pool can contain two, three, four, or more constructs.

In some embodiments, the DR sequence is at least 16, at least 17, at least 18, at least 19, at least 20, at least 25, at least 30, or at least 40, or at least 50 nucleotides in length, or is between 16-30, or between 16-25, or between 16-20 nucleotides in length. In an embodiment, the DR is 20 nucleotides in length. In some embodiments, the length of the DR sequences in the engineered polynucleotide can be the same. In some embodiments, the DR sequences in the engineered polynucleotide can be the different.

The position of the mutation in a DR sequence can vary. In general, useful mutations will be those that generate engineered polynucleotides that direct higher levels of CRISPR activity than does the same polynucleotide comprising two corresponding wild type DR sequences. In an embodiment, the mutation is a substitution. In an embodiment, the mutation is an insertion, or a deletion. In an embodiment, the mutation can comprise a chemical modification of a nucleotide. Exemplary chemical modifications can be 5'-methylcytidine in place of cytosine and/or psuedouridine, dihydrouridine or dideoxyuracil in place of uracil.

In certain embodiments, the DR sequence forms a stem loop, preferably a single stem loop. In an embodiment, the mutation in the DR sequence is in a loop. In an embodiment, the mutation in the DR sequence is in a stem loop. In an embodiment, stem base pairing is maintained in the mutant DR sequence. In an embodiment, mutant DR1 is not complementary with mutant DR2 over the stem-loop region over 2 bases, over 3 bases, over 4 bases, over 5 bases, over 6 bases, over 7 bases, over 8 bases or more.

Direct repeats have been identified for many different CRISPR loci. Wild type direct repeats that have been identified for any of the CRISPR loci encoding the CRISPR proteins, for example, a CpF1 polypeptide disclosed herein can be used in the construction of the engineered polynucleotides disclosed herein. The exemplary Cpf1 polypeptides are listed in Tables 1 and 2.

In some embodiments, direct repeats may be identified in silico by searching for repetitive motifs that fulfill any or all of the following criteria: 1. found in a 2 Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

An exemplary DR sequence utilized by AsCas12a, a Cpf1 polypeptide, is TAATTTCTACTCTTGTAGAT (SEQ ID NO: 83). In an embodiment, the DR sequence TTTCTACTCTTGTAGAT (SEQ ID NO: 84) can have a mutation at position 12, position 14, or position 16. In an embodiment, the DR sequence TTTCTACTCTTGTAGAT (SEQ ID NO: 85) can have a mutation at position 1 and/or 6 and/or 9 and/or 19. In an embodiment, the mutation can be A or G or T at position 12. In an embodiment, the mutation can be A or G at position 12. In an embodiment, the mutation can be A or G at position 1 and/or C at position 6 and/or C at position 9 and/or C or A or G at position 14 and/or G at position 16 and/or G at position 19. In an embodiment, the mutation can be G at position 12, C at position 14; or A at position 12, C at position 14; or A at position 1, A at position 14; or A at position 12, A at position 14; or T at position 12, C at position 14; or A at position 1, A at position 12; or A at position 12, G at position 14; or G at position 1, C at position 14; or C at position 6, G at position 19; or G at position 1, A at position 14; or C at position 9, G at position 16; or G at position 1, G at position 14; or T at position 12, A at position 14; or C at position 9, A at position 12, G at position 16; or C at position 9, A at position 14, G at position 16; or A at position 1, C at position 9, G at position 16; or C at position 6, A at position 14, G at position 19; or A at position 1, C at position 9, C at position 14, position G at position 16; or G at position 1, C at position 9, C at position 14, position G at position 16; or G at position 1, C at position 6, A at position 12, position G at position 19; or A at position 1, C at position 9, A at position 14, G at position 16; or A at position 1, C at position 6, C at position 14, G at position 19.

A wild type DR can be mutated using various methods. Useful DR mutants can be identified by functional screening. As described herein (see, for example, Example 2) a library of engineered polynucleotide sequences comprising a first DR sequence (DR1) and a second DR sequence (DR2) along with a first guide sequence and a second guide sequence can be synthesized. In an embodiment, DR1 is a wild type DR sequence and DR2 comprises a sequence in which at least one mutation has been introduced into the corresponding wild type sequence of DR1. In an embodiment, DR2 is a wild type DR sequence and DR1 comprises a sequence in which at least one mutation has been introduced into the corresponding wild type sequence of DR2. Regardless of the order of the direct repeat sequences, the library can be cloned into a suitable vector, for example, a lentiviral vector, which is then used to infect a cell line, for example, a mammalian cell line, that has been engineered to express a CRISPR polypeptide. In an embodiment, the CRISPR polypeptide can be a Cpf1 polypeptide, for example, AsCas12a. the transfected cells can be cultured and then analyzed by a suitable method to identify specific DR sequences that direct CRISPR activity, e.g., Cpf1 activity, in a way that is superior to that obtained by a control polynucleotide in which both DR sequences are wild type.

The functional assay can vary depending upon function of the gene targeted by the guide sequences. In an embodiment, functional genomic methods, which involve identifying cellular interactions by introducing multiple combinatorial perturbations and correlating observed genomic, genetic, proteomic, epigenetic and/or phenotypic effects with the perturbation detected in single cells, also referred to as "perturb-seq" can be suitable screening methods. These methods can be used for combinatorial probing of cellular circuits, for dissecting cellular circuitry, for delineating molecular pathways, and/or for identifying relevant targets for therapeutics development. In an embodiment, such a screening method can be based on identifying redundant genes in general, for example, MAPK1 and MAPK3. In an embodiment such a screening method can be based on genes having a symbiotic lethal relationship, for example, BRCA1 and PARP1.

In an embodiment, the guide sequences can comprise a sequence targeting genes relevant to cancer, specifically to apoptotic pathways that are often altered in cancer cells. In an embodiment, the guide sequences can be sequences found in MCL1 and BCL2L1. In an embodiment, Cpf1 expressing cells that has been infected with a lentiviral vector comprising a library expressing the engineered polynucleotide 5' DR1-G1-DR2-G2 3', wherein DR1 is a first direct repeat, G1 is a first guide, DR2 is a second direct repeat, G2 is a second guide and DR1 is a wild type DR sequence, DR2 is a sequence comprising at least one mutation relative to the wild type sequence of DR1, G1 is an MCL1 guide, and G2 is a BCL2L1 guide. In an embodiment, DR1 is a first direct repeat, G1 is a first guide, DR2 is a second direct repeat, G2 is a second guide and DR1 is a wild type DR sequence, DR2 is a sequence comprising at least one mutation relative to the wild type sequence of DR1, G1 is an BCL2L1 guide, and G2 is a MCL1 guide. In an embodiment, transcription of engineered polynucleotide can be driven by and RNA polymerase III promoter, for example, a U6 promoter. The cells can be cultured under conditions that permit CRISPR-directed ablation of BCL2L1 and MCL1 activity. The cells can then be recovered, the genomic DNA can be extracted, and the extracted genomic DNA can be analyzed, for example by sequencing, to identify mutant DR sequences that conferred enhanced CRISPR-directed ablation of BCL2L1 and MCL1 activity.

Guides

The engineered polynucleotides disclosed herein can include two or more guide sequences. A guide sequence can target, for example, without limitation, genes related to 6-thioguanine metabolism, e.g., HPRT1, and NUDT5; SB63845 metabolism, e.g., BCL2L1; A1331852 metabolism, e.g., MCL1, BAX, PMAIP, BAK1, BCL2L2; a cell surface marker, e.g., CD33, CD81, FAS, ICAM1; Talazoparib metabolism, e.g., BRCA1, BRCA2.; Vemurafenib metabolism, e.g., CUL3, NF1, NF2, MED12; a cell-specific lethal gene, e.g., ARNT, PAX8, SLC25A26, STEAP3, TNFSF10, ERBB2, FOXA2, KRAS, NFE2L2, PIK3CA, HRAS, NRAS, PEX10, SOX10, ELOF1, FBXO42, RNH1, YAP1; or a pan-essential gene, e.g., EEF2, HNRNPU, KPNB1, POLR1C, PSMA6, RPS20, SF3B1, SNRPD1, TFRC. Selection of guides as well as modified guide sequences, for example, inducible guides, protected guides, escorted guides, and self-inactivating guides, are discussed herein below.

In general, a "nucleic acid-targeting system" as used in the present application refers collectively to transcripts and other elements involved in the expression of or directing the activity of nucleic acid-targeting CRISPR-associated ("Cas") genes (also referred to herein as an effector protein), including sequences encoding a nucleic acid-targeting Cas (effector) protein and a guide RNA (comprising crRNA sequence and a trans-activating CRISPR/Cas system RNA (tracrRNA) sequence), or other sequences and transcripts from a nucleic acid-targeting CRISPR locus. In some embodiments, one or more elements of a nucleic acid-targeting system are derived from a Type V/Type VI nucleic acid-targeting CRISPR system. In some embodiments, one or more elements of a nucleic acid-targeting system is derived from a particular organism comprising an endogenous nucleic acid-targeting CRISPR system. In general, a nucleic acid-targeting system is characterized by elements that promote the formation of a nucleic acid-targeting complex at the site of a target sequence. In the context of formation of a nucleic acid-targeting complex, "target sequence" refers to a sequence to which a guide sequence is designed to have complementarity, where hybridization between a target sequence and a guide RNA promotes the formation of a DNA or RNA-targeting complex. Full complementarity is not necessarily required, provided there is sufficient complementarity to cause hybridization and promote formation of a nucleic acid-targeting complex. A target sequence may comprise RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing RNA" or "editing sequence". In aspects of the invention, an exogenous template RNA may be referred to as an editing template. In an aspect of the invention the recombination is homologous recombination.

Typically, in the context of an endogenous nucleic acid-targeting system, formation of a nucleic acid-targeting complex (comprising a guide RNA hybridized to a target sequence and complexed with one or more nucleic acid-targeting effector proteins) results in cleavage of one or both RNA strands in or near (e.g. within 1, 2, 3, 4, 5, 6, 7, 8, 9, 10, 20, 50, or more base pairs from) the target sequence. In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector protein and a guide RNA could each be operably linked to separate regulatory elements on separate vectors. Alternatively, two or more of the elements expressed from the same or different regulatory elements, may be combined in a single vector, with one or more additional vectors providing any components of the nucleic acid-targeting system not included in the first vector. Nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector protein and a guide RNA embedded within one or more intron sequences (e.g. each in a different intron, two or more in at least one intron, or all in a single intron). In some embodiments, the nucleic acid-targeting effector protein and guide RNA are operably linked to and expressed from the same promoter.

In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to target, e.g. have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides and is comprised within a target locus of interest. In some embodiments, a target sequence is located in the nucleus or cytoplasm of a cell.

In general, the term "guide sequence" is any polynucleotide sequence having sufficient complementarity with a target polynucleotide sequence to hybridize with the target sequence and direct sequence-specific binding of a nucleic acid-targeting complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, CA), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a nucleic acid-targeting complex to a target sequence may be assessed by any suitable assay (as described in EP3009511 or US2016208243). For example, the components of a nucleic acid-targeting system sufficient to form a nucleic acid-targeting complex, including the guide sequence to be tested, may be provided to a host cell having the corresponding target sequence, such as by transfection with vectors encoding the components of the nucleic acid-targeting CRISPR sequence, followed by an assessment of preferential cleavage within or in the vicinity of the target sequence, such as by Surveyor assay as described herein. Similarly, cleavage of a target polynucleotide sequence (or a sequence in the vicinity thereof) may be evaluated in a test tube by providing the target sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art.

A guide sequence may be selected to target any target sequence. In some embodiments, the target sequence is a sequence within a gene transcript or mRNA. In some embodiments, the target sequence is a sequence within a genome of a cell.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and P A Carr and G M Church, 2009, *Nature Biotechnology* 27(12): 1151-62). Further algorithms may be found in U.S. application Ser. No. 61/836,080, to which U.S. Patent Application Publication No. U.S. 2015/0356239 claims priority; incorporated herein by reference.

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence. For the Cpf1 orthologs identified to date, the direct repeat is located upstream 5' of the guide sequence.

In relation to a nucleic acid-targeting complex or system preferably, the crRNA sequence has one or more stem loops or hairpins and is 30 or more nucleotides in length, 40 or more nucleotides in length, or 50 or more nucleotides in length; In certain embodiments, the crRNA sequence is between 42 and 44 nucleotides in length, and the nucleic acid-targeting Cas protein is Cpf1 of *Francisella tularensis* subsp.novocida U112. In certain embodiments, the crRNA comprises, consists essentially of, or consists of 19 nucleotides of a direct repeat and between 23 and 25 nucleotides of spacer sequence, and the nucleic acid-targeting Cas protein is Cpf1 of *Francisella tularensis* subsp.novocida U112.

CRISPR Proteins
Overview

In one aspect, embodiments disclosed herein are directed to engineered CRISPR-Cas effector proteins that comprise at least one modification compared to an unmodified CRISPR-Cas effector protein that enhances binding of the of the CRISPR complex to the binding site and/or alters editing preference as compared to wild type. In certain example embodiments, the CRISPR-Cas effector protein is a Type V effector protein. In certain other example embodiments, the Type V effector protein is Cpf1. Example Cpf1 proteins suitable for use in the embodiments disclosed herein are discussed in further detail below.

In another aspect, embodiments disclosed herein are directed to viral vectors for delivery of CRISPR-Cas effector proteins, including Cpf1. In certain example embodiments, the vectors are designed so as to allow packaging of the CRISPR-Cas effector protein within a single vector. There is also an increased interest in the design of compact promoters for packing and thus expressing larger transgenes for targeted delivery and tissue-specificity. Thus, in another aspect certain embodiments disclosed herein are directed to delivery vectors, constructs, and methods of delivering larger genes for systemic delivery.

In another aspect, the present invention relates to methods for developing or designing CRISPR-Cas systems. In an aspect, the present invention relates to methods for developing or designing optimized CRISPR-Cas systems a wide range of applications including, but not limited to, therapeutic development, bioproduction, and plant and agricultural applications. In certain based therapy or therapeutics. The present invention in particular relates to methods for improving CRISPR-Cas systems, such as CRISPR-Cas system based therapy or therapeutics. Key characteristics of successful CRISPR-Cas systems, such as CRISPR-Cas system based therapy or therapeutics involve high specificity, high efficacy, and high safety. High specificity and high safety can be achieved among others by reduction of off-target effects. Improved specificity and efficacy likewise may be used to improve applications in plants and bioproduction.

Accordingly, in an aspect, the present invention relates to methods for increasing specificity of CRISPR-Cas systems, such as CRISPR-Cas system-based therapy or therapeutics. In a further aspect, the invention relates to methods for increasing efficacy of CRISPR-Cas systems, such as CRISPR-Cas system-based therapy or therapeutics. In a further aspect, the invention relates to methods for increasing safety of CRISPR-Cas systems, such as CRISPR-Cas system-based therapy or therapeutics. In a further aspect, the present invention relates to methods for increasing specificity, efficacy, and/or safety, preferably all, of CRISPR-Cas systems, such as CRISPR-Cas system-based therapy or therapeutics.

In certain embodiments, the CRISPR-Cas system comprises a CRISPR effector as defined herein elsewhere.

The methods of the present invention in particular involve optimization of selected parameters or variables associated with the CRISPR-Cas system and/or its functionality, as described herein further elsewhere. Optimization of the CRISPR-Cas system in the methods as described herein may depend on the target(s), such as the therapeutic target or therapeutic targets, the mode or type of CRISPR-Cas system modulation, such as CRISPR-Cas system based therapeutic target(s) modulation, modification, or manipulation, as well as the delivery of the CRISPR-Cas system components. One or more targets may be selected, depending on the genotypic and/or phenotypic outcome. For instance, one or more therapeutic targets may be selected, depending on (genetic) disease etiology or the desired therapeutic outcome. The (therapeutic) target(s) may be a single gene, locus, or other genomic site, or may be multiple genes, loci or other genomic sites. A single gene, locus, or other genomic site may be targeted more than once, such as by use of multiple gRNAs.

CRISPR-Cas system activity, such as CRISPR-Cas system design may involve target disruption, such as target mutation, such as leading to gene knockout. CRISPR-Cas system activity, such as CRISPR-Cas system design may involve replacement of particular target sites, such as leading to target correction. CISPR-Cas system design may involve removal of particular target sites, such as leading to target deletion. CRISPR-Cas system activity may involve modulation of target site functionality, such as target site activity or accessibility, leading for instance to (transcriptional and/or epigenetic) gene or genomic region activation or gene or genomic region silencing. The skilled person will understand that modulation of target site functionality may involve CRISPR effector mutation (such as for instance generation of a catalytically inactive CRISPR effector) and/or functionalization (such as for instance fusion of the CRISPR effector with a heterologous functional domain, such as a transcriptional activator or repressor), as described herein elsewhere.

Engineered CRISPR-Cas Systems

In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Halocarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

General Features of Cpf1 Effector Protein

The present invention encompasses the use of a Cpf1 effector protein, derived from a Cpf1 locus denoted as subtype V-A. Herein such effector proteins are also referred to as "Cpf1p", e.g., a Cpf1 protein (and such effector protein or Cpf1 protein or protein derived from a Cpf1 locus is also called "CRISPR enzyme"). Presently, the subtype V-A loci encompasses cas1, cas2, a distinct gene denoted cpf1 and a CRISPR array. Cpf1 (CRISPR-associated protein Cpf1, subtype PREFRAN) is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in all Cas9 proteins, and the RuvC-like domain is contiguous in the Cpf1 sequence, in contrast to Cas9 where it contains long inserts including the HNH domain. Accordingly, in particular embodiments, the CRISPR-Cas enzyme comprises only a RuvC-like nuclease domain.

Orthologs of Cpf1

The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. doi: 10.1002/pro.2225.). See also Shmakov et al. (2015) for application in the field of CRISPR-Cas loci. Homologous proteins may but need not be structurally related, or are only partially structurally related. Exemplary Cpf1 orthologs are listed in Table 1.

TABLE 1

Cpf1 Orthologs
Cpf1 orthologs

| Species | Sequence |
|---|---|
| *Franscisella tularensis* subsp. *novicida* U112 (FnCpf1) | gi\|489130501 WP_003040289.1 |
| *Lachnospiraceae* bacterium MC2017 (Lb3Cpf1) | gi\|1175286431 WP_081834226.1 |
| *Butyrivibrio proteoclasticus* (BpCpf1) | gi\|503048015 WP_013282991.1 |
| *Peregrinibacteria* bacterium GW2011_GWA_33_10 (PeCpf1) | gi\|818249855 KKP36646.1 |
| *Parcubacteria* bacterium GWC2011_GWC2_44_17 (PbCpf1) | gi\|818703647 KKT48220.1 |
| *Smithella* sp. SC_K08D17 (SsCpf1) | gi\|745626783 KIE18657.1 |
| *Acidaminococcus* sp. BV3L6 (AsCpf1) | gi\|545612232 WP_021736722.1 |
| *Lachnospiraceae* bacterium MA2020 (Lb2Cpf1) | gi\|769142322 WP_044919442.1 |
| *Candidatus Methanoplasma termitum* (CMtCpf1) | gi\|851218172 WP_048112740.1 |
| *Eubacterium eligens* (EeCpf1) | gi\|502240446 WP_012739647.1 |
| *Moraxella bovoculi* 237 (MbCpf1) | gi\|918722523 WP_052585281.1 |
| *Leptospira inadai* (LiCpf1) | gi\|537834683 WP_020988726.1 |
| *Lachnospiraceae* bacterium ND2006 (LbCpf1) | gi\|917059416 WP_051666128.1 |
| *Porphyromonas crevioricanis* (PcCpf1) | gi\|739008549 WP_036890108.1 |
| *Prevotella disiens* (PdCpf1) | gi\|915400855 WP_050786240.1 |

TABLE 1-continued

Cpf1 Orthologs
Cpf1 orthologs

| Species | Sequence |
|---|---|
| *Porphyromonas macacae* (PmCpf1) | gi\|517171043 WP_018359861.1 |
| *Thiomicrospira* sp. XS5 (TsCpf1) | gi\|1057283858 WP_068647445.1 |
| *Moraxella bovoculi* AAX08_00205 (Mb2Cpf1) | gi\|818916199 WP_046697655.1 |
| *Moraxella bovoculi* AAX11_00205 (Mb3Cpf1) | gi\|818853245 WP_046695838.1 |
| *Butyrivibrio* sp. NC3005 (BsCpf1) | gi\|737831580 WP_035798880.1 |
| *Prevotella brevis* ATCC 19188 | gi\|941888538\| WP_055225123.1 |
| *Eubacterium rectale* | gi\|941908238 WP_055237260.1 |
| *Eubacterium rectale* | gi\|942035338 WP_055272206.1 |
| *Eubacterium* sp. 41_20 | gi\|1125050969 OLA16049.1 |
| *Eubacterium rectale* | gi\|1469346808 WP_117685196.1 |
| *Eubacterium rectale* | gi\|1469351724 WP_117689699.1 |
| *Eubacterium rectale* | gi\|1469378426 WP_117689699.1 |
| *Eubacterium rectale* | gi\|1473947471 WP_118371518.1 |
| *Eubacterium rectale* | gi\|1473752862 WP_118190996.1 |
| *Eubacterium rectale* | gi\|1473543641 WP_117996653.1 |
| *Eubacterium rectale* | gi\|1473459431 WP_117918179.1 |
| *Bacteroidetes* bacterium GWF2_33_38 | OFY19591.1 |
| *Nitrospinae* bacterium | OGW03971.1 |
| *Planctomycetes* bacterium GWC2_39_26 | OHB41002.1 |
| *Bacteroidales* bacterium KA00251 | WP_066040075.1 |
| *Clostridium* sp. | SCH47915.1 |
| *Lachnospira pectinoschiza* | WP_055306762.1 |
| *Clostridium* sp. | SCH45297.1 |
| *Succiniclasticum ruminis* | WP_093729503.1 |
| *Coprococcus eutactus* | WP_082431329.1 |
| *Lachnospira pectinoschiza* | WP_082421630.1 |
| *Candidatus Ryanbacteria* bacterium RIFCSPHIGHO2_01_FULL_48_27 | OGZ45678.1 |
| *Candidatus Falkowbacteria* bacterium RBG_13_39_14 | OGF20863.1 |
| *Arcobacter butzleri* | WP_052943011.1 |
| *Treponema* endosymbiont of *Eucomonympha* sp. | WP_062376669.1 |
| *Bacteroidetes* oral taxon 274 str. F0058 | WP_009217842.1 |
| *Butyrivibrio fibrisolvens* | WP_027216152.1 |
| *Lachnospiraceae* bacterium COE1 | WP_016301126.1 |
| *Flavobacterium branchiophilum* FL-15 | WP_014085038.1 |
| *Flavobacterium* sp. 316 | WP_045971446.1 |
| Candidate division WS6 bacterium GW2011_GWA2_37_6 US52_C0007 | KKQ36153.1 |
| *Helcococcus kunzii* ATCC 51366 | WP_005398606.1 |
| *Lachnospiraceae* bacterium NC2008 | WP_027109509.1 |
| *Lachnospiraceae* bacterium MC2017 | WP_044910713.1 |
| *Candidatus Methanomethylophilus alvus* Mx1201 | WP_015504779.1 |
| *Moraxella caprae* DSM 19149 | WP_036388671.1 |
| *Oribacterium* sp. NK2B42 | WP_049895985.1 |
| *Parcubacteria* bacterium GW2011 | KKT50231.1 |
| *Prevotella bryantii* B14 | WP_006283774.1 |
| *Prevotella albensis* | WP_024988992.1 |
| *Pseudobutyrivibrio ruminis* | WP_028248456.1 |
| *Proteocatella sphenisci* | WP_084502895.1 |
| *Anaerovibrio* sp. RM50 | WP_027407524.1 |
| *Succinivibrio dextrinosolvens* H5 | WP_031492824.1 |
| *Synergistes jonesii* strain 78-1 | WP_081839471.1 |
| *Smithella* sp. SCADC | KFO67989.1 |
| Uncultured bacterium (gcode 4) ACD_3C00058 | EKE28449.1 |
| *Microgenomates* (*Roizmanbacteria*) bacterium GW2011_GWA2_37_7 | KKQ38174.1 |
| *Eubacterium* sp. CAG:76 | CDF09621.1 |
| *Parcubacteria* bacterium GW2011_GWA2_41_14 | KKR91555.1 |

TABLE 1-continued

Cpf1 Orthologs
Cpf1 orthologs

| Species | Sequence |
|---|---|
| *Francisella tularensis* subsp. *novicida* F6168 | WP_003034647.1 |
| *Francisella novicida* | WP_004339290.1 |
| *Francisella* cf. *novicida* Fx1 | WP_014550095.1 |
| *Moraxella lacunata* | WP_065256572.1 |
| *Pseudobutyrivibrio xylanivorans* | SCZ76797.1 |
| *Sneathia amnii* | AKC95493.1 |
| *Candidatus Campbellbacteria* bacterium | OGD68774.1 |
| *Candidatus Wildermuthbacteria* bacterium | OHA63117.1 |
| *Treponema porcinum* | WP_078933213.1 |
| *Eubacterium coprostanoligenes* | WP_078767700.1 |
| *Butyrivibrio hungatei* | WP_071177645.1 |
| *Coprococcus eutactus* | WP_082431329.1 |
| *Candidatus Gracilibacteria* bacterium CG1_02_38_174 | OIO75780.1 |
| *Eubacterium* sp. 41_20 | OLA16049.1 |
| *Bacteroides galacturonicus* | WP_116443914.1 |
| *Eubacterium* sp. CAG76_36_125 | |

The Cpf1 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this putative novel CRISPR-Cas system appears to be similar to that of type II-B. Furthermore, similar to Cas9, the Cpf1 protein contains a readily identifiable C-terminal region that is homologous to the transposon ORF-B and includes an active RuvC-like nuclease, an arginine-rich region, and a Zn finger (absent in Cas9). However, unlike Cas9, Cpf1 is also present in several genomes without a CRISPR-Cas context and its relatively high similarity with ORF-B suggests that it might be a transposon component. It was suggested that if this was a genuine CRISPR-Cas system and Cpf1 is a functional analog of Cas9 it would be a novel CRISPR-Cas type, namely type V (See Annotation and Classification of CRISPR-Cas Systems. Makarova K S, Koonin E V. Methods Mol Biol. 2015; 1311:47-75). However, as described herein, Cpf1 is denoted to be in subtype V-A to distinguish it from C2clp which does not have an identical domain structure and is hence denoted to be in subtype V-B.

In particular embodiments, the effector protein is a Cpf1 effector protein from an organism from a genus comprising Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opituticaceae, Tuberibacillus, Bacillus, Brevibacillus, Methylobacterium or Acidaminococcus.

In further particular embodiments, the Cpf1 effector protein is from an organism selected from S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii.

The effector protein may comprise a chimeric effector protein comprising a first fragment from a first effector protein (e.g., a Cpf1) ortholog and a second fragment from a second effector (e.g., a Cpf1) protein ortholog, and wherein the first and second effector protein orthologs are different.

At least one of the first and second effector protein (e.g., a Cpf1) orthologs may comprise an effector protein (e.g., a Cpf1) from an organism comprising Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium or Acidaminococcus; e.g., a chimeric effector protein comprising a first fragment and a second fragment wherein each of the first and second fragments is selected from a Cpf1 of an organism comprising Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Clostridiaridium, Leptotrichia, Francisella, Legionella, Alicyclobacillus, Methanomethyophilus, Porphyromonas, Prevotella, Bacteroidetes, Helcococcus, Letospira, Desulfovibrio, Desulfonatronum, Opitutaceae, Tuberibacillus, Bacillus, Brevibacilus, Methylobacterium or Acidaminococcus wherein the first and second fragments are not from the same bacteria; for instance a chimeric effector protein comprising a first fragment and a second fragment wherein each of the first and second fragments is selected from a Cpf1 of S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis 1, Prevotella albensis, Lachnospiraceae bacterium MC2017 1, Butyrivibrio proteoclasticus, Peregrinibacteria bacterium GW2011_GWA2_33_10, Parcubacteria bacterium GW2011_GWC2_44_17, Smithella sp. SCADC, Acidaminococcus sp. BV3L6, Lachnospiraceae bacterium MA2020, Candidatus Methanoplasma termitum, Eubacterium eligens, Moraxella bovoculi 237, Leptospira inadai, Lachnospiraceae bacterium ND2006, Porphyromonas crevioricanis 3, Prevotella disiens and Porphyromonas macacae, wherein the first and second fragments are not from the same bacteria.

In a more preferred embodiment, the Cpf1p is derived from a bacterial species selected from Francisella tularensis 1, Prevotella albensis, Lachnospiraceae bacterium MC2017 1, Butyrivibrio proteoclasticus, Peregrinibacteria bacterium GW2011_GWA2_33_10, Parcubacteria bacterium GW2011_GWC2_44_17, Smithella sp. SCADC, Acidaminococcus sp. BV3L6, Lachnospiraceae bacterium MA2020, Candidatus Methanoplasma termitum, Eubacterium eligens, Moraxella bovoculi 237, Leptospira inadai, Lachnospiraceae bacterium ND2006, Porphyromonas crevioricanis 3, Prevotella disiens and Porphyromonas macacae. In certain embodiments, the Cpf1p is derived from a bacterial species selected from Acidaminococcus sp. BV3L6, Lachnospiraceae bacterium MA2020. In certain embodiments, the effector protein is derived from a subspecies of Francisella tularensis 1, including but not limited to Francisella tularensis subsp. Novicida.

In particular embodiments, the homologue or orthologue of Cpf1 as referred to herein has a sequence homology or identity of at least 80%, more preferably at least 85%, even more preferably at least 90%, such as for instance at least 95% with Cpf1. In further embodiments, the homologue or orthologue of Cpf1 as referred to herein has a sequence identity of at least 80%, more preferably at least 85%, even more preferably at least 90%, such as for instance at least 95% with the wild type Cpf1. Where the Cpf1 has one or more mutations (mutated), the homologue or orthologue of said Cpf1 as referred to herein has a sequence identity of at least 80%, more preferably at least 85%, even more preferably at least 90%, such as for instance at least 95% with the mutated Cpf1.

In an embodiment, the Cpf1 protein may be an ortholog of an organism of a genus which includes, but is not limited to, Acidaminococcus sp, Lachnospiraceae bacterium or Moraxella bovoculi; in particular embodiments, the type V Cas protein may be an ortholog of an organism of a species which includes, but is not limited to, Acidaminococcus sp. BV3L6; Lachnospiraceae bacterium ND2006 (LbCpf1) or Moraxella bovoculi 237. In particular embodiments, the homologue or orthologue of Cpf1 as referred to herein has a sequence homology or identity of at least 80%, more preferably at least 85%, even more preferably at least 90%, such as for instance at least 95% with one or more of the Cpf1 sequences disclosed herein. In further embodiments, the homologue or orthologue of Cpf as referred to herein has a sequence identity of at least 80%, more preferably at least 85%, even more preferably at least 90%, such as for instance at least 95% with the wild type FnCpf1, AsCpf1 or LbCpf1.

In particular embodiments, the Cpf1 protein of the invention has a sequence homology or identity of at least 60%, more particularly at least 70, such as at least 80%, more preferably at least 85%, even more preferably at least 90%, such as for instance at least 95% with FnCpf1, AsCpf1 or LbCpf1. In further embodiments, the Cpf1 protein as referred to herein has a sequence identity of at least 60%, such as at least 70%, more particularly at least 80%, more preferably at least 85%, even more preferably at least 90%, such as for instance at least 95% with the wild type AsCpf1 or LbCpf1. In particular embodiments, the Cpf1 protein of the present invention has less than 60% sequence identity with FnCpf1. The skilled person will understand that this includes truncated forms of the Cpf1 protein whereby the sequence identity is determined over the length of the truncated form.

In an embodiment of the invention, the effector protein comprises at least one HEPN domain, including but not limited to HEPN domains described herein, HEPN domains known in the art, and domains recognized to be HEPN domains by comparison to consensus sequences and motifs.

Determination of PAM

Determination of PAM can be ensured as follows This experiment closely parallels similar work in E. coli for the heterologous expression of StCas9 (Sapranauskas, R. et al. Nucleic Acids Res 39, 9275-9282 (2011)). Applicants introduce a plasmid containing both a PAM and a resistance gene into the heterologous E. coli, and then plate on the corresponding antibiotic. If there is DNA cleavage of the plasmid, Applicants observe no viable colonies.

In further detail, the assay is as follows for a DNA target. Two E. coli strains are used in this assay. One carries a plasmid that encodes the endogenous effector protein locus from the bacterial strain. The other strain carries an empty plasmid (e.g. pACYC184, control strain). All possible 7 or 8 bp PAM sequences are presented on an antibiotic resistance plasmid (pUC19 with ampicillin resistance gene). The PAM is located next to the sequence of proto-spacer 1 (the DNA target to the first spacer in the endogenous effector protein locus). Two PAM libraries were cloned. One has an 8 random bp 5' of the proto-spacer (e.g., total of 65536 different PAM sequences=complexity). The other library has 7 random bp 3' of the proto-spacer (e.g. total complexity is 16384 different PAMs). Both libraries were cloned to have in average 500 plasmids per possible PAM. Test strain and control strain were transformed with 5'PAM and 3'PAM library in separate transformations and transformed cells were plated separately on ampicillin plates. Recognition and subsequent cutting/interference with the plasmid renders a cell vulnerable to ampicillin and prevents growth. Approximately 12 h after transformation, all colonies formed by the test and control strains where harvested and plasmid DNA was isolated. Plasmid DNA was used as template for PCR amplification and subsequent deep sequencing. Representation of all PAMs in the untransformed libraries showed the expected representation of PAMs in transformed cells. Representation of all PAMs found in control strains showed the actual representation. Representation of all PAMs in test strain showed which PAMs are not recognized by the enzyme and comparison to the control strain allows extracting the sequence of the depleted PAM.

For the Cpf1 orthologues identified to date, the following PAMs have been identified: the *Acidaminococcus* sp. BV3L6 Cpf1 (AsCpf1) and Lachnospiraceae bacterium ND2006 Cpf1 (LbCpf1) can cleave target sites preceded by a TTTV PAM, FnCpf1p, can cleave sites preceded by TTN, where N is A/C/G or T.

Codon Optimized Nucleic Acid Sequences

Where the effector protein is to be administered as a nucleic acid, the application envisages the use of codon-optimized Cpf1 sequences. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667) as an example of a codon optimized sequence (from knowledge in the art and this disclosure, codon optimizing coding nucleic acid molecule(s), especially as to effector protein (e.g., Cpf1) is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA/RNA-targeting Cas protein is codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at http://www.yeastgenome.org/community/codon_usage.shtml, or Codon selection in yeast, Bennetzen and Hall, J Biol Chem. 1982 Mar. 25; 257(6):3026-31. As to codon usage in plants including algae, reference is made to Codon usage in higher plants, green algae, and cyanobacteria, Campbell and Gowri, Plant Physiol. 1990 January; 92(1): 1-11.; as well as Codon usage in plant genes, Murray et al, Nucleic Acids Res. 1989 Jan. 25; 17(2):477-98; or Selection on the codon bias of chloroplast and cyanelle genes in different plant and algal lineages, Morton B R, J Mol Evol. 1998 April; 46(4):449-59. Exemplary amino acid sequences of human codon optimized Cpf1 orthologs are shown in FIG. 13. The sequences also include at their C termini nuclear localization signals (NLS) (italics), a glycine-serine (GS) linker, and a 3×HA tag.

Modified Cpf1 Polypeptides

In particular embodiments, it is of interest to make an engineered Cpf1 protein as defined herein, such as Cpf1, wherein the protein complexes with a nucleic acid molecule comprising RNA to form a CRISPR complex, wherein when in the CRISPR complex, the nucleic acid molecule targets one or more target polynucleotide loci, the protein comprises at least one modification compared to unmodified Cpf1 protein, and wherein the CRISPR complex comprising the modified protein has altered activity as compared to the complex comprising the unmodified Cpf1 protein. It is to be understood that when referring herein to CRISPR "protein", the Cpf1 protein preferably is a modified CRISPR enzyme (e.g. having increased or decreased (or no) enzymatic activity, such as without limitation including Cpf1. The term "CRISPR protein" may be used interchangeably with "CRISPR enzyme", irrespective of whether the CRISPR protein has altered, such as increased or decreased (or no) enzymatic activity, compared to the wild type CRISPR protein.

Computational analysis of the primary structure of Cpf1 nucleases reveals three distinct regions. First, a C-terminal RuvC like domain, which is the only functional characterized domain. Second, a N-terminal alpha-helical region and third a mixed alpha and beta region, located between the RuvC like domain and the alpha-helical region.

Several small stretches of unstructured regions are predicted within the Cpf1 primary structure. Unstructured regions, which are exposed to the solvent and not conserved within different Cpf1 orthologs, are preferred sides for splits and insertions of small protein sequences. In addition, these sides can be used to generate chimeric proteins between Cpf1 orthologs.

In certain example embodiments, a modified Cpf1 protein comprises at least one modification that alters editing preference as compared to wild type. In certain example embodiments, the editing preference is for a specific insert or deletion within the target region. In certain example embodiments, the at least one modification increases formation of one or more specific indels. In certain example embodiments, the at least one modification is in a C-terminal RuvC like domain, the N-terminal alpha-helical region, the mixed alpha and beta region, or a combination thereof. In certain example embodiments, the altered editing preference is indel formation. In certain example embodiments, the at least one modification increases formation of one or more specific insertions.

In certain example embodiments, the at least one modification increases formation of one or more specific insertions. In certain example embodiments, the at least one modification results in an insertion of an A adjacent to an A, T, G, or C in the target region. In another example embodiment, the at least one modification results in insertion of a T adjacent to an A, T, G, or C in the target region. In another example embodiment, the at least one modification results in insertion of a G adjacent to an A, T, G, or C in the target region. In another example embodiment, the at least one modification results in insertion of a C adjacent to an A, T, C, or G in the target region. The insertion may be 5' or 3' to the adjacent nucleotide. In one example embodiment, the one or more modification direct insertion of a T adjacent to an existing T. In certain example embodiments, the existing T corresponds to the 4th position in the binding region of a guide sequence. In certain example embodiments, the one or more modifications result in an enzyme which ensures more precise one-base insertions or deletions, such as those described above. More particularly, the one or more modifications may reduce the formations of other types of indels by the enzyme. The ability to generate one-base insertions or deletions can be of interest in a number of applications, such as correction of genetic mutants in diseases caused by small deletions, more particularly where HDR is not possible. For example, correction of the F508del mutation in CFTR via delivery of three sRNA directing insertion of three T's, which is the most common genotype of cystic fibrosis, or correction of Alia Jafar's single nucleotide deletion in CDKL5 in the brain. As the editing method only requires NHEJ, the editing would be possible in post-mitotic cells such as the brain. The ability to generate one base pair insertions/deletions may also be useful in genome-wide CRISPR-Cas negative selection screens. In certain example embodiments, the at least one modification, is a mutation. In certain other example embodiment, the one or more modification may be combined with one or more additional modifications or mutations described below including modifications to increase binding specificity and/or decrease off-target effects.

In certain example embodiments, the engineered CRISPR-Cas effector comprising at least one modification that alters editing preference as compared to wild type may further comprise one or more additional modifications that alters the binding property as to the nucleic acid molecule comprising RNA or the target polypeptide loci, altering binding kinetics as to the nucleic acid molecule or target molecule or target polynucleotide or alters binding specificity as to the nucleic acid molecule. Example of such modifications are summarized in the following paragraph. Based on the above information, mutants can be generated which lead to inactivation of the enzyme or which modify the double strand nuclease to nickase activity. In alternative embodiments, this information is used to develop enzymes with reduced off-target effects (described elsewhere herein).

In certain of the above-described Cpf1 enzymes, the enzyme is modified by mutation of one or more residues including but not limited to positions D917, E1006, E1028, D1227, D1255A, N1257, according to FnCpf1 protein or any corresponding ortholog. In an aspect, the invention provides a herein-discussed composition wherein the Cpf1 enzyme is an inactivated enzyme which comprises one or more mutations selected from the group consisting of D917A, E1006A, E1028A, D1227A, D1255A, N1257A, D917A, E1006A, E1028A, D1227A, D1255A and N1257A according to FnCpf1 protein or corresponding positions in a Cpf1 ortholog. In an aspect, the invention provides a herein-discussed composition, wherein the CRISPR enzyme comprises D917, or E1006 and D917, or D917 and D1255, according to FnCpf1 protein or a corresponding position in a Cpf1 ortholog.

In certain of the above-described Cpf1 enzymes, the enzyme is modified by mutation of one or more residues (in the RuvC domain) including but not limited to positions R909, R912, R930, R947, K949, R951, R955, K965, K968, K1000, K1002, R1003, K1009, K1017, K1022, K1029, K1035, K1054, K1072, K1086, R1094, K1095, K1109, K1118, K1142, K1150, K1158, K1159, R1220, R1226, R1242, and/or R1252 with reference to amino acid position numbering of AsCpf1 (*Acidaminococcus* sp. BV3L6).

In certain of the above-described non-naturally-occurring CRISPR enzymes, the enzyme is modified by mutation of one or more residues (in the RAD50) domain including but not limited positions K324, K335, K337, R331, K369, K370, R386, R392, R393, K400, K404, K406, K408, K414, K429, K436, K438, K459, K460, K464, R670, K675, R681, K686, K689, R699, K705, R725, K729, K739, K748, and/or K752 with reference to amino acid position numbering of AsCpf1 (*Acidaminococcus* sp. BV3L6).

In certain of the Cpf1 enzymes, the enzyme is modified by mutation of one or more residues including but not limited positions R912, T923, R947, K949, R951, R955, K965, K968, K1000, R1003, K1009, K1017, K1022, K1029, K1072, K1086, F1103, R1226, and/or R1252 with reference to amino acid position numbering of AsCpf1 (*Acidaminococcus* sp. BV3L6).

In certain embodiments, the Cpf1 enzyme is modified by mutation of one or more residues including but not limited positions R833, R836, K847, K879, K881, R883, R887, K897, K900, K932, R935, K940, K948, K953, K960, K984, K1003, K1017, R1033, R1138, R1165, and/or R1252 with reference to amino acid position numbering of LbCpf1 (Lachnospiraceae bacterium ND2006).

In certain embodiments, the Cpf1 enzyme is modified by mutation of one or more residues including but not limited positions K15, R18, K26, Q34, R43, K48, K51, R56, R84, K85, K87, N93, R103, N104, T118, K123, K134, R176, K177, R192, K200, K226, K273, K275, T291, R301, K307, K369, S404, V409, K414, K436, K438, K468, D482, K516, R518, K524, K530, K532, K548, K559, K570, R574, K592, D596, K603, K607, K613, C647, R681, K686, H720, K739, K748, K757, K766, K780, R790, P791, K796, K809, K815, T816, K860, R862, R863, K868, K897, R909, R912, T923, R947, K949, R951, R955, K965, K968, K1000, R1003, K1009, K1017, K1022, K1029, A1053, K1072, K1086, F1103, S1209, R1226, R1252, K1273, K1282, and/or K1288 with reference to amino acid position numbering of AsCpf1 (*Acidaminococcus* sp. BV3L6).

In certain embodiments, the enzyme is modified by mutation of one or more residues including but not limited positions K15, R18, K26, R34, R43, K48, K51, K56, K87, K88, D90, K96, K106, K107, K120, Q125, K143, R186, K187, R202, K210, K235, K296, K298, K314, K320, K326, K397, K444, K449, E454, A483, E491, K527, K541, K581, R583, K589, K595, K597, K613, K624, K635, K639, K656, K660, K667, K671, K677, K719, K725, K730, K763, K782, K791, R800, K809, K823, R833, K834, K839, K852, K858, K859, K869, K871, R872, K877, K905, R918, R921, K932, I960, K962, R964, R968, K978, K981, K1013, R1016, K1021, K1029, K1034, K1041, K1065, K1084, and/or K1098 with reference to amino acid position numbering of FnCpf1 (*Francisella novicida* U112).

In certain embodiments, the enzyme is modified by mutation of one or more residues including but not limited positions K15, R18, K26, K34, R43, K48, K51, R56, K83, K84, R86, K92, R102, K103, K116, K121, R158, E159, R174, R182, K206, K251, K253, K269, K271, K278, P342, K380, R385, K390, K415, K421, K457, K471, A506, R508, K514, K520, K522, K538, Y548, K560, K564, K580, K584, K591, K595, K601, K634, K640, R645, K679, K689, K707, T716, K725, R737, R747, R748, K753, K768, K774, K775, K785, K787, R788, Q793, K821, R833, R836, K847, K879, K881, R883, R887, K897, K900, K932, R935, K940, K948, K953, K960, K984, K1003, K1017, R1033, K1121, R1138, R1165, K1190, K1199, and/or K1208 with reference to amino acid position numbering of LbCpf1 (Lachnospiraceae bacterium ND2006).

In certain embodiments, the enzyme is modified by mutation of one or more residues including but not limited positions K14, R17, R25, K33, M42, Q47, K50, D55, K85, N86, K88, K94, R104, K105, K118, K123, K131, R174, K175, R190, R198, I221, K267, Q269, K285, K291, K297, K357, K403, K409, K414, K448, K460, K501, K515, K550, R552, K558, K564, K566, K582, K593, K604, K608, K623, K627, K633, K637, E643, K780, Y787, K792, K830, Q846, K858, K867, K876, K890, R900, K901, M906, K921, K927, K928, K937, K939, R940, K945, Q975, R987, R990, K1001, R1034, I1036, R1038, R1042, K1052, K1055, K1087, R1090, K1095, N1103, K1108, K1115, K1139, K1158, R1172, K1188, K1276, R1293, A1319, K1340, K1349, and/or K1356 with reference to amino acid position numbering of MbCpf1 (*Moraxella bovoculi* 237).

Thus, exemplary inactivating mutations for *Francisella tularensis* subsp. *novicida* U112: are D917A, E1006A; exemplary inactivating mutations for *Acidaminococcus* sp. BV3L6 are D908A, E933A; exemplary inactivating mutations for Lachnospiraceae bacterium MA2020 are D815A, E906A; exemplary inactivating mutations for *Candidatus Methanoplasma* termituma are D859A, E944A; exemplary inactivating mutations for *Moraxella bovoculi* 237 are D986A, E1080A; exemplary inactivating mutations for Lachnospiraceae bacterium ND2006 are D832A, E925A; exemplary inactivating mutations for *Porphyromonas crevioricanis* are D878A, E963A; exemplary inactivating mutations for *Prevotella disiens* are D943A, E1032A.

Recently, a method was described for the generation of Cas9 orthologs with enhanced specificity (Slaymaker et al. 2015). This strategy can be used to enhance the specificity of Cpf1 orthologs. The following modifications are presently considered to provide enhanced Cpf1 specificity.

TABLE 2

Conserved Lysine and Arginine residues within RuvC

| AsCpf1 | LbCpf1 |
|---|---|
| R912 | R833 |
| T923 | R836 |
| R947 | K847 |
| K949 | K879 |
| R951 | K881 |
| R955 | R883 |
| K965 | R887 |
| K968 | K897 |
| K1000 | K900 |
| R1003 | K932 |
| K1009 | R935 |
| K1017 | K940 |
| K1022 | K948 |
| K1029 | K953 |
| K1072 | K960 |
| K1086 | K984 |
| F1103 | K1003 |
| R1226 | K1017 |
| R1252 | R1033 |
|  | R1138 |
|  | R1165 |

Additional candidates are positive charged residues that are conserved between different orthologs (Table 3).

TABLE 3

Conserved Lysine and Arginine residues

| Residue | AsCpf1 | FnCpf1 | LbCpf1 | MbCpf1 |
|---|---|---|---|---|
| Lys | K15 | K15 | K15 | K14 |
| Arg | R18 | R18 | R18 | R17 |
| Lys/Arg | K26 | K26 | K26 | R25 |
| Lys/Arg | Q34 | R34 | K34 | K33 |
| Arg | R43 | R43 | R43 | M42 |
| Lys | K48 | K48 | K48 | Q47 |
| Lys | K51 | K51 | K51 | K50 |
| Lys/Arg | R56 | K56 | R56 | D55 |
| Lys/Arg | K84 | K87 | K83 | K85 |
| Lys/Arg | K85 | K88 | K84 | N86 |
| Lys/Arg | K87 | D90 | R86 | K88 |
| Arg | N93 | K96 | K92 | K94 |
| Lys/Arg | R103 | K106 | R102 | R104 |
| Lys | N104 | K107 | K103 | K105 |
| Lys | T118 | K120 | K116 | K118 |
| Lys/Arg | K123 | Q125 | K121 | K123 |
| Lys | K134 | K143 | — | K131 |
| Arg | R176 | R186 | R158 | R174 |
| Lys | K177 | K187 | E159 | K175 |
| Arg | R192 | R202 | R174 | R190 |
| Lys/Arg | K200 | K210 | R182 | R198 |
| Lys | K226 | K235 | K206 | I221 |
| Lys | K273 | K296 | K251 | K267 |
| Lys | K275 | K298 | K253 | Q269 |
| Lys | T291 | K314 | K269 | K285 |
| Lys/Arg | R301 | K320 | K271 | K291 |
| Lys | K307 | K326 | K278 | K297 |
| Lys | K369 | K397 | P342 | K357 |
| Lys | S404 | K444 | K380 | K403 |
| Lys/Arg | V409 | K449 | R385 | K409 |
| Lys | K414 | E454 | K390 | K414 |
| Lys | K436 | A483 | K415 | K448 |
| Lys | K438 | E491 | K421 | K460 |
| Lys | K468 | K527 | K457 | K501 |
| Lys | D482 | K541 | K471 | K515 |
| Lys | K516 | K581 | A506 | K550 |
| Arg | R518 | R583 | R508 | R552 |
| Lys | K524 | K589 | K514 | K558 |
| Lys | K530 | K595 | K520 | K564 |
| Lys | K532 | K597 | K522 | K566 |
| Lys | K548 | K613 | K538 | K582 |
| Lys | K559 | K624 | Y548 | K593 |
| Lys | K570 | K635 | K560 | K604 |

TABLE 3-continued

Conserved Lysine and Arginine residues

| Residue | AsCpf1 | FnCpf1 | LbCpf1 | MbCpf1 |
|---|---|---|---|---|
| Lys/Arg | R574 | K639 | K564 | K608 |
| Lys | K592 | K656 | K580 | K623 |
| Lys | D596 | K660 | K584 | K627 |
| Lys | K603 | K667 | K591 | K633 |
| Lys | K607 | K671 | K595 | K637 |
| Lys | K613 | K677 | K601 | E643 |
| Lys | C647 | K719 | K634 | K780 |
| Lys/Arg | R681 | K725 | K640 | Y787 |
| Lys/Arg | K686 | K730 | R645 | K792 |
| Lys | H720 | K763 | K679 | K830 |
| Lys | K739 | K782 | K689 | Q846 |
| Lys | K748 | K791 | K707 | K858 |
| Lys/Arg | K757 | R800 | T716 | K867 |
| Lys/Arg | T766 | K809 | K725 | K876 |
| Lys/Arg | K780 | K823 | K737 | K890 |
| Arg | R790 | R833 | R747 | R900 |
| Lys/Arg | P791 | K834 | R748 | K901 |
| Lys | K796 | K839 | K753 | M906 |
| Lys | K809 | K852 | K768 | K921 |
| Lys | K815 | K858 | K774 | K927 |
| Lys | T816 | K859 | K775 | K928 |
| Lys | K860 | K869 | K785 | K937 |
| Lys/Arg | R862 | K871 | K787 | K939 |
| Arg | R863 | R872 | R788 | R940 |
| Lys | K868 | K877 | Q793 | K945 |
| Lys | K897 | K905 | K821 | Q975 |
| Arg | R909 | R918 | R833 | R987 |
| Arg | R912 | R921 | R836 | R990 |
| Lys | T923 | K932 | K847 | K1001 |
| Lys/Arg | R947 | I960 | K879 | R1034 |
| Lys | K949 | K962 | K881 | I1036 |
| Arg | R951 | R964 | R883 | R1038 |
| Arg | R955 | R968 | R887 | R1042 |
| Lys | K965 | K978 | K897 | K1052 |
| Lys | K968 | K981 | K900 | K1055 |
| Lys | K1000 | K1013 | K932 | K1087 |
| Arg | R1003 | R1016 | R935 | R1090 |
| Lys | K1009 | K1021 | K940 | K1095 |
| Lys | K1017 | K1029 | K948 | N1103 |
| Lys | K1022 | K1034 | K953 | K1108 |
| Lys | K1029 | K1041 | K960 | K1115 |
| Lys | A1053 | K1065 | K984 | K1139 |
| Lys | K1072 | K1084 | K1003 | K1158 |
| Lys/Arg | K1086 | K1098 | K1017 | R1172 |
| Lys/Arg | F1103 | K1114 | R1033 | K1188 |
| Lys | S1209 | K1201 | K1121 | K1276 |
| Arg | R1226 | R1218 | R1138 | R1293 |
| Arg | R1252 | R1244 | R1165 | A1319 |
| Lys | K1273 | K1265 | K1190 | K1340 |
| Lys | K1282 | K1274 | K1199 | K1349 |
| Lys | K1288 | K1281 | K1208 | K1356 |

Table 3 provides the positions of conserved Lysine and Arginine residues in an alignment of Cpf1 nuclease from *Francisella novicida* U112 (FnCpf1), *Acidaminococcus* sp. BV3L6 (AsCpf1), Lachnospiraceae bacterium ND2006 (LbCpf1) and *Moraxella bovoculi* 237 (MbCpf1). These can be used to generate Cpf1 mutants with enhanced specificity.

With a similar strategy used to improve Cas9 specificity, specificity of Cpf1 can be improved by mutating residues that stabilize the non-targeted DNA strand. This may be accomplished without a crystal structure by using linear structure alignments to predict 1) which domain of Cpf1 binds to which strand of DNA and 2) which residues within these domains contact DNA.

However, this approach may be limited due to poor conservation of Cpf1 with known proteins. Thus, it may be desirable to probe the function of all likely DNA interacting amino acids (lysine, histidine and arginine).

Positively charged residues in the RuvC domain are more conserved throughout Cpf1s than those in the Rad50 domain indicating that RuvC residues are less evolutionarily flexible. This suggests that rigid control of nucleic acid binding is needed in this domain (relative to the Rad50 domain). Therefore, it is possible this domain cuts the targeted DNA strand because of the requirement for RNA:DNA duplex stabilization (precedent in Cas9). Furthermore, more arginines are present in the RuvC domain (5% of RuvC residues 904 to 1307 vs 3.8% in the proposed Rad50 domains) suggesting again that RuvC targets the DNA strand complexed with the guide RNA. Arginines are more involved in binding nucleic acid major and minor grooves (Rohs et al. Nature (2009): Vol 461: 1248-1254). Major/minor grooves would only be present in a duplex (such as DNA:RNA targeting duplex), further suggesting that RuvC cuts the "targeted strand".

From these specific observations about AsCpf1 we can identify similar residues in Cpf1 from other species by sequence alignments.

Crystal structures of two similar domains as those found in Cpf1 (RuvC holiday junction resolvase and Rad50 DNA repair protein) have been described. Based on these structures, it can be deduced what the relevant domains look like in Cpf1, and infer which regions and residues may contact DNA. In each structure residues are highlighted that contact DNA. The list of residues in Table 4 are those found in the two binding domains.

TABLE 4 list of probable DNA interacting residues

| RuvC domain probable DNA interacting residues: AsCpf1 | Rad50 domain probable DNA interacting residues: AsCpf1 |
|---|---|
| R909 | K324 |
| R912 | K335 |
| R930 | K337 |
| R947 | R331 |
| K949 | K369 |
| R951 | K370 |
| R955 | R386 |
| K965 | R392 |
| K968 | R393 |
| K1000 | K400 |
| K1002 | K404 |
| R1003 | K406 |
| K1009 | K408 |
| K1017 | K414 |
| K1022 | K429 |
| K1029 | K436 |
| K1035 | K438 |
| K1054 | K459 |
| K1072 | K460 |
| K1086 | K464 |
| R1094 | R670 |
| K1095 | K675 |
| K1109 | R681 |
| K1118 | K686 |
| K1142 | K689 |
| K1150 | R699 |
| K1158 | K705 |
| K1159 | R725 |
| R1220 | K729 |
| R1226 | K739 |
| R1242 | K748 |
| R1252 | K752 |
|  | R670 |

Deactivated/Inactivated Cpf1 Protein

Where the Cpf1 protein has nuclease activity, the Cpf1 protein may be modified to have diminished nuclease activity e.g., nuclease inactivation of at least 70%, at least 80%, at least 90%, at least 95%, at least 97%, or 100% as compared with the wild type enzyme; or to put in another way, a Cpf1 enzyme having advantageously about 0% of the nuclease activity of the non-mutated or wild type Cpf1 enzyme or CRISPR enzyme, or no more than about 3% or about 5% or about 10% of the nuclease activity of the non-mutated or wild type Cpf1 enzyme, e.g. of the non-mutated or wild type *Francisella novicida* U112 (FnCpf1), *Acidaminococcus* sp. BV3L6 (AsCpf1), Lachnospiraceae bacterium ND2006 (LbCpf1) or *Moraxella bovoculi* 237 (MbCpf1 Cpf1 enzyme or CRISPR enzyme. This is possible by introducing mutations into the nuclease domains of the Cpf1 and orthologs thereof.

In certain embodiments, the CRISPR enzyme is engineered and can comprise one or more mutations that reduce or eliminate a nuclease activity. The amino acid positions in the FnCpf1p RuvC domain include but are not limited to D917A, E1006A, E1028A, D1227A, D1255A, N1257A, D917A, E1006A, E1028A, D1227A, D1255A and N1257A. Applicants have also identified a putative second nuclease domain which is most similar to PD-(D/E)XK (SEQ ID NO: 128) nuclease superfamily and HincII endonuclease like. The point mutations to be generated in this putative nuclease domain to substantially reduce nuclease activity include, but are not limited to, N580A, N584A, T587A, W609A, D610A, K613A, E614A, D616A, K624A, D625A, K627A and Y629A. In a preferred embodiment, the mutation in the FnCpf1p RuvC domain is D917A or E1006A, wherein the D917A or E1006A mutation completely inactivates the DNA cleavage activity of the FnCpf1 effector protein. In another embodiment, the mutation in the FnCpf1p RuvC domain is D1255A, wherein the mutated FnCpf1 effector protein has significantly reduced nucleolytic activity.

More particularly, the inactivated Cpf1 enzymes include enzymes mutated in amino acid positions As908, As993, As1263 of AsCpf1 or corresponding positions in Cpf1 orthologs. Additionally, the inactivated Cpf1 enzymes include enzymes mutated in amino acid position Lb832, 925, 947 or 1180 of LbCpf1 or corresponding positions in Cpf1 orthologs. More particularly, the inactivated Cpf1 enzymes include enzymes comprising one or more of mutations AsD908A, AsE993A, AsD1263A of AsCpf1 or corresponding mutations in Cpf1 orthologs. Additionally, the inactivated Cpf1 enzymes include enzymes comprising one or more of mutations LbD832A, E925A, D947A or D1180A of LbCpf1 or corresponding mutations in Cpf1 orthologs.

Mutations can also be made at neighboring residues, e.g., at amino acids near those indicated above that participate in the nuclease activity. In some embodiments, only the RuvC domain is inactivated, and in other embodiments, another putative nuclease domain is inactivated, wherein the effector protein complex functions as a nickase and cleaves only one DNA strand. In a preferred embodiment, the other putative nuclease domain is a HincII-like endonuclease domain. In some embodiments, two FnCpf1, AsCpf1 or LbCpf1 variants (each a different nickase) are used to increase specificity, two nickase variants are used to cleave DNA at a target (where both nickases cleave a DNA strand, while minimizing or eliminating off-target modifications where only one DNA strand is cleaved and subsequently repaired). In preferred embodiments, the Cpf1 effector protein cleaves sequences associated with or at a target locus of interest as a homodimer comprising two Cpf1 effector protein molecules. In a preferred embodiment, the homodimer may comprise two Cpf1 effector protein molecules comprising a different mutation in their respective RuvC domains.

The inactivated Cpf1 CRISPR enzyme may have associated (e.g., via fusion protein) one or more functional domains, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that gRNAs are designed to provide proper spacing for functional use (Fok1) as specifically described in Tsai et al. Nature Biotechnology, Vol. 32, Number 6, June 2014). The adaptor protein may utilize known linkers to attach such functional domains. In some cases, it is advantageous that additionally at least one NLS is provided. In some instances, it is advantageous to position the NLS at the N terminus. When more than one functional domain is included, the functional domains may be the same or different.

In general, the positioning of the one or more functional domain on the inactivated Cpf1 enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the CRISPR enzyme.

In some embodiments, the nucleic acid-targeting effector protein is part of a fusion protein comprising one or more heterologous protein domains (e.g., about or more than about 1, 2, 3, 4, 5, 6, 7, 8, 9, 10, or more domains in addition to the nucleic acid-targeting effector protein). In some embodiments, the CRISPR effector protein is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include, but is not limited to, electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283 and WO 2014/018423 and U.S. Pat. Nos. 8,889,418, 8,895,308, US20140186919, US20140242700, US20140273234, US20140335620, WO2014093635, which is hereby incorporated by reference in its entirety.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by an Cpf1 mediated cleavage event. In an embodiment, the template nucleic acid may include sequence that corresponds to both, a first site on the target sequence that is cleaved in a first Cpf1 mediated event, and a second site on the target sequence that is cleaved in a second Cpf1 mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In certain embodiments, a template nucleic acid for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Suzuki et al. describe in vivo genome editing via CRISPR/Cas9 mediated homology-independent targeted integration (2016, Nature 540:144-149).

Accordingly, when referring to the CRISPR system herein, in some aspects or embodiments, the CRISPR system comprises (i) a CRISPR protein or a polynucleotide encoding a CRISPR effector protein and (ii) one or more polynucleotides engineered to: complex with the CRISPR protein to form a CRISPR complex; and to complex with the target sequence.

In some embodiments, the therapeutic is for delivery (or application or administration) to a eukaryotic cell, either in vivo or ex vivo.

In some embodiments, the CRISPR protein is a nuclease directing cleavage of one or both strands at the location of the target sequence, or wherein the CRISPR protein is a nickase directing cleavage at the location of the target sequence.

In some embodiments, the CRISPR protein is a Cpf1 protein complexed with a CRISPR-Cas system RNA polynucleotide sequence, wherein the polynucleotide sequence comprises: a) a guide RNA polynucleotide capable of hybridizing to a target HBV sequence; and (b) a direct repeat RNA polynucleotide.

In some embodiments, the CRISPR protein is a Cpf1, and the system comprises: I. a CRISPR-Cas system RNA polynucleotide sequence, wherein the polynucleotide sequence comprises: (a) a guide RNA polynucleotide capable of hybridizing to a target sequence, and (b) a direct repeat RNA polynucleotide, and II. a polynucleotide sequence encoding the Cpf1, optionally comprising at least one or more nuclear localization sequences, wherein the direct repeat sequence hybridizes to the guide sequence and directs sequence-specific binding of a CRISPR complex to the target sequence, and wherein the CRISPR complex comprises the CRISPR protein complexed with (1) the guide sequence that is hybridized or hybridizable to the target sequence, and (2) the direct repeat sequence, and the polynucleotide sequence encoding a CRISPR protein is DNA or RNA.

In some embodiments, the CRISPR protein is a Cpf1 from *Acidaminococcus* sp. BV3L6 (AsCpf1), Lachnospiraceae bacterium ND2006 (LbCpf1) or *Moraxella bovoculi* 237.

In some embodiments, the CRISPR protein further comprises one or more nuclear localization sequences (NLSs) capable of driving the accumulation of the CRISPR protein to a detectable amount in the nucleus of the cell of the organism.

In some embodiments, the CRISPR protein comprises one or more mutations.

In some embodiments, the CRISPR protein has one or more mutations in a catalytic domain, and wherein the protein further comprises a functional domain.

In some embodiments, the CRISPR system is comprised within a delivery system, optionally: a vector system comprising one or more vectors, optionally wherein the vectors comprise one or more viral vectors, optionally wherein the one or more viral vectors comprise one or more lentiviral, adenoviral or adeno-associated viral (AAV) vectors; or a particle or lipid particle, optionally wherein the CRISPR protein is complexed with the polynucleotides to form the CRISPR complex.

In some embodiments, the system, complex or protein is for use in a method of modifying an organism or a non-human organism by manipulation of a target sequence in a genomic locus of interest.

In some embodiments, the polynucleotides encoding the sequence encoding or providing the CRISPR system are delivered via liposomes, particles, cell penetrating peptides, exosomes, microvesicles, or a gene-gun. In some embodiments, a delivery system is included. In some embodiments, the delivery system comprises: a vector system comprising one or more vectors comprising the engineered polynucleotides and polynucleotide encoding the CRISPR protein, optionally wherein the vectors comprise one or more viral vectors, optionally wherein the one or more viral vectors comprise one or more lentiviral, adenoviral or adeno-associated viral (AAV) vectors; or a particle or lipid particle, containing the CRISPR system or the CRISPR complex.

In some embodiments, the CRISPR protein has one or more mutations in a catalytic domain, and wherein the enzyme further comprises a functional domain.

In some embodiments, a recombination/repair template is provided.

In certain example embodiments, the engineered CRISPR-Cas effector comprising at least one modification that alters editing preference as compared to wild type may further comprise one or more additional modifications that alters the binding property as to the nucleic acid molecule comprising RNA or the target polypeptide loci, altering binding kinetics as to the nucleic acid molecule or target molecule or target polynucleotide or alters binding specificity as to the nucleic acid molecule. Example of such modifications are summarized in the following paragraph. Based on the above information, mutants can be generated which lead to inactivation of the enzyme or which modify the double strand nuclease to nickase activity. In alternative embodiments, this information is used to develop enzymes with reduced off-target effects (described elsewhere herein).

For the invention described herein, the following criteria may be taken into account when optimizing the respective parameters or variables.

CRISPR Effector Choice
Size
Currently, CRISPR single nuclease effectors demonstrating high efficiency mammalian genome editing range from 1053 amino acids (SaCas9) to 1368 amino acids (SpCas9), (AsCpf1, 1307aa; and LbCpf1, 1246). While smaller orthologs of Cas9 do exist and cleave DNA with high efficiency in vitro, Cas9 orthologs smaller than SaCas9 have shown diminished mammalian DNA cleavage efficiency. The large size of current single effector CRISPR nucleases is challenging for both nanoparticle protein delivery and viral vector delivery strategies. For protein delivery, payload per particle is a function of 3-D protein size, and for viral delivery of single effectors, large gene size limits flexibility for multiplexing or use of large cell-type specific promoters. Considerations relating to delivery are described detailed further herein below.

Protein Search
The ability of the CRISPR effector to access regions of high chromatin complexity can be viewed in two ways 1) this increases the versatility of the CRISPR effector as a tool for genome editing or 2) this may be undesirable due to cellular dysregulation resulting from perturbation of the genomic structure of cells contacted with the CRISPR effector. There have been reports that the most active Cas9 guides are ones that target low nucleosomal occupancy positions: https://elifesciences.org/content/5/e12677, and https://elifesciences.org/content/5/e13450; however, over a longer time scale, cleavage can still occur (also cleavage can occur during replication when the nucleosomal occupancy is moved). Considerations relating to choice of Cpf1 and modifications thereof are described detailed further herein below.

Efficacy
Overall efficiency: robust and uniform enzyme activity across genomic targets in regions of open chromatin is generally desirable for all single effector nucleases. On the other hand, robust and uniform enzyme activity across genomic targets with varying chromatin complexity and epigenetic marks may not be desirable for research and therapeutic applications. It has been shown that Cas9 shows robust cleavage of methylated DNA, and this increases the utility of the enzyme. On the other hand, CRISPR effector binding or cleavage at loci enriched for epigenetic marks may dysregulate cellular processes. A further aspect to be considered is whether enzymes that do not disturb chromatin structure are desirable. If cleaving a locus in a terminally differentiated cell, it may be desirable to utilize enzymes that are not capable of penetrating silenced regions of the genome. Alternatively, when cleaving a locus in a precursor of a differentiated cell type, then it may be advantageous to be able to penetrate regions of the genome inactive at the time of editing.

Specificity: Mismatch Bulge Tolerance
Naturally occurring Cas9 orthologs: naturally occurring CRISPR effectors show tolerance of mismatches or bulges between the RNA guide and DNA target. This tolerance is generally undesirable for therapeutic applications. For therapeutic applications, patients should be individually screened for perfect target guide RNA complementarity, and tolerance of bulges and mismatches will only increase the likelihood of off-target DNA cleavage. High specificity engineered variants have been developed, such as eSpCas9 and Cas9-HF1 for Cas9; these variants show decreased tolerance of mismatches between DNA targets and the RNA guide (relevant to mismatches in approximately the PAM distal 12-14 nucleotides of the guide RNA given 20 nt of guide RNA target complementarity).

PAM Choice
Natural PAM vs. Modified PAM: Targets for each single effector CRISPR DNA endonuclease discovered so far require a protospacer adjacent motif (PAM) flanking the guide RNA complimentary region of the target. For the DNA endonucleases discovered so far, the PAM motifs have at least 2 nucleotides of specificity, such as 2, 3, 4, 5 or more nucleotides of specificity, such as 2-4 or 2-5 nucleotides of specificity, which curtails the fraction of possible targets in the genome that can be cleaved with a single natural enzyme. Mutation of naturally occurring DNA endonucleases has resulted in protein variants with modified PAM specificities. Cumulatively, the more such variants exist for a given protein targeting different PAMs, the greater the density of genomic targets are available for use in therapeutic design (See population efficacy). Nucleotide content: Nucleotide content of PAMs can affect what fraction of the genome can be targeted with an individual protein due to differences in the abundance of a particular motif in the genome or in a specific therapeutic locus of the genome. Additionally, nucleotide content can affect PAM mutation frequencies in the genome (See population efficacy). Cpf1 proteins with altered PAM specificity can address this issue (as described further herein). Influence of PAM length/complexity on target specificity: Cas9 interrogates the genome by first binding to a PAM site before attempting to create a stable RNA/DNA duplex by melting the double stranded DNA. Since the complexity of the PAM limits the possible space of targets interrogated, a more complex PAM will have fewer possible sites at which off-target cleavage can occur.

crRNA Processing Capabilities of the Enzyme: Multiplexing
For multiplexing, crRNA processing capabilities are desirable, as a transcript expressed from a single promoter can contain multiple different crRNAs. This transcript is then processed into multiple constituent crRNAs by the protein, and multiplexed editing proceeds for each target specified by the crRNA. On the other hand, the rules for RNA endonucleolytic processing of multi crRNA transcripts into crRNAs are not fully understood. Hence, for therapeutic applications, crRNA processing may be undesirable due to off-target cleavage of endogenous RNA transcripts.

Target Choice
Target Length
Although most protospacer elements observed in naturally occurring Cas9 and Cpf1 CRISPR arrays are longer than 20 nt, protospacer complimentary regions of resulting crRNA products are often processed to 20 nt (Cas9) or do not confer specificity beyond 20 nt (Cpf1). Extension of the target complimentary region of the guide RNA beyond 20 nt likely is positioned outside of the footprint of the protein on the guide RNA and is often processed away by exonucleases (See protected guide RNAs for further discussion).

Efficiency Screening
Screening for CRISPR effector efficacy has been performed by studying the efficacy of knockdown of cell surface proteins using different DNA targets. These studies show some evidence that position dependent nucleotide content in CRISPR effector targets and flanking nucleotides affects the efficacy of target cleavage.

Specificity Screening
Unbiased investigation of genome-wide CRISPR nuclease activity suggests that most off-target activity occurs at loci with at most three mismatches to the RNA guide.

Current approaches for CRISPR effector target selection rank off-target candidates found in the reference human genome by both the number and position of RNA guide mismatches, with the assumption that loci containing less than 3 mismatches or containing PAM distal mismatches are more likely to be cleaved. However, in a population of individuals, this strategy is complicated by the existence of multiple haplotypes (sets of associated variants), which will contain different positions or numbers of mismatches at candidate off-target sites (See: population safety).

Guide RNA Design

Several technologies have been developed to address different aspects of efficacy and specificity.

Tru Guide

Trimming 1-3 nt off from the 3' end of the target complimentary region of the gRNA often decreases activity at off-target loci containing at least one mismatch to the guide RNA. Likely, with fewer nucleotides of base-pairing between the off-target and gRNA, each mismatch has a greater thermodynamic consequence to the stability of the CRISPR effector-gRNA complex with the off-target DNA. Percentage of successfully cleaved targets may be reduced in using tru guides: i.e., some sites that worked with a 20 nt guide may not cut efficiently with a 17 nt guide; but the ones that do work with 17 nt generally cleavage as efficiently.

Protected Guide

Protected guides utilize an extended guide RNA and/or trans RNA/DNA elements to 1) create stable structures in the sgRNA that compete with sgRNA base-pairing at a target or off-target site or 2) (optionally) extend complimentary nucleotides between the gRNA and target. For extended RNA implementations, secondary structure results from complementarity between the 3' extension of the guide RNA and another target complimentary region of the guide RNA. For trans implementations, DNA or RNA elements bind the extended or normal length guide RNA partially obscuring the target complimentary region of the sgRNA.

Dosage

The dosage of the CRISPR components should take into account the following factors:

Target Search

CRISPR effector/guide RNA-enzyme complexes use 3-D stochastic search to locate targets. Given equal genomic accessibility, the probability of the complex finding an off-target or on-target is similar.

Binding (Target Dwell Time)

Once located, the binding kinetics of the complex at an on-target or an off-target with few mismatches differs only slightly. Hence, target search and binding are likely not the rate-limiting steps for DNA cleavage at on-target or off-target loci. ChIP data suggests that complex dwell time does decrease accompanying increasing mismatches between the off-target locus and RNA guide, particularly in the PAM-proximal 'seed' region of the RNA guide.

Cutting (Thermodynamic Barrier to Assuming an Active Conformation)

A major rate-limiting step for CRISPR effector enzymatic activity appears to be configuration of the target DNA and guide RNA-protein complex in an active conformation for DNA cleavage. Increasing mismatches at off-target loci decrease the likelihood of the complex achieving an active conformation at off-target loci.

The difference between binding and cutting is why ChIP has very low predictive power as a tool for evaluating the off-target cleavage of Cpf1.

If the probability of finding an off-target or on-target is similar, then the difference in rate of on and off-target cleavage is likely due to the fact that the probability of cleavage at an on-target sites is greater than off target sites. (See temporal control) The stochastic search means that Cpf1 suggests that an incorrect model is to view Cpf1 as preferentially cleaving the on-target site first and only moving onto off-target sites after on-target cleavage is saturated; instead, all sites are interrogated at random, and the probability of progression to cutting after PAM binding is what differentiates the propensity of on vs. off-target cutting.

Repetition in DNA Modification at an Individual Locus

NHEJ repair of DNA double strand breaks is generally high fidelity (Should find exact error rate). Hence, it is likely that a nuclease must cut an individual locus many times before an error in NHEJ results in an indel at the cut site. The probability of observing an indel is the compounding probability of observing a double strand break based on 1) target search probability, 2) target dwell time, and 3) overcoming the thermodynamic barrier to DNA cleavage.

Enzyme Concentration

Even at very low concentrations, search may still encounter an off-target prior to an on-target. Thereafter, the number and location of mismatches in an off-target, and likely the nucleotide content of the target will influence the likelihood of DNA cleavage.

Thinking about on/off target cleavage in probabilistic terms, each interaction that Cas9 or Cpf1 has with the genome can be thought of as having some probability of successful cleavage. Reducing the dose will reduce the number of effector molecules available for interacting with the genome, and thus will limit the additive probability of repeated interactions at off-target sites.

Temporal and Spatial Control of the CRISPR System

Various technologies have been developed which provide additional options for addressing efficacy, specificity and safety issues. More particularly these options can be used to allow for temporal control. More particularly these technologies allow for temporal/spatial control (as described further herein):

1. Double nickases
2. Escorted guides
3. Split-effector protein
4. "Self-inactivating" systems or "governing guides"

In the following, the different variables and how they influence the design of a CRISPR-based editing system are described in more detail.

Specificity—Select Most Specific Guide RNA

Guide Specificity

While early reports were fairly contradictory on the ability to accurately predict guide RNAs with limited off-target activity, statistical analysis based on a large number of data has made it possible to identify rules governing off-target effects. Doench et al. (Nat Biotechnol. 2016 February; 34(2):184-91) describe the profiling of the off-target activity of thousands of sgRNAs and the development of a metric to predict off-target sites.

Accordingly, in particular embodiments, the methods of the invention involve selecting a guide RNA which, based on statistical analysis, is less likely to generate off-target effects.

Guide Complementarity

It is generally envisaged that the degree of complementarity between a guide sequence and its corresponding target sequence should be as high as possible, such as more than about 50%, 60%, 75%, 80%, 85%, 90%, 95%, 97.5%, 99%, or 100%. However, in particular embodiments, a particular concern is reducing off-target interactions, e.g., reducing the guide interacting with a target sequence having low complementarity. It has been shown that certain mutations result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in particular embodiments, the guide is selected such that the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

Select Guide Enzyme Concentration

For minimization of toxicity and off-target effect, it will be important to control the concentration of Cpf1 protein and guide RNA delivered. Optimal concentrations of Cpf1 protein and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 86) in the EMX1 gene of the human genome, deep sequencing can be used to assess the level of modification at the following two off-target loci, 1: 5'-GAGTCCTAGCAG-GAGAAGAA-3' (SEQ ID NO: 87) and 2: 5'-GAGTCTAAGCAGAAGAAGAA-3' (SEQ ID NO: 88). The concentration that gives the highest level of on-target modification while minimizing the level of off-target modification should be chosen for in vivo delivery.

Specificity—Select Most Specific Enzyme

Enzyme Modifications to Enhance Specificity

In particular embodiments, a reduction of off-target cleavage is ensured by destabilizing strand separation, more particularly by introducing mutations in the Cpf1 enzyme decreasing the positive charge in the DNA interacting regions (as described herein and further exemplified for Cas9 by Slaymaker et al. 2016 (Science, 1; 351(6268):84-8). In further embodiments, a reduction of off-target cleavage is ensured by introducing mutations into Cpf1 enzyme which affect the interaction between the target strand and the guide RNA sequence, more particularly disrupting interactions between Cpf1 and the phosphate backbone of the target DNA strand in such a way as to retain target specific activity but reduce off-target activity (as described for Cas9 by Kleinstiver et al. 2016, Nature, 28; 529(7587):490-5). In particular embodiments, the off-target activity is reduced by way of a modified Cpf1 wherein both interaction with target strand and non-target strand are modified compared to wild-type Cpf1.

The methods and mutations which can be employed in various combinations to increase or decrease activity and/or specificity of on-target vs. off-target activity, or increase or decrease binding and/or specificity of on-target vs. off-target binding, can be used to compensate or enhance mutations or modifications made to promote other effects. Such mutations or modifications made to promote other effects include mutations or modification to the Cpf1 effector protein and or mutation or modification made to a guide RNA.

With a similar strategy used to improve Cas9 specificity (Slaymaker et al. 2015 "Rationally engineered Cas9 nucleases with improved specificity"), specificity of Cpf1 can be improved by mutating residues that stabilize the non-targeted DNA strand. This may be accomplished without a crystal structure by using linear structure alignments to predict 1) which domain of Cpf1 binds to which strand of DNA and 2) which residues within these domains contact DNA.

However, this approach may be limited due to poor conservation of Cpf1 with known proteins. Thus, it may be desirable to probe the function of all likely DNA interacting amino acids (lysine, histidine and arginine).

Positively charged residues in the RuvC domain are more conserved throughout Cpf1s than those in the Rad50 domain indicating that RuvC residues are less evolutionarily flexible. This suggests that rigid control of nucleic acid binding is needed in this domain (relative to the Rad50 domain). Therefore, it is possible this domain cuts the targeted DNA strand because of the requirement for RNA:DNA duplex stabilization (precedent in Cas9). Furthermore, more arginines are present in the RuvC domain (5% of RuvC residues 904 to 1307 vs 3.8% in the proposed Rad50 domains) suggesting again that RuvC targets one of the DNA strands. Arginines are more involved in binding nucleic acid major and minor grooves (Rohs Nature 2009: http://rohslab.cmb.usc.edu/Papers/Rohs_etal_Nature.pdf). Major/minor grooves would only be present in a duplex (such as DNA: RNA targeting duplex), further suggesting that RuvC may be involved in cutting.

Based on the structural analysis of the RuvC and Rad50 domains, it can be deduced what the relevant domains look like in Cpf1, and infer which regions and residues may contact DNA. Accordingly, in certain embodiments the Cpf1 enzyme is modified by mutation of one or more residues (in the RuvC domain) including but not limited positions R909, R912, R930, R947, K949, R951, R955, K965, K968, K1000, K1002, R1003, K1009, K1017, K1022, K1029, K1035, K1054, K1072, K1086, R1094, K1095, K1109, K1118, K1142, K1150, K1158, K1159, K1220, R1226, R1242, and/or R1252 with reference to amino acid position numbering of AsCpf1 (*Acidaminococcus* sp. BV3L6). Additionally or alternatively, in certain embodiments, the Cpf1 enzyme is modified by mutation of one or more residues (in the RAD50) domain including but not limited positions K324, K335, K337, R331, K369, K370, R386, R392, R393, K400, K404, K406, K408, K414, K429, K436, K438, K459, K460, K464, R670, K675, R681, K686, K689, R699, K705, R725, K729, K739, K748, and/or K752 with reference to amino acid position numbering of AsCpf1 (*Acidaminococcus* sp. BV3L6).

From these specific observations about AsCpf1 similar residues can be identified in Cpf1 from other species by sequence alignments. In certain embodiments, the Cpf1 enzyme is modified by mutation of one or more residues including but not limited positions R912, T923, R947, K949, R951, R955, K965, K968, K1000, R1003, K1009, K1017, K1022, K1029, K1072, K1086, F1103, R1226, and/or R1252 with reference to amino acid position numbering of AsCpf1 (*Acidaminococcus* sp. BV3L6). In certain embodiments, the enzyme is modified by mutation of one or more residues including but not limited positions R833, R836, K847, K879, K881, R883, R887, K897, K900, K932, R935, K940, K948, K953, K960, K984, K1003, K1017, R1033, R1138, R1165, and/or R1252 with reference to amino acid position numbering of LbCpf1 (Lachnospiraceae bacterium ND2006).

Selecting Suitable PAM Recognition

The requirement of a protospacer adjacent motif (PAM) of most CRISPR effector proteins, ensures another level of specificity in that only the target which is preceded by the relevant motif for the enzyme, will be cleaved. Thus, in particular embodiments, where available it may be of interest to select an effector protein with a stringent PAM so as to reduce off-target effects. Such an effector protein may be a Cpf1 ortholog or an effector protein having altered specificity.

On the other hand, the use of a Cpf1 effector protein can be limited by its protospacer adjacent motif (PAM), in that it will only be able to robustly cleave target sites preceded by said motif. For instance, the Acidaminococcus sp. BV3L6 Cpf1 (AsCpf1), which has been successfully harnessed for genome editing can only cleave target sites precede by a TTTV protospacer adjacent motif (PAM), which limits its practical utility. Where broad applicability is desirable or required for multiplexing, the selection of an effector protein with a different PAM specificity may be of interest. Again, this altered specificity may be found in a Cpf1 ortholog; However, it has been found that the Cpf1 effector protein can be mutated to modify its PAM specificity.

Modification of PAM specificity has been performed by a structure-guided saturation mutagenesis screen to increase the targeting range of Cpf1 (Linyi et al. 2016, BioRxiv, http://dx.doi.org/10.1101/091611). Two variants of AsCpf1 were engineered with the mutations S542R/K607R and S542R/K548V/N552R that can cleave target sites with TYCV/CCCC and TATV PAMs, respectively, with enhanced activities in vitro and in human cells. Genome-wide assessment of off-target activity indicated that these variants retain a high level of DNA targeting specificity. It was found that by the provision of the additional AsCpf1 effector protein variants, this results in the addition of one cleavage site for every ~8.7 bp in non-repetitive regions of the human genome.

Further Cpf1 mutants are also envisaged herein. In particular embodiments, a mutated Cpf1 is used wherein said mutated Cpf1 comprises one or more mutated amino acid residue at position 11, 12, 13, 14, 15, 16, 17, 34, 36, 39, 40, 43, 46, 47, 50, 54, 57, 58, 111, 126, 127, 128, 129, 130, 131, 132, 133, 134, 135, 136, 157, 158, 159, 160, 161, 162, 163, 164, 165, 166, 167, 168, 169, 170, 171, 172, 173, 174, 175, 176, 177, 178, 532, 533, 534, 535, 536, 537, 538, 539, 540, 541, 542, 543, 544, 545, 546, 547, 548, 549, 550, 551, 552, 553, 554, 555, 556, 565, 566, 567, 568, 569, 570, 571, 572, 573, 574, 575, 592, 593, 594, 595, 596, 597, 598, 599, 600, 601, 602, 603, 604, 605, 606, 607, 608, 609, 610, 611, 612, 613, 614, 615, 616, 617, 618, 619, 620, 626, 627, 628, 629, 630, 631, 632, 633, 634, 635, 636, 637, 638, 642, 643, 644, 645, 646, 647, 648, 649, 651, 652, 653, 654, 655, 656, 676, 679, 680, 682, 683, 684, 685, 686, 687, 688, 689, 690, 691, 692, 693, 707, 711, 714, 715, 716, 717, 718, 719, 720, 721, 722, 739, 765, 768, 769, 773, 777, 778, 779, 780, 781, 782, 783, 784, 785, 786, 871, 872, 873, 874, 875, 876, 877, 878, 879, 880, 881, 882, 883, 884, or 1048; preferably, one or more mutated amino acid residue at position 130, 131, 132, 133, 134, 135, 136, 162, 163, 164, 165, 166, 167, 168, 169, 170, 171, 172, 173, 174, 175, 176, 177, 536, 537, 538, 539, 540, 541, 542, 543, 544, 545, 546, 547, 548, 549, 550, 551, 552, 570, 571, 572, 573, 595, 596, 597, 598, 599, 600, 601, 602, 603, 604, 605, 606, 607, 608, 609, 610, 611, 612, 613, 614, 615, 630, 631, 632, 646, 647, 648, 649, 650, 651, 652, 653, 683, 684, 685, 686, 687, 688, 689, or 690; more preferably one or more mutated amino acid residue at position 539, 542, 547, 548, 550, 551, 552, 167, 604, and/or 607 of AsCpf1, or the corresponding position of an AsCpf1 orthologue, homologue, or variant, preferably mutated amino acid residues at positions 542 or 542 and 607, wherein said mutations preferably are 542R and 607R, such as S542R and K607R; or preferably mutated amino acid residues at positions 542 and 548 (and optionally 552), wherein said mutations preferably are 542R and 548V (and optionally 552R), such as S542R and K548V (and optionally N552R); or at position 532, 538, 542, and/or 595 of LbCpf1, or the corresponding position of an AsCpf1 orthologue, homologue, or variant, preferably mutated amino acid residues at positions 532 or 532 and 595, wherein said mutations preferably are 532R and 595R, such as G532R and K595R; or preferably mutated amino acid residues at positions 532 and 538 (and optionally 542), wherein said mutations preferably are 532R and 538V (and optionally 542R), such as G532R and K538V (and optionally Y542R).

Accordingly, these variants increase the targeting range, providing a useful addition to the CRISPR/Cas genome engineering toolbox. At the same time, the provision of Cpf1 effector proteins with alternative PAM specificity allows for the selection of a particular variant with optimal specificity for a particular target sequence.

System Approaches to Reduce Off-Target Effects

Double Nickase

Alternatively, to minimize the level of toxicity and off-target effect, a Cpf1 nickase can be used with a pair of guide RNAs targeting a site of interest. Guide sequences and strategies to minimize toxicity and off-target effects can be as in WO 2014/093622 (PCT/US2013/074667); or, via mutation as described herein.

The invention thus contemplates methods of using two or more nickases, in particular a dual or double nickase approach. In some aspects and embodiments, a single type FnCpf1, AsCpf1 or LbCpf1 nickase may be delivered, for example a modified FnCpf1, AsCpf1 or LbCpf1 or a modified FnCpf1, AsCpf1 or LbCpf1 nickase as described herein. This results in the target DNA being bound by two FnCpf1 nickases. In addition, it is also envisaged that different orthologs may be used, e.g., an FnCpf1, AsCpf1 or LbCpf1 nickase on one strand (e.g., the coding strand) of the DNA and an ortholog on the non-coding or opposite DNA strand. The ortholog can be, but is not limited to, a Cpf1 nickase such as a AsCpf1 nickase or a LbCpf1 nickase or FnCpf1 nickase. It may be advantageous to use two different orthologs that require different PAMs and may also have different guide requirements, thus allowing a greater deal of control for the user. In certain embodiments, DNA cleavage will involve at least four types of nickases, wherein each type is guided to a different sequence of target DNA, wherein each pair introduces a first nick into one DNA strand and the second introduces a nick into the second DNA strand. In such methods, at least two pairs of single stranded breaks are introduced into the target DNA wherein upon introduction of first and second pairs of single-strand breaks, target sequences between the first and second pairs of single-strand breaks are excised. In certain embodiments, one or both of the orthologs is controllable, i.e. inducible.

Escorted Guides

The methods provided herein may also involve the use of escorted Cpf1 CRISPR-Cas systems or complexes, especially such a system involving an escorted Cpf1 CRISPR-Cas system guide. By "escorted" is meant that the Cpf1 CRISPR-Cas system or complex or guide is delivered to a selected time or place within a cell, so that activity of the Cpf1 CRISPR-Cas system or complex or guide is spatially or temporally controlled. For example, the activity and destination of the Cpf1 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time. The principle of escorted guides and embodiments thereof are described in detail in WO2016094874 incorporated by reference herein.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4). The aptamers used in this aspect are designed to improve gRNA delivery, including delivery across the cellular membrane, to intracellular compartments, or into the nucleus. Such a structure can include, either in addition to the one or more aptamer(s) or without such one or more aptamer(s), moiety(ies) so as to render the guide deliverable, inducible or responsive to a selected effector. In particular embodiments, a gRNA is designed that responds to normal or pathological physiological conditions, including without limitation pH, hypoxia, O2 concentration, temperature, protein concentration, enzymatic concentration, lipid structure, light exposure, mechanical disruption (e.g. ultrasound waves), magnetic fields, electric fields, or electromagnetic radiation. Accordingly, in particular embodiments, the escort aptamer has binding affinity for an aptamer ligand on or in the cell, or the escort aptamer is responsive to a localized aptamer effector on or in the cell, wherein the presence of the aptamer ligand or effector on or in the cell is spatially or temporally restricted.

Once intended alterations have been introduced, such as by editing intended copies of a gene in the genome of a cell, continued CRISRP/Cpf1 expression in that cell is no longer necessary. Indeed, sustained expression would be undesirable in certain cases in case of off-target effects at unintended genomic sites, etc. Thus time-limited expression is of interest.

Inducible expression offers one approach, but in addition Applicants have engineered a Self-Inactivating Cpf1 CRISPR-Cas system that relies on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Simply, the self-inactivating Cpf1 CRISPR-Cas system includes additional RNA (i.e., guide RNA) that targets the coding sequence for the CRISPR enzyme itself or that targets one or more non-coding guide target sequences complementary to unique sequences present in one or more of the following: (a) within the promoter driving expression of the non-coding RNA elements, (b) within the promoter driving expression of the Cpf1 gene, (c) within 100 bp of the ATG translational start codon in the Cpf1 coding sequence, (d) within the inverted terminal repeat (iTR) of a viral delivery vector, e.g., in an AAV genome.

Examples of inducible systems are light responsive systems. Light responsiveness of an inducible system can be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Crytochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

In particular embodiments, energy sources such as electromagnetic radiation, sound energy or thermal energy can induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm2. In a preferred embodiment, a stimulation paradigm of as low as 0.25 sec every 15 sec should result in maximal activation.

In particular embodiments, the system is chemically inducible. Exemplary designs of chemical inducible systems include: 1. ABI-PYL based system inducible by Abscisic Acid (ABA) (see, e.g., http://stke.sciencemag.org/cgi/content/abstract/sigtrans; 4/164/rs2), 2. FKBP-FRB based system inducible by rapamycin (or related chemicals based on rapamycin) (see, e.g., http://www.nature.com/nmeth/journal/v2/n6/full/nmeth763.html), 3. GID1-GAI based system inducible by Gibberellin (GA) (see, e.g., http://www.nature.com/nchembio/journal/v8/n5/full/nchembio.922.html). Another chemical inducible system is an estrogen receptor (ER) based system inducible by 4-hydroxytamoxifen (40HT) (see, e.g., http://www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

In particular embodiments, the chemical inducible system is based on change in sub-cellular localization. The polypeptide can include a DNA binding domain comprising at least five or more Transcription activator-like effector (TALE) monomers and at least one or more half-monomers specifically ordered to target the genomic locus of interest linked to at least one or more effector domains are further linker to a chemical or energy sensitive protein. This protein will lead to a change in the sub-cellular localization of the entire polypeptide (i.e. transportation of the entire polypeptide from cytoplasm into the nucleus of the cells) upon the binding of a chemical or energy transfer to the chemical or energy sensitive protein. This transportation of the entire polypeptide from one sub-cellular compartments or organelles, in which its activity is sequestered due to lack of substrate for the effector domain, into another one in which the substrate is present would allow the entire polypeptide to come in contact with its desired substrate (i.e. genomic DNA in the mammalian nucleus) and result in activation or repression of target gene expression.

Another inducible system is based on the design using Transient receptor potential (TRP) ion channel-based system inducible by energy, heat or radio-wave (see, e.g., http://www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cpf1 CRISPR-Cas complex or system, and the binding will induce the change of sub-cellular localization of the polypeptide, leading to the entire polypeptide entering the nucleus of cells. Once inside the nucleus, the guide protein and the other components of the Cpf1 CRISPR-Cas complex will be active and modulating target gene expression in cells. This type of system could also be used to induce the cleavage of a genomic locus of interest in a cell; and, in this regard, it is noted that the Cpf1 enzyme is a nuclease. The light could be generated with a laser or other forms of energy sources. The heat could be generated by raise of temperature results from an energy source, or from nano-particles that release heat after absorbing energy from an energy source delivered in the form of radio-wave.

Photoinducibility provides the potential for spatial precision. Taking advantage of the development of optrode technology, a stimulating fiber optic lead may be placed in a precise brain region. Stimulation region size may then be tuned by light intensity. This may be done in conjunction with the delivery of the Cpf1 CRISPR-Cas system or complex of the invention, or, in the case of transgenic Cpf1 animals, guide RNA of the invention may be delivered and the optrode technology can allow for the modulation of gene expression in precise brain regions. A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S(Nichirei), TFBM-01 (Nichirei), ASF104, among others. Suitable culture media for specific cell types may be found at the American Type Culture Collection (ATCC) or the European Collection of Cell Cultures (ECACC). Culture media may be supplemented with amino acids such as L-glutamine, salts, anti-fungal or anti-bacterial agents such as Fungizone®, penicillin-streptomycin, animal serum, and the like. The cell culture medium may optionally be serum-free.

Temporal precision can also be achieved in vivo. This may be used to alter gene expression during a particular stage of development. This may be used to time a genetic cue to a particular experimental window. For example, genes implicated in learning may be overexpressed or repressed only during the learning stimulus in a precise region of the intact rodent or primate brain. Further, the invention may be used to induce gene expression changes only during particular stages of disease development. For example, an oncogene may be overexpressed only once a tumor reaches a particular size or metastatic stage. Conversely, proteins suspected in the development of Alzheimer's may be knocked down only at defined time points in the animal's life and within a particular brain region. Although these examples do not exhaustively list the potential applications of the invention, they highlight some of the areas in which the invention may be a powerful technology.

Protected Guide RNAs

In one aspect, it is of interest to further enhance the specificity of Cpf1 given individual guide RNAs through thermodynamic tuning of the binding specificity of the guide RNA to target DNA. This is a general approach of introducing mismatches, elongation or truncation of the guide sequence to increase/decrease the number of complimentary bases vs. mismatched bases shared between a genomic target and its potential off-target loci, in order to give thermodynamic advantage to targeted genomic loci over genomic off-targets. Thus, it can be of interest to modify the guide sequence by secondary structure to increase the specificity of the Cpf1 CRISPR-Cas system whereby the secondary structure can protect against exonuclease activity. This can be ensured by hybridizing a "protector RNA" to a guide sequence, wherein the "protector RNA" is an RNA strand complementary to the 5' end of the guide RNA (gRNA), to thereby generate a partially double-stranded gRNA. Protecting the mismatched bases with a perfectly complementary protector sequence decreases the likelihood of target DNA binding to the mismatched base pairs at the 3' end. In particular embodiments, additional sequences comprising an extended length may also be present. The principle of using protected guide RNAs is described in detail in WO/2016/094867, which is incorporated herein by reference.

Guide RNA (gRNA) extensions matching the genomic target provide gRNA protection and enhance specificity. Extension of the gRNA with matching sequence distal to the end of the spacer seed for individual genomic targets thus provides enhanced specificity. In particular embodiments, stable forms arise from protective states, where the extension forms a closed loop with the gRNA seed due to complimentary sequences in the spacer extension and the spacer seed. Thus, the protected guide concept also includes sequences matching the genomic target sequence distal of the 20mer spacer-binding region. Thermodynamic prediction can be used to predict completely matching or partially matching guide extensions that result in protected gRNA states as described in WO/2016/094867.

An extension sequence which corresponds to the extended length (ExL) may optionally be attached directly to the guide sequence at the 3' end of the protected guide sequence.

The extension sequence may be 2 to 12 nucleotides in length. Preferably, ExL may be denoted as 0, 2, 4, 6, 8, 10 or 12 nucleotides in length. In a preferred embodiment, the ExL is denoted as 0 or 4 nucleotides in length. In a more preferred embodiment, the ExL is 4 nucleotides in length. The extension sequence may or may not be complementary to the target sequence. An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence.

In an embodiment, the engineered polynucleotide can include a 5' extension that is connected to 5' DR1-G1-DR2-G2 3' by a cleavable bond. The 5' extension hybridizes to the guide sequence, for example, G1 or G2 and thus blocks the activity of CpF1. Upon exposure to the appropriate agent, for example light or other energy, the bond cleaves and CpF1 can bind to the engineered polynucleotide. In some embodiments, the inducer can be a polypeptide. See, for example, Ferry et al., "Rational design of inducible CRISPR guide RNAs for de novo assembly of transcriptional programs." Nature Communications 8: 14633 (2017).

Formation of a RISC Through Guide Engineering

In some embodiments, the guide may be a protected guide (e.g. a pgRNA) or an escorted guide (e.g. an esgRNA) as described herein. Both of these, in some embodiments, make use of RISC. A RISC is a key component of RNAi. RISC (RNA-induced silencing complex) is a multiprotein, specifically a ribonucleoprotein, complex which incorporates one strand of a double-stranded RNA (dsRNA) fragment, such as small interfering RNA (siRNA) or microRNA (miRNA), which acts as a template for RISC to recognize a complementary messenger RNA (mRNA) transcript. The mRNA is thus cleaved by one of the components of the RISC.

As such, the formation of a RISC is advantageous in some embodiments. Guide RNAs according to various aspects of the present invention, including but not limited to protected and/or escorted guide RNAs, may be adapted to include RNA nucleotides that promote formation of a RISC, for example in combination with an siRNA or miRNA that may be provided or may, for instance, already be expressed in a cell. This may be useful, for instance, as a self-inactivating system to clear or degrade the guide.

Thus, the guide RNA may comprise a sequence complementary to a target miRNA or an siRNA, which may or may not be present within a cell. In this way, only when the miRNA or siRNA is present, for example through expression (by the cell or through human intervention), is there binding of the RNA sequence to the miRNA or siRNA which then results in cleavage of the guide RNA an RNA-induced silencing complex (RISC) within the cell. Therefore, in some embodiments, the guide RNA comprises an RNA sequence complementary to a target miRNA or siRNA, and binding of the guide RNA sequence to the target miRNA or siRNA results in cleavage of the guide RNA by an RNA-induced silencing complex (RISC) within the cell. RISC formation through use of escorted guides is described in WO2016094874, RISC formation through use of protected guides is described in WO/2016/094867.

Use of Inducible Systems

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, and WO 2014/018423 A2 which is hereby incorporated by reference in its entirety.

Use of Inducible/Split Effector Enzymes

In an aspect the invention provides a (non-naturally occurring or engineered) inducible CRISPR protein according to the invention as described herein (CRISPR-Cas system), comprising: a first CRISPR protein fusion construct attached to a first half of an inducible dimer and a second CRISPR protein fusion construct attached to a second half of the inducible dimer, wherein the first Cpf1 fusion construct is operably linked to one or more nuclear localization signals, wherein the second CRISPR protein fusion construct is operably linked to one or more nuclear export signals, wherein contact with an inducer energy source brings the first and second halves of the inducible dimer together, wherein bringing the first and second halves of the inducible dimer together allows the first and second CRISPR protein fusion constructs to constitute a functional CRISPR protein (optionally wherein the CRISPR-Cas system comprises a guide RNA (gRNA) comprising a guide sequence capable of hybridizing to a target sequence in a genomic locus of interest in a cell, and wherein the functional CRISPR-Cas system binds to the target sequence and, optionally, edits the genomic locus to alter gene expression).

In an aspect of the invention in the inducible CRISPR-Cas system, the inducible dimer is or comprises or consists essentially of or consists of an inducible heterodimer. In an aspect, in inducible CRISPR-Cas system, the first half or a first portion or a first fragment of the inducible heterodimer is or comprises or consists of or consists essentially of an FKBP, optionally FKBP12. In an aspect of the invention, in the inducible CRISPR-Cas system, the second half or a second portion or a second fragment of the inducible heterodimer is or comprises or consists of or consists essentially of FRB. In an aspect of the invention, in the inducible CRISPR-Cas system, the arrangement of the first CRISPR fusion construct is or comprises or consists of or consists essentially of N' terminal CRISPR part-FRB-NES. In an aspect of the invention, in the inducible CRISPR-Cas system, the arrangement of the first CRISP fusion construct is or comprises or consists of or consists essentially of NES-N' terminal CRISP part-FRB-NES. In an aspect of the invention, in the inducible CRISPR-Cas system, the arrangement of the second CRISP fusion construct is or comprises or consists essentially of or consists of C' terminal CRISP part-FKBP-NLS. In an aspect the invention provides in the inducible Cpf1 CRISPR-Cas system, the arrangement of the second CRISP fusion construct is or comprises or consists of or consists essentially of NLS-C' terminal CRISP part-FKBP-NLS. In an aspect, in inducible CRISPR-Cas system there can be a linker that separates the CRISP part from the half or portion or fragment of the inducible dimer. In an aspect, in the inducible CRISPR-Cas system, the inducer energy source is or comprises or consists essentially of or consists of rapamycin. In an aspect, in inducible CRISPR-Cas system, the inducible dimer is an inducible homodimer. In an aspect, in an inducible Cpf1 CRISPR-Cas system, the Cpf1 is AsCpf1, LbCpf1 or FnCpf1.

In an aspect, the invention provides a (non-naturally occurring or engineered) inducible CRISPR-Cas system, comprising: a first CRISPR fusion construct attached to a first half of an inducible heterodimer and a second CRISPR fusion construct attached to a second half of the inducible heterodimer, wherein the first CRISPR fusion construct is operably linked to one or more nuclear localization signals, wherein the second CRISPR fusion construct is operably linked to a nuclear export signal, wherein contact with an inducer energy source brings the first and second halves of the inducible heterodimer together, wherein bringing the first and second halves of the inducible heterodimer together allows the first and second CRISPR fusion constructs to constitute a functional CRISPR (optionally wherein the CRISPR-Cas system comprises a guide RNA (gRNA) comprising a guide sequence capable of hybridizing to a target sequence in a genomic locus of interest in a cell, and wherein the functional CRISPR-Cas system edits the genomic locus to alter gene expression).

Accordingly, the invention comprehends inter alia homodimers as well as heterodimers, dead-CRISPR or CRISPR protein having essentially no nuclease activity, e.g., through mutation, systems or complexes wherein there is one or more NLS and/or one or more NES; functional domain(s) linked to split Cas9; methods, including methods of treatment, and uses.

An inducer energy source may be considered to be simply an inducer or a dimerizing agent. The term 'inducer energy source' is used herein throughout for consistency. The inducer energy source (or inducer) acts to reconstitute the enzyme. In some embodiments, the inducer energy source brings the two parts of the enzyme together through the action of the two halves of the inducible dimer. The two halves of the inducible dimer therefore are brought tougher in the presence of the inducer energy source. The two halves of the dimer will not form into the dimer (dimerize) without the inducer energy source.

Thus, the two halves of the inducible dimer cooperate with the inducer energy source to dimerize the dimer. This in turn reconstitutes the CRISPR by bringing the first and second parts of the CRISPR together.

The CRISPR protein fusion constructs each comprise one part of the split CRISPR protein. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer.

The CRISPR protein is split in the sense that the two parts of the CRISPR protein enzyme substantially comprise a functioning CRISPR protein. That CRISPR protein may function as a genome editing enzyme (when forming a complex with the target DNA and the guide), such as a nickase or a nuclease (cleaving both strands of the DNA), or it may be a dead-CRISPR protein which is essentially a DNA-binding protein with very little or no catalytic activity, due to typically mutation(s) in its catalytic domains.

The two parts of the split CRISPR protein can be thought of as the N' terminal part and the C' terminal part of the split CRISPR protein. The fusion is typically at the split point of the CRISPR protein. In other words, the C' terminal of the N' terminal part of the split CRISPR protein is fused to one of the dimer halves, whilst the N' terminal of the C' terminal part is fused to the other dimer half.

The CRISPR protein does not have to be split in the sense that the break is newly created. The split point is typically designed in silico and cloned into the constructs. Together, the two parts of the split CRISPR protein, the N' terminal and C' terminal parts, form a full CRISPR protein, comprising preferably at least 70% or more of the wildtype amino acids (or nucleotides encoding them), preferably at least 80% or more, preferably at least 90% or more, preferably at least 95% or more, and most preferably at least 99% or more of the wildtype amino acids (or nucleotides encoding them). Some trimming may be possible, and mutants are envisaged. Non-functional domains may be removed entirely. What is important is that the two parts may be brought together and that the desired CRISPR protein function is restored or reconstituted.

The dimer may be a homodimer or a heterodimer.

One or more, preferably two, NLSs may be used in operable linkage to the first CRISPR protein construct. One or more, preferably two, NESs may be used in operable linkage to the first Cpf1 construct. The NLSs and/or the NESs preferably flank the split Cpf1-dimer (i.e., half dimer) fusion, i.e., one NLS may be positioned at the N' terminal of the first CRISPR protein construct and one NLS may be at the C' terminal of the first CRISPR protein construct. Similarly, one NES may be positioned at the N' terminal of the second CRISPR construct and one NES may be at the C' terminal of the second CRISPR construct. Where reference is made to N' or C' terminals, it will be appreciated that these correspond to 5' ad 3' ends in the corresponding nucleotide sequence.

A preferred arrangement is that the first CRISPR protein construct is arranged 5'-NLS-(N' terminal CRISPR protein part)-linker-(first half of the dimer)-NLS-3'. A preferred arrangement is that the second CRISPR protein construct is arranged 5'-NES-(second half of the dimer)-linker-(C' terminal CRISPR protein part)-NES-3'. A suitable promoter is preferably upstream of each of these constructs. The two constructs may be delivered separately or together.

In some embodiments, one or all of the NES(s) in operable linkage to the second CPf1 construct may be swapped out for an NLS. However, this may be typically not preferred and, in other embodiments, the localization signal in operable linkage to the second Cpf1 construct is one or more NES(s).

It will also be appreciated that the NES may be operably linked to the N' terminal fragment of the split CRISPR protein and that the NLS may be operably linked to the C' terminal fragment of the split CRISPR protein. However, the arrangement where the NLS is operably linked to the N' terminal fragment of the split Cpf1 and that the NES is operably linked to the C' terminal fragment of the split CRISPR protein may be preferred.

The NES functions to localize the second CRISPR protein fusion construct outside of the nucleus, at least until the inducer energy source is provided (e.g., at least until an energy source is provided to the inducer to perform its function). The presence of the inducer stimulates dimerization of the two CRISPR protein fusions within the cytoplasm and makes it thermodynamically worthwhile for the dimerized, first and second, CRISPR protein fusions to localize to the nucleus. Without being bound by theory, Applicants believe that the NES sequesters the second CRISPR protein fusion to the cytoplasm (i.e., outside of the nucleus). The NLS on the first CRISPR protein fusion localizes it to the nucleus. In both cases, Applicants use the NES or NLS to shift an equilibrium (the equilibrium of nuclear transport) to a desired direction. The dimerization typically occurs outside of the nucleus (a very small fraction might happen in the nucleus) and the NLSs on the dimerized complex shift the equilibrium of nuclear transport to nuclear localization, so the dimerized and hence reconstituted CRISPR protein enters the nucleus.

Beneficially, Applicants are able to reconstitute function in the split CRISPR protein. Transient transfection is used to prove the concept and dimerization occurs in the background in the presence of the inducer energy source. No activity is seen with separate fragments of the CRISPR protein. Stable expression through lentiviral delivery is then used to develop this and show that a split CRISPR protein approach can be used.

This present split CRISPR protein approach is beneficial as it allows the CRISPR protein activity to be inducible, thus allowing for temporal control. Furthermore, different localization sequences may be used (i.e., the NES and NLS as preferred) to reduce background activity from auto-assembled complexes. Tissue specific promoters, for example one for each of the first and second CRISPR protein fusion constructs, may also be used for tissue-specific targeting, thus providing spatial control. Two different tissue specific promoters may be used to exert a finer degree of control if required. The same approach may be used in respect of stage-specific promoters or there may a mixture of stage and tissue specific promoters, where one of the first and second Cpf1 fusion constructs is under the control of (i.e. operably linked to or comprises) a tissue-specific promoter, whilst the other of the first and second Cpf1 fusion constructs is under the control of (i.e. operably linked to or comprises) a stage-specific promoter.

The inducible CRISPR protein CRISPR-Cas system comprises one or more nuclear localization sequences (NLSs), as described herein, for example as operably linked to the first CRISPR protein fusion construct. These nuclear localization sequences are ideally of sufficient strength to drive accumulation of said first CRISPR protein fusion construct in a detectable amount in the nucleus of a eukaryotic cell. Without wishing to be bound by theory, it is believed that a nuclear localization sequence is not necessary for CRISPR-Cas complex activity in eukaryotes, but that including such sequences enhances activity of the system, especially as to targeting nucleic acid molecules in the nucleus, and assists with the operation of the present 2-part system.

Equally, the second CRISPR protein fusion construct is operably linked to a nuclear export sequence (NES). Indeed, it may be linked to one or more nuclear export sequences. In other words, the number of export sequences used with the second CRISPR protein fusion construct is preferably 1 or 2 or 3. Typically 2 is preferred, but 1 is enough and so is preferred in some embodiments. Suitable examples of NLS and NES are known in the art. For example, a preferred nuclear export signal (NES) is human protein tyrosine kinase 2. Preferred signals will be species specific.

Where the FRB and FKBP system are used, the FKBP is preferably flanked by nuclear localization sequences (NLSs). Where the FRB and FKBP system are used, the preferred arrangement is N' terminal CRISPR protein-FRB-NES. C' terminal Cpf1-FKBP-NLS. Thus, the first CRISPR protein fusion construct would comprise the C' terminal CRISPR protein part and the second CRISPR protein fusion construct would comprise the N' terminal CRISPR protein part.

Another beneficial aspect to the present invention is that it may be turned on quickly, i.e. that is has a rapid response. It is believed, without being bound by theory, that CRISPR protein activity can be induced through dimerization of existing (already present) fusion constructs (through contact with the inducer energy source) more rapidly than through the expression (especially translation) of new fusion constructs. As such, the first and second CRISPR protein fusion constructs may be expressed in the target cell ahead of time, i.e. before CRISPR protein activity is required. CRISPR protein activity can then be temporally controlled and then quickly constituted through addition of the inducer energy source, which ideally acts more quickly (to dimerize the heterodimer and thereby provide CRISPR protein activity) than through expression (including induction of transcription) of CRISPR protein delivered by a vector, for example.

Applicants demonstrate that CRISPR protein can be split into two components, which reconstitute a functional nuclease when brought back together. Employing rapamycin sensitive dimerization domains, Applicants generate a chemically inducible CRISPR protein for temporal control of CRISPR protein-mediated genome editing and transcription modulation. Put another way, Applicants demonstrate that CRISPR protein can be rendered chemically inducible by being split into two fragments and that rapamycin-sensitive dimerization domains may be used for controlled reassembly of the CRISPR protein. Applicants show that the re-assembled CRISPR protein may be used to mediate genome editing (through nuclease/nickase activity) as well as transcription modulation (as a DNA-binding domain, the so-called "dead CRISPR protein").

As such, the use of rapamycin-sensitive dimerization domains is preferred. Reassembly of the CRISPR protein is preferred. Reassembly can be determined by restoration of binding activity. Where the CRISPR protein is a nickase or induces a double-strand break, suitable comparison percentages compared to a wildtype are described herein.

Rapamycin treatments can last 12 days. The dose can be 200 nM. This temporal and/or molar dosage is an example of an appropriate dose for Human embryonic kidney 293FT (HEK293FT) cell lines and this may also be used in other cell lines. This figure can be extrapolated out for therapeutic use in vivo into, for example, mg/kg. However, it is also envisaged that the standard dosage for administering rapamycin to a subject is used here as well. By the "standard dosage", it is meant the dosage under rapamycin's normal therapeutic use or primary indication (i.e. the dose used when rapamycin is administered for use to prevent organ rejection).

It is noteworthy that the preferred arrangement of CRISPR protein –FRB/FKBP pieces are separate and inactive until rapamycin-induced dimerization of FRB and FKBP results in reassembly of a functional full-length CRISPR protein nuclease. Thus, it is preferred that first CRISPR protein fusion construct attached to a first half of an inducible heterodimer is delivered separately and/or is localized separately from the second Cpf1 fusion construct attached to a first half of an inducible heterodimer.

To sequester the CRISPR protein (N)-FRB fragment in the cytoplasm, where it is less likely to dimerize with the nuclear-localized Cpf1(C)-FKBP fragment, it is preferable to use on CRISPR protein (N)-FRB a single nuclear export sequence (NES) from the human protein tyrosin kinase 2 (CRISPR protein (N)—FRB-NES). In the presence of rapamycin, CRISPR protein (N)-FRB-NES dimerizes with CRISPR protein (C)-FKBP-2×NLS to reconstitute a complete CRISPR protein, which shifts the balance of nuclear trafficking toward nuclear import and allows DNA targeting.

In some aspects or embodiments, an inducible system for providing a CRISPR protein may be used. In some embodiments, the CRISPR protein is capable, in the presence of an inducer energy source, of forming a CRISPR complex with a target sequence and polynucleotides engineered to complex with the CRISPR protein and the target sequence. In some embodiments, the inducible system comprises: a first fusion protein, or polynucleotides encoding it; and a second fusion protein, or polynucleotides encoding it. In some embodiments, the first fusion protein comprises a first portion of the CRISPR protein, a first half of an inducible dimer and one or more Nuclear Localisation Sequences (NLS); and the second fusion protein comprises a second portion of the CRISPR protein, a second half of the inducible dimer and one or more Nuclear Export Sequences (NES). In some embodiments, contact with the inducer energy source brings the first and second portions of the inducible dimer together, so as to bring the first and second portions of the CRISPR protein together, such that the CRISPR protein is thereby capable of forming the CRISPR complex. In some embodiments, the CRISPR protein or the CRISPR system is inducible. In some embodiments, the CRISPR protein may be provided as a single 'part.' In some embodiments, delivery of the CRISPR protein is in protein (including in RNP complex with the polynucleotides) or in nucleotide form (including in mRNA form). In some embodiments, polynucleotides encoding the first fusion protein and polynucleotides encoding second fusion protein are provided on same or different constructs. WO 2015/089427 describes an inducible CRISPR-Cas system based on an inducible dimer, which can be a homodimer or heterodimer. The system is also described in Zetsche et al. (Nature Biotechnology 33: 139-142 (2015) DOI: doi:10.1038/nbt.3149). Basically, the CRISPR effector protein is split into two parts, each of which is fused to one half of an inducible dimer, whereby contact with an inducer energy source brings the first and second halves of the inducible dimer together, and bringing the first and second halves of the inducible dimer together allows the first and second CRISPR effector fusion constructs to constitute a functional CRISPR-Cas system, wherein the CRISPR-Cas system comprises a guide RNA (gRNA) comprising a guide sequence capable of hybridizing to a target sequence in a genomic locus of interest in a cell, and wherein the functional CRISPR-Cas system binds to the genomic locus. In particular embodiments, the functional CRISPR-Cas system edits the genomic locus to alter gene expression. In particular embodiments the first half is an FKBP and the second half is an FRB. An inducer energy source may be considered to be simply an inducer or a dimerizing agent as it acts to reconstitute the CRISPR effector protein.

Examples of inducers include light and hormones. A preferred example of first and second light-inducible dimer halves is the CIB1 and CRY2 system. The CIB1 domain is a heterodimeric binding partner of the light-sensitive Cryptochrome 2 (CRY2). In another example, the blue light-responsive Magnet dimerization system (pMag and nMag) may be fused to the two parts of a split Cpf1 protein. In response to light stimulation, pMag and nMag dimerize and Cpf1 reassembles. For example, such system is described in connection with Cas9 in Nihongaki et al. (Nat. Biotechnol. 33, 755-790, 2015). The inducer energy source may be heat, ultrasound, electromagnetic energy or chemical. In a preferred embodiment the inducer energy source may be an antibiotic, a small molecule, a hormone, a hormone derivative, a steroid or a steroid derivative. In a more preferred embodiment, the inducer energy source maybe abscisic acid (ABA), doxycycline (DOX), cumate, rapamycin, 4-hydroxytamoxifen (4OHT), estrogen or ecdysone. The at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4OHT/estrogen inducible systems, ecdysone-based inducible systems and FKBP12/FRAP (FKBP12-rapamycin complex) inducible systems. Such inducers are also discussed herein and in PCT/US2013/051418, incorporated herein by reference.

Also, it is described in WO2015/089427 that the half of an inducible dimer can be linked to the effector protein with a linker. Optionally, the CRISPR effector protein has reduced or no nuclease activity, e.g. contains one or more inactivating mutations. Further it is described that one or more functional domains can be associated with one or both parts of the effector protein, WO2015/089427 identifies split points within SpCas9. Similar suitable split points can be identified for Cpf1.

Table 5 presents non-limiting potential split regions within As and LbCpf1. A split site within such a region may be opportune.

TABLE 5

| Split region | AsCpf1 | LbCpf1 |
| --- | --- | --- |
| 1 | 575-588 | 566-571 |
| 2 | 631-645 | 754-757 |
| 3 | 653-664 | — |
| 4 | 818-844 | — |

For Fn, As and Lb Cpf1 mutants, it should be readily apparent what the corresponding position for a potential split site is, for example, based on a sequence alignment. For non-Fn, As and Lb enzymes one can use the crystal structure of an ortholog if a relatively high degree of homology exists between the ortholog and the intended Cpf1, or one can use computational prediction.

Further it is described that the first and second fusion constructs of the CRISPR effector protein can be delivered in the same or separate vectors. In particular embodiments, a first half of the inducible dimer is fused to one or more nuclear localization constructs while the second half is fused to one or more nuclear export signals.

The therapeutic methods which involve the use of the inducible dimer comprise the step of administering the vectors comprising the first and second fusion constructs to the subject and administering an inducer energy source to the subject. In particular embodiments, the inducer energy source is rapamycin. It is further envisaged that the methods can involve administering, a repair template, in the same or a different vector as the inducible dimer fragments. An exemplary treatment regimen with Rapamycin can last 12 days.

The use of the split Cpf1 effector protein system described herein allows a further control of the CRISPR-Cas activity. More particularly the use of an inducible system allows for temporal control. In addition, the use of different localization sequences (i.e., the NES and NLS as preferred) can reduce background activity from auto-assembled complexes. Tissue specific promoters, allow for spatial control. Two different tissue specific promoters may be used to exert a finer degree of control if required.

Use of Self-Inactivating Systems

Once all copies of a gene in the genome of a cell have been edited, continued CRISPR/Cpf1 expression in that cell is no longer necessary. Indeed, sustained expression is undesirable to avoid off-target effects and other toxicity issues. WO 2015089351 describes self-Inactivating CRISPR systems which rely on the use of a non-coding guide target sequence within the CRISPR vector itself. Thus, after expression begins, the CRISPR system will lead to its own destruction, but before destruction is complete it will have time to edit the genomic copies of the target gene (which, with a normal point mutation in a diploid cell, requires at most two edits). Accordingly, the methods may involve the use of a self-inactivating CRISPR-Cas system which includes one additional RNA (i.e., guide RNA) that targets the coding sequence for the CRISPR enzyme itself or that targets one or more non-coding guide target sequences complementary to unique sequences present in within the promoter driving expression of the non-coding RNA elements, within the promoter driving expression of the Cpf1 gene, within 100 bp of the ATG translational start codon in the Cpf1 coding sequence, or within the inverted terminal repeat (iTR) of a viral delivery vector, e.g., in the AAV genome.

Similarly, self-inactivating systems which make use of "governing guides" are exemplified in relation to Cas9 in US2015232881A1 (also published as WO2015070083 (A1) referenced elsewhere herein and incorporated herein by reference, and may be extrapolated to Cpf1. More particularly Methods and compositions that use, or include, a nucleic acid, e.g., a DNA, that encodes a Cpf1 molecule or a gRNA molecule, can, in addition, use or include a "governing gRNA molecule." The governing gRNA molecule can complex with the Cpf1 molecule to inactivate or silence a component of a Cpf1 system. The additional gRNA molecule, referred to herein as a governing gRNA molecule, comprises a targeting domain which targets a component of the Cpf1 system. In an embodiment, the governing gRNA molecule targets and silences (1) a nucleic acid that encodes a Cpf1 molecule (i.e., a Cpf1-targeting gRNA molecule), (2) a nucleic acid that encodes a gRNA molecule (i.e., a gRNA-targeting gRNA molecule), or (3) a nucleic acid sequence engineered into the Cpf1 components that is designed with minimal homology to other nucleic acid sequences in the cell to minimize off-target cleavage (i.e., an engineered control sequence-targeting gRNA molecule).

The targeting sequence for the governing gRNA can be selected to increase regulation or control of the Cpf1 system and/or to reduce or minimize off-target effects of the system. For example, a governing gRNA can minimize undesirable cleavage, e.g., "recleavage" after Cpf1 mediated alteration of a target nucleic acid or off-target cutting of Cpf1, by inactivating (e.g., cleaving) a nucleic acid that encodes a Cpf1 molecule. In an embodiment, a governing gRNA places temporal or other limit(s) on the level of expression or activity of the Cpf1 molecule/gRNA molecule complex. In an embodiment, the governing gRNA reduces off-target or other unwanted activity.

The additional guide RNA can be delivered via a vector, e.g., a separate vector or the same vector that is encoding the CRISPR complex. When provided by a separate vector, the CRISPR RNA that targets Cpf1 expression can be administered sequentially or simultaneously. When administered sequentially, the CRISPR RNA that targets Cpf1 expression is to be delivered after the CRISPR RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas enzyme associates with a first gRNA capable of hybridizing to a first target, such as a genomic locus or loci of interest and undertakes the function(s) desired of the CRISPR-Cas system (e.g., gene engineering); and subsequently the Cpf1 enzyme may then associate with the second gRNA capable of hybridizing to the sequence comprising at least part of the Cpf1 or CRISPR cassette. Where the gRNA targets the sequences encoding expression of the Cpf1 protein, the enzyme becomes impeded and the system becomes self-inactivating. In the same manner, CRISPR RNA that targets Cpf1 expression applied via, for example liposome, lipofection, nanoparticles, microvesicles as explained herein, may be administered sequentially or simultaneously. Similarly, self-inactivation may be used for inactivation of one or more guide RNA used to target one or more targets.

In some embodiments, a single gRNA is provided that is capable of hybridization to a sequence downstream of a CRISPR enzyme start codon, whereby after a period of time there is a loss of the CRISPR enzyme expression. In some embodiments, one or more gRNA(s) are provided that are capable of hybridization to one or more coding or non-coding regions of the polynucleotide encoding the CRISPR-Cas system, whereby after a period of time there is a inactivation of one or more, or in some cases all, of the CRISPR-Cas systems. In some aspects of the system, and not to be limited by theory, the cell may comprise a plurality of CRISPR-Cas complexes, wherein a first subset of CRISPR complexes comprise a first chiRNA capable of targeting a genomic locus or loci to be edited, and a second subset of CRISPR complexes comprise at least one second chiRNA capable of targeting the polynucleotide encoding the CRISPR-Cas system, wherein the first subset of CRISPR-Cas complexes mediate editing of the targeted genomic locus or loci and the second subset of CRISPR complexes eventually inactivate the CRISPR-Cas system, thereby inactivating further CRISPR-Cas expression in the cell.

Thus, the invention provides a CRISPR-Cas system comprising one or more vectors for delivery to a eukaryotic cell, wherein the vector(s) encode(s): (i) a CRISPR enzyme; (ii) a first guide RNA capable of hybridizing to a target sequence in the cell; (iii) a second guide RNA capable of hybridizing to one or more target sequence(s) in the vector which encodes the CRISPR enzyme; (iv) at least one tracr mate sequence; and (v) at least one tracr sequence. The first and second complexes can use the same tracr and tracr mate, thus differing only by the guide sequence, wherein, when expressed within the cell: the first guide RNA directs sequence-specific binding of a first CRISPR complex to the target sequence in the cell; the second guide RNA directs sequence-specific binding of a second CRISPR complex to the target sequence in the vector which encodes the CRISPR enzyme; the CRISPR complexes comprise (a) a tracr mate sequence hybridised to a tracr sequence and (b) a CRISPR enzyme bound to a guide RNA, such that a guide RNA can hybridize to its target sequence; and the second CRISPR complex inactivates the CRISPR-Cas system to prevent continued expression of the CRISPR enzyme by the cell. The CRISPR enzyme can be Cpf1, particularly FnCpf1 or AsCpf1.

Further characteristics of the vector(s), the encoded enzyme, the guide sequences, etc. are disclosed elsewhere herein. For instance, one or both of the guide sequence(s) can be part of a chiRNA sequence which provides the guide, tracr mate and tracr sequences within a single RNA, such that the system can encode (i) a CRISPR enzyme; (ii) a first chiRNA comprising a sequence capable of hybridizing to a first target sequence in the cell, a first tracr mate sequence, and a first tracr sequence; (iii) a second guide RNA capable of hybridizing to the vector which encodes the CRISPR enzyme, a second tracr mate sequence, and a second tracr sequence. Similarly, the enzyme can include one or more NLS, etc.

The various coding sequences (CRISPR enzyme, guide RNAs, tracr and tracr mate) can be included on a single vector or on multiple vectors. For instance, it is possible to encode the enzyme on one vector and the various RNA sequences on another vector, or to encode the enzyme and one chiRNA on one vector, and the remaining chiRNA on another vector, or any other permutation. In general, a system using a total of one or two different vectors is preferred.

Where multiple vectors are used, it is possible to deliver them in unequal numbers, and ideally with an excess of a vector which encodes the first guide RNA relative to the second guide RNA, thereby assisting in delaying final inactivation of the CRISPR system until genome editing has had a chance to occur.

Thus, the target sequence in the vector must be capable of inactivating expression of the CRISPR effector protein. Suitable target sequences can be, for instance, near to or within the translational start codon for the Cpf1 coding sequence, in a non-coding sequence in the promoter driving expression of the non-coding RNA elements, within the promoter driving expression of the Cpf1 gene, within 100 bp of the ATG translational start codon in the Cpf1 coding sequence, and/or within the inverted terminal repeat (iTR) of a viral delivery vector, e.g., in the AAV genome. A double stranded break near this region can induce a frame shift in the Cpf1 coding sequence, causing a loss of protein expression. An alternative target sequence for the "self-inactivating" guide RNA would aim to edit/inactivate regulatory regions/sequences needed for the expression of the CRISPR-Cpf1 system or for the stability of the vector. For instance, if the promoter for the Cpf1 coding sequence is disrupted then transcription can be inhibited or prevented. Similarly, if a vector includes sequences for replication, maintenance or stability then it is possible to target these. For instance, in a AAV vector a useful target sequence is within the iTR. Other useful sequences to target can be promoter sequences, polyadenlyation sites, etc.

Furthermore, if the guide RNAs are expressed in array format, the "self-inactivating" guide RNAs that target both promoters simultaneously will result in the excision of the intervening nucleotides from within the CRISPR-Cas expression construct, effectively leading to its complete inactivation. Similarly, excision of the intervening nucleotides will result where the guide RNAs target both ITRs, or targets two or more other CRISPR-Cas components simultaneously. Self-inactivation as explained herein is applicable, in general, with CRISPR-Cpf1 systems in order to provide regulation of the CRISPR-Cpf1. For example, self-inactivation as explained herein may be applied to the CRISPR repair of mutations, for example expansion disorders, as explained herein. As a result of this self-inactivation, CRISPR repair is only transiently active.

Addition of non-targeting nucleotides to the 5' end (e.g. 1-10 nucleotides, preferably 1-5 nucleotides) of the "self-inactivating" guide RNA can be used to delay its processing and/or modify its efficiency as a means of ensuring editing at the targeted genomic locus prior to CRISPR-Cpf1 shutdown.

In one aspect of the self-inactivating AAV-CRISPR-Cpf1 system, plasmids that co-express one or more sgRNA targeting genomic sequences of interest (e.g. 1-2, 1-5, 1-10, 1-15, 1-20, 1-30) may be established with "self-inactivating" sgRNAs that target a Cpf1 sequence at or near the engineered ATG start site (e.g. within 5 nucleotides, within 15 nucleotides, within 30 nucleotides, within 50 nucleotides, within 100 nucleotides). A regulatory sequence in the U6 promoter region can also be targeted with an sgRNA. The U6-driven sgRNAs may be designed in an array format such that multiple sgRNA sequences can be simultaneously released. When first delivered into target tissue/cells (left cell) sgRNAs begin to accumulate while Cpf1 protein levels rise in the nucleus. Cpf1 complexes with all of the sgRNAs to mediate genome editing and self-inactivation of the CRISPR-Cpf1 plasmids.

One aspect of a self-inactivating CRISPR-Cpf1 system is expression of singly or in tandem array format from 1 up to 4 or more different guide sequences; e.g. up to about 20 or about 30 guides sequences. Each individual self-inactivating guide sequence may target a different target. Such may be processed from, e.g. one chimeric pol3 transcript. Pol3 promoters such as U6 or H1 promoters may be used. Pol2 promoters such as those mentioned throughout herein. Inverted terminal repeat (iTR) sequences may flank the Pol3 promoter-sgRNA(s)-Pol2 promoter-Cas9.

In particular embodiments, one or more guide(s) edit the one or more target(s) while one or more self-inactivating guides inactivate the CRISPR/Cpf1 system. Thus, for example, the described CRISPR-Cpf1 system for repairing expansion disorders may be directly combined with the self-inactivating CRISPR-Cpf1 system described herein. Such a system may, for example, have two guides directed to the target region for repair as well as at least a third guide directed to self-inactivation of the CRISPR-Cpf1. Reference is made to Application Ser. No. PCT/US2014/069897, entitled "Compositions and Methods of Use of Crispr-Cas Systems in Nucleotide Repeat Disorders," published Dec. 12, 2014, as WO/2015/089351.

In particular embodiments, the gene editing systems described herein are placed under the control of a passcode kill switch, which is a mechanism which efficiently kills the host cell when the conditions of the cell are altered. This is ensured by introducing hybrid LacI-GalR family transcription factors, which require the presence of IPTG to be switched on (Chan et al. 2015 Nature Chemical Biology doi:10.1038/nchembio.1979 which can be used to drive a gene encoding an enzyme critical for cell-survival. By combining different transcription factors sensitive to different chemicals, a "code" can be generated. This system can be used to spatially and temporally control the extent of CRISPR-induced genetic modifications, which can be of interest in different fields including therapeutic applications and may also be of interest to avoid the "escape" of GMOs from their intended environment.

Use of "Off-Switches"

In particular embodiments, it may be possible to make use of specific inhibitors and/or agonist of Cpf1. Off-switches and On-switches may be any molecules (i.e. peptides, proteins, small molecules, nucleic acids) capable of interfering with or acting as an agonist for any aspect of the Cas9 effector protein. For instance, Pawluck et al. 2016 (Cell 167, 1-10) describe mobile elements from bacteria that encode protein inhibitors of Cas9. Three families of anti-CRISPRs were found to inhibit *N. meningitidis* Cas9 in vivo and in vitro. The anti-CRISPRs bind directly to NmeCas9. These proteins are described to be potent "off-switches" for Nme-Cas9 genome editing in human cells. Methods for identifying small molecules which affect efficiency of Cas9 are described for example by Yu et al. (Cell Stem Cell 16, 142-147, 2015). In certain embodiments small molecules may be used for control Cas9. Maji et al. describe a small molecule-regulated protein degron domain to control Cas9 system editing. Maji et al. "Multidimensional chemical control of CRISPR-Cas9" Nature Chemical Biology (2017) 13:9-12. In certain example embodiments, the inhibitor may be a bacteriophage derived protein. See Rauch et al. "Inhibition of CRISPR-Cas9 with Bacteriophage Proteins" Cell (2017) 168(2):150-158. In certain example embodiments, the anti-CRISPR may inhibit CRISPR-Cas systems by binding to guide molecules. See Shin et al. "Disabling Cas9 by an anti-CRISPR DNA mimic" bioRxiv, Apr. 22, 2017, doi:http://dx.doi.org/10.1101/129627.

In particular embodiments, intracellular DNA is removed by genetically encoded DNai which responds to a transcriptional input and degrades user-defined DNA as described in Caliando & Voigt, Nature Communications 6: 6989 (2015).

Efficacy

Enzyme Stability

The level of expression of a protein is dependent on many factors, including the quantity of mRNA, its stability and rates of ribosome initiation. The stability or degradation of mRNA is an important factor. Several strategies have been described to increase mRNA stability. One aspect is codon-optimization. It has been found that GC-rich genes are expressed several-fold to over a 100-fold more efficiently than their GC-poor counterparts. This effect could be directly attributed to increased steady-state mRNA levels, and more particularly to efficient transcription or mRNA processing (not decreased degradation) (Kudla et al. Plos Biology http://dx.doi.org/10.1371/journal.pbio.0040180). Also, it has been found that ribosomal density has a significant effect on the transcript half-life. More particularly, it was found that an increase in stability can be achieved through the incorporation of nucleotide sequences that are capable of forming secondary structures, which often recruit ribosomes, which impede mRNA degrading enzymes. WO2011/141027 describes that slowly-read codons can be positioned in such a way as to cause high ribosome occupancy across a critical region of the 5' end of the mRNA can increase the half-life of a message by as much as 25%, and produce a similar uplift in protein production. In contrast, positioning even a single slow-read codon before this critical region can significantly destabilize the mRNA and result in an attenuation of protein expression. This understanding enables the design of mRNAs so as to suit the desired functionality. In addition, chemical modifications such as those described for guide sequences herein can be envisaged to increase mRNA stability.

Guide Stability

In certain embodiments, the methods make use of chemically modified guide RNAs. Examples of guide RNA chemical modifications include, without limitation, incorporation of 2'-O-methyl (M), 2'-O-methyl 3'phosphorothioate (MS), or 2'-O-methyl 3'thioPACE (MSP) at one or more terminal nucleotides. Such chemically modified guide RNAs can comprise increased stability and increased activity as compared to unmodified guide RNAs, though on-target vs. off-target specificity is not predictable. (See, Hendel, 2015, Nat Biotechnol. 33(9):985-9, doi: 10.1038/nbt.3290, published online 29 Jun. 2015). Chemically modified guide RNAs father include, without limitation, RNAs with phosphorothioate linkages and locked nucleic acid (LNA) nucleotides comprising a methylene bridge between the 2' and 4' carbons of the ribose ring.

Select Best Target Site in Gene

Selection within a Target Gene

Studies to date suggest that while sgRNA activity can be quite high, there is significant variability among sgRNAs in their ability to generate the desired target cleavage. Efforts have been made to identify design criteria to maximize guide RNA efficacy. Doench et al. (Nat Biotechnol. 2014 December; 32(12): 1262-1267 and Nat Biotechnol. PubMed PMID: 26780180) describe the development of a quantitative model to optimize sgRNA activity prediction, and a tool to use this model for sgRNA design. Accordingly, in particular embodiments, the methods provided herein comprise identifying an optimal guide sequence based on a statistical comparison of active guide RNAs, such as described by Doench et al. (above). In particular embodiments, at least five gRNAs are designed per target and these are tested empirically in cells to generate at least one which has sufficiently high activity.

*Note that there is mention of a manual entitled "How to design CRISPR crRNA for gene disruption" from integrated technologies which apparently mentions concept of "targeting an early 5' exon of your gene reduces the chances of functional [off-target]" but this link is no longer working.

Identification of Suitable Guide Sequence

Currently RNA guides are designed using the reference human genome; however, failing to take into account variation in the human population may confound the therapeutic outcome for a given RNA guide. The recently released ExAC dataset, based on 60,706 individuals, contains on average one variant per eight nucleotides in the human exome (Lek, M. et al. Analysis of protein-coding genetic variation in 60,706 humans. Nature 536, 285-291 (2016)). This highlights the potential for genetic variation to impact the efficacy of certain RNA guides across patient populations for CRISPR-based gene therapy, due to the presence of mismatches between the RNA guide and variants present in the target site of specific patients. To assess this impact, we use the ExAC dataset to catalog variants present in all possible targets in the human reference exome that either (i) disrupt the target PAM sequence or (ii) introduce mismatches between the RNA guide and the genomic DNA, which can collectively be termed target variation. For treatment of a patient population, avoiding target variation for RNA guides administered to individual patients will maximize the consistency of outcomes for a genome editing therapeutic. The demonstration of the impact of target variation is illustrated in the examples section herein.

Ideally, personalized genomic medicine would tailor RNA-guided endonuclease therapeutics for each patient. However, it would likely be cost-prohibitive and infeasible from a regulatory standpoint to design an individual RNA guide for each patient receiving a genome editing therapy. The analysis of the impact of genetic variation on the efficacy and safety of RNA-guided endonucleases motivates the following framework to streamline the design and testing of genome editing therapeutics. First, use of RNA guides for platinum targets would ensure perfect targeting for 99.99% of patients. Second, these RNA guides need to be further selected to minimize the number of off-target candidates occurring on high frequency haplotypes in the patient population. Third, low frequency variation captured in large scale sequencing datasets can be used to estimate the number of guide RNA-enzyme combinations required to effectively and safely treat different sizes of patient populations. Growth of large-scale sequencing datasets will improve the accuracy of these estimates. Fourth, pre-therapeutic whole genome sequencing of individual patients will be needed to select a single approved guide RNA-enzyme combination for treatment. This combination should be a perfect match to the patient's genome and be free of patient-specific off-target candidates. This framework, in combination with rapidly accumulating human sequencing data, which will further refine these selection criteria, will enable the design and validation of genome editing therapeutics minimizing both the number of guide RNA-enzyme combinations necessary for approval and the cost of delivering effective and safe gene therapies to patients.

Accordingly, in particular embodiments, the methods provided herein comprise one or more of the following steps: (1) identifying platinum targets, (2) selection of the guides to minimize the number of off-target candidates occurring on high frequency haplotypes in the patient population; (3) select guide (and/or effector protein) based low frequency variation captured in large scale sequencing datasets to estimate the number of guide RNA-enzyme combinations required to effectively and safely treat different sizes of patient populations, and (4) confirm or select guide based on pre-therapeutic whole genome sequencing of individual patient. In particular embodiments, a "platinum" target is one that does not contain variants occurring at ≥0.01% allele frequency.

Methods for Determining on/Off-Target Activity and Selecting Suitable Target Sequences/Guides.

In certain example embodiments, parameters such as, but not limited to, off-target candidates, PAM restrictiveness, target cleavage efficiency, or effector protein specific may be determined using sequencing-based double-strand break (DSB) detection assays. Example sequencing-based DSB detection assay sChIP-seq (Szilard et al. Nat. Struct. Mol. Biol. 18, 299-305 (2010); Iacovoni et al. EMBO J. 29, 1446-1457 (2010)), BLESS (Crosetto et al. Nat. Methods 10, 361-365 (2013); Ran et al. Nature 520, 186-191 (2015); Slaymaker et al. Science 351, 84-88 (2016)), GUIDEseq (Tsai et al. Nat. Biotech 33, 187-197 (2015)), Digenome-seq (Kim et al. Nat. Methods 12, 237-43 (2015)), IDLV-mediated DNA break capture (Wang et al. Nat. Biotechnol. 33, 179-186 (2015), HTGTS (Frock et al. Nat. Biotechnol. 33, 179-186 (2015)), End-Seq (Canela et al. Mol. Cell 63, 898-911 (2016), and DSBCapture (Lensing et al. Nat. Methods 13, 855-857 (2016). Additional methods that may be used to assess target cleavage efficiency include SITE-Seq (Cameron et al. Nature Methods, 14, 600-606 (2017), and CIRCLE-seq (Tsai et al. Nature Methods 14, 607-614 (2017)).

Methods useful for assessing Cpf1 RNase activity include those disclosed in Zhong et al. Nature Chemical Biology Jun. 19, 2017 doi: 10.1038/NCHEMBIO.2410. Increased RNase activity and the ability to excise multiple CRISPR RNAs (crRNA) from a single RNA polymerase II-driven RNA transcript can simplify modification of multiple genomic targets and can be used to increase the efficiency of Cpf1-mediated editing.

BLISS: Other suitable assays include those described in Yan et al. ("BLISS: quantitative and versatile genome-wide profiling of DNA breaks in situ", BioRxiv, Dec. 4, 2016, doi: http://dx.doi.org/10.1101/091629) describe a versatile, sensitive and quantitative method for detecting DSBs applicable to low-input specimens of both cells and tissues that is scalable for high-throughput DSB mapping in multiple samples. Breaks Labeling In Situ and Sequencing (BLISS), features efficient in situ DSB labeling in fixed cells or tissue sections immobilized onto a solid surface, linear amplification of tagged DSBs via T7-mediated in vitro transcription (IVT) for greater sensitivity, and accurate DSB quantification by incorporation of unique molecular identifiers (UMIs).

Curtain. A further method, has been developed which may also be useful in assessing certain parameters disclosed herein. The method allowing on target and off target cutting of a nuclease to be assessed in a direct and unbiased way using in vitro cutting of immobilized nucleic acid molecules. Further reference is made to International Patent Application No. PCT/US2017/028009 entitled "Unbiased Detection of Nucleic Acid Modifictions" filed on Jun. 16, 2017.

This method may also be used to select a suitable guide RNA. The method allows the detection of a nucleic acid modification, by performing the following steps: i) contacting one or more nucleic acid molecules immobilized on a solid support (immobilized nucleic acid molecules) with an agent capable of inducing a nucleic acid modification; and ii) sequencing at least part of said one or more immobilized nucleic acid molecules that comprises the nucleic acid modification using a primer specifically binding to a primer binding site. This method further allows the selection of a guide RNA from a plurality of guide RNAs specific for a selected target sequence. In particular embodiments, the method comprises contacting a plurality of nucleic acid molecules immobilized on a solid support (immobilized nucleic acid molecules) with a plurality of RNA-guided nuclease complexes capable of inducing a nucleic acid break, said plurality of RNA-guided nuclease complexes comprising a plurality of different guide RNA's, thereby inducing one or more nucleic acid breaks; attaching an adapter comprising a primer binding site to said one or more immobilized nucleic acid molecules comprising a nucleic acid break; sequencing at least part of said one or more immobilized nucleic acid molecules comprising a nucleic acid break using a primer specifically binding to said primer binding site; and selecting a guide RNA based on location and/or amount of said one or more breaks.

In particular embodiments, the method comprises determining one or more locations in said one or more immobilized nucleic acid molecules comprising a break other than a location comprising said selected target sequence (off-target breaks) and selecting a guide RNA based on said one or more locations. In particular embodiments, step v comprises determining a number of sites in said one or more immobilized nucleic acid molecules comprising off-target breaks and selecting a guide RNA based on said number of sites. In a further embodiment, step iv comprises both determining the location of off-targets breaks and the number of locations of off-target breaks.

Safety
Select Protein with Shortest Half-Life
Inherent Half-Life of the Effector Protein The extended presence of an effector protein after having performed its function at the target site is a potential safety concern, both for off-target effects and direct toxicity of the effector protein. It has been reported that upon direct delivery to the cell by LNP, CRISPR effector proteins degrade rapidly within the cell (Kim et al. Genome Res. 2014 June; 24(6): 1012-1019). Where the effector protein is to be expressed from a plasmid, strategies to actively reduce the half-life of the protein may be of interest.

Use of Destabilized Domains

In certain embodiments, the methods provided herein involve the use of a Cpf1 effector protein which is associated with or fused to a destabilization domain (DD). The technology relating to the use of destabilizing domains is described in detail in WO2016/106244, which is incorporated by reference herein.

Destabilizing domains (DD) are domains which can confer instability to a wide range of proteins; see, e.g., Miyazaki, J Am Chem Soc. Mar. 7, 2012; 134(9): 3942-3945, and Chung H Nature Chemical Biology Vol. 11 Sep. 2015 pgs 713-720, incorporated herein by reference. DD can be associated with, e.g., fused to, advantageously with a linker, to a CRISPR enzyme, whereby the DD can be stabilized in the presence of a ligand and when there is the absence thereof the DD can become destabilized, whereby the CRISPR enzyme is entirely destabilized, or the DD can be stabilized in the absence of a ligand and when the ligand is present the DD can become destabilized; the DD allows the Cpf1 effector to be regulated or controlled, thereby providing means for regulation or control of the system. For instance, when a protein of interest is expressed as a fusion with the DD tag, it is destabilized and rapidly degraded in the cell, e.g., by proteasomes. Thus, absence of stabilizing ligand leads to a DD-associated Cpf1 being degraded. Peak activity of the Cpf1 effector is relevant to reduce off-target effects and for the general safety of the system. Advantages of the DD system include that it can be dosable, orthogonal (e.g., a ligand only affects its cognate DD so two or more systems can operate independently), transportable (e.g., may work in different cell types or cell lines) and allows for temporal control.

Suitable DD—stabilizing ligand pairs are known in the art and also described in WO2016/106244. The size of Destabilization Domain varies but is typically approx.-approx. 100-300 amino acids in size. Suitable examples include ER50 and/or DHFR50. A corresponding stabilizing ligand for ER50 is, for example, 4HT or CMP8. In some embodiments, one or two DDs may be fused to the N-terminal end of the CRISPR enzyme with one or two DDs fused to the C-terminal of the CRISPR enzyme. While the DD can be provided directly at N and/or C terminal(s) of the Cpf1 effector protein, they can also be fused via a linker, such as a GlySer linker, or an NLS and/or NES. A commercially available DD system is the CloneTech, ProteoTuner™ system; the stabilizing ligand is Shield1. In some embodiments, the stabilizing ligand is a 'small molecule', preferably it is cell-permeable and has a high affinity for its corresponding DD.

Select Least Immunogenic RNP

When administering an agent to a mammal, there is always the risk of an immune response to the agent and/or its delivery vehicle. Circumventing the immune response is a major challenge for most delivery vehicles. Viral vectors, which express immunogenic epitopes within the organism typically induce an immune response. Nanoparticle and lipid-based vectors to some extent address this problem. Yin et al. demonstrate a therapeutic approach combining viral delivery of the guide RNA with lipid nanoparticle-mediated delivery of the CRISPR effector protein (Nature Biotechnology 34:328-33(2016)). Ziris et al. describes cationin-lipid mediated delivery of Cas9:guideRNA nuclease complexes to cells. The CRISPR effector proteins, which are of bacterial origin, also inherently carry the risk of eliciting an immune response. This may be addressed by humanizing the Cpf1 effector protein.

Introduce Modifications in Guide RNA to Minimize Immunogenicity

Chemical modifications of RNAs have been used to avoid reactions of the innate immune system. Judge et al. (2006) demonstrated that immune stimulation by synthetic siRNA can be completely abrogated by selective incorporation of 2'-O-methyl (2'OMe) uridine or guanosine nucleosides into one strand of the siRNA duplex (Mol. Ther., 13 (2006), pp. 494-505). Cekaite et al. (J. Mol. Biol., 365 (2007), pp. 90-108) observed that replacement of only uridine bases of siRNA with either 2'-fluoro or 2'-O-methyl modified counterparts abrogated upregulation of genes involved in the regulation of the immune response. Similarly, Hendel et al. tested sgRNAs with both backbone and sugar modifications that confer nuclease stability and can reduce immunostimulatory effects (Hendel et al., Nat. Biotechnol., 33 (2015), pp. 985-989).

Accordingly, in particular embodiments, the methods comprise modifying the guide RNA so as to minimize immunogenicity using one or more of these methods.

Identify Optimal Dosage to Minimize Toxicity and Maximize Specificity

It is generally accepted that the dosage of CRISPR components will be relevant to toxicity and specificity of the system (Pattanayak et al. Nat Biotechnol. 2013 September; 31(9): 839-843). Hsu et al. (Nat Biotechnol. 2013 September; 31(9): 827-832) demonstrated that the dosage of SpCas9 and sgRNA can be titrated to address these issues. In certain example embodiments, toxicity is minimized by saturating complex with guide by either pre-forming complex, putting guide under control of a strong promoter, or via timing of delivery to ensure saturating conditions available during expression of the effector protein.

Delivery Methods

In some embodiments, the one or more components of the CRISPR system described herein may be delivered in various form, such as combinations of DNA/RNA or RNA/RNA or protein/RNA. For example, the Cpf1 may be delivered as a DNA-coding polynucleotide or an RNA-coding polynucleotide or as a protein. The guide may be delivered as a DNA-coding polynucleotide or an RNA. All possible combinations are envisioned, including mixed forms of delivery.

In some aspects, the invention provides methods comprising delivering one or more polynucleotides, such as or one or more vectors as described herein, one or more transcripts thereof, and/or one or proteins transcribed therefrom, to a host cell.

Vectors

Conventional viral and non-viral based gene transfer methods can be used to introduce nucleic acids in mammalian cells or target tissues. Such methods can be used to administer nucleic acids encoding components of a nucleic acid-targeting system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

Plasmid delivery involves the cloning of a guide RNA into a CRISPR effector protein expressing plasmid and transfecting the DNA in cell culture. Plasmid backbones are available commercially and no specific equipment is required. They have the advantage of being modular, capable of carrying different sizes of CRISPR effector coding sequences (including those encoding larger sized proteins) as well as selection markers. Both an advantage of plasmids is that they can ensure transient, but sustained expression. However, delivery of plasmids is not straightforward such that in vivo efficiency is often low. The sustained expression can also be disadvantageous in that it can increase off-target editing. In addition, excess build-up of the CRISPR effector protein can be toxic to the cells. Finally, plasmids always hold the risk of random integration of the dsDNA in the host genome, more particularly in view of the double-stranded breaks being generated (on and off-target).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). This is discussed more in detail below.

The advantages and disadvantages of Plasmid delivery are described by Plasmid delivery involves the cloning of a guide RNA into a CRISPR effector protein expressing plasmid and transfecting the DNA in cell culture. Plasmid backbones are available commercially and no specific equipment is required. They have the advantage of being modular, capable of carrying different sizes of CRISPR effector coding sequences (including those encoding larger sized proteins) as well as selection markers. Both an advantage of plasmids is that they can ensure transient, but sustained expression. However, delivery of plasmids is not straightforward such that in vivo efficiency is often low. The sustained expression can also be disadvantageous in that it can increase off-target editing. In addition, excess build-up of the CRISPR effector protein can be toxic to the cells. Finally, plasmids always hold the risk of random integration of the dsDNA in the host genome, more particularly in view of the double-stranded breaks being generated (on and off-target).The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). This is discussed more in detail below.

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

The invention provides AAV that contains or consists essentially of an exogenous nucleic acid molecule encoding a CRISPR system, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cas9 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator ... Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas9 and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator ... Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn). In another embodiment, multiple gRNA expression cassettes along with the Cas9 expression cassette can be delivered in a high-capacity adenoviral vector (HCAdV), from which all AAV coding genes have been removed. See e.g, Schiwon et al., "One-Vector System for Multiplexed CRISPR/Cas9 against Hepatitis B Virus cccDNA Utilizing High-Capacity Adenoviral Vectors" Mol Ther Nucleic Acids. 2018 Sep. 7; 12: 242-253; and Ehrke-Schulz et al., "CRISPR/Cas9 delivery with one single adenoviral vector devoid of all viral genes" Sci Rep. 2017; 7: 17113. Additional methods for the delivery of nucleic acids to cells are known to those skilled in the art. See, for example, US20030087817, incorporated herein by reference.

Also contemplated is delivery by dual vector systems. In one embodiment, expression cassettes of Cas9 and gRNA can be delivered via a dual vector system. Such systems can include, for example, a first AAV vector encoding a gRNA and an N-terminal Cas9 and a second AAV vector containing a C-terminal Cas9. See, e.g. Moreno et al., "In Situ Gene Therapy via AAV—CRISPR-Cas9-Mediated Targeted Gene Regulation" Mol Ther. 2018 Jul. 5; 26(7):1818-1827. In another embodiment, Cas9 protein can be separated into two parts that are expressed individually and reunited in the cell by various means, including use of 1) the gRNA as a scaffold for Cas9 assembly; 2) the rapamycin-controlled FKBP/FRB system; 3) the light-regulated Magnet system; or 4) inteins. See, e.g. Schmelas et al., "Split Cas9, Not Hairs—Advancing the Therapeutic Index of CRISPR Technology" Biotechnol J. 2018 September; 13(9):e1700432. doi: 10.1002/biot.201700432. Epub 2018 Feb. 2.

In some embodiments, an AAV vector can include additional sequence information encoding sequences that facilitate transduction or that assist in evasion of the host immune system. In one embodiment, CRISPR-Cas9 can be delivered to astrocytes using an AAV vector that includes a synthetic surface peptide for transduction of astrocytes. See, e.g. Kunze et al., "Synthetic AAV/CRISPR vectors for blocking HIV-1 expression in persistently infected astrocytes" Glia. 2018 February; 66(2):413-427. In another embodiment, CRISPR-Cas9 can be delivered in a capsid engineered AAV, for example an AAV that has been engineered to include "chemical handles" on the AAV surface and be complexed with lipids to produce a "cloaked AAV" that is resistant to endogenous neutralizing antibodies in the host. See, e.g. Katrekar et al., "Oligonucleotide conjugated multi-functional adeno-associated viruses" Sci Rep. 2018; 8: 3589.

In another embodiment, Cocal vesiculovirus envelope pseudotyped retroviral vector particles are contemplated (see, e.g., US Patent Publication No. 20120164118 assigned to the Fred Hutchinson Cancer Research Center). Cocal virus is in the Vesiculovirus genus, and is a causative agent of vesicular stomatitis in mammals. Cocal virus was originally isolated from mites in Trinidad (Jonkers et al., Am. J. Vet. Res. 25:236-242 (1964)), and infections have been identified in Trinidad, Brazil, and Argentina from insects, cattle, and horses. Many of the vesiculoviruses that infect mammals have been isolated from naturally infected arthropods, suggesting that they are vector-borne. Antibodies to vesiculoviruses are common among people living in rural areas where the viruses are endemic and laboratory-acquired; infections in humans usually result in influenza-like symptoms. The Cocal virus envelope glycoprotein shares 71.5% identity at the amino acid level with VSV-G Indiana, and phylogenetic comparison of the envelope gene of vesiculoviruses shows that Cocal virus is serologically distinct from, but most closely related to, VSV-G Indiana strains among the vesiculoviruses. Jonkers et al., Am. J. Vet. Res. 25:236-242 (1964) and Travassos da Rosa et al., Am. J. Tropical Med. & Hygiene 33:999-1006 (1984). The Cocal vesiculovirus envelope pseudotyped retroviral vector particles may include for example, lentiviral, alpharetroviral, betaretroviral, gammaretroviral, deltaretroviral, and epsilonretroviral vector particles that may comprise retroviral Gag, Pol, and/or one or more accessory protein(s) and a Cocal vesiculovirus envelope protein. Within certain aspects of these embodiments, the Gag, Pol, and accessory proteins are lentiviral and/or gammaretroviral.

In some embodiments, a host cell is transiently or non-transiently transfected with one or more vectors described herein. In some embodiments, a cell is transfected as it naturally occurs in a subject optionally to be reintroduced therein. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr–/–, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments it is envisaged to introduce the RNA and/or protein directly to the host cell. For instance, the CRISPR effector can be delivered as CRISPR effector-encoding mRNA together with an in vitro transcribed guide RNA. Such methods can reduce the time to ensure effect of the CRISPR effector protein and further prevents long-term expression of the CRISPR system components.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver Cpf1 and gRNA (and, for instance, HR repair template) into cells using liposomes or nanoparticles. Thus, delivery of the CRISPR enzyme, such as a Cpf1 and/or delivery of the RNAs of the invention may be in RNA form and via microvesicles, liposomes or particle or particles. For example, Cpf1 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via particles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purified and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA) filled with phosphate-buffered saline (PBS) or free Tocsi-BACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 μmol of CRISPR Cas targeted to the brain may be contemplated. Zou et al. ((HUMAN GENE THERAPY 22:465-475 (April 2011)) describes a method of lentiviral-mediated delivery of short-hairpin RNAs targeting PKC7 for in vivo gene silencing in the spinal cord of rats. Zou et al. administered about 10 μl of a recombinant lentivirus having a titer of 1×10' transducing units (TU)/ml by an intrathecal catheter. A similar dosage of CRISPR Cas expressed in a lentiviral vector targeted to the brain may be contemplated for humans in the present invention, for example, about 10-50 ml of CRISPR Cas targeted to the brain in a lentivirus having a titer of 1×10' transducing units (TU)/ml may be contemplated.

Vector delivery, e.g., plasmid, viral delivery: The CRISPR enzyme, for instance a Cpf1, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Cpf1 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein, the delivery is via an adenovirus, which may be at a single booster dose containing at least 1×105 particles (also referred to as particle units, pu) of adenoviral vector. In an embodiment herein, the dose preferably is at least about $1\times10^6$ particles (for example, about $1\times10^6$-$1\times10^{12}$ particles), more preferably at least about $1\times10^7$ particles, more preferably at least about $1\times10^8$ particles (e.g., about $1\times10^8 1\times10^{11}$ particles or about $1\times10^8$-$1\times10^{12}$ particles), and most preferably at least about $1\times100$ particles (e.g., about $1\times10^9$-$1\times10^{10}$ particles or about $1\times10^9$-$1\times10^{12}$ particles), or even at least about $1\times10^{10}$ particles (e.g., about $1\times10^{10}$-$1\times10^{12}$ particles) of the adenoviral vector. Alternatively, the dose comprises no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ articles). Thus, the dose may contain a single dose of adenoviral vector with, for example, about $1\times10^6$ particle units (pu), about $2\times10^6$ pu, about $4\times10^6$ pu, about $1\times10^7$ pu, about $2\times10^7$ pu, about $4\times10^7$ pu, about $1\times10^8$ pu, about $2\times10^8$ pu, about $4\times10^8$ pu, about $1\times10^9$ pu, about $2\times10^9$ pu, about $4\times10^9$ pu, about $1\times10^{10}$ pu, about $2\times10^{10}$ pu, about $4\times10^{10}$ pu, about $1\times10^{11}$ pu, about $2\times10^{11}$ pu, about $4\times10^{11}$ pu, about $1\times10^{12}$ pu, about $2\times10^{12}$ pu, or about $4\times10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1\times10^{10}$ to about $1\times10^{10}$ functional AAV/ml solution. The dosage may be adjusted to balance the therapeutic benefit against any side effects. In an embodiment herein, the AAV dose is generally in the range of concentrations of from about $1\times10^5$ to $1\times10^{50}$ genomes AAV, from about $1\times10^8$ to $1\times10^{20}$ genomes AAV, from about $1\times10^{10}$ to about $1\times10^{16}$ genomes, or about $1\times10^{11}$ to about $1\times10^{16}$ genomes AAV. A human dosage may be about $1\times10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

Among vectors that may be used in the practice of the invention, integration in the host genome of a cell is possible with retrovirus gene transfer methods, often resulting in long term expression of the inserted transgene. In a preferred embodiment the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that may be used in the practice of the invention include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700). Zou et al. administered about 10 µl of a recombinant lentivirus having a titer of $1\times10^9$ transducing units (TU)/ml by an intrathecal catheter. These sort of dosages can be adapted or extrapolated to use of a retroviral or lentiviral vector in the present invention.

Vector Packaging of CRISPR Proteins

Described herein are suitable methods of packaging and/or otherwise including polynucleotides and/or polypeptides of the CRISPR-Cas system described in greater detail elsewhere herein into a vector, such as any of those described herein (including but not limited to viral vectors) to mediate genome modification in vivo. In some embodiments, described herein are methods of packaging one or more polynucleotides of the CRISPR-Cas system described herein into a viral particle, which can be subsequently used to deliver the packaged polynucleotide to a subject. In some embodiments, NHEJ-mediate gene modification (e.g. knock out, knock in, and gene editing) can be achieved.

The one or more CRISPR-Cas system polynucleotides described elsewhere herein can be included in a single viral vector, vector containing two or more expression cassettes, and/or double virus vector. In some embodiments, the vector can contain a promoter operably coupled to a Cas polypeptide coding polynucleotide and a terminator. In some embodiments, the vector can contain a promoter operably coupled to one or more guide polynucleotides. In some vector systems the vector systems can include a first vector having a promoter operably coupled to a Cas polypeptide coding polynucleotide, 1-100 more additional vectors each having 1-100 or more guide polynucleotides each operably coupled to one or more promoters and optionally a terminator sequence. In some embodiments, the vector containing the Cas polypeptide encoding polynucleotide also includes one or more guide polynucleotides. The vector system can also include one or more vectors that include an expression cassette capable of driving expression of a Cas polypeptide. The Cas polypeptide can be any Cas polypeptide, such as any of those described herein. In some embodiments, the Cas polypeptide is a Cas 12 polypeptide or a Cas9 polypeptide. In some embodiments, the vector can be configured to drive NHEJ recombination. In some embodiments, the vector can be configured to drive homology-directed repair.

In addition to the single and double virus vector approaches described above, an additional vector can be used to deliver a homology-directed repair template.

The promoter used to drive Cpf1 coding nucleic acid molecule expression can include: (a) AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cpf1. (b) For ubiquitous expression, promoters that can be used include: CMV, CAG, CBh, PGK, SV40, Ferritin heavy or light chains, etc.

In some embodiments, a SynapsinI promoter can be used for neuron specific expression. In some embodiments, a CaMKIIalpha promoter can be used for excitatory neuron specific expression. In some embodiments, GAD67 or GAD65 or VGAT promoter can be used for GABAergic neuron specific expression.

In some embodiments, an albumin promoter can be used for liver specific expression.

In some embodiments, an SP-B promoter can be used for lung specific expression.

In some embodiments, an ICAM promoter can be used for endothelial cell specific expression.

In some embodiments, an IFN beta or CD45 promoter can be used for hematopoietic cell specific expression.

In some embodiments, an OG-2 promoter can be used for osteoblast specific expression.

The promoter used to drive guide RNA can include: one or more Pol III promoters, such as U6 or H1. In some embodiments, the promoter used to drive gRNA expression can be a Pol II promoter. In some embodiments, one or more intronic cassettes can be used to express gRNA Additional suitable promoters to drive expression of one or more components of the CRISPR-Cas systems herein are described elsewhere herein.

Adeno Associated Virus (AAV)

Cpf1 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cpf1 can be driven by a cell-type specific promoter. For example, liver-specific expression might use the Albumin promoter and neuron-specific expression (e.g. for targeting CNS disorders) might use the Synapsin I promoter.

In terms of in vivo delivery, AAV is advantageous over other viral vectors for a couple of reasons:

Low toxicity (this may be due to the purification method not requiring ultra-centrifugation of cell particles that can activate the immune response) and Low probability of causing insertional mutagenesis because it doesn't integrate into the host genome.

AAV has a packaging limit of 4.5 or 4.75 Kb. This means that Cpf1 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore, embodiments of the invention include utilizing homologs of Cpf1 that are shorter. Non-limiting examples are shown in Table 6.

TABLE 6

| Species | Cas9 Size (nt) |
|---|---|
| *Corynebacter diphtheriae* | 3252 |
| *Eubacterium ventriosum* | 3321 |
| *Streptococcus pasteurianus* | 3390 |
| *Lactobacillus farciminis* | 3378 |
| *Sphaerochaeta globus* | 3537 |
| *Azospirillum* B510 | 3504 |
| *Gluconacetobacter diazotrophicus* | 3150 |
| *Neisseria cinerea* | 3246 |
| *Roseburia intestinalis* | 3420 |
| *Parvibaculum lavamentivorans* | 3111 |

TABLE 6-continued

| Species | Cas9 Size (nt) |
|---|---|
| *Staphylococcus aureus* | 3159 |
| *Nitratifractor salsuginis* DSM 16511 | 3396 |
| *Campylobacter lari* CF89-12 | 3009 |
| *Campylobacter jejuni* | 2952 |
| *Streptococcus thermophilus* LMD-9 | 3396 | rAAV vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

These species are therefore, in general, preferred Cpf1 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV 1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows (Table 7):

TABLE 7

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 ug of psPAX2 (gag/pol/rev/tat). Transfection was done in 4 mL OptiMEM with a cationic lipid delivery agent (50 uL Lipofectamine 2000 and 100 ul Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 um low protein binding (PVDF) filter. They were then spun in an ultracentrifuge for 2 hours at 24,000 rpm. Viral pellets were resuspended in 50 ul of DMEM overnight at 4 C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of 2.5×106 CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos.

US20110293571; US20110293571, US20040013648, US20070025970, US20090111106 and U.S. Pat. No. 7,259, 015.

Use of Minimal Promoters

The present application provides a vector for delivering an effector protein and at least one CRISPR guide RNA to a cell comprising a minimal promoter operably linked to a polynucleotide sequence encoding the effector protein and a second minimal promoter operably linked to a polynucleotide sequence encoding at least one guide RNA, wherein the length of the vector sequence comprising the minimal promoters and polynucleotide sequences is less than 4.4 Kb. In an embodiment, the vector is an AAV vector. In another embodiment, the effector protein is a CRISPR enzyme. In a further embodiment, the CRISPR enzyme is SaCas9, Cpf1, Cas13b or C2c2.

In a related aspect, the invention provides a lentiviral vector for delivering an effector protein and at least one CRISPR guide RNA to a cell comprising a promoter operably linked to a polynucleotide sequence encoding Cpf1 and a second promoter operably linked to a polynucleotide sequence encoding at least one guide RNA, wherein the polynucleotide sequences are in reverse orientation.

In another aspect, the invention provides a method of expressing an effector protein and guide RNA in a cell comprising introducing the vector according any of the vector delivery systems disclosed herein. In an embodiment of the vector for delivering an effector protein, the minimal promoter is the Mecp2 promoter, tRNA promoter, or U6. In a further embodiment, the minimal promoter is tissue specific.

Dosage of Vectors

In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^0$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^{11}$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^1$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In some embodiments, the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 µg to about 10 µg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

The dosage used for the compositions provided herein include dosages for repeated administration or repeat dosing. In particular embodiments, the administration is repeated within a period of several weeks, months, or years. Suitable assays can be performed to obtain an optimal dosage regime. Repeated administration can allow the use of lower dosage, which can positively affect off-target modifications.

RNA Delivery

In particular embodiments, RNA based delivery is used. In these embodiments, mRNA of the CRISPR effector protein is delivered together with in vitro transcribed guide RNA. Liang et al. describes efficient genome editing using RNA based delivery (Protein Cell. 2015 May; 6(5): 363-372).

RNA delivery: The CRISPR enzyme, for instance a Cpf1, and/or any of the present RNAs, for instance a guide RNA, can also be delivered in the form of RNA. Cpf1 mRNA can be generated using in vitro transcription. For example, Cpf1 mRNA can be synthesized using a PCR cassette containing the following elements: T7_promoter-kozak sequence (GC-CACC)-Cpf1-3' UTR from beta globin-polyA tail (a string of 120 or more adenines). The cassette can be used for transcription by T7 polymerase. Guide RNAs can also be transcribed using in vitro transcription from a cassette containing T7_promoter-GG-guide RNA sequence.

To enhance expression and reduce possible toxicity, the CRISPR enzyme-coding sequence and/or the guide RNA can be modified to include one or more modified nucleoside e.g. using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

RNP

In particular embodiments, pre-complexed guide RNA and CRISPR effector protein are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4): 910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly, these polypeptides can be used for the delivery of CRISPR-effector based RNPs in eukaryotic cells.

Indeed, RNA delivery is a useful method of in vivo delivery. It is possible to deliver Cpf1 and gRNA (and, for instance, HR repair template) into cells using liposomes or particles. Thus, delivery of the CRISPR enzyme, such as a Cpf1 and/or delivery of the RNAs of the invention may be in RNA form and via microvesicles, liposomes or particles. For example, Cpf1 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purified and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, CA) filled with phosphate-buffered saline (PBS) or free Tocsi-BACE or Toc-siBACE/HDL and connected with Brain Infusion Kit 3 (Alzet). A brain-infusion cannula was placed about 0.5 mm posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR Cas conjugated to α-tocopherol and co-administered with HDL targeted to the brain may be contemplated for humans in the present invention, for example, about 3 nmol to about 3 µmol of CRISPR Cas targeted to the brain may be contemplated.

Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of 1×109 transducing units (TU)/ml by an intrathecal catheter. A similar dosage of CRISPR Cas expressed in a lentiviral vector may be contemplated for humans in the present invention, for example, about 10-50 ml of CRISPR Cas in a lentivirus having a titer of 1×109 transducing units (TU)/ml may be contemplated. A similar dosage of CRISPR Cas expressed in a lentiviral vector targeted to the brain may be contemplated for humans in the present invention, for example, about 10-50 ml of CRISPR Cas targeted to the brain in a lentivirus having a titer of 1×109 transducing units (TU)/ml may be contemplated.

Anderson et al. (US 20170079916) provides a modified dendrimer nanoparticle for the delivery of therapeutic, prophylactic and/or diagnostic agents to a subject, comprising: one or more zero to seven generation alkylated dendrimers; one or more amphiphilic polymers; and one or more therapeutic, prophylactic and/or diagnostic agents encapsulated therein. One alkylated dendrimer may be selected from the group consisting of poly(ethyleneimine), poly(polyproylenimine), diaminobutane amine polypropylenimine tetramine and poly(amido amine). The therapeutic, prophylactic and diagnostic agent may be selected from the group consisting of proteins, peptides, carbohydrates, nucleic acids, lipids, small molecules and combinations thereof.

Anderson et al. (US 20160367686) provides a compound of Formula (I):

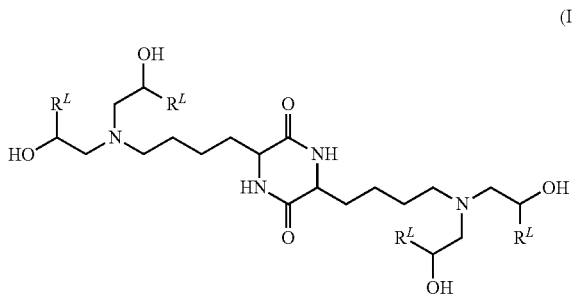

(I)

and salts thereof, wherein each instance of $R^L$ is independently optionally substituted C6-C40 alkenyl, and a composition for the delivery of an agent to a subject or cell comprising the compound, or a salt thereof, an agent; and optionally, an excipient. The agent may be an organic molecule, inorganic molecule, nucleic acid, protein, peptide, polynucleotide, targeting agent, an isotopically labeled chemical compound, vaccine, an immunological agent, or an agent useful in bioprocessing. The composition may further comprise cholesterol, a PEGylated lipid, a phospholipid, or an apolipoprotein.

Anderson et al. (US20150232883) provides a delivery particle formulations and/or systems, preferably nanoparticle delivery formulations and/or systems, comprising (a) a CRISPR-Cas system RNA polynucleotide sequence; or (b) Cas9; or (c) both a CRISPR-Cas system RNA polynucleotide sequence and Cas9; or (d) one or more vectors that contain nucleic acid molecule(s) encoding (a), (b) or (c), wherein the CRISPR-Cas system RNA polynucleotide sequence and the Cas9 do not naturally occur together. The delivery particle formulations may further comprise a surfactant, lipid or protein, wherein the surfactant may comprise a cationic lipid.

Anderson et al. (US20050123596) provides examples of microparticles that are designed to release their payload when exposed to acidic conditions, wherein the microparticles comprise at least one agent to be delivered, a pH triggering agent, and a polymer, wherein the polymer is selected from the group of polymethacrylates and polyacrylates.

Anderson et al (US 20020150626) provides lipid-protein-sugar particles for delivery of nucleic acids, wherein the polynucleotide is encapsulated in a lipid-protein-sugar matrix by contacting the polynucleotide with a lipid, a protein, and a sugar; and spray drying mixture of the polynucleotide, the lipid, the protein, and the sugar to make microparticles.

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Particles

In some aspects or embodiments, a composition comprising a delivery particle formulation may be used. In some aspects or embodiments, the formulation comprises a CRISPR complex, the complex comprising a CRISPR protein and a guide which directs sequence-specific binding of the CRISPR complex to a target sequence. In some embodiments, the delivery particle comprises a lipid-based particle, optionally a lipid nanoparticle, or cationic lipid and optionally biodegradable polymer. In some embodiments, the cationic lipid comprises 1,2-dioleoyl-3-trimethylammonium-propane (DOTAP). In some embodiments, the hydrophilic polymer comprises ethylene glycol or polyethylene glycol. In some embodiments, the delivery particle further comprises a lipoprotein, preferably cholesterol. In some embodiments, the delivery particles are less than 500 nm in diameter, optionally less than 250 nm in diameter, optionally less than 100 nm in diameter, optionally about 35 nm to about 60 nm in diameter.

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100-nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

In terms of this invention, it is preferred to have one or more components of CRISPR complex, e.g., CRISPR enzyme or mRNA or guide RNA delivered using nanoparticles or lipid envelopes. Other delivery systems or vectors are may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. It will be appreciated that reference made herein to particles or nanoparticles can be interchangeable, where appropriate.

It will be understood that the size of the particle will differ depending as to whether it is measured before or after loading. Accordingly, in particular embodiments, the term "nanoparticles" may apply only to the particles preloading.

Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarization interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

CRISPR enzyme mRNA and guide RNA may be delivered simultaneously using particles or lipid envelopes; for instance, CRISPR enzyme and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano.2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1×PBS; and separately, DOTAP, DMPC, PEG, and cholesterol as applicable for the formulation are dissolved in alcohol, e.g., 100% ethanol; and, the two solutions are mixed together to form particles containing the complexes).

Nucleic acid-targeting effector proteins (such as a Type V protein such Cpf1) mRNA and guide RNA may be delivered simultaneously using particles or lipid envelopes. Examples of suitable particles include but are not limited to those described in U.S. Pat. No. 9,301,923.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

Liu et al. (US 20110212179) provides bimodal porous polymer microspheres comprising a base polymer, wherein the particle comprises macropores having a diameter ranging from about 20 to about 500 microns and micropores having a diameter ranging from about 1 to about 70 microns, and wherein the microspheres have a diameter ranging from about 50 to about 1100 microns.

Berg et al. (US20160174546) a nanolipid delivery system, in particular a nano-particle concentrate, comprising: a composition comprising a lipid, oil or solvent, the composition having a viscosity of less than 100 cP at 25.degrees C. and a Kauri Butanol solvency of greater than 25 Kb; and at least one amphipathic compound selected from the group consisting of an alkoxylated lipid, an alkoxylated fatty acid, an alkoxylated alcohol, a heteroatomic hydrophilic lipid, a heteroatomic hydrophilic fatty acid, a heteroatomic hydrophilic alcohol, a diluent, and combinations thereof, wherein the compound is derived from a starting compound having a viscosity of less than 1000 cP at 50.degrees C., wherein the concentrate is configured to provide a stable nano emulsion having a D50 and a mean average particle size distribution of less than 100 nm when diluted.

Liu et al. (US 20140301951) provides a protocell nanostructure comprising: a porous particle core comprising a plurality of pores; and at least one lipid bilayer surrounding the porous particle core to form a protocell, wherein the protocell is capable of loading one or more cargo components to the plurality of pores of the porous particle core and releasing the one or more cargo components from the porous particle core across the surrounding lipid bilayer.

Chromy et al. (US 20150105538) provides methods and systems for assembling, solubilizing and/or purifying a membrane associated protein in a nanolipoprotein particle, which comprise a temperature transition cycle performed in presence of a detergent, wherein during the temperature transition cycle the nanolipoprotein components are brought to a temperature above and below the gel to liquid crystalling transition temperature of the membrane forming lipid of the nanolipoprotein particle.

Bader et al. (US 20150250725), provides a method for producing a lipid particle comprising the following: i) providing a first solution comprising denatured apolipoprotein, ii) adding the first solution to a second solution comprising at least two lipids and a detergent but no apolipoprotein, and iii) removing the detergent from the solution obtained in ii) and thereby producing a lipid particle.

Mirkin et al., (US20100129793) provides a method of preparing a composite particle comprising the steps of (a) admixing a dielectric component and a magnetic component to form a first intermediate, (b) admixing the first intermediate and gold seeds to form a second intermediate, and (c) forming a gold shell on the second intermediate by admixing the second intermediate with a gold source and a reducing agent to form said composite particle.

Other gold nanoparticle-based systems are also contemplated. In one embodiment, Cas9 RNP can be delivered in a vehicle composed of gold nanoparticles conjugated with DNA, which are complexed with donor DNA, Cas9 RNP, and the endosomal disruptive polymer PAsp(DET). See, e.g. Lee et al., "Nanoparticle delivery of Cas9 ribonucleoprotein and donor DNA in vivo induces homology-directed DNA repair" Nat Biomed Eng. 2017; 1: 889-901. In another embodiment, Cas9 RNP can be delivered into the cell cytoplasm and nucleus using arginine-functionalized gold nanoparticles. See, e.g. Mout et al., "Cytosolic and Nuclear Delivery of CRISPR/Cas9-ribonucleoprotein for Gene Editing Using Arginine Functionalized Gold Nanoparticles" Bio Protoc. 2017 Oct. 20; 7 (20).

In one embodiment, particles/nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5 (5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles/nanoparticles that can deliver RNA to a cancer cell to stop tumor growth developed by Dan Anderson's lab at MIT may be used/and or adapted to the CRISPR Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

The lipid particles developed by the Qiaobing Xu's lab at Tufts University may be used/adapted to the present delivery system for cancer therapy. See Wang et al., J. Control Release, 2017 Jan. 31. pii: 50168-3659(17)30038-X. doi: 10.1016/j.jconrel.2017.01.037. [Epub ahead of print]; Altmoglu et al., Biomater Sci., 4(12):1773-80, Nov. 15, 2016; Wang et al., PNAS, 113(11):2868-73 Mar. 15, 2016; Wang et al., PloS One, 10(11): e0141860. doi: 10.1371/journal.pone.0141860. eCollection 2015, Nov. 3, 2015; Takeda et al., Neural Regen Res. 10(5):689-90, May 2015; Wang et al., Adv. Healthc Mater., 3(9):1398-403, September 2014; and Wang et al., Agnew Chem Int Ed Engl., 53(11): 2893-8, Mar. 10, 2014.

US patent application 20110293703 relates to lipidoid compounds are also particularly useful in the administration of polynucleotides, which may be applied to deliver the CRISPR Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR Cas system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

Zhu et al. (US20140348900) provides for a process for preparing liposomes, lipid discs, and other lipid nanoparticles using a multi-port manifold, wherein the lipid solution stream, containing an organic solvent, is mixed with two or more streams of aqueous solution (e.g., buffer). In some aspects, at least some of the streams of the lipid and aqueous solutions are not directly opposite of each other. Thus, the process does not require dilution of the organic solvent as an additional step. In some embodiments, one of the solutions may also contain an active pharmaceutical ingredient (API). This invention provides a robust process of liposome manufacturing with different lipid formulations and different payloads. Particle size, morphology, and the manufacturing scale can be controlled by altering the port size and number of the manifold ports, and by selecting the flow rate or flow velocity of the lipid and aqueous solutions.

Cullis et al. (US 20140328759) provides limit size lipid nanoparticles with a diameter from 10-100 nm, in particular comprising a lipid bilayer surrounding an aqueous core. Methods and apparatus for preparing such limit size lipid nanoparticles are also disclosed.

Manoharan et al. (US 20140308304) provides cationic lipids of formula (II)

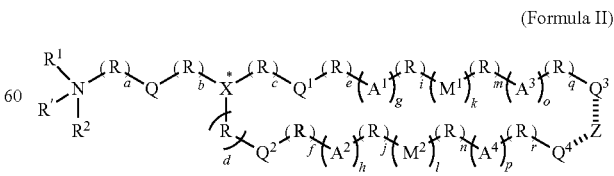

(Formula II)

or a salt thereof, wherein X is N or P; R' is absent, hydrogen, or alkyl; with respect to $R^1$ and $R^2$, (i) $R^1$ and $R^2$ are each, independently, optionally substituted alkyl, alkenyl, alkynyl, cycloalkyl, cycloalkylalkyl, heterocycle or $R^{10}$; (ii) $R^1$ and $R^2$, together with the nitrogen atom to which they are attached, form an optionally substituted heterocylic ring; or (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl with (a) the adjacent nitrogen atom and (b) the $(R)_a$ group adjacent to the nitrogen atom; each occurrence of R is, independently, —$(CR^3R^4)$—; each occurrence of $R^3$ and $R^4$ are, independently H, halogen, OH, alkyl, alkoxy, —NH.sub.2, alkylamino, or dialkylamino; or $R^3$ and $R^4$, together with the carbon atom to which they are directly attached, form a cycloalkyl group, wherein no more than three R groups in each chain attached to the atom X* are cycloalkyl; each occurrence of R.sup.10 is independently selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two $R^{10}$ groups; Q is absent or is —O—, —NH—, —S—, —C(O) O—, —OC(O)—, —C(O)N($R^4$)—, —N($R^5$)C(O)—, —S—S—, —OC(O)O—, —O—N.dbd.C($R^5$)—, —C($R^5$).dbd.N—O—, —OC(O)N($R^5$)—, —N($R^5$)C(O)N ($R^5$)—, —N($R^5$)C(O)O—, —C(O)S—, —C(S)O— or —C($R^5$).dbd.N—O—C(O)—; $Q^1$ and $Q^2$ are each, independently, absent, —O—, —S—, —OC(O)—, —C(O)O—, —SC(O)—, —C(O)S—, —OC(S)—, —C(S)O—, —S—S—, —C(O)(N$R^5$)—, —N($R^5$)C(O)—, —C(S)(N$R^5$)—, —N($R^5$)C(O)—, —N($R^5$)C(O)N($R^5$)—, or —OC(O)O—; $Q^3$ and $Q^4$ are each, independently, H, —$(CR^3R^4)$—, aryl, or a cholesterol moiety; each occurrence of $A^1$, $A^2$, $A^3$ and $A^4$ is, independently, —$(CR^5R^5$—$CR^5$.dbd.$CR^5)$—; each occurrence of $R^5$ is, independently, H or alkyl; $M^1$ and $M^2$ are each, independently, a biodegradable group (e.g., —OC (O)—, —C(O)O—, —SC(O)—, —C(O)S—, —OC(S)—, —C(S)O—, —S—S—, —C($R^5$).dbd.N—, —N.dbd.C ($R^5$)—, —C($R^5$).dbd.N—O—, —O—N.dbd.C($R^5$)—C(O) (N$R^5$)—, —N($R^5$)C(O)—, —C(S)(N$R^5$)—, —N($R^5$)C (O)—, —N($R^5$)C(O)N($R^5$)—, —OC(O)O—, —OSi($R^5$).sub.20-, —C(O)($CR^3R^4$)C(O)O—, or —OC(O) ($CR^3R^4$)C(O)—); Z is absent, alkylene or —O—P(O) (OH)—O—; each — attached to Z is an optional bond, such that when Z is absent, $Q^3$ and $Q^4$ are not directly covalently bound together; a is 1, 2, 3, 4, 5 or 6; b is 0, 1, 2, or 3; c, d, e, f, i, j, m, n, q and r are each, independently, 0, 1, 2, 3, 4, 5, 6, 7, 8, 9, or 10; g and h are each, independently, 0, 1 or 2; k and l are each, independently, 0 or 1, where at least one of k and l is 1; and o and p are each, independently, 0, 1 or 2, wherein $Q^3$ and $Q^4$ are each, independently, separated from the tertiary atom marked with an asterisk (X*) by a chain of 8 or more atoms. The cationic lipid can be used with other lipid components such as cholesterol and PEG-lipids to form lipid nanoparticles with oligonucleotides, to facilitate the cellular uptake and endosomal escape, and to knockdown target mRNA both in vitro and in vivo.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 µg/ml of LNP or CRISPR-Cas RNA in or associated with the LNP may be contemplated, especially for a formulation containing DLinKC2-DMA.

Preparation of LNPs and CRISPR Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ω-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, MO). The specific CRISPR Cas RNA may be encapsulated in LNPs containing DLinDAP, DLinDMA, DLinK-DMA, and DLinKC2-DMA (cationic lipid:DSPC: CHOL:PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a CRISPR-Cas system or components thereof.

Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate: DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-μm syringe filter.

Preassembled recombinant CRISPR-Cpf1 complexes comprising Cpf1 and crRNA may be transfected, for example by electroporation, resulting in high mutation rates and absence of detectable off-target mutations. Hur, J. K. et al, Targeted mutagenesis in mice by electroporation of Cpf1 ribonucleoproteins, Nat Biotechnol. 2016 Jun. 6. doi: 10.1038/nbt.3596. [Epub ahead of print].

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

In some embodiments, sugar-based particles may be used, for example GalNAc, as described herein and with reference to WO2014118272 (incorporated herein by reference) and Nair, J K et al., 2014, Journal of the American Chemical Society 136 (49), 16958-16961) and the teaching herein, especially in respect of delivery applies to all particles unless otherwise apparent. This may be considered to be a sugar-based particle and further details on other particle delivery systems and/or formulations are provided herein. GalNAc can therefore be considered to be a particle in the sense of the other particles described herein, such that general uses and other considerations, for instance delivery of said particles, apply to GalNAc particles as well. A solution-phase conjugation strategy may for example be used to attach triantennary GalNAc clusters (mol. wt. ~2000) activated as PFP (pentafluorophenyl) esters onto 5'-hexylamino modified oligonucleotides (5'-HA ASOs, mol. wt. ~8000 Da; Østergaard et al., Bioconjugate Chem., 2015, 26 (8), pp 1451-1455). Similarly, poly(acrylate) polymers have been described for in vivo nucleic acid delivery (see WO2013158141 incorporated herein by reference). In further alternative embodiments, pre-mixing CRISPR nanoparticles (or protein complexes) with naturally occurring serum proteins may be used in order to improve delivery (Akinc A et al, 2010, Molecular Therapy vol. 18 no. 7, 1357-1364).

Additional nanoparticle configurations are also contemplated. In another embodiment, Cas9 protein and sgRNA can be delivered into cells using "CRISPR-delivery particles," (CriPs), composed of nano-size complexes of Cas9 protein and sgRNA that are coated with an amphipathic peptide called Endo-Porter (EP) an amphipathic α-helical peptide composed of leucine and histidine residues that mediates entry into cells. See, e.g. Shen et al., "CRISPR-delivery particles targeting nuclear receptor-interacting protein 1 (Nrip1) in adipose cells to enhance energy expenditure" J Biol Chem. 2018 Nov. 2; 293(44):17291-17305. In another embodiment, Cas9 plasmids and synthesized sgRNAs can be delivered into cells encapsulated in PEGylated nanoparticles (named P-HNPs) based on the cationic α-helical polypeptide poly(γ-4-((2-(piperidin-1-yl)ethyl)aminomethyl)benzyl-1-glutamate). See, e.g. Wang et al., "Nonviral gene editing via CRISPR/Cas9 delivery by membrane-disruptive and endosomolytic helical polypeptide" Proc Natl Acad Sci USA. 2018 May 8; 115(19): 4903-4908. In another embodiment, a CRISPR-Cas9 plasmid can be incorporated into a self assembled nanoparticle. The plasmid can be complexed with protamine sulfate and the resulting complex decorated by a multi-functional outer layer composed of an endosomolytic peptide (KALA) and aptamer AS1411 incorporated carboxymethyl chitosan. See, e.g. Liu et al., "Tumor targeted genome editing mediated by a multi-functional gene vector for regulating cell behaviors." J Control Release. 2018 Dec. 10; 291:90-98.In another embodiment, spCas9 and sgRNA RNP complexes can be delivered via a vesicle decorated with the fusogenic glycoprotein of the vesicular stomatitis virus (VSV-G). See, e.g. "VSV-G-Enveloped Vesicles for Traceless Delivery of CRISPR-Cas9" Montagna et al., Sci Rep. 2018 Nov. 2; 8(1):16304. In another embodiment, Cas9 RNP can be delivered by encapsulation in a nanoscale zeolitic imidazole framework (ZIF), in which enhanced endosomal escape is promoted by the protonated imidazole moieties. See, e.g. Alsaiari et al., "Endosomal Escape and Delivery of CRISPR/Cas9 Genome Editing Machinery Enabled by Nanoscale Zeolitic Imidazolate Framework" J Am Chem Soc. 2018 Jan. 10; 140(1): 143-146.

Also contemplated are filtration-based systems. In one embodiment, Cas9 and sgRNA RNP complexes can be delivered into patient-derived hematopoietic stem and progenitor cells (HSPCs) ex vivo using TRansmembrane Internalization Assisted by Membrane Filtration (TRIAMF), a method to deliver RNPs into HSPCs by passing a RNP and cell mixture through a filter membrane. See, e.g. Yen et al., "TRIAMF: A New Method for Delivery of Cas9 Ribonucleoprotein Complex to Human Hematopoietic Stem Cells" Sci Rep. 2018 Nov. 2; 8(1):16304.

Nanoclews

Further, the CRISPR system may be delivered using nanoclews, for example as described in Sun W et al, *Cocoon-like self-degradable DNA nanoclew for anticancer drug delivery.*, J Am Chem Soc. 2014 Oct. 22; 136(42): 14722-5. doi: 10.1021/ja5088024. Epub 2014 Oct. 13; or in Sun W et al, *Self-Assembled DNA Nanoclews for the Efficient Delivery of CRISPR-Cas9 for Genome Editing.*, Angew Chem Int Ed Engl. 2015 Oct. 5; 54(41):12029-33. doi: 10.1002/anie.201506030. Epub 2015 Aug. 27.

LNP

In some embodiments, delivery is by encapsulation of the Cpf1 protein or mRNA form in a lipid particle such as an LNP. In some embodiments, therefore, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR Cas system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 μg/ml of LNP or CRISPR-Cas RNA in or associated with the LNP may be contemplated, especially for a formulation containing DLinKC2-DMA.

Preparation of LNPs and CRISPR Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-[(ʃ-methoxy-poly(ethylene glycol)2000] carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, MO). The specific CRISPR Cas RNA may be encapsulated in LNPs containing DLinDAP, DLinDMA, DLinK-DMA, and DLinKC2-DMA (cationic lipid:DSPC:CHOL:PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/l. This ethanol solution of lipid may be added drop-wise to 50 mmol/l citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/l citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, CA). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, VA). In conjunction with the herein discussion of LNPs and PEG lipids, PEGylated liposomes or LNPs are likewise suitable for delivery of a CRISPR-Cas system or components thereof.

A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/l, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Spherical Nucleic Acid (SNA™) constructs and other nanoparticles (particularly gold nanoparticles) are also contemplated as a means to delivery CRISPR-Cas system to intended targets. Significant data show that AuraSense Therapeutics' Spherical Nucleic Acid (SNA™) constructs, based upon nucleic acid-functionalized gold nanoparticles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 $10^9$:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR Cas is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclododecane-1,4,7,10-tetraacetic acid mono(N-hydroxysuccinimide ester) (DOTA-NHSester) was ordered from Macrocyclics (Dallas, TX). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, CA) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a RNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+ 5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumors, Davis et al. investigated biopsies from three patients from three different dosing cohorts; patients A, B and C, all of whom had metastatic melanoma and received CALAA-01 doses of 18, 24 and 30 mg m-2 siRNA, respectively. Similar doses may also be contemplated for the CRISPR Cas system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 μm and 30 μm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable particles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can be envisioned that such conjugated lipomers can be used in the context of the CRISPR-Cas system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano.2014.84). C71 was synthesized by reacting C15 epoxide-terminated lipids with PEI600 at a 14:1 molar ratio, and was formulated with C14PEG2000 to produce nanoparticles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

In some embodiments, the LNP for delivering the RNA molecules is prepared by methods known in the art, such as those described in, for example, WO 2005/105152 (PCT/EP2005/004920), WO 2006/069782 (PCT/EP2005/014074), WO 2007/121947 (PCT/EP2007/003496), and WO 2015/082080 (PCT/EP2014/003274), which are herein incorporated by reference. LNPs aimed specifically at the enhanced and improved delivery of siRNA into mammalian cells are described in, for example, Aleku et al., Cancer Res., 68(23): 9788-98 (Dec. 1, 2008), Strumberg et al., Int. J. Clin. Pharmacol. Ther., 50(1): 76-8 (January 2012), Schultheis et al., J. Clin. Oncol., 32(36): 4141-48 (Dec. 20, 2014), and Fehring et al., Mol. Ther., 22(4): 811-20 (Apr. 22, 2014), which are herein incorporated by reference and may be applied to the present technology.

In some embodiments, the LNP includes any LNP disclosed in WO 2005/105152 (PCT/EP2005/004920), WO 2006/069782 (PCT/EP2005/014074), WO 2007/121947 (PCT/EP2007/003496), and WO 2015/082080 (PCT/EP2014/003274).

In some embodiments, the LNP includes at least one lipid having Formula III:

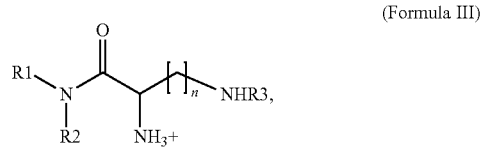

(Formula III)

wherein $R^1$ and $R^2$ are each and independently selected from the group comprising alkyl, n is any integer between 1 and 4, and $R^3$ is an acyl selected from the group comprising lysyl, ornithyl, 2,4-diaminobutyryl, histidyl and an acyl moiety according to Formula IV:

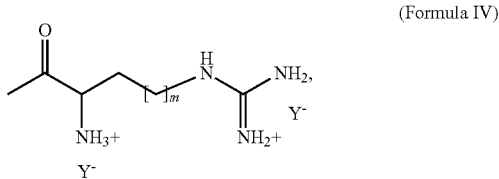

(Formula IV)

wherein m is any integer from 1 to 3 and $Y^-$ is a pharmaceutically acceptable anion. In some embodiments, a lipid according to Formula I includes at least two asymmetric C atoms. In some embodiments, enantiomers of Formula I include, but are not limited to, R-R; S-S; R—S and S-R enantiomer.

In some embodiments, R1 is lauryl and R2 is myristyl. In another embodiment, R1 is palmityl and R2 is oleyl. In some embodiments, m is 1 or 2. In some embodiments, $Y^-$ is selected from halogenids, acetate or trifluoroacetate.

In some embodiments, the LNP comprises one or more lipids select from:

β-arginyl-2,3-diamino propionic acid-N-palmityl-N-oleyl-amide trihydrochloride (Formula V):

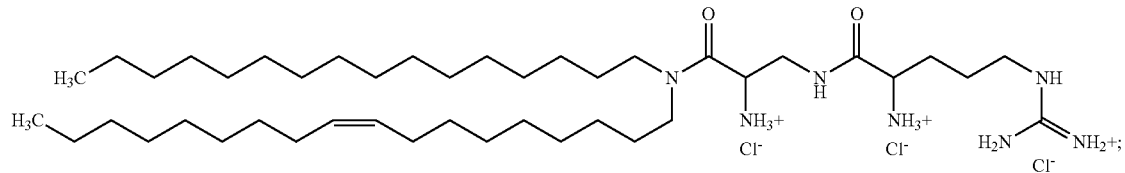

(Formula V)

β-arginyl-2,3-diamino propionic acid-N-lauryl-N-myristyl-amide trihydrochloride (Formula VI):

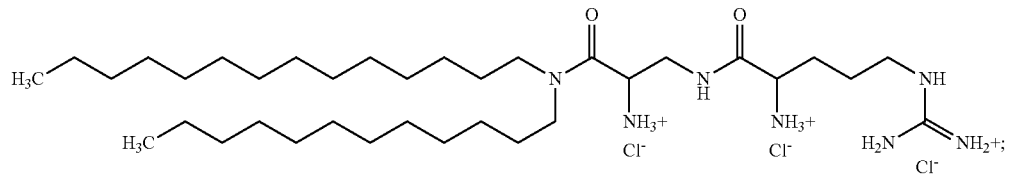

(Formula VI)

ε-arginyl-lysine-N-lauryl-N-myristyl-amide trihydrochloride (Formula VII):

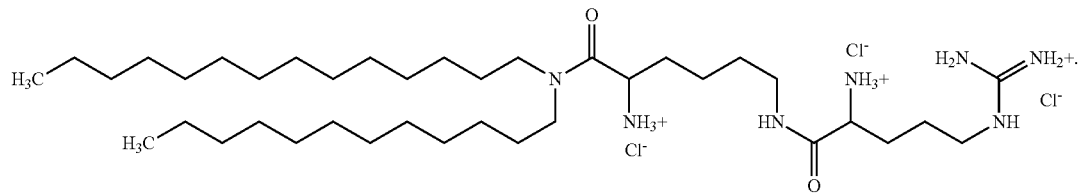

(Formula VII)

In some embodiments, the LNP also includes a constituent. By way of example, but not by way of limitation, in some embodiments, the constituent is selected from peptides, proteins, oligonucleotides, polynucleotides, nucleic acids, or a combination thereof. In some embodiments, the constituent is an antibody, e.g., a monoclonal antibody. In some embodiments, the constituent is a nucleic acid selected from, e.g., ribozymes, aptamers, spiegelmers, DNA, RNA, PNA, LNA, or a combination thereof. In some embodiments, the nucleic acid is gRNA and/or mRNA.

In some embodiments, the constituent of the LNP comprises an mRNA encoding a CRIPSR effector protein. In some embodiments, the constituent of the LNP comprises an mRNA encoding a Type-II, Type-V, or Type-VI CRIPSR effector protein. In some embodiments, the constituent of the LNP comprises an mRNA encoding an RNA-guided DNA binding protein. In some embodiments, the constituent of the LNP comprises an mRNA encoding an RNA-guided RNA binding protein.

In some embodiments, the constituent of the LNP further comprises one or more guide RNA. In some embodiments, the LNP is configured to deliver the aforementioned mRNA and guide RNA to vascular endothelium. In some embodiments, the LNP is configured to deliver the aforementioned mRNA and guide RNA to pulmonary endothelium. In some embodiments, the LNP is configured to deliver the aforementioned mRNA and guide RNA to liver. In some embodiments, the LNP is configured to deliver the aforementioned mRNA and guide RNA to lung. In some embodiments, the LNP is configured to deliver the aforementioned mRNA and guide RNA to hearts. In some embodiments, the LNP is configured to deliver the aforementioned mRNA and guide RNA to spleen. In some embodiments, the LNP is configured to deliver the aforementioned mRNA and guide RNA to kidney. In some embodiments, the LNP is configured to deliver the aforementioned mRNA and guide RNA to pancrea. In some embodiments, the LNP is configured to deliver the aforementioned mRNA and guide RNA to brain. In some embodiments, the LNP is configured to deliver the aforementioned mRNA and guide RNA to macrophages.

In some embodiments, the LNP also includes at least one helper lipid. In some embodiments, the helper lipid is selected from phospholipids and steroids. In some embodiments, the phospholipids are di- and/or monoester of the phosphoric acid. In some embodiments, the phospholipids are phosphoglycerides and/or sphingolipids. In some embodiments, the steroids are naturally occurring and/or synthetic compounds based on the partially hydrogenated cyclopenta[a]phenanthrene. In some embodiments, the steroids contain 21 to 30 C atoms. In some embodiments, the steroid is cholesterol. In some embodiments, the helper lipid is selected from 1,2-diphytanoyl-sn-glycero-3-phosphoethanolamine (DPhyPE), ceramide, and 1,2-dioleylsn-glycero-3-phosphoethanolamine (DOPE).

In some embodiments, the at least one helper lipid comprises a moiety selected from the group comprising a PEG moiety, a HEG moiety, a polyhydroxyethyl starch (polyHES) moiety and a polypropylene moiety. In some embodiments, the moiety has a molecule weight between about 500 to 10,000 Da or between about 2,000 to 5,000 Da. In some embodiments, the PEG moiety is selected from 1,2-distearoyl-sn-glycero-3 phosphoethanolamine, 1,2-dialkyl-sn-glycero-3-phosphoethanolamine, and Ceramide-PEG. In some embodiments, the PEG moiety has a molecular weight between about 500 to 10,000 Da or between about 2,000 to 5,000 Da. In some embodiments, the PEG moiety has a molecular weight of 2,000 Da.

In some embodiments, the helper lipid is between about 20 mol % to 80 mol % of the total lipid content of the composition. In some embodiments, the helper lipid component is between about 35 mol % to 65 mol % of the total lipid content of the LNP. In some embodiments, the LNP includes lipids at 50 mol % and the helper lipid at 50 mol % of the total lipid content of the LNP.

In some embodiments, the LNP includes any of β-3-arginyl-2,3-diaminopropionic acid-N-palmityl-N-oleyl-amide trihydrochloride, β-arginyl-2,3-diaminopropionic acid-N-lauryl-N-myristyl-amide trihydrochloride or arginyl-lysine-N-lauryl-N-myristyl-amide trihydrochloride in combination with DPhyPE, wherein the content of DPhyPE is about 80 mol %, 65 mol %, 50 mol % and 35 mol % of the overall lipid content of the LNP. In some embodiments, the LNP includes β-3-arginyl-2,3-diaminopropionic acid-N-palmityl-N-oleyl-amide trihydrochloride (lipid) and 1,2-diphytanoyl-sn-glycero-3-phosphoethanolamine (helper lipid). In some embodiments, the LNP includes β-3-arginyl-2,3-diaminopropionic acid-N-palmityl-N-oleyl-amide trihydrochloride (lipid), 1,2-diphytanoyl-sn-glycero-3-phosphoethanolamine (first helper lipid), and 1,2-disteroyl-sn-glycero-3-phosphoethanolamine-PEG2000 (second helper lipid).

In some embodiments, the second helper lipid is between about 0.05 mol % to 4.9 mol % or between about 1 mol % to 3 mol % of the total lipid content. In some embodiments, the LNP includes lipids at between about 45 mol % to 50 mol % of the total lipid content, a first helper lipid between about 45 mol % to 50 mol % of the total lipid content, under the proviso that there is a PEGylated second helper lipid between about 0.1 mol % to 5 mol %, between about 1 mol % to 4 mol %, or at about 2 mol % of the total lipid content, wherein the sum of the content of the lipids, the first helper lipid, and of the second helper lipid is 100 mol % of the total lipid content and wherein the sum of the first helper lipid and the second helper lipid is 50 mol % of the total lipid content. In some embodiments, the LNP comprises: (a) 50 mol % of arginyl-2,3-diamino propionic acid-N-palmityl-N-oleyl-amide trihydrochloride, 48 mol % of 1,2-diphytanoyl-sn-glycero-3-phosphoethanolamine; and 2 mol % 1,2-distearoyl-sn-glycero-3-phosphoethanolamine-PEG2000; or (b) 50 mol % of β-3-arginyl-2,3-diaminopropionic acid-N-palmityl-N-oleyl-amide trihydrochloride, 49 mol % 1,2-diphytanoyl-sn-glycero-3-phosphoethanolamine; and 1 mol % N(Carbonyl-methoxypolyethylenglycol-2000)-1,2-distearoyl-sn-glycero3-phosphoethanolamine, or a sodium salt thereof.

In some embodiments, the LNP contains a nucleic acid, wherein the charge ratio of nucleic acid backbone phosphates to cationic lipid nitrogen atoms is about 1: 1.5-7 or about 1:4.

In some embodiments, the LNP also includes a shielding compound, which is removable from the lipid composition under in vivo conditions. In some embodiments, the shielding compound is a biologically inert compound. In some embodiments, the shielding compound does not carry any charge on its surface or on the molecule as such. In some embodiments, the shielding compounds are polyethylenglycoles (PEGs), hydroxyethylglucose (HEG) based polymers, polyhydroxyethyl starch (polyHES) and polypropylene. In some embodiments, the PEG, HEG, polyHES, and a polypropylene weight between about 500 to 10,000 Da or between about 2000 to 5000 Da. In some embodiments, the shielding compound is PEG2000 or PEG5000.

In some embodiments, the LNP includes at least one lipid, a first helper lipid, and a shielding compound that is removable from the lipid composition under in vivo conditions. In some embodiments, the LNP also includes a second helper lipid. In some embodiments, the first helper lipid is ceramide. In some embodiments, the second helper lipid is ceramide. In some embodiments, the ceramide comprises at least one short carbon chain substituent of from 6 to 10 carbon atoms. In some embodiments, the ceramide comprises 8 carbon atoms. In some embodiments, the shielding compound is attached to a ceramide. In some embodiments, the shielding compound is attached to a ceramide. In some embodiments, the shielding compound is covalently attached to the ceramide. In some embodiments, the shielding compound is attached to a nucleic acid in the LNP. In some embodiments, the shielding compound is covalently attached to the nucleic acid. In some embodiments, the shielding compound is attached to the nucleic acid by a linker. In some embodiments, the linker is cleaved under physiological conditions. In some embodiments, the linker is selected from ssRNA, ssDNA, dsRNA, dsDNA, peptide, S-S-linkers and pH sensitive linkers. In some embodiments, the linker moiety is attached to the 3' end of the sense strand of the nucleic acid. In some embodiments, the shielding compound comprises a pH-sensitive linker or a pH-sensitive moiety. In some embodiments, the pH-sensitive linker or pH-sensitive moiety is an anionic linker or an anionic moiety. In some embodiments, the anionic linker or anionic moiety is less anionic or neutral in an acidic environment. In some embodiments, the pH-sensitive linker or the pH-sensitive moiety is selected from the oligo (glutamic acid), oligophenolate(s) and diethylene triamine penta acetic acid.

In any of the LNP embodiments in the previous paragraph, the LNP can have an osmolality between about 50 to 600 mosmole/kg, between about 250 to 350 mosmole/kg, or between about 280 to 320 mosmole/kg, and/or wherein the LNP formed by the lipid and/or one or two helper lipids and the shielding compound have a particle size between about 20 to 200 nm, between about 30 to 100 nm, or between about 40 to 80 nm.

In some embodiments, the shielding compound provides for a longer circulation time in vivo and allows for a better biodistribution of the nucleic acid containing LNP. In some embodiments, the shielding compound prevents immediate interaction of the LNP with serum compounds or compounds of other bodily fluids or cytoplasma membranes, e.g., cytoplasma membranes of the endothelial lining of the vasculature, into which the LNP is administered. Additionally or alternatively, in some embodiments, the shielding compounds also prevent elements of the immune system from immediately interacting with the LNP. Additionally or alternatively, in some embodiments, the shielding compound acts as an anti-opsonizing compound. Without wishing to be bound by any mechanism or theory, in some embodiments, the shielding compound forms a cover or coat that reduces the surface area of the LNP available for interaction with its environment. Additionally or alternatively, in some embodiments, the shielding compound shields the overall charge of the LNP.

In another embodiment, the LNP includes at least one cationic lipid having Formula VIII:

(Formula VIII)

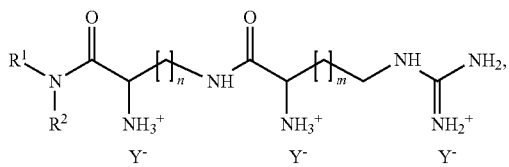

wherein n is 1, 2, 3, or 4, wherein m is 1, 2, or 3, wherein Y⁻ is anion, wherein each of $R^1$ and $R^2$ is individually and independently selected from the group consisting of linear C12-C18 alkyl and linear C12-C18 alkenyl, a sterol compound, wherein the sterol compound is selected from the group consisting of cholesterol and stigmasterol, and a PEGylated lipid, wherein the PEGylated lipid comprises a PEG moiety, wherein the PEGylated lipid is selected from the group consisting of:

a PEGylated phosphoethanolamine of Formula IX:

(Formula IX)

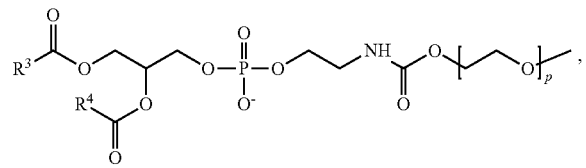

wherein $R^3$ and $R^4$ are individually and independently linear C13-C17 alkyl, and p is any integer between 15 to 130;

a PEGylated ceramide of Formula X:

wherein $R^5$ is linear C7-C15 alkyl, and q is any number between 15 to 130; and a PEGylated diacylglycerol of Formula XI:

(Formula XI)

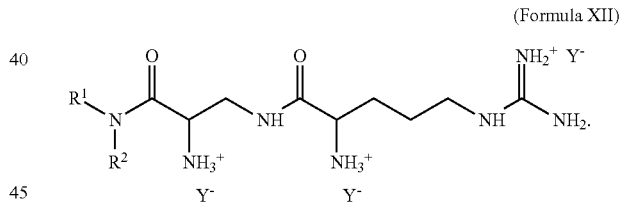

wherein each of $R^6$ and $R^7$ is individually and independently linear C11-C17 alkyl, and r is any integer from 15 to 130.

In some embodiments, $R^1$ and $R^2$ are different from each other. In some embodiments, $R^1$ is palmityl and $R^2$ is oleyl. In some embodiments, $R^1$ is lauryl and $R^2$ is myristyl. In some embodiments, $R^1$ and $R^2$ are the same. In some embodiments, each of $R^1$ and $R^2$ is individually and independently selected from the group consisting of C12 alkyl, C14 alkyl, C16 alkyl, C18 alkyl, C12 alkenyl, C14 alkenyl, C16 alkenyl and C18 alkenyl. In some embodiments, each of C12 alkenyl, C14 alkenyl, C16 alkenyl and C18 alkenyl comprises one or two double bonds. In some embodiments, C18 alkenyl is C18 alkenyl with one double bond between C9 and C10. In some embodiments, C18 alkenyl is cis-9-octadecyl.

In some embodiments, the cationic lipid is a compound of Formula XII:

(Formula XII)

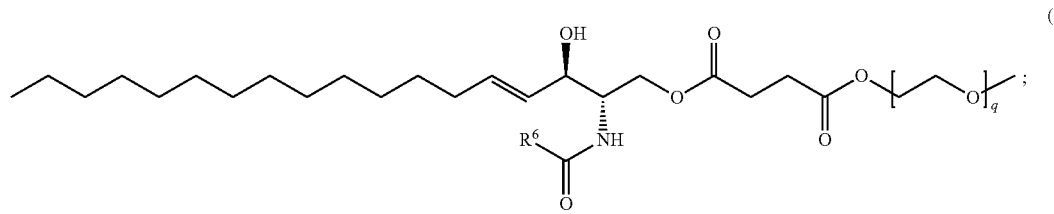

In some embodiments, Y⁻ is selected from halogenids, acetate and trifluoroacetate. In some embodiments, the cationic lipid is β-arginyl-2,3-diamino propionic acid-N-palmityl-N-oleyl-amide trihydrochloride of Formula XIII:

(Formula X)

(Formula XIII)

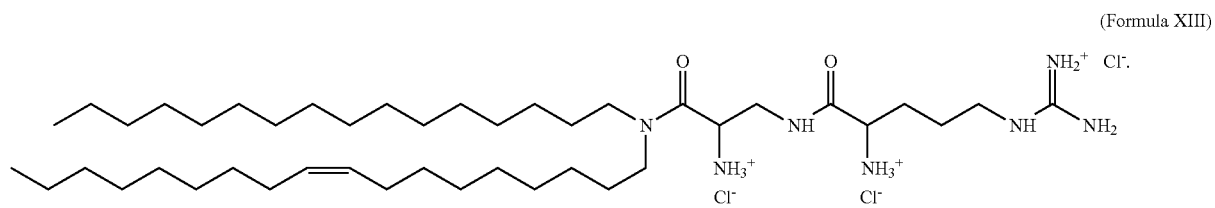

In some embodiments, the cationic lipid is β-arginyl-2,3-diamino propionic acid-N-lauryl-N-myristyl-amide trihydrochloride of Formula XIV:

(Formula XIV)

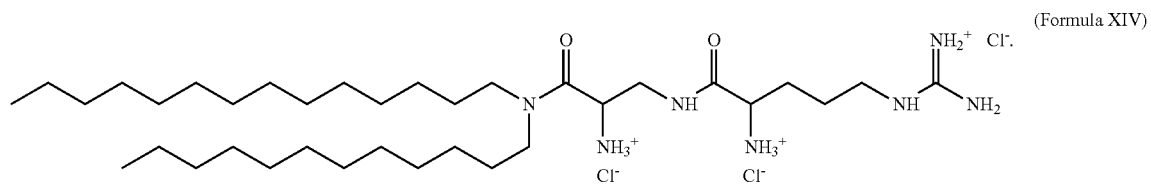

In some embodiments, the cationic lipid is s-arginyl-lysine-N-lauryl-N-myristyl-amide trihydrochloride of Formula XV:

(Formula XV)

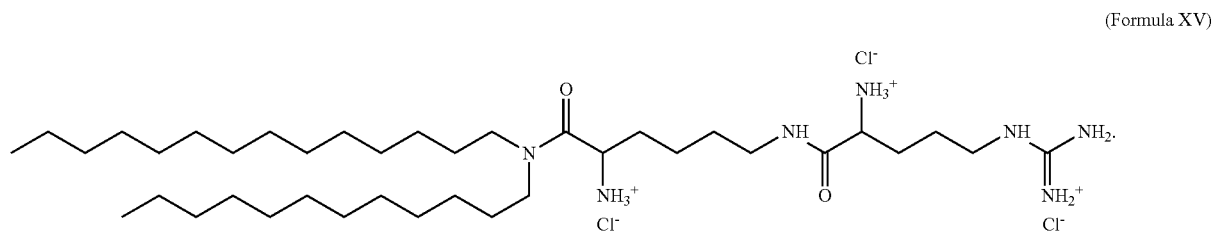 [SMILES: [Cl-] ; CCCCCCCCCCCCCCN(CCCCCCCCCCCC)C(=O)C([NH3+])CCCCNC(=O)C([NH3+])CCCNC(N)=[NH2+] ; [Cl-] ; [Cl-]]

In some embodiments, the sterol compound is cholesterol. In some embodiments, the sterol compound is stigmasterin.

In some embodiments, the PEG moiety of the PEGylated lipid has a molecular weight from about 800 to 5,000 Da. In some embodiments, the molecular weight of the PEG moiety of the PEGylated lipid is about 800 Da. In some embodiments, the molecular weight of the PEG moiety of the PEGylated lipid is about 2,000 Da. In some embodiments, the molecular weight of the PEG moiety of the PEGylated lipid is about 5,000 Da. In some embodiments, the PEGylated lipid is a PEGylated phosphoethanolamine of Formula VII, wherein each of $R^3$ and $R^4$ is individually and independently linear C13-C17 alkyl, and p is any integer from 18, 19 or 20, or from 44, 45 or 46 or from 113, 114 or 115. In some embodiments, $R^3$ and $R^4$ are the same. In some embodiments, $R^3$ and $R^4$ are different. In some embodiments, each of $R^3$ and $R^4$ is individually and independently selected from the group consisting of C13 alkyl, C15 alkyl and C17 alkyl. In some embodiments, the PEGylated phosphoethanolamine of Formula XVI is 1,2-distearoyl-sn-glycero-3-phosphoethanolamine-N-[methoxy(polyethylene glycol)-2000](ammonium salt):

(Formula XVI)

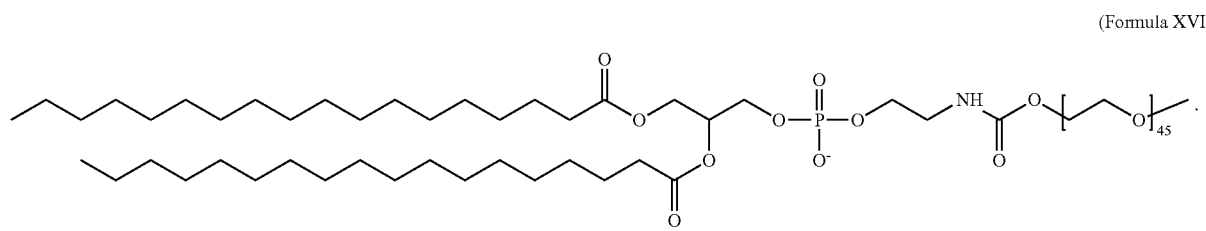

In some embodiments, the PEGylated phosphoethanolamine of Formula XVII is 1,2-distearoyl-sn-glycero-3-phosphoethanolamine-N-[methoxy(polyethylene glycol)-5000](ammonium salt):

(Formula XVII)

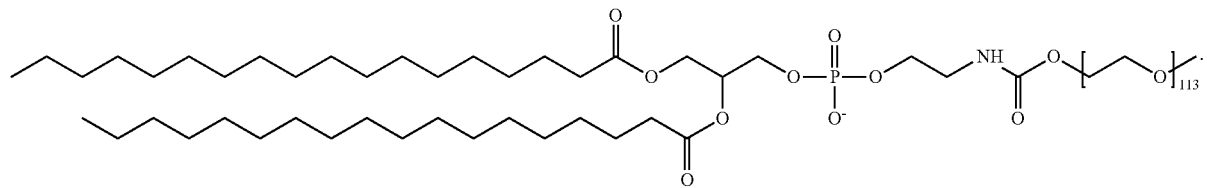

In some embodiments, the PEGylated lipid is a PEGylated ceramide of Formula XVIII, wherein $R^5$ is linear C7-C15 alkyl, and q is any integer from 18, 19 or 20, or from 44, 45 or 46 or from 113, 114 or 115. In some embodiments, $R^5$ is linear C7 alkyl. In some embodiments, $R^5$ is linear C15 alkyl. In some embodiments, the PEGylated ceramide of Formula XVIII is N-octanoyl-sphingosine-1-{succinyl [methoxy(polyethylene glycol)2000]}:

(Formula XXIII)

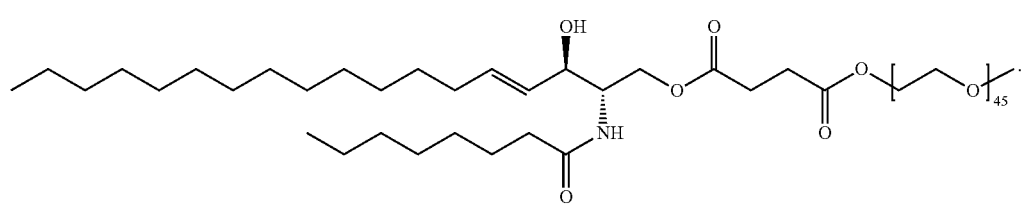

In some embodiments, the PEGylated ceramide of Formula XIX is N-palmitoyl-sphingosine-1-{succinyl [methoxy(polyethylene glycol)2000]}

(Formula XIX)

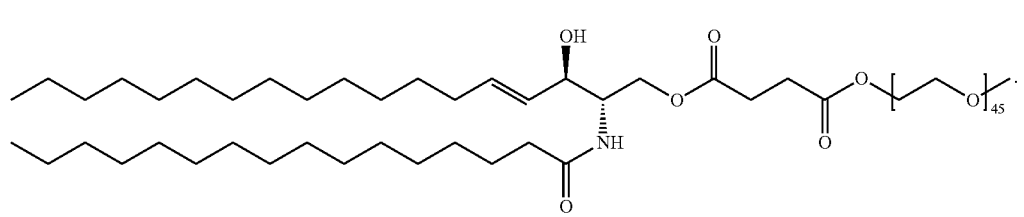

In some embodiments, the PEGylated lipid is a PEGylated diacylglycerol of Formula XX, wherein each of $R^6$ and $R^7$ is individually and independently linear C11-C17 alkyl, and r is any integer from 18, 19 or 20, or from 44, 45 or 46 or from 113, 114 or 115. In some embodiments, $R^6$ and $R^7$ are the same. In some embodiments, $R^6$ and $R^7$ are different. In some embodiments, each of $R^6$ and $R^7$ is individually and independently selected from the group consisting of linear C17 alkyl, linear C15 alkyl and linear C13 alkyl. In some embodiments, the PEGylated diacylglycerol of Formula XX 1,2-Distearoyl-sn-glycerol [methoxy(polyethylene glycol) 2000]:

(Formula XX)

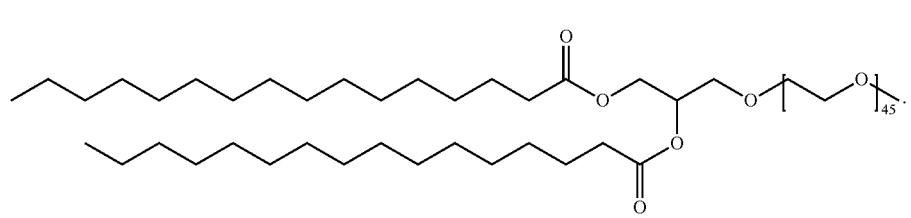

In some embodiments, the PEGylated diacylglycerol of Formula XXI is 1,2-Dipalmitoyl-sn-glycerol [methoxy (polyethylene glycol)2000]:

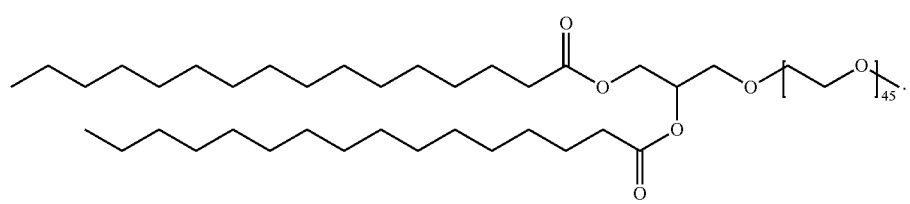

(Formula XXI)

In some embodiments, the PEGylated diacylglycerol of Formula XXII is:

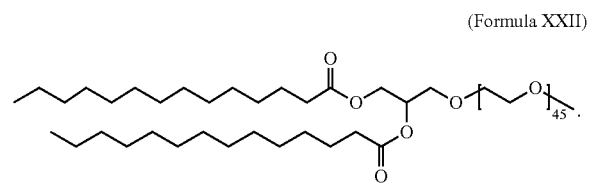

(Formula XXII)

In some embodiments, the LNP includes at least one cationic lipid selected from of Formulas III, IV, and V, at least one sterol compound selected from a cholesterol and stigmasterin, and wherein the PEGylated lipid is at least one selected from Formulas XI and XII. In some embodiments, the LNP includes at least one cationic lipid selected from Formulas III, IV, and V, at least one sterol compound selected from a cholesterol and stigmasterin, and wherein the PEGylated lipid is at least one selected from Formulas XIII and XIV. In some embodiments, the LNP includes at least one cationic lipid selected from Formulas III, IV, and V, at least one sterol compound selected from a cholesterol and stigmasterin, and wherein the PEGylated lipid is at least one selected from Formulas XV and XVI. In some embodiments, the LNP includes a cationic lipid of Formula III, a cholesterol as the sterol compound, and wherein the PEGylated lipid is Formula XI.

In any of the LNP embodiments in the previous paragraph, wherein the content of the cationic lipid composition is between about 65 mole % to 75 mole %, the content of the sterol compound is between about 24 mole % to 34 mole % and the content of the PEGylated lipid is between about 0.5 mole % to 1.5 mole %, wherein the sum of the content of the cationic lipid, of the sterol compound and of the PEGylated lipid for the lipid composition is 100 mole %. In some embodiments, the cationic lipid is about 70 mole %, the content of the sterol compound is about 29 mole % and the content of the PEGylated lipid is about 1 mole %. In some embodiments, the LNP is 70 mole % of Formula III, 29 mole % of cholesterol, and 1 mole % of Formula XI.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 μg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 μF resulted in the greatest retention of RNA and was used for all subsequent experiments.

Alvarez-Erviti et al. administered 150 μg of each BACE1 siRNA encapsulated in 150 μg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVGexosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas system of the present invention to therapeutic targets, especially neurodegenerative diseases. A dosage of about 100 to 1000 mg of CRISPR Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mm filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR Cas into exosomes may be conducted similarly to siRNA. The exosomes may be co-cultured with monocytes and lymphocytes isolated from the peripheral blood of healthy donors. Therefore, it may be contemplated that exosomes containing CRISPR Cas may be introduced to monocytes and lymphocytes of and autologously reintroduced into a human. Accordingly, delivery or administration according to the invention may be performed using plasma exosomes.

Liposomes

The lipid, lipid particle, or lipid bilayer or lipid entity of the invention can be prepared by methods well known in the art. See Wang et al., ACS Synthetic Biology, 1, 403-07 (2012); Wang et al., PNAS, 113(11) 2868-2873 (2016); Manoharan, et al., WO 2008/042973; Zugates et al., U.S. Pat. No. 8,071,082; Xu et al., WO 2014/186366 A1 (US20160082126). Xu et provides a way to make a nanocomplex for the delivery of saporin wherein the nanocomplex comprising saporin and a lipid-like compound, and wherein the nanocomplex has a particle size of 50 nm to 1000 nm; the saporin binds to the lipid-like compound via non-covalent interaction or covalent bonding; and the lipid-like compound has a hydrophilic moiety, a hydrophobic moiety, and a linker joining the hydrophilic moiety and the hydrophobic moiety, the hydrophilic moiety being optionally charged and the hydrophobic moiety having 8 to 24 carbon atoms. Xu et al., WO 2014/186348 (US20160129120) provides examples of nanocomplexes of modified peptides or proteins comprising a cationic delivery agent and an anionic pharmaceutical agent, wherein the nanocomplex has a particle size of 50 to 1000 nm, the cationic delivery agent binds to the anionic pharmaceutical agent, and the anionic pharmaceutical agent is a modified peptide or protein formed of a peptide and a protein and an added chemical moiety that contains an anionic group. The added chemical moiety is linked to the peptide or protein via an amide group, an ester group, an ether group, a thioether group, a disulfide group, a hydrazone group, a sulfenate ester group, an amidine group, a urea group, a carbamate group, an imidoester group, or a carbonate group. More particularly these documents provide examples of lipid or lipid-like compounds that can be used to make the particle delivery system of the present invention, including compounds of the formula $B_1-K_1-A-K_2-B_2$, in which A, the hydrophilic moiety, is

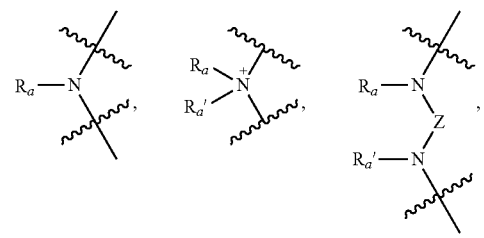

-continued

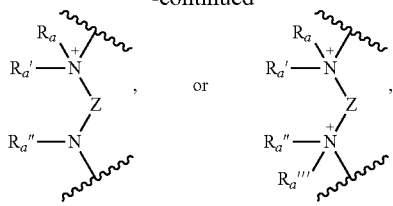

each of $R_a$, $R_a'$, $R_a''$, and $R_a'''$, independently, being a $C_1$-$C_{20}$ monovalent aliphatic radical, a $C_1$-$C_{20}$ $_O$ monovalent heteroaliphatic radical, a monovalent aryl radical, or a monovalent heteroaryl radical; and Z being a $C_1$-$C_{20}$ bivalent aliphatic radical, a $C_1$-$C_{20}$ bivalent heteroaliphatic radical, a bivalent aryl radical, or a bivalent heteroaryl radical; each of $B_1$, the hydrophobic moiety, and $B_2$, also the hydrophobic moiety, independently, is a $C_{12-20}$ aliphatic radical or a $c_{12-20}$ heteroaliphatic radical; and each of $K_1$, the linker, and $K_2$, also the linker, independently, is O, S, Si, $C_1$-$C_6$ alkylene

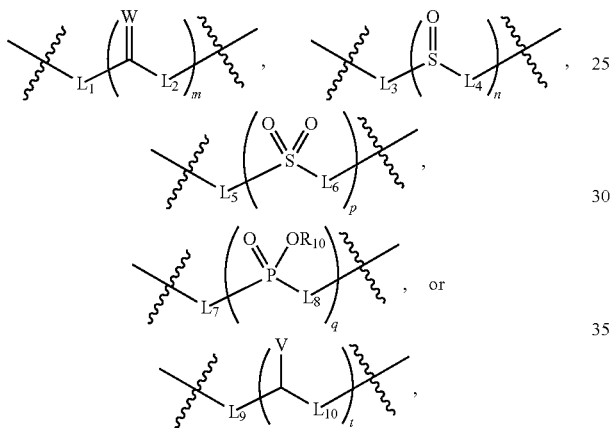

in which each of m, n, p, q, and t, independently, is 1-6; W is O, S, or $NR_C$; each of $L_1$, $L_3$, $L_5$, $L_7$, and $L_9$, independently, is a bond, O, S, or $NR_d$; each of L2, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical and specific compounds:

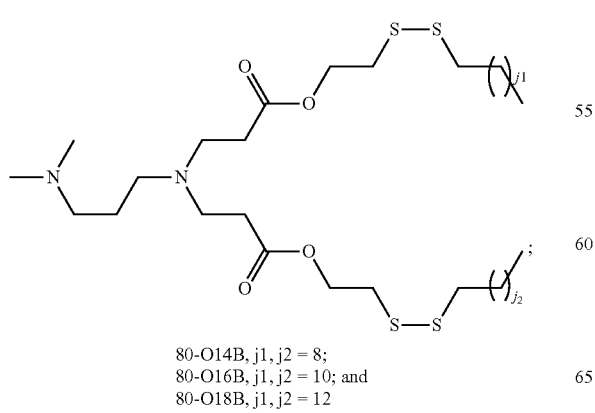

80-O14B, j1, j2 = 8;
80-O16B, j1, j2 = 10; and
80-O18B, j1, j2 = 12

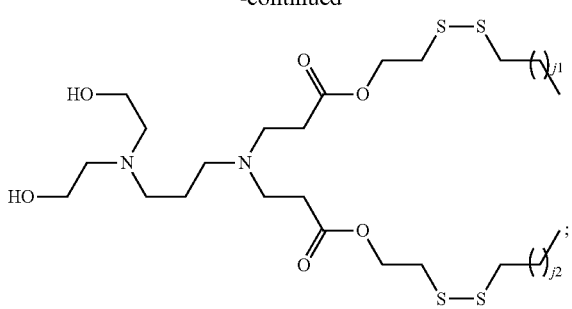

87-O14B, j1, j2 = 8;
87-O16B, j1, J2 = 10; and
87-O18B, j1, j2 = 12

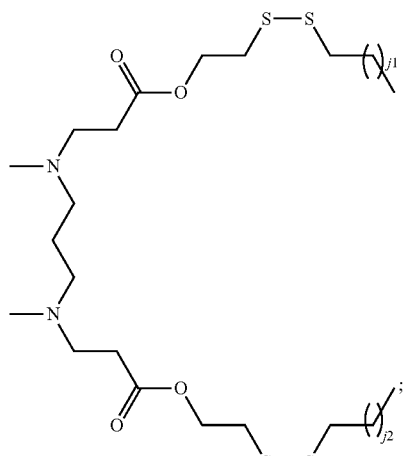

1-O16B, j1, j2 = 10; and
1-O18B, j1, j2 = 12

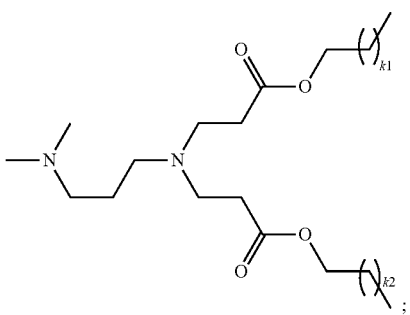

80-O14, k1, 12;
80-O16, k1, 14; and
80-O18, k1, 16

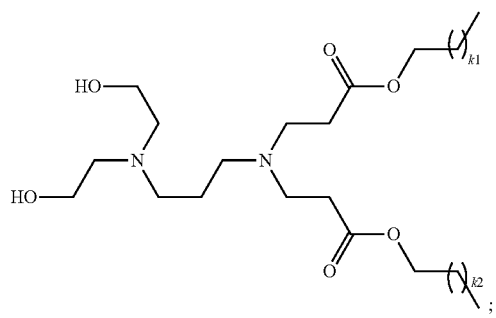

87-O14, k1, k2 = 12;
87-O16, k1, k2 = 14; and
87-O18, k1, k2 = 16.

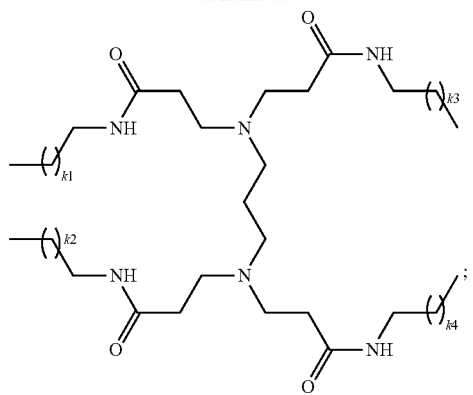

1-N16, k1, k2, k3, k4 = 14
1-N18, k1 = 12, k2 = 13, k3 = 15, and k4 = 16

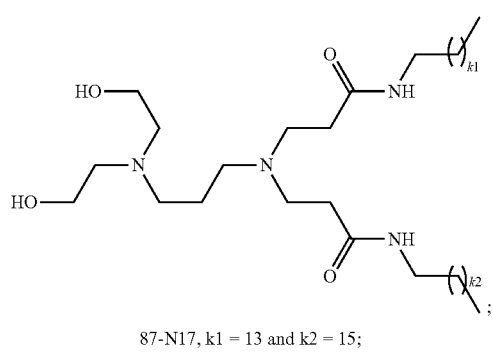

87-N17, k1 = 13 and k2 = 15;
87-N16, k1, k2 = 14; and
87-N18, k1, k2 = 16.

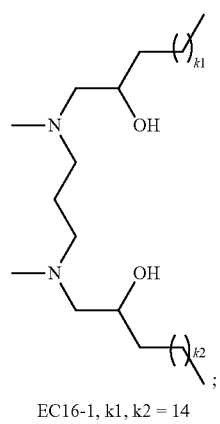

EC16-1, k1, k2 = 14

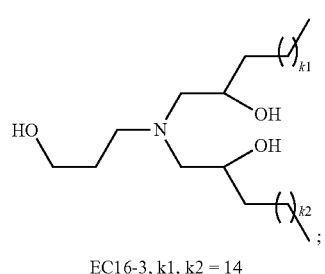

EC16-3, k1, k2 = 14

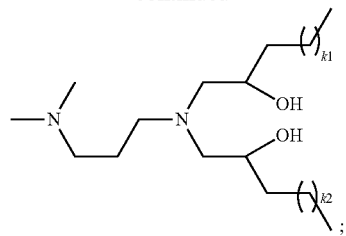

EC16-12, k1, k2 = 14

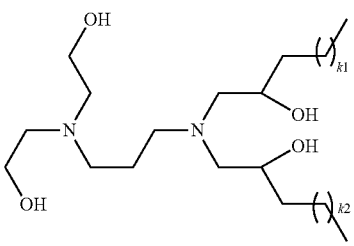

EC16-14, k1, k2 = 14; and

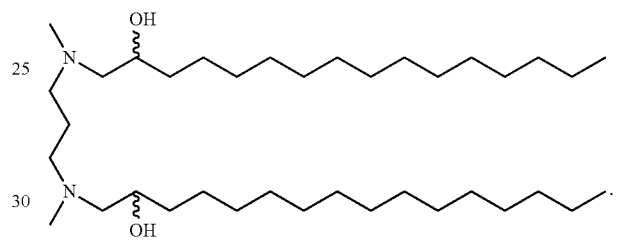

EC16-63

Additional examples of cationic lipid that can be used to make the particle delivery system of the invention can be found in US20150140070, wherein the cationic lipid has the formula XXIII

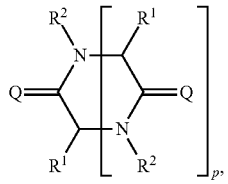

(Formula XXIII)

wherein p is an integer between 1 and 9, inclusive; each instance of Q is independently O, S, or $NR^Q$; $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii) or (iii); each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, —$OR^{41}$, —$N(R^{41})_2$, —$SR^{41}$, or a group of formula:

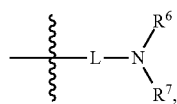

L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and each of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii); each occurrence of $R^{A}i$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{A}I$ groups, together with the nitrogen atom to which they are attached, are joined to form an optionally substituted heterocyclic or optionally substituted heteroaryl ring; each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii); Formulae (i), (ii), and (iii) are:

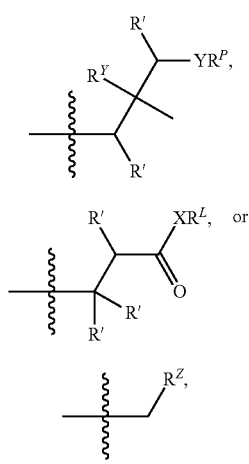

each instance of R' is independently hydrogen or optionally substituted alkyl; X is O, S, or $NR^X$; $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; Y is O, S, or $NR^Y$; $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; $R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; $R^L$ is optionally substituted $C_{1-50}$ alkyl, optionally substituted $C_{2-50}$ alkenyl, optionally substituted $C_{2-50}$ alkynyl, optionally substituted hetero$C_{1-50}$ alkyl, optionally substituted hetero$C_{2-50}$ alkenyl, optionally substituted hetero$C_{2-50}$ alkynyl, or a polymer; provided that at least one instance of $R^Q$, $R^2$, $R^6$, or $R^7$ is a group of the formula (i), (ii), or (iii); in Liu et al., (US 20160200779, US 20150118216, US 20150071903, and US 20150071903), which provide examples of cationic lipids to include polyethylenimine, polyamidoamine (PAMAM) starburst dendrimers, Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3.beta.-[N—(N',N'-dimethylaminoethane)carbamoyl]cholesterol (DC-Chol), 2,3,-dioleyloxy-N-[2(sperminecarboxamido)ethyl]-N,N-dimethyl-1-propanamin-ium trifluoroacetate (DOSPA), 1,2-dimyristyloxypropyl-3-dimethyl-hydroxyethyl ammonium bromide; and dimethyldioctadecylammonium bromide (DDAB); in WO2013/093648 which provides cationic lipids of formula XXIV

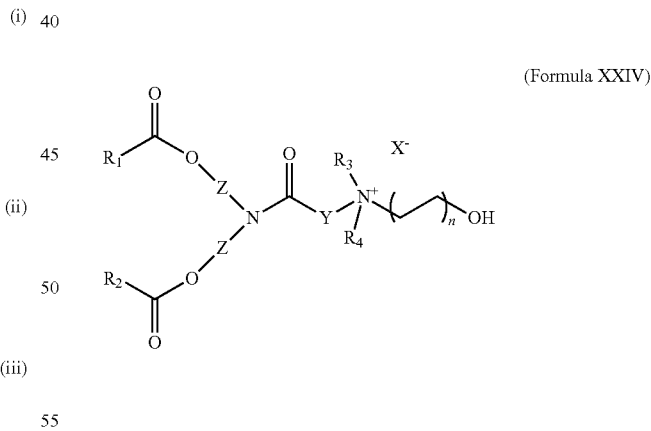

(Formula XXIV)

in which Z=an alkyl linker, $C_2$-$C_4$ alkyl, Y=an alkyl linker, $C_1$-$C_6$ alkyl, $R_1$ and $R_2$ are each independently $C_{10}$-$C_{30}$alkyl, $C_{10}$-$C_{30}$alkenyl, or $C_{10}$-$C_{30}$alkynyl, $C_{10}$-$C_{30}$alkyl, $C_{10}$-$C_{20}$alkyl, $C_{12}$-$C_{18}$alkyl, $C_{13}$-$C_{17}$alkyl, $C_{13}$alkyl, $C_{10}$-$C_{30}$alkenyl, $C_{10}$-$C_{20}$alkenyl, $C_{12}$-$C_{15}$alkenyl, $C_{13}$-$C_{17}$alkenyl, $C_{17}$alkenyl; $R^3$ and $R^4$ are each independently hydrogen, $C_1$-$C_6$ alkyl, or —$CH_2CH_2OH$, $C_1$-$C_6$ alkyl, $C_1$-$C_3$alkyl; n is 1-6; and X is a counterion, including any nitrogen counterion, as that term is readily understood in the art, and specific cationic lipids including (Formula XXV)

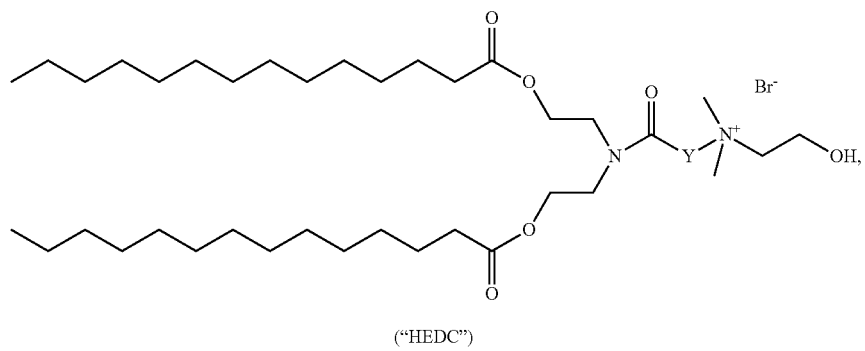

("HEDC")

(Formula XXVI)

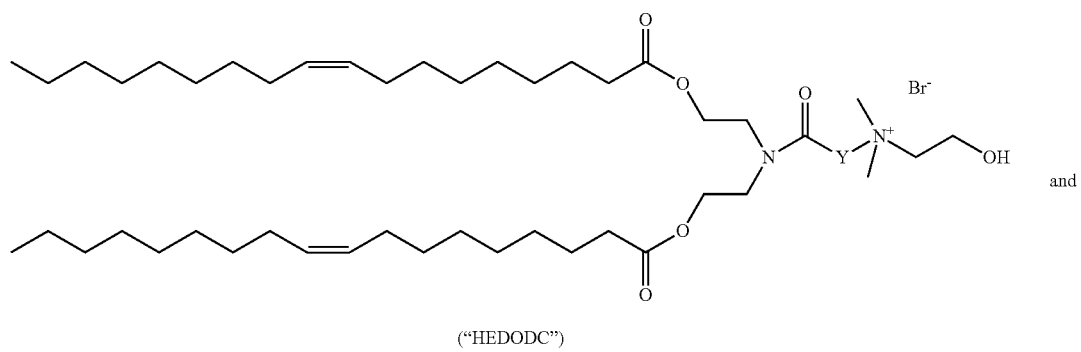

("HEDODC")

and (Formula XXVII)

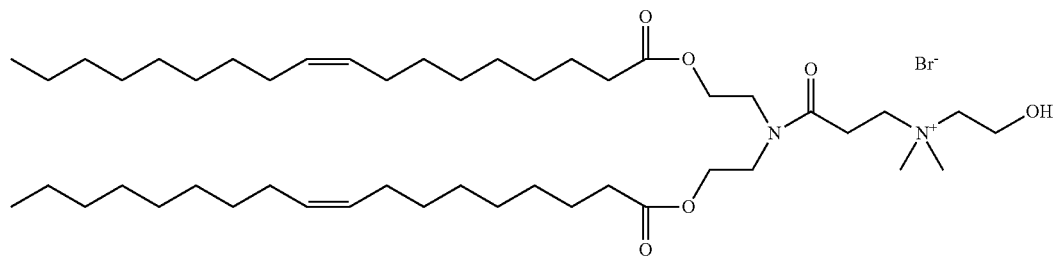

("HE-Et-DODC")

WO2013/093648 also provides examples of other cationic charged lipids at physiological pH including N,N-dioleyl-N,N-dimethylammonium chloride (DODAC), N,N-distearyl-N,N-dimethylammonium bromide (DDAB); N-(1,2-dimyristyloxyprop-3-yl)-N,N-dimethyl-N-hydroxyethylammonium bromide (DMRIE) and dioctadecylamidoglycyl carboxyspermidine (DOGS); in US 20160257951, which provides cationic lipids with a general formula (Formula XXVIII)

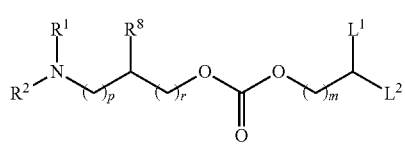

or a pharmacologically acceptable salt thereof, wherein $R^1$ and $R^2$ are each independently a hydrogen atom, a $C_1$-$C_6$ alkyl group optionally substituted with one or more substituents selected from substituent group a, a $C_2$-$C_6$ alkenyl group optionally substituted with one or more substituents selected from substituent group α, a $C_2$-$C_6$ alkynyl group optionally substituted with one or more substituents selected from substituent group α, or a $C_3$-$C_7$ cycloalkyl group optionally substituted with one or more substituents selected from substituent group α, or $R^1$ and $R^2$ form a 3- to 10-membered heterocyclic ring together with the nitrogen atom bonded thereto, wherein the heterocyclic ring is optionally substituted with one or more substituents selected from substituent group α and optionally contains one or more atoms selected from a nitrogen atom, an oxygen atom, and a sulfur atom, in addition to the nitrogen atom bonded to $R^1$ and $R^2$, as atoms constituting the heterocyclic ring; $R^8$ is a hydrogen atom or a $C_1$-$C_6$ alkyl group optionally substituted with one or more substituents selected from substituent group α; or $R^1$ and $R^8$ together are the group —$(CH_2)_q$—; substituent group α consists of a halogen atom, an oxo group, a hydroxy group, a sulfanyl group, an amino group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_6$ alkylamino group, and a $C_1$-$C_7$ alkanoyl group; $L^1$ is a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, or a $(C_1$-$C_{10}$ alkyl)-$(Q)_k$-$(C_1$-$C_{10}$ alkyl) group optionally substituted with one or more substituents selected from substituent group β1; $L^2$ is, independently of $L^1$, a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, a $(C_1$-$C_{10}$ alkyl)-$(Q)_k$-$(C_1$-$C_{10}$ alkyl) group optionally substituted with having one or more substituents selected from substituent group β1, a $(C_{10}$-$C_{24}$ alkoxy)methyl group optionally substituted with one or more substituents selected from substituent group β1, a $(C_{10}$-$C_{24}$ alkenyl)oxymethyl group optionally substituted with one or more substituents selected from substituent group β1, a $(C_3$-$C_{24}$ alkynyl)oxymethyl group optionally substituted with one or more substituents selected from substituent group β1, or a $(C_1$-$C_{10}$ alkyl)-$(Q)_k$-$(C_1$-$C_{10}$ alkoxy)methyl group optionally substituted with one or more substituents selected from substituent group β1; substituent group β1 consists of a halogen atom, an oxo group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_7$ alkanoyl group, a $C_1$-$C_7$ alkanoyloxy group, a $C_3$-$C_7$ alkoxyalkoxy group, a $(C_1$-$C_6$ alkoxy)carbonyl group, a $(C_1$-$C_6$ alkoxy)carboxyl group, a $(C_1$-$C_6$ alkoxy)carbamoyl group, and a $(C_1$-$C_6$ alkylamino)carboxyl group; Q is a group of formula:

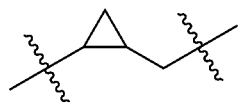 [SMILES: *CC1CC1*]

when $L^1$ and $L^2$ are each substituted with one or more substituents selected from substituent group β1 and substituent group β1 is a $C_1$-$C_6$ alkyl group, a $C_1$-$C_6$ alkoxy group, a $C_1$-$C_6$ alkylsulfanyl group, a $C_1$-$C_7$ alkanoyl group, or a $C_1$-$C_7$ alkanoyloxy group, the substituent or substituents selected from substituent group β1 in $L^1$ and the substituent or substituents selected from substituent group β1 in $L^2$ optionally bind to each other to form a cyclic structure; k is 1, 2, 3, 4, 5, 6, or 7; m is 0 or 1; p is 0, 1, or 2; q is 1, 2, 3, or 4; and r is 0, 1, 2, or 3, provided that p+r is 2 or larger, or q+r is 2 or larger, and specific cationic lipids including

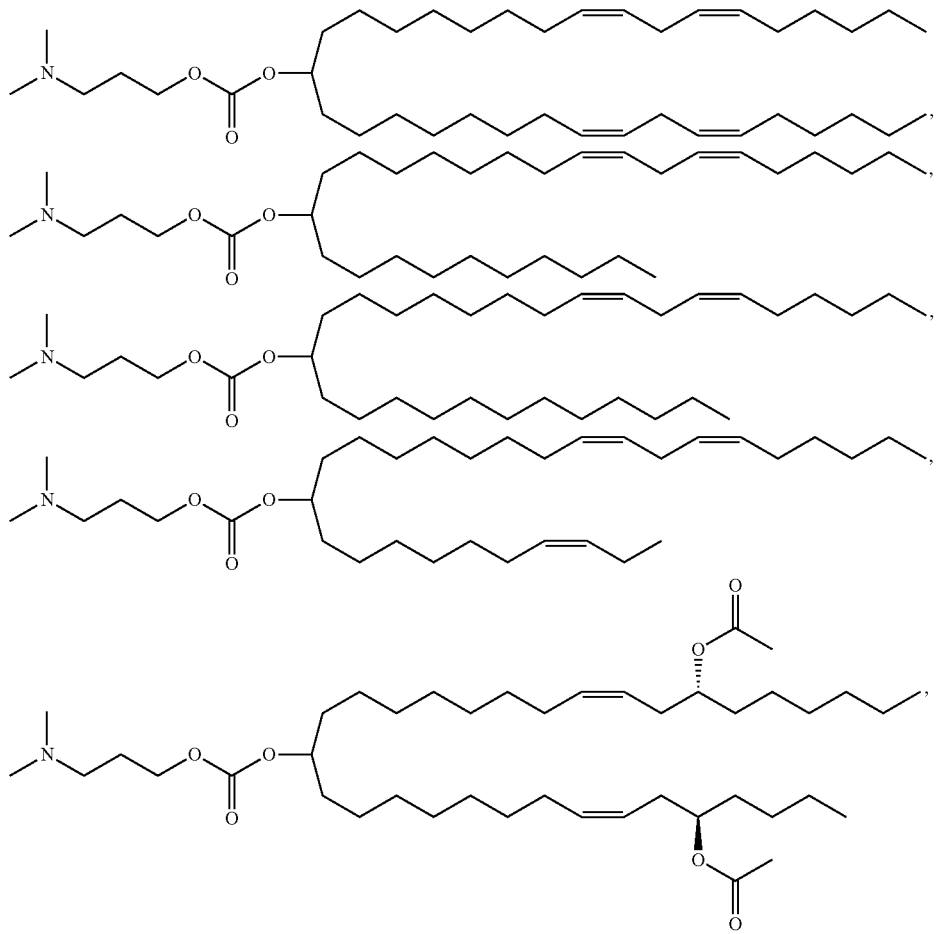

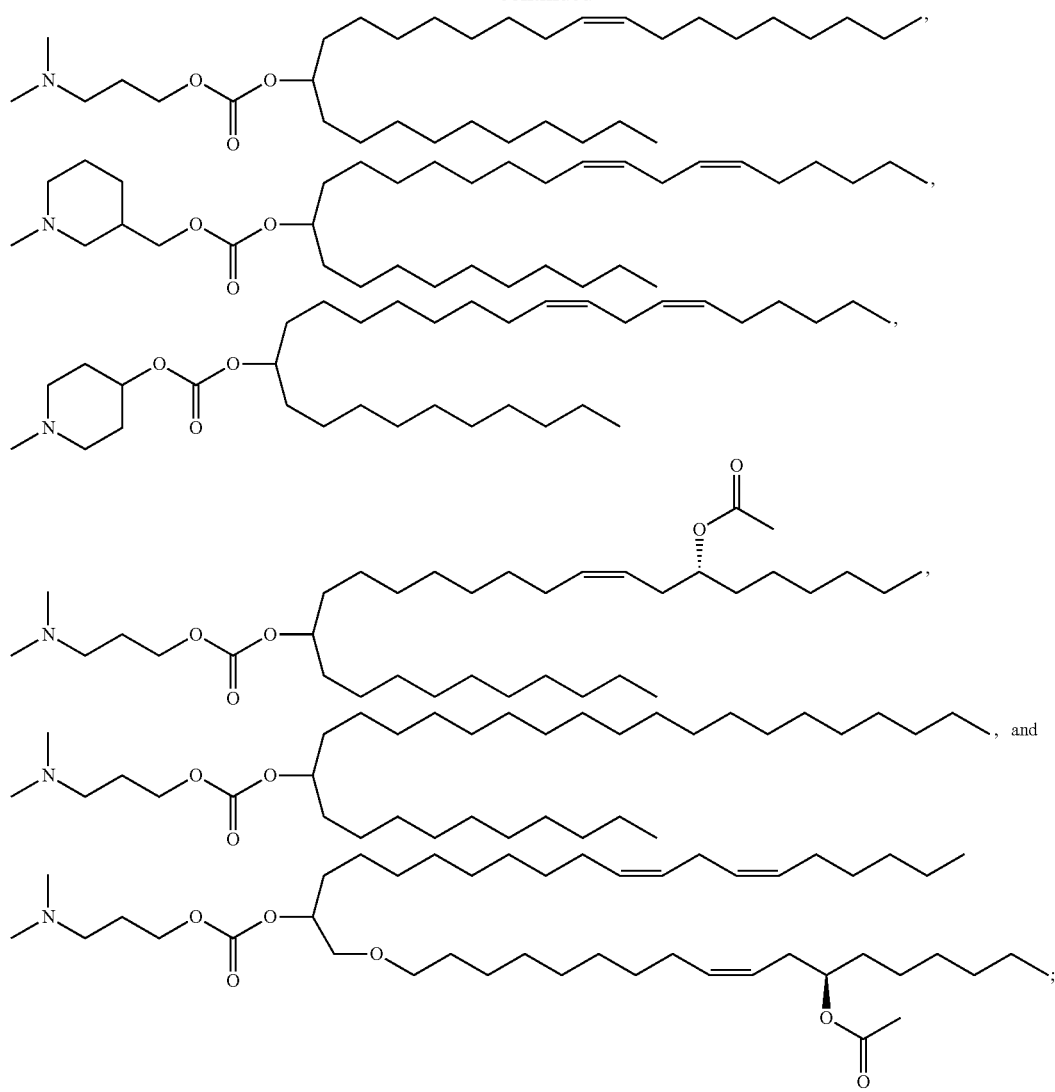

and in US 20160244761, which provides cationic lipids that include 1,2-distearyloxy-N,N-dimethyl-3-aminopropane (DSDMA), 1,2-dioleyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), 1,2-di-.gamma.-linolenyloxy-N, N-dimethylaminopropane (.gamma.-DLenDMA), 1,2-dilinoleyloxy-keto-N,N-dimethyl-3-aminopropane (DLin-K-DMA), 1,2-dilinoleyl-4-(2-dimethylaminoethyl)-[1,3]-dioxolane (DLin-K—C2-DMA) (also known as DLin-C2K-DMA, XTC2, and C2K), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K—C4-DMA), 1,2-dilinolenyloxy-4-(2-dimethylaminoethyl)-[1,3]-dioxolane (DLen-C2K-DMA), 1,2-di-.gamma.-linolenyloxy-4-(2-dimethylaminoethyl)-[1,3]-dioxolane (.gamma.-DLen-C2K-DMA), dilinoleylmethyl-3-dimethylaminopropionate (DLin-M-C2-DMA) (also known as MC2), (6Z,9Z,28Z,31Z)-heptatriaconta-6,9,28,31-tetraen-19-yl 4-(dimethylamino) butanoate (DLin-M-C3-DMA) (also known as MC3) and 3-(dilinoleylmethoxy)-N, N-dimethylpropan-1-amine (DLin-MP-DMA) (also known as 1-B1 1).

In one embodiment, the lipid compound is preferably a bio-reducible material, e.g., a bio-reducible polymer and a bio-reducible lipid-like compound.

In embodiment, the lipid compound comprises a hydrophilic head, and a hydrophobic tail, and optionally a linker.

In one embodiment, the hydrophilic head contains one or more hydrophilic functional groups, e.g., hydroxyl, carboxyl, amino, sulfhydryl, phosphate, amide, ester, ether, carbamate, carbonate, carbamide and phosphodiester. These groups can form hydrogen bonds and are optionally positively or negatively charged, in particular at physiological conditions such as physiological pH.

In one embodiment, the hydrophobic tail is a saturated or unsaturated, linear or branched, acyclic or cyclic, aromatic or nonaromatic hydrocarbon moiety, wherein the saturated or unsaturated, linear or branched, acyclic or cyclic, aromatic or nonaromatic hydrocarbon moiety optionally contains a disulfide bond and/or 8-24 carbon atoms. One or more of the carbon atoms can be replaced with a heteroatom, such as N, O, P, B, S, Si, Sb, Al, Sn, As, Se, and Ge. The lipid or lipid-like compounds containing disulfide bond can be bioreducible.

In one embodiment, the linker of the lipid or lipid-like compound links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate phosphate, phosphite, sulfate, sulfite, and thiosulfate.

The lipid or lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumarate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

Delivery or administration according to the invention can be performed with liposomes. Liposomes are spherical vesicle structures composed of a uni- or multilamellar lipid bilayer surrounding internal aqueous compartments and a relatively impermeable outer lipophilic phospholipid bilayer. Liposomes have gained considerable attention as drug delivery carriers because they are biocompatible, nontoxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2-distearoryl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at http://cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the CRISPR Cas system or components thereof may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR Cas targeted in a SNALP are contemplated. The daily treatment may be over about three days and then weekly for about five weeks. In another embodiment, a specific CRISPR Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, MO, USA), dipalmitoylphosphatidylcholine (Avanti Polar Lipids, Alabaster, AL, USA), 3-N-[(w-methoxy poly(ethylene glycol) 2000)carbamoyl]-1,2-dimyrestyloxypropylamine, and cationic 1,2-dilinoleyloxy-3-N,Ndimethylaminopropane (see, e.g., Geisbert et al., Lancet 2010; 375: 1896-905). A dosage of about 2 mg/kg total CRISPR Cas per dose administered as, for example, a bolus intravenous infusion may be contemplated.

In yet another embodiment, a SNALP may comprise synthetic cholesterol (Sigma-Aldrich), 1,2-distearoyl-snglycero-3-phosphocholine (DSPC; Avanti Polar Lipids Inc.), PEG-cDMA, and 1,2-dilinoleyloxy-3-(N,N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC) both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-C-DMA used at a molar ratio of 57.1:7.1:34.3:1.4. Upon formation of the loaded particles, SNALP were dialyzed against PBS and filter sterilized through a 0.2 μm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR Cas or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11+0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the CRISPR Cas system of the present invention or component(s) thereof or nucleic acid molecule(s) coding therefor to form lipid nanoparticles (LNPs). Lipids include, but are not limited to, DLin-KC2-DMA4, C12-200 and colipids disteroylphosphatidyl choline, cholesterol, and PEG-DMG may be formulated with CRISPR Cas instead of siRNA (see, e.g., Novobrantseva, Molecular Therapy-Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/disteroylphosphatidyl choline/cholesterol/PEG-DMG). The final lipid:siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The CRISPR Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesized from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine. and phosphorous containing compounds with a mixture of amine/amide or $N-P(O_2)S$ as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterized by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR Cas system(s) or component(s) thereof or nucleic acid molecule(s) coding therefor.

Additional delivery system formulations and particle types are also contemplated. In one embodiment, plasmids containing Cas9 and gRNA sequences can be delivered in a formulation that includes polyethyleneimine (PEI), specifically branched PEI 25 kD. See, e.g. Ryu et al., "Effective PEI-mediated delivery of CRISPR-Cas9 complex for targeted gene therapy" Nanomedicine. 2018 October; 14(7): 2095-2102. In another embodiment, plasmids can be delivered in a formulation in which the plasmids are complexed with stearyl polyethylenimine as the core of human serum albumin nanoparticles noncovalently bound to CRISPR/Cas9 plasmids or siRNA for disrupting or silencing PD-L1 expression for immunotherapy. See, e.g. Cheng et al., Int J Nanomedicine. 2018 Nov. 2; 13:7079-7094. 2018. In another embodiment, plasmids containing Cas9 and gRNA sequences can be delivered in a hybrid nanoparticle produced by encapsulating the plasmid in an exosome, which is then fused with a liposome, to allow uptake by cell types that are not efficiently transfected using liposomes. See, e.g. Lin et al., "Exosome-Liposome Hybrid Nanoparticles Deliver CRISPR/Cas9 System in MSCs" Adv Sci (Weinh). 2018 April; 5(4): 1700611. In another embodiment, a Cas9 plasmid can be delivered in a formulation that includes a novel fluorinated acid-labile branched hydroxyl-rich polycation (ARP-F). See, e.g. Qi et al., "Fluorinated Acid-Labile Branched Hydroxyl-Rich Nanosystems for Flexible and Robust Delivery of Plasmids." Small. 2018 October; 14(42): e1803061.

Supercharged Proteins

Supercharged proteins are a class of engineered or naturally occurring proteins with unusually high positive or negative net theoretical charge and may be employed in delivery of CRISPR Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified+36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116) (However, pilot experiments varying the dose of protein and RNA should be performed to optimize the procedure for specific cell lines):

(1) One day before treatment, plate $1 \times 10^5$ cells per well in a 48-well plate.
(2) On the day of treatment, dilute purified+36 GFP protein in serum free media to a final concentration 200 nM. Add RNA to a final concentration of 50 nM. Vortex to mix and incubate at room temperature for 10 min.
(3) During incubation, aspirate media from cells and wash once with PBS.
(4) Following incubation of +36 GFP and RNA, add the protein-RNA complexes to cells.
(5) Incubate cells with complexes at 37° C. for 4 h.
(6) Following incubation, aspirate the media and wash three times with 20 U/mL heparin PBS. Incubate cells with serum-containing media for a further 48 h or longer depending upon the assay for activity.
(7) Analyze cells by immunoblot, qPCR, phenotypic assay, or other appropriate method.

+36 GFP can be an effective plasmid delivery reagent in a range of cells. As plasmid DNA is a larger cargo than siRNA, proportionately more+36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications: (1) One day before treatment, plate $1 \times 10^5$ per well in a 48-well plate. (2) On the day of treatment, dilute purified b36 GFP protein in serum free media to a final concentration 2 mM. Add 1 mg of plasmid DNA. Vortex to mix and incubate at room temperature for 10 min. (3) During incubation, aspirate media from cells and wash once with PBS. (4) Following incubation of b36 GFP and plasmid DNA, gently add the protein-DNA complexes to cells. (5) Incubate cells with complexes at 37 C for 4 h. (6) Following incubation, aspirate the media and wash with PBS. Incubate cells in serum-containing media and incubate for a further 24-48 h. (7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR Cas system of the present invention. These systems of Dr. Lui and documents herein in conjunction with herein teaching can be employed in the delivery of CRISPR Cas system(s) or component(s) thereof or nucleic acid molecule(s) coding therefor.

Cell Penetrating Peptides (CPPs)

In yet another embodiment, cell penetrating peptides (CPPs) are contemplated for the delivery of the CRISPR Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles, including nanoparticles, liposomes, chromophores, small molecules and radioactive materials. In aspects of the invention, the cargo may also comprise any component of the CRISPR Cas system or the entire functional CRISPR Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intrarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the CRISPR-Cas system or components thereof. That CPPs can be employed to deliver the CRISPR-Cas system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Implantable Devices

In another embodiment, implantable devices are also contemplated for delivery of the CRISPR Cas system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the CRISPR Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically, a few devices are implanted during the same treatment procedure.

US Patent Publication 20110195123, provides a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m$^3$ to 1000 mm$^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, nondegradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system of US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mm to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof.

For example, the composition (optionally with the device) is optionally implanted within or in the proximity to pancreas, prostate, breast, liver, via the nipple, within the vascular system and so forth.

The target location is optionally selected from the group comprising, consisting essentially of, or consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear—auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR Cas system of the present invention.

As another example of a specific application, neuro and muscular degenerative diseases develop due to abnormal gene expression. Local delivery of RNAs may have therapeutic properties for interfering with such abnormal gene expression. Local delivery of anti-apoptotic, anti-inflammatory and anti-degenerative drugs including small drugs and macromolecules may also optionally be therapeutic. In such cases the Loder is applied for prolonged release at constant rate and/or through a dedicated device that is implanted separately. All of this may be used and/or adapted to the CRISPR Cas system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR Cas system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the CRISPR Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable devices may also include cells, such as epidermal progenitor cells that have been edited or modified to express the CRISPR-Cas systems disclosed herein and embedded with an implantable device, such as a patch. See. Yue et al. "Engineered Epidermal Progenitor Cells Can Correct Diet-Induced Obesity and Diabetes" Cell Stem Cell (2017) 21(2):256-263.

Implantable device technology herein discussed can be employed with herein teachings and hence by this disclosure and the knowledge in the art, CRISPR-Cas system or components thereof or nucleic acid molecules thereof or encoding or providing components may be delivered via an implantable device.

Aerosol Delivery

Subjects treated for a lung disease may for example receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector.

Hybrid Viral Capsid Delivery Systems

In one aspect, the invention provides a particle delivery system comprising a hybrid virus capsid protein or hybrid viral outer protein, wherein the hybrid virus capsid or outer protein comprises a virus capsid or outer protein attached to at least a portion of a non-capsid protein or peptide. The genetic material of a virus is stored within a viral structure called the capsid. The capsid of certain viruses is enclosed in a membrane called the viral envelope. The viral envelope is made up of a lipid bilayer embedded with viral proteins including viral glycoproteins. As used herein, an "envelope protein" or "outer protein" means a protein exposed at the surface of a viral particle that is not a capsid protein. For example, envelope or outer proteins typically comprise proteins embedded in the envelope of the virus. Non-limiting examples of outer or envelope proteins include, without limit, gp41 and gp120 of HIV, hemagglutinin, neuraminidase and M2 proteins of influenza virus.

In one example embodiment of the delivery system, the non-capsid protein or peptide has a molecular weight of up to a megadalton, or has a molecular weight in the range of 110 to 160 kDa, 160 to 200 kDa, 200 to 250 kDa, 250 to 300 kDa, 300 to 400 kDa, or 400 to 500 kDa, the non-capsid protein or peptide comprises a CRISPR protein.

The present application provides a vector for delivering an effector protein and at least one CRISPR guide RNA to a cell comprising a minimal promoter operably linked to a polynucleotide sequence encoding the effector protein and a second minimal promoter operably linked to a polynucleotide sequence encoding at least one guide RNA, wherein the length of the vector sequence comprising the minimal promoters and polynucleotide sequences is less than 4.4 Kb. In an embodiment, the virus is an adeno-associated virus (AAV) or an adenovirus. In another embodiment, the effector protein is a CRISPR enzyme. In a further embodiment, the CRISPR enzyme is SaCas9, Cpf1, Cas13b or C2c2.

In a related aspect, the invention provides a lentiviral vector for delivering an effector protein and at least one CRISPR guide RNA to a cell comprising a promoter operably linked to a polynucleotide sequence encoding Cpf1 and a second promoter operably linked to a polynucleotide sequence encoding at least one guide RNA, wherein the polynucleotide sequences are in reverse orientation.

In an embodiment of the delivery system, the virus is lentivirus or murine leukemia virus (MuMLV).

In an embodiment of the delivery system, the virus is an Adenoviridae or a Parvoviridae or a retrovirus or a Rhabdoviridae or an enveloped virus having a glycoprotein protein (G protein).

In an embodiment of the delivery system, the virus is VSV or rabies virus.

In an embodiment of the delivery system, the capsid or outer protein comprises a capsid protein having VP1, VP2 or VP3.

In an embodiment of the delivery system, the capsid protein is VP3, and the non-capsid protein is inserted into or attached to VP3 loop 3 or loop 6.

In an embodiment of the delivery system, the virus is delivered to the interior of a cell.

In an embodiment of the delivery system, the capsid or outer protein and the non-capsid protein can dissociate after delivery into a cell.

In an embodiment of the delivery system, the capsid or outer protein is attached to the protein by a linker.

In an embodiment of the delivery system, the linker comprises amino acids.

In an embodiment of the delivery system, the linker is a chemical linker.

In an embodiment of the delivery system, the linker is cleavable.

In an embodiment of the delivery system, the linker is biodegradable.

In an embodiment of the delivery system, the linker comprises $(GGGGS)_{1-3}$ (SEQ ID NOs: 89-91), ENLYFQG (SEQ ID NO: 92), or a disulfide.

In an embodiment, the delivery system comprises a protease or nucleic acid molecule(s) encoding a protease that is expressed, said protease being capable of cleaving the linker, whereby there can be cleavage of the linker. In an embodiment of the invention, a protease is delivered with a particle component of the system, for example packaged, mixed with, or enclosed by lipid and or capsid. Entry of the particle into a cell is thereby accompanied or followed by cleavage and dissociation of payload from particle. In certain embodiments, an expressible nucleic acid encoding a protease is delivered, whereby at entry or following entry of the particle into a cell, there is protease expression, linker cleavage, and dissociation of payload from capsid. In certain embodiments, dissociation of payload occurs with viral replication. In certain embodiments, dissociation of payload occurs in the absence of productive virus replication.

In an embodiment of the delivery system, each terminus of a CRISPR protein is attached to the capsid or outer protein by a linker.

In an embodiment of the delivery system, the non-capsid protein is attached to the exterior portion of the capsid or outer protein.

In an embodiment of the delivery system, the non-capsid protein is attached to the interior portion of the capsid or outer protein.

In an embodiment of the delivery system, the capsid or outer protein and the non-capsid protein are a fusion protein.

In an embodiment of the delivery system, the non-capsid protein is encapsulated by the capsid or outer protein.

In an embodiment of the delivery system, the non-capsid protein is attached to a component of the capsid protein or a component of the outer protein prior to formation of the capsid or the outer protein.

In an embodiment of the delivery system, the protein is attached to the capsid or outer protein after formation of the capsid or outer protein.

In an embodiment, the delivery system comprises a targeting moiety, such as active targeting of a lipid entity of the invention, e.g., lipid particle or nanoparticle or liposome or lipid bylayer of the invention comprising a targeting moiety for active targeting.

With regard to targeting moieties, mention is made of Deshpande et al, "Current trends in the use of liposomes for tumor targeting," Nanomedicine (Lond). 8(9), doi:10.2217/nnm.13.118 (2013), and the documents it cites, all of which are incorporated herein by reference. Mention is also made of WO/2016/027264, and the documents it cites, all of which are incorporated herein by reference. And mention is made of Lorenzer et al, "Going beyond the liver: Progress and challenges of targeted delivery of siRNA therapeutics," Journal of Controlled Release, 203: 1-15 (2015), and the documents it cites, all of which are incorporated herein by reference.

An actively targeting lipid particle or nanoparticle or liposome or lipid bylayer delivery system (generally as to embodiments of the invention, "lipid entity of the invention" delivery systems) are prepared by conjugating targeting moieties, including small molecule ligands, peptides and monoclonal antibodies, on the lipid or liposomal surface; for example, certain receptors, such as folate and transferrin (Tf) receptors (TfR), are overexpressed on many cancer cells and have been used to make liposomes tumor cell specific. Liposomes that accumulate in the tumor microenvironment can be subsequently endocytosed into the cells by interacting with specific cell surface receptors. To efficiently target liposomes to cells, such as cancer cells, it is useful that the targeting moiety have an affinity for a cell surface receptor and to link the targeting moiety in sufficient quantities to have optimum affinity for the cell surface receptors; and determining these aspects are within the ambit of the skilled artisan. In the field of active targeting, there are a number of cell-, e.g., tumor-, specific targeting ligands.

Also, as to active targeting, with regard to targeting cell surface receptors such as cancer cell surface receptors, targeting ligands on liposomes can provide attachment of liposomes to cells, e.g., vascular cells, via a non-internalizing epitope; and this can increase the extracellular concentration of that which is being delivered, thereby increasing the amount delivered to the target cells. A strategy to target cell surface receptors, such as cell surface receptors on cancer cells, such as overexpressed cell surface receptors on cancer cells, is to use receptor-specific ligands or antibodies. Many cancer cell types display upregulation of tumor-specific receptors. For example, TfRs and folate receptors (FRs) are greatly overexpressed by many tumor cell types in response to their increased metabolic demand. Folic acid can be used as a targeting ligand for specialized delivery owing to its ease of conjugation to nanocarriers, its high affinity for FRs and the relatively low frequency of FRs, in normal tissues as compared with their overexpression in activated macrophages and cancer cells, e.g., certain ovarian, breast, lung, colon, kidney and brain tumors. Overexpression of FR on macrophages is an indication of inflammatory diseases, such as psoriasis, Crohn's disease, rheumatoid arthritis and atherosclerosis; accordingly, folate-mediated targeting of the invention can also be used for studying, addressing or treating inflammatory disorders, as well as cancers. Folate-linked lipid particles or nanoparticles or liposomes or lipid bilayers of the invention ("lipid entity of the invention") deliver their cargo intracellularly through receptor-mediated endocytosis. Intracellular trafficking can be directed to acidic compartments that facilitate cargo release, and, most importantly, release of the cargo can be altered or delayed until it reaches the cytoplasm or vicinity of target organelles. Delivery of cargo using a lipid entity of the invention having a targeting moiety, such as a folate-linked lipid entity of the invention, can be superior to nontargeted lipid entity of the invention. The attachment of folate directly to the lipid head groups may not be favorable for intracellular delivery of folate-conjugated lipid entity of the invention, since they may not bind as efficiently to cells as folate attached to the lipid entity of the invention surface by a spacer, which may can enter cancer cells more efficiently. A lipid entity of the invention coupled to folate can be used for the delivery of complexes of lipid, e.g., liposome, e.g., anionic liposome and virus or capsid or envelope or virus outer protein, such as those herein discussed such as adenovirous or AAV. Tf is a monomeric serum glycoprotein of approximately 80 KDa involved in the transport of iron throughout the body. Tf binds to the TfR and translocates into cells via receptor-mediated endocytosis. The expression of TfR is can be higher in certain cells, such as tumor cells (as compared with normal cells and is associated with the increased iron demand in rapidly proliferating cancer cells. Accordingly, the invention comprehends a TfR-targeted lipid entity of the invention, e.g., as to liver cells, liver cancer, breast cells such as breast cancer cells, colon such as colon cancer cells, ovarian cells such as ovarian cancer cells, head, neck and lung cells, such as head, neck and non-small-cell lung cancer cells, cells of the mouth such as oral tumor cells.

Also, as to active targeting, a lipid entity of the invention can be multifunctional, i.e., employ more than one targeting moiety such as CPP, along with Tf; a bifunctional system; e.g., a combination of Tf and poly-L-arginine which can provide transport across the endothelium of the blood-brain barrier. EGFR, is a tyrosine kinase receptor belonging to the ErbB family of receptors that mediates cell growth, differentiation and repair in cells, especially non-cancerous cells, but EGF is overexpressed in certain cells such as many solid tumors, including colorectal, non-small-cell lung cancer, squamous cell carcinoma of the ovary, kidney, head, pancreas, neck and prostate, and especially breast cancer. The invention comprehends EGFR-targeted monoclonal antibody(ies) linked to a lipid entity of the invention. HER-2 is often overexpressed in patients with breast cancer, and is also associated with lung, bladder, prostate, brain and stomach cancers. HER-2, encoded by the ERBB2 gene. The invention comprehends a HER-2-targeting lipid entity of the invention, e.g., an anti-HER-2-antibody (or binding fragment thereof)-lipid entity of the invention, a HER-2-targeting-PEGylated lipid entity of the invention (e.g., having an anti-HER-2-antibody or binding fragment thereof), a HER-2-targeting-maleimide-PEG polymer-lipid entity of the invention (e.g., having an anti-HER-2-antibody or binding fragment thereof). Upon cellular association, the receptor-antibody complex can be internalized by formation of an endosome for delivery to the cytoplasm. With respect to receptor-mediated targeting, the skilled artisan takes into consideration ligand/target affinity and the quantity of receptors on the cell surface, and that PEGylation can act as a barrier against interaction with receptors. The use of antibody-lipid entity of the invention targeting can be advantageous. Multivalent presentation of targeting moieties can also increase the uptake and signaling properties of antibody fragments. In practice of the invention, the skilled person takes into account ligand density (e.g., high ligand densities on a lipid entity of the invention may be advantageous for increased binding to target cells). Preventing early by macrophages can be addressed with a sterically stabilized lipid entity of the invention and linking ligands to the terminus of molecules such as PEG, which is anchored in the lipid entity of the invention (e.g., lipid particle or nanoparticle or liposome or lipid bilayer). The microenvironment of a cell mass such as a tumor microenvironment can be targeted; for instance, it may be advantageous to target cell mass vasculature, such as the tumor vasculature microenvironment. Thus, the invention comprehends targeting VEGF. VEGF and its receptors are well-known proangiogenic molecules and are well-characterized targets for antiangiogenic therapy. Many small-molecule inhibitors of receptor tyrosine kinases, such as VEGFRs or basic FGFRs, have been developed as anticancer agents and the invention comprehends coupling any one or more of these peptides to a lipid entity of the invention, e.g., phage IVO peptide(s) (e.g., via or with a PEG terminus), tumor-homing peptide APRPG such as APRPG-PEG-modified. VCAM, the vascular endothelium plays a key role in the pathogenesis of inflammation, thrombosis and atherosclerosis. CAMs are involved in inflammatory disorders, including cancer, and are a logical target, E- and P-selectins, VCAM-1 and ICAMs. Can be used to target a lipid entity of the invention., e.g., with PEGylation. Matrix metalloproteases (MMPs) belong to the family of zinc-dependent endopeptidases. They are involved in tissue remodeling, tumor invasiveness, resistance to apoptosis and metastasis. There are four MMP inhibitors called TIMP1-4, which determine the balance between tumor growth inhibition and metastasis; a protein involved in the angiogenesis of tumor vessels is MT1-MMP, expressed on newly formed vessels and tumor tissues. The proteolytic activity of MT1-MMP cleaves proteins, such as fibronectin, elastin, collagen and laminin, at the plasma membrane and activates soluble MMPs, such as MMP-2, which degrades the matrix. An antibody or fragment thereof such as a Fab' fragment can be used in the practice of the invention such as for an antihuman MT1-MMP monoclonal antibody linked to a lipid entity of the invention, e.g., via a spacer such as a PEG spacer. αβ-integrins or integrins are a group of transmembrane glycoprotein receptors that mediate attachment between a cell and its surrounding tissues or extracellular matrix. Integrins contain two distinct chains (heterodimers) called α- and β-subunits. The tumor tissue-specific expression of integrin receptors can be been utilized for targeted delivery in the invention, e.g., whereby the targeting moiety can be an RGD peptide such as a cyclic RGD. Aptamers are ssDNA or RNA oligonucleotides that impart high affinity and specific recognition of the target molecules by electrostatic interactions, hydrogen bonding and hydro phobic interactions as opposed to the Watson-Crick base pairing, which is typical for the bonding interactions of oligonucleotides. Aptamers as a targeting moiety can have advantages over antibodies: aptamers can demonstrate higher target antigen recognition as compared with antibodies; aptamers can be more stable and smaller in size as compared with antibodies; aptamers can be easily synthesized and chemically modified for molecular conjugation; and aptamers can be changed in sequence for improved selectivity and can be developed to recognize poorly immunogenic targets. Such moieties as a sgc8 aptamer can be used as a targeting moiety (e.g., via covalent linking to the lipid entity of the invention, e.g., via a spacer, such as a PEG spacer). The targeting moiety can be stimuli-sensitive, e.g., sensitive to an externally applied stimuli, such as magnetic fields, ultrasound or light; and pH-triggering can also be used, e.g., a labile linkage can be used between a hydrophilic moiety such as PEG and a hydrophobic moiety such as a lipid entity of the invention, which is cleaved only upon exposure to the relatively acidic conditions characteristic of the a particular environment or microenvironment such as an endocytic vacuole or the acidic tumor mass. pH-sensitive copolymers can also be incorporated in embodiments of the invention can provide shielding; diortho esters, vinyl esters, cysteine-cleavable lipopolymers, double esters and hydrazones are a few examples of pH-sensitive bonds that are quite stable at pH 7.5, but are hydrolyzed relatively rapidly at pH 6 and below, e.g., a terminally alkylated copolymer of N-isopropylacrylamide and methacrylic acid that copolymer facilitates destabilization of a lipid entity of the invention and release in compartments with decreased pH value; or, the invention comprehends ionic polymers for generation of a pH-responsive lipid entity of the invention (e.g., poly (methacrylic acid), poly(diethylaminoethyl methacrylate), poly(acrylamide) and poly(acrylic acid)). Temperature-triggered delivery is also within the ambit of the invention. Many pathological areas, such as inflamed tissues and tumors, show a distinctive hyperthermia compared with normal tissues. Utilizing this hyperthermia is an attractive strategy in cancer therapy since hyperthermia is associated with increased tumor permeability and enhanced uptake. This technique involves local heating of the site to increase microvascular pore size and blood flow, which, in turn, can result in an increased extravasation of embodiments of the invention. Temperature-sensitive lipid entity of the invention can be prepared from thermosensitive lipids or polymers with a low critical solution temperature. Above the low critical solution temperature (e.g., at site such as tumor site or inflamed tissue site), the polymer precipitates, disrupting the liposomes to release. Lipids with a specific gel-to-liquid phase transition temperature are used to prepare these lipid entities of the invention; and a lipid for a thermosensitive embodiment can be dipalmitoylphosphatidylcholine. Thermosensitive polymers can also facilitate destabilization followed by release, and a useful thermosensitive polymer is poly (N-isopropylacrylamide). Another temperature triggered system can employ lysolipid temperature-sensitive liposomes. The invention also comprehends redox-triggered delivery: The difference in redox potential between normal and inflamed or tumor tissues, and between the intra- and extra-cellular environments has been exploited for delivery; e.g., GSH is a reducing agent abundant in cells, especially in the cytosol, mitochondria and nucleus. The GSH concentrations in blood and extracellular matrix are just one out of 100 to one out of 1000 of the intracellular concentration, respectively. This high redox potential difference caused by GSH, cysteine and other reducing agents can break the reducible bonds, destabilize a lipid entity of the invention and result in release of payload. The disulfide bond can be used as the cleavable/reversible linker in a lipid entity of the invention, because it causes sensitivity to redox owing to the disulfide-to-thiol reduction reaction; a lipid entity of the invention can be made reduction sensitive by using two (e.g., two forms of a disulfide-conjugated multifunctional lipid as cleavage of the disulfide bond (e.g., via tris(2-carboxyethyl)phosphine, dithiothreitol, L-cysteine or GSH), can cause removal of the hydrophilic head group of the conjugate and alter the membrane organization leading to release of payload. Calcein release from reduction-sensitive lipid entity of the invention containing a disulfide conjugate can be more useful than a reduction-insensitive embodiment. Enzymes can also be used as a trigger to release payload. Enzymes, including MMPs (e.g. MMP2), phospholipase A2, alkaline phosphatase, transglutaminase or phosphatidylinositol-specific phospholipase C, have been found to be overexpressed in certain tissues, e.g., tumor tissues. In the presence of these enzymes, specially engineered enzyme-sensitive lipid entity of the invention can be disrupted and release the payload. an MMP2-cleavable octapeptide (Gly-Pro-Leu-Gly-Ile-Ala-Gly-Gln) (SEQ ID NO: 129) can be incorporated into a linker, and can have antibody targeting, e.g., antibody 2C5. The invention also comprehends light- or energy-triggered delivery, e.g., the lipid entity of the invention can be light-sensitive, such that light or energy can facilitate structural and conformational changes, which lead to direct interaction of the lipid entity of the invention with the target cells via membrane fusion, photo-isomerism, photofragmentation or photopolymerization; such a moiety therefor can be benzoporphyrin photosensitizer. Ultrasound can be a form of energy to trigger delivery; a lipid entity of the invention with a small quantity of particular gas, including air or perfluorated hydrocarbon can be triggered to release with ultrasound, e.g., low-frequency ultrasound (LFUS). Magnetic delivery: A lipid entity of the invention can be magnetized by incorporation of magnetites, such as Fe3O4 or γ-Fe2O3, e.g., those that are less than 10 nm in size. Targeted delivery can be then by exposure to a magnetic field.

Also, as to active targeting, the invention also comprehends intracellular delivery. Since liposomes follow the endocytic pathway, they are entrapped in the endosomes (pH 6.5-6) and subsequently fuse with lysosomes (pH<5), where they undergo degradation that results in a lower therapeutic potential. The low endosomal pH can be taken advantage of to escape degradation. Fusogenic lipids or peptides, which destabilize the endosomal membrane after the conformational transition/activation at a lowered pH. Amines are protonated at an acidic pH and cause endosomal swelling and rupture by a buffer effect Unsaturated dioleoylphosphatidylethanolamine (DOPE) readily adopts an inverted hexagonal shape at a low pH, which causes fusion of liposomes to the endosomal membrane. This process destabilizes a lipid entity containing DOPE and releases the cargo into the cytoplasm; fusogenic lipid GALA, cholesteryl-GALA and PEG-GALA may show a highly efficient endosomal release; a pore-forming protein listeriolysin O may provide an endosomal escape mechanism; and, histidine-rich peptides have the ability to fuse with the endosomal membrane, resulting in pore formation, and can buffer the proton pump causing membrane lysis.

Also, as to active targeting, cell-penetrating peptides (CPPs) facilitate uptake of macromolecules through cellular membranes and, thus, enhance the delivery of CPP-modified molecules inside the cell. CPPs can be split into two classes: amphipathic helical peptides, such as transportan and MAP, where lysine residues are major contributors to the positive charge; and Arg-rich peptides, such as TATp, Antennapedia or penetratin. TATp is a transcription-activating factor with 86 amino acids that contains a highly basic (two Lys and six Arg among nine residues) protein transduction domain, which brings about nuclear localization and RNA binding. Other CPPs that have been used for the modification of liposomes include the following: the minimal protein transduction domain of Antennapedia, a Drosophilia homeoprotein, called penetratin, which is a 16-mer peptide (residues 43-58) present in the third helix of the homeodomain; a 27-amino acid-long chimeric CPP, containing the peptide sequence from the amino terminus of the neuropeptide galanin bound via the Lys residue, mastoparan, a wasp venom peptide; VP22, a major structural component of HSV-1 facilitating intracellular transport and transportan (18-mer) amphipathic model peptide that translocates plasma membranes of mast cells and endothelial cells by both energy-dependent and -independent mechanisms. The invention comprises a lipid entity of the invention modified with CPP(s), for intracellular delivery that may proceed via energy dependent macropinocytosis followed by endosomal escape. The invention further comprises organelle-specific targeting. A lipid entity of the invention surface-functionalized with the triphenylphosphonium (TPP) moiety or a lipid entity of the invention with a lipophilic cation, rhodamine 123 can be effective in delivery of cargo to mitochondria. DOPE/sphingomyelin/stearyl-octa-arginine can delivers cargos to the mitochondrial interior via membrane fusion. A lipid entity of the invention surface modified with a lysosomotropic ligand, octadecyl rhodamine B can deliver cargo to lysosomes. Ceramides are useful in inducing lysosomal membrane permeabilization; the invention comprehends intracellular delivery of a lipid entity of the invention having a ceramide. The invention further comprehends a lipid entity of the invention targeting the nucleus, e.g., via a DNA-intercalating moiety. The invention also comprehends multifunctional liposomes for targeting, i.e., attaching more than one functional group to the surface of the lipid entity of the invention, for instance to enhances accumulation in a desired site and/or promotes organelle-specific delivery and/or target a particular type of cell and/or respond to the local stimuli such as temperature (e.g., elevated), pH (e.g., decreased), respond to externally applied stimuli such as a magnetic field, light, energy, heat or ultrasound and/or promote intracellular delivery of the cargo. All of these are considered actively targeting moieties.

An embodiment of the invention includes the delivery system comprising an actively targeting lipid particle or nanoparticle or liposome or lipid bilayer delivery system; or comprising a lipid particle or nanoparticle or liposome or lipid bilayer comprising a targeting moiety whereby there is active targeting or wherein the targeting moiety is an actively targeting moiety. A targeting moiety can be one or more targeting moieties, and a targeting moiety can be for any desired type of targeting such as, e.g., to target a cell such as any herein-mentioned; or to target an organelle such as any herein-mentioned; or for targeting a response such as to a physical condition such as heat, energy, ultrasound, light, pH, chemical such as enzymatic, or magnetic stimuli; or to target to achieve a particular outcome such as delivery of payload to a particular location, such as by cell penetration.

It should be understood that as to each possible targeting or active targeting moiety herein-discussed, there is an aspect of the invention wherein the delivery system comprises such a targeting or active targeting moiety. Likewise, the following table provides exemplary targeting moieties that can be used in the practice of the invention an as to each an aspect of the invention provides a delivery system that comprises such a targeting moiety (see e.g. Table 8).

TABLE 8

| Targeting Moiety | Target Molecule | Target Cell or Tissue |
|---|---|---|
| folate | folate receptor | cancer cells |
| transferrin | transferrin receptor | cancer cells |
| Antibody CC52 | rat CC531 | rat colon adenocarcinoma CC531 |
| anti-HER2 antibody | HER2 | HER2-overexpressing tumors |
| anti-GD2 | GD2 | neuroblastoma, melanoma |
| anti-EGFR | EGFR | tumor cells overexpressing EGFR |
| pH-dependent fusogenic peptide diINF-7 | | ovarian carcinoma |
| anti-VEGFR | VEGF Receptor | tumor vasculature |
| anti-CD19 | CD19 (B cell marker) | leukemia, lymphoma |
| cell-penetrating peptide | | blood-brain barrier |
| cyclic arginine-glycine-aspartic acid-tyrosine-cysteine peptide (c(RGDyC)-LP) | $\alpha v \beta 3$ | glioblastoma cells, human umbilical vein endothelial cells, tumor angiogenesis |
| ASSHN peptide | | endothelial progenitor cells; anti-cancer |
| PR_b peptide | $\alpha_5\beta_1$ integrin | cancer cells |
| AG86 peptide | $\alpha_6\beta_4$ integrin | cancer cells |
| KCCYSL (P6.1 peptide) | HER-2 receptor | cancer cells |
| affinity peptide LN (YEVGHRC) | Aminopeptidase N (APN/CD13) | APN-positive tumor |

TABLE 8-continued

| Targeting Moiety | Target Molecule | Target Cell or Tissue |
|---|---|---|
| synthetic somatostatin analogue | Somatostatin receptor 2 (SSTR2) | breast cancer |
| anti-CD20 monoclonal antibody | B-lymphocytes | B cell lymphoma |

Thus, in an embodiment of the delivery system, the targeting moiety comprises a receptor ligand, such as, for example, hyaluronic acid for CD44 receptor, galactose for hepatocytes, or antibody or fragment thereof such as a binding antibody fragment against a desired surface receptor, and as to each of a targeting moiety comprising a receptor ligand, or an antibody or fragment thereof such as a binding fragment thereof, such as against a desired surface receptor, there is an aspect of the invention wherein the delivery system comprises a targeting moiety comprising a receptor ligand, or an antibody or fragment thereof such as a binding fragment thereof, such as against a desired surface receptor, or hyaluronic acid for CD44 receptor, galactose for hepatocytes (see, e.g., Surace et al, "Lipoplexes targeting the CD44 hyaluronic acid receptor for efficient transfection of breast cancer cells," J. Mol Pharm 6(4):1062-73; doi: 10.1021/mp800215d (2009); Sonoke et al, "Galactose-modified cationic liposomes as a liver-targeting delivery system for small interfering RNA," Biol Pharm Bull. 34(8): 1338-42 (2011); Torchilin, "Antibody-modified liposomes for cancer chemotherapy," Expert Opin. Drug Deliv. 5 (9), 1003-1025 (2008); Manjappa et al, "Antibody derivatization and conjugation strategies: application in preparation of stealth immunoliposome to target chemotherapeutics to tumor," J. Control. Release 150 (1), 2-22 (2011); Sofou S "Antibody-targeted liposomes in cancer therapy and imaging," Expert Opin. Drug Deliv. 5 (2): 189-204 (2008); Gao J et al, "Antibody-targeted immunoliposomes for cancer treatment," Mini. Rev. Med. Chem. 13(14): 2026-2035 (2013); Molavi et al, "Anti-CD30 antibody conjugated liposomal doxorubicin with significantly improved therapeutic efficacy against anaplastic large cell lymphoma," Biomaterials 34(34):8718-25 (2013), each of which and the documents cited therein are hereby incorporated herein by reference).

Moreover, in view of the teachings herein the skilled artisan can readily select and apply a desired targeting moiety in the practice of the invention as to a lipid entity of the invention. The invention comprehends an embodiment wherein the delivery system comprises a lipid entity having a targeting moiety.

In an embodiment of the delivery system, the protein comprises a CRISPR protein, or portion thereof.

In some embodiments a non-capsid protein or protein that is not a virus outer protein or a virus envelope (sometimes herein shorthanded as "non-capsid protein"), such as a CRISPR protein or portion thereof, can have one or more functional moiety(ies) thereon, such as a moiety for targeting or locating, such as an NLS or NES, or an activator or repressor.

In an embodiment of the delivery system, a protein or portion thereof can comprise a tag.

In an aspect, the invention provides a virus particle comprising a capsid or outer protein having one or more hybrid virus capsid or outer proteins comprising the virus capsid or outer protein attached to at least a portion of a non-capsid protein or a CRISPR protein.

In an aspect, the invention provides an in vitro method of delivery comprising contacting the delivery system with a cell, optionally a eukaryotic cell, whereby there is delivery into the cell of constituents of the delivery system.

In an aspect, the invention provides an in vitro, a research or study method of delivery comprising contacting the delivery system with a cell, optionally a eukaryotic cell, whereby there is delivery into the cell of constituents of the delivery system, obtaining data or results from the contacting, and transmitting the data or results.

In an aspect, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results.

In an aspect, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results; and wherein the cell product is altered compared to the cell not contacted with the delivery system, for example altered from that which would have been wild type of the cell but for the contacting.

In an embodiment, the cell product is non-human or animal.

In one aspect, the invention provides a particle delivery system comprising a composite virus particle, wherein the composite virus particle comprises a lipid, a virus capsid protein, and at least a portion of a non-capsid protein or peptide. The non-capsid peptide or protein can have a molecular weight of up to one megadalton.

In one embodiment, the particle delivery system comprises a virus particle adsorbed to a liposome or lipid particle or nanoparticle. In one embodiment, a virus is adsorbed to a liposome or lipid particle or nanoparticle either through electrostatic interactions, or is covalently linked through a linker. The lipid particle or nanoparticles (1 mg/ml) dissolved in either sodium acetate buffer (pH 5.2) or pure $H_2O$ (pH 7) are positively charged. The isoelectropoint of most viruses is in the range of 3.5-7. They have a negatively charged surface in either sodium acetate buffer (pH 5.2) or pure $H_2O$. The electrostatic interaction between the virus and the liposome or synthetic lipid nanoparticle is the most significant factor driving adsorption. By modifying the charge density of the lipid nanoparticle, e.g. inclusion of neutral lipids into the lipid nanoparticle, it is possible to modulate the interaction between the lipid nanoparticle and the virus, hence modulating the assembly. In one embodiment, the liposome comprises a cationic lipid.

In one embodiment, the liposome of the particle delivery system comprises a CRISPR system component.

In one aspect, the invention provides a delivery system comprising one or more hybrid virus capsid proteins in combination with a lipid particle, wherein the hybrid virus capsid protein comprises at least a portion of a virus capsid protein attached to at least a portion of a non-capsid protein.

In one embodiment, the virus capsid protein of the delivery system is attached to a surface of the lipid particle. When the lipid particle is a bilayer, e.g., a liposome, the lipid particle comprises an exterior hydrophilic surface and an interior hydrophilic surface. In one embodiment, the virus capsid protein is attached to a surface of the lipid particle by an electrostatic interaction or by hydrophobic interaction.

In one embodiment, the particle delivery system has a diameter of 50-1000 nm, preferably 100-1000 nm.

In one embodiment, the delivery system comprises a non-capsid protein or peptide, wherein the non-capsid protein or peptide has a molecular weight of up to a megadalton. In one embodiment, the non-capsid protein or peptide has a molecular weight in the range of 110 to 160 kDa, 160 to 200 kDa, 200 to 250 kDa, 250 to 300 kDa, 300 to 400 kDa, or 400 to 500 kDa.

In one embodiment, the delivery system comprises a non-capsid protein or peptide, wherein the protein or peptide comprises a CRISPR protein or peptide. In one embodiment, the protein or peptide comprises a Cas9, a Cpf1 or a C2c2/Cas13a.

In one embodiment, a weight ratio of hybrid capsid protein to wild-type capsid protein is from 1:10 to 1:1, for example, 1:1, 1:2, 1:3, 1:4, 1:5, 1:6, 1:7, 1:8, 1:9 and 1:10.

In one embodiment, the virus of the delivery system is an Adenoviridae or a Parvoviridae or a Rhabdoviridae or an enveloped virus having a glycoprotein protein. In one embodiment, the virus is an adeno-associated virus (AAV) or an adenovirus or a VSV or a rabies virus. In one embodiment, the virus is a retrovirus or a lentivirus. In one embodiment, the virus is murine leukemia virus (MuMLV).

In one embodiment, the virus capsid protein of the delivery system comprises VP1, VP2 or VP3.

In one embodiment, the virus capsid protein of the delivery system is VP3, and the non-capsid protein is inserted into or tethered or connected to VP3 loop 3 or loop 6.

In one embodiment, the virus of the delivery system is delivered to the interior of a cell.

In one embodiment, the virus capsid protein and the non-capsid protein are capable of dissociating after delivery into a cell.

In one aspect of the delivery system, the virus capsid protein is attached to the non-capsid protein by a linker. In one embodiment, the linker comprises amino acids. In one embodiment, the linker is a chemical linker. In another embodiment, the linker is cleavable or biodegradable. In one embodiment, the linker comprises (GGGGS)$_{13}$ (SEQ ID NOs: 89-91, ENLYFQG (SEQ ID NO: 92), or a disulfide.

In one embodiment of the delivery system, each terminus of the non-capsid protein is attached to the capsid protein by a linker moiety.

In one embodiment, the non-capsid protein is attached to the exterior portion of the virus capsid protein. As used herein, "exterior portion" as it refers to a virus capsid protein means the outer surface of the virus capsid protein when it is in a formed virus capsid.

In one embodiment, the non-capsid protein is attached to the interior portion of the capsid protein or is encapsulated within the lipid particle. As used herein, "interior portion" as it refers to a virus capsid protein means the inner surface of the virus capsid protein when it is in a formed virus capsid. In one embodiment, the virus capsid protein and the non-capsid protein are a fusion protein.

In one embodiment, the fusion protein is attached to the surface of the lipid particle.

In one embodiment, the non-capsid protein is attached to the virus capsid protein prior to formation of the capsid.

In one embodiment, the non-capsid protein is attached to the virus capsid protein after formation of the capsid.

In one embodiment, the non-capsid protein comprises a targeting moiety.

In one embodiment, the targeting moiety comprises a receptor ligand.

In an embodiment, the non-capsid protein comprises a tag.

In an embodiment, the non-capsid protein comprises one or more heterologous nuclear localization signals(s) (NLSs).

In an embodiment, the protein or peptide comprises a Type II CRISPR protein or a Type V CRISPR protein.

In an embodiment, the delivery system further comprises guide RNS, optionally complexed with the CRISPR protein.

In an embodiment, the delivery system comprises a protease or nucleic acid molecule(s) encoding a protease that is expressed, whereby the protease cleaves the linker. In certain embodiments, there is protease expression, linker cleavage, and dissociation of payload from capsid in the absence of productive virus replication.

In an aspect, the invention provides a delivery system comprising a first hybrid virus capsid protein and a second hybrid virus capsid protein, wherein the first hybrid virus capsid protein comprises a virus capsid protein attached to a first part of a protein, and wherein the second hybrid virus capsid protein comprises a second virus capsid protein attached to a second part of the protein, wherein the first part of the protein and the second part of the protein are capable of associating to form a functional protein.

In an aspect, the invention provides a delivery system comprising a first hybrid virus capsid protein and a second hybrid virus capsid protein, wherein the first hybrid virus capsid protein comprises a virus capsid protein attached to a first part of a CRISPR protein, and wherein the second hybrid virus capsid protein comprises a second virus capsid protein attached to a second part of a CRISPR protein, wherein the first part of the CRISPR protein and the second part of the CRISPR protein are capable of associating to form a functional CRISPR protein.

In an embodiment of the delivery system, the first hybrid virus capsid protein and the second virus capsid protein are on the surface of the same virus particle.

In an embodiment of the delivery system, the first hybrid virus capsule protein is located at the interior of a first virus particle and the second hybrid virus capsid protein is located at the interior of a second virus particle.

In an embodiment of the delivery system, the first part of the protein or CRISPR protein is linked to a first member of a ligand pair, and the second part of the protein or CRISPR protein is linked to a second member of a ligand pair, wherein the first part of the ligand pair binds to the second part of the ligand pair in a cell. In an embodiment, the binding of the first part of the ligand pair to the second part of the ligand pair is inducible.

In an embodiment of the delivery system, either or both of the first part of the protein or CRISPR protein and the second part of the protein or CRISPR protein comprise one or more NLSs.

In an embodiment of the delivery system, either or both of the first part of the protein or CRISPR protein and the second part of the protein or CRISPR protein comprise one or more nuclear export signals (NESs).

In certain embodiments, the virus structural component comprises one or more capsid proteins including an entire capsid. In certain embodiments, such as wherein a viral capsid comprises multiple copies of different proteins, the delivery system can provide one or more of the same protein or a mixture of such proteins. For example, AAV comprises 3 capsid proteins, VP1, VP2, and VP3, thus delivery systems of the invention can comprise one or more of VP1, and/or one or more of VP2, and/or one or more of VP3. Accordingly, the present invention is applicable to a virus within the family Adenoviridae, such as Atadenovirus, e.g., Ovine atadenovirus D, Aviadenovirus, e.g., Fowl aviadenovirus A, Ichtadenovirus, e.g., Sturgeon ichtadenovirus A, Mastadenovirus (which includes adenoviruses such as all human adenoviruses), e.g., Human mastadenovirus C, and Siadenovirus, e.g., Frog siadenovirus A. Thus, a virus of within the family Adenoviridae is contemplated as within the invention with discussion herein as to adenovirus applicable to other family members. Target-specific AAV capsid variants can be used or selected. Non-limiting examples include capsid variants selected to bind to chronic myelogenous leukemia cells, human CD34 PBPC cells, breast cancer cells, cells of lung, heart, dermal fibroblasts, melanoma cells, stem cell, glioblastoma cells, coronary artery endothelial cells and keratinocytes. See, e.g., Buning et al, 2015, Current Opinion in Pharmacology 24, 94-104. From teachings herein and knowledge in the art as to modifications of adenovirus (see, e.g., U.S. Pat. Nos. 9,410,129, 7,344,872, 7,256,036, 6,911,199, 6,740,525; Matthews, "Capsid-Incorporation of Antigens into Adenovirus Capsid Proteins for a Vaccine Approach," Mol Pharm, 8(1): 3-11 (2011)), as well as regarding modifications of AAV, the skilled person can readily obtain a modified adenovirus that has a large payload protein or a CRISPR-protein, despite that heretofore it was not expected that such a large protein could be provided on an adenovirus. And as to the viruses related to adenovirus mentioned herein, as well as to the viruses related to AAV mentioned herein, the teachings herein as to modifying adenovirus and AAV, respectively, can be applied to those viruses without undue experimentation from this disclosure and the knowledge in the art.

In another aspect, the invention provides a non-naturally occurring or engineered CRISPR protein associated with Adeno Associated Virus (AAV), e.g., an AAV comprising a CRISPR protein as a fusion, with or without a linker, to or with an AAV capsid protein such as VP1, VP2, and/or VP3; and, for shorthand purposes, such a non-naturally occurring or engineered CRISPR protein is herein termed a "AAV-CRISPR protein" More in particular, modifying the knowledge in the art, e.g., Rybniker et al., "Incorporation of Antigens into Viral Capsids Augments Immunogenicity of Adeno-Associated Virus Vector-Based Vaccines," J Virol. December 2012; 86 (24): 13800-13804, Lux K, et al. 2005. Green fluorescent protein-tagged adeno-associated virus particles allow the study of cytosolic and nuclear trafficking. J. Virol. 79:11776-11787, Munch R C, et al. 2012. "Displaying high-affinity ligands on adeno-associated viral vectors enables tumor cell-specific and safe gene transfer." Mol. Ther. [Epub ahead of print.] doi:10.1038/mt.2012.186 and Warrington K H, Jr, et al. 2004. Adeno-associated virus type 2 VP2 capsid protein is nonessential and can tolerate large peptide insertions at its N terminus. J. Virol. 78:6595-6609, each incorporated herein by reference, one can obtain a modified AAV capsid of the invention. It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3). One can modify the cap gene to have expressed at a desired location a non-capsid protein advantageously a large payload protein, such as a CRISPR-protein. Likewise, these can be fusions, with the protein, e.g., large payload protein such as a CRISPR-protein fused in a manner analogous to prior art fusions. See, e.g., US Patent Publication 20090215879; Nance et al., "Perspective on Adeno-Associated Virus Capsid Modification for Duchenne Muscular Dystrophy Gene Therapy," Hum Gene Ther. 26(12):786-800 (2015) and documents cited therein, incorporated herein by reference. The skilled person, from this disclosure and the knowledge in the art can make and use modified AAV or AAV capsid as in the herein invention, and through this disclosure one knows now that large payload proteins can be fused to the AAV capsid. Applicants provide AAV capsid-CRISPR protein (e.g., Cas, Cas9, dCas9, Cpf1, Cas13a, Cas13b) fusions and those AAV-capsid CRISPR protein (e.g., Cas, Cas9) fusions can be a recombinant AAV that contains nucleic acid molecule(s) encoding or providing CRISPR-Cas or CRISPR system or complex RNA guide(s), whereby the CRISPR protein (e.g., Cas, Cas9) fusion delivers a CRISPR-Cas or CRISPR system complex (e.g., the CRISPR protein or Cas or Cas9 or Cpf1 is provided by the fusion, e.g., VP1, VP2, pr VP3 fusion, and the guide RNA is provided by the coding of the recombinant virus, whereby in vivo, in a cell, the CRISPR-Cas or CRISPR system is assembled from the nucleic acid molecule(s) of the recombinant providing the guide RNA and the outer surface of the virus providing the CRISPR-Enzyme or Cas or Cas9. Such as complex may herein be termed an "AAV-CRISPR system" or an "AAV-CRISPR-Cas" or "AAV-CRISPR complex" or "AAV-CRISPR-Cas complex." Accordingly, the instant invention is also applicable to a virus in the genus Dependoparvovirus or in the family Parvoviridae, for instance, AAV, or a virus of Amdoparvovirus, e.g., Carnivore amdoparvovirus 1, a virus of Aveparvovirus, e.g., Galliform aveparvovirus 1, a virus of Bocaparvovirus, e.g., Ungulate bocaparvovirus 1, a virus of Copiparvovirus, e.g., Ungulate copiparvovirus 1, a virus of Dependoparvovirus, e.g., Adeno-associated dependoparvovirus A, a virus of Erythroparvovirus, e.g., Primate erythroparvovirus 1, a virus of Protoparvovirus, e.g., Rodent protoparvovirus 1, a virus of Tetraparvovirus, e.g., Primate tetraparvovirus 1. Thus, a virus of within the family Parvoviridae or the genus Dependoparvovirus or any of the other foregoing genera within Parvoviridae is contemplated as within the invention with discussion herein as to AAV applicable to such other viruses.

In one aspect, the invention provides a non-naturally occurring or engineered composition comprising a CRISPR enzyme which is part of or tethered to a AAV capsid domain, i.e., VP1, VP2, or VP3 domain of Adeno-Associated Virus (AAV) capsid. In some embodiments, part of or tethered to a AAV capsid domain includes associated with associated with a AAV capsid domain. In some embodiments, the CRISPR enzyme may be fused to the AAV capsid domain. In some embodiments, the fusion may be to the N-terminal end of the AAV capsid domain. As such, in some embodiments, the C-terminal end of the CRISPR enzyme is fused to the N-terminal end of the AAV capsid domain. In some embodiments, an NLS and/or a linker (such as a GlySer linker) may be positioned between the C-terminal end of the CRISPR enzyme and the N-terminal end of the AAV capsid domain. In some embodiments, the fusion may be to the C-terminal end of the AAV capsid domain. In some embodiments, this is not preferred due to the fact that the VP1, VP2 and VP3 domains of AAV are alternative splices of the same RNA and so a C-terminal fusion may affect all three domains. In some embodiments, the AAV capsid domain is truncated. In some embodiments, some or all of the AAV capsid domain is removed. In some embodiments, some of the AAV capsid domain is removed and replaced with a linker (such as a GlySer linker), typically leaving the N-terminal and C-terminal ends of the AAV capsid domain intact, such as the first 2, 5 or 10 amino acids. In this way, the internal (non-terminal) portion of the VP3 domain may be replaced with a linker. It is particularly preferred that the linker is fused to the CRISPR protein. A branched linker may be used, with the CRISPR protein fused to the end of one of the branches. This allows for some degree of spatial separation between the capsid and the CRISPR protein. In this way, the CRISPR protein is part of (or fused to) the AAV capsid domain.

Alternatively, the CRISPR enzyme may be fused in frame within, i.e. internal to, the AAV capsid domain. Thus, in some embodiments, the AAV capsid domain again preferably retains its N-terminal and C-terminal ends. In this case, a linker is preferred, in some embodiments, either at one or both ends of the CRISPR enzyme. In this way, the CRISPR enzyme is again part of (or fused to) the AAV capsid domain. In certain embodiments, the positioning of the CRISPR enzyme is such that the CRISPR enzyme is at the external surface of the viral capsid once formed. In one aspect, the invention provides a non-naturally occurring or engineered composition comprising a CRISPR enzyme associated with a AAV capsid domain of Adeno-Associated Virus (AAV) capsid. Here, associated may mean in some embodiments fused, or in some embodiments bound to, or in some embodiments tethered to. The CRISPR protein may, in some embodiments, be tethered to the VP1, VP2, or VP3 domain. This may be via a connector protein or tethering system such as the biotin-streptavidin system. In one example, a biotinylation sequence (15 amino acids) could therefore be fused to the CRISPR protein. When a fusion of the AAV capsid domain, especially the N-terminus of the AAV AAV capsid domain, with streptavidin is also provided, the two will therefore associate with very high affinity. Thus, in some embodiments, provided is a composition or system comprising a CRISPR protein-biotin fusion and a streptavidin-AAV capsid domain arrangement, such as a fusion. The CRISPR protein-biotin and streptavidin-AAV capsid domain forms a single complex when the two parts are brought together. NLSs may also be incorporated between the CRISPR protein and the biotin; and/or between the streptavidin and the AAV capsid domain.

An alternative tether may be to fuse or otherwise associate the AAV capsid domain to an adaptor protein which binds to or recognizes to a corresponding RNA sequence or motif. In some embodiments, the adaptor is or comprises a binding protein which recognizes and binds (or is bound by) an RNA sequence specific for said binding protein. In some embodiments, a preferred example is the MS2 (see Konermann et al. December 2014, cited infra, incorporated herein by reference) binding protein which recognizes and binds (or is bound by) an RNA sequence specific for the MS2 protein.

With the AAV capsid domain associated with the adaptor protein, the CRISPR protein may, in some embodiments, be tethered to the adaptor protein of the AAV capsid domain. The CRISPR protein may, in some embodiments, be tethered to the adaptor protein of the AAV capsid domain via the CRISPR enzyme being in a complex with a modified guide, see Konermann et al. The modified guide is, in some embodiments, a sgRNA. In some embodiments, the modified guide comprises a distinct RNA sequence; see, e.g., PCT/US14/70175, incorporated herein by reference.

In some embodiments, distinct RNA sequence is an aptamer. Thus, corresponding aptamer-adaptor protein systems are preferred. One or more functional domains may also be associated with the adaptor protein. An example of a preferred arrangement would be:

[AAV AAV capsid domain-adaptor protein]-[modified guide-CRISPR protein]

In certain embodiments, the positioning of the CRISPR protein is such that the CRISPR protein is at the internal surface of the viral capsid once formed. In one aspect, the invention provides a non-naturally occurring or engineered composition comprising a CRISPR protein associated with an internal surface of an AAV capsid domain. Here again, associated may mean in some embodiments fused, or in some embodiments bound to, or in some embodiments tethered to. The CRISPR protein may, in some embodiments, be tethered to the VP1, VP2, or VP3 domain such that it locates to the internal surface of the viral capsid once formed. This may be via a connector protein or tethering system such as the biotin-streptavidin system as described above.

When the CRISPR protein fusion is designed so as to position the CRISPR protein at the internal surface of the capsid once formed, the CRISPR protein will fill most or all of internal volume of the capsid. In some embodiments, the CRISPR protein may be modified or divided so as to occupy a less of the capsid internal volume. Accordingly, in certain embodiments, the invention provides a CRISRP protein divided in two portions, one portion comprises in one viral particle or capsid and the second portion comprised in a second viral particle or capsid. In certain embodiments, by splitting the CRISPR protein in two portions, space is made available to link one or more heterologous domains to one or both CRISPR protein portions.

Split CRISPR proteins are set forth herein and in documents incorporated herein by reference in further detail herein. In certain embodiments, each part of a split CRISRP proteins are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In general, according to the invention, CRISPR proteins may preferably split between domains, leaving domains intact. Preferred, non-limiting examples of such CRISPR proteins include, without limitation, Cas9, Cpf1, C2c2, Cas13a, Cas13b, and orthologues. Preferred, non-limiting examples of split points include, with reference to SpCas9: a split position between 202A/203S; a split position between 255F/256D; a split position between 310E/311I; a split position between 534R/535K; a split position between 572E/573C; a split position between 713S/714G; a split position between 1003L/104E; a split position between 1054G/1055E; a split position between 1114N/1115S; a split position between 1152K/1153S; a split position between 1245K/1246G; or a split between 1098 and 1099.

In some embodiments, any AAV serotype is preferred. In some embodiments, the VP2 domain associated with the CRISPR enzyme is an AAV serotype 2 VP2 domain. In some embodiments, the VP2 domain associated with the CRISPR enzyme is an AAV serotype 8 VP2 domain. The serotype can be a mixed serotype as is known in the art.

The CRISPR enzyme may form part of a CRISPR-Cas system, which further comprises a guide RNA (sgRNA) comprising a guide sequence capable of hybridizing to a target sequence in a genomic locus of interest in a cell. In some embodiments, the functional CRISPR-Cas system binds to the target sequence. In some embodiments, the functional CRISPR-Cas system may edit the genomic locus to alter gene expression. In some embodiments, the functional CRISPR-Cas system may comprise further functional domains.

In some embodiments, the CRISPR enzyme is a Cpf1. In some embodiments, the CRISPR enzyme is an FnCpf1. In some embodiments, the CRISPR enzyme is an AsCpf1, although other orthologs are envisaged. FnCpf1 and AsCpf1 are particularly preferred, in some embodiments.

In some embodiments, the CRISPR enzyme is external to the capsid or virus particle. In the sense that it is not inside the capsid (enveloped or encompassed with the capsid), but is externally exposed so that it can contact the target genomic DNA). In some embodiments, the CRISPR enzyme cleaves both strands of DNA to produce a double strand break (DSB). In some embodiments, the CRISPR enzyme is a nickase. In some embodiments, the CRISPR enzyme is a dual nickase. In some embodiments, the CRISPR enzyme is a deadCpf1. In some general embodiments, the CRISPR enzyme is associated with one or more functional domains. In some more specific embodiments, the CRISPR enzyme is a deadCpf1 and is associated with one or more functional domains. In some embodiments, the CRISPR enzyme comprises a Rec2 or HD2 truncation. In some embodiments, the CRISPR enzyme is associated with the AAV VP2 domain by way of a fusion protein. In some embodiments, the CRISPR enzyme is fused to Destabilization Domain (DD). In other words, the DD may be associated with the CRISPR enzyme by fusion with said CRISPR enzyme. The AAV can then, by way of nucleic acid molecule(s) deliver the stabilizing ligand (or such can be otherwise delivered) In some embodiments, the enzyme may be considered to be a modified CRISPR enzyme, wherein the CRISPR enzyme is fused to at least one destabilization domain (DD) and VP2. In some embodiments, the association may be considered to be a modification of the VP2 domain. Where reference is made herein to a modified VP2 domain, then this will be understood to include any association discussed herein of the VP2 domain and the CRISPR enzyme. In some embodiments, the AAV VP2 domain may be associated (or tethered) to the CRISPR enzyme via a connector protein, for example using a system such as the streptavidin-biotin system. As such, provided is a fusion of a CRISPR enzyme with a connector protein specific for a high affinity ligand for that connector, whereas the AAV VP2 domain is bound to said high affinity ligand. For example, streptavidin may be the connector fused to the CRISPR enzyme, while biotin may be bound to the AAV VP2 domain. Upon co-localization, the streptavidin will bind to the biotin, thus connecting the CRISPR enzyme to the AAV VP2 domain. The reverse arrangement is also possible. In some embodiments, a biotinylation sequence (15 amino acids) could therefore be fused to the AAV VP2 domain, especially the N-terminus of the AAV VP2 domain. A fusion of the CRISPR enzyme with streptavidin is also preferred, in some embodiments. In some embodiments, the biotinylated AAV capsids with streptavidin-CRISPR enzyme are assembled in vitro. This way the AAV capsids should assemble in a straightforward manner and the CRISPR enzyme-streptavidin fusion can be added after assembly of the capsid. In other embodiments a biotinylation sequence (15 amino acids) could therefore be fused to the CRISPR enzyme, together with a fusion of the AAV VP2 domain, especially the N-terminus of the AAV VP2 domain, with streptavidin. For simplicity, a fusion of the CRISPR enzyme and the AAV VP2 domain is preferred in some embodiments. In some embodiments, the fusion may be to the N-terminal end of the CRISPR enzyme. In other words, in some embodiments, the AAV and CRISPR enzyme are associated via fusion. In some embodiments, the AAV and CRISPR enzyme are associated via fusion including a linker. Suitable linkers are discussed herein, but include GlySer linkers. Fusion to the N-term of AAV VP2 domain is preferred, in some embodiments. In some embodiments, the CRISPR enzyme comprises at least one Nuclear Localization Signal (NLS). In an aspect, the present invention provides a polynucleotide encoding the present CRISPR enzyme and associated AAV VP2 domain.

Viral delivery vectors, for example modified viral delivery vectors, are hereby provided. While the AAV may advantageously be a vehicle for providing RNA of the CRISPR-Cas Complex or CRISPR system, another vector may also deliver that RNA, and such other vectors are also herein discussed. In one aspect, the invention provides a non-naturally occurring modified AAV having a VP2-CRISPR enzyme capsid protein, wherein the CRISPR enzyme is part of or tethered to the VP2 domain. In some preferred embodiments, the CRISPR enzyme is fused to the VP2 domain so that, in another aspect, the invention provides a non-naturally occurring modified AAV having a VP2-CRISPR enzyme fusion capsid protein. The following embodiments apply equally to either modified AAV aspect, unless otherwise apparent. Thus, reference herein to a VP2-CRISPR enzyme capsid protein may also include a VP2-CRISPR enzyme fusion capsid protein. In some embodiments, the VP2-CRISPR enzyme capsid protein further comprises a linker. In some embodiments, the VP2-CRISPR enzyme capsid protein further comprises a linker, whereby the VP2-CRISPR enzyme is distanced from the remainder of the AAV. In some embodiments, the VP2-CRISPR enzyme capsid protein further comprises at least one protein complex, e.g., CRISPR complex, such as CRISPR-Cpf1 complex guide RNA that targets a particular DNA, TALE, etc. A CRISPR complex, such as CRISPR-Cas system comprising the VP2-CRISPR enzyme capsid protein and at least one CRISPR complex, such as CRISPR-Cpf1 complex guide RNA that targets a particular DNA, is also provided in one aspect. In general, in some embodiments, the AAV further comprises a repair template. It will be appreciated that comprises here may mean encompassed thin the viral capsid or that the virus encodes the comprised protein. In some embodiments, one or more, preferably two or more guide RNAs, may be comprised/encompassed within the AAV vector. Two may be preferred, in some embodiments, as it allows for multiplexing or dual nickase approaches. Particularly for multiplexing, two or more guides may be used. In fact, in some embodiments, three or more, four or more, five or more, or even six or more guide RNAs may be comprised/encompassed within the AAV. More space has been freed up within the AAV by virtue of the fact that the AAV no longer needs to comprise/encompass the CRISPR enzyme. In each of these instances, a repair template may also be provided comprised/encompassed within the AAV. In some embodiments, the repair template corresponds to or includes the DNA target.

In a further aspect, the present invention provides compositions comprising the CRISPR enzyme and associated AAV VP2 domain or the polynucleotides or vectors described herein. Also provides are CRISPR-Cas systems comprising guide RNAs.

Also provided is a method of treating a subject in need thereof, comprising inducing gene editing by transforming the subject with the polynucleotide encoding the system or any of the present vectors. A suitable repair template may also be provided, for example delivered by a vector comprising said repair template. In some embodiments, a single vector provides the CRISPR enzyme through (association with the viral capsid) and at least one of: guide RNA; and/or a repair template. Also provided is a method of treating a subject in need thereof, comprising inducing transcriptional activation or repression by transforming the subject with the polynucleotide encoding the present system or any of the present vectors, wherein said polynucleotide or vector encodes or comprises the catalytically inactive CRISPR enzyme and one or more associated functional domains. Compositions comprising the present system for use in said method of treatment are also provided. A kit of parts may be provided including such compositions. Use of the present system in the manufacture of a medicament for such methods of treatment are also provided.

Also provided is a pharmaceutical composition comprising the CRISPR enzyme which is part of or tethered to a VP2 domain of Adeno-Associated Virus (AAV) capsid; or the non-naturally occurring modified AAV; or a polynucleotide encoding them.

Also provided is a complex of the CRISPR enzyme with a guideRNA, such as sgRNA. The complex may further include the target DNA.

A split CRISPR enzyme, most preferably Cpf1, approach may be used. The so-called 'split Cpf1' approach Split Cpf1 allows for the following. The Cpf1 is split into two pieces and each of these are fused to one half of a dimer. Upon dimerization, the two parts of the Cpf1 are brought together and the reconstituted Cpf1 has been shown to be functional. Thus, one part of the split Cpf1 may be associated with one VP2 domain and second part of the split Cpf1 may be associated with another VP2 domain. The two VP2 domains may be in the same or different capsid. In other words, the split parts of the Cpf1 could be on the same virus particle or on different virus particles.

In some embodiments, one or more functional domains may be associated with or tethered to CRISPR enzyme and/or may be associated with or tethered to modified guides via adaptor proteins. These can be used irrespective of the fact that the CRISPR enzyme may also be tethered to a virus outer protein or capsid or envelope, such as a VP2 domain or a capsid, via modified guides with aptamer RAN sequences that recognize correspond adaptor proteins.

In some embodiments, one or more functional domains comprise a transcriptional activator, repressor, a recombinase, a transposase, a histone remodeler, a demethylase, a DNA methyltransferase, a cryptochrome, a light inducible/controllable domain, a chemically inducible/controllable domain, an epigenetic modifying domain, or a combination thereof. Advantageously, the functional domain comprises an activator, repressor or nuclease.

In some embodiments, a functional domain can have methylase activity, demethylase activity, transcription activation activity, transcription repression activity, transcription release factor activity, histone modification activity, RNA cleavage activity or nucleic acid binding activity, or activity that a domain identified herein has.

Examples of activators include P65, a tetramer of the herpes simplex activation domain VP16, termed VP64, optimized use of VP64 for activation through modification of both the sgRNA design and addition of additional helper molecules, MS2, P65 and HSF1 in the system called the synergistic activation mediator (SAM) (Konermann et al, "Genome-scale transcriptional activation by an engineered CRISPR-Cas9 complex," Nature 517(7536):583-8 (2015)); and examples of repressors include the KRAB (Kruppel-associated box) domain of Kox1 or SID domain (e.g. SID4X); and an example of a nuclease or nuclease domain suitable for a functional domain comprises Fok1.

Suitable functional domains for use in practice of the invention, such as activators, repressors or nucleases are also discussed in documents incorporated herein by reference, including the patents and patent publications herein-cited and incorporated herein by reference regarding general information on CRISPR-Cas Systems.

In some embodiments, the CRISPR enzyme comprises or consists essentially of or consists of a localization signal as, or as part of, the linker between the CRISPR enzyme and the AAV capsid, e.g., VP2. HA or Flag tags are also within the ambit of the invention as linkers as well as Glycine Serine linkers as short as GS up to $(GGGGS)_3$ (SEQ ID NO: 91). In this regard it is mentioned that tags that can be used in embodiments of the invention include affinity tags, such as chitin binding protein (CBP), maltose binding protein (MBP), glutathione-S-transferase (GST), poly(His) tag; solubilization tags such as thioredoxin (TRX) and poly (NANP), MBP, and GST; chromatography tags such as those consisting of polyanionic amino acids, such as FLAG-tag; epitope tags such as V5-tag, Myc-tag, HA-tag and NE-tag; fluorescence tags, such as GFP and mCherry; protein tags that may allow specific enzymatic modification (such as biotinylation by biotin ligase) or chemical modification (such as reaction with FlAsH-EDT2 for fluorescence imaging).

Also provided is a method of treating a subject, e.g, a subject in need thereof, comprising inducing gene editing by transforming the subject with the AAV-CRISPR enzyme advantageously encoding and expressing in vivo the remaining portions of the CRISPR system (e.g., RNA, guides). A suitable repair template may also be provided, for example delivered by a vector comprising said repair template. Also provided is a method of treating a subject, e.g., a subject in need thereof, comprising inducing transcriptional activation or repression by transforming the subject with the AAV-CRISPR enzyme advantageously encoding and expressing in vivo the remaining portions of the CRISPR system (e.g., RNA, guides); advantageously in some embodiments the CRISPR enzyme is a catalytically inactive CRISPR enzyme and comprises one or more associated functional domains. Where any treatment is occurring ex vivo, for example in a cell culture, then it will be appreciated that the term 'subject' may be replaced by the phrase "cell or cell culture."

Compositions comprising the present system for use in said method of treatment are also provided. A kit of parts may be provided including such compositions. Use of the present system in the manufacture of a medicament for such methods of treatment are also provided. Use of the present system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again.

In one aspect, the invention provides an engineered, non-naturally occurring CRISPR-Cas system comprising a AAV-Cas protein and a guide RNA that targets a DNA molecule encoding a gene product in a cell, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type II CRISPR-Cas protein and in a preferred embodiment the Cas protein is a Cpf1 protein. The invention further comprehends the coding for the Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to a CRISPR-Cas system guide RNA that targets a DNA molecule encoding a gene product and an AAV-Cas protein. The components may be located on same or different vectors of the system, or may be the same vector whereby the AAV-Cas protein also delivers the RNA of the CRISPR system. The guide RNA targets the DNA molecule encoding the gene product in a cell and the AAV-Cas protein may cleaves the DNA molecule encoding the gene product (it may cleave one or both strands or have substantially no nuclease activity), whereby expression of the gene product is altered; and, wherein the AAV-Cas protein and the guide RNA do not naturally occur together. The invention comprehends the guide RNA comprising a guide sequence fused to a tracr sequence. In an embodiment of the invention the AAV-Cas protein is a type II AAV-CRISPR-Cas protein and in a preferred embodiment the AAV-Cas protein is an AAV-Cpf1 protein. The invention further comprehends the coding for the AAV-Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides a method of expressing an effector protein and guide RNA in a cell comprising introducing the vector according any of the vector delivery systems disclosed herein. In an embodiment of the vector for delivering an effector protein, the minimal promoter is the Mecp2 promoter, tRNA promoter, or U6. In a further embodiment, the minimal promoter is tissue specific.

The one or more polynucleotide molecules may be comprised within one or more vectors. The invention comprehends such polynucleotide molecule(s), for instance such polynucleotide molecules operably configured to express the protein and/or the nucleic acid component(s), as well as such vector(s).

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of an AAV-CRISPR complex to a target sequence in a eukaryotic cell, wherein the CRISPR complex comprises a AAV-CRISPR enzyme complexed with (1) the guide sequence that is hybridized to the target sequence, and (2) the tracr mate sequence that is hybridized to the tracr sequence; and (b) said AAV-CRISPR enzyme comprising at least one nuclear localization sequence and/or at least one NES; wherein components (a) and (b) are located on or in the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of an AAV-CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publicly and commercially available alignment algorithms and programs such as, but not limited to, ClustalW, Smith-Waterman in matlab, Bowtie, Geneious, Biopython and SeqMan. In some embodiments, the AAV-CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for AAV-CRISPR complex activity in eukaryotes, but that including such sequences enhances activity of the system, especially as to targeting nucleic acid molecules in the nucleus and/or having molecules exit the nucleus. In some embodiments, the AAV-CRISPR enzyme is a type II AAV-CRISPR system enzyme. In some embodiments, the AAV-CRISPR enzyme is an AAV-Cpf1 enzyme. In some embodiments, the AAV-Cpf1 enzyme is derived from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis*, Lachnospiraceae bacterium MC2017 1, *Butyrivibrio proteoclasticus*, Peregrinibacteria bacterium GW201 1_GWA2_33_10, Parcubacteria bacterium GW2011_GWC2_44_17, Smithella sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae* (e.g., a Cpf1 of one of these organisms modified to have or be associated with at least one AAV), and may include further mutations or alterations or be a chimeric Cpf1. The enzyme may be an AAV-Cpf1 homolog or ortholog. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks DNA strand cleavage activity. In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Again, the RNA of the CRISPR System, while advantageously delivered via the AAV-CRISPR enzyme can also be delivered separately, e.g. via a separate vector.

In one aspect, the invention provides an AAV-CRISPR enzyme comprising one or more nuclear localization sequences and/or NES. In some embodiments, said AAV-CRISPR enzyme includes a regulatory element that drives transcription of component(s) of the CRISPR system (e.g., RNA, such as guide RNA and/or HR template nucleic acid molecule) in a eukaryotic cell such that said AAV-CRISPR enzyme delivers the CRISPR system accumulates in a detectable amount in the nucleus of the eukaryotic cell and/or is exported from the nucleus. In some embodiments, the regulatory element is a polymerase II promoter. In some embodiments, the AAV-CRISPR enzyme is a type II AAV-CRISPR system enzyme. In some embodiments, the AAV-CRISPR enzyme is an AAV-Cpf1 enzyme. In some embodiments, the AAV-Cpf1 enzyme is derived from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, Smithella sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae* (e.g., Cpf1 modified to have or be associated with at least one AAV), and may include further alteration or mutation of the Cpf1, and can be a chimeric Cpf1. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild-type enzyme or enzyme not having the mutation or alteration that decreases nuclease activity).

In one aspect, the invention provides an AAV-CRISPR enzyme comprising one or more nuclear localization sequences of sufficient strength to drive accumulation of said AAV-CRISPR enzyme in a detectable amount in the nucleus of a eukaryotic cell. In some embodiments, the AAV-CRISPR enzyme is a type II AAV-CRISPR system enzyme. In some embodiments, the AAV-CRISPR enzyme is an AAV-Cpf1 enzyme. In some embodiments, the AAV-Cpf1 enzyme is derived from *S. mutans, S. agalactiae, S. equisimilis, S. sanguinis, S. pneumonia; C. jejuni, C. coli*; N. *salsuginis*, N. tergarcus; S. *auricularis*, S. *carnosus*; N. *meningitides*, N. gonorrhoeae; L. monocytogenes, L. ivanovii; C. botulinum, C. difficile, C. tetani, C. sordellii; Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, Smithella sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae* (e.g., Cpf1 modified to have or be associated with at least one AAV), and may include further alteration or mutation of the Cpf1, and can be a chimeric Cpf1. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity).

In one aspect, the invention provides a eukaryotic host cell comprising (a) a first regulatory element operably linked to a tracr mate sequence and one or more insertion sites for inserting one or more guide sequences upstream of the tracr mate sequence, wherein when expressed, the guide sequence directs sequence-specific binding of an AAV-CRISPR complex to a target sequence in a eukaryotic cell, wherein the AAV-CRISPR complex comprises an AAV-CRISPR enzyme complexed with (1) the guide sequence that is hybridized to the target sequence, and (2) the tracr mate sequence that is hybridized to the tracr sequence; and/or (b) a said AAV-CRISPR enzyme optionally comprising at least one nuclear localization sequence and/or NES. In some embodiments, the host cell comprises components (a) and (b). In some embodiments, component (a), component (b), or components (a) and (b) are stably integrated into a genome of the host eukaryotic cell. In some embodiments, component (b) includes or contains component (a). In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of an AAV-CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the AAV-CRISPR enzyme comprises one or more nuclear localization sequences and/or nuclear export sequences of sufficient strength to drive accumulation of said CRISPR enzyme in a detectable amount in of the nucleus of a eukaryotic cell. In some embodiments, the AAV-CRISPR enzyme is a type II CRISPR system enzyme. In some embodiments, the CRISPR enzyme is a Cpf1 enzyme. In some embodiments, the AAV-Cpf1 enzyme is derived from *S. mutans, S. agalactiae, S. equisimilis, S. sanguinis, S. pneumonia; C. jejuni, C. coli*; N. *salsuginis*, N. tergarcus; S. *auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, Smithella sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae* (e.g., Cpf1 modified to have or be associated with at least one AAV), and may include further alteration or mutation of the Cpf1, and can be a chimeric Cpf1. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example, a mammal. Also, the organism may be an arthropod such as an insect. The organism also may be a plant. Further, the organism may be a fungus. Advantageously, the organism is a host of AAV.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) said AAV-CRISPR enzyme optionally comprising a nuclear localization sequence. In some embodiments, the kit comprises components (a) and (b) located on or in the same or different vectors of the system, e.g., (a) can be contained in (b). In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cpf1 enzyme. In some embodiments, the Cpf1 enzyme is derived from *S. mutans, S. agalactiae, S. equisimilis, S. sanguinis, S. pneumonia; C. jejuni, C. coli*; N. *salsuginis*, N. tergarcus; S. *auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis*, Lachnospiraceae bacterium MC2017 1, *Butyrivibrio proteoclasticus*, Peregrinibacteria bacterium GW2011_GWA2_33_10, Parcubacteria bacterium GW2011_GWC2_44_17, Smithella sp. SCADC, *Acidaminococcus* sp. BV3L6, Lachnospiraceae bacterium MA2020, *Candidatus Methanoplasma termitum, Eubacterium eligens, Moraxella bovoculi* 237, *Leptospira inadai*, Lachnospiraceae bacterium ND2006, *Porphyromonas crevioricanis* 3, *Prevotella disiens* and *Porphyromonas macacae* (e.g., Cpf1 modified to have or be associated with at least one AAV), and may include further alteration or mutation of the Cpf1, and can be a chimeric Cpf1. In some embodiments, the coding for the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In one aspect, the invention provides a method of modifying a target polynucleotide in a eukaryotic cell. In some embodiments, the method comprises allowing an AAV-CRISPR complex to bind to the target polynucleotide, e.g., to effect cleavage of said target polynucleotide, thereby modifying the target polynucleotide, wherein the AAV-CRISPR complex comprises a AAV-CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said AAV-CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein one or more vectors comprise the AAV-CRISPR enzyme and one or more vectors drive expression of one or more of: the guide sequence linked to the tracr mate sequence, and the tracr sequence. In some embodiments, said AAV-CRISPR enzyme drive expression of one or more of: the guide sequence linked to the tracr mate sequence, and the tracr sequence. In some embodiments such AAV-CRISPR enzyme are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing an AAV-CRISPR complex to bind to the polynucleotide such that said binding results in increased or decreased expression of said polynucleotide; wherein the AAV-CRISPR complex comprises a AAV-CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors are the AAV-CRISPR enzyme and/or drive expression of one or more of: the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors comprise the AAV-CRISPR enzyme and/or drive expression of one or more of: a guide sequence linked to a tracr mate sequence, and a tracr sequence; and (b) allowing an AAV-CRISPR complex to bind to a target polynucleotide, e.g., to effect cleavage of the target polynucleotide within said disease gene, wherein the AAV-CRISPR complex comprises the AAV-CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. Thus, in some embodiments the AAV-CRISPR enzyme contains nucleic acid molecules for and drives expression of one or more of: a guide sequence linked to a tracr mate sequence, and a tracr sequence and/or a Homologous Recombination template and/or a stabilizing ligand if the CRISPR enzyme has a destabilization domain. In some embodiments, said cleavage comprises cleaving one or two strands at the location of the target sequence by said AAV-CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of an AAV-CRISPR complex to a corresponding target sequence present in a eukaryotic cell. The polynucleotide can be carried within and expressed in vivo from the AAV-CRISPR enzyme. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors comprise an AAV-CRISPR enzyme and/or drive expression of one or more of: a guide sequence linked to a tracr mate sequence, a tracr sequence, and an editing template; wherein, for example that which is being expressed is within and expressed in vivo by the AAV-CRISPR enzyme and/or the editing template comprises the one or more mutations that abolish AAV-CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the AAV-CRISPR complex comprises the AAV-CRISPR enzyme complexed with (1) the guide sequence that is hybridized to the target sequence within the target polynucleotide, and (2) the tracr mate sequence that is hybridized to the tracr sequence, wherein binding of the AAV-CRISPR complex to the target polynucleotide induces cell death, thereby allowing one or more cell(s) in which one or more mutations have been introduced to be selected. In a preferred embodiment, the AAV-CRISPR enzyme is AAV-Cpf1. In another aspect of the invention the cell to be selected may be a eukaryotic cell. Aspects of the invention allow for selection of specific cells without requiring a selection marker or a two-step process that may include a counter-selection system. The cell(s) may be prokaryotic or eukaryotic cells.

With respect to mutations of the AAV-CRISPR enzyme, mutations may be made at any or all residues corresponding to positions 908, 993, and 1263 with reference to amino acid position numbering of AsCpf1 (which may be ascertained for instance by standard sequence comparison tools), or 917 and 1006 with reference to amino acid numbering of FnCpf1, or 832, 925, 947, 1180 with reference to amino acid position numbering of LbCpf1. In particular, any or all of the following mutations are preferred in AsCpf1: D908A, E993A, and D1263; in FnCpf1: D917A and H1006A; in LbCpf1: D832A, E925A, D947A, and D1180A; as well as conservative substitution for any of the replacement amino acids is also envisaged. In an aspect the invention provides as to any or each or all embodiments herein-discussed wherein the AAV-CRISPR enzyme comprises at least one or more, or at least two or more mutations, wherein the at least one or more mutation or the at least two or more mutations is as to D908, E993, or D1263 according to AsCpf1 protein, e.g., D908A, E993A, or D1263 as to AsCpf1, or D917 or H1006 according to FnCpf1, e.g., D917A or H1006A as to FnCpf1, or D832, E925, D947, or D1180 according to LbCpf1, e.g., D832A, E925A, D947A, or D 1180A as to LbCpf1, or any corresponding mutation(s) in a Cpf1 of an ortholog to As or Fn or Lb, or the CRISPR enzyme comprises at least one mutation wherein at least D908A, E993A, or D1263 as to AsCpf1 or D917A or H1006A as to FnCpf1 or D832A, E925A, D947A, or D1180A as to LbCpf1 is mutated; or any corresponding mutation(s) in a Cpf1 of an ortholog to As protein or Fn protein or Lb protein.

Aspects of the invention encompass a non-naturally occurring or engineered composition that may comprise a guide RNA (sgRNA) comprising a guide sequence capable of hybridizing to a target sequence in a genomic locus of interest in a cell and an AAV-CRISPR enzyme that may comprise at least one or more nuclear localization sequences, wherein the AAV-CRISPR enzyme comprises one or two or more mutations, such that the enzyme has altered or diminished nuclease activity compared with the wild type enzyme, wherein at least one loop of the sgRNA is modified by the insertion of distinct RNA sequence(s) that bind to one or more adaptor proteins, and wherein the adaptor protein further recruits one or more heterologous functional domains. In an embodiment of the invention the AAV-CRISPR enzyme comprises one or two or more mutations in a residue selected from the group comprising, consisting essentially of, or consisting of D908, E993, or D1263 according to AsCpf1 protein; D917 or H1006 according to FnCpf1; or D832, E925, D947, or D1180 according to LbCpf1. In a further embodiment the AAV-CRISPR enzyme comprises one or two or more mutations selected from the group comprising D908A, E993A, or D1263 as to AsCpf1; D917A or H1006A as to FnCpf1; or D832A, E925A, D947A, or D1180A as to LbCpf1. In another embodiment, the functional domain can comprise, consist of, or consist essentially of a transcriptional activation domain, e.g., VP64. In another embodiment, the functional domain can comprise, consist of, or consist essentially of a transcriptional repressor domain, e.g., KRAB domain, SID domain or a SID4X domain. In embodiments of the invention, the one or more heterologous functional domains have one or more activities selected from the group comprising, consisting essentially of, or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, QP, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In another embodiment, the at least one loop of the sgRNA is tetraloop and/or loop2. An aspect of the invention encompasses methods of modifying a genomic locus of interest to change gene expression in a cell by introducing into the cell any of the compositions described herein. An aspect of the invention is that the above elements are comprised in a single composition or comprised in individual compositions, e.g., the AAV-CRISPR enzyme delivers the enzyme as discussed as well as the guide. These compositions may advantageously be applied to a host to elicit a functional effect on the genomic level. In general, the sgRNA are modified in a manner that provides specific binding sites (e.g., aptamers) for adapter proteins comprising one or more functional domains (e.g., via fusion protein) to bind to. The modified sgRNA are modified such that once the sgRNA forms an AAV-CRISPR complex (i.e. AAV-CRISPR enzyme binding to sgRNA and target) the adapter proteins bind and, the functional domain on the adapter protein is positioned in a spatial orientation which is advantageous for the attributed function to be effective. For example, if the functional domain can comprise, consist of, or consist essentially of a transcription activator (e.g., VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partially cleave the target. Again, the AAV-CRISPR enzyme can deliver both the enzyme and the modified guide. The skilled person will understand that modifications to the sgRNA which allow for binding of the adapter+functional domain but not proper positioning of the adapter+functional domain (e.g., due to steric hindrance within the three-dimensional structure of the CRISPR complex) are modifications which are not intended. The one or more modified sgRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). In some cases, it is advantageous that additionally at least one NLS is provided. In some instances, it is advantageous to position the NLS at the N terminus. When more than one functional domain is included, the functional domains may be the same or different.

The sgRNA may be designed to include multiple binding recognition sites (e.g., aptamers) specific to the same or different adapter protein. The sgRNA may be designed to bind to the promoter region −1000-+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified sgRNA may be one or more modified sgRNAs targeted to one or more target loci (e.g., at least 1 sgRNA, at least 2 sgRNA, at least 5 sgRNA, at least 10 sgRNA, at least 20 sgRNA, at least 30 sg RNA, at least 50 sgRNA) comprised in a composition.

Further, the AAV-CRISPR enzyme with diminished nuclease activity is most effective when the nuclease activity is inactivated (e.g., nuclease inactivation of at least 70%, at least 80%, at least 90%, at least 95%, at least 97%, or 100% as compared with the wild type enzyme; or to put in another way, a AAV-Cpf1 enzyme or AAV-CRISPR enzyme having advantageously about 0% of the nuclease activity of the non-mutated or wild type Cpf1 enzyme or CRISPR enzyme, or no more than about 3% or about 5% or about 10% of the nuclease activity of the non-mutated or wild type Cpf1 enzyme or CRISPR enzyme). This is possible by introducing mutations into the RuvC and HNH nuclease domains of the AsCpf1 and orthologs thereof. For example utilizing mutations in a residue selected from the group comprising, consisting essentially of, or consisting of D908, E993, or D1263 according to AsCpf1 protein; D917 or H1006 according to FnCpf1; or D832, E925, D947, or D1180 according to LbCpf1, and more preferably introducing one or more of the mutations selected from the group comprising, consisting essentially of, or consisting of D908A, E993A, or D1263 as to AsCpf1; D917A or H1006A as to FnCpf1; or D832A, E925A, D947A, or D1180A as to LbCpf1. The inactivated CRISPR enzyme may have associated (e.g., via fusion protein) one or more functional domains, e.g., at least one destabilizing domain; or, for instance like those as described herein for the modified sgRNA adaptor proteins, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that sgRNAs are designed to provide proper spacing for functional use (Fok1) as specifically described in Tsai et al. Nature Biotechnology, Vol. 32, Number 6, June 2014). The adaptor protein may utilize known linkers to attach such functional domains. In some cases, it is advantageous that additionally at least one NLS is provided. In some instances, it is advantageous to position the NLS at the N terminus. When more than one functional domain is included, the functional domains may be the same or different. In general, the positioning of the one or more functional domain on the inactivated AAV-CRISPR enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the AAV-CRISPR enzyme. Positioning the functional domain in the Rec domain, the Rec2 domain, the HNH domain, or the PI domain of the AsCpf1 protein or any ortholog corresponding to these domains is advantageous; and again, it is mentioned that the functional domain can be a DD. Positioning of the functional domains to the Rec domain or the Rec2 domain, of the AsCpf1 protein or any ortholog corresponding to these domains, in some instances may be preferred. Fok1 functional domain may be attached at the N terminus. When more than one functional domain is included, the functional domains may be the same or different.

An adaptor protein may be any number of proteins that binds to an aptamer or recognition site introduced into the modified sgRNA and which allows proper positioning of one or more functional domains, once the sgRNA has been incorporated into the AAV-CRISPR complex, to affect the target with the attributed function. As explained in detail in this application such may be coat proteins, preferably bacteriophage coat proteins. The functional domains associated with such adaptor proteins (e.g., in the form of fusion protein) may include, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains. Such linkers may be used to associate the AAV (e.g., capsid or VP2) with the CRISPR enzyme or have the CRISPR enzyme comprise the AAV (or vice versa).

Thus, sgRNA, e.g., modified sgRNA, the inactivated AAV-CRISPR enzyme (with or without functional domains), and the binding protein with one or more functional domains, may each individually be comprised in a composition and administered to a host individually or collectively. Alternatively, these components may be provided in a single composition for administration to a host, e.g., the AAV-CRISPR enzyme can deliver the RNA or guide or sgRNA or modified sgRNA and/or other components of the CRISPR system. Administration to a host may be performed via viral vectors, advantageously using the AAV-CRISPR enzyme as the delivery vehicle, although other vehicles can be used to deliver components other than the enzyme of the CRISPR system, and such viral vectors can be, for example, lentiviral vector, adenoviral vector, AAV vector. Several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; lossof-function modeling; the use the compositions of the invention to establish cell lines and transgenic animals for optimization and screening purposes).

In an aspect, the invention provides a particle delivery system or the delivery system or the virus particle of any one of any one of the above embodiments or the cell of any one of the above embodiments for use in medicine or in therapy; or for use in a method of modifying an organism or a non-human organism by manipulation of a target sequence in a genomic locus associated with a disease or disorder; or for use in a method of treating or inhibiting a condition caused by one or more mutations in a genetic locus associated with a disease in a eukaryotic organism or a non-human organism.; or for use in in vitro, ex vivo or in vivo gene or genome editing; or for use in in vitro, ex vivo or in vivo gene therapy.

In an aspect, the invention provides a pharmaceutical composition comprising the particle delivery system or the delivery system or the virus particle of any one of the above embodiments, or the cell of any one of the above embodiments.

In an aspect, the invention provides a method of treating or inhibiting a condition or a disease caused by one or more mutations in a genomic locus in a eukaryotic organism or a non-human organism comprising manipulation of a target sequence within a coding, non-coding or regulatory element of said genomic locus in a target sequence in a subject or a non-human subject in need thereof comprising modifying the subject or a non-human subject by manipulation of the target sequence and wherein the condition or disease is susceptible to treatment or inhibition by manipulation of the target sequence comprising providing treatment comprising delivering a composition comprising the particle delivery system or the delivery system or the virus particle of any one of the above embodiment or the cell of any one of the above embodiment.

In an aspect, the invention provides use of the particle delivery system or the delivery system or the virus particle of any one of the above embodiments or the cell of any one of the above embodiments in ex vivo or in vivo gene or genome editing; or for use in in vitro, ex vivo or in vivo gene therapy.

In an aspect, the invention provides use of the particle delivery system or the delivery system or the virus particle of any one of the above embodiment or the cell of any one of the above embodiment in the manufacture of a medicament for in vitro, ex vivo or in vivo gene or genome editing or for use in in vitro, ex vivo or in vivo gene therapy or for use in a method of modifying an organism or a non-human organism by manipulation of a target sequence in a genomic locus associated with a disease or in a method of treating or inhibiting a condition or disease caused by one or more mutations in a genomic locus in a eukaryotic organism or a non-human organism.

In an aspect, the invention provides a method of individualized or personalized treatment of a genetic disease in a subject in need of such treatment comprising: (a) introducing one or more mutations ex vivo in a tissue, organ or a cell line, or in vivo in a transgenic non-human mammal, comprising delivering to cell(s) of the tissue, organ, cell or mammal a composition comprising the particle delivery system or the delivery system or the virus particle of any one of the above embodiment or the cell of any one of the above embodiment, wherein the specific mutations or precise sequence substitutions are or have been correlated to the genetic disease; (b) testing treatment(s) for the genetic disease on the cells to which the vector has been delivered that have the specific mutations or precise sequence substitutions correlated to the genetic disease; and (c) treating the subject based on results from the testing of treatment(s) of step (b).

In an aspect, the invention provides a method of modeling a disease associated with a genomic locus in a eukaryotic organism or a non-human organism comprising manipulation of a target sequence within a coding, non-coding or regulatory element of said genomic locus comprising delivering a non-naturally occurring or engineered composition comprising a viral vector system comprising one or more viral vectors operably encoding a composition for expression thereof, wherein the composition comprises particle delivery system or the delivery system or the virus particle of any one of the above embodiments or the cell of any one of the above embodiment.

In an aspect, the method provides a method of modifying an organism or a non-human organism by manipulation of a target sequence in a genomic locus of interest comprising administering a composition comprising the particle delivery system or the delivery system or the virus particle of any one of the above embodiments or the cell of any one of the above embodiments.

In any of the described methods the strand break may be a single strand break or a double strand break.

Regulatory elements may comprise inducible promotors. Polynucleotides and/or vector systems may comprise inducible systems.

The invention also provides a vector system comprising one or more vectors, the one or more vectors comprising one or more polynucleotide molecules encoding components of a non-naturally occurring or engineered composition which is a composition having the characteristics as discussed herein or defined in any of the herein described methods.

The invention also provides a non-naturally occurring or engineered composition, or one or more polynucleotides encoding components of said composition, or vector systems comprising one or more polynucleotides encoding components of said composition for use in a therapeutic method of treatment. The therapeutic method of treatment may comprise gene or genome editing, or gene therapy.

The nucleic acids-targeting systems, the vector systems, the vectors and the compositions described herein may be used in various nucleic acids-targeting applications, altering or modifying synthesis of a gene product, such as a protein, nucleic acids cleavage, nucleic acids editing, nucleic acids splicing; trafficking of target nucleic acids, tracing of target nucleic acids, isolation of target nucleic acids, visualization of target nucleic acids, etc.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Vectors for and that result in expression in a eukaryotic cell can be referred to herein as "eukaryotic expression vectors." Common expression vectors of utility in recombinant DNA techniques are often in the form of plasmids.

In certain embodiments, a vector system includes promoter-guide expression cassette in reverse order.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adeno-associated viruses, and types of such vectors can also be selected for targeting particular types of cells.

In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector module and a nucleic acid-targeting guide RNA could each be operably linked to separate regulatory elements on separate vectors. RNA(s) of the nucleic acid-targeting system can be delivered to a transgenic nucleic acid-targeting effector module animal or mammal, e.g., an animal or mammal that constitutively or inducibly or conditionally expresses nucleic acid-targeting effector module; or an animal or mammal that is otherwise expressing nucleic acid-targeting effector modules or has cells containing nucleic acid-targeting effector modules, such as by way of prior administration thereto of a vector or vectors that code for and express in vivo nucleic acid-targeting effector modules. Alternatively, two or more of the elements expressed from the same or different regulatory elements, may be combined in a single vector, with one or more additional vectors providing any components of the nucleic acid-targeting system not included in the first vector. nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector module and the nucleic acid-targeting guide RNA, embedded within one or more intron sequences (e.g., each in a different intron, two or more in at least one intron, or all in a single intron). In some embodiments, the nucleic acid-targeting effector module and the nucleic acid-targeting guide RNA may be operably linked to and expressed from the same promoter.

In an aspect, the invention provides in a vector system comprising one or more vectors, wherein the one or more vectors comprises: a) a first regulatory element operably linked to a nucleotide sequence encoding the engineered CRISPR protein as defined herein; and optionally b) a second regulatory element operably linked to one or more nucleotide sequences encoding one or more nucleic acid molecules comprising a guide RNA comprising a guide sequence, a direct repeat sequence, optionally wherein components (a) and (b) are located on same or different vectors. The invention also provides an engineered, non-naturally occurring Clustered Regularly Interspersed Short Palindromic Repeats (CRISPR)-CRISPR associated (Cas effector module) (CRISPR-Cas effector module) vector system comprising one or more vectors comprising: a) a first regulatory element operably linked to a nucleotide sequence encoding a non-naturally-occurring CRISPR enzyme of any one of the inventive constructs herein; and b) a second regulatory element operably linked to one or more nucleotide sequences encoding one or more of the guide RNAs, the guide RNA comprising a guide sequence, a direct repeat sequence, wherein: components (a) and (b) are located on same or different vectors, the CRISPR complex is formed; the guide RNA targets the target polynucleotide loci and the enzyme alters the polynucleotide loci, and the enzyme in the CRISPR complex has reduced capability of modifying one or more off-target loci as compared to an unmodified enzyme and/or whereby the enzyme in the CRISPR complex has increased capability of modifying the one or more target loci as compared to an unmodified enzyme.

As used herein, a CRISPR Cas effector module or CRISRP effector module includes, but is not limited to, Cas9, Cpf1, C2c2, Group 13b, and C2c1. In some embodiments, the CRISPR-Cas effector module may be engineered.

In such a system, component (II) may comprise a first regulatory element operably linked to a polynucleotide sequence which comprises the guide sequence, the direct repeat sequence, and wherein component (II) may comprise a second regulatory element operably linked to a polynucleotide sequence encoding the CRISPR enzyme. In such a system, where applicable the guide RNA may comprise a chimeric RNA.

In such a system, component (I) may comprise a first regulatory element operably linked to the guide sequence and the direct repeat sequence, and wherein component (II) may comprise a second regulatory element operably linked to a polynucleotide sequence encoding the CRISPR enzyme. Such a system may comprise more than one guide RNA, and each guide RNA has a different target whereby there is multiplexing. Components (a) and (b) may be on the same vector.

In any such systems comprising vectors, the one or more vectors may comprise one or more viral vectors, such as one or more retrovirus, lentivirus, adenovirus, adeno-associated virus or herpes simplex virus.

In any such systems comprising regulatory elements, at least one of said regulatory elements may comprise a tissue-specific promoter. The tissue-specific promoter may direct expression in a mammalian blood cell, in a mammalian liver cell or in a mammalian eye.

In any of the above-described compositions or systems the direct repeat sequence, may comprise one or more protein-interacting RNA aptamers. The one or more aptamers may be located in the tetraloop. The one or more aptamers may be capable of binding MS2 bacteriophage coat protein.

In any of the above-described compositions or systems the cell may be a eukaryotic cell or a prokaryotic cell; wherein the CRISPR complex is operable in the cell, and whereby the enzyme of the CRISPR complex has reduced capability of modifying one or more off-target loci of the cell as compared to an unmodified enzyme and/or whereby the enzyme in the CRISPR complex has increased capability of modifying the one or more target loci as compared to an unmodified enzyme.

The invention also provides a CRISPR complex of any of the above-described compositions or from any of the above-described systems.

The invention also provides a method of modifying a locus of interest in a cell comprising contacting the cell with any of the herein-described engineered CRISPR enzymes (e.g. engineered Cas effector module), compositions or any of the herein-described systems or vector systems, or wherein the cell comprises any of the herein-described CRISPR complexes present within the cell. In such methods the cell may be a prokaryotic or eukaryotic cell, preferably a eukaryotic cell. In such methods, an organism may comprise the cell. In such methods the organism may not be a human or other animal.

In certain embodiment, the invention also provides a non-naturally-occurring, engineered composition (e.g., engineered Cas9, Cpf1, C2c2, C2c1, Group 29/30, 13b, or any Cas protein which can fit into an AAV vector). Reference is made to FIGS. 19A, 19B, 19C, 19D, and 20A-F in U.S. Pat. No. 8,697,359 herein incorporated by reference to provide a list and guidance for other proteins which may also be used.

Any such method may be ex vivo or in vitro.

Gene Editing or Altering a Target Loci with a Cas 12 (Cpf1) Enzyme

In an embodiment, the template nucleic acid alters the structure of the target position by participating in homologous recombination. In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by a Cpf1 mediated cleavage event. In an embodiment, the template nucleic acid may include sequence that corresponds to both, a first site on the target sequence that is cleaved in a first Cpf1 mediated event, and a second site on the target sequence that is cleaved in a second Cpf1 mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

A template nucleic acid comprises the following components: [5' homology arm]-[replacement sequence]-[3' homology arm]. The homology arms provide for recombination into the chromosome, thus replacing the undesired element, e.g., a mutation or signature, with the replacement sequence. In an embodiment, the homology arms flank the most distal cleavage sites. In an embodiment, the 3' end of the 5' homology arm is the position next to the 5' end of the replacement sequence. In an embodiment, the 5' homology arm can extend at least 10, 20, 30, 40, 50, 100, 200, 300, 400, 500, 600, 700, 800, 900, 1000, 1500, or 2000 nucleotides 5' from the 5' end of the replacement sequence. In an embodiment, the 5' end of the 3' homology arm is the position next to the 3' end of the replacement sequence. In an embodiment, the 3' homology arm can extend at least 10, 20, 30, 40, 50, 100, 200, 300, 400, 500, 600, 700, 800, 900, 1000, 1500, or 2000 nucleotides 3' from the 3' end of the replacement sequence.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In certain embodiments, a template nucleic acid for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Non-Homologous End-Joining by a Cas 12 (Cpf1) Enzyme or System

In certain embodiments, nuclease-induced non-homologous end-joining (NHEJ) can be used to target gene-specific knockouts. Nuclease-induced NHEJ can also be used to remove (e.g., delete) sequence in a gene of interest. Generally, NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily be greater than 50 bp, e.g., they can easily reach greater than about 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it may also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving Cpf1 molecules and single strand, or nickase, Cpf1 molecules can be used in the methods and compositions described herein to generate NHEJ-mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In an embodiment, in which a guide RNA and Cpf1 nuclease generate a double strand break for the purpose of inducing NHEJ-mediated indels, a guide RNA may be configured to position one double-strand break in close proximity to a nucleotide of the target position. In an embodiment, the cleavage site may be between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two guide RNAs complexing with Cpf1 nickases induce two single strand breaks for the purpose of inducing NHEJ-mediated indels, two guide RNAs may be configured to position two single-strand breaks to provide for NHEJ repair a nucleotide of the target position.

Delivery of Functional Effectors by a Cas 12 (Cpf1) Enzyme Complex

Unlike CRISPR-Cas-mediated gene knockout, which permanently eliminates expression by mutating the gene at the DNA level, CRISPR-Cas knockdown allows for temporary reduction of gene expression through the use of artificial transcription factors. Mutating key residues in both DNA cleavage domains of the Cpf1 protein, such as FnCpf1 protein (e.g. the D917A and H1006A mutations of the FnCpf1 protein or D908A, E993A, D1263A according to AsCpf1 protein or D832A, E925A, D947A or D1180A according to LbCpf1 protein) results in the generation of a catalytically inactive Cpf1. A catalytically inactive Cpf1 complexes with a guide RNA and localizes to the DNA sequence specified by that guide RNA's targeting domain, however, it does not cleave the target DNA. Fusion of the inactive Cpf1 protein, such as FnCpf1 protein (e.g. the D917A and H1006A mutations) to an effector domain, e.g., a transcription repression domain, enables recruitment of the effector to any DNA site specified by the guide RNA. In certain embodiments, Cpf1 may be fused to a transcriptional repression domain and recruited to the promoter region of a gene. Especially for gene repression, it is contemplated herein that blocking the binding site of an endogenous transcription factor would aid in downregulating gene expression. In another embodiment, an inactive Cpf1 can be fused to a chromatin modifying protein. Altering chromatin status can result in decreased expression of the target gene.

In an embodiment, a guide RNA molecule can be targeted to a known transcription response element (e.g., promoters, enhancers, etc.), a known upstream activating sequences, and/or sequences of unknown or known function that are suspected of being able to control expression of the target DNA.

In some methods, a target polynucleotide can be inactivated to affect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In certain embodiments, the CRISPR enzyme comprises one or more mutations selected from the group consisting of D917A, E1006A and D1225A and/or the one or more mutations is in a RuvC domain of the CRISPR enzyme or is a mutation as otherwise as discussed herein. In some embodiments, the CRISPR enzyme has one or more mutations in a catalytic domain, wherein when transcribed, the direct repeat sequence forms a single stem loop and the guide sequence directs sequence-specific binding of a CRISPR complex to the target sequence, and wherein the enzyme further comprises a functional domain. In some embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

Methods of Detection Using Cas 12 (Cpf1) Enzymes

In one aspect, the invention provides an engineered, non-naturally occurring CRISPR-Cas system comprising a catalytically inactivate Cas protein described herein, preferably an inactivate Cpf1 (dCpf1), and use this system in detection methods such as fluorescence in situ hybridization (FISH). dCpf1 which lacks the ability to produce DNA double-strand breaks may be fused with a marker, such as fluorescent protein, such as the enhanced green fluorescent protein (eEGFP) and co-expressed with small guide RNAs to target pericentric, centric and teleomeric repeats in vivo. The dCpf1 system can be used to visualize both repetitive sequences and individual genes in the human genome. Such new applications of labelled dCpf1 CRISPR-cas systems may be important in imaging cells and studying the functional nuclear architecture, especially in cases with a small nucleus volume or complex 3-D structures. (Chen B, Gilbert L A, Cimini B A, Schnitzbauer J, Zhang W, Li G W, Park J, Blackburn E H, Weissman J S, Qi L S, Huang B. 2013. Dynamic imaging of genomic loci in living human cells by an optimized CRISPR/Cas system. Cell 155(7):1479-91. doi: 10.1016/j.cell.2013.12.001.)

Nucleic Acids, Amino Acids and Proteins, Regulatory Sequences, Vectors

The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques in Biochemistry and Molecular Biology-Hybridization with Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridizing to the reference sequence under highly stringent conditions. Generally, in order to maximize the hybridization rate, relatively low-stringency hybridization conditions are selected: about 20 to 250 C lower than the thermal melting point (Tm). The Tm is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the Tm. In order to require at least about 70% nucleotide complementarity of hybridized sequences, moderately-stringent washing conditions are selected to be about 15 to 30° C. lower than the Tm. Highly permissive (very low stringency) washing conditions may be as low as 500 C below the Tm, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

As used herein the term "wild type" is a term of the art understood by skilled persons and means the typical form of an organism, strain, gene or characteristic as it occurs in nature as distinguished from mutant or variant forms. A "wild type" can be a base line.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. In all aspects and embodiments, whether they include these terms or not, it will be understood that, preferably, the may be optional and thus preferably included or not preferably not included. Furthermore, the terms "non-naturally occurring" and "engineered" may be used interchangeably and so can therefore be used alone or in combination and one or other may replace mention of both together. In particular, "engineered" is preferred in place of "non-naturally occurring" or "non-naturally occurring and/or engineered."

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However, it can be preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4th Ed. -Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according Table 9 which describes a generally accepted Venn diagram grouping of amino acids.

TABLE 9

| Set | | Sub-set | |
|---|---|---|---|
| Hydrophobic | F W Y H K M I L V A G C (SEQ ID NO: 93) | Aromatic | F W Y H (SEQ ID NO: 96) |
| | | Aliphatic | I L V |
| Polar | W Y H K R E D C S T N Q (SEQ ID NO: 94) | Charged | H K R E D (SEQ ID NO: 97) |
| | | Positively charged | H K R |
| | | Negatively charged | E D |
| Small | V C A G S P T N D (SEQ ID NO: 95) | Tiny | A G S |

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R.I. Freshney, ed. (1987)).

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Homology modelling: Corresponding residues in other Cpf1 orthologs can be identified by the methods of Zhang et al., 2012 (Nature; 490(7421): 556-60) and Chen et al., 2015 (PLoS Comput Biol; 11(5): e1004248)—a computational protein-protein interaction (PPI) method to predict interactions mediated by domain-motif interfaces. PrePPI (Predicting PPI), a structure-based PPI prediction method, combines structural evidence with non-structural evidence using a Bayesian statistical framework. The method involves taking a pair of query proteins and using structural alignment to identify structural representatives that correspond to either their experimentally determined structures or homology models. Structural alignment is further used to identify both close and remote structural neighbors by considering global and local geometric relationships. Whenever two neighbors of the structural representatives form a complex reported in the Protein Data Bank, this defines a template for modelling the interaction between the two query proteins. Models of the complex are created by superimposing the representative structures on their corresponding structural neighbor in the template. This approach is further described in Dey et al., 2013 (Prot Sci; 22: 359-66).

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR.

Functional Domains

In some embodiments, one or more functional domains are associated with the Cpf1 effector protein. In some embodiments, one or more functional domains are associated with an adaptor protein, for example as used with the modified guides of Konnerman et al. (Nature 517, 583-588, 29 Jan. 2015). In some embodiments, one or more functional domains are associated with a dead gRNA (dRNA). In some embodiments, a dRNA complex with active Cpf1 effector protein directs gene regulation by a functional domain at on gene locus while an gRNA directs DNA cleavage by the active Cpf1 effector protein at another locus, for example as described analogously in CRISPR-Cas9 systems by Dahlman et al., 'Orthogonal gene control with a catalytically active Cas9 nuclease' (in press). In some embodiments, dRNAs are selected to maximize selectivity of regulation for a gene locus of interest compared to off-target regulation. In some embodiments, dRNAs are selected to maximize target gene regulation and minimize target cleavage.

For the purposes of the following discussion, reference to a functional domain could be a functional domain associated with the Cpf1 effector protein or a functional domain associated with the adaptor protein.

In the practice of the invention, loops of the gRNA may be extended, without colliding with the Cpf1 protein by the insertion of distinct RNA loop(s) or distinct sequence(s) that may recruit adaptor proteins that can bind to the distinct RNA loop(s) or distinct sequence(s). The adaptor proteins may include, but are not limited to, orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease. In some preferred embodiments, the functional domain is a transcriptional activation domain, such as, without limitation, VP64, p65, MyoD1, HSF1, RTA, SET7/9 or a histone acetyltransferase. In some embodiments, the functional domain is a transcription repression domain, preferably KRAB. In some embodiments, the transcription repression domain is SID, or concatemers of SID (e.g. SID4X). In some embodiments, the functional domain is an epigenetic modifying domain, such that an epigenetic modifying enzyme is provided. In some embodiments, the functional domain is an activation domain, which may be the P65 activation domain.

In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. Other references herein to activation (or activator) domains in respect of those associated with the CRISPR enzyme include any known transcriptional activation domain and specifically VP64, p65, MyoD1, HSF1, RTA, SET7/9 or a histone acetyltransferase.

In some embodiments, the one or more functional domains is a transcriptional repressor domain. In some embodiments, the transcriptional repressor domain is a KRAB domain. In some embodiments, the transcriptional repressor domain is a NuE domain, NcoR domain, SID domain or a SID4X domain.

In some embodiments, the one or more functional domains have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

Histone modifying domains are also preferred in some embodiments. Exemplary histone modifying domains are discussed below. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains. Histone acetyltransferases are preferred in some embodiments.

In some embodiments, the DNA cleavage activity is due to a nuclease. In some embodiments, the nuclease comprises a Fok1 nuclease. See, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In some embodiments, the one or more functional domains is attached to the Cpf1 effector protein so that upon binding to the sgRNA and target the functional domain is in a spatial orientation allowing for the functional domain to function in its attributed function.

In some embodiments, the one or more functional domains is attached to the adaptor protein so that upon binding of the Cpf1 effector protein to the gRNA and target, the functional domain is in a spatial orientation allowing for the functional domain to function in its attributed function.

In an aspect the invention provides a composition as herein discussed wherein the one or more functional domains is attached to the Cpf1 effector protein or adaptor protein via a linker, optionally a GlySer linker, as discussed herein.

Endogenous transcriptional repression is often mediated by chromatin modifying enzymes such as histone methyltransferases (HMTs) and deacetylases (HDACs). Repressive histone effector domains are known and an exemplary list is provided below. In the exemplary table, preference was given to proteins and functional truncations of small size to facilitate efficient viral packaging (for instance via AAV). In general, however, the domains may include HDACs, histone methyltransferases (HMTs), and histone acetyltransferase (HAT) inhibitors, as well as HDAC and HMT recruiting proteins. The functional domain may be or include, in some embodiments, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains (Table 10).

TABLE 10

HDAC Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| HDAC I | HDAC8 | — | — | X. laevis | 325 | 1-325 | 325 | 1-272: HDAC |
| HDAC I | RPD3 | — | — | S. cerevisiae | 433 | 19-340 (Vannier) | 322 | 19-331: HDAC |
| HDAC IV | MesoLo4 | — | — | M. loti | 300 | 1-300 (Gregoretti) | 300 | — |
| HDAC IV | HDAC11 | — | — | H. sapiens | 347 | 1-347 (Gao) | 347 | 14-326: HDAC |
| HD2 | HDT1 | — | — | A. thatiana | 245 | 1-211 (Wu) | 211 | — |
| SIRT I | SIRT3 | H3K9Ac H4K16Ac H3K56Ac | — | H. sapiens | 399 | 143-399 (Scher) | 257 | 126-382: SIRT |
| SIRT I | HST2 | — | — | C. albicans | 331 | 1-331 (Hnisz) | 331 | — |
| SIRT I | CobB | — | — | E. coli (K12) | 242 | 1-242 (Landry) | 242 | — |
| SIRT I | HST2 | — | — | S. cerevisiaie | 357 | 8-298 (Wilson) | 291 | — |
| SIRT III | SIRT5 | H4K8Ac H4K16Ac | — | H. sapiens | 310 | 37-310 (Gertz) | 274 | 41-309: SIRT |
| SIRT III | Sir2A | — | — | P. falciparum | 273 | 1-273 (Zhu) | 273 | 19-273: SIRT |
| SIRT IV | SIRT6 | H3K9Ac H3K56Ac | — | H. sapiens | 355 | 1-289 (Tennen) | 289 | 35-274: SIRT |

Accordingly, the repressor domains of the present invention may be selected from histone methyltransferases (HMNTs), histone deacetylases (HIDACs), histone acetyltransferase (HAT) inhibitors, as well as HIDAC and HMNT recruiting proteins.

The THDAC domain may be any of those in the table above, namely: HIDAC8, RPD3, MesoLo4, HIDAC11, HIDT1, SIRT3, HST2, CobB, HST2, SIRT5, Sir2A, or SIRT6.

In some embodiment, the functional domain may be a THDAC Recruiter Effector Domain. Preferred examples include those in Table 11, namely MeCP2, MBD2b, Sin3a, NcoR, SALL1, RCOR1. NcoR is exemplified in the present Examples and, although preferred, it is envisaged that others in the class will also be useful.

TABLE 11

HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | MeCP2 | — | — | R. norvegicus | 492 | 207-492 (Nan) | 286 | — |
| Sin3a | MBD2b | — | — | H. sapiens | 262 | 45-262 (Boeke) | 218 | — |

TABLE 11-continued

| | | | | | | | |
|---|---|---|---|---|---|---|---|
| | | | | HDAC Recruiter Effector Domains | | | |
| Subtype/ Complex | Name | Substrate (if known) | Modification (if known) | Organism | Full size (aa) | Selected truncation (aa) | Final size (aa) | Catalytic domain |
| Sin3a | Sin3a | — | — | H. sapiens | 1273 | 524-851 (Laherty) | 328 | 627-829: HDAC1 interaction |
| NcoR | NcoR | — | — | H. sapiens | 2440 | 420-488 (Zhang) | 69 | — |
| NuRD | SALL1 | — | — | M. musculus | 1322 | 1-93 (Lauberth) | 93 | — |
| CoREST | RCOR1 | — | — | H. sapiens | 482 | 81-300 (Gu, Ouyang) | 220 | — |

In some embodiment, the functional domain may be a Methyltransferase (TBDoT) Effector Domain. Preferred examples include those in the Table 12, namely NUE, vSET, ETIMT2/G9A, SUV39H1, dim-5, KYP, SUVR4, SET4, SET1, SETD8, and TgSET8. NUE is exemplified in the present Examples and, although preferred, it is envisaged that others in the class will also be useful and can be included in various embodiments of the present invention.

TABLE 12

| | | | | | | | | |
|---|---|---|---|---|---|---|---|---|
| | | | | Histone Methyltransferase (HMT) Effector Domains | | | | |
| Subtype/ Complex | Name | Substrate (if known) | Modification (if known) | Organism | Full size (aa) | Selected truncation (aa) | Final size (aa) | Catalytic domain |
| SET | NUE | H2B, H3, H4 | — | C. trachomatis | 219 | 1-219 (Pennini) | 219 | — |
| SET | vSET | — | H3K27me3 | P. bursaria chlorella virus | 119 | 1-119 (Mujtaba) | 119 | 4-112: SET2 |
| SUV39 family | EHMT2/ G9A | H1.4K2, H3K9, H3K27 | H3K9me1/2, H1K25me1 | M. musculus | 1263 | 969-1263 (Tachibana) | 295 | 1025-1233: preSET, SET, postSET |
| SUV39 | SUV39H1 | — | H3K9me2/3 | H. sapiens | 412 | 79-412 (Snowden) | 334 | 172-412: preSET, SET, postSET |
| Suvar3-9 | dim-5 | — | H3K9me3 | N. crassa | 331 | 1-331 (Rathert) | 331 | 77-331: preSET, SET, postSET |
| Suvar3-9 (SUVH subfamily) | KYP | — | H3K9me1/2 | A. thaliana | 624 | 335-601 | 267 (Jackson) | — |
| Suvar3-9 (SUVR subfamily) | SUVR4 | H3K9me1 | H3K9me2/3 | A. thaliana | 492 | 180-492 | 313 (Thorstensen) | 192-462: preSET, SET, postSET |
| Suvar4-20 | SET4 | — | H4K20me3 | C. elegans | 288 | 1-288 (Vielle) | 288 | — |
| SET8 | SET1 | — | H4K20me1 | C. elegans | 242 | 1-242 (Vielle) | 242 | — |
| SET8 | SETD8 | — | H4K20me1 | H. sapiens | 393 | 185-393 (Couture) | 209 | 256-382: SET |
| SET8 | TgSET8 | — | H4K20me1/2/3 | T. gondii | 1893 | 1590-1893 (Sautel) | 304 | 1749-1884: SET |

In some embodiment, the functional domain may be a Histone Methyltransferase (TBMT) Recruiter Effector Domain. Preferred examples include those in the Table 13, namely Hp1a, PHF19, and NIPP1.

TABLE 13

Histone Methyltransferase (HMT) Recruiter Effector Domains

| Subtype/<br>Complex | Name | Substrate<br>(if known) | Modification<br>(if known) | Organism | Full<br>size<br>(aa) | Selected<br>truncation<br>(aa) | Final<br>size<br>(aa) | Catalytic<br>domain |
|---|---|---|---|---|---|---|---|---|
| — | Hp1a | — | H3K9me3 | M. musculus | 191 | 73-191 | 119<br>(Hathaway) | 121-179:<br>chromoshadow |
| — | PHF19 | — | H3K27me3 | H. sapiens | 580 | (1-250) +<br>GGSG<br>linker +<br>(500-580) | 335<br>(Ballaré) | 163-250:<br>PHD2 |
| — | NIPP1 | — | H3K27me3 | H. sapiens | 351 | 1-329<br>(Jin) | 329 | 310-329:<br>EED |

In some embodiment, the functional domain may be Histone Acetyltransferase Inhibitor Effector Domain. Preferred examples include SET/TAF-1β listed in the Table 14.

TABLE 14

Histone Acetyltransferase Inhibitor Effector Domains

| Subtype/<br>Complex | Name | Substrate<br>(if known) | Modification<br>(if known) | Organism | Full<br>size<br>(aa) | Selected<br>truncation<br>(aa) | Final<br>size<br>(aa) | Catalytic<br>domain |
|---|---|---|---|---|---|---|---|---|
| — | SET/TAF-1β | — | — | M. musculus | 289 | 1-289<br>(Cervoni) | 289 | — |

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100 kb away. Targeting of known control elements can be used to activate or repress the gene of interest. In some cases, a single control element can influence the transcription of multiple target genes. Targeting of a single control element could therefore be used to control the transcription of multiple genes simultaneously.

Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100 kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome readout by e.g. RNAseq or microarray. This would allow for the identification of likely candidate genes involved in the disease phenotype. Such candidate genes could be useful as novel drug targets.

Histone acetyltransferase (HAT) inhibitors are mentioned herein. However, an alternative in some embodiments is for the one or more functional domains to comprise an acetyltransferase, preferably a histone acetyltransferase. These are useful in the field of epigenomics, for example in methods of interrogating the epigenome. Methods of interrogating the epigenome may include, for example, targeting epigenomic sequences. Targeting epigenomic sequences may include the guide being directed to an epigenomic target sequence. Epigenomic target sequence may include, in some embodiments, include a promoter, silencer or an enhancer sequence.

Use of a functional domain linked to a Cpf1 effector protein as described herein, preferably a dead-Cpf1 effector protein, more preferably a dead-FnCpf1 effector protein, to target epigenomic sequences can be used to activate or repress promoters, silencer or enhancers.

Examples of acetyltransferases are known but may include, in some embodiments, histone acetyltransferases. In some embodiments, the histone acetyltransferase may comprise the catalytic core of the human acetyltransferase p300 (Gerbasch & Reddy, Nature Biotech 6th April 2015).

In some preferred embodiments, the functional domain is linked to a dead-Cpf1 effector protein to target and activate epigenomic sequences such as promoters or enhancers. One or more guides directed to such promoters or enhancers may also be provided to direct the binding of the CRISPR enzyme to such promoters or enhancers.

The term "associated with" is used here in relation to the association of the functional domain to the Cpf1 effector protein or the adaptor protein. It is used in respect of how one molecule 'associates' with respect to another, for example between an adaptor protein and a functional domain, or between the Cpf1 effector protein and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the Cpf1 effector protein or adaptor protein is associated with a functional domain by binding thereto. In other embodiments, the Cpf1 effector protein or adaptor protein is associated with a functional domain because the two are fused together, optionally via an intermediate linker.

Attachment of a functional domain or fusion protein can be via a linker, e.g., a flexible glycine-serine (GlyGlyGly-Ser) (SEQ ID NO: 98) or (GGGS)$_3$ (SEQ ID NO: 99) or a rigid alpha-helical linker such as (Ala(GluAlaAlaAlaLys)Ala) (SEQ ID NO: 100). Linkers such as (GGGGS)$_3$ (SEQ ID NO: 91) are preferably used herein to separate protein or peptide domains. (GGGGS)$_3$ (SEQ ID NO: 91) is preferable because it is a relatively long linker (15 amino acids). The glycine residues are the most flexible and the serine residues enhance the chance that the linker is on the outside of the protein. (GGGGS)$_6$ (SEQ ID NO: 101) (GGGGS)$_9$ (SEQ ID NO: 102) or (GGGGS)$_{12}$ (SEQ ID NO: 103) may preferably be used as alternatives. Other preferred alternatives are (GGGGS)$_1$ (SEQ ID NO: 89), (GGGGS)$_2$ (SEQ ID NO: 90), (GGGGS)$_4$ (SEQ ID NO: 104), (GGGGS)$_5$ (SEQ ID NO: 105), (GGGGS)$_7$ (SEQ ID NO: 106), (GGGGS)s SEQ ID NO: 107), (GGGGS)$_{10}$ (SEQ ID NO: 108), or (GGGGS)ii (SEQ ID NO: 109). Alternative linkers are available, but highly flexible linkers are thought to work best to allow for maximum opportunity for the 2 parts of the Cpf1 to come together and thus reconstitute Cpf1 activity. One alternative is that the NLS of nucleoplasmin can be used as a linker. For example, a linker can also be used between the Cpf1 and any functional domain. Again, a (GGGGS)$_3$ (SEQ ID NO: 91) linker may be used here (or rsions therefore) or the NLS of nucleoplasmin can be used as a linker between Cpf1 and the functional domain.

Methods of Use

The methods and compositions disclosed herein are useful for treatment of diseases and disorders in both human and nonhuman animal species as well as in plants, particularly plants of agricultural importance. The multiplexing polynucleotides disclosed herein provide methods of targeting multiple sequences for improved therapeutic benefit. The multiplexing polynucleotides disclosed herein are also as screening tools to identify sequences that may be implicated in diseases or disorders both human and nonhuman animal species as well as plant species.

Use of Cas12 (Cpf1) Effector Proteins and Systems in Non-Animal Organisms

The methods and compositions disclosed herein are useful for treatment or analysis of nonanimal organisms. The Cpf1 effector protein system(s) (e.g., single or multiplexed) can be used in conjunction with recent advances in crop genomics. The systems described herein can be used to perform efficient and cost-effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. The Cpf1 effector protein system(s) can be used with regard to plants in Site-Directed Integration (SDI) or Gene Editing (GE) or any Near Reverse Breeding (NRB) or Reverse Breeding (RB) techniques. Aspects of utilizing the herein described Cpf1 effector protein systems may be analogous to the use of the CRISPR-Cas (e.g. CRISPR-Cas9) system in plants, and mention is made of the University of Arizona website "CRISPR-PLANT" (http://www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR-Cas system," Plant Methods 2013, 9:39 (doi:10.1186/1746-4811-9-39); Brooks, "Efficient gene editing in tomato in the first generation using the CRISPR-Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061 —*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent; and, the enzymes herein having reduced off-target effects and systems employing such enzymes can be used in plant applications, including those mentioned herein.

Use of Cpf1-CRISPR Systems in Plants and Yeast

Definitions. In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, eucalyptus, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, papaya, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. The term plant also encompasses Algae, which are mainly photoautotrophs unified primarily by their lack of roots, leaves and other organs that characterize higher plants.

The methods for genome editing using the Cpf1 system as described herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the methods and CRISPR-Cas systems can be used over a broad range of plants, such as for example with dicotyledonous plants belonging to the orders Magniolales, Illiciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales; the methods and CRISPR-Cas systems can be used with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales, or with plants belonging to Gymnospermae, e.g those belonging to the orders Pinales, Ginkgoales, Cycadales, Araucariales, Cupressales and Gnetales.

The Cpf1 CRISPR systems and methods of use described herein can be used over a broad range of plant species, included in the non-limitative list of dicot, monocot or gymnosperm genera hereunder: *Atropa, Alseodaphne, Anacardium, Arachis, Beilschmiedia, Brassica, Carthamus, Cocculus, Croton, Cucumis, Citrus, Citrullus, Capsicum, Cath-aranthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis,* and *Vigna*; and the genera *Allium, Andropogon, Aragrostis, Asparagus, Avena, Cynodon, Elaeis, Festuca, Festulolium, Heterocallis, Hordeum, Lemna, Lolium, Musa, Oryza, Panicum, Pannesetum, Phleum, Poa, Secale, Sorghum, Triticum, Zea, Abies, Cunninghamia, Ephedra, Picea, Pinus,* and *Pseudotsuga*.

The Cpf1 CRISPR systems and methods of use can also be used over a broad range of "algae" or "algae cells"; including for example algea selected from several eukaryotic phyla, including the Rhodophyta (red algae), Chlorophyta (green algae), Phaeophyta (brown algae), Bacillariophyta (diatoms), Eustigmatophyta and dinoflagellates as well as the prokaryotic phylum Cyanobacteria (blue-green algae). The term "algae" includes for example algae selected from: *Amphora, Anabaena, Anikstrodesmis, Botryococcus, Chaetoceros, Chlamydomonas, Chlorella, Chlorococcum, Cyclotella, Cylindrotheca, Dunaliella, Emiliana, Euglena, Hematococcus, Isochrysis, Monochrysis, Monoraphidium, Nannochloris, Nannnochloropsis, Navicula, Nephrochloris, Nephroselmis, Nitzschia, Nodularia, Nostoc, Oochromonas, Oocystis, Oscillartoria, Pavlova, Phaeodactylum, Playtmonas, Pleurochrysis, Porhyra, Pseudoanabaena, Pyramimonas, Stichococcus, Synechococcus, Synechocystis, Tetraselmis, Thalassiosira,* and *Trichodesmium*.

A part of a plant, i.e., a "plant tissue" may be treated according to the methods of the present invention to produce an improved plant. Plant tissue also encompasses plant cells. The term "plant cell" as used herein refers to individual units of a living plant, either in an intact whole plant or in an isolated form grown in in vitro tissue cultures, on media or agar, in suspension in a growth media or buffer or as a part of higher organized unites, such as, for example, plant tissue, a plant organ, or a whole plant.

A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The term "transformation" broadly refers to the process by which a plant host is genetically modified by the introduction of DNA by means of Agrobacteria or one of a variety of chemical or physical methods. As used herein, the term "plant host" refers to plants, including any cells, tissues, organs, or progeny of the plants. Many suitable plant tissues or plant cells can be transformed and include, but are not limited to, protoplasts, somatic embryos, pollen, leaves, seedlings, stems, calli, stolons, microtubers, and shoots. A plant tissue also refers to any clone of such a plant, seed, progeny, propagule whether generated sexually or asexually, and descendants of any of these, such as cuttings or seed.

The term "transformed" as used herein, refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is transmitted to the subsequent progeny. In these embodiments, the "transformed" or "transgenic" cell or plant may also include progeny of the cell or plant and progeny produced from a breeding program employing such a transformed plant as a parent in a cross and exhibiting an altered phenotype resulting from the presence of the introduced DNA molecule. Preferably, the transgenic plant is fertile and capable of transmitting the introduced DNA to progeny through sexual reproduction.

The term "progeny", such as the progeny of a transgenic plant, is one that is born of, begotten by, or derived from a plant or the transgenic plant. The introduced DNA molecule may also be transiently introduced into the recipient cell such that the introduced DNA molecule is not inherited by subsequent progeny and thus not considered "transgenic". Accordingly, as used herein, a "non-transgenic" plant or plant cell is a plant which does not contain a foreign DNA stably integrated into its genome.

The term "plant promoter" as used herein is a promoter capable of initiating transcription in plant cells, whether or not its origin is a plant cell. Exemplary suitable plant promoters include, but are not limited to, those that are obtained from plants, plant viruses, and bacteria such as *Agrobacterium* or *Rhizobium* which comprise genes expressed in plant cells.

As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerervisiae, Kluyveromyces marxianus*, or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis*, a.k.a. *Pichia kudriavzevii* and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains may include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest. Without wishing to be bound to theory, it is thought that the abundance of guideRNA may more often be a rate-limiting component in genome engineering of polyploid cells than in haploid cells, and thus the methods using the Cpf1 CRISPRS system described herein may take advantage of using a certain fungal cell type.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in in Yeast Protocols, 2nd edition, Xiao, W., ed. (Humana Press, New York, 2007) and Buckholz, R. G. and Gleeson, M.A. (1991) Biotechnology (NY) 9(11): 1067-72. Yeast vectors may contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2 plasmids, yeast integrative plasmids, yeast replicative plasmids, shuttle vectors, and episomal plasmids.

Stable Integration of Cpf1 CRISPR System Components in the Genome of Plants and Plant Cells In particular embodiments, it is envisaged that the polynucleotides encoding the components of the Cpf1 CRISPR system are introduced for stable integration into the genome of a plant cell. In these embodiments, the design of the transformation vector or the expression system can be adjusted depending on for when, where and under what conditions the guide RNA and/or the Cpf1 gene are expressed.

In particular embodiments, it is envisaged to introduce the components of the Cpf1 CRISPR system stably into the genomic DNA of a plant cell. Additionally or alternatively, it is envisaged to introduce the components of the Cpf1 CRISPR system for stable integration into the DNA of a plant organelle such as, but not limited to a plastid, e mitochondrion or a chloroplast.

The expression system for stable integration into the genome of a plant cell may contain one or more of the following elements: a promoter element that can be used to express the RNA and/or Cpf1 enzyme in a plant cell; a 5' untranslated region to enhance expression; an intron element to further enhance expression in certain cells, such as monocot cells; a multiple-cloning site to provide convenient restriction sites for inserting the guide RNA and/or the Cpf1 gene sequences and other desired elements; and a 3' untranslated region to provide for efficient termination of the expressed transcript.

The elements of the expression system may be on one or more expression constructs which are either circular such as a plasmid or transformation vector, or non-circular such as linear double stranded DNA.

In a particular embodiment, a Cfp1 CRISPR expression system comprises at least: a nucleotide sequence encoding a guide RNA (gRNA) that hybridizes with a target sequence in a plant, and wherein the guide RNA comprises a guide sequence and a direct repeat sequence, and a nucleotide sequence encoding a Cpf1 protein, wherein components (a) or (b) are located on the same or on different constructs, and whereby the different nucleotide sequences can be under control of the same or a different regulatory element operable in a plant cell.

DNA construct(s) containing the components of the Cpf1 CRISPR system, and, where applicable, template sequence may be introduced into the genome of a plant, plant part, or plant cell by a variety of conventional techniques. The process generally comprises the steps of selecting a suitable host cell or host tissue, introducing the construct(s) into the host cell or host tissue, and regenerating plant cells or plants therefrom.

In particular embodiments, the DNA construct may be introduced into the plant cell using techniques such as but not limited to electroporation, microinjection, aerosol beam injection of plant cell protoplasts, or the DNA constructs can be introduced directly to plant tissue using biolistic methods, such as DNA particle bombardment (see also Fu et al., Transgenic Res. 2000 February; 9(1):11-9). The basis of particle bombardment is the acceleration of particles coated with gene/s of interest toward cells, resulting in the penetration of the protoplasm by the particles and typically stable integration into the genome. (see e.g. Klein et al, Nature (1987), Klein et ah, Bio/Technology (1992), Casas et ah, Proc. Natl. Acad. Sci. USA (1993).).

In particular embodiments, the DNA constructs containing components of the Cpf1 CRISPR system may be introduced into the plant by *Agrobacterium*-mediated transformation. The DNA constructs may be combined with suitable T-DNA flanking regions and introduced into a conventional *Agrobacterium tumefaciens* host vector. The foreign DNA can be incorporated into the genome of plants by infecting the plants or by incubating plant protoplasts with *Agrobacterium* bacteria, containing one or more Ti (tumor-inducing) plasmids. (see e.g. Fraley et al., (1985), Rogers et al., (1987) and U.S. Pat. No. 5,563,055).

Plant Promoters

In order to ensure appropriate expression in a plant cell, the components of the Cpf1 CRISPR system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. "Regulated promoter" refers to promoters that direct gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In particular embodiments, one or more of the Cpf1 CRISPR components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the Cpf1 CRISPR system are found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc.), or light inducible systems (Phytochrome, LOV domains, or cryptochrome)., such as a Light Inducible Transcriptional Effector (LITE) that direct changes in transcriptional activity in a sequence-specific manner. The components of a light inducible system may include a Cpf1 CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736, 465 and U.S. 61/721,283, which is hereby incorporated by reference in its entirety.

In particular embodiments, transient or inducible expression can be achieved by using, for example, chemical-regulated promotors, i.e. whereby the application of an exogenous chemical induces gene expression. Modulating of gene expression can also be obtained by a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-ll-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

Translocation to and/or Expression in Specific Plant Organelles

The expression system may comprise elements for translocation to and/or expression in a specific plant organelle.

Chloroplast Targeting

In particular embodiments, it is envisaged that the Cpf1 CRISPR system is used to specifically modify chloroplast genes or to ensure expression in the chloroplast. For this purpose, use is made of chloroplast transformation methods or compartmentalization of the Cpf1 CRISPR components to the chloroplast. For instance, the introduction of genetic modifications in the plastid genome can reduce biosafety issues such as gene flow through pollen.

Methods of chloroplast transformation are known in the art and include Particle bombardment, PEG treatment, and microinjection. Additionally, methods involving the translocation of transformation cassettes from the nuclear genome to the plastid can be used as described in WO2010061186.

Alternatively, it is envisaged to target one or more of the Cpf1 CRISPR components to the plant chloroplast. This is achieved by incorporating in the expression construct a sequence encoding a chloroplast transit peptide (CTP) or plastid transit peptide, operably linked to the 5' region of the sequence encoding the Cpf1 protein. The CTP is removed in a processing step during translocation into the chloroplast. Chloroplast targeting of expressed proteins is well known to the skilled artisan (see for instance Protein Transport into Chloroplasts, 2010, Annual Review of Plant Biology, Vol. 61: 157-180). In such embodiments, it is also desired to target the guide RNA to the plant chloroplast. Methods and constructs which can be used for translocating guide RNA into the chloroplast by means of a chloroplast localization sequence are described, for instance, in US 20040142476, incorporated herein by reference. Such variations of constructs can be incorporated into the expression systems of the invention to efficiently translocate the Cpf1-guide RNA.

Introduction of Polynucleotides Encoding the CRISPR-Cpf1 System in Algal Cells

Transgenic algae (or other plants such as rape) may be particularly useful in the production of vegetable oils or biofuels such as alcohols (especially methanol and ethanol) or other products. These may be engineered to express or overexpress high levels of oil or alcohols for use in the oil or biofuel industries.

U.S. Pat. No. 8,945,839 describes a method for engineering Micro-Algae (*Chlamydomonas reinhardtii* cells) species) using Cas9. Using similar tools, the methods of the Cpf1 CRISPR system described herein can be applied on *Chlamydomonas* species and other algae. In particular embodiments, Cpf1 and guide RNA are introduced in algae expressed using a vector that expresses Cpf1 under the control of a constitutive promoter such as Hsp70A-Rbc S2 or Beta2-tubulin. Guide RNA is optionally delivered using a vector containing T7 promoter. Alternatively, Cpf1 mRNA and in vitro transcribed guide RNA can be delivered to algal cells. Electroporation protocols are available to the skilled person such as the standard recommended protocol from the GeneArt *Chlamydomonas* Engineering kit.

In particular embodiments, the endonuclease used herein is a Split Cpf1 enzyme. Split Cpf1 enzymes are preferentially used in Algae for targeted genome modification as has been described for Cas9 in WO 2015086795. Use of the Cpf1 split system is particularly suitable for an inducible method of genome targeting and avoids the potential toxic effect of the Cpf1 overexpression within the algae cell. In particular embodiments, said Cpf1 split domains (RuvC and HNH domains) can be simultaneously or sequentially introduced into the cell such that said split Cpf1 domain(s) process the target nucleic acid sequence in the algae cell. The reduced size of the split Cpf1 compared to the wild type Cpf1 allows other methods of delivery of the CRISPR system to the cells, such as the use of Cell Penetrating Peptides as described herein. This method is of particular interest for generating genetically modified algae.

Introduction of Polynucleotides Encoding Cpf1 Components in Yeast Cells

In particular embodiments, the invention relates to the use of the Cpf1 CRISPR system for genome editing of yeast cells. Methods for transforming yeast cells which can be used to introduce polynucleotides encoding the Cpf1 CRISPR system components are well known to the artisan and are reviewed by Kawai et al., 2010, Bioeng. Bugs. 2010 November-December; 1(6): 395-403). Non-limiting examples include transformation of yeast cells by lithium acetate treatment (which may further include carrier DNA and PEG treatment), bombardment or by electroporation.

Transient Expression of Cpf1 CRISP System Components in Plants and Plant Cell

In particular embodiments, it is envisaged that the guide RNA and/or Cpf1 gene are transiently expressed in the plant cell. In these embodiments, the Cpf1 CRISPR system can ensure modification of a target gene only when both the guide RNA and the Cpf1 protein is present in a cell, such that genomic modification can further be controlled. As the expression of the Cpf1 enzyme is transient, plants regenerated from such plant cells typically contain no foreign DNA. In particular embodiments, the Cpf1 enzyme is stably expressed by the plant cell and the guide sequence is transiently expressed.

In particular embodiments, the Cpf1 CRISPR system components can be introduced in the plant cells using a plant viral vector (Scholthof et al. 1996, Annu Rev Phytopathol. 1996; 34:299-323). In further particular embodiments, said viral vector is a vector from a DNA virus. For example, geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., Faba bean necrotic yellow virus). In other particular embodiments, said viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

In particular embodiments, the vector used for transient expression of Cpf1 CRISPR constructs is for instance a pEAQ vector, which is tailored for *Agrobacterium*-mediated transient expression (Sainsbury F. et al., Plant Biotechnol J. 2009 September; 7(7):682-93) in the protoplast. Precise targeting of genomic locations was demonstrated using a modified Cabbage Leaf Curl virus (CaLCuV) vector to express gRNAs in stable transgenic plants expressing a CRISPR enzyme (Scientific Reports 5, Article number: 14926 (2015), doi:10.1038/srep14926).

In particular embodiments, double-stranded DNA fragments encoding the guide RNA and/or the Cpf1 gene can be transiently introduced into the plant cell. In such embodiments, the introduced double-stranded DNA fragments are provided in sufficient quantity to modify the cell but do not persist after a contemplated period of time has passed or after one or more cell divisions. Methods for direct DNA transfer in plants are known by the skilled artisan (see for instance Davey et al. Plant Mol Biol. 1989 September; 13(3):273-85.)

In other embodiments, an RNA polynucleotide encoding the Cpf1protein is introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13; 119-122).

Combinations of the different methods described above are also envisaged.

Delivery of Cpf1 CRISPR Components to the Plant Cell

In particular embodiments, it is of interest to deliver one or more components of the Cpf1 CRISPR system directly to the plant cell. This is of interest, inter alia, for the generation of non-transgenic plants (see below). In particular embodiments, one or more of the Cpf1 components is prepared outside the plant or plant cell and delivered to the cell. For instance, in particular embodiments, the Cpf1 protein is prepared in vitro prior to introduction to the plant cell. Cpf1 protein can be prepared by various methods known by one of skill in the art and include recombinant production. After expression, the Cpf1 protein is isolated, refolded if needed, purified and optionally treated to remove any purification tags, such as a His-tag. Once crude, partially purified, or more completely purified Cpf1 protein is obtained, the protein may be introduced to the plant cell.

In particular embodiments, the Cpf1 protein is mixed with guide RNA targeting the gene of interest to form a pre-assembled ribonucleoprotein.

The individual components or pre-assembled ribonucleoprotein can be introduced into the plant cell via electroporation, by bombardment with Cpf1-associated gene product coated particles, by chemical transfection or by some other means of transport across a cell membrane. For instance, transfection of a plant protoplast with a pre-assembled CRISPR ribonucleoprotein has been demonstrated to ensure targeted modification of the plant genome (as described by Woo et al. Nature Biotechnology, 2015; DOI: 10.1038/nbt.3389).

In particular embodiments, the Cpf1 CRISPR system components are introduced into the plant cells using nanoparticles. The components, either as protein or nucleic acid or in a combination thereof, can be uploaded onto or packaged in nanoparticles and applied to the plants (such as for instance described in WO 2008042156 and US 20130185823). In particular, embodiments of the invention comprise nanoparticles uploaded with or packed with DNA molecule(s) encoding the Cpf1 protein, DNA molecules encoding the guide RNA and/or isolated guide RNA as described in WO2015089419.

Further means of introducing one or more components of the Cpf1 CRISPR system to the plant cell is by using cell penetrating peptides (CPP). Accordingly, in particular, embodiments the invention comprises compositions comprising a cell penetrating peptide linked to the Cpf1 protein. In particular embodiments of the present invention, the Cpf1 protein and/or guide RNA is coupled to one or more CPPs to effectively transport them inside plant protoplasts; see also Ramakrishna (20140Genome Res. 2014 June; 24(6): 1020-7 for Cas9 in human cells). In other embodiments, the Cpf1 gene and/or guide RNA are encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic peptides, peptides having proline-rich and anti-microbial sequence, and chimeric or bipartite peptides (Pooga and Langel 2005). CPPs are able to penetrate biological membranes and as such trigger the movement of various biomolecules across cell membranes into the cytoplasm and to improve their intracellular routing, and hence facilitate interaction of the biomolecule with the target. Examples of CPP include amongst others: Tat, a nuclear transcriptional activator protein required for viral replication by HIV type1, penetratin, Kaposi fibroblast growth factor (FGF) signal peptide sequence, integrin 33 signal peptide sequence; polyarginine peptide Args sequence, Guanine rich-molecular transporters, sweet arrow peptide, etc.

Methods of Making Genetically Modified Non-Transgenic Plants Using Cpf1 CRISPR Systems In particular embodiments, the methods described herein are used to modify endogenous genes or to modify their expression without the permanent introduction into the genome of the plant of any foreign gene, including those encoding CRISPR components, so as to avoid the presence of foreign DNA in the genome of the plant. This can be of interest as the regulatory requirements for non-transgenic plants are less rigorous.

In particular embodiments, this is ensured by transient expression of the Cpf1 CRISPR components. In particular embodiments, one or more of the CRISPR components are expressed on one or more viral vectors which produce sufficient Cpf1 protein and guide RNA to consistently steadily ensure modification of a gene of interest according to a method described herein.

In particular embodiments, transient expression of Cpf1 CRISPR constructs is ensured in plant protoplasts and thus not integrated into the genome. The limited window of expression can be sufficient to allow the Cpf1 CRISPR system to ensure modification of a target gene as described herein.

In particular embodiments, the different components of the Cpf1 CRISPR system are introduced in the plant cell, protoplast or plant tissue either separately or in mixture, with the aid of particulate delivering molecules such as nanoparticles or CPP molecules as described herein above.

The expression of the Cpf1 CRISPR components can induce targeted modification of the genome, either by direct activity of the Cpf1 nuclease and optionally introduction of template DNA or by modification of genes targeted using the Cpf1 CRISPR system as described herein. The different strategies described herein above allow Cpf1-mediated targeted genome editing without requiring the introduction of the Cpf1 CRISPR components into the plant genome. Components which are transiently introduced into the plant cell are typically removed upon crossing.

Detecting Genome Modifications in Plants Using a Cpf1 CRISPR System

In particular embodiments, where the method involves modification of an endogenous target gene of the plant genome, any suitable method can be used to determine, after the plant, plant part or plant cell is infected or transfected with the Cpf1 CRISPR system, whether gene targeting or targeted mutagenesis has occurred at the target site. Where the method involves introduction of a transgene, a transformed plant cell, callus, tissue or plant may be identified and isolated by selecting or screening the engineered plant material for the presence of the transgene or for traits encoded by the transgene. Physical and biochemical methods may be used to identify plant or plant cell transformants containing inserted gene constructs or an endogenous DNA modification. These methods include, but are not limited to: 1) Southern analysis or PCR amplification for detecting and determining the structure of the recombinant DNA insert or modified endogenous genes; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct or expression is affected by the genetic modification; 4) protein gel electrophoresis, Western blot techniques, immunoprecipitation, or enzyme-linked immunoassays, where the gene construct or endogenous gene products are proteins. Additional techniques, such as in situ hybridization, enzyme staining, and immunostaining, also may be used to detect the presence or expression of the recombinant construct or detect a modification of endogenous gene in specific plant organs and tissues. The methods for doing all these assays are well known to those skilled in the art.

Additionally (or alternatively), the expression system encoding the Cpf1 CRISPR components is typically designed to comprise one or more selectable or detectable markers that provide a means to isolate or efficiently select cells that contain and/or have been modified by the Cpf1 CRISPR system at an early stage and on a large scale.

In the case of *Agrobacterium*-mediated transformation, the marker cassette may be adjacent to or between flanking T-DNA borders and contained within a binary vector. In another embodiment, the marker cassette may be outside of the T-DNA. A selectable marker cassette may also be within or adjacent to the same T-DNA borders as the expression cassette or may be somewhere else within a second T-DNA on the binary vector (e.g., a 2 T-DNA system).

For particle bombardment or with protoplast transformation, the expression system can comprise one or more isolated linear fragments or may be part of a larger construct that might contain bacterial replication elements, bacterial selectable markers or other detectable elements. The expression cassette(s) comprising the polynucleotides encoding the guide and/or Cpf1 may be physically linked to a marker cassette or may be mixed with a second nucleic acid molecule encoding a marker cassette. The marker cassette is comprised of necessary elements to express a detectable or selectable marker that allows for efficient selection of transformed cells.

The selection procedure for the cells based on the selectable marker will depend on the nature of the marker gene. In particular embodiments, use is made of a selectable marker, i.e. a marker which allows a direct selection of the cells based on the expression of the marker. A selectable marker can confer positive or negative selection and is conditional or non-conditional on the presence of external substrates (Miki et al. 2004, 107(3): 193-232). Most commonly, antibiotic or herbicide resistance genes are used as a marker, whereby selection is be performed by growing the engineered plant material on media containing an inhibitory amount of the antibiotic or herbicide to which the marker gene confers resistance. Examples of such genes are genes that confer resistance to antibiotics, such as hygromycin (hpt) and kanamycin (nptII), and genes that confer resistance to herbicides, such as phosphinothricin (bar) and chlorosulfuron (als).

Transformed plants and plant cells may also be identified by screening for the activities of a visible marker, typically an enzyme capable of processing a colored substrate (e.g., the β-glucuronidase, luciferase, B or C1 genes). Such selection and screening methodologies are well known to those skilled in the art.

Plant Cultures and Regeneration

In particular embodiments, plant cells which have a modified genome and that are produced or obtained by any of the methods described herein, can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g., Evans et al. (1983), Handbook of Plant Cell Culture, Klee et al (1987) Ann. Rev. of Plant Phys.).

In particular embodiments, transformed or improved plants as described herein can be self-pollinated to provide seed for homozygous improved plants of the invention (homozygous for the DNA modification) or crossed with non-transgenic plants or different improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the improved plants and comprising the genetic modification (which can be a recombinant DNA) are referred to herein as "progeny". Progeny plants are plants descended from the original transgenic plant and containing the genome modification or recombinant DNA molecule introduced by the methods provided herein. Alternatively, genetically modified plants can be obtained by one of the methods described supra using the Cfp1 enzyme whereby no foreign DNA is incorporated into the genome. Progeny of such plants, obtained by further breeding may also contain the genetic modification. Breedings are performed by any breeding methods that are commonly used for different crops (e.g., Allard, Principles of Plant Breeding, John Wiley & Sons, NY, U. of CA, Davis, CA, 50-98 (1960).

Generation of Plants with Enhanced Agronomic Traits

The Cpf1 based CRISPR systems provided herein can be used to introduce targeted double-strand or single-strand breaks and/or to introduce gene activator and or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

In particular embodiments, the Cpf1 CRISPR system as described herein is used to introduce targeted double-strand breaks (DSB) in an endogenous DNA sequence. The DSB activates cellular DNA repair pathways, which can be harnessed to achieve desired DNA sequence modifications near the break site. This is of interest where the inactivation of endogenous genes can confer or contribute to a desired trait. In particular embodiments, homologous recombination with a template sequence is promoted at the site of the DSB, in order to introduce a gene of interest.

In particular embodiments, the Cpf1 CRISPR system may be used as a generic nucleic acid binding protein with fusion to or being operably linked to a functional domain for activation and/or repression of endogenous plant genes. Exemplary functional domains may include but are not limited to translational initiator, translational activator, translational repressor, nucleases, in particular ribonucleases, a spliceosome, beads, a light inducible/controllable domain or a chemically inducible/controllable domain. In some of these embodiments, the Cpf1 protein comprises at least one mutation, such that it has no more than 5% of the activity of the Cpf1 protein not having the at least one mutation; the guide RNA comprises a guide sequence capable of hybridizing to a target sequence.

The methods described herein generally result in the generation of "improved plants" in that they have one or more desirable traits compared to the wildtype plant. In particular embodiments, the plants, plant cells or plant parts obtained are transgenic plants, comprising an exogenous DNA sequence incorporated into the genome of all or part of the cells of the plant. In particular embodiments, non-transgenic genetically modified plants, plant parts or cells are obtained, in that no exogenous DNA sequence is incorporated into the genome of any of the plant cells of the plant. In such embodiments, the improved plants are non-transgenic. Where only the modification of an endogenous gene is ensured and no foreign genes are introduced or maintained in the plant genome, the resulting genetically modified crops contain no foreign genes and can thus basically be considered non-transgenic. The different applications of the Cpf1 CRISPR system for plant genome editing are described more in detail below:

Introduction of One or More Foreign Genes to Confer an Agricultural Trait of Interest The invention provides methods of genome editing or modifying sequences associated with or at a target locus of interest wherein the method comprises introducing a Cpf1 effector protein complex into a plant cell, whereby the Cpf1 effector protein complex effectively functions to integrate a DNA insert, e.g. encoding a foreign gene of interest, into the genome of the plant cell. In preferred embodiments the integration of the DNA insert is facilitated by HR with an exogenously introduced DNA template or repair template. Typically, the exogenously introduced DNA template or repair template is delivered together with the Cpf1 effector protein complex or one component or a polynucleotide vector for expression of a component of the complex.

The Cpf1 CRISPR systems provided herein allow for targeted gene delivery. It has become increasingly clear that the efficiency of expressing a gene of interest is to a great extent determined by the location of integration into the genome. The present methods allow for targeted integration of the foreign gene into a desired location in the genome. The location can be selected based on information of previously generated events or can be selected by methods disclosed elsewhere herein.

In particular embodiments, the methods provided herein include (a) introducing into the cell a Cpf1 CRISPR complex comprising a guide RNA, comprising a direct repeat and a guide sequence, wherein the guide sequence hybridizes to a target sequence that is endogenous to the plant cell; (b) introducing into the plant cell a Cpf1 effector molecule which complexes with the guide RNA when the guide sequence hybridizes to the target sequence and induces a double strand break at or near the sequence to which the guide sequence is targeted; and (c) introducing into the cell a nucleotide sequence encoding an HDR repair template which encodes the gene of interest and which is introduced into the location of the DS break as a result of HDR. In particular embodiments, the step of introducing can include delivering to the plant cell one or more polynucleotides encoding Cpf1 effector protein, the guide RNA and the repair template. In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the Cpf1 effector protein, the guide RNA and the repair template, where the delivering is via *Agrobacterium*. The nucleic acid sequence encoding the Cpf1 effector protein can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the repair template i.e. the gene of interest has been introduced. In particular embodiments, the methods include the step of regenerating a plant from the plant cell. In further embodiments, the methods include cross breeding the plant to obtain a genetically desired plant lineage. Examples of foreign genes encoding a trait of interest are listed below.

Editing of Endogenous Genes to Confer an Agricultural Trait of Interest

The invention provides methods of genome editing or modifying sequences associated with or at a target locus of interest wherein the method comprises introducing a Cpf1 effector protein complex into a plant cell, whereby the Cpf1 complex modifies the expression of an endogenous gene of the plant. This can be achieved in different ways. In particular embodiments, the elimination of expression of an endogenous gene is desirable and the Cpf1 CRISPR complex is used to target and cleave an endogenous gene so as to modify gene expression. In these embodiments, the methods provided herein include (a) introducing into the plant cell a Cpf1 CRISPR complex comprising a guide RNA, comprising a direct repeat and a guide sequence, wherein the guide sequence hybridizes to a target sequence within a gene of interest in the genome of the plant cell; and (b) introducing into the cell a Cpf1 effector protein, which upon binding to the guide RNA comprises a guide sequence that is hybridized to the target sequence, ensures a double strand break at or near the sequence to which the guide sequence is targeted; In particular embodiments, the step of introducing can include delivering to the plant cell one or more polynucleotides encoding Cpf1 effector protein and the guide RNA.

In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the Cpf1 effector protein and the guide RNA, where the delivering is via *Agrobacterium*. The polynucleotide sequence encoding the components of the Cpf1 CRISPR system can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the expression of the gene of interest has been modified. In particular embodiments, the methods include the step of regenerating a plant from the plant cell. In further embodiments, the methods include cross breeding the plant to obtain a genetically desired plant lineage.

In particular embodiments of the methods described above, disease resistant crops are obtained by targeted mutation of disease susceptibility genes or genes encoding negative regulators (e.g. Mlo gene) of plant defense genes. In a particular embodiment, herbicide-tolerant crops are generated by targeted substitution of specific nucleotides in plant genes such as those encoding acetolactate synthase (ALS) and protoporphyrinogen oxidase (PPO). In particular embodiments drought and salt tolerant crops by targeted mutation of genes encoding negative regulators of abiotic stress tolerance, low amylose grains by targeted mutation of Waxy gene, rice or other grains with reduced rancidity by targeted mutation of major lipase genes in aleurone layer, etc. In particular embodiments. A more extensive list of endogenous genes encoding traits of interest are listed below
Modulating Endogenous Genes Using a Cpf1 CRISPR System to Confer an Agricultural Trait of Interest Also provided herein are methods for modulating (i.e. activating or repressing) endogenous gene expression using the Cpf1 protein provided herein. Such methods make use of distinct RNA sequence(s) which are targeted to the plant genome by the Cpf1 complex. More particularly the distinct RNA sequence(s) bind to two or more adaptor proteins (e.g. aptamers) whereby each adaptor protein is associated with one or more functional domains and wherein at least one of the one or more functional domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity; The functional domains are used to modulate expression of an endogenous plant gene so as to obtain the desired trait. Typically, in these embodiments, the Cpf1 effector protein has one or more mutations such that it has no more than 5% of the nuclease activity of the Cpf1 effector protein not having the at least one mutation.

In particular embodiments, the methods provided herein include the steps of (a) introducing into the cell a Cpf1 CRISPR complex comprising a guide RNA, comprising a direct repeat and a guide sequence, wherein the guide sequence hybridizes to a target sequence that is endogenous to the plant cell; (b) introducing into the plant cell a Cpf1 effector molecule which complexes with the guide RNA when the guide sequence hybridizes to the target sequence; and wherein either the guide RNA is modified to comprise a distinct RNA sequence (aptamer) binding to a functional domain and/or the Cpf1 effector protein is modified in that it is linked to a functional domain. In particular embodiments, the step of introducing can include delivering to the plant cell one or more polynucleotides encoding the (modified) Cpf1 effector protein and the (modified) guide RNA. The details the components of the Cpf1 CRISPR system for use in these methods are described elsewhere herein.

In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the Cpf1 effector protein and the guide RNA, where the delivering is via *Agrobacterium*. The nucleic acid sequence encoding the one or more components of the Cpf1 CRISPR system can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the expression of the gene of interest has been modified. In particular embodiments, the methods include the step of regenerating a plant from the plant cell. In further embodiments, the methods include cross breeding the plant to obtain a genetically desired plant lineage. A more extensive list of endogenous genes encoding traits of interest are listed below.
Use of Cpf1 to Modify Polyploid Plants Many plants are polyploid, which means they carry duplicate copies of their genomes-sometimes as many as six, as in wheat. The methods according to the present invention, which make use of the Cpf1 CRISPR effector protein can be "multiplexed" to affect all copies of a gene, or to target dozens of genes at once. For instance, in particular embodiments, the methods of the present invention are used to simultaneously ensure a loss of function mutation in different genes responsible for suppressing defenses against a disease. In particular embodiments, the methods of the present invention are used to simultaneously suppress the expression of the TaMLO-A1, TaMLO-B1 and TaMLO-D1 nucleic acid sequence in a wheat plant cell and regenerating a wheat plant therefrom, in order to ensure that the wheat plant is resistant to powdery mildew (see also WO2015109752).
Exemplary Genes Conferring Agronomic Traits As described herein above, in particular embodiments, the invention encompasses the use of the Cpf1 CRISPR system as described herein for the insertion of a DNA of interest, including one or more plant expressible gene(s). In further particular embodiments, the invention encompasses methods and tools using the Cpf1 system as described herein for partial or complete deletion of one or more plant expressed gene(s). In other further particular embodiments, the invention encompasses methods and tools using the Cpf1 system as described herein to ensure modification of one or more plant-expressed genes by mutation, substitution, insertion of one of more nucleotides. In other particular embodiments, the invention encompasses the use of Cpf1 CRISPR system as described herein to ensure modification of expression of one or more plant-expressed genes by specific modification of one or more of the regulatory elements directing expression of said genes.

In particular embodiments, the invention encompasses methods which involve the introduction of exogenous genes and/or the targeting of endogenous genes and their regulatory elements, such as listed below:
Genes that Confer Resistance to Pests or Diseases:

Plant disease resistance genes. A plant can be transformed with cloned resistance genes to engineer plants that are resistant to specific pathogen strains. See, e.g., Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (Arabidopsmay be RSP2 gene for resistance to *Pseudomonas syringae*). A plant gene that is upregulated or down regulated during pathogen infection can be engineered for pathogen resistance. See, e.g., Thomazella et al., bioRxiv 064824; doi: https://doi.org/10.1101/064824 Epub. Jul. 23, 2016 (tomato plants with deletions in the SlDMR6-1 which is normally upregulated during pathogen infection).

Genes conferring resistance to a pest, such as soybean cyst nematode. See e.g., PCT Application WO 96/30517; PCT Application WO 93/19181.

*Bacillus thuringiensis* proteins see, e.g., Geiser et al., Gene 48:109 (1986).

Lectins, see, for example, Van Damme et al., Plant Molec. Biol. 24:25 (1994.

Vitamin-binding protein, such as avidin, see PCT application US93/06487, teaching the use of avidin and avidin homologues as larvicides against insect pests.

Enzyme inhibitors such as protease or proteinase inhibitors or amylase inhibitors. See, e.g., Abe et al., J. Biol. Chem. 262:16793 (1987), Huub et al., Plant Molec. Biol. 21:985 (1993)), Sumitani et al., Biosci. Biotech. Biochem. 57:1243 (1993) and U.S. Pat. No. 5,494,813.

Insect-specific hormones or pheromones such as ecdysteroid or juvenile hormone, a variant thereof, a mimetic based thereon, or an antagonist or agonist thereof. See, for example Hammock et al., Nature 344:458 (1990).

Insect-specific peptides or neuropeptides which, upon expression, disrupts the physiology of the affected pest. For example, Regan, J. Biol. Chem. 269:9 (1994) and Pratt et al., Biochem. Biophys. Res. Comm. 163:1243 (1989). See also U.S. Pat. No. 5,266,317.

Insect-specific venom produced in nature by a snake, a wasp, or any other organism. For example, see Pang et al., Gene 116: 165 (1992).

Enzymes responsible for a hyperaccumulation of a monoterpene, a sesquiterpene, a steroid, hydroxamic acid, a phenylpropanoid derivative or another nonprotein molecule with insecticidal activity.

Enzymes involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO93/02197, Kramer et al., Insect Biochem. Molec. Biol. 23:691 (1993) and Kawalleck et al., Plant Molec. Biol. 21:673 (1993).

Molecules that stimulates signal transduction. For example, see Botella et al., Plant Molec. Biol. 24:757 (1994), and Griess et al., Plant Physiol. 104:1467 (1994).

Viral-invasive proteins or a complex toxin derived therefrom. See Beachy et al., Ann. rev. Phytopathol. 28:451 (1990).

Developmental-arrestive proteins produced in nature by a pathogen or a parasite. See Lamb et al., Bio/Technology 10:1436 (1992) and Toubart et al., Plant J. 2:367 (1992).

A developmental-arrestive protein produced in nature by a plant. For example, Logemann et al., Bio/Technology 10:305 (1992).

In plants, pathogens are often host-specific. For example, some *Fusarium* species will cause tomato wilt but attacks only tomato, and other *Fusarium* species attack only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible or there can be partial resistance against all races of a pathogen, typically controlled by many genes and/or also complete resistance to some races of a pathogen but not to other races. Such resistance is typically controlled by a few genes. Using methods and components of the CRISP-cpf1 system, a new tool now exists to induce specific mutations in anticipation hereon. Accordingly, one can analyze the genome of sources of resistance genes, and in plants having desired characteristics or traits, use the method and components of the Cpf1 CRISPR system to induce the rise of resistance genes. The present systems can do so with more precision than previous mutagenic agents and hence accelerate and improve plant breeding programs.

Genes Involved in Plant Diseases

In some embodiments, the gene(s) that is/are modified, inserted, or deleted can be any of those involved in development or pathology of a plant disease. Such diseases and/or genes can be any of those described and discussed herein and/or those listed in WO 2012046247.

Rice diseases: *Magnaporthe grisea, Cochliobolus miyabeanus, Rhizoctonia solani, Gibberella fujikuroi*; Wheat diseases: *Erysiphe graminis, Fusarium graminearum, F. avenaceum, F. culmorum, Microdochium nivale, Puccinia striiformis, P. graminis, P. recondita, Micronectriella nivale, Typhula* sp., *Ustilago tritici, Tilletia caries, Pseudocercosporella herpotrichoides, Mycosphaerella graminicola, Stagonospora nodorum, Pyrenophora tritici-repentis*; Barley diseases: *Erysiphe graminis, Fusarium graminearum, F. avenaceum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea, Rhizoctonia solani*; Maize diseases: *Ustilago maydis, Cochliobolus heterostrophus, Gloeocercospora sorghi, Puccinia polysora, Cercospora zeae-maydis, Rhizoctonia solani;*

Citrus diseases: *Diaporthe citri, Elsinoe fawcetti, Penicillium digitatum, P. italicum, Phytophthora parasitica, Phytophthora citrophthora*; Apple diseases: *Monilinia mali, Valsa ceratosperma, Podosphaera leucotricha, Alternaria alternata* apple pathotype, *Venturia inaequalis, Colletotrichum acutatum, Phytophtora cactorum;*

Pear diseases: *Venturia nashicola, V. pirina, Alternaria alternata* Japanese pear pathotype, *Gymnosporangium haraeanum, Phytophtora cactorum;*

Peach diseases: *Monilinia fructicola, Cladosporium carpophilum, Phomopsis* sp.;

Grape diseases: *Elsinoe ampelina, Glomerella cingulata, Uninula necator, Phakopsora ampelopsidis, Guignardia bidwellii, Plasmopara viticola;*

Persimmon diseases: *Gloesporium kaki, Cercospora kaki, Mycosphaerela nawae;*

Gourd diseases: *Colletotrichum lagenarium, Sphaerotheca fuliginea, Mycosphaerella melonis, Fusarium oxysporum, Pseudoperonospora cubensis, Phytophthora* sp., *Pythium* sp.;

Tomato diseases: *Alternaria solani, Cladosporium fulvum, Phytophthora infestans*; *Pseudomonas syringae* pv. Tomato; *Phytophthora capsici*; *Xanthomonas*;

Eggplant diseases: *Phomopsis vexans, Erysiphe cichoracearum*; Brassicaceous vegetable diseases: *Alternaria japonica, Cercosporella brassicae, Plasmodiophora brassicae, Peronospora parasitica;*

Welsh onion diseases: *Puccinia allii, Peronospora destructor;*

Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani, Corynespora casiicola, Sclerotinia sclerotiorum;*

Kidney bean diseases: *Colletrichum lindemthianum;*

Peanut diseases: *Cercospora personata, Cercospora arachidicola, Sclerotium rolfsii;*

Pea diseases pea: *Erysiphe pisi;*

Potato diseases: *Alternaria solani, Phytophthora infestans, Phytophthora erythroseptica, Spongospora subterranean,* f. sp. Subterranean;

Strawberry diseases: *Sphaerotheca humuli, Glomerella cingulata;*

Tea diseases: *Exobasidium reticulatum, Elsinoe leucospila, Pestalotiopsis* sp., *Colletotrichum theae-sinensis;*

Tobacco diseases: *Alternaria longipes, Erysiphe cichoracearum, Colletotrichum tabacum, Peronospora tabacina, Phytophthora nicotianae;*

Rapeseed diseases: *Sclerotinia sclerotiorum, Rhizoctonia solani;*

Cotton diseases: *Rhizoctonia solani;*

Beet diseases: *Cercospora beticola, Thanatephorus cucumeris, Thanatephorus cucumeris, Aphanomyces cochlioides;*

Rose diseases: *Diplocarpon rosae, Sphaerotheca pannosa, Peronospora sparsa;*

Diseases of chrysanthemum and asteraceae: *Bremia lactuca, Septoria chrysanthemi-indici, Puccinia horiana;*

Diseases of various plants: *Pythium aphanidermatum, Pythium debarianum, Pythium graminicola, Pythium irregulare, Pythium ultimum, Botrytis cinerea, Sclerotinia sclerotiorum;*

Radish diseases: *Alternaria brassicicola;*

Zoysia diseases: *Sclerotinia homeocarpa, Rhizoctonia solani;*

Banana diseases: *Mycosphaerella fijiensis, Mycosphaerella musicola;*

Sunflower diseases: *Plasmopara halstedii;*

Seed diseases or diseases in the initial stage of growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Rhoma* spp., *Rhizoctonia* spp., *Diplodia* spp., or the like;

Virus diseases of various plants mediated by *Polymixa* spp., *Olpidium* spp., or the like.

Examples of genes that confer resistance to herbicides:

Resistance to herbicides that inhibit the growing point or meristem, such as an imidazolinone or a sulfonylurea, for example, by Lee et al., EMBO J. 7:1241 (1988), and Miki et al., Theor. Appl. Genet. 80:449 (1990), respectively.

Glyphosate tolerance (resistance conferred by, e.g., mutant 5-enolpyruvylshikimate-3-phosphate synthase (EPSPs) genes, aroA genes and glyphosate acetyl transferase (GAT) genes, respectively), or resistance to other phosphono compounds such as by glufosinate (phosphinothricin acetyl transferase (PAT) genes from *Streptomyces* species, including *Streptomyces hygroscopicus* and *Streptomyces viridichromogenes*), and to pyridinoxy or phenoxy proprionic acids and cyclohexones by ACCase inhibitor-encoding genes. See, for example, U.S. Pat. Nos. 4,940,835 and 6,248,876, 4,769,061, EP No. 0 333 033 and U.S. Pat. No. 4,975,374. See also EP No. 0242246, DeGreef et al., Bio/Technology 7:61 (1989), Marshall et al., Theor. Appl. Genet. 83:435 (1992), WO 2005012515 to Castle et. al. and WO 2005/107437.

Resistance to herbicides that inhibit photosynthesis, such as a triazine (psbA and gs+ genes) or a benzonitrile (nitrilase gene), and glutathione S-transferase in Przibila et al., Plant Cell 3:169 (1991), U.S. Pat. No. 4,810,648, and Hayes et al., Biochem. J. 285: 173 (1992).

Genes encoding Enzymes detoxifying the herbicide or a mutant glutamine synthase enzyme that is resistant to inhibition, e.g. U.S. patent application Ser. No. 11/760,602. Or a detoxifying enzyme is an enzyme encoding a phosphinothricin acetyltransferase (such as the bar or pat protein from *Streptomyces* species). Phosphinothricin acetyltransferases are, for example, described in U.S. Pat. Nos. 5,561,236; 5,648,477; 5,646,024; 5,273,894; 5,637,489; 5,276,268; 5,739,082; 5,908,810 and 7,112,665.

Hydroxyphenylpyruvatedioxygenases (HPPD) inhibitors, i.e., naturally occurring HPPD resistant enzymes, or genes encoding a mutated or chimeric HPPD enzyme as described in WO 96/38567, WO 99/24585, and WO 99/24586, WO 2009/144079, WO 2002/046387, or U.S. Pat. No. 6,768,044.

Genes Involved in Abiotic Stress Tolerance

In some embodiments, the gene(s) that are deleted, inserted, and/or otherwise modulated can be involved in abiotic stress tolerance in plants. Such genes can be any one or more of the following.

Transgene capable of reducing the expression and/or the activity of poly(ADP-ribose) polymerase (PARP) gene in the plant cells or plants as described in WO 00/04173 or, WO 2006/045633.

Transgenes capable of reducing the expression and/or the activity of the PARG encoding genes of the plants or plants cells, as described e.g. in WO 2004/090140.

Transgenes coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphorybosyltransferase as described e.g. in EP 04077624.7, WO 2006/133827, PCT/EP07/002433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, the production of alpha-1,6 branched alpha-1,4-glucans, as disclosed in WO 00/73422, the production of alternan, as disclosed in e.g. WO 00/47727, WO 00/73422, EP 06077301.7, U.S. Pat. No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

Genes that improve drought resistance. For example, WO 2013/122472 discloses that the absence or reduced level of functional Ubiquitin Protein Ligase protein (UPL) protein, more specifically, UPL3, leads to a decreased need for water or improved resistance to drought of said plant. Other examples of transgenic plants with increased drought tolerance are disclosed in, for example, US 2009/0144850, US 2007/0266453, and WO 2002/083911. US2009/0144850 describes a plant displaying a drought tolerance phenotype due to altered expression of a DR02 nucleic acid. US 2007/0266453 describes a plant displaying a drought tolerance phenotype due to altered expression of a DR03 nucleic acid and WO 2002/083911 describes a plant having an increased tolerance to drought stress due to a reduced activity of an ABC transporter which is expressed in guard cells. Another example is the work by Kasuga and co-authors (1999), who describe that overexpression of cDNA encoding DREB1 A in transgenic plants activated the expression of many stress tolerance genes under normal growing conditions and resulted in improved tolerance to drought, salt loading, and freezing. However, the expression of DREB1A also resulted in severe growth retardation under normal growing conditions (Kasuga (1999) Nat Biotechnol 17(3) 287-291).

In further particular embodiments, crop plants can be improved by influencing specific plant traits. For example, by developing pesticide-resistant plants, improving disease resistance in plants, improving plant insect and nematode resistance, improving plant resistance against parasitic weeds, improving plant drought tolerance, improving plant nutritional value, improving plant stress tolerance, avoiding self-pollination, plant forage digestibility biomass, grain yield etc. A few specific non-limiting examples are provided hereinbelow.

In addition to targeted mutation of single genes, Cpf1CRISPR complexes can be designed to allow targeted mutation of multiple genes, deletion of chromosomal fragment, site-specific integration of transgene, site-directed mutagenesis in vivo, and precise gene replacement or allele swapping in plants. Therefore, the methods described herein have broad applications in gene discovery and validation, mutational and cisgenic breeding, and hybrid breeding. These applications facilitate the production of a new generation of genetically modified crops with various improved agronomic traits such as herbicide resistance, disease resistance, abiotic stress tolerance, high yield, and superior quality.

Methods of Making Sterile Plants Using Cpf1-CRISPR Systems

Hybrid plants typically have advantageous agronomic traits compared to inbred plants. However, for self-pollinating plants, the generation of hybrids can be challenging. In different plant types, genes have been identified which are important for plant fertility, more particularly male fertility. For instance, in maize, at least two genes have been identified which are important in fertility (Amitabh Mohanty International Conference on New Plant Breeding Molecular Technologies Technology Development And Regulation, Oct. 9-10, 2014, Jaipur, India; Svitashev et al. Plant Physiol. 2015 October; 169(2):931-45; Djukanovic et al. Plant J. 2013 December; 76(5):888-99). The methods provided herein can be used to target genes required for male fertility so as to generate male sterile plants which can easily be crossed to generate hybrids. In particular embodiments, the Cpf1 CRISPR system provided herein is used for targeted mutagenesis of the cytochrome P450-like gene (MS26) or the meganuclease gene (MS45) thereby conferring male sterility to the maize plant. Maize plants which are as such genetically altered can be used in hybrid breeding programs.

Increasing the Fertility Stage in Plants Using a CRISPR-Cas System

In particular embodiments, the methods provided herein are used to prolong the fertility stage of a plant such as of a rice plant. For instance, a rice fertility stage gene such as Ehd3 can be targeted in order to generate a mutation in the gene and plantlets can be selected for a prolonged regeneration plant fertility stage (as described in CN 104004782). In some embodiments, the methods include using one or more CRISPR-Cas systems described herein to increase the fertility stage in a plant.

Generating Genetic Variation Using a CRISPR-Cas System in Plants

The availability of wild germplasm and genetic variations in crop plants is the key to crop improvement programs, but the available diversity in germplasms from crop plants is limited. The present invention envisages methods for generating a diversity of genetic variations in a germplasm of interest. In this application of the Cpf1 CRISPR system a library of guide RNAs targeting different locations in the plant genome is provided and is introduced into plant cells together with the Cpf1 effector protein. In this way a collection of genome-scale point mutations and gene knockouts can be generated. In particular embodiments, the methods comprise generating a plant part or plant from the cells so obtained and screening the cells for a trait of interest. The target genes can include both coding and non-coding regions. In particular embodiments, the trait is stress tolerance, and the method is a method for the generation of stress-tolerant crop varieties Modulating Fruit-Ripening Using a CRISPR-Cas System Ripening is a normal phase in the maturation process of fruits and vegetables. Only a few days after it starts it renders a fruit or vegetable inedible. This process brings significant losses to both farmers and consumers. In particular embodiments, the methods of the present invention are used to reduce ethylene production. This is ensured by ensuring one or more of the following: a. Suppression of ACC synthase gene expression. ACC (1-aminocyclopropane-1-carboxylic acid) synthase is the enzyme responsible for the conversion of S-adenosylmethionine (SAM) to ACC; the second to the last step in ethylene biosynthesis. Enzyme expression is hindered when an antisense ("mirror-image") or truncated copy of the synthase gene is inserted into the plant's genome; b. Insertion of the ACC deaminase gene. The gene coding for the enzyme is obtained from *Pseudomonas chlororaphis*, a common nonpathogenic soil bacterium. It converts ACC to a different compound thereby reducing the amount of ACC available for ethylene production; c. Insertion of the SAM hydrolase gene. This approach is similar to ACC deaminase wherein ethylene production is hindered when the amount of its precursor metabolite is reduced; in this case SAM is converted to homoserine. The gene coding for the enzyme is obtained from *E. coli* T3 bacteriophage and d. Suppression of ACC oxidase gene expression. ACC oxidase is the enzyme which catalyzes the oxidation of ACC to ethylene, the last step in the ethylene biosynthetic pathway. Using the methods described herein, down regulation of the ACC oxidase gene results in the suppression of ethylene production, thereby delaying fruit ripening. In particular embodiments, additionally or alternatively to the modifications described above, the methods described herein are used to modify ethylene receptors, so as to interfere with ethylene signals obtained by the fruit. In particular embodiments, expression of the ETR1 gene, encoding an ethylene binding protein is modified, more particularly suppressed. In particular embodiments, additionally or alternatively to the modifications described above, the methods described herein are used to modify expression of the gene encoding Polygalacturonase (PG), which is the enzyme responsible for the breakdown of pectin, the substance that maintains the integrity of plant cell walls. Pectin breakdown occurs at the start of the ripening process resulting in the softening of the fruit. Accordingly, in particular embodiments, the methods described herein are used to introduce a mutation in the PG gene or to suppress activation of the PG gene in order to reduce the amount of PG enzyme produced thereby delaying pectin degradation.

In particular embodiments, the methods comprise the use of the Cpf1 CRISPR system to ensure one or more modifications of the genome of a plant cell such as described above, and regenerating a plant therefrom. In particular embodiments, the plant is a tomato plant.

Increasing Storage Life of Plants Using a CRISPR-Cas System

In particular embodiments, the methods of the present invention are used to modify genes involved in the production of compounds which affect storage life of the plant or plant part. More particularly, the modification is in a gene that prevents the accumulation of reducing sugars in potato tubers. Upon high-temperature processing, these reducing sugars react with free amino acids, resulting in brown, bitter-tasting products and elevated levels of acrylamide, which is a potential carcinogen. In particular embodiments, the methods provided herein are used to reduce or inhibit expression of the vacuolar invertase gene (VInv), which encodes a protein that breaks down sucrose to glucose and fructose (Clasen et al. DOI: 10.1111/pbi.12370).

Generating Functional Foods using a CRISPR-Cas System

In particular embodiments the Cpf1 CRISPR system is used to produce nutritionally improved agricultural crops. In particular embodiments, the methods provided herein are adapted to generate "functional foods", i.e. a modified food or food ingredient that may provide a health benefit beyond the traditional nutrients it contains and or "nutraceutical", i.e. substances that may be considered a food or part of a food and provides health benefits, including the prevention and treatment of disease. In particular embodiments, the nutraceutical is useful in the prevention and/or treatment of one or more of cancer, diabetes, cardiovascular disease, and hypertension.

Examples of nutritionally improved crops include (Newell-McGloughlin, Plant Physiology, July 2008, Vol. 147, pp. 939-953):

Modified protein quality, content and/or amino acid composition, such as have been described for Bahiagrass (Luciani et al. 2005, Florida Genetics Conference Poster), Canola (Roesler et al., 1997, Plant Physiol 113 75-81), Maize (Cromwell et al, 1967, 1969 J Anim Sci 26 1325-1331, O'Quin et al. 2000 J Anim Sci 78 2144-2149, Yang et al. 2002, Transgenic Res 11 11-20, Young et al. 2004, Plant J 38 910-922), Potato (Yu J and Ao, 1997 Acta Bot Sin 39 329-334; Chakraborty et al. 2000, Proc Natl Acad Sci USA 97 3724-3729; L$^1$ et al. 2001) Chin Sci Bull 46 482-484, Rice (Katsube et al. 1999, Plant Physiol 120 1063-1074), Soybean (Dinkins et al. 2001, Rapp 2002, In Vitro Cell Dev Biol Plant 37 742-747), Sweet Potato (Egnin and Prakash 1997, In Vitro Cell Dev Biol 33 52A).

Essential amino acid content, such as has been described for Canola (Falco et al. 1995, Bio/Technology 13 577-582), Lupin (White et al. 2001, J Sci Food Agric 81 147-154), Maize (Lai and Messing, 2002, Agbios 2008 GM crop database (Mar. 11, 2008)), Potato (Zeh et al. 2001, Plant Physiol 127 792-802), Sorghum (Zhao et al. 2003, Kluwer Academic Publishers, Dordrecht, The Netherlands, pp 413-416), Soybean (Falco et al. 1995 Bio/Technology 13 577-582; Galili et al. 2002 Crit Rev Plant Sci 21 167-204).

Oils and Fatty acids such as for Canola (Dehesh et al. (1996) Plant J 9 167-172 [PubMed]; Del Vecchio (1996) INFORM International News on Fats, Oils and Related Materials 7 230-243; Roesler et al. (1997) Plant Physiol 113 75-81 [PMC free article] [PubMed]; Froman and Ursin (2002, 2003) Abstracts of Papers of the American Chemical Society 223 U35; James et al. (2003) Am J Clin Nutr 77 1140-1145 [PubMed]; Agbios (2008, above); coton (Chapman et al. (2001). J Am Oil Chem Soc 78 941-947; Liu et al. (2002) J Am Coll Nutr 21 205S-211S [PubMed]; O'Neill (2007) Australian Life Scientist. http://www.biotechnews-.com.au/index.php/id;866694817;fp;4;fpid;2 (Jun. 17, 2008), Linseed (Abbadi et al., 2004, Plant Cell 16: 2734-2748), Maize (Young et al., 2004, Plant J 38 910-922), oil palm (Jalani et al. 1997, J Am Oil Chem Soc 74 1451-1455; Parveez, 2003, AgBiotechNet 113 1-8), Rice (Anai et al., 2003, Plant Cell Rep 21 988-992), Soybean (Reddy and Thomas, 1996, Nat Biotechnol 14 639-642; Kinney and Kwolton, 1998, Blackie Academic and Professional, London, pp 193-213), Sunflower (Arcadia, Biosciences 2008)

Carbohydrates, such as Fructans described for Chicory (Smeekens (1997) Trends Plant Sci 2 286-287, Sprenger et al. (1997) FEBS Lett 400 355-358, Sevenier et al. (1998) Nat Biotechnol 16 843-846), Maize (Caimi et al. (1996) Plant Physiol 110 355-363), Potato (Hellwege et al., 1997 Plant J 12 1057-1065), Sugar Beet (Smeekens et al. 1997, above), Inulin, such as described for Potato (Hellewege et al. 2000, Proc Natl Acad Sci USA 97 8699-8704), Starch, such as described for Rice (Schwall et al. (2000) Nat Biotechnol 18 551-554, Chiang et al. (2005) Mol Breed 15 125-143), Vitamins and carotenoids, such as described for Canola (Shintani and DellaPenna (1998) Science 282 2098-2100), Maize (Rocheford et al. (2002). J Am Coll Nutr 21 191S-198S, Cahoon et al. (2003) Nat Biotechnol 21 1082-1087, Chen et al. (2003) Proc Natl Acad Sci USA 100 3525-3530), Mustardseed (Shewmaker et al. (1999) Plant J 20 401-412, Potato (Ducreux et al., 2005, J Exp Bot 56 81-89), Rice (Ye et al. (2000) Science 287 303-305, Strawberry (Agius et al. (2003), Nat Biotechnol 21 177-181), Tomato (Rosati et al. (2000) Plant J 24 413-419, Fraser et al. (2001) J Sci Food Agric 81 822-827, Mehta et al. (2002) Nat Biotechnol 20 613-618, Diaz de la Garza et al. (2004) Proc Natl Acad Sci USA 101 13720-13725, Enfissi et al. (2005) Plant Biotechnol J 3 17-27, DellaPenna (2007) Proc Natl Acad Sci USA 104 3675-3676.

Functional secondary metabolites, such as described for Apple (stilbenes, Szankowski et al. (2003) Plant Cell Rep 22: 141-149), Alfalfa (resveratrol, Hipskind and Paiva (2000) Mol Plant Microbe Interact 13 551-562), Kiwi (resveratrol, Kobayashi et al. (2000) Plant Cell Rep 19 904-910), Maize and Soybean (flavonoids, Yu et al. (2000) Plant Physiol 124 781-794), Potato (anthocyanin and alkaloid glycoside, Lukaszewicz et al. (2004) J Agric Food Chem 52 1526-1533), Rice (flavonoids & resveratrol, Stark-Lorenzen et al. (1997) Plant Cell Rep 16 668-673, Shin et al. (2006) Plant Biotechnol J 4 303-315), Tomato (+resveratrol, chlorogenic acid, flavonoids, stilbene; Rosati et al. (2000) above, Muir et al. (2001) Nature 19 470-474, Niggeweg et al. (2004) Nat Biotechnol 22 746-754, Giovinazzo et al. (2005) Plant Biotechnol J 3 57-69), wheat (caffeic and ferulic acids, resveratrol; United Press International (2002)); and Mineral availabilities such as described for Alfalfa (phytase, Austin-Phillips et al. (1999) http://www.molecularfarming.com/nonmedical.html), Lettuce (iron, Goto et al. (2000) Theor Appl Genet 100 658-664), Rice (iron, Lucca et al. (2002) J Am Coll Nutr 21 184S-190S), Maize, Soybean and wheat (phytase, Drakakaki et al. (2005) Plant Mol Biol 59 869-880, Denbow et al. (1998) Poult Sci 77 878-881, Brinch-Pedersen et al. (2000) Mol Breed 6 195-206).

In particular embodiments, the value-added trait is related to the envisaged health benefits of the compounds present in the plant. For instance, in particular embodiments, the value-added crop is obtained by applying the methods of the invention to ensure the modification of or induce/increase the synthesis of one or more of the following compounds:

Carotenoids, such as α-Carotene present in carrots which neutralizes free radicals that may cause damage to cells or β-Carotene present in various fruits and vegetables which neutralizes free radicals, Lutein, which is present in green vegetables and may contribute to maintenance of healthy vision, Lycopene, which is present in tomato and tomato products and can reduce the risk of prostate cancer, Zeaxanthin, present in citrus and maize, which can contribute to maintenance of healthy vision, Dietary fiber, such as insoluble fiber present in wheat bran, which may reduce the risk of breast and/or colon cancer and β-Glucan, which is present in oat, soluble fiber present in Psyllium and whole cereal grains, which may reduce the risk of cardiovascular disease (CVD), Fatty acids, such as ω-3 fatty acids, which may reduce the risk of CVD and improve mental and visual functions, conjugated linoleic acid, which may improve body composition, may decrease risk of certain cancers, and GLA which may reduce inflammation risk of cancer and CVD, may improve body composition, Flavonoids, such as Hydroxycinnamates, present in wheat which have Antioxidant-like activities, may reduce risk of degenerative diseases, flavonols, catechins and tannins present in fruits and vegetables which neutralize free radicals and may reduce risk of cancer, Glucosinolates, indoles, isothiocyanates, such as Sulforaphane, present in Cruciferous vegetables (broccoli, kale), horseradish, which neutralize free radicals, may reduce risk of cancer, Phenolics, such as stilbenes present in grape which May reduce risk of degenerative diseases, heart disease, and cancer, may have longevity effect and caffeic acid and ferulic acid present in vegetables and citrus which have Antioxidant-like activities, may reduce risk of degenerative diseases, heart disease, and eye disease, and epicatechin present in cacao which has Antioxidant-like activities, may reduce risk of degenerative diseases and heart disease, Plant stanols/sterols present in maize, soy, wheat and wooden oils, which may reduce risk of coronary heart disease by lowering blood cholesterol levels, Fructans, inulins, fructo-oligosaccharides, which is present in Jerusalem artichoke, shallot, onion powder which may improve gastrointestinal health, Saponins, which are present in soybean, which may lower LDL cholesterol, Soybean protein, which may reduce risk of heart disease, Phytoestrogens, such as isoflavones present in soybean, which may reduce menopause symptoms, such as hot flashes, may reduce osteoporosis and CVD and lignans present in flax, rye and vegetables, which may protect against heart disease and some cancers, may lower LDL cholesterol, and/or lower total cholesterol, Sulfides and thiols such as diallyl sulphide present in onion, garlic, olive, leek and scallion and Allyl methyl trisulfide, dithiolthiones, which are present in cruciferous vegetables which, may lower LDL cholesterol and/or can help to maintain healthy immune system, Tannins, such as proanthocyanins, present in cranberry, cocoa, which may improve urinary tract health and/or may reduce risk of CVD and high blood pressure.

In addition, the methods of the present invention also envisage modifying protein/starch functionality, shelf life, taste/aesthetics, fiber quality, and allergen, antinutrient, and toxin reduction traits.

Accordingly, the invention encompasses methods for producing plants with nutritional added value, said methods comprising introducing into a plant cell a gene encoding an enzyme involved in the production of a component of added nutritional value using the Cpf1 CRISPR system as described herein and regenerating a plant from said plant cell, said plant characterized in an increase expression of said component of added nutritional value. In particular embodiments, the Cpf1 CRISPR system is used to modify the endogenous synthesis of these compounds indirectly, e.g. by modifying one or more transcription factors that controls the metabolism of this compound. Methods for introducing a gene of interest into a plant cell and/or modifying an endogenous gene using the Cpf1 CRISPR system are described herein above.

Some specific examples of modifications in plants that have been modified to confer value-added traits are: plants with modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992). Another example involves decreasing phytate content, for example by cloning and then reintroducing DNA associated with the single allele which may be responsible for maize mutants characterized by low levels of phytic acid. See Raboy et al, Maydica 35:383 (1990).

Similarly, expression of the maize (*Zea mays*) Tfs C1 and R, which regulate the production of flavonoids in maize aleurone layers under the control of a strong promoter, resulted in a high accumulation rate of anthocyanins in *Arabidopsis* (*Arabidopsis thaliana*), presumably by activating the entire pathway (Bruce et al., 2000, Plant Cell 12:65-80). DellaPenna (Welsch et al., 2007 Annu Rev Plant Biol 57: 711-738) found that Tf RAP2.2 and its interacting partner SINAT2 increased carotenogenesis in *Arabidopsis* leaves. Expressing the Tf Dof1 induced the up-regulation of genes encoding enzymes for carbon skeleton production, a marked increase of amino acid content, and a reduction of the Glc level in transgenic *Arabidopsis* (Yanagisawa, 2004 Plant Cell Physiol 45: 386-391), and the DOF Tf AtDof1.1

(OBP2) up-regulated all steps in the glucosinolate biosynthetic pathway in *Arabidopsis* (Skirycz et al., 2006 Plant J 47: 10-24).

Reducing Allergen(s) in Plants Using a CRISPR-Cas System

In particular embodiments, the methods provided herein are used to generate plants with a reduced level of allergens, making them safer for the consumer. In particular embodiments, the methods comprise modifying expression of one or more genes responsible for the production of plant allergens. For instance, in particular embodiments, the methods comprise down-regulating expression of a Lol p5 gene in a plant cell, such as a ryegrass plant cell and regenerating a plant therefrom so as to reduce allergenicity of the pollen of said plant (Bhalla et al. 1999, Proc. Natl. Acad. Sci. USA Vol. 96: 11676-11680).

Peanut allergies and allergies to legumes generally are a real and serious health concern. The Cpf1 effector protein system of the present invention can be used to identify and then edit or silence genes encoding allergenic proteins of such legumes. Without limitation as to such genes and proteins, Nicolaou et al. identifies allergenic proteins in peanuts, soybeans, lentils, peas, lupin, green beans, and mung beans. See, Nicolaou et al., Current Opinion in Allergy and Clinical Immunology 2011; 11(3):222).

Methods of Screening a Plant Genome Using a CRISPR-Cas System

The methods provided herein further allow the identification of genes of value encoding enzymes involved in the production of a component of added nutritional value or generally genes affecting agronomic traits of interest, across species, phyla, and plant kingdom. By selectively targeting e.g., genes encoding enzymes of metabolic pathways in plants using the Cpf1 CRISPR system as described herein, the genes responsible for certain nutritional aspects of a plant can be identified. Similarly, by selectively targeting genes which may affect a desirable agronomic trait, the relevant genes can be identified. Accordingly, the present invention encompasses screening methods for genes encoding enzymes involved in the production of compounds with a particular nutritional value and/or agronomic traits.

Further Applications of the Cpf1 CRISPR System in Non-Animal Organisms

Use of Cpf1 CRISPR Systems in Biofuel Production

The term "biofuel" as used herein is an alternative fuel made from plant and plant-derived resources. Renewable biofuels can be extracted from organic matter whose energy has been obtained through a process of carbon fixation or are made through the use or conversion of biomass. This biomass can be used directly for biofuels or can be converted to convenient energy containing substances by thermal conversion, chemical conversion, and biochemical conversion. This biomass conversion can result in fuel in solid, liquid, or gas form. There are two types of biofuels: bioethanol and biodiesel. Bioethanol is mainly produced by the sugar fermentation process of cellulose (starch), which is mostly derived from maize and sugar cane. Biodiesel on the other hand is mainly produced from oil crops such as rapeseed, palm, and soybean. Biofuels are used mainly for transportation.

Enhancing Plant Properties for Biofuel Production

In particular embodiments, the methods using the Cpf1 CRISPR system as described herein are used to alter the properties of the cell wall in order to facilitate access by key hydrolysing agents for a more efficient release of sugars for fermentation. In particular embodiments, the biosynthesis of cellulose and/or lignin are modified. Cellulose is the major component of the cell wall. The biosynthesis of cellulose and lignin are co-regulated. By reducing the proportion of lignin in a plant the proportion of cellulose can be increased. In particular embodiments, the methods described herein are used to downregulate lignin biosynthesis in the plant so as to increase fermentable carbohydrates. More particularly, the methods described herein are used to downregulate at least a first lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH) as disclosed in WO 2008064289 A2.

In particular embodiments, the methods described herein are used to produce plant mass that produces lower levels of acetic acid during fermentation (see also WO 2010096488). More particularly, the methods disclosed herein are used to generate mutations in homologs to CaslL to reduce polysaccharide acetylation.

Modifying Yeast for Biofuel Production

In particular embodiments, the Cpf1 enzyme provided herein is used for bioethanol production by recombinant micro-organisms. For instance, Cpf1 can be used to engineer micro-organisms, such as yeast, to generate biofuel or biopolymers from fermentable sugars and optionally to be able to degrade plant-derived lignocellulose derived from agricultural waste as a source of fermentable sugars. More particularly, the invention provides methods whereby the Cpf1 CRISPR complex is used to introduce foreign genes required for biofuel production into micro-organisms and/or to modify endogenous genes why may interfere with the biofuel synthesis. More particularly the methods involve introducing into a micro-organism such as a yeast one or more nucleotide sequence encoding enzymes involved in the conversion of pyruvate to ethanol or another product of interest. In particular embodiments the methods ensure the introduction of one or more enzymes which allows the micro-organism to degrade cellulose, such as a cellulase. In yet further embodiments, the Cpf1 CRISPR complex is used to modify endogenous metabolic pathways which compete with the biofuel production pathway.

Accordingly, in more particular embodiments, the methods described herein are used to modify a micro-organism as follows:

to introduce at least one heterologous nucleic acid or increase expression of at least one endogenous nucleic acid encoding a plant cell wall degrading enzyme, such that said micro-organism is capable of expressing said nucleic acid and of producing and secreting said plant cell wall degrading enzyme;

to introduce at least one heterologous nucleic acid or increase expression of at least one endogenous nucleic acid encoding an enzyme that converts pyruvate to acetaldehyde optionally combined with at least one heterologous nucleic acid encoding an enzyme that converts acetaldehyde to ethanol such that said host cell is capable of expressing said nucleic acid; and/or;

to modify at least one nucleic acid encoding for an enzyme in a metabolic pathway in said host cell, wherein said pathway produces a metabolite other than acetaldehyde from pyruvate or ethanol from acetaldehyde, and wherein said modification results in a reduced production of said metabolite, or to introduce at least one nucleic acid encoding for an inhibitor of said enzyme.

Modifying Algae and Plants for Production of Vegetable Oils or Biofuels

Transgenic algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

According to particular embodiments of the invention, the Cpf1 CRISPR system is used to generate lipid-rich diatoms which are useful in biofuel production.

In particular embodiments it is envisaged to specifically modify genes that are involved in the modification of the quantity of lipids and/or the quality of the lipids produced by the algal cell. Examples of genes encoding enzymes involved in the pathways of fatty acid synthesis can encode proteins having for instance acetyl-CoA carboxylase, fatty acid synthase, 3-ketoacyl_acyl-carrier protein synthase III, glycerol-3-phospate deshydrogenase (G3PDH), Enoyl-acyl carrier protein reductase (Enoyl-ACP-reductase), glycerol-3-phosphate acyltransferase, lysophosphatidic acyl transferase or diacylglycerol acyltransferase, phospholipid:diacylglycerol acyltransferase, phoshatidate phosphatase, fatty acid thioesterase such as palmitoyl protein thioesterase, or malic enzyme activities. In further embodiments it is envisaged to generate diatoms that have increased lipid accumulation. This can be achieved by targeting genes that decrease lipid catabolisation. Of particular interest for use in the methods of the present invention are genes involved in the activation of both triacylglycerol and free fatty acids, as well as genes directly involved in β-oxidation of fatty acids, such as acyl-CoA synthetase, 3-ketoacyl-CoA thiolase, acyl-CoA oxidase activity and phosphoglucomutase. The Cpf1 CRISPR system and methods described herein can be used to specifically activate such genes in diatoms as to increase their lipid content.

Organisms such as microalgae are widely used for synthetic biology. Stovicek et al. (Metab. Eng. Comm., 2015; 2:13 describes genome editing of industrial yeast, for example, *Saccharomyces cerevisiae*, to efficiently produce robust strains for industrial production. Stovicek used a CRISPR-Cas9 system codon-optimized for yeast to simultaneously disrupt both alleles of an endogenous gene and knock in a heterologous gene. Cas9 and gRNA were expressed from genomic or episomal 2µ-based vector locations. The authors also showed that gene disruption efficiency could be improved by optimization of the levels of Cas9 and gRNA expression. Hlavová et al. (Biotechnol. Adv. 2015) discusses development of species or strains of microalgae using techniques such as CRISPR to target nuclear and chloroplast genes for insertional mutagenesis and screening. The methods of Stovicek and Hlavová may be applied to the Cpf1 effector protein system of the present invention.

U.S. Pat. No. 8,945,839 describes a method for engineering Micro-Algae (*Chlamydomonas reinhardtii* cells) species) using Cas9. Using similar tools, the methods of the Cpf1 CRISPR system described herein can be applied on *Chlamydomonas* species and other algae. In particular embodiments, Cpf1 and guide RNA are introduced in algae expressed using a vector that expresses Cpf1 under the control of a constitutive promoter such as Hsp70A-Rbc S2 or Beta2-tubulin. Guide RNA will be delivered using a vector containing T7 promoter. Alternatively, Cpf1 mRNA and in vitro transcribed guide RNA can be delivered to algal cells. Electroporation protocol follows standard recommended protocol from the GeneArt Chlamydomonas Engineering kit.

Use of Cpf1 in the Generation of Micro-Organisms Capable of Fatty Acid Production In particular embodiments, the methods of the invention are used for the generation of genetically engineered microorganisms capable of the production of fatty esters, such as fatty acid methyl esters ("FAME") and fatty acid ethyl esters ("FAEE"), Typically, host cells can be engineered to produce fatty esters from a carbon source, such as an alcohol, present in the medium, by expression or overexpression of a gene encoding a thioesterase, a gene encoding an acyl-CoA synthase, and a gene encoding an ester synthase. Accordingly, the methods provided herein are used to modify a micro-organism so as to overexpress or introduce a thioesterase gene, a gene enclonding an acyl-CoA synthase, and a gene encoding an ester synthase. In particular embodiments, the thioesterase gene is selected from tesA, 'tesA, tesB, fatB, fatB2, fatB3, fatA1, or fatA. In particular embodiments, the gene encoding an acyl-CoA synthase is selected from fadDJadK, BH3103, pfl-4354, EAV15023, fadD1, fadD2, RPC_4074, fadDD35, fadDD22, faa39, or an identified gene encoding an enzyme having the same properties. In particular embodiments, the gene encoding an ester synthase is a gene encoding a synthase/acyl-CoA:diacylglycerl acyltransferase from *Simmondsia chinensis*, *Acinetobacter* sp. ADP, *Alcanivorax borkumensis*, *Pseudomonas aeruginosa*, *Fundibacter jadensis*, *Arabidopsis thaliana*, or *Alkaligenes eutrophus*, or a variant thereof. Additionally, or alternatively, the methods provided herein are used to decrease expression in said micro-organism of at least one of a gene encoding an acyl-CoA dehydrogenase, a gene encoding an outer membrane protein receptor, and a gene encoding a transcriptional regulator of fatty acid biosynthesis. In particular embodiments one or more of these genes is inactivated, such as by introduction of a mutation. In particular embodiments, the gene encoding an acyl-CoA dehydrogenase is fadE. In particular embodiments, the gene encoding a transcriptional regulator of fatty acid biosynthesis encodes a DNA transcription repressor, for example, fabR.

Additionally, or alternatively, said micro-organism is modified to reduce expression of at least one of a gene encoding a pyruvate formate-lyase, a gene encoding a lactate dehydrogenase, or both. In particular embodiments, the gene encoding a pyruvate formate lyase is pflB. In particular embodiments, the gene encoding a lactate dehydrogenase is IdhA. In particular embodiments one or more of these genes is inactivated, such as by introduction of a mutation therein.

In particular embodiments, the micro-organism is selected from the genus *Escherichia*, *Bacillus*, *Lactobacillus*, *Rhodococcus*, *Synechococcus*, *Synechoystis*, *Pseudomonas*, *Aspergillus*, *Trichoderma*, *Neurospora*, *Fusarium*, *Humicola*, *Rhizomucor*, *Kluyveromyces*, *Pichia*, *Mucor*, *Myceliophtora*, *Penicillium*, *Phanerochaete*, *Pleurotus*, *Trametes*, *Chrysosporium*, *Saccharomyces*, *Stenotrophamonas*, *Schizosaccharomyces*, *Yarrowia*, or *Streptomyces*.

Use of Cpf1 in the Generation of Micro-Organisms Capable of Organic Acid Production The methods provided herein are further used to engineer micro-organisms capable of organic acid production, more particularly from pentose or hexose sugars. In particular embodiments, the methods comprise introducing into a micro-organism an exogenous LDH gene. In particular embodiments, the organic acid production in said micro-organisms is additionally or alternatively increased by inactivating endogenous genes encoding proteins involved in an endogenous metabolic pathway which produces a metabolite other than the organic acid of interest and/or wherein the endogenous metabolic pathway consumes the organic acid. In particular embodiments, the modification ensures that the production of the metabolite other than the organic acid of interest is reduced. According to particular embodiments, the methods are used to introduce at least one engineered gene deletion and/or inactivation of an endogenous pathway in which the organic acid is consumed or a gene encoding a product involved in an endogenous pathway which produces a metabolite other than the organic acid of interest. In particular embodiments, the at least one engineered gene deletion or inactivation is in one or more gene encoding an enzyme selected from the group consisting of pyruvate decarboxylase (pdc), fumarate reductase, alcohol dehydrogenase (adh), acetaldehyde dehydrogenase, phosphoenolpyruvate carboxylase (ppc), D-lactate dehydrogenase (d-ldh), L-lactate dehydrogenase (l-ldh), lactate 2-monooxygenase. In further embodiments the at least one engineered gene deletion and/or inactivation is in an endogenous gene encoding pyruvate decarboxylase (pdc).

In further embodiments, the micro-organism is engineered to produce lactic acid and the at least one engineered gene deletion and/or inactivation is in an endogenous gene encoding lactate dehydrogenase. Additionally or alternatively, the micro-organism comprises at least one engineered gene deletion or inactivation of an endogenous gene encoding a cytochrome-dependent lactate dehydrogenase, such as a cytochrome B2-dependent L-lactate dehydrogenase.

Use of Cpf1 in the Generation of Improved Xylose or Cellobiose Utilizing Yeasts Strains In particular embodiments, the Cpf1 CRISPR system may be applied to select for improved xylose or cellobiose utilizing yeast strains. Error-prone PCR can be used to amplify one (or more) genes involved in the xylose utilization or cellobiose utilization pathways. Examples of genes involved in xylose utilization pathways and cellobiose utilization pathways may include, without limitation, those described in Ha, S. J., et al. (2011) Proc. Natl. Acad. Sci. USA 108(2):504-9 and Galazka, J. M., et al. (2010) Science 330(6000):84-6. Resulting libraries of double-stranded DNA molecules, each comprising a random mutation in such a selected gene could be co-transformed with the components of the Cpf1 CRISPR system into a yeast strain (for instance S288C) and strains can be selected with enhanced xylose or cellobiose utilization capacity, as described in WO2015138855.

Use of Cpf1 in the Generation of Improved Yeasts Strains for Use in Isoprenoid Biosynthesis Tadas Jakočiūnas et al. described the successful application of a multiplex CRISPR/Cas9 system for genome engineering of up to 5 different genomic loci in one transformation step in baker's yeast *Saccharomyces cerevisiae* (Metabolic Engineering Volume 28, March 2015, Pages 213-222) resulting in strains with high mevalonate production, a key intermediate for the industrially important isoprenoid biosynthesis pathway. In particular embodiments, the Cpf1 CRISPR system may be applied in a multiplex genome engineering method as described herein for identifying additional high producing yeast strains for use in isoprenoid synthesis.

Use of Cpf1 in the Generation of Lactic Acid Producing Yeasts Strains

In another embodiment, successful application of a multiplex Cpf1 CRISPR system is encompassed. In analogy with Vratislav Stovicek et al. (Metabolic Engineering Communications, Volume 2, December 2015, Pages 13-22), improved lactic acid-producing strains can be designed and obtained in a single transformation event. In a particular embodiment, the Cpf1 CRISPR system is used for simultaneously inserting the heterologous lactate dehydrogenase gene and disruption of two endogenous genes PDC1 and PDC5 genes.

Further Applications of the Cpf1 CRISPR System in Plants

In particular embodiments, the CRISPR system, and preferably the Cpf1 CRISPR system described herein, can be used for visualization of genetic element dynamics. For example, CRISPR imaging can visualize either repetitive or non-repetitive genomic sequences, report telomere length change and telomere movements and monitor the dynamics of gene loci throughout the cell cycle (Chen et al., Cell, 2013). These methods may also be applied to plants.

Other applications of the CRISPR system, and preferably the Cpf1 CRISPR system described herein, is the targeted gene disruption positive-selection screening in vitro and in vivo (Malina et al., Genes and Development, 2013). These methods may also be applied to plants.

In particular embodiments, fusion of inactive Cpf1 endonucleases with histone-modifying enzymes can introduce custom changes in the complex epigenome (Rusk et al., Nature Methods, 2014). These methods may also be applied to plants.

In particular embodiments, the CRISPR system, and preferably the Cpf1 CRISPR system described herein, can be used to purify a specific portion of the chromatin and identify the associated proteins, thus elucidating their regulatory roles in transcription (Waldrip et al., Epigenetics, 2014). These methods may also be applied to plants.

In particular embodiments, present invention can be used as a therapy for virus removal in plant systems as it is able to cleave both viral DNA and RNA. Previous studies in human systems have demonstrated the success of utilizing CRISPR in targeting the single strand RNA virus, hepatitis C (A. Price, et al., Proc. Natl. Acad. Sci, 2015) as well as the double stranded DNA virus, hepatitis B (V. Ramanan, et al., Sci. Rep, 2015). These methods may also be adapted for using the Cpf1 CRISPR system in plants.

In particular embodiments, present invention could be used to alter genome complexity. In further particular embodiment, the CRISPR system, and preferably the Cpf1 CRISPR system described herein, can be used to disrupt or alter chromosome number and generate haploid plants, which only contain chromosomes from one parent. Such plants can be induced to undergo chromosome duplication and converted into diploid plants containing only homozygous alleles (Karimi-Ashtiyani et al., PNAS, 2015; Anton et al., Nucleus, 2014). These methods may also be applied to plants.

In particular embodiments, the Cpf1 CRISPR system described herein, can be used for self-cleavage. In these embodiments, the promotor of the Cpf1 enzyme and gRNA can be a constitutive promotor and a second gRNA is introduced in the same transformation cassette, but controlled by an inducible promoter. This second gRNA can be designated to induce site-specific cleavage in the Cpf1 gene in order to create a non-functional Cpf1. In a further particular embodiment, the second gRNA induces cleavage on both ends of the transformation cassette, resulting in the removal of the cassette from the host genome. This system offers a controlled duration of cellular exposure to the Cas enzyme and further minimizes off-target editing. Furthermore, cleavage of both ends of a CRISPR/Cas cassette can be used to generate transgene-free TO plants with bi-allelic mutations (as described for Cas9 e.g. Moore et al., Nucleic Acids Research, 2014; Schaeffer et al., Plant Science, 2015). The methods of Moore et al. may be applied to the Cpf1 CRISPR systems described herein.

Sugano et al. (Plant Cell Physiol. 2014 March; 55(3):475-81. doi: 10.1093/pcp/pcu014. Epub 2014 Jan. 18) reports the application of CRISPR-Cas9 to targeted mutagenesis in the liverwort *Marchantia polymorpha* L., which has emerged as a model species for studying land plant evolution. The U6 promoter of *M. polymorpha* was identified and cloned to express the gRNA. The target sequence of the gRNA was designed to disrupt the gene encoding auxin response factor 1 (ARF1) in *M. polymorpha*. Using *Agrobacterium*-mediated transformation, Sugano et al. isolated stable mutants in the gametophyte generation of *M. polymorpha*. CRISPR-Cas9-based site-directed mutagenesis in vivo was achieved using either the Cauliflower mosaic virus 35S or *M. polymorpha* EF1α promoter to express Cas9. Isolated mutant individuals showing an auxin-resistant phenotype were not chimeric. Moreover, stable mutants were produced by asexual reproduction of T1 plants. Multiple arf1 alleles were easily established using CRIPSR-Cas9-based targeted mutagenesis. The methods of Sugano et al. may be applied to the Cpf1 effector protein system of the present invention.

Kabadi et al. (Nucleic Acids Res. 2014 Oct. 29; 42 (19):e147. doi: 10.1093/nar/gku749. Epub 2014 Aug. 13) developed a single lentiviral system to express a Cas9 variant, a reporter gene and up to four sgRNAs from independent RNA polymerase III promoters that are incorporated into the vector by a convenient Golden Gate cloning method. Each sgRNA was efficiently expressed and can mediate multiplex gene editing and sustained transcriptional activation in immortalized and primary human cells. The methods of Kabadi et al. may be applied to the Cpf1 effector protein system of the present invention.

Ling et al. (BMC Plant Biology 2014, 14:327) developed a CRISPR-Cas9 binary vector set based on the pGreen or pCAMBIA backbone, as well as a gRNA This toolkit requires no restriction enzymes besides BsaI to generate final constructs harboring maize-codon optimized Cas9 and one or more gRNAs with high efficiency in as little as one cloning step. The toolkit was validated using maize protoplasts, transgenic maize lines, and transgenic *Arabidopsis* lines and was shown to exhibit high efficiency and specificity. More importantly, using this toolkit, targeted mutations of three *Arabidopsis* genes were detected in transgenic seedlings of the T1 generation. Moreover, the multiple-gene mutations could be inherited by the next generation. (guide RNA) module vector set, as a toolkit for multiplex genome editing in plants. The toolbox of Lin et al. may be applied to the Cpf1 effector protein system of the present invention.

Protocols for targeted plant genome editing via CRISPR-Cpf1 are also available based on those disclosed for the CRISPR-Cas9 system in volume 1284 of the series Methods in Molecular Biology pp 239-255 10 Feb. 2015. A detailed procedure to design, construct, and evaluate dual gRNAs for plant codon optimized Cas9 (pcoCas9) mediated genome editing using *Arabidopsis thaliana* and *Nicotiana benthamiana* protoplasts s model cellular systems are described. Strategies to apply the CRISPR-Cas9 system to generating targeted genome modifications in whole plants are also discussed. The protocols described in the chapter may be applied to the Cpf1 effector protein system of the present invention.

Ma et al. (Mol Plant. 2015 Aug. 3; 8(8):1274-84. doi: 10.1016/j.molp.2015.04.007) reports robust CRISPR-Cas9 vector system, utilizing a plant codon optimized Cas9 gene, for convenient and high-efficiency multiplex genome editing in monocot and dicot plants. Ma et al. designed PCR-based procedures to rapidly generate multiple sgRNA expression cassettes, which can be assembled into the binary CRISPR-Cas9 vectors in one round of cloning by Golden Gate ligation or Gibson Assembly. With this system, Ma et al. edited 46 target sites in rice with an average 85.4% rate of mutation, mostly in biallelic and homozygous status. Ma et al. provide examples of loss-of-function gene mutations in TO rice and T1*Arabidopsis* plants by simultaneous targeting of multiple (up to eight) members of a gene family, multiple genes in a biosynthetic pathway, or multiple sites in a single gene. The methods of Ma et al. may be applied to the Cpf1 effector protein system of the present invention.

Lowder et al. (Plant Physiol. 2015 Aug. 21. pii: pp. 00636.2015) also developed a CRISPR-Cas9 toolbox enables multiplex genome editing and transcriptional regulation of expressed, silenced or non-coding genes in plants. This toolbox provides researchers with a protocol and reagents to quickly and efficiently assemble functional CRISPR-Cas9 T-DNA constructs for monocots and dicots using Golden Gate and Gateway cloning methods. It comes with a full suite of capabilities, including multiplexed gene editing and transcriptional activation or repression of plant endogenous genes. T-DNA based transformation technology is fundamental to modern plant biotechnology, genetics, molecular biology and physiology. As such, Applicants developed a method for the assembly of Cpf1 (WT, nickase or dCpf1) and gRNA(s) into a T-DNA destination-vector of interest. The assembly method is based on both Golden Gate assembly and MultiSite Gateway recombination. Three modules are required for assembly. The first module is a Cpf1 entry vector, which contains promoterless Cpf1 or its derivative genes flanked by attL1 and attR5 sites. The second module is a gRNA entry vector which contains entry gRNA expression cassettes flanked by attL5 and attL2 sites. The third module includes attR1-attR2-containing destination T-DNA vectors that provide promoters of choice for Cpf1 expression. The toolbox of Lowder et al. may be applied to the Cpf1 effector protein system of the present invention.

Wang et al. (bioRxiv 051342; doi: https://doi.org/10.1101/051342; Epub. May 12, 2016) demonstrate editing of homologous copies of four genes affecting important agronomic traits in hexaploid wheat using a multiplexed gene editing construct with several gRNA-tRNA units under the control of a single promoter.

In an advantageous embodiment, the plant may be a tree. The present invention may also utilize the herein disclosed CRISPR Cas system for herbaceous systems (see, e.g., Belhaj et al., Plant Methods 9: 39 and Harrison et al., Genes & Development 28: 1859-1872). In a particularly advantageous embodiment, the CRISPR Cas system of the present invention may target single nucleotide polymorphisms (SNPs) in trees (see, e.g., Zhou et al., New Phytologist, Volume 208, Issue 2, pages 298-301, October 2015). In the Zhou et al. study, the authors applied a CRISPR Cas system in the woody perennial Populus using the 4-coumarate:CoA ligase (4CL) gene family as a case study and achieved 100% mutational efficiency for two 4CL genes targeted, with every transformant examined carrying biallelic modifications. In the Zhou et al., study, the CRISPR-Cas9 system was highly sensitive to single nucleotide polymorphisms (SNPs), as cleavage for a third 4CL gene was abolished due to SNPs in the target sequence. These methods may be applied to the Cpf1 effector protein system of the present invention.

The methods of Zhou et al. (New Phytologist, Volume 208, Issue 2, pages 298-301, October 2015) may be applied to the present invention as follows. Two 4CL genes, 4CL1 and 4CL2, associated with lignin and flavonoid biosynthesis, respectively are targeted for CRISPR-Cas9 editing. The Populus tremula×alba clone 717-1B4 routinely used for transformation is divergent from the genome-sequenced Populus trichocarpa. Therefore, the 4CL1 and 4CL2 gRNAs designed from the reference genome are interrogated with in-house 717 RNA-Seq data to ensure the absence of SNPs which could limit Cas efficiency. A third gRNA designed for 4CL5, a genome duplicate of 4CL1, is also included. The corresponding 717 sequence harbors one SNP in each allele near/within the PAM, both of which are expected to abolish targeting by the 4CL5-gRNA. All three gRNA target sites are located within the first exon. For 717 transformation, the gRNA is expressed from the Medicago U6.6 promoter, along with a human codon-optimized Cas under control of the CaMV 35S promoter in a binary vector. Transformation with the Cas-only vector can serve as a control. Randomly selected 4CL1 and 4CL2 lines are subjected to amplicon-sequencing. The data is then processed and biallelic mutations are confirmed in all cases. These methods may be applied to the Cpf1 effector protein system of the present invention.

In plants, pathogens are often host-specific. For example, Fusarium oxysporum f. sp. lycopersici causes tomato wilt but attacks only tomato, and F. oxysporum f. dianthii Puccinia graminis f. sp. tritici attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

Table 15 provides additional references and related fields for which the CRISPR-Cas complexes, modified effector proteins, systems, and methods of optimization may be used to improve bioproduction.

TABLE 15

| | | |
|---|---|---|
| Feb. 17, 2014 | PCT/US15/63434 (WO2016/099887) | Compositions and methods for efficient gene editing in E. coli using guide RNA/Cas endonuclease systems in combination with circular polynucleotide modification templates. |
| Aug. 13, 2014 | PCT/US15/41256 (WO2016/025131) | Genetic targeting in non-conventional yeast using an RNA-guided endonuclease. |
| Nov. 6, 2014 | PCT/US15/58760 (WO2016/073433) | Peptide-mediated delivery of RNA-guided endonuclease into cells. |
| Oct. 12, 2015 | PCT/US16/56404 (WO2017/066175) | Protected DNA templates for gene modification and increased homologous recombination in cells and methods of use. |
| Dec. 11, 2015 | PCT/US16/65070 (WO2017/100158) | Methods and compositions for enhanced nuclease-mediated genome modification and reduced off-target site effects. |
| Dec. 18, 2015 | PCT/US16/65537 (WO 2017/105991) | Methods and compositions for T-RNA based guide RNA expression. |
| Dec. 18, 2015 | PCT/US16/66772 (WO2017/106414) | Methods and compositions for polymerase II (Pol-II) based guide RNA expression. |
| Dec. 16, 2014 | PCT/US15/65693 (WO2016/100272) | Fungal genome modification systems and methods of use. |
| Dec. 16, 2014 | PCT/US15/66195 (WO2016/100571) | Fungal genome modification systems and methods of use |
| Dec. 16, 2014 | PCT/US15/66192 (WO 2016/100568) | Fungal genome modification systems and methods of use. |
| Dec. 16, 2014 | PCT/US15/66178 (WO 2016/100562) | Use of a helper strain with silenced NHEJ to improve homologous integration of targeted DNA cassettes in Trichoderma reesei. |
| Jul. 28, 2015 | PCT/US16/44489 (WO 2017/019867) | Genome editing systems and methods of use. |

Modified Plants and Yeast Cells

The present invention also provides plants and yeast cells obtainable and obtained by the methods provided herein. The improved plants obtained by the methods described herein may be useful in food or feed production through expression of genes which, for instance ensure tolerance to plant pests, herbicides, drought, low or high temperatures, excessive water, etc.

The improved plants obtained by the methods described herein, especially crops and algae may be useful in food or feed production through expression of, for instance, higher protein, carbohydrate, nutrient or vitamin levels than would normally be seen in the wildtype. In this regard, improved plants, especially pulses and tubers are preferred.

Improved algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

The invention also provides for improved parts of a plant. Plant parts include, but are not limited to, leaves, stems, roots, tubers, seeds, endosperm, ovule, and pollen. Plant parts as envisaged herein may be viable, nonviable, regeneratable, and/or non-regeneratable.

It is also encompassed herein to provide plant cells and plants generated according to the methods of the invention. Gametes, seeds, embryos, either zygotic or somatic, progeny or hybrids of plants comprising the genetic modification, which are produced by traditional breeding methods, are also included within the scope of the present invention. Such plants may contain a heterologous or foreign DNA sequence inserted at or instead of a target sequence. Alternatively, such plants may contain only an alteration (mutation, deletion, insertion, substitution) in one or more nucleotides. As such, such plants will only be different from their progenitor plants by the presence of the particular modification.

Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

The methods for genome editing using the Cpf1 system as described herein can be used to confer desired traits on essentially any plant, algae, fungus, yeast, etc. A wide variety of plants, algae, fungus, yeast, etc and plant algae, fungus, yeast cell or tissue systems may be engineered for the desired physiological and agronomic characteristics described herein using the nucleic acid constructs of the present disclosure and the various transformation methods mentioned above.

In particular embodiments, the methods described herein are used to modify endogenous genes or to modify their expression without the permanent introduction into the genome of the plant, algae, fungus, yeast, etc. of any foreign gene, including those encoding CRISPR components, so as to avoid the presence of foreign DNA in the genome of the plant. This can be of interest as the regulatory requirements for non-transgenic plants are less rigorous.

The CRISPR systems provided herein can be used to introduce targeted double-strand or single-strand breaks and/or to introduce gene activator and or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

The methods described herein generally result in the generation of "improved plants, algae, fungi, yeast, etc" in that they have one or more desirable traits compared to the wildtype plant. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified plants, algae, fungi, yeast, etc., parts or cells are obtained, in that no exogenous DNA sequence is incorporated into the genome of any of the cells of the plant. In such embodiments, the improved plants, algae, fungi, yeast, etc. are non-transgenic. Where only the modification of an endogenous gene is ensured and no foreign genes are introduced or maintained in the plant, algae, fungi, yeast, etc. genome, the resulting genetically modified crops contain no foreign genes and can thus basically be considered non-transgenic. The different applications of the Cpf1 CRISPR system for plant, algae, fungi, yeast, etc. genome editing include, but are not limited to: introduction of one or more foreign genes to confer an agricultural trait of interest; editing of endogenous genes to confer an agricultural trait of interest; modulating of endogenous genes by the Cpf1 CRISPR system to confer an agricultural trait of interest. Exemplary genes conferring agronomic traits include, but are not limited to genes that confer resistance to pests or diseases; genes involved in plant diseases, such as those listed in WO 2013 046247; genes that confer resistance to herbicides, fungicides, or the like; genes involved in (abiotic) stress tolerance. Other aspects of the use of the CRISPR-Cas system include, but are not limited to: create (male) sterile plants; increasing the fertility stage in plants/algae etc.; generate genetic variation in a crop of interest; affect fruit-ripening; increasing storage life of plants/algae etc.; reducing allergen in plants/algae etc.; ensure a value added trait (e.g. nutritional improvement); Screening methods for endogenous genes of interest; biofuel, fatty acid, organic acid, etc. production.

Using CRISPR-Cas Systems and Components Thereof in Non-Human Organisms/Animals

In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example, a mammal. Also, the organism may be an arthropod such as an insect. The present invention may also be extended to other agricultural applications such as, for example, farm and production animals. For example, pigs have many features that make them attractive as biomedical models, especially in regenerative medicine. In particular, pigs with severe combined immunodeficiency (SCID) may provide useful models for regenerative medicine, xenotransplantation (discussed also elsewhere herein), and tumor development and will aid in developing therapies for human SCID patients. Lee et al., (Proc Natl Acad Sci USA. 2014 May 20; 111(20):7260-5) utilized a reporter-guided transcription activator-like effector nuclease (TALEN) system to generated targeted modifications of recombination activating gene (RAG) 2 in somatic cells at high efficiency, including some that affected both alleles. The Cpf1 effector protein may be applied to a similar system.

The methods of Lee et al., (Proc Natl Acad Sci USA. 2014 May 20; 111(20):7260-5) may be applied to the present invention analogously as follows. Mutated pigs are produced by targeted modification of RAG2 in fetal fibroblast cells followed by SCNT and embryo transfer. Constructs coding for CRISPR Cas and a reporter are electroporated into fetal-derived fibroblast cells. After 48 h, transfected cells expressing the green fluorescent protein are sorted into individual wells of a 96-well plate at an estimated dilution of a single cell per well. Targeted modification of RAG2 are screened by amplifying a genomic DNA fragment flanking any CRISPR Cas cutting sites followed by sequencing the PCR products. After screening and ensuring lack of off-site mutations, cells carrying targeted modification of RAG2 are used for SCNT. The polar body, along with a portion of the adjacent cytoplasm of oocyte, presumably containing the metaphase II plate, are removed, and a donor cell are placed in the perivitelline. The reconstructed embryos are then electrically porated to fuse the donor cell with the oocyte and then chemically activated. The activated embryos are incubated in Porcine Zygote Medium 3 (PZM3) with 0.5 µM Scriptaid (S7817; Sigma-Aldrich) for 14-16 h. Embryos are then washed to remove the Scriptaid and cultured in PZM3 until they were transferred into the oviducts of surrogate pigs.

The present invention is also applicable to modifying SNPs of other animals, such as cows. Tan et al. (Proc Natl Acad Sci USA. 2013 Oct. 8; 110(41): 16526-16531) expanded the livestock gene editing toolbox to include transcription activator-like (TAL) effector nuclease (TALEN)- and clustered regularly interspaced short palindromic repeats (CRISPR)/Cas9-stimulated homology-directed repair (HDR) using plasmid, rAAV, and oligonucleotide templates. Gene specific gRNA sequences were cloned into the Church lab gRNA vector (Addgene ID: 41824) according to their methods (Mali P, et al. (2013) RNA-Guided Human Genome Engineering via Cas9. Science 339(6121):823-826). The Cas9 nuclease was provided either by co-transfection of the hCas9 plasmid (Addgene ID: 41815) or mRNA synthesized from RCIScript-hCas9. This RCIScript-hCas9 was constructed by sub-cloning the XbaI-AgeI fragment from the hCas9 plasmid (encompassing the hCas9 cDNA) into the RCIScript plasmid.

Heo et al. (Stem Cells Dev. 2015 Feb. 1; 24(3):393-402. doi: 10.1089/scd.2014.0278. Epub 2014 Nov. 3) reported highly efficient gene targeting in the bovine genome using bovine pluripotent cells and clustered regularly interspaced short palindromic repeat (CRISPR)/Cas9 nuclease. First, Heo et al. generate induced pluripotent stem cells (iPSCs) from bovine somatic fibroblasts by the ectopic expression of Yamanaka factors and GSK3β and MEK inhibitor (2i) treatment. Heo et al. observed that these bovine iPSCs are highly similar to naïve pluripotent stem cells with regard to gene expression and developmental potential in teratomas. Moreover, CRISPR-Cas9 nuclease, which was specific for the bovine NANOG locus, showed highly efficient editing of the bovine genome in bovine iPSCs and embryos.

Igenity® provides a profile analysis of animals, such as cows, to perform and transmit traits of economic traits of economic importance, such as carcass composition, carcass quality, maternal and reproductive traits and average daily gain. The analysis of a comprehensive Igenity® profile begins with the discovery of DNA markers (most often single nucleotide polymorphisms or SNPs). All the markers behind the Igenity® profile were discovered by independent scientists at research institutions, including universities, research organizations, and government entities such as USDA. Markers are then analyzed at Igenity® in validation populations. Igenity® uses multiple resource populations that represent various production environments and biological types, often working with industry partners from the seedstock, cow-calf, feedlot and/or packing segments of the beef industry to collect phenotypes that are not commonly available. Cattle genome databases are widely available, see, e.g., the NAGRP Cattle Genome Coordination Program (http://www.animalgenome.org/cattle/maps/db.html). Thus, the present invention maybe applied to target bovine SNPs. One of skill in the art may utilize the above protocols for targeting SNPs and apply them to bovine SNPs as described, for example, by Tan et al. or Heo et al.

Qingjian Zou et al. (Journal of Molecular Cell Biology Advance Access published Oct. 12, 2015) demonstrated increased muscle mass in dogs by targeting the first exon of the dog Myostatin (MSTN) gene (a negative regulator of skeletal muscle mass). First, the efficiency of the sgRNA was validated, using cotransfection of the sgRNA targeting MSTN with a Cas9 vector into canine embryonic fibroblasts (CEFs). Thereafter, MSTN KO dogs were generated by micro-injecting embryos with normal morphology with a mixture of Cas9 mRNA and MSTN sgRNA and auto-transplantation of the zygotes into the oviduct of the same female dog. The knock-out puppies displayed an obvious muscular phenotype on thighs compared with its wild-type littermate sister. This can also be performed using the Cpf1 CRISPR systems provided herein.

Livestock—Pigs

Viral targets in livestock may include, in some embodiments, porcine CD163, for example on porcine macrophages. CD163 is associated with infection (thought to be through viral cell entry) by PRRSv (Porcine Reproductive and Respiratory Syndrome virus, an arterivirus). Infection by PRRSv, especially of porcine alveolar macrophages (found in the lung), results in a previously incurable porcine syndrome ("Mystery swine disease" or "blue ear disease") that causes suffering, including reproductive failure, weight loss and high mortality rates in domestic pigs. Opportunistic infections, such as enzootic pneumonia, meningitis and ear oedema, are often seen due to immune deficiency through loss of macrophage activity. It also has significant economic and environmental repercussions due to increased antibiotic use and financial loss (an estimated $660m per year).

As reported by Kristin M Whitworth and Dr Randall Prather et al. (Nature Biotech 3434 published online 7 Dec. 2015) at the University of Missouri and in collaboration with Genus Plc, CD163 was targeted using CRISPR-Cas9 and the offspring of edited pigs were resistant when exposed to PRRSv. One founder male and one founder female, both of whom had mutations in exon 7 of CD163, were bred to produce offspring. The founder male possessed an 11-bp deletion in exon 7 on one allele, which results in a frameshift mutation and missense translation at amino acid 45 in domain 5 and a subsequent premature stop codon at amino acid 64. The other allele had a 2-bp addition in exon 7 and a 377-bp deletion in the preceding intron, which were predicted to result in the expression of the first 49 amino acids of domain 5, followed by a premature stop code at amino acid 85. The sow had a 7 bp addition in one allele that when translated was predicted to express the first 48 amino acids of domain 5, followed by a premature stop codon at amino acid 70. The sow's other allele was unamplifiable. Selected offspring were predicted to be a null animal (CD163−/−), i.e. a CD163 knock out.

Accordingly, in some embodiments, porcine alveolar macrophages may be targeted by the CRISPR protein. In some embodiments, porcine CD163 may be targeted by the CRISPR protein. In some embodiments, porcine CD163 may be knocked out through induction of a DSB or through insertions or deletions, for example targeting deletion or modification of exon 7, including one or more of those described above, or in other regions of the gene, for example deletion or modification of exon 5.

An edited pig and its progeny are also envisaged, for example a CD163 knock out pig. This may be for livestock, breeding or modelling purposes (i.e. a porcine model). Semen comprising the gene knock out is also provided.

CD163 is a member of the scavenger receptor cysteine-rich (SRCR) superfamily. Based on in vitro studies SRCR domain 5 of the protein is the domain responsible for unpackaging and release of the viral genome. As such, other members of the SRCR superfamily may also be targeted in order to assess resistance to other viruses. PRRSV is also a member of the mammalian arterivirus group, which also includes murine lactate dehydrogenase-elevating virus, simian hemorrhagic fever virus and equine arteritis virus. The arteriviruses share important pathogenesis properties, including macrophage tropism and the capacity to cause both severe disease and persistent infection. Accordingly, arteriviruses, and in particular murine lactate dehydrogenase-elevating virus, simian hemorrhagic fever virus and equine arteritis virus, may be targeted, for example through porcine CD163 or homologues thereof in other species, and murine, simian and equine models and knockout also provided.

Indeed, this approach may be extended to viruses or bacteria that cause other livestock diseases that may be transmitted to humans, such as Swine Influenza Virus (SIV) strains which include influenza C and the subtypes of influenza A known as H1N1, H1N2, H2N1, H3N1, H3N2, and H2N3, as well as pneumonia, meningitis and oedema mentioned above.

Cpf1 effector protein complexes can be used in non-animal organisms, such as plants, algae, fungi, yeasts, etc.

The methods for genome editing using the Cpf1 system as described herein can be used to confer desired traits on essentially any plant, algae, fungus, yeast, etc. A wide variety of plants, algae, fungus, yeast, etc. and plant algae, fungus, yeast cell or tissue systems may be engineered for the desired physiological and agronomic characteristics described herein using the nucleic acid constructs of the present disclosure and the various transformation methods mentioned above.

In particular embodiments, the methods described herein are used to modify endogenous genes or to modify their expression without the permanent introduction into the genome of the plant, algae, fungus, yeast, etc. of any foreign gene, including those encoding CRISPR components, so as to avoid the presence of foreign DNA in the genome of the plant. This can be of interest as the regulatory requirements for non-transgenic plants are less rigorous.

The CRISPR systems provided herein can be used to introduce targeted double-strand or single-strand breaks and/or to introduce gene activator and or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

The methods described herein generally result in the generation of "modulated and/or improved plants, algae, fungi, yeast, etc." in that they have one or more desirable traits compared to the wildtype plant. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified plants, algae, fungi, yeast, etc., parts or cells are obtained, in that no exogenous DNA sequence is incorporated into the genome of any of the cells of the plant. In such embodiments, the improved plants, algae, fungi, yeast, etc. are non-transgenic. Where only the modification of an endogenous gene is ensured and no foreign genes are introduced or maintained in the plant, algae, fungi, yeast, etc. genome, the resulting genetically modified crops contain no foreign genes and can thus basically be considered non-transgenic. The different applications of the Cpf1 CRISPR system for plant, algae, fungi, yeast, etc. genome editing include, but are not limited to: introduction of one or more foreign genes to confer an agricultural trait of interest; editing of endogenous genes to confer an agricultural trait of interest; modulating of endogenous genes by the Cpf1 CRISPR system to confer an agricultural trait of interest. Exemplary genes conferring agronomic traits include, but are not limited to genes that confer resistance to pests or diseases; genes involved in plant diseases, such as those listed in WO 2013046247; genes that confer resistance to herbicides, fungicides, or the like; genes involved in (abiotic) stress tolerance. Other aspects of the use of the CRISPR-Cas system include, but are not limited to: create (male) sterile plants; increasing the fertility stage in plants/algae etc.; generate genetic variation in a crop of interest; affect fruit-ripening; increasing storage life of plants/algae etc.; reducing allergen in plants/algae etc.; ensure a value added trait (e.g. nutritional improvement); screening methods for endogenous genes of interest; biofuel, fatty acid, organic acid, etc.

Treating and/or Preventing Diseases Using a CRISRP-Cas System and/or Component Thereof As will be apparent, it is envisaged that the present system can be used to target any polynucleotide sequence of interest. The invention provides a non-naturally occurring or engineered composition, or one or more polynucleotides encoding components of said composition, or vector or delivery systems comprising one or more polynucleotides encoding components of said composition for use in a modifying a target cell in vivo, ex vivo or in vitro and, may be conducted in a manner alters the cell such that once modified the progeny or cell line of the CRISPR modified cell retains the altered phenotype. The modified cells and progeny may be part of a multi-cellular organism such as a plant or animal with ex vivo or in vivo application of CRISPR system to desired cell types. The CRISPR invention may be a therapeutic method of treatment. The therapeutic method of treatment may comprise gene or genome editing, or gene therapy.

Treating Pathogens Such as Bacterial, Fungal and Parasitic Pathogens

The present invention may also be applied to treat bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

Jiang et al. ("RNA-guided editing of bacterial genomes using CRISPR-Cas systems," Nature Biotechnology vol. 31, p. 233-9, March 2013) used a CRISPR-Cas9 system to mutate or kill S. pneumoniae and E. coli. The work, which introduced precise mutations into the genomes, relied on dual-RNA:Cas9-directed cleavage at the targeted genomic site to kill unmutated cells and circumvented the need for selectable markers or counter-selection systems. CRISPR systems have be used to reverse antibiotic resistance and eliminate the transfer of resistance between strains. Bickard et al. showed that Cas9, reprogrammed to target virulence genes, kills virulent, but not avirulent, S. aureus. Reprogramming the nuclease to target antibiotic resistance genes destroyed staphylococcal plasmids that harbor antibiotic resistance genes and immunized against the spread of plasmid-borne resistance genes. (see, Bikard et al., "Exploiting CRISPR-Cas nucleases to produce sequence-specific antimicrobials," Nature Biotechnology vol. 32, 1146-1150, doi: 10.1038/nbt.3043, published online 5 Oct. 2014.) Bikard showed that CRISPR-Cas9 antimicrobials function in vivo to kill S. aureus in a mouse skin colonization model.

Similarly, Yosef et al. used a CRISPR system to target genes encoding enzymes that confer resistance to β-lactam antibiotics (see Yousef et al., "Temperate and lytic bacteriophages programmed to sensitize and kill antibiotic-resistant bacteria," Proc. Natl. Acad. Sci. USA, vol. 112, p. 7267-7272, doi: 10.1073/pnas.1500107112 published online May 18, 2015).

CRISPR systems can be used to edit genomes of parasites that are resistant to other genetic approaches. For example, a CRISPR-Cas9 system was shown to introduce double-stranded breaks into the in the *Plasmodium yoelii* genome (see, Zhang et al., "Efficient Editing of Malaria Parasite Genome Using the CRISPR/Cas9 System," mBio. vol. 5, e01414-14, July-August 2014). Ghorbal et al. ("Genome editing in the human malaria parasite *Plasmodium falciparum* using the CRISPR-Cas9 system," Nature Biotechnology, vol. 32, p. 819-821, doi: 10.1038/nbt.2925, published online Jun. 1, 2014) modified the sequences of two genes, orc1 and kelch13, which have putative roles in gene silencing and emerging resistance to artemisinin, respectively. Parasites that were altered at the appropriate sites were recovered with very high efficiency, despite there being no direct selection for the modification, indicating that neutral or even deleterious mutations can be generated using this system. CRISPR-Cas9 is also used to modify the genomes of other pathogenic parasites, including *Toxoplasma gondii* (see Shen et al., "Efficient gene disruption in diverse strains of *Toxoplasma gondii* using CRISPR/CAS9," mBio vol. 5:e01114-14, 2014; and zSidik et al., "Efficient Genome Engineering of *Toxoplasma gondii* Using CRISPR/Cas9," PLoS One vol. 9, e100450, doi: 10.1371/journal.pone.0100450, published online Jun. 27, 2014).

Vyas et al. ("A *Candida albicans* CRISPR system permits genetic engineering of essential genes and gene families," Science Advances, vol. 1, e1500248, DOI: 10.1126/sciadv.1500248, Apr. 3, 2015) employed a CRISPR system to overcome long-standing obstacles to genetic engineering in *C. albicans* and efficiently mutate in a single experiment both copies of several different genes. In an organism where several mechanisms contribute to drug resistance, Vyas produced homozygous double mutants that no longer displayed the hyper-resistance to fluconazole or cycloheximide displayed by the parental clinical isolate Can90. Vyas also obtained homozygous loss-of-function mutations in essential genes of *C. albicans* by creating conditional alleles. Null alleles of DCR1, which is required for ribosomal RNA processing, are lethal at low temperature but viable at high temperature. Vyas used a repair template that introduced a nonsense mutation and isolated dcr1/dcr1 mutants that failed to grow at 16° C.

The CRISPR system of the present invention for use in *P. falciparum* by disrupting chromosomal loci. Ghorbal et al. ("Genome editing in the human malaria parasite *Plasmodium falciparum* using the CRISPR-Cas9 system", Nature Biotechnology, 32, 819-821 (2014), DOI: 10.1038/nbt.2925, Jun. 1, 2014) employed a CRISPR system to introduce specific gene knockouts and single-nucleotide substitutions in the malaria genome. To adapt the CRISPR-Cas9 system to *P. falciparum*, Ghorbal et al. generated expression vectors for under the control of plasmodial regulatory elements in the pUF1-Cas9 episome that also carries the drug-selectable marker yDHODH, which gives resistance to DSM1, a *P. falciparum* dihydroorotate dehydrogenase (PfDHODH) inhibitor and for transcription of the sgRNA, used *P. falciparum* U6 small nuclear (sn)RNA regulatory elements placing the guide RNA and the donor DNA template for homologous recombination repair on the same plasmid, pL7. See also, Zhang C. et al. ("Efficient editing of malaria parasite genome using the CRISPR/Cas9 system", MBio, 2014 Jul. 1; 5 (4):E01414-14, doi: 10.1 128/MbIO.01414-14) and Wagner et al. ("Efficient CRISPR-Cas9-mediated genome editing in *Plasmodium falciparum*, Nature Methods 11, 915-918 (2014), DOI: 10.1038/nmeth.3063).

Treating Pathogens, e.g., Viral Pathogens Such as HIV

Cas-mediated genome editing might be used to introduce protective mutations in somatic tissues to combat nongenetic or complex diseases. For example, NHEJ-mediated inactivation of the CCR5 receptor in lymphocytes (Lombardo et al., Nat Biotechnol. 2007 November; 25(11):1298-306) may be a viable strategy for circumventing HIV infection, whereas deletion of PCSK9 (Cohen et al., Nat Genet. 2005 February; 37(2):161-5) orangiopoietin (Musunuru et al., N Engl J Med. 2010 Dec. 2; 363(23):2220-7) may provide therapeutic effects against statin-resistant hypercholesterolemia or hyperlipidemia. Although these targets may be also addressed using siRNA-mediated protein knockdown, a unique advantage of NHEJ-mediated gene inactivation is the ability to achieve permanent therapeutic benefit without the need for continuing treatment. As with all gene therapies, it will of course be important to establish that each proposed therapeutic use has a favorable benefit-risk ratio.

Hydrodynamic delivery of plasmid DNA encoding Cas9 nd guide RNA along with a repair template into the liver of an adult mouse model of tyrosinemia was shown to be able to correct the mutant Fah gene and rescue expression of the wild-type Fah protein in ~1 out of 250 cells (Nat Biotechnol. 2014 June; 32(6):551-3). In addition, clinical trials successfully used ZF nucleases to combat HIV infection by ex vivo knockout of the CCR5 receptor. In all patients, HIV DNA levels decreased, and in one out of four patients, HIV RNA became undetectable (Tebas et al., N Engl J Med. 2014 Mar. 6; 370(10):901-10). Both of these results demonstrate the promise of programmable nucleases as a new therapeutic platform.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of 2.5×106 CD34+ cells per kilogram patient weight may be collected and prestimulated for 16 to 20 hours in X-VIVO 15 medium (Lonza) containing 2 μmol/L-glutamine, stem cell factor (100 ng/ml), Flt-3 ligand (Flt-3L) (100 ng/ml), and thrombopoietin (10 ng/ml) (Cell-Genix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

With the knowledge in the art and the teachings in this disclosure the skilled person can correct HSCs as to immunodeficiency condition such as HIV/AIDS comprising contacting an HSC with a CRISPR-Cpf1 system that targets and knocks out CCR5. A guide RNA (and advantageously a dual guide approach, e.g., a pair of different guide RNAs; for instance, guide RNAs targeting of two clinically relevant genes, B2M and CCR5, in primary human CD4+ T cells and CD34+ hematopoietic stem and progenitor cells (HSPCs)) that targets and knocks out CCR5-and-Cpf1 protein containing particle is contacted with HSCs. The so contacted cells can be administered; and optionally treated/expanded; cf. Cartier. See also Kiem, "Hematopoietic stem cell-based gene therapy for HIV disease," Cell Stem Cell. Feb. 3, 2012;

10(2): 137-147; incorporated herein by reference along with the documents it cites; Mandal et al, "Efficient Ablation of Genes in Human Hematopoietic Stem and Effector Cells using CRISPR/Cas9," Cell Stem Cell, Volume 15, Issue 5, p643-652, 6 Nov. 2014; incorporated herein by reference along with the documents it cites. Mention is also made of Ebina, "CRISPR/Cas9 system to suppress HIV-1 expression by editing HIV-1 integrated proviral DNA" SCIENTIFIC REPORTS |3: 2510| DOI: 10.1038/srep02510, incorporated herein by reference along with the documents it cites, as another means for combatting HIV/AIDS using a CRISPR-Cpf1 system.

The rationale for genome editing for HIV treatment originates from the observation that individuals homozygous for loss of function mutations in CCR5, a cellular co-receptor for the virus, are highly resistant to infection and otherwise healthy, suggesting that mimicking this mutation with genome editing could be a safe and effective therapeutic strategy [Liu, R., et al. Cell 86, 367-377 (1996)]. This idea was clinically validated when an HIV infected patient was given an allogeneic bone marrow transplant from a donor homozygous for a loss of function CCR5 mutation, resulting in undetectable levels of HIV and restoration of normal CD4 T-cell counts [Hutter, G., et al. The New England journal of medicine 360, 692-698 (2009)]. Although bone marrow transplantation is not a realistic treatment strategy for most HIV patients, due to cost and potential graft vs. host disease, HIV therapies that convert a patient's own T-cells into CCR5 are desirable.

Early studies using ZFNs and NHEJ to knockout CCR5 in humanized mouse models of HIV showed that transplantation of CCR5 edited CD4 T cells improved viral load and CD4 T-cell counts [Perez, E. E., et al. Nature biotechnology 26, 808-816 (2008)]. Importantly, these models also showed that HIV infection resulted in selection for CCR5 null cells, suggesting that editing confers a fitness advantage and potentially allowing a small number of edited cells to create a therapeutic effect.

As a result of this and other promising preclinical studies, genome editing therapy that knocks out CCR5 in patient T cells has now been tested in humans [Holt, N., et al. Nature biotechnology 28, 839-847 (2010); Li, L., et al. Molecular therapy: the journal of the American Society of Gene Therapy 21, 1259-1269 (2013)]. In a recent phase I clinical trial, CD4+ T cells from patients with HIV were removed, edited with ZFNs designed to knockout the CCR5 gene, and autologously transplanted back into patients [Tebas, P., et al. The New England journal of medicine 370, 901-910 (2014)].

In another study (Mandal et al., Cell Stem Cell, Volume 15, Issue 5, p643-652, 6 Nov. 2014), CRISPR-Cas9 has targeted two clinically relevant genes, B2M and CCR5, in human CD4+ T cells and CD34+ hematopoietic stem and progenitor cells (HSPCs). Use of single RNA guides led to highly efficient mutagenesis in HSPCs but not in T cells. A dual guide approach improved gene deletion efficacy in both cell types. HSPCs that had undergone genome editing with CRISPR-Cas9 retained multilineage potential. Predicted on- and off-target mutations were examined via target capture sequencing in HSPCs and low levels of off-target mutagenesis were observed at only one site. These results demonstrate that CRISPR-Cas9 can efficiently ablate genes in HSPCs with minimal off-target mutagenesis, which have broad applicability for hematopoietic cell-based therapy.

Wang et al. (PLoS One. 2014 Dec. 26; 9 (12):e115987. doi: 10.1371/journal.pone.0115987) silenced CCR5 via CRISPR associated protein 9 (Cas9) and single guided RNAs (guide RNAs) with lentiviral vectors expressing Cas9 and CCR5 guide RNAs. Wang et al. showed that a single round transduction of lentiviral vectors expressing Cas9 and CCR5 guide RNAs into HIV-1 susceptible human CD4+ cells yields high frequencies of CCR5 gene disruption. CCR5 gene-disrupted cells are not only resistant to R5-tropic HIV-1, including transmitted/founder (T/F) HIV-1 isolates, but also have selective advantage over CCR5 gene-undisrupted cells during R5-tropic HIV-1 infection. Genome mutations at potential off-target sites that are highly homologous to these CCR5 guide RNAs in stably transduced cells even at 84 days post transduction were not detected by a T7 endonuclease I assay.

Fine et al. (Sci Rep. 2015 Jul. 1; 5:10777. doi: 10.1038/srep10777) identified a two-cassette system expressing pieces of the S. pyogenes Cas9 (SpCas9) protein which splice together in cellula to form a functional protein capable of site-specific DNA cleavage. With specific CRISPR guide strands, Fine et al. demonstrated the efficacy of this system in cleaving the HBB and CCR5 genes in human HEK-293T cells as a single Cas9 and as a pair of Cas9 nickases. The trans-spliced SpCas9 (tsSpCas9) displayed ~35% of the nuclease activity compared with the wild-type SpCas9 (wt-SpCas9) at standard transfection doses, but had substantially decreased activity at lower dosing levels. The greatly reduced open reading frame length of the tsSpCas9 relative to wtSpCas9 potentially allows for more complex and longer genetic elements to be packaged into an AAV vector including tissue-specific promoters, multiplexed guide RNA expression, and effector domain fusions to SpCas9.

$L^1$ et al. (J Gen Virol. 2015 August; 96(8):2381-93. doi: 10.1099/vir.0.000139. Epub 2015 Apr. 8) demonstrated that CRISPR-Cas9 can efficiently mediate the editing of the CCR5 locus in cell lines, resulting in the knockout of CCR5 expression on the cell surface. Next-generation sequencing revealed that various mutations were introduced around the predicted cleavage site of CCR5. For each of the three most effective guide RNAs that were analyzed, no significant off-target effects were detected at the 15 top-scoring potential sites. By constructing chimeric Ad5F35 adenoviruses carrying CRISPR-Cas9 components, Li et al. efficiently transduced primary CD4+T-lymphocytes and disrupted CCR5 expression, and the positively transduced cells were conferred with HIV-1 resistance.

One of skill in the art may utilize the above studies of, for example, Holt, N., et al. Nature biotechnology 28, 839-847 (2010), Li, L., et al. Molecular therapy: the journal of the American Society of Gene Therapy 21, 1259-1269 (2013), Mandal et al., Cell Stem Cell, Volume 15, Issue 5, p643-652, 6 Nov. 2014, Wang et al. (PLoS One. 2014 Dec. 26; 9 (12):e115987. doi: 10.1371/journal.pone.0115987), Fine et al. (Sci Rep. 2015 Jul. 1; 5:10777. doi: 10.1038/srep10777) and Li et al. (J Gen Virol. 2015 August; 96(8):2381-93. doi: 10.1099/vir.0.000139. Epub 2015 Apr. 8) for targeting CCR5 with the CRISPR Cas system of the present invention.

Treating Pathogens, e.g., Viral Pathogens, Such as HBV

The present invention may also be applied to treat hepatitis B virus (HBV). However, the CRISPR Cas system must be adapted to avoid the shortcomings of RNAi, such as the risk of oversatring endogenous small RNA pathways, by for example, optimizing dose and sequence (see, e.g., Grimm et al., Nature vol. 441, 26 May 2006). For example, low doses, such as about $1$-$10 \times 10^{14}$ particles per human are contemplated. In another embodiment, the CRISPR Cas system directed against HBV may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of CRISPR Cas targeted to HBV RNA in a SNALP are contemplated. The daily treatment may be over about three days and then weekly for about five weeks. In another embodiment, the system of Chen et al. (Gene Therapy (2007) 14, 11-19) may be used/and or adapted for the CRISPR Cas system of the present invention. Chen et al. use a double-stranded adeno-associated virus 8-pseudotyped vector (dsAAV2/8) to deliver shRNA. A single administration of dsAAV2/8 vector (1×1012 vector genomes per mouse), carrying HBV-specific shRNA, effectively suppressed the steady level of HBV protein, mRNA and replicative DNA in liver of HBV transgenic mice, leading to up to 2-3 log 10 decrease in HBV load in the circulation. Significant HBV suppression sustained for at least 120 days after vector administration. The therapeutic effect of shRNA was target sequence dependent and did not involve activation of interferon. For the present invention, a CRISPR Cas system directed to HBV may be cloned into an AAV vector, such as a dsAAV2/8 vector and administered to a human, for example, at a dosage of about 1×1015 vector genomes to about 1×1016 vector genomes per human. In another embodiment, the method of Wooddell et al. (Molecular Therapy vol. 21 no. 5, 973-985 May 2013) may be used/and or adapted to the CRISPR Cas system of the present invention. Woodell et al. show that simple coinjection of a hepatocyte-targeted, N-acetyl galactosamine-conjugated melittin-like peptide (NAG-MLP) with a liver-tropic cholesterol-conjugated siRNA (chol-siRNA) targeting coagulation factor VII (F7) results in efficient F7 knockdown in mice and nonhuman primates without changes in clinical chemistry or induction of cytokines. Using transient and transgenic mouse models of HBV infection, Wooddell et al. show that a single coinjection of NAG-MLP with potent chol-siRNAs targeting conserved HBV sequences resulted in multilog repression of viral RNA, proteins, and viral DNA with long duration of effect. Intravenous coinjections, for example, of about 6 mg/kg of NAG-MLP and 6 mg/kg of HBV specific CRISPR Cas may be envisioned for the present invention. In the alternative, about 3 mg/kg of NAG-MLP and 3 mg/kg of HBV specific CRISPR Cas may be delivered on day one, followed by administration of about 2-3 mg/kg of NAG-MLP and 2-3 mg/kg of HBV specific CRISPR Cas two weeks later.

In some embodiments, the target sequence is an HBV sequence. In some embodiments, the target sequences are comprised in an episomal viral nucleic acid molecule which is not integrated into the genome of the organism to thereby manipulate the episomal viral nucleic acid molecule. In some embodiments, the episomal nucleic acid molecule is a double-stranded DNA polynucleotide molecule or is a covalently closed circular DNA (cccDNA). In some embodiments, the CRISPR complex is capable of reducing the amount of episomal viral nucleic acid molecule in a cell of the organism compared to the amount of episomal viral nucleic acid molecule in a cell of the organism in the absence of providing the complex, or is capable of manipulating the episomal viral nucleic acid molecule to promote degradation of the episomal nucleic acid molecule. In some embodiments, the target HBV sequence is integrated into the genome of the organism. In some embodiments, when formed within the cell, the CRISPR complex is capable of manipulating the integrated nucleic acid to promote excision of all or part of the target HBV nucleic acid from the genome of the organism. In some embodiments, said at least one target HBV nucleic acid is comprised in a double-stranded DNA polynucleotide cccDNA molecule and/or viral DNA integrated into the genome of the organism and wherein the CRISPR complex manipulates at least one target HBV nucleic acid to cleave viral cccDNA and/or integrated viral DNA. In some embodiments, said cleavage comprises one or more double-strand break(s) introduced into the viral cccDNA and/or integrated viral DNA, optionally at least two double-strand break(s). In some embodiments, said cleavage is via one or more single-strand break(s) introduced into the viral cccDNA and/or integrated viral DNA, optionally at least two single-strand break(s). In some embodiments, said one or more double-strand break(s) or said one or more single-strand break(s) leads to the formation of one or more insertion or deletion mutations (INDELs) in the viral cccDNA sequences and/or integrated viral DNA sequences.

Lin et al. (Mol Ther Nucleic Acids. 2014 Aug. 19; 3:e186. doi: 10.1038/mtna.2014.38) designed eight gRNAs against HBV of genotype A. With the HBV-specific gRNAs, the CRISPR-Cas9 system significantly reduced the production of HBV core and surface proteins in Huh-7 cells transfected with an HBV-expression vector. Among eight screened gRNAs, two effective ones were identified. One gRNA targeting the conserved HBV sequence acted against different genotypes. Using a hydrodynamics-HBV persistence mouse model, Lin et al. further demonstrated that this system could cleave the intrahepatic HBV genome-containing plasmid and facilitate its clearance in vivo, resulting in reduction of serum surface antigen levels. These data suggest that the CRISPR-Cas9 system could disrupt the HBV-expressing templates both in vitro and in vivo, indicating its potential in eradicating persistent HBV infection.

Dong et al. (Antiviral Res. 2015 June; 118:110-7. doi: 10.1016/j.antiviral.2015.03.015. Epub 2015 Apr. 3) used the CRISPR-Cas9 system to target the HBV genome and efficiently inhibit HBV infection. Dong et al. synthesized four single-guide RNAs (guide RNAs) targeting the conserved regions of HBV. The expression of these guide RNAS with Cas9 reduced the viral production in Huh7 cells as well as in HBV-replication cell HepG2.2.15. Dong et al. further demonstrated that CRISPR-Cas9 direct cleavage and cleavage-mediated mutagenesis occurred in HBV cccDNA of transfected cells. In the mouse model carrying HBV cccDNA, injection of guide RNA-Cas9 plasmids via rapid tail vein resulted in the low level of cccDNA and HBV protein.

Liu et al. (J Gen Virol. 2015 August; 96(8):2252-61. doi: 10.1099/vir.0.000159. Epub 2015 Apr. 22) designed eight guide RNAs (gRNAs) that targeted the conserved regions of different HBV genotypes, which could significantly inhibit HBV replication both in vitro and in vivo to investigate the possibility of using the CRISPR-Cas9 system to disrupt the HBV DNA templates. The HBV-specific gRNA/Cpf1 system could inhibit the replication of HBV of different genotypes in cells, and the viral DNA was significantly reduced by a single gRNA/Cpf1 system and cleared by a combination of different gRNA/Cpf1 systems.

Wang et al. (World J Gastroenterol. 2015 Aug. 28; 21(32): 9554-65. doi: 10.3748/wjg.v21.i32.9554) designed 15 gRNAs against HBV of genotypes A-D. Eleven combinations of two above gRNAs (dual-gRNAs) covering the regulatory region of HBV were chosen. The efficiency of each gRNA and 11 dual-gRNAs on the suppression of HBV (genotypes A-D) replication was examined by the measurement of HBV surface antigen (HBsAg) or e antigen (HBeAg) in the culture supernatant. The destruction of HBV-expressing vector was examined in HuH7 cells co-transfected with dual-gRNAs and HBV-expressing vector using polymerase chain reaction (PCR) and sequencing method, and the destruction of cccDNA was examined in HepAD38 cells using KCl precipitation, plasmid-safe ATP-dependent DNase (PSAD) digestion, rolling circle amplification and quantitative PCR combined method. The cytotoxicity of these gRNAs was assessed by a mitochondrial tetrazolium assay. All of gRNAs could significantly reduce HBsAg or HBeAg production in the culture supernatant, which was dependent on the region in which gRNA against. All of dual gRNAs could efficiently suppress HBsAg and/or HBeAg production for HBV of genotypes A-D, and the efficacy of dual gRNAs in suppressing HBsAg and/or HBeAg production was significantly increased when compared to the single gRNA used alone. Furthermore, by PCR direct sequencing we confirmed that these dual gRNAs could specifically destroy HBV expressing template by removing the fragment between the cleavage sites of the two used gRNAs. Most importantly, gRNA-5 and gRNA-12 combination not only could efficiently suppress HBsAg and/or HBeAg production, but also destroy the cccDNA reservoirs in HepAD38 cells.

Karimova et al. (Sci Rep. 2015 Sep. 3; 5:13734. doi: 10.1038/srep13734) identified cross-genotype conserved HBV sequences in the S and X region of the HBV genome that were targeted for specific and effective cleavage by a Cas9 nickase. This approach disrupted not only episomal cccDNA and chromosomally integrated HBV target sites in reporter cell lines, but also HBV replication in chronically and de novo infected hepatoma cell lines.

One of skill in the art may utilize the above studies of, for example, Lin et al. (Mol Ther Nucleic Acids. 2014 Aug. 19; 3:e186. doi: 10.1038/mtna.2014.38), Dong et al. (Antiviral Res. 2015 June; 118:110-7. doi: 10.1016/j.antiviral.2015.03.015. Epub 2015 Apr. 3), Liu et al. (J Gen Virol. 2015 August; 96(8):2252-61. doi: 10.1099/vir.0.000159. Epub 2015 Apr. 22), Wang et al. (World J Gastroenterol. 2015 Aug. 28; 21(32):9554-65. doi: 10.3748/wjg.v21.i32.9554) and Karimova et al. (Sci Rep. 2015 Sep. 3; 5:13734. doi: 10.1038/srep13734) for targeting HBV with the CRISPR Cas system of the present invention.

Chronic hepatitis B virus (HBV) infection is prevalent, deadly, and seldom cured due to the persistence of viral episomal DNA (cccDNA) in infected cells. Ramanan et al. (Ramanan V, Shlomai A, Cox D B, Schwartz R E, Michailidis E, Bhatta A, Scott D A, Zhang F, Rice C M, Bhatia S N, Sci Rep. 2015 Jun. 2; 5:10833. doi: 10.1038/srep10833, published online 2nd June 2015.) showed that the CRISPR/Cas9 system can specifically target and cleave conserved regions in the HBV genome, resulting in robust suppression of viral gene expression and replication. Upon sustained expression of Cas9 and appropriately chosen guide RNAs, they demonstrated cleavage of cccDNA by Cas9 and a dramatic reduction in both cccDNA and other parameters of viral gene expression and replication. Thus, they showed that directly targeting viral episomal DNA is a novel therapeutic approach to control the virus and possibly cure patients. This is also described in WO 2015/089465 A1, in the name of The Broad Institute et al., the contents of which are hereby incorporated by reference As such targeting viral episomal DNA in HBV is preferred in some embodiments.

The present invention may also be applied to treat pathogens, e.g. bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

The present invention may also be applied to treat hepatitis C virus (HCV). The methods of Roelvinki et al. (Molecular Therapy vol. 20 no. 9, 1737-1749 September 2012) may be applied to the CRISPR Cas system. For example, an AAV vector such as AAV8 may be a contemplated vector and for example a dosage of about 1.25×1011 to 1.25×1013 vector genomes per kilogram body weight (vg/kg) may be contemplated. The present invention may also be applied to treat pathogens, e.g. bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

Jiang et al. ("RNA-guided editing of bacterial genomes using CRISPR-Cas systems," Nature Biotechnology vol. 31, p. 233-9, March 2013) used a CRISPR-Cas9 system to mutate or kill *S. pneumoniae* and *E. coli*. The work, which introduced precise mutations into the genomes, relied on dual-RNA:Cas9-directed cleavage at the targeted genomic site to kill unmutated cells and circumvented the need for selectable markers or counter-selection systems. CRISPR systems have be used to reverse antibiotic resistance and eliminate the transfer of resistance between strains. Bickard et al. showed that Cas9, reprogrammed to target virulence genes, kills virulent, but not avirulent, *S. aureus*. Reprogramming the nuclease to target antibiotic resistance genes destroyed staphylococcal plasmids that harbor antibiotic resistance genes and immunized against the spread of plasmid-borne resistance genes. (see Bikard et al., "Exploiting CRISPR-Cas nucleases to produce sequence-specific antimicrobials," Nature Biotechnology vol. 32, 1146-1150, doi: 10.1038/nbt.3043, published online 5 Oct. 2014.) Bikard showed that CRISPR-Cas9 antimicrobials function in vivo to kill *S. aureus* in a mouse skin colonization model. Similarly, Yosef et al used a CRISPR system to target genes encoding enzymes that confer resistance to β-lactam antibiotics (see Yousef et al., "Temperate and lytic bacteriophages programmed to sensitize and kill antibiotic-resistant bacteria," Proc. Natl. Acad. Sci. USA, vol. 112, p. 7267-7272, doi: 10.1073/pnas.1500107112 published online May 18, 2015).

CRISPR systems can be used to edit genomes of parasites that are resistant to other genetic approaches. For example, a CRISPR-Cas9 system was shown to introduce double-stranded breaks into the in the *Plasmodium yoelii* genome (see, Zhang et al., "Efficient Editing of Malaria Parasite Genome Using the CRISPR/Cas9 System," mBio. vol. 5, e01414-14, July-August 2014). Ghorbal et al. ("Genome editing in the human malaria parasite *Plasmodium falciparum* using the CRISPR-Cas9 system," Nature Biotechnology, vol. 32, p. 819-821, doi: 10.1038/nbt.2925, published online Jun. 1, 2014) modified the sequences of two genes, orc1 and kelch13, which have putative roles in gene silencing and emerging resistance to artemisinin, respectively. Parasites that were altered at the appropriate sites were recovered with very high efficiency, despite there being no direct selection for the modification, indicating that neutral or even deleterious mutations can be generated using this system. CRISPR-Cas9 is also used to modify the genomes of other pathogenic parasites, including *Toxo-*

*plasma gondii* (see Shen et al., "Efficient gene disruption in diverse strains of *Toxoplasma gondii* using CRISPR/CAS9," mBio vol. 5:e01114-14, 2014; and Sidik et al., "Efficient Genome Engineering of *Toxoplasma gondii* Using CRISPR/Cas9," PLoS One vol. 9, e100450, doi: 10.1371/journal-.pone.0100450, published online Jun. 27, 2014).

Vyas et al. ("A *Candida albicans* CRISPR system permits genetic engineering of essential genes and gene families," Science Advances, vol. 1, e1500248, DOI: 10.1126/sciadv.1500248, Apr. 3, 2015) employed a CRISPR system to overcome long-standing obstacles to genetic engineering in *C. albicans* and efficiently mutate in a single experiment both copies of several different genes. In an organism where several mechanisms contribute to drug resistance, Vyas produced homozygous double mutants that no longer displayed the hyper-resistance to fluconazole or cycloheximide displayed by the parental clinical isolate Can90. Vyas also obtained homozygous loss-of-function mutations in essential genes of *C. albicans* by creating conditional alleles. Null alleles of DCR1, which is required for ribosomal RNA processing, are lethal at low temperature but viable at high temperature. Vyas used a repair template that introduced a nonsense mutation and isolated dcr1/dcr1 mutants that failed to grow at 16° C.

Treating Diseases with Genetic or Epigenetic Aspects

The CRISPR-Cas systems of the present invention can be used to correct genetic mutations that were previously attempted with limited success using TALEN and ZFN and have been identified as potential targets for Cas9 systems, including as in published applications of Editas Medicine describing methods to use Cas9 systems to target loci to therapeutically address diseaes with gene therapy, including, WO 2015/048577 CRISPR-RELATED METHODS AND COMPOSITIONS of Gluckmann et al.; WO 2015/070083 CRISPR-RELATED METHODS AND COMPOSITIONS WITH GOVERNING gRNAS of Glucksmann et al. In some embodiments, the treatment, prophylaxis or diagnosis of Primary Open Angle Glaucoma (POAG) is provided. The target is preferably the MYOC gene. This is described in WO2015153780, the disclosure of which is hereby incorporated by reference.

Mention is made of WO2015/134812 CRISPR/CAS-RELATED METHODS AND COMPOSITIONS FOR TREATING USHER SYNDROME AND RETINITIS PIGMENTOSA of Maeder et al. Through the teachings herein the invention comprehends methods and materials of these documents applied in conjunction with the teachings herein. In an aspect of ocular and auditory gene therapy, methods and compositions for treating Usher Syndrome and Retinis-Pigmentosa may be adapted to the CRISPR-Cas system of the present invention (see, e.g., WO 2015/134812). In an embodiment, the WO 2015/134812 involves a treatment or delaying the onset or progression of Usher Syndrome type IIA (USH2A, USH11A) and retinitis pigmentosa 39 (RP39) by gene editing, e.g., using CRISPR-Cas9 mediated methods to correct the guanine deletion at position 2299 in the USH2A gene (e.g., replace the deleted guanine residue at position 2299 in the USH2A gene). A similar effect can be achieved with Cpf1. In a related aspect, a mutation is targeted by cleaving with either one or more nuclease, one or more nickase, or a combination thereof, e.g., to induce HDR with a donor template that corrects the point mutation (e.g., the single nucleotide, e.g., guanine, deletion). The alteration or correction of the mutant USH2A gene can be mediated by any mechanism. Exemplary mechanisms that can be associated with the alteration (e.g., correction) of the mutant HSH2A gene include, but are not limited to, non-homologous end joining, microhomology-mediated end joining (MMEJ), homology-directed repair (e.g., endogenous donor template mediated), SDSA (synthesis dependent strand annealing), single-strand annealing or single strand invasion. In an embodiment, the method used for treating Usher Syndrome and Retinis-Pigmentosa can include acquiring knowledge of the mutation carried by the subject, e.g., by sequencing the appropriate portion of the USH2A gene.

Accordingly, in some embodiments, the treatment, prophylaxis or diagnosis of Retinitis Pigmentosa is provided. A number of different genes are known to be associated with or result in Retinitis Pigmentosa, such as RP1, RP2 and so forth. These genes are targeted in some embodiments and either knocked out or repaired through provision of suitable a template. In some embodiments, delivery is to the eye by injection.

One or more Retinitis Pigmentosa genes can, in some embodiments, be selected from: RP1 (Retinitis pigmentosa-1), RP2 (Retinitis pigmentosa-2), RPGR (Retinitis pigmentosa-3), PRPH2 (Retinitis pigmentosa-7), RP9 (Retinitis pigmentosa-9), IMPDH1 (Retinitis pigmentosa-10), PRPF31 (Retinitis pigmentosa-11), CRB1 (Retinitis pigmentosa-12, autosomal recessive), PRPF8 (Retinitis pigmentosa-13), TULP1 (Retinitis pigmentosa-14), CA4 (Retinitis pigmentosa-17), HPRPF3 (Retinitis pigmentosa-18), ABCA4 (Retinitis pigmentosa-19), EYS (Retinitis pigmentosa-25), CERKL (Retinitis pigmentosa-26), FSCN2 (Retinitis pigmentosa-30), TOPORS (Retinitis pigmentosa-31), SNRNP200 (Retinitis pigmentosa 33), SEMA4A (Retinitis pigmentosa-35), PRCD (Retinitis pigmentosa-36), NR2E3 (Retinitis pigmentosa-37), MERTK (Retinitis pigmentosa-38), USH2A (Retinitis pigmentosa-39), PROM1 (Retinitis pigmentosa-41), KLHL7 (Retinitis pigmentosa-42), CNGB1 (Retinitis pigmentosa-45), BEST1 (Retinitis pigmentosa-50), TTC8 (Retinitis pigmentosa 51), C2orf71 (Retinitis pigmentosa 54), ARL6 (Retinitis pigmentosa 55), ZNF513 (Retinitis pigmentosa 58), DHDDS (Retinitis pigmentosa 59), BEST1 (Retinitis pigmentosa, concentric), PRPH2 (Retinitis pigmentosa, digenic), LRAT (Retinitis pigmentosa, juvenile), SPATA7 (Retinitis pigmentosa, juvenile, autosomal recessive), CRX (Retinitis pigmentosa, late-onset dominant), and/or RPGR (Retinitis pigmentosa, X-linked, and sinorespiratory infections, with or without deafness).

In some embodiments, the Retinitis Pigmentosa gene is MERTK (Retinitis pigmentosa-38) or USH2A (Retinitis pigmentosa-39).

Mention is also made of WO 2015/138510 and through the teachings herein the invention (using a CRISPR-Cas9 system) comprehends providing a treatment or delaying the onset or progression of Leber's Congenital Amaurosis 10 (LCA 10). LCA 10 is caused by a mutation in the CEP290 gene, e.g., a c.2991+1655, adenine to guanine mutation in the CEP290 gene which gives rise to a cryptic splice site in intron 26. This is a mutation at nucleotide 1655 of intron 26 of CEP290, e.g., an A to G mutation. CEP290 is also known as: CT87; MKS4; POC3; rdl6; BBS14; JBTS5; LCAJO; NPHP6; SLSN6; and 3H11Ag (see, e.g., WO 2015/138510). In an aspect of gene therapy, the invention involves introducing one or more breaks near the site of the LCA target position (e.g., c.2991+1655; A to G) in at least one allele of the CEP290 gene. Altering the LCA10 target position refers to (1) break-induced introduction of an indel (also referred to herein as NHEJ-mediated introduction of an indel) in close proximity to or including a LCA10 target position (e.g., c.2991+1655A to G), or (2) break-induced deletion (also referred to herein as NHEJ-mediated deletion) of genomic sequence including the mutation at a LCA10 target position (e.g., c.2991+1655A to G). Both approaches give rise to the loss or destruction of the cryptic splice site resulting from the mutation at the LCA 10 target position. Accordingly, the use of Cpf1 in the treatment of LCA is specifically envisaged.

Researchers are contemplating whether gene therapies could be employed to treat a wide range of diseases. The CRISPR systems of the present invention based on Cpf1 effector protein are envisioned for such therapeutic uses including, but not limited to, further exemplified targeted areas and with delivery methods as below. Some examples of conditions or diseases that might be usefully treated using the present system are included in the examples of genes and references included herein and are currently associated with those conditions are also provided there. The genes and conditions exemplified are not exhaustive.

Treating Diseases of the Circulatory System

The present invention also contemplates delivering the CRISPR-Cas system, specifically the novel CRISPR effector protein systems described herein, to the blood or hematopoetic stem cells. The plasma exosomes of Wahlgren et al. (Nucleic Acids Research, 2012, Vol. 40, No. 17 e130) were previously described and may be utilized to deliver the CRISPR Cas system to the blood. The nucleic acid-targeting system of the present invention is also contemplated to treat hemoglobinopathies, such as thalassemias and sickle cell disease. See, e.g., International Patent Publication No. WO 2013/126794 for potential targets that may be targeted by the CRISPR Cas system of the present invention.

Drakopoulou, "Review Article, The Ongoing Challenge of Hematopoietic Stem Cell-Based Gene Therapy for β-Thalassemia," Stem Cells International, Volume 2011, Article ID 987980, 10 pages, doi:10.4061/2011/987980, incorporated herein by reference along with the documents it cites, as if set out in full, discuss modifying HSCs using a lentivirus that delivers a gene for β-globin or γ-globin. In contrast to using lentivirus, with the knowledge in the art and the teachings in this disclosure, the skilled person can correct HSCs as to β-Thalassemia using a CRISPR-Cas system that targets and corrects the mutation (e.g., with a suitable HDR template that delivers a coding sequence for β-globin or γ-globin, advantageously non-sickling β-globin or γ-globin); specifically, the guide RNA can target mutation that give rise to β-Thalassemia, and the HDR can provide coding for proper expression of β-globin or γ-globin. A guide RNA that targets the mutation-and-Cas protein containing particle is contacted with HSCs carrying the mutation. The particle also can contain a suitable HDR template to correct the mutation for proper expression of β-globin or γ-globin; or the HSC can be contacted with a second particle or a vector that contains or delivers the HDR template. The so contacted cells can be administered; and optionally treated/expanded; cf. Cartier. In this regard mention is made of: Cavazzana, "Outcomes of Gene Therapy for β-Thalassemia Major via Transplantation of Autologous Hematopoietic Stem Cells Transduced Ex Vivo with a Lentiviral βA-T87Q-Globin Vector." tif2014.org/abstractFiles/Jean %20Antoine %20Ribeil_Abstract.pdf; Cavazzana-Calvo, "Transfusion independence and HMGA2 activation after gene therapy of human 0-thalassaemia", Nature 467, 318-322 (16 Sep. 2010) doi:10.1038/nature09328; Nienhuis, "Development of Gene Therapy for Thalassemia, Cold Spring Harbor Perpsectives in Medicine, doi: 10.1101/cshperspect.a011833 (2012), LentiGlobin BB305, a lentiviral vector containing an engineered β-globin gene (βA-T87Q); and Xie et al., "Seamless gene correction of 0-thalassaemia mutations in patient-specific iPSCs using CRISPR/Cas9 and piggyback" Genome Research gr.173427.114 (2014) http://www.genome.org/cgi/doi/10.1101/gr.173427.114 (Cold Spring Harbor Laboratory Press); that is the subject of Cavazzana work involving human 0-thalassaemia and the subject of the Xie work, are all incorporated herein by reference, together with all documents cited therein or associated therewith. In the instant invention, the HDR template can provide for the HSC to express an engineered β-globin gene (e.g., βA-T87Q), or β-globin as in Xie.

Xu et al. (Sci Rep. 2015 Jul. 9; 5:12065. doi: 10.1038/srep12065) have designed TALENs and CRISPR-Cas9 to directly target the intron2 mutation site IVS2-654 in the globin gene. Xu et al. observed different frequencies of double-strand breaks (DSBs) at IVS2-654 loci using TALENs and CRISPR-Cas9, and TALENs mediated a higher homologous gene targeting efficiency compared to CRISPR-Cas9 when combined with the piggyBac transposon donor. In addition, more obvious off-target events were observed for CRISPR-Cas9 compared to TALENs. Finally, TALENs-corrected iPSC clones were selected for erythroblast differentiation using the OP9 co-culture system and detected relatively higher transcription of HBB than the uncorrected cells.

Song et al. (Stem Cells Dev. 2015 May 1; 24(9):1053-65. doi: 10.1089/scd.2014.0347. Epub 2015 Feb. 5) used CRISPR/Cas9 to correct β-Thal iPSCs; gene-corrected cells exhibit normal karyotypes and full pluripotency as human embryonic stem cells (hESCs) showed no off-targeting effects. Then, Song et al. evaluated the differentiation efficiency of the gene-corrected β-Thal iPSCs. Song et al. found that during hematopoietic differentiation, gene-corrected β-Thal iPSCs showed an increased embryoid body ratio and various hematopoietic progenitor cell percentages. More importantly, the gene-corrected β-Thal iPSC lines restored HBB expression and reduced reactive oxygen species production compared with the uncorrected group. Song et al.'s study suggested that hematopoietic differentiation efficiency of β-Thal iPSCs was greatly improved once corrected by the CRISPR-Cas9 system. Similar methods may be performed utilizing the CRISPR-Cas systems described herein, e.g. systems comprising Cpf1 effector proteins.

Sickle cell anemia is an autosomal recessive genetic disease in which red blood cells become sickle-shaped. It is caused by a single base substitution in the β-globin gene, which is located on the short arm of chromosome 11. As a result, valine is produced instead of glutamic acid causing the production of sickle hemoglobin (HbS). This results in the formation of a distorted shape of the erythrocytes. Due to this abnormal shape, small blood vessels can be blocked, causing serious damage to the bone, spleen and skin tissues. This may lead to episodes of pain, frequent infections, hand-foot syndrome or even multiple organ failure. The distorted erythrocytes are also more susceptible to hemolysis, which leads to serious anemia. As in the case of β-thalassaemia, sickle cell anemia can be corrected by modifying HSCs with the CRISPR-Cas system. The system allows the specific editing of the cell's genome by cutting its DNA and then letting it repair itself. The Cas protein is inserted and directed by an RNA guide to the mutated point and then it cuts the DNA at that point. Simultaneously, a healthy version of the sequence is inserted. This sequence is used by the cell's own repair system to fix the induced cut. In this way, the CRISPR-Cas allows the correction of the mutation in the previously obtained stem cells. With the knowledge in the art and the teachings in this disclosure, the skilled person can correct HSCs as to sickle cell anemia using a CRISPR-Cas system that targets and corrects the mutation (e.g., with a suitable HDR template that delivers a coding sequence for β-globin, advantageously non-sickling β-globin); specifically, the guide RNA can target mutation that give rise to sickle cell anemia, and the HDR can provide coding for proper expression of β-globin. A guide RNA that targets the mutation-and-Cas protein containing particle is contacted with HSCs carrying the mutation. The particle also can contain a suitable HDR template to correct the mutation for proper expression of β-globin; or the HSC can be contacted with a second particle or a vector that contains or delivers the HDR template. The so contacted cells can be administered; and optionally treated/expanded; cf. Cartier. The HDR template can provide for the HSC to express an engineered β-globin gene (e.g., βA-T87Q), or β-globin as in Xie.

Williams, "Broadening the Indications for Hematopoietic Stem Cell Genetic Therapies," Cell Stem Cell 13:263-264 (2013), incorporated herein by reference along with the documents it cites, as if set out in full, report lentivirus-mediated gene transfer into HSC/P cells from patients with the lysosomal storage disease metachromatic leukodystrophy disease (MLD), a genetic disease caused by deficiency of arylsulfatase A (ARSA), resulting in nerve demyelination; and lentivirus-mediated gene transfer into HSCs of patients with Wiskott-Aldrich syndrome (WAS) (patients with defective WAS protein, an effector of the small GTPase CDC42 that regulates cytoskeletal function in blood cell lineages and thus suffer from immune deficiency with recurrent infections, autoimmune symptoms, and thrombocytopenia with abnormally small and dysfunctional platelets leading to excessive bleeding and an increased risk of leukemia and lymphoma). In contrast to using lentivirus, with the knowledge in the art and the teachings in this disclosure, the skilled person can correct HSCs as to MLD (deficiency of arylsulfatase A (ARSA)) using a CRISPR-Cas system that targets and corrects the mutation (deficiency of arylsulfatase A (ARSA)) (e.g., with a suitable HDR template that delivers a coding sequence for ARSA); specifically, the guide RNA can target mutation that gives rise to MLD (deficient ARSA), and the HDR can provide coding for proper expression of ARSA. A guide RNA that targets the mutation-and-Cas protein containing particle is contacted with HSCs carrying the mutation. The particle also can contain a suitable HDR template to correct the mutation for proper expression of ARSA; or the HSC can be contacted with a second particle or a vector that contains or delivers the HDR template. The so contacted cells can be administered; and optionally treated/expanded; cf. Cartier. In contrast to using lentivirus, with the knowledge in the art and the teachings in this disclosure, the skilled person can correct HSCs as to WAS using a CRISPR-Cas system that targets and corrects the mutation (deficiency of WAS protein) (e.g., with a suitable HDR template that delivers a coding sequence for WAS protein); specifically, the guide RNA can target mutation that gives rise to WAS (deficient WAS protein), and the HDR can provide coding for proper expression of WAS protein. A guide RNA that targets the mutation-and-Cpf1 protein containing particle is contacted with HSCs carrying the mutation. The particle also can contain a suitable HDR template to correct the mutation for proper expression of WAS protein; or the HSC can be contacted with a second particle or a vector that contains or delivers the HDR template. The so contacted cells can be administered; and optionally treated/expanded; cf. Cartier.

Watts, "Hematopoietic Stem Cell Expansion and Gene Therapy" Cytotherapy 13(10):1164-1171. doi:10.3109/14653249.2011.620748 (2011), incorporated herein by reference along with the documents it cites, as if set out in full, discusses hematopoietic stem cell (HSC) gene therapy, e.g., virus-mediated HSC gene therapy, as highly attractive treatment option for many disorders including hematologic conditions, immunodeficiencies including HIV/AIDS, and other genetic disorders like lysosomal storage diseases, including SCID-X1, ADA-SCID, β-thalassemia, X-linked CGD, Wiskott-Aldrich syndrome, Fanconi anemia, adrenoleukodystrophy (ALD), and metachromatic leukodystrophy (MLD).

US Patent Publication Nos. 20110225664, 20110091441, 20100229252, 20090271881 and 20090222937 assigned to Cellectis, relates to CREI variants, wherein at least one of the two I-CreI monomers has at least two substitutions, one in each of the two functional subdomains of the LAGLIDADG (SEQ ID NO: 127) core domain situated respectively from positions 26 to 40 and 44 to 77 of I-CreI, said variant being able to cleave a DNA target sequence from the human interleukin-2 receptor gamma chain (IL2RG) gene also named common cytokine receptor gamma chain gene or gamma C gene. The target sequences identified in US Patent Publication Nos. 20110225664, 20110091441, 20100229252, 20090271881 and 20090222937 may be utilized for the nucleic acid-targeting system of the present invention.

Severe Combined Immune Deficiency (SCID) results from a defect in lymphocytes T maturation, always associated with a functional defect in lymphocytes B (Cavazzana-Calvo et al., Annu. Rev. Med., 2005, 56, 585-602; Fischer et al., Immunol. Rev., 2005, 203, 98-10$^9$). Overall incidence is estimated to 1 in 75 000 births. Patients with untreated SCID are subject to multiple opportunist micro-organism infections, and do generally not live beyond one year. SCID can be treated by allogenic hematopoietic stem cell transfer, from a familial donor. Histocompatibility with the donor can vary widely. In the case of Adenosine Deaminase (ADA) deficiency, one of the SCID forms, patients can be treated by injection of recombinant Adenosine Deaminase enzyme.

Since the ADA gene has been shown to be mutated in SCID patients (Giblett et al., Lancet, 1972, 2, 1067-1069), several other genes involved in SCID have been identified (Cavazzana-Calvo et al., Annu. Rev. Med., 2005, 56, 585-602; Fischer et al., Immunol. Rev., 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., Cell, 1993, 73, 147-157), a common component of at least five interleukin receptor complexes. These receptors activate several targets through the JAK3 kinase (Macchi et al., Nature, 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes involved in this process, result in the absence of mature T and B lymphocytes; and (iv) Mutations in other genes such as CD45, involved in T cell specific signaling have also been reported, although they represent a minority of cases (Cavazzana-Calvo et al., Annu.

Rev. Med., 2005, 56, 585-602; Fischer et al., Immunol. Rev., 2005, 203, 98-109). Since when their genetic bases have been identified, the different SCID forms have become a paradigm for gene therapy approaches (Fischer et al., Immunol. Rev., 2005, 203, 98-109) for two major reasons. First, as in all blood diseases, an ex vivo treatment can be envisioned. Hematopoietic Stem Cells (HSCs) can be recovered from bone marrow, and keep their pluripotent properties for a few cell divisions. Therefore, they can be treated in vitro, and then reinjected into the patient, where they repopulate the bone marrow. Second, since the maturation of lymphocytes is impaired in SCID patients, corrected cells have a selective advantage. Therefore, a small number of corrected cells can restore a functional immune system. This hypothesis was validated several times by (i) the partial restoration of immune functions associated with the reversion of mutations in SCID patients (Hirschhorn et al., Nat. Genet., 1996, 13, 290-295; Stephan et al., N. Engl. J. Med., 1996, 335, 1563-1567; Bousso et al., Proc. Natl., Acad. Sci. USA, 2000, 97, 274-278; Wada et al., Proc. Natl. Acad. Sci. USA, 2001, 98, 8697-8702; Nishikomori et al., Blood, 2004, 103, 4565-4572), (ii) the correction of SCID-X1 deficiencies in vitro in hematopoietic cells (Candotti et al., Blood, 1996, 87, 3097-3102; Cavazzana-Calvo et al., Blood, 1996, Blood, 88, 3901-3909; Taylor et al., Blood, 1996, 87, 3103-3107; Hacein-Bey et al., Blood, 1998, 92, 4090-4097), (iii) the correction of SCID-X1 (Soudais et al., Blood, 2000, 95, 3071-3077; Tsai et al., Blood, 2002, 100, 72-79), JAK-3 (Bunting et al., Nat. Med., 1998, 4, 58-64; Bunting et al., Hum. Gene Ther., 2000, 11, 2353-2364) and RAG2 (Yates et al., Blood, 2002, 100, 3942-3949) deficiencies in vivo in animal models and (iv) by the result of gene therapy clinical trials (Cavazzana-Calvo et al., Science, 2000, 288, 669-672; Aiuti et al., Nat. Med., 2002; 8, 423-425; Gaspar et al., Lancet, 2004, 364, 2181-2187).

US Patent Publication No. 20110182867 assigned to the Children's Medical Center Corporation and the President and Fellows of Harvard College relates to methods and uses of modulating fetal hemoglobin expression (HbF) in a hematopoietic progenitor cells via inhibitors of BCL11A expression or activity, such as RNAi and antibodies. The targets disclosed in US Patent Publication No. 20110182867, such as BCL11A, may be targeted by the CRISPR Cas system of the present invention for modulating fetal hemoglobin expression. See also Bauer et al. (Science 11 Oct. 2013: Vol. 342 no. 6155 pp. 253-257) and Xu et al. (Science 18 Nov. 2011: Vol. 334 no. 6058 pp. 993-996) for additional BCL11A targets.

With the knowledge in the art and the teachings in this disclosure, the skilled person can correct HSCs as to a genetic hematologic disorder, e.g., β-Thalassemia, Hemophilia, or a genetic lysosomal storage disease.

Delivery to and Editing of Hematopoietic Stem Cells Using a CRISPR-Cas System and/or Component Thereof The term "Hematopoietic Stem Cell" or "HSC" is meant to include broadly those cells considered to be an HSC, e.g., blood cells that give rise to all the other blood cells and are derived from mesoderm; located in the red bone marrow, which is contained in the core of most bones. HSCs of the invention include cells having a phenotype of hematopoietic stem cells, identified by small size, lack of lineage (lin) markers, and markers that belong to the cluster of differentiation series, like: CD34, CD38, CD90, CD133, CD105, CD45, and also c-kit,—the receptor for stem cell factor. Hematopoietic stem cells are negative for the markers that are used for detection of lineage commitment, and are, thus, called Lin-; and, during their purification by FACS, a number of up to 14 different mature blood-lineage markers, e.g., CD13 & CD33 for myeloid, CD71 for erythroid, CD19 for B cells, CD61 for megakaryocytic, etc. for humans; and, B220 (murine CD45) for B cells, Mac-1 (CD11b/CD18) for monocytes, Gr-1 for Granulocytes, Ter119 for erythroid cells, Il7Ra, CD3, CD4, CD5, CD8 for T cells, etc. Mouse HSC markers: CD34lo/-, SCA-1+, Thy1.1+/lo, CD38+, C-kit+, lin-, and Human HSC markers: CD34+, CD59+, Thy1/CD90+, CD38lo/-, C-kit/CD117+, and lin-. HSCs are identified by markers. Hence in embodiments discussed herein, the HSCs can be CD34+ cells. HSCs can also be hematopoietic stem cells that are CD34-/CD38-. Stem cells that may lack c-kit on the cell surface that are considered in the art as HSCs are within the ambit of the invention, as well as CD133+ cells likewise considered HSCs in the art.

The CRISPR-Cas (e.g., Cpf1) system may be engineered to target genetic locus or loci in HSCs. Cas (e.g., Cpf1) protein, advantageously codon-optimized for a eukaryotic cell and especially a mammalian cell, e.g., a human cell, for instance, HSC, and sgRNA targeting a locus or loci in HSC, e.g., the gene EMX1, may be prepared. These may be delivered via particles. The particles may be formed by the Cas (e.g., Cpf1) protein and the gRNA being admixed. The gRNA and Cas (e.g., Cpf1) protein mixture may for example be admixed with a mixture comprising or consisting essentially of or consisting of surfactant, phospholipid, biodegradable polymer, lipoprotein and alcohol, whereby particles containing the gRNA and Cas (e.g., Cpf1) protein may be formed. The invention comprehends so making particles and particles from such a method as well as uses thereof.

More generally, particles may be formed using an efficient process. First, Cas (e.g., Cpf1) protein and gRNA targeting the gene EMX1 or the control gene LacZ may be mixed together at a suitable, e.g., 3:1 to 1:3 or 2:1 to 1:2 or 1:1 molar ratio, at a suitable temperature, e.g., 15-30° C., e.g., 20-25° C., e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol may be dissolved in an alcohol, advantageously a C1-6 alkyl alcohol, such as methanol, ethanol, isopropanol, e.g., 100% ethanol. The two solutions may be mixed together to form particles containing the Cas (e.g., Cpf1)-gRNA complexes. In certain embodiments, the particle can contain an HDR template. That can be a particle co-administered with gRNA+Cas (e.g., Cpf1) protein-containing particle, or i.e., in addition to contacting an HSC with an gRNA+Cas (e.g., Cpf1) protein-containing particle, the HSC is contacted with a particle containing an HDR template; or the HSC is contacted with a particle containing all of the gRNA, Cas (e.g., Cpf1) and the HDR template. The HDR template can be administered by a separate vector, whereby in a first instance the particle penetrates an HSC cell, and the separate vector also penetrates the cell, wherein the HSC genome is modified by the gRNA+Cas (e.g., Cpf1) and the HDR template is also present, whereby a genomic locus is modified by the HDR; for instance, this may result in correcting a mutation.

After the particles form, HSCs in 96 well plates may be transfected with 15 μg Cas (e.g., Cpf1) protein per well. Three days after transfection, HSCs may be harvested, and the number of insertions and deletions (indels) at the EMX1 locus may be quantified.

This illustrates how HSCs can be modified using CRISPR-Cas (e.g., Cpf1) targeting a genomic locus or loci of interest in the HSC. The HSCs that are to be modified can be in vivo, i.e., in an organism, for example a human or a non-human eukaryote, e.g., animal, such as fish, e.g., zebra fish, mammal, e.g., primate, e.g., ape, chimpanzee, macaque, rodent, e.g., mouse, rabbit, rat, canine or dog, livestock (cow/bovine, sheep/ovine, goat or pig), fowl or poultry, e.g., chicken. The HSCs that are to be modified can be in vitro, i.e., outside of such an organism. And, modified HSCs can be used ex vivo, i.e., one or more HSCs of such an organism can be obtained or isolated from the organism, optionally the HSC(s) can be expanded, the HSC(s) are modified by a composition comprising a CRISPR-Cas (e.g., Cpf1) that targets a genetic locus or loci in the HSC, e.g., by contacting the HSC(s) with the composition, for instance, wherein the composition comprises a particle containing the CRISPR enzyme and one or more gRNA that targets the genetic locus or loci in the HSC, such as a particle obtained or obtainable from admixing an gRNA and Cas (e.g., Cpf1) protein mixture with a mixture comprising or consisting essentially of or consisting of surfactant, phospholipid, biodegradable polymer, lipoprotein and alcohol (wherein one or more gRNA targets the genetic locus or loci in the HSC), optionally expanding the resultant modified HSCs and administering to the organism the resultant modified HSCs. In some instances, the isolated or obtained HSCs can be from a first organism, such as an organism from a same species as a second organism, and the second organism can be the organism to which the resultant modified HSCs are administered, e.g., the first organism can be a donor (such as a relative as in a parent or sibling) to the second organism. Modified HSCs can have genetic modifications to address or alleviate or reduce symptoms of a disease or condition state of an individual or subject or patient. Modified HSCs, e.g., in the instance of a first organism donor to a second organism, can have genetic modifications to have the HSCs have one or more proteins e.g. surface markers or proteins more like that of the second organism. Modified HSCs can have genetic modifications to simulate a disease or condition state of an individual or subject or patient and would be re-administered to a non-human organism so as to prepare an animal model. Expansion of HSCs is within the ambit of the skilled person from this disclosure and knowledge in the art, see e.g., Lee, "Improved ex vivo expansion of adult hematopoietic stem cells by overcoming CUL4-mediated degradation of HOXB4." Blood. 2013 May 16; 121(20):4082-9. doi: 10.1182/blood-2012-09-455204. Epub 2013 Mar. 21.

As indicated to improve activity, gRNA may be pre-complexed with the Cas (e.g., Cpf1) protein, before formulating the entire complex in a particle. Formulations may be made with a different molar ratio of different components known to promote delivery of nucleic acids into cells (e.g., 1,2-dioleoyl-3-trimethylammonium-propane (DOTAP), 1,2-ditetradecanoyl-sn-glycero-3-phosphocholine (DMPC), polyethylene glycol (PEG), and cholesterol) For example, DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. The invention accordingly comprehends admixing gRNA, Cas (e.g., Cpf1) protein and components that form a particle; as well as particles from such admixing.

In a preferred embodiment, particles containing the Cas (e.g., Cpf1)-gRNA complexes may be formed by mixing Cas (e.g., Cpf1) protein and one or more gRNAs together, preferably at a 1:1 molar ratio, enzyme: guide RNA. Separately, the different components known to promote delivery of nucleic acids (e.g., DOTAP, DMPC, PEG, and cholesterol) are dissolved, preferably in ethanol. The two solutions are mixed together to form particles containing the Cas (e.g., Cpf1)-gRNA complexes. After the particles are formed, Cas (e.g., Cpf1)-gRNA complexes may be transfected into cells (e.g., HSCs). Bar coding may be applied. The particles, the Cas-9 and/or the gRNA may be barcoded.

The invention in an embodiment comprehends a method of preparing an gRNA-and-Cas (e.g., Cpf1) protein containing particle comprising admixing an gRNA and Cas (e.g., Cpf1) protein mixture with a mixture comprising or consisting essentially of or consisting of surfactant, phospholipid, biodegradable polymer, lipoprotein and alcohol. An embodiment comprehends an gRNA-and-Cas (e.g., Cpf1) protein containing particle from the method. The invention in an embodiment comprehends use of the particle in a method of modifying a genomic locus of interest, or an organism or a non-human organism by manipulation of a target sequence in a genomic locus of interest, comprising contacting a cell containing the genomic locus of interest with the particle wherein the gRNA targets the genomic locus of interest; or a method of modifying a genomic locus of interest, or an organism or a non-human organism by manipulation of a target sequence in a genomic locus of interest, comprising contacting a cell containing the genomic locus of interest with the particle wherein the gRNA targets the genomic locus of interest. In these embodiments, the genomic locus of interest is advantageously a genomic locus in an HSC.

Considerations for Therapeutic Applications of a CRISPR-Cas System

A consideration in genome editing therapy is the choice of sequence-specific nuclease, such as a variant of a Cpf1 nuclease. Each nuclease variant may possess its own unique set of strengths and weaknesses, many of which must be balanced in the context of treatment to maximize therapeutic benefit. Thus far, two therapeutic editing approaches with nucleases have shown significant promise: gene disruption and gene correction. Gene disruption involves stimulation of NHEJ to create targeted indels in genetic elements, often resulting in loss of function mutations that are beneficial to patients. In contrast, gene correction uses HDR to directly reverse a disease-causing mutation, restoring function while preserving physiological regulation of the corrected element. HDR may also be used to insert a therapeutic transgene into a defined 'safe harbor' locus in the genome to recover missing gene function. For a specific editing therapy to be efficacious, a sufficiently high level of modification must be achieved in target cell populations to reverse disease symptoms. This therapeutic modification 'threshold' is determined by the fitness of edited cells following treatment and the amount of gene product necessary to reverse symptoms. With regard to fitness, editing creates three potential outcomes for treated cells relative to their unedited counterparts: increased, neutral, or decreased fitness. In the case of increased fitness, for example in the treatment of SCID-X1, modified hematopoietic progenitor cells selectively expand relative to their unedited counterparts. SCID-X1 is a disease caused by mutations in the IL2RG gene, the function of which is required for proper development of the hematopoietic lymphocyte lineage [Leonard, W. J., et al. Immunological reviews 138, 61-86 (1994); Kaushansky, K. & Williams, W. J. Williams hematology, (McGraw-Hill Medical, New York, 2010)]. In clinical trials with patients who received viral gene therapy for SCID-X1, and a rare example of a spontaneous correction of SCID-X1 mutation, corrected hematopoietic progenitor cells may be able to overcome this developmental block and expand relative to their diseased counterparts to mediate therapy [Bousso, P., et al. Proceedings of the National Academy of Sciences of the United States of America 97, 274-278 (2000); Hacein-Bey-Abina, S., et al. The New England journal of medicine 346, 1185-1193 (2002); Gaspar, H. B., et al. Lancet 364, 2181-2187 (2004)]. In this case, where edited cells possess a selective advantage, even low numbers of edited cells can be amplified through expansion, providing a therapeutic benefit to the patient. In contrast, editing for other hematopoietic diseases, like chronic granulomatous disorder (CGD), would induce no change in fitness for edited hematopoietic progenitor cells, increasing the therapeutic modification threshold. CGD is caused by mutations in genes encoding phagocytic oxidase proteins, which are normally used by neutrophils to generate reactive oxygen species that kill pathogens [Mukherjee, S. & Thrasher, A. J. Gene 525, 174-181 (2013)]. As dysfunction of these genes does not influence hematopoietic progenitor cell fitness or development, but only the ability of a mature hematopoietic cell type to fight infections, there would be likely no preferential expansion of edited cells in this disease. Indeed, no selective advantage for gene corrected cells in CGD has been observed in gene therapy trials, leading to difficulties with long-term cell engraftment [Malech, H. L., et al. Proceedings of the National Academy of Sciences of the United States of America 94, 12133-12138 (1997); Kang, H. J., et al. Molecular therapy: the journal of the American Society of Gene Therapy 19, 2092-2101 (2011)]. As such, significantly higher levels of editing would be required to treat diseases like CGD, where editing creates a neutral fitness advantage, relative to diseases where editing creates increased fitness for target cells. If editing imposes a fitness disadvantage, as would be the case for restoring function to a tumor suppressor gene in cancer cells, modified cells would be outcompeted by their diseased counterparts, causing the benefit of treatment to be low relative to editing rates. This latter class of diseases would be particularly difficult to treat with genome editing therapy.

In addition to cell fitness, the amount of gene product necessary to treat disease also influences the minimal level of therapeutic genome editing that must be achieved to reverse symptoms. Haemophilia B is one disease where a small change in gene product levels can result in significant changes in clinical outcomes. This disease is caused by mutations in the gene encoding factor IX, a protein normally secreted by the liver into the blood, where it functions as a component of the clotting cascade. Clinical severity of haemophilia B is related to the amount of factor IX activity. Whereas severe disease is associated with less than 1% of normal activity, milder forms of the diseases are associated with greater than 1% of factor IX activity [Kaushansky, K. & Williams, W. J. Williams hematology, (McGraw-Hill Medical, New York, 2010); Lofqvist, T., et al. Journal of internal medicine 241, 395-400 (1997)]. This suggests that editing therapies that can restore factor IX expression to even a small percentage of liver cells could have a large impact on clinical outcomes. A study using ZFNs to correct a mouse model of haemophilia B shortly after birth demonstrated that 3-7% correction was sufficient to reverse disease symptoms, providing preclinical evidence for this hypothesis [Li, H., et al. Nature 475, 217-221 (2011)].

Disorders where a small change in gene product levels can influence clinical outcomes and diseases where there is a fitness advantage for edited cells, are ideal targets for genome editing therapy, as the therapeutic modification threshold is low enough to permit a high chance of success given the current technology. Targeting these diseases has now resulted in successes with editing therapy at the preclinical level and a phase I clinical trial. Improvements in DSB repair pathway manipulation and nuclease delivery are needed to extend these promising results to diseases with a neutral fitness advantage for edited cells, or where larger amounts of gene product are needed for treatment Table 16 shows some examples of applications of genome editing to therapeutic models, and the references of Table 16 and the documents cited in those references are hereby incorporated herein by reference as if set out in full.

TABLE 16

| Disease Type | Nuclease Platform Employed | Therapeutic Strategy | References |
|---|---|---|---|
| Hemophilia B | ZFN | HDR-mediated insertion of correct gene sequence | Li, H., et al. Nature 475, 217-221 (2011) |
| SCID | ZFN | HDR-mediated insertion of correct gene sequence | Genovese, P., et al. Nature 510, 235-240 (2014) |
| Hereditary tyrosinemia | CRISPR | HDR-mediated correction of mutation in liver | Yin, H., et al. Nature biotechnology 32, 551-553 (2014) |

Addressing each of the conditions of the foregoing table, using the CRISPR-Cas (eg Cpf1) system to target by either HDR-mediated correction of mutation, or HDR-mediated insertion of correct gene sequence, advantageously via a delivery system as herein, e.g., a particle delivery system, is within the ambit of the skilled person from this disclosure and the knowledge in the art. Thus, an embodiment comprehends contacting a Hemophilia B, SCID (e.g., SCID-X1, ADA-SCID) or Hereditary tyrosinemia mutation-carrying HSC with an gRNA-and-Cas (eg Cpf1) protein containing particle targeting a genomic locus of interest as to Hemophilia B, SCID (e.g., SCID-X1, ADA-SCID) or Hereditary tyrosinemia (e.g., as in Li, Genovese or Yin). The particle also can contain a suitable HDR template to correct the mutation; or the HSC can be contacted with a second particle or a vector that contains or delivers the HDR template. In this regard, it is mentioned that Haemophilia B is an X-linked recessive disorder caused by loss-of-function mutations in the gene encoding Factor IX, a crucial component of the clotting cascade. Recovering Factor IX activity to above 1% of its levels in severely affected individuals can transform the disease into a significantly milder form, as infusion of recombinant Factor IX into such patients prophylactically from a young age to achieve such levels largely ameliorates clinical complications. With the knowledge in the art and the teachings in this disclosure, the skilled person can correct HSCs as to Haemophilia B using a CRISPR-Cas (eg Cpf1) system that targets and corrects the mutation (X-linked recessive disorder caused by loss-of-function mutations in the gene encoding Factor IX) (e.g., with a suitable HDR template that delivers a coding sequence for Factor IX); specifically, the gRNA can target mutation that give rise to Haemophilia B, and the HDR can provide coding for proper expression of Factor IX. An gRNA that targets the mutation-and-Cas (eg Cpf1) protein containing particle is contacted with HSCs carrying the mutation. The particle also can contain a suitable HDR template to correct the mutation for proper expression of Factor IX; or the HSC can be contacted with a second particle or a vector that contains or delivers the HDR template. The so contacted cells can be administered; and optionally treated/expanded; cf. Cartier, discussed herein.

In Cartier, "MINI-SYMPOSIUM: X-Linked Adrenoleukodystrophy, Hematopoietic Stem Cell Transplantation and Hematopoietic Stem Cell Gene Therapy in X-Linked Adrenoleukodystrophy," Brain Pathology 20 (2010) 857-862, incorporated herein by reference along with the documents it cites, as if set out in full, there is recognition that allogeneic hematopoietic stem cell transplantation (HSCT) was utilized to deliver normal lysosomal enzyme to the brain of a patient with Hurler's disease, and a discussion of HSC gene therapy to treat ALD. In two patients, peripheral CD34+ cells were collected after granulocyte-colony stimulating factor (G-CSF) mobilization and transduced with a myeloproliferative sarcoma virus enhancer, negative control region deleted, dl587rev primer binding site substituted (MND)-ALD lentiviral vector. CD34+ cells from the patients were transduced with the MND-ALD vector during 16 h in the presence of cytokines at low concentrations. Transduced CD34+ cells were frozen after transduction to perform on 5% of cells various safety tests that included in particular three replication-competent lentivirus (RCL) assays. Transduction efficacy of CD34+ cells ranged from 35% to 50% with a mean number of lentiviral integrated copy between 0.65 and 0.70. After the thawing of transduced CD34+ cells, the patients were reinfused with more than 4.106 transduced CD34+ cells/kg following full myeloablation with busulfan and cyclophosphamide. The patient's HSCs were ablated to favor engraftment of the gene-corrected HSCs. Hematological recovery occurred between days 13 and 15 for the two patients. Nearly complete immunological recovery occurred at 12 months for the first patient, and at 9 months for the second patient. In contrast to using lentivirus, with the knowledge in the art and the teachings in this disclosure, the skilled person can correct HSCs as to ALD using a CRISPR-Cas (Cpf1) system that targets and corrects the mutation (e.g., with a suitable HDR template); specifically, the gRNA can target mutations in ABCD1, a gene located on the X chromosome that codes for ALD, a peroxisomal membrane transporter protein, and the HDR can provide coding for proper expression of the protein. An gRNA that targets the mutation-and-Cas (Cpf1) protein containing particle is contacted with HSCs, e.g., CD34+ cells carrying the mutation as in Cartier. The particle also can contain a suitable HDR template to correct the mutation for expression of the peroxisomal membrane transporter protein; or the HSC can be contacted with a second particle or a vector that contains or delivers the HDR template. The so contacted cells optimally can be treated as in Cartier. The so contacted cells can be administered as in Cartier.

Mention is made of WO 2015/148860, through the teachings herein the invention comprehends methods and materials of these documents applied in conjunction with the teachings herein. In an aspect of blood-related disease gene therapy, methods and compositions for treating beta thalassemia may be adapted to the CRISPR-Cas system of the present invention (see, e.g., WO 2015/148860). In an embodiment, WO 2015/148860 involves the treatment or prevention of beta thalassemia, or its symptoms, e.g., by altering the gene for B-cell CLL/lymphoma 11A (BCL11A). The BCL11A gene is also known as B-cell CLL/lymphoma 11A, BCL11A -L, BCL11A -S, BCL11AXL, CTIP 1, HBFQTL5 and ZNF. BCL11A encodes a zinc-finger protein that is involved in the regulation of globin gene expression. By altering the BCL11A gene (e.g., one or both alleles of the BCL11A gene), the levels of gamma globin can be increased. Gamma globin can replace beta globin in the hemoglobin complex and effectively carry oxygen to tissues, thereby ameliorating beta thalassemia disease phenotypes.

Mention is also made of WO 2015/148863 and through the teachings herein the invention comprehends methods and materials of these documents which may be adapted to the CRISPR-Cas system of the present invention. In an aspect of treating and preventing sickle cell disease, which is an inherited hematologic disease, WO 2015/148863 comprehends altering the BCL11A gene. By altering the BCL11A gene (e.g., one or both alleles of the BCL11A gene), the levels of gamma globin can be increased. Gamma globin can replace beta globin in the hemoglobin complex and effectively carry oxygen to tissues, thereby ameliorating sickle cell disease phenotypes.

In an aspect of the invention, methods and compositions which involve editing a target nucleic acid sequence, or modulating expression of a target nucleic acid sequence, and applications thereof in connection with cancer immunotherapy are comprehended by adapting the CRISPR-Cas system of the present invention. Reference is made to the application of gene therapy in WO 2015/161276 which involves methods and compositions which can be used to affect T-cell proliferation, survival and/or function by altering one or more T-cell expressed genes, e.g., one or more of FAS, BID, CTLA4, PDCD1, CBLB, PTPN6, TRAC and/or TRBC genes. In a related aspect, T-cell proliferation can be affected by altering one or more T-cell expressed genes, e.g., the CBLB and/or PTPN6 gene, FAS and/or BID gene, CTLA4 and/or PDCDI and/or TRAC and/or TRBC gene.

Chimeric antigen receptor (CAR)19 T-cells exhibit anti-leukemic effects in patient malignancies. However, leukemia patients often do not have enough T-cells to collect, meaning that treatment must involve modified T cells from donors. Accordingly, there is interest in establishing a bank of donor T-cells. Qasim et al. ("First Clinical Application of Talen Engineered Universal CAR19 T Cells in B-ALL" ASH 57th Annual Meeting and Exposition, Dec. 5-8, 2015, Abstract 2046 (https://ash.confex.com/ash/2015/webprogram/Paper81653.html published online November 2015) discusses modifying CAR19 T cells to eliminate the risk of graft-versus-host disease through the disruption of T-cell receptor expression and CD52 targeting. Furthermore, CD52 cells were targeted such that they became insensitive to Alemtuzumab, and thus allowed Alemtuzumab to prevent host-mediated rejection of human leukocyte antigen (HLA) mismatched CAR19 T-cells. Investigators used third generation self-inactivating lentiviral vector encoding a 4 g7 CAR19 (CD19 scFv-4-1BB-CD3ζ) linked to RQR8, then electroporated cells with two pairs of TALEN mRNA for multiplex targeting for both the T-cell receptor (TCR) alpha constant chain locus and the CD52 gene locus. Cells which were still expressing TCR following ex vivo expansion were depleted using CliniMacs a/P TCR depletion, yielding a T-cell product (UCART19) with <1% TCR expression, 85% of which expressed CAR19, and 64% becoming CD52 negative. The modified CAR19 T cells were administered to treat a patient's relapsed acute lymphoblastic leukemia. The teachings provided herein provide effective methods for providing modified hematopoietic stem cells and progeny thereof, including but not limited to cells of the myeloid and lymphoid lineages of blood, including T cells, B cells, monocytes, macrophages, neutrophils, basophils, eosinophils, erythrocytes, dendritic cells, and megakaryocytes or platelets, and natural killer cells and their precursors and progenitors. Such cells can be modified by knocking out, knocking in, or otherwise modulating targets, for example to remove or modulate CD52 as described above, and other targets, such as, without limitation, CXCR4, and PD-1. Thus compositions, cells, and method of the invention can be used to modulate immune responses and to treat, without limitation, malignancies, viral infections, and immune disorders, in conjunction with modification of administration of T cells or other cells to patients.

Mention is made of WO 2015/148670 and through the teachings herein the invention comprehends methods and materials of this document applied in conjunction with the teachings herein. In an aspect of gene therapy, methods and compositions for editing of a target sequence related to or in connection with Human Immunodeficiency Virus (HIV) and Acquired Immunodeficiency Syndrome (AIDS) are comprehended. In a related aspect, the invention described herein comprehends prevention and treatment of HIV infection and AIDS, by introducing one or more mutations in the gene for C-C chemokine receptor type 5 (CCR5). The CCR5 gene is also known as CKR5, CCR-5, CD195, CKR-5, CCCKR5, CMKBR5, IDDM22, and CC-CKR-5. In a further aspect, the invention described herein comprehends provide for prevention or reduction of HIV infection and/or prevention or reduction of the ability for HIV to enter host cells, e.g., in subjects who are already infected. Exemplary host cells for HIV include, but are not limited to, CD4 cells, T cells, gut associated lymphatic tissue (GALT), macrophages, dendritic cells, myeloid precursor cell, and microglia. Viral entry into the host cells requires interaction of the viral glycoproteins gp41 and gp120 with both the CD4 receptor and a co-receptor, e.g., CCR5. If a co-receptor, e.g., CCR5, is not present on the surface of the host cells, the virus cannot bind and enter the host cells. The progress of the disease is thus impeded. By knocking out or knocking down CCR5 in the host cells, e.g., by introducing a protective mutation (such as a CCR5 delta 32 mutation), entry of the HIV virus into the host cells is prevented.

X-linked Chronic granulomatous disease (CGD) is a hereditary disorder of host defense due to absent or decreased activity of phagocyte NADPH oxidase. Using a CRISPR-Cas (Cpf1) system that targets and corrects the mutation (absent or decreased activity of phagocyte NADPH oxidase) (e.g., with a suitable HDR template that delivers a coding sequence for phagocyte NADPH oxidase); specifically, the gRNA can target mutation that gives rise to CGD (deficient phagocyte NADPH oxidase), and the HDR can provide coding for proper expression of phagocyte NADPH oxidase. An gRNA that targets the mutation-and-Cas (Cpf1) protein containing particle is contacted with HSCs carrying the mutation. The particle also can contain a suitable HDR template to correct the mutation for proper expression of phagocyte NADPH oxidase; or the HSC can be contacted with a second particle or a vector that contains or delivers the HDR template. The so contacted cells can be administered; and optionally treated/expanded; cf. Cartier.

Fanconi anemia: Mutations in at least 15 genes (FANCA, FANCB, FANCC, FANCD1/BRCA2, FANCD2, FANCE, FANCF, FANCG, FANCI, FANCJ/BACH1/BRIP1, FANCL/PHF9/POG, FANCM, FANCN/PALB2, FANCO/Rad51C, and FANCP/SLX4/BTBD12) can cause Fanconi anemia. Proteins produced from these genes are involved in a cell process known as the FA pathway. The FA pathway is turned on (activated) when the process of making new copies of DNA, called DNA replication, is blocked due to DNA damage. The FA pathway sends certain proteins to the area of damage, which trigger DNA repair so DNA replication can continue. The FA pathway is particularly responsive to a certain type of DNA damage known as interstrand cross-links (ICLs). ICLs occur when two DNA building blocks (nucleotides) on opposite strands of DNA are abnormally attached or linked together, which stops the process of DNA replication. ICLs can be caused by a buildup of toxic substances produced in the body or by treatment with certain cancer therapy drugs. Eight proteins associated with Fanconi anemia group together to form a complex known as the FA core complex. The FA core complex activates two proteins, called FANCD2 and FANCI. The activation of these two proteins brings DNA repair proteins to the area of the ICL so the cross-link can be removed and DNA replication can continue. the FA core complex. More in particular, the FA core complex is a nuclear multiprotein complex consisting of FANCA, FANCB, FANCC, FANCE, FANCF, FANCG, FANCL, and FANCM, functions as an E3 ubiquitin ligase and mediates the activation of the ID complex, which is a heterodimer composed of FANCD2 and FANCI. Once monoubiquitinated, it interacts with classical tumor suppressors downstream of the FA pathway including FANCD1/BRCA2, FANCN/PALB2, FANCJ/BRIP1, and FANCO/Rad51C and thereby contributes to DNA repair via homologous recombination (HR). Eighty to 90 percent of FA cases are due to mutations in one of three genes, FANCA, FANCC, and FANCG. These genes provide instructions for producing components of the FA core complex. Mutations in such genes associated with the FA core complex will cause the complex to be nonfunctional and disrupt the entire FA pathway. As a result, DNA damage is not repaired efficiently and ICLs build up over time. Geiselhart, "Review Article, Disrupted Signaling through the Fanconi Anemia Pathway Leads to Dysfunctional Hematopoietic Stem Cell Biology: Underlying Mechanisms and Potential Therapeutic Strategies," Anemia Volume 2012 (2012), Article ID 265790, http://dx.doi.org/10.1155/2012/265790 discussed FA and an animal experiment involving intrafemoral injection of a lentivirus encoding the FANCC gene resulting in correction of HSCs in vivo. Using a CRISPR-Cas (Cpf1) system that targets and one or more of the mutations associated with FA, for instance a CRISPR-Cas (Cpf1) system having gRNA(s) and HDR template(s) that respectively targets one or more of the mutations of FANCA, FANCC, or FANCG that give rise to FA and provide corrective expression of one or more of FANCA, FANCC or FANCG; e.g., the gRNA can target a mutation as to FANCC, and the HDR can provide coding for proper expression of FANCC. An gRNA that targets the mutation(s) (e.g., one or more involved in FA, such as mutation(s) as to any one or more of FANCA, FANCC or FANCG)-and-Cas (Cpf1) protein containing particle is contacted with HSCs carrying the mutation(s). The particle also can contain a suitable HDR template(s) to correct the mutation for proper expression of one or more of the proteins involved in FA, such as any one or more of FANCA, FANCC or FANCG; or the HSC can be contacted with a second particle or a vector that contains or delivers the HDR template. The so contacted cells can be administered; and optionally treated/expanded; cf. Cartier.

The particle in the herein discussion (e.g., as to containing gRNA(s) and Cas (Cpf1), optionally HDR template(s), or HDR template(s); for instance as to Hemophilia B, SCID, SCID-X1, ADA-SCID, Hereditary tyrosinemia, 0-thalassemia, X-linked CGD, Wiskott-Aldrich syndrome, Fanconi anemia, adrenoleukodystrophy (ALD), metachromatic leukodystrophy (MLD), HIV/AIDS, Immunodeficiency disorder, Hematologic condition, or genetic lysosomal storage disease) is advantageously obtained or obtainable from admixing an gRNA(s) and Cas (Cpf1) protein mixture (optionally containing HDR template(s) or such mixture only containing HDR template(s) when separate particles as to template(s) is desired) with a mixture comprising or consisting essentially of or consisting of surfactant, phospholipid, biodegradable polymer, lipoprotein and alcohol (wherein one or more gRNA targets the genetic locus or loci in the HSC).

Indeed, the invention is especially suited for treating hematopoietic genetic disorders with genome editing, and immunodeficiency disorders, such as genetic immunodeficiency disorders, especially through using the particle technology herein-discussed. Genetic immunodeficiencies are diseases where genome editing interventions of the instant invention can successful. The reasons include: Hematopoietic cells, of which immune cells are a subset, are therapeutically accessible. They can be removed from the body and transplanted autologously or allogenically. Further, certain genetic immunodeficiencies, e.g., severe combined immunodeficiency (SCID), create a proliferative disadvantage for immune cells. Correction of genetic lesions causing SCID by rare, spontaneous 'reverse' mutations indicates that correcting even one lymphocyte progenitor may be sufficient to recover immune function in patients . . . / . . . / . . . / Users/t_kowalski/AppData/Local/Microsoft/Windows/Temporary Internet Files/Content.Outlook/GA8VY8LK/Treating SCID for Ellen.docx—_ENREF_1 See Bousso, P., et al. Diversity, functionality, and stability of the T cell repertoire derived in vivo from a single human T cell precursor. Proceedings of the National Academy of Sciences of the United States of America 97, 274-278 (2000). The selective advantage for edited cells allows for even low levels of editing to result in a therapeutic effect. This effect of the instant invention can be seen in SCID, Wiskott-Aldrich Syndrome, and the other conditions mentioned herein, including other genetic hematopoietic disorders such as alpha- and beta-thalassemia, where hemoglobin deficiencies negatively affect the fitness of erythroid progenitors.

The activity of NHEJ and HDR DSB repair varies significantly by cell type and cell state. NHEJ is not highly regulated by the cell cycle and is efficient across cell types, allowing for high levels of gene disruption in accessible target cell populations. In contrast, HDR acts primarily during S/G2 phase, and is therefore restricted to cells that are actively dividing, limiting treatments that require precise genome modifications to mitotic cells [Ciccia, A. & Elledge, S. J. Molecular cell 40, 179-204 (2010); Chapman, J. R., et al. Molecular cell 47, 497-510 (2012)].

The efficiency of correction via HDR may be controlled by the epigenetic state or sequence of the targeted locus, or the specific repair template configuration (single vs. double stranded, long vs. short homology arms) used [Hacein-Bey-Abina, S., et al. The New England journal of medicine 346, 1185-1193 (2002); Gaspar, H. B., et al. Lancet 364, 2181-2187 (2004); Beumer, K. J., et al. G3 (2013)]. The relative activity of NHEJ and HDR machineries in target cells may also affect gene correction efficiency, as these pathways may compete to resolve DSBs [Beumer, K. J., et al. Proceedings of the National Academy of Sciences of the United States of America 105, 19821-19826 (2008)]. HDR also imposes a delivery challenge not seen with NHEJ strategies, as it requires the concurrent delivery of nucleases and repair templates. In practice, these constraints have so far led to low levels of HDR in therapeutically relevant cell types. Clinical translation has therefore largely focused on NHEJ strategies to treat disease, although proof-of-concept preclinical HDR treatments have now been described for mouse models of haemophilia B and hereditary tyrosinemia [Li, H., et al. Nature 475, 217-221 (2011); Yin, H., et al. Nature biotechnology 32, 551-553 (2014)].

Any given genome editing application may comprise combinations of proteins, small RNA molecules, and/or repair templates, making delivery of these multiple parts substantially more challenging than small molecule therapeutics. Two main strategies for delivery of genome editing tools have been developed: ex vivo and in vivo. In ex vivo treatments, diseased cells are removed from the body, edited and then transplanted back into the patient. Ex vivo editing has the advantage of allowing the target cell population to be well defined and the specific dosage of therapeutic molecules delivered to cells to be specified. The latter consideration may be particularly important when off-target modifications are a concern, as titrating the amount of nuclease may decrease such mutations (Hsu et al., 2013). Another advantage of ex vivo approaches is the typically high editing rates that can be achieved, due to the development of efficient delivery systems for proteins and nucleic acids into cells in culture for research and gene therapy applications.

There may be drawbacks with ex vivo approaches that limit application to a small number of diseases. For instance, target cells must be capable of surviving manipulation outside the body. For many tissues, like the brain, culturing cells outside the body is a major challenge, because cells either fail to survive, or lose properties necessary for their function in vivo. Thus, in view of this disclosure and the knowledge in the art, ex vivo therapy as to tissues with adult stem cell populations amenable to ex vivo culture and manipulation, such as the hematopoietic system, by the CRISPR-Cas (Cpf1) system are enabled. [Bunn, H.F. & Aster, J. Pathophysiology of blood disorders, (McGraw-Hill, New York, 2011)]

In vivo genome editing involves direct delivery of editing systems to cell types in their native tissues. In vivo editing allows diseases in which the affected cell population is not amenable to ex vivo manipulation to be treated. Furthermore, delivering nucleases to cells in situ allows for the treatment of multiple tissue and cell types. These properties probably allow in vivo treatment to be applied to a wider range of diseases than ex vivo therapies.

To date, in vivo editing has largely been achieved through the use of viral vectors with defined, tissue-specific tropism. Such vectors are currently limited in terms of cargo carrying capacity and tropism, restricting this mode of therapy to organ systems where transduction with clinically useful vectors is efficient, such as the liver, muscle and eye [Kotterman, M. A. & Schaffer, D. V. Nature reviews. Genetics 15, 445-451 (2014); Nguyen, T. H. & Ferry, N. Gene therapy 11 Suppl 1, S76-84 (2004); Boye, S. E., et al. Molecular therapy: the journal of the American Society of Gene Therapy 21, 509-519 (2013)].

A potential barrier for in vivo delivery is the immune response that may be created in response to the large amounts of virus necessary for treatment, but this phenomenon is not unique to genome editing and is observed with other virus-based gene therapies [Bessis, N., et al. Gene therapy 11 Suppl 1, S10-17 (2004)]. It is also possible that peptides from editing nucleases themselves are presented on MHC Class I molecules to stimulate an immune response, although there is little evidence to support this happening at the preclinical level. Another major difficulty with this mode of therapy is controlling the distribution and consequently the dosage of genome editing nucleases in vivo, leading to off-target mutation profiles that may be difficult to predict. However, in view of this disclosure and the knowledge in the art, including the use of virus- and particle-based therapies being used in the treatment of cancers, in vivo modification of HSCs, for instance by delivery by either particle or virus, is within the ambit of the skilled person.

Ex Vivo Editing Therapy

The long-standing clinical expertise with the purification, culture and transplantation of hematopoietic cells has made diseases affecting the blood system such as SCID, Fanconi anemia, Wiskott-Aldrich syndrome and sickle cell anemia the focus of ex vivo editing therapy. Another reason to focus on hematopoietic cells is that, thanks to previous efforts to design gene therapy for blood disorders, delivery systems of relatively high efficiency already exist. With these advantages, this mode of therapy can be applied to diseases where edited cells possess a fitness advantage, so that a small number of engrafted, edited cells can expand and treat disease. One such disease is HIV, where infection results in a fitness disadvantage to CD4+ T cells.

Ex vivo editing therapy has been recently extended to include gene correction strategies. The barriers to HDR ex vivo were overcome in a recent paper from Genovese and colleagues, who achieved gene correction of a mutated IL2RG gene in hematopoietic stem cells (HSCs) obtained from a patient suffering from SCID-X1 [Genovese, P., et al. Nature 510, 235-240 (2014)]. Genovese et. al. accomplished gene correction in HSCs using a multimodal strategy. First, HSCs were transduced using integration-deficient lentivirus containing an HDR template encoding a therapeutic cDNA for IL2RG. Following transduction, cells were electroporated with mRNA encoding ZFNs targeting a mutational hotspot in IL2RG to stimulate HDR based gene correction. To increase HDR rates, culture conditions were optimized with small molecules to encourage HSC division. With optimized culture conditions, nucleases and HDR templates, gene corrected HSCs from the SCID-X1 patient were obtained in culture at therapeutically relevant rates. HSCs from unaffected individuals that underwent the same gene correction procedure could sustain long-term hematopoiesis in mice, the gold standard for HSC function. HSCs are capable of giving rise to all hematopoietic cell types and can be autologously transplanted, making them an extremely valuable cell population for all hematopoietic genetic disorders [Weissman, I. L. & Shizuru, J. A. Blood 112, 3543-3553 (2008)]. Gene corrected HSCs could, in principle, be used to treat a wide range of genetic blood disorders making this study an exciting breakthrough for therapeutic genome editing.

In Vivo Editing Therapy

In vivo editing can be used advantageously from this disclosure and the knowledge in the art. For organ systems where delivery is efficient, there have already been a number of exciting preclinical therapeutic successes. The first example of successful in vivo editing therapy was demonstrated in a mouse model of Haemophilia B [Li, H., et al. Nature 475, 217-221 (2011)]. As noted earlier, Haemophilia B is an X-linked recessive disorder caused by loss-of-function mutations in the gene encoding Factor IX, a crucial component of the clotting cascade. Recovering Factor IX activity to above 1% of its levels in severely affected individuals can transform the disease into a significantly milder form, as infusion of recombinant Factor IX into such patients prophylactically from a young age to achieve such levels largely ameliorates clinical complications [Lofqvist, T., et al. Journal of internal medicine 241, 395-400 (1997)]. Thus, only low levels of HDR gene correction are necessary to change clinical outcomes for patients. In addition, Factor IX is synthesized and secreted by the liver, an organ that can be transduced efficiently by viral vectors encoding editing systems.

Using hepatotropic adeno-associated viral (AAV) serotypes encoding ZFNs and a corrective HDR template, up to 7% gene correction of a mutated, humanized Factor IX gene in the murine liver was achieved [Li, H., et al. Nature 475, 217-221 (2011)]. This resulted in improvement of clot formation kinetics, a measure of the function of the clotting cascade, demonstrating for the first time that in vivo editing therapy is not only feasible, but also efficacious. As discussed herein, the skilled person is positioned from the teachings herein and the knowledge in the art, e.g., Li to address Haemophilia B with a particle-containing HDR template and a CRISPR-Cas (Cpf1) system that targets the mutation of the X-linked recessive disorder to reverse the loss-of-function mutation.

Building on this study, other groups have recently used in vivo genome editing of the liver with CRISPR-Cas to successfully treat a mouse model of hereditary tyrosinemia and to create mutations that provide protection against cardiovascular disease. These two distinct applications demonstrate the versatility of this approach for disorders that involve hepatic dysfunction [Yin, H., et al. Nature biotechnology 32, 551-553 (2014); Ding, Q., et al. Circulation research 115, 488-492 (2014)]. Application of in vivo editing to other organ systems are necessary to prove that this strategy is widely applicable. Currently, efforts to optimize both viral and non-viral vectors are underway to expand the range of disorders that can be treated with this mode of therapy [Kotterman, M. A. & Schaffer, D. V. Nature reviews. Genetics 15, 445-451 (2014); Yin, H., et al. Nature reviews. Genetics 15, 541-555 (2014)]. As discussed herein, the skilled person is positioned from the teachings herein and the knowledge in the art, e.g., Yin to address hereditary tyrosinemia with a particle-containing HDR template and a CRISPR-Cas (Cpf1) system that targets the mutation.

Targeted deletion, therapeutic applications: Targeted deletion of genes may be preferred. Preferred are, therefore, genes involved in immunodeficiency disorder, hematologic condition, or genetic lysosomal storage disease, e.g., Hemophilia B, SCID, SCID-X1, ADA-SCID, Hereditary tyrosinemia, 0-thalassemia, X-linked CGD, Wiskott-Aldrich syndrome, Fanconi anemia, adrenoleukodystrophy (ALD), metachromatic leukodystrophy (MLD), HIV/AIDS, other metabolic disorders, genes encoding mis-folded proteins involved in diseases, genes leading to loss-of-function involved in diseases; generally, mutations that can be targeted in an HSC, using any herein-discussed delivery system, with the particle system considered advantageous.

In the present invention, the immunogenicity of the CRISPR enzyme in particular may be reduced following the approach first set out in Tangri et al with respect to erythropoietin and subsequently developed. Accordingly, directed evolution or rational design may be used to reduce the immunogenicity of the CRISPR enzyme (for instance a Cpf1) in the host species (human or other species).

Genome editing: The CRISPR/Cas (Cpf1) systems of the present invention can be used to correct genetic mutations that were previously attempted with limited success using TALEN and ZFN and lentiviruses, including as herein discussed; see also WO2013163628.

Treating Diseases of the Brain, Central Nervous and Immune Systems

The present invention also contemplates delivering the CRISPR-Cas system to the brain or neurons. For example, RNA interference (RNAi) offers therapeutic potential for this disorder by reducing the expression of HTT, the disease-causing gene of Huntington's disease (see, e.g., McBride et al., Molecular Therapy vol. 19 no. 12 Dec. 2011, pp. 2152-2162), therefore Applicant postulates that it may be used/and or adapted to the CRISPR-Cas system. The CRISPR-Cas system may be generated using an algorithm to reduce the off-targeting potential of antisense sequences. The CRISPR-Cas sequences may target either a sequence in exon 52 of mouse, rhesus or human huntingtin and expressed in a viral vector, such as AAV. Animals, including humans, may be injected with about three microinjections per hemisphere (six injections total): the first 1 mm rostral to the anterior commissure (12 μl) and the two remaining injections (12 μl and 10 μl, respectively) spaced 3 and 6 mm caudal to the first injection with 1e12 vg/ml of AAV at a rate of about 1 l/minute, and the needle was left in place for an additional 5 minutes to allow the injectate to diffuse from the needle tip.

DiFiglia et al. (PNAS, Oct. 23, 2007, vol. 104, no. 43, 17204-17209) observed that single administration into the adult striatum of an siRNA targeting Htt can silence mutant Htt, attenuate neuronal pathology, and delay the abnormal behavioral phenotype observed in a rapid-onset, viral transgenic mouse model of HD. DiFiglia injected mice intrastriatally with 2 μl of Cy3-labeled cc-siRNA-Htt or unconjugated siRNA-Htt at 10 μM. A similar dosage of CRISPR Cas targeted to Htt may be contemplated for humans in the present invention, for example, about 5-10 ml of 10 μM CRISPR Cas targeted to Htt may be injected intrastriatally.

In another example, Boudreau et al. (Molecular Therapy vol. 17 no. 6 Jun. 2009) injects 5 μl of recombinant AAV serotype 2/1 vectors expressing htt-specific RNAi virus (at 4×1012 viral genomes/ml) into the striatum. A similar dosage of CRISPR Cas targeted to Htt may be contemplated for humans in the present invention, for example, about 10-20 ml of 4×1012 viral genomes/ml) CRISPR Cas targeted to Htt may be injected intrastriatally.

In another example, a CRISPR Cas targeted to HTT may be administered continuously (see, e.g., Yu et al., Cell 150, 895-908, Aug. 31, 2012). Yu et al. utilizes osmotic pumps delivering 0.25 ml/hr (Model 2004) to deliver 300 mg/day of ss-siRNA or phosphate-buffered saline (PBS) (Sigma Aldrich) for 28 days, and pumps designed to deliver 0.5 μl/hr (Model 2002) were used to deliver 75 mg/day of the positive control MOE ASO for 14 days. Pumps (Durect Corporation) were filled with ss-siRNA or MOE diluted in sterile PBS and then incubated at 37 C for 24 or 48 (Model 2004) hours prior to implantation. Mice were anesthetized with 2.5% isofluorane, and a midline incision was made at the base of the skull. Using stereotaxic guides, a cannula was implanted into the right lateral ventricle and secured with Loctite adhesive. A catheter attached to an Alzet osmotic mini pump was attached to the cannula, and the pump was placed subcutaneously in the midscapular area. The incision was closed with 5.0 nylon sutures. A similar dosage of CRISPR Cas targeted to Htt may be contemplated for humans in the present invention, for example, about 500 to 1000 g/day CRISPR Cas targeted to Htt may be administered.

In another example of continuous infusion, Stiles et al. (Experimental Neurology 233 (2012) 463-471) implanted an intraparenchymal catheter with a titanium needle tip into the right putamen. The catheter was connected to a SynchroMed® II Pump (Medtronic Neurological, Minneapolis, MN) subcutaneously implanted in the abdomen. After a 7-day infusion of phosphate buffered saline at 6 μL/day, pumps were re-filled with test article and programmed for continuous delivery for 7 days. About 2.3 to 11.52 mg/d of siRNA were infused at varying infusion rates of about 0.1 to 0.5 μL/min. A similar dosage of CRISPR Cas targeted to Htt may be contemplated for humans in the present invention, for example, about 20 to 200 mg/day CRISPR Cas targeted to Htt may be administered. In another example, the methods of US Patent Publication No. 20130253040 assigned to Sangamo may also be also be adapted from TALES to the nucleic acid-targeting system of the present invention for treating Huntington's Disease.

In another example, the methods of US Patent Publication No. 20130253040 (WO2013130824) assigned to Sangamo may also be also be adapted from TALES to the CRISPR Cas system of the present invention for treating Huntington's Disease.

WO2015089354 A1 in the name of The Broad Institute et al., hereby incorporated by reference, describes a target(s) for Huntington's Disease (HP). Possible target genes of CRISPR complex in regard to Huntington's Disease: PRKCE; IGF1; EP300; RCOR1; PRKCZ; HDAC4; and TGM2. Accordingly, one or more of PRKCE; IGF1; EP300; RCOR1; PRKCZ; HDAC4; and TGM2 may be selected as targets for Huntington's Disease in some embodiments of the present invention.

Other trinucleotide repeat disorders. These may include any of the following: Category I includes Huntington's disease (HD) and the spinocerebellar ataxias; Category II expansions are phenotypically diverse with heterogeneous expansions that are generally small in magnitude, but also found in the exons of genes; and Category III includes fragile X syndrome, myotonic dystrophy, two of the spinocerebellar ataxias, juvenile myoclonic epilepsy, and Friedreich's ataxia.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

The methods of US Patent Publication No. 20110158957 assigned to Sangamo BioSciences, Inc. involved in inactivating T cell receptor (TCR) genes may also be modified to the CRISPR Cas system of the present invention. In another example, the methods of US Patent Publication No. 20100311124 assigned to Sangamo BioSciences, Inc. and US Patent Publication No. 20110225664 assigned to Cellectis, which are both involved in inactivating glutamine synthetase gene expression genes may also be modified to the CRISPR Cas system of the present invention.

Delivery options for the brain include encapsulation of CRISPR enzyme and guide RNA in the form of either DNA or RNA into liposomes and conjugating to molecular Trojan horses for trans-blood brain barrier (BBB) delivery. Molecular Trojan horses have been shown to be effective for delivery of B-gal expression vectors into the brain of non-human primates. The same approach can be used to delivery vectors containing CRISPR enzyme and guide RNA. For instance, Xia C F and Boado R J, Pardridge W M ("Antibody-mediated targeting of siRNA via the human insulin receptor using avidin-biotin technology." Mol Pharm. 2009 May-June; 6(3):747-51. doi: 10.1021/mp800194) describes how delivery of short interfering RNA (siRNA) to cells in culture, and in vivo, is possible with combined use of a receptor-specific monoclonal antibody (mAb) and avidin-biotin technology. The authors also report that because the bond between the targeting mAb and the siRNA is stable with avidin-biotin technology, and RNAi effects at distant sites such as brain are observed in vivo following an intravenous administration of the targeted siRNA.

Zhang et al. (Mol Ther. 2003 January; 7(1):11-8.)) describe how expression plasmids encoding reporters such as luciferase were encapsulated in the interior of an "artificial virus" comprised of an 85 nm pegylated immunoliposome, which was targeted to the rhesus monkey brain in vivo with a monoclonal antibody (MAb) to the human insulin receptor (HIR). The HIRMAb enables the liposome carrying the exogenous gene to undergo transcytosis across the blood-brain barrier and endocytosis across the neuronal plasma membrane following intravenous injection. The level of luciferase gene expression in the brain was 50-fold higher in the rhesus monkey as compared to the rat. Widespread neuronal expression of the beta-galactosidase gene in primate brain was demonstrated by both histochemistry and confocal microscopy. The authors indicate that this approach makes feasible reversible adult transgenics in 24 hours. Accordingly, the use of immunoliposome is preferred. These may be used in conjunction with antibodies to target specific tissues or cell surface proteins.

Alzheimer's Disease

US Patent Publication No. 20110023153, describes use of zinc finger nucleases to genetically modify cells, animals and proteins associated with Alzheimer's Disease. Once modified cells and animals may be further tested using known methods to study the effects of the targeted mutations on the development and/or progression of AD using measures commonly used in the study of AD—such as, without limitation, learning and memory, anxiety, depression, addiction, and sensory motor functions as well as assays that measure behavioral, functional, pathological, metabolic and biochemical function.

The present disclosure comprises editing of any chromosomal sequences that encode proteins associated with AD. The AD-related proteins are typically selected based on an experimental association of the AD-related protein to an AD disorder. For example, the production rate or circulating concentration of an AD-related protein may be elevated or depressed in a population having an AD disorder relative to a population lacking the AD disorder. Differences in protein levels may be assessed using proteomic techniques including but not limited to Western blot, immunohistochemical staining, enzyme linked immunosorbent assay (ELISA), and mass spectrometry. Alternatively, the AD-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Examples of Alzheimer's disease associated proteins may include the very low-density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

By way of non-limiting example, proteins associated with AD include but are not limited to the proteins listed as follows: Chromosomal Sequence Encoded Protein ALAS2 Delta-aminolevulinate synthase 2 (ALAS2) ABCA1 ATP-binding cassette transporter (ABCA1) ACE Angiotensin I-converting enzyme (ACE) APOE Apolipoprotein E precursor (APOE) APP amyloid precursor protein (APP) AQP1 aquaporin 1 protein (AQP1) BIN1 Myc box-dependent-interacting protein 1 or bridging integrator 1 protein (BIN1) BDNF brain-derived neurotrophic factor (BDNF) BTNL8 Butyrophilin-like protein 8 (BTNL8) C1ORF49 chromosome 1 open reading frame 49 CDH4 Cadherin-4 CHRNB2 Neuronal acetylcholine receptor subunit beta-2 CKLFSF2 CKLF-like MARVEL transmembrane domain-containing protein 2 (CKLFSF2) CLEC4E C-type lectin domain family 4, member e (CLEC4E) CLU clusterin protein (also known as apolipoprotein J) CR1 Erythrocyte complement receptor 1 (CR1, also known as CD35, $C_3b/C_4b$ receptor and immune adherence receptor) CR1L Erythrocyte complement receptor 1 (CR1L) CSF3R granulocyte colony-stimulating factor 3 receptor (CSF3R) CST3 Cystatin C or cystatin 3 CYP2C Cytochrome P450 2C DAPK1 Death-associated protein kinase 1 (DAPK1) ESR1 Estrogen receptor 1 FCAR Fc fragment of IgA receptor (FCAR, also known as CD89) FCGR3B Fc fragment of IgG, low affinity IIIb, receptor (FCGR3B or CD16b) FFA2 Free fatty acid receptor 2 (FFA2) FGA Fibrinogen (Factor I) GAB2 GRB2-associated-binding protein 2 (GAB2) GAB2 GRB2-associated-binding protein 2 (GAB2) GALP Galanin-like peptide GAPDHS Glyceraldehyde-3-phosphate dehydrogenase, spermatogenic (GAPDHS) GMPB GMBP HP Haptoglobin (HP) HTR7 5-hydroxytryptamine (serotonin) receptor 7 (adenylate cyclase-coupled) IDE Insulin degrading enzyme IF127 IF127 IFI6 Interferon, alpha-inducible protein 6 (IFI6) IFIT2 Interferon-induced protein with tetratricopeptide repeats 2 (IFIT2) IL1RN interleukin-1 receptor antagonist (IL-iRA) IL8RA Interleukin 8 receptor, alpha (IL8RA or CD181) IL8RB Interleukin 8 receptor, beta (IL8RB) JAG1 Jagged 1 (JAG1) KCNJ15 Potassium inwardly-rectifying channel, subfamily J, member 15 (KCNJ15) LRP6 Low-density lipoprotein receptor-related protein 6 (LRP6) MAPT microtubule-associated protein tau (MAPT) MARK4 MAP/microtubule affinity-regulating kinase 4 (MARK4) MPHOSPH1 M-phase phosphoprotein 1 MTHFR 5,10-methylenetetrahydrofolate reductase MX2 Interferon-induced GTP-binding protein Mx2 NBN Nibrin, also known as NBN NCSTN Nicastrin NIACR2 Niacin receptor 2 (NIACR2, also known as GPR109B) NMNAT3 nicotinamide nucleotide adenylyltransferase 3 NTM Neurotrimin (or HNT) ORM1 Orosmucoid 1 (ORM1) or Alpha-1-acid glycoprotein 1 P2RY13 P2Y purinoceptor 13 (P2RY13) PBEF1 Nicotinamide phosphoribosyltransferase (NAmPRTase or Nampt) also known as pre-B-cell colony-enhancing factor 1 (PBEF1) or visfatin PCK1 Phosphoenolpyruvate carboxykinase PICALM phosphatidylinositol binding clathrin assembly protein (PICALM) PLAU Urokinase-type plasminogen activator (PLAU) PLXNC1 Plexin $C_1$ (PLXNC1) PRNP Prion protein PSEN1 presenilin 1 protein (PSEN1) PSEN2 presenilin 2 protein (PSEN2) PTPRA protein tyrosine phosphatase receptor type A protein (PTPRA) RALGPS2 Ral GEF with PH domain and SH3 binding motif 2 (RALGPS2) RGSL2 regulator of G-protein signaling like 2 (RGSL2) SELENBP1 Selenium binding protein 1 (SELNBP1) SLC25A37 Mitoferrin-1 SORL1 sortilin-related receptor L (DLR class) A repeats-containing protein (SORL1) TF Transferrin TFAM Mitochondrial transcription factor A TNF Tumor necrosis factor TNFRSF10C Tumor necrosis factor receptor superfamily member 10C (TNFRSF10C) TNFSF10 Tumor necrosis factor receptor superfamily, (TRAIL) member 10a (TNFSF10) UBA1 ubiquitin-like modifier activating enzyme 1 (UBA1) UBA3 NEDD8-activating enzyme E1 catalytic subunit protein (UBE1C) UBB ubiquitin B protein (UBB) UBQLN1 Ubiquilin-1 UCHL1 ubiquitin carboxyl-terminal esterase L1 protein (UCHL1) UCHL3 ubiquitin carboxyl-terminal hydrolase isozyme L3 protein (UCHL3) VLDLR very low density lipoprotein receptor protein (VLDLR).

In exemplary embodiments, the proteins associated with AD whose chromosomal sequence is edited may be the very low density lipoprotein receptor protein (VLDLR) encoded by the VLDLR gene, the ubiquitin-like modifier activating enzyme 1 (UBA1) encoded by the UBA1 gene, the NEDD8-activating enzyme E1 catalytic subunit protein (UBE1C) encoded by the UBA3 gene, the aquaporin 1 protein (AQP1) encoded by the AQP1 gene, the ubiquitin carboxyl-terminal esterase L1 protein (UCHL1) encoded by the UCHL1 gene, the ubiquitin carboxyl-terminal hydrolase isozyme L3 protein (UCHL3) encoded by the UCHL3 gene, the ubiquitin B protein (UBB) encoded by the UBB gene, the microtubule-associated protein tau (MAPT) encoded by the MAPT gene, the protein tyrosine phosphatase receptor type A protein (PTPRA) encoded by the PTPRA gene, the phosphatidylinositol binding clathrin assembly protein (PICALM) encoded by the PICALM gene, the clusterin protein (also known as apolipoprotein J) encoded by the CLU gene, the presenilin 1 protein encoded by the PSEN1 gene, the presenilin 2 protein encoded by the PSEN2 gene, the sortilin-related receptor L (DLR class) A repeats-containing protein (SORL1) protein encoded by the SORL1 gene, the amyloid precursor protein (APP) encoded by the APP gene, the Apolipoprotein E precursor (APOE) encoded by the APOE gene, or the brain-derived neurotrophic factor (BDNF) encoded by the BDNF gene. In an exemplary embodiment, the genetically modified animal is a rat, and the edited chromosomal sequence encoding the protein associated with AD is as follows: APP amyloid precursor protein (APP) NM_019288 AQP1 aquaporin 1 protein (AQP1) NM_012778 BDNF Brain-derived neurotrophic factor NM_012513 CLU clusterin protein (also known as NM_053021 apolipoprotein J) MAPT microtubule-associated protein NM_017212 tau (MAPT) PICALM phosphatidylinositol binding NM_053554 clathrin assembly protein (PICALM) PSEN1 presenilin 1 protein (PSEN1) NM 019163 PSEN2 presenilin 2 protein (PSEN2) NM_031087 PTPRA protein tyrosine phosphatase NM_012763 receptor type A protein (PTPRA) SORL1 sortilin-related receptor L (DLR NM_053519, class) A repeats-containing XM_001065506, protein (SORL1) XM_217115 UBA1 ubiquitin-like modifier activating NM_001014080 enzyme 1 (UBA1) UBA3 NEDD8-activating enzyme E1 NM_057205 catalytic subunit protein (UBE1C) UBB ubiquitin B protein (UBB) NM_138895 UCHL1 ubiquitin carboxyl-terminal NM_017237 esterase L1 protein (UCHL1) UCHL3 ubiquitin carboxyl-terminal NM_001110165 hydrolase isozyme L3 protein (UCHL3) VLDLR very low density lipoprotein NM_013155 receptor protein (VLDLR)

The animal or cell may comprise 1, 2, 3, 4, 5, 6, 7, 8, 9, 10, 11, 12, 13, 14, 15 or more disrupted chromosomal sequences encoding a protein associated with AD and zero, 1, 2, 3, 4, 5, 6, 7, 8, 9, 10, 11, 12, 13, 14, 15 or more chromosomally integrated sequences encoding a protein associated with AD.

The edited or integrated chromosomal sequence may be modified to encode an altered protein associated with AD. A number of mutations in AD-related chromosomal sequences have been associated with AD. For instance, the V7171 (i.e. valine at position 717 is changed to isoleucine) missense mutation in APP causes familial AD. Multiple mutations in the presenilin-1 protein, such as H163R (i.e. histidine at position 163 is changed to arginine), A246E (i.e. alanine at position 246 is changed to glutamate), L286V (i.e. leucine at position 286 is changed to valine) and C410Y (i.e. cysteine at position 410 is changed to tyrosine) cause familial Alzheimer's type 3. Mutations in the presenilin-2 protein, such as N141 I (i.e. asparagine at position 141 is changed to isoleucine), M239V (i.e. methionine at position 239 is changed to valine), and D439A (i.e. aspartate at position 439 is changed to alanine) cause familial Alzheimer's type 4. Other associations of genetic variants in AD-associated genes and disease are known in the art. See, for example, Waring et al. (2008) Arch. Neurol. 65:329-334, the disclosure of which is incorporated by reference herein in its entirety.

Secretase Disorders

US Patent Publication No. 20110023146, describes use of zinc finger nucleases to genetically modify cells, animals and proteins associated with secretase-associated disorders. Secretases are essential for processing pre-proteins into their biologically active forms. Defects in various components of the secretase pathways contribute to many disorders, particularly those with hallmark amyloidogenesis or amyloid plaques, such as Alzheimer's disease (AD).

A secretase disorder and the proteins associated with these disorders are a diverse set of proteins that effect susceptibility for numerous disorders, the presence of the disorder, the severity of the disorder, or any combination thereof. The present disclosure comprises editing of any chromosomal sequences that encode proteins associated with a secretase disorder. The proteins associated with a secretase disorder are typically selected based on an experimental association of the secretase-related proteins with the development of a secretase disorder. For example, the production rate or circulating concentration of a protein associated with a secretase disorder may be elevated or depressed in a population with a secretase disorder relative to a population without a secretase disorder. Differences in protein levels may be assessed using proteomic techniques including but not limited to Western blot, immunohistochemical staining, enzyme linked immunosorbent assay (ELISA), and mass spectrometry. Alternatively, the protein associated with a secretase disorder may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with a secretase disorder include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), BACE1 (beta-site APP-cleaving enzyme 1), ITM2B (integral membrane protein 2B), CTSD (cathepsin D), NOTCH1 (Notch homolog 1, translocation-associated (*Drosophila*)), TNF (tumor necrosis factor (TNF superfamily, member 2)), INS (insulin), DYT10 (dystonia 10), ADAM17 (ADAM metallopeptidase domain 17), APOE (apolipoprotein E), ACE (angiotensin I converting enzyme (peptidyl-dipeptidase A) 1), STN (statin), TP53 (tumor protein p53), IL6 (interleukin 6 (interferon, beta 2)), NGFR (nerve growth factor receptor (TNFR superfamily, member 16)), IL1B (interleukin 1, beta), ACHE (acetylcholinesterase (Yt blood group)), CTNNB1 (catenin (cadherin-associated protein), beta 1, 88 kDa), IGF1 (insulin-like growth factor 1 (somatomedin C)), IFNG (interferon, gamma), NRG1 (neuregulin 1), CASP3 (caspase 3, apoptosis-related cysteine peptidase), MAPK1 (mitogen-activated protein kinase 1), CDH1 (cadherin 1, type 1, E-cadherin (epithelial)), APBB1 (amyloid beta (A4) precursor protein-binding, family B, member 1 (Fe65)), HMGCR (3-hydroxy-3-methylglutaryl-Coenzyme A reductase), CREB1 (cAMP responsive element binding protein 1), PTGS2 (prostaglandin-endoperoxide synthase 2 (prostaglandin G/H synthase and cyclooxygenase)), HES1 (hairy and enhancer of split 1, (*Drosophila*)), CAT (catalase), TGFB1 (transforming growth factor, beta 1), ENO2 (enolase 2 (gamma, neuronal)), ERBB4 (v-erb-a erythroblastic leukemia viral oncogene homolog 4 (avian)), TRAPPC10 (trafficking protein particle complex 10), MAOB (monoamine oxidase B), NGF (nerve growth factor (beta polypeptide)), MMP12 (matrix metallopeptidase 12 (macrophage elastase)), JAG1 (jagged 1 (Alagille syndrome)), CD40LG (CD40 ligand), PPARG (peroxisome proliferator-activated receptor gamma), FGF2 (fibroblast growth factor 2 (basic)), IL3 (interleukin 3 (colony-stimulating factor, multiple)), LRP1 (low density lipoprotein receptor-related protein 1), NOTCH4 (Notch homolog 4 (*Drosophila*)), MAPK8 (mitogen-activated protein kinase 8), PREP (prolyl endopeptidase), NOTCH3 (Notch homolog 3 (*Drosophila*)), PRNP (prion protein), CTSG (cathepsin G), EGF (epidermal growth factor (beta-urogastrone)), REN (renin), CD44 (CD44 molecule (Indian blood group)), SELP (selectin P (granule membrane protein 140 kDa, antigen CD62)), GHR (growth hormone receptor), ADCYAP1 (adenylate cyclase activating polypeptide 1 (pituitary)), INSR (insulin receptor), GFAP (glial fibrillary acidic protein), MMP3 (matrix metallopeptidase 3 (stromelysin 1, progelatinase)), MAPK10 (mitogen-activated protein kinase 10), SP1 (Sp1 transcription factor), MYC (v-myc myelocytomatosis viral oncogene homolog (avian)), CTSE (cathepsin E), PPARA (peroxisome proliferator-activated receptor alpha), JUN (jun oncogene), TIMP1 (TIMP metallopeptidase inhibitor 1), IL5 (interleukin 5 (colony-stimulating factor, eosinophil)), IL1A (interleukin 1, alpha), MMP9 (matrix metallopeptidase 9 (gelatinase B, 92 kDa gelatinase, 92 kDa type IV collagenase)), HTR4 (5-hydroxytryptamine (serotonin) receptor 4), HSPG2 (heparan sulfate proteoglycan 2), KRAS (v-Ki-ras2 Kirsten rat sarcoma viral oncogene homolog), CYCS (cytochrome c, somatic), SMG1 (SMG1 homolog, phosphatidylinositol 3-kinase-related kinase (*C. elegans*)), IL1R1 (interleukin 1 receptor, type I), PROK1 (prokineticin 1), MAPK3 (mitogen-activated protein kinase 3), NTRK1 (neurotrophic tyrosine kinase, receptor, type 1), IL13 (interleukin 13), MME (membrane metallo-endopeptidase), TKT (transketolase), CXCR2 (chemokine (C-X-C motif) receptor 2), IGF1R (insulin-like growth factor 1 receptor), RARA (retinoic acid receptor, alpha), CREBBP (CREB binding protein), PTGS1 (prostaglandin-endoperoxide synthase 1 (prostaglandin G/H synthase and cyclooxygenase)), GALT (galactose-1-phosphate uridylyltransferase), CHRM1 (cholinergic receptor, muscarinic 1), ATXN1 (ataxin 1), PAWR (PRKC, apoptosis, WT1, regulator), NOTCH2 (Notch homolog 2 (*Drosophila*)), M6PR (mannose-6-phosphate receptor (cation dependent)), CYP46A1 (cytochrome P450, family 46, subfamily A, polypeptide 1), CSNK1 D (casein kinase 1, delta), MAPK14 (mitogen-activated protein kinase 14), PRG2 (proteoglycan 2, bone marrow (natural killer cell activator, eosinophil granule major basic protein)), PRKCA (protein kinase C, alpha), L1 CAM (L1 cell adhesion molecule), CD40 (CD40 molecule, TNF receptor superfamily member 5), NR1I2 (nuclear receptor subfamily 1, group I, member 2), JAG2 (jagged 2), CTNND1 (catenin (cadherin-associated protein), delta 1), CDH2 (cadherin 2, type 1, N-cadherin (neuronal)), CMA1 (chymase 1, mast cell), SORT1 (sortilin 1), DLK1 (delta-like 1 homolog (*Drosophila*)), THEM4 (thioesterase superfamily member 4), JUP (junction plakoglobin), CD46 (CD46 molecule, complement regulatory protein), CCL11 (chemokine (C-C motif) ligand 11), CAV3 (caveolin 3), RNASE3 (ribonuclease, RNase A family, 3 (eosinophil cationic protein)), HSPA8 (heat shock 70 kDa protein 8), CASP9 (caspase 9, apoptosis-related cysteine peptidase), CYP3A4 (cytochrome P450, family 3, subfamily A, polypeptide 4), CCR3 (chemokine (C-C motif) receptor 3), TFAP2A (transcription factor AP-2 alpha (activating enhancer binding protein 2 alpha)), SCP2 (sterol carrier protein 2), CDK4 (cyclin-dependent kinase 4), HIF1A (hypoxia inducible factor 1, alpha subunit (basic helix-loop-helix transcription factor)), TCF7L2 (transcription factor 7-like 2 (T-cell specific, HMG-box)), IL1R2 (interleukin 1 receptor, type II), B3GALTL (beta 1,3-galactosyltransferase-like), MDM2 (Mdm2 p53 binding protein homolog (mouse)), RELA (v-rel reticuloendotheliosis viral oncogene homolog A (avian)), CASP7 (caspase 7, apoptosis-related cysteine peptidase), IDE (insulin-degrading enzyme), FABP4 (fatty acid binding protein 4, adipocyte), CASK (calcium/calmodulin-dependent serine protein kinase (MAGUK family)), ADCYAP1R1 (adenylate cyclase activating polypeptide 1 (pituitary) receptor type I), ATF4 (activating transcription factor 4 (tax-responsive enhancer element B67)), PDGFA (platelet-derived growth factor alpha polypeptide), C21 or f33 (chromosome 21 open reading frame 33), SCG5 (secretogranin V (7B2 protein)), RNF123 (ring finger protein 123), NFKB1 (nuclear factor of kappa light polypeptide gene enhancer in B-cells 1), ERBB2 (v-erb-b2 erythroblastic leukemia viral oncogene homolog 2, neuro/glioblastoma derived oncogene homolog (avian)), CAV1 (caveolin 1, caveolae protein, 22 kDa), MMP7 (matrix metallopeptidase 7 (matrilysin, uterine)), TGFA (transforming growth factor, alpha), RXRA (retinoid X receptor, alpha), STX1A (syntaxin 1A (brain)), PSMC4 (proteasome (prosome, macropain) 26S subunit, ATPase, 4), P2RY2 (purinergic receptor P2Y, G-protein coupled, 2), TNFRSF21 (tumor necrosis factor receptor superfamily, member 21), DLG1 (discs, large homolog 1 (*Drosophila*)), NUMBL (numb homolog (*Drosophila*)-like), SPN (sialophorin), PLSCR1 (phospholipid scramblase 1), UBQLN2 (ubiquilin 2), UBQLN1 (ubiquilin 1), PCSK7 (proprotein convertase subtilisin/kexin type 7), SPON1 (spondin 1, extracellular matrix protein), SILV (silver homolog (mouse)), QPCT (glutaminyl-peptide cyclotransferase), HES5 (hairy and enhancer of split 5 (*Drosophila*)), GCC1 (GRIP and coiled-coil domain containing 1), and any combination thereof.

The genetically modified animal or cell may comprise 1, 2, 3, 4, 5, 6, 7, 8, 9, 10 or more disrupted chromosomal sequences encoding a protein associated with a secretase disorder and zero, 1, 2, 3, 4, 5, 6, 7, 8, 9, 10 or more chromosomally integrated sequences encoding a disrupted protein associated with a secretase disorder.

ALS

US Patent Publication No. 20110023144, describes use of zinc finger nucleases to genetically modify cells, animals and proteins associated with amyotrophic lateral sclerosis (ALS) disease. ALS is characterized by the gradual steady degeneration of certain nerve cells in the brain cortex, brain stem, and spinal cord involved in voluntary movement.

Motor neuron disorders and the proteins associated with these disorders are a diverse set of proteins that effect susceptibility for developing a motor neuron disorder, the presence of the motor neuron disorder, the severity of the motor neuron disorder or any combination thereof. The present disclosure comprises editing of any chromosomal sequences that encode proteins associated with ALS disease, a specific motor neuron disorder. The proteins associated with ALS are typically selected based on an experimental association of ALS-related proteins to ALS. For example, the production rate or circulating concentration of a protein associated with ALS may be elevated or depressed in a population with ALS relative to a population without ALS. Differences in protein levels may be assessed using proteomic techniques including but not limited to Western blot, immunohistochemical staining, enzyme linked immunosorbent assay (ELISA), and mass spectrometry. Alternatively, the proteins associated with ALS may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with ALS include but are not limited to the following proteins: SOD1 superoxide dismutase 1, ALS3 amyotrophic lateral soluble sclerosis 3 SETX senataxin ALS5 amyotrophic lateral sclerosis 5 FUS fused in sarcoma ALS7 amyotrophic lateral sclerosis 7 ALS2 amyotrophic lateral DPP6 Dipeptidyl-peptidase 6 sclerosis 2 NEFH neurofilament, heavy PTGS1 prostaglandin-polypeptide endoperoxide synthase 1 SLC1A2 solute carrier family 1 TNFRSF10B tumor necrosis factor (glial high affinity receptor superfamily, glutamate transporter), member 10b member 2 PRPH peripherin HSP90AA1 heat shock protein 90 kDa alpha (cytosolic), class A member 1 GRIA2 glutamate receptor, IFNG interferon, gamma ionotropic, AMPA 2 S100B S100 calcium binding FGF2 fibroblast growth factor 2 protein B AOX1 aldehyde oxidase 1 CS citrate synthase TARDBP TAR DNA binding protein TXN thioredoxin RAPH1 Ras association MAP3K5 mitogen-activated protein (RalGDS/AF-6) and kinase 5 pleckstrin homology domains 1 NBEAL1 neurobeachin-like 1 GPX1 glutathione peroxidase 1 ICA1L islet cell autoantigen RAC1 ras-related $C_3$ botulinum 1.69 kDa-like toxin substrate 1 MAPT microtubule-associated ITPR2 inositol 1,4,5-protein tau triphosphate receptor, type 2 ALS2CR4 amyotrophic lateral GLS glutaminase sclerosis 2 (juvenile) chromosome region, candidate 4 ALS2CR8 amyotrophic lateral CNTFR ciliary neurotrophic factor sclerosis 2 (juvenile) receptor chromosome region, candidate 8 ALS2CR11 amyotrophic lateral FOLH1 folate hydrolase 1 sclerosis 2 (juvenile) chromosome region, candidate 11 FAM117B family with sequence P4HB prolyl 4-hydroxylase, similarity 117, member B beta polypeptide CNTF ciliary neurotrophic factor SQSTM1 sequestosome 1 STRADB STE20-related kinase NAIP NLR family, apoptosis adaptor beta inhibitory protein YWHAQ tyrosine 3-SLC33A1 solute carrier family 33 monooxygenase/tryptophan (acetyl-CoA transporter), an 5-monooxygenase member 1 activation protein, theta polypeptide TRAK2 trafficking protein, homolog, SAC1 kinesin binding 2 lipid phosphatase domain containing NIF3L1 NIF3 NGG1 interacting INA internexin neuronal factor 3-like 1 intermediate filament protein, alpha PARD3B par-3 partitioning COX8A cytochrome c oxidase defective 3 homolog B subunit VIIIA CDK15 cyclin-dependent kinase HECW1 HECT, $C_2$ and WW 15 domain containing E3 ubiquitin protein ligase 1 NOS1 nitric oxide synthase 1 MET met proto-oncogene SOD2 superoxide dismutase 2, HSPB1 heat shock 27 kDa mitochondrial protein 1 NEFL neurofilament, light CTSB cathepsin B polypeptide ANG angiogenin, HSPA8 heat shock 70 kDa ribonuclease, RNase A protein 8 family, 5 VAPB VAMP (vesicle-ESR1 estrogen receptor 1 associated membrane protein)-associated protein B and C SNCA synuclein, alpha HGF hepatocyte growth factor CAT catalase ACTB actin, beta NEFM neurofilament, medium TH tyrosine hydroxylase polypeptide BCL2 B-cell CLL/lymphoma 2 FAS Fas (TNF receptor superfamily, member 6) CASP3 caspase 3, apoptosis-CLU clusterin related cysteine peptidase SMN1 survival of motor neuron G6PD glucose-6-phosphate 1, telomeric dehydrogenase BAX BCL2-associated X HSF1 heat shock transcription protein factor 1 RNF19A ring finger protein 19A JUN jun oncogene ALS2CR12 amyotrophic lateral HSPA5 heat shock 70 kDa sclerosis 2 (juvenile) protein 5 chromosome region, candidate 12 MAPK14 mitogen-activated protein IL10 interleukin 10 kinase 14 APEX1 APEX nuclease TXNRD1 thioredoxin reductase 1 (multifunctional DNA repair enzyme) 1 NOS2 nitric oxide synthase 2, TIMP1 TIMP metallopeptidase inducible inhibitor 1 CASP9 caspase 9, apoptosis-XIAP X-linked inhibitor of related cysteine apoptosis peptidase GLG1 golgi glycoprotein 1 EPO erythropoietin VEGFA vascular endothelial ELN elastin growth factor A GDNF glial cell derived NFE2L2 nuclear factor (erythroid-neurotrophic factor derived 2)-like 2 SLC6A3 solute carrier family 6 HSPA4 heat shock 70 kDa (neurotransmitter protein 4 transporter, dopamine), member 3 APOE apolipoprotein E PSMB8 proteasome (prosome, macropain) subunit, beta type, 8 DCTN1 dynactin 1 TIMP3 TIMP metallopeptidase inhibitor 3 KIFAP3 kinesin-associated SLC1A1 solute carrier family 1 protein 3 (neuronal/epithelial high affinity glutamate transporter, system Xag), member 1 SMN2 survival of motor neuron CCNC cyclin C 2, centromeric MPP4 membrane protein, STUB1 STIP1 homology and U-palmitoylated 4 box containing protein 1 ALS2 amyloid beta (A4) PRDX6 peroxiredoxin 6 precursor protein SYP synaptophysin CABIN1 calcineurin binding protein 1 CASP1 caspase 1, apoptosis-GART phosphoribosylglycinami related cysteine de formyltransferase, peptidase phosphoribosylglycinami de synthetase, phosphoribosylaminoimidazole synthetase CDK5 cyclin-dependent kinase 5 ATXN3 ataxin 3 RTN4 reticulon 4 C1QB complement component 1, q subcomponent, B chain VEGFC nerve growth factor HTT huntingtin receptor PARK7 Parkinson disease 7 XDH xanthine dehydrogenase GFAP glial fibrillary acidic MAP2 microtubule-associated protein 2 CYCS cytochrome c, somatic FCGR3B Fc fragment of IgG, low affinity IIIb, CCS copper chaperone for UBL5 ubiquitin-like 5 superoxide dismutase MMP9 matrix metallopeptidase SLC18A3 solute carrier family 18 9 ((vesicular acetylcholine), member 3 TRPM7 transient receptor HSPB2 heat shock 27 kDa potential cation channel, protein 2 subfamily M, member 7 AKT 1 v-akt murine thymoma DERL 1 Derl-like domain family, viral oncogene homolog 1 member 1 CCL2 chemokine (C-C motif) NGRN neugrin, neurite ligand 2 outgrowth associated GSR glutathione reductase TPPP3 tubulin polymerization-promoting protein family member 3 APAF1 apoptotic peptidase BTBD10 BTB (POZ) domain activating factor 1 containing 10 GLUD1 glutamate CXCR4 chemokine (C—X—C motif) dehydrogenase 1 receptor 4 SLC1A3 solute carrier family 1 FLT1 fms-related tyrosine (glial high affinity glutamate transporter), member 3 kinase 1 PON1 paraoxonase 1 AR androgen receptor LIF leukemia inhibitory factor ERBB3 v-erb-b2 erythroblastic leukemia viral oncogene homolog 3 LGALS1 lectin, galactoside-CD44 CD44 molecule binding, soluble, 1 TP53 tumor protein p53 TLR3 toll-like receptor 3 GRIA1 glutamate receptor, GAPDH glyceraldehyde-3-ionotropic, AMPA 1 phosphate dehydrogenase GRIK1 glutamate receptor, DES desmin ionotropic, kainate 1 CHAT choline acetyltransferase FLT4 fms-related tyrosine kinase 4 CHMP2B chromatin modifying BAG1 BCL2-associated protein 2B athanogene MT3 metallothionein 3 CHRNA4 cholinergic receptor, nicotinic, alpha 4 GSS glutathione synthetase BAK1 BCL2-antagonist/killer 1 KDR kinase insert domain GSTP1 glutathione S-transferase receptor (a type III pi 1 receptor tyrosine kinase) OGG1 8-oxoguanine DNA IL6 interleukin 6 (interferon, glycosylase beta 2).

The animal or cell may comprise 1, 2, 3, 4, 5, 6, 7, 8, 9, 10 or more disrupted chromosomal sequences encoding a protein associated with ALS and zero, 1, 2, 3, 4, 5, 6, 7, 8, 9, 10 or more chromosomally integrated sequences encoding the disrupted protein associated with ALS. Preferred proteins associated with ALS include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Autism

US Patent Publication No. 20110023145, describes use of zinc finger nucleases to genetically modify cells, animals and proteins associated with autism spectrum disorders (ASD). Autism spectrum disorders (ASDs) are a group of disorders characterized by qualitative impairment in social interaction and communication, and restricted repetitive and stereotyped patterns of behavior, interests, and activities. The three disorders, autism, Asperger syndrome (AS) and pervasive developmental disorder-not otherwise specified (PDD-NOS) are a continuum of the same disorder with varying degrees of severity, associated intellectual functioning and medical conditions. ASDs are predominantly genetically determined disorders with a heritability of around 90%.

US Patent Publication No. 20110023145 comprises editing of any chromosomal sequences that encode proteins associated with ASD which may be applied to the CRISPR Cas system of the present invention. The proteins associated with ASD are typically selected based on an experimental association of the protein associated with ASD to an incidence or indication of an ASD. For example, the production rate or circulating concentration of a protein associated with ASD may be elevated or depressed in a population having an ASD relative to a population lacking the ASD. Differences in protein levels may be assessed using proteomic techniques including but not limited to Western blot, immunohistochemical staining, enzyme linked immunosorbent assay (ELISA), and mass spectrometry. Alternatively, the proteins associated with ASD may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Non-limiting examples of disease states or disorders that may be associated with proteins associated with ASD include autism, Asperger syndrome (AS), pervasive developmental disorder-not otherwise specified (PDD-NOS), Rett's syndrome, tuberous sclerosis, phenylketonuria, Smith-Lemli-Opitz syndrome and fragile X syndrome. By way of non-limiting example, proteins associated with ASD include but are not limited to the following proteins: ATP10C aminophospholipid-MET MET receptor transporting ATPase tyrosine kinase (ATP10C) BZRAP1 MGLUR5 (GRM5) Metabotropic glutamate receptor 5 (MGLUR5) CDH10 Cadherin-10 MGLUR6 (GRM6) Metabotropic glutamate receptor 6 (MGLUR6) CDH9 Cadherin-9 NLGN1 Neuroligin-1 CNTN4 Contactin-4 NLGN2 Neuroligin-2 CNTNAP2 Contactin-associated SEMA5A Neuroligin-3 protein-like 2 (CNTNAP2) DHCR7 7-dehydrocholesterol NLGN4X Neuroligin-4 X-reductase (DHCR7) linked DOC2A Double C2-like domain-NLGN4Y Neuroligin-4 Y-containing protein alpha linked DPP6 Dipeptidyl NLGN5 Neuroligin-5 aminopeptidase-like protein 6 EN2 engrailed 2 (EN2) NRCAM Neuronal cell adhesion molecule (NRCAM) MDGA2 fragile X mental retardation NRXN1 Neurexin-1 1 (MDGA2) FMR2 (AFF2) AF4/FMR2 family member 2 OR4M2 Olfactory receptor (AFF2) 4M2 FOXP2 Forkhead box protein P2 OR4N4 Olfactory receptor (FOXP2) 4N4 FXR1 Fragile X mental OXTR oxytocin receptor retardation, autosomal (OXTR) homolog 1 (FXR1) FXR2 Fragile X mental PAH phenylalanine retardation, autosomal hydroxylase (PAH) homolog 2 (FXR2) GABRA1 Gamma-aminobutyric acid PTEN Phosphatase and receptor subunit alpha-1 tensin homologue (GABRA1) (PTEN) GABRA5 GABAA (.gamma.-aminobutyric PTPRZ1 Receptor-type acid) receptor alpha 5 tyrosine-protein subunit (GABRA5) phosphatase zeta (PTPRZ1) GABRB1 Gamma-aminobutyric acid RELN Reelin receptor subunit beta-1 (GABRB1) GABRB3 GABAA (.gamma.-aminobutyric RPL10 60S ribosomal acid) receptor.beta.3 subunit protein L10 (GABRB3) GABRGI Gamma-aminobutyric acid SEMA5A Semaphorin-5A receptor subunit gamma-1 (SEMA5A) (GABRGI) HIRIP3 HIRA-interacting protein 3 SEZ6L2 seizure related 6 homolog (mouse)-like 2 HOXA1 Homeobox protein Hox-A1 SHANK3 SH3 and multiple (HOXA1) ankyrin repeat domains 3 (SHANK3) IL6 Interleukin-6 SHBZRAPI SH3 and multiple ankyrin repeat domains 3 (SHBZRAPI) LAMB1 Laminin subunit beta-1 SLC6A4 Serotonin (LAMB1) transporter (SERT) MAPK3 Mitogen-activated protein TAS2R1 Taste receptor kinase 3 type 2 member 1 TAS2R1 MAZ Myc-associated zinc finger TSC1 Tuberous sclerosis protein protein 1 MDGA2 MAM domain containing TSC2 Tuberous sclerosis glycosylphosphatidylinositol protein 2 anchor 2 (MDGA2) MECP2 Methyl CpG binding UBE3A Ubiquitin protein 2 (MECP2) ligase E3A (UBE3A) MECP2 methyl CpG binding WNT2 Wingless-type protein 2 (MECP2) MMTV integration site family, member 2 (WNT2).

The identity of the protein associated with ASD whose chromosomal sequence is edited can and will vary. In preferred embodiments, the proteins associated with ASD whose chromosomal sequence is edited may be the benzodiazapine receptor (peripheral) associated protein 1 (BZRAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, the fragile X mental retardation autosomal homolog 2 protein (FXR2) encoded by the FXR2 gene, the MAM domain containing glycosylphosphatidylinositol anchor 2 protein (MDGA2) encoded by the MDGA2 gene, the methyl CpG binding protein 2 (MECP2) encoded by the MECP2 gene, the metabotropic glutamate receptor 5 (MGLUR5) encoded by the MGLUR5-1 gene (also termed GRM5), the neurexin 1 protein encoded by the NRXN1 gene, or the semaphorin-5A protein (SEMA5A) encoded by the SEMA5A gene. In an exemplary embodiment, the genetically modified animal is a rat, and the edited chromosomal sequence encoding the protein associated with ASD is as listed below: BZRAP1 benzodiazepine receptor XM_002727789, (peripheral) associated XM_213427, protein 1 (BZRAP1) XM_002724533, XM_001081125 AFF2 (FMR2) AF4/FMR2 family member 2 XM_219832, (AFF2) XM_001054673 FXR1 Fragile X mental NM_001012179 retardation, autosomal homolog 1 (FXR1) FXR2 Fragile X mental NM_001100647 retardation, autosomal homolog 2 (FXR2) MDGA2 MAM domain containing NM_199269 glycosylphosphatidylinositol anchor 2 (MDGA2) MECP2 Methyl CpG binding NM_022673 protein 2 (MECP2) MGLUR5 Metabotropic glutamate NM_017012 (GRM5) receptor 5 (MGLUR5) NRXN1 Neurexin-1 NM_021767 SEMA5A Semaphorin-5A (SEMA5A) NM_001107659.

Trinucleotide Repeat Expansion Disorders

US Patent Publication No. 20110016540, describes use of zinc finger nucleases to genetically modify cells, animals and proteins associated with trinucleotide repeat expansion disorders. Trinucleotide repeat expansion disorders are complex, progressive disorders that involve developmental neurobiology and often affect cognition as well as sensori-motor functions.

Trinucleotide repeat expansion proteins are a diverse set of proteins associated with susceptibility for developing a trinucleotide repeat expansion disorder, the presence of a trinucleotide repeat expansion disorder, the severity of a trinucleotide repeat expansion disorder or any combination thereof. Trinucleotide repeat expansion disorders are divided into two categories determined by the type of repeat. The most common repeat is the triplet CAG, which, when present in the coding region of a gene, codes for the amino acid glutamine (Q). Therefore, these disorders are referred to as the polyglutamine (polyQ) disorders and comprise the following diseases: Huntington Disease (HD); Spinobulbar Muscular Atrophy (SBMA); Spinocerebellar Ataxias (SCA types 1, 2, 3, 6, 7, and 17); and Dentatorubro-Pallidoluysian Atrophy (DRPLA). The remaining trinucleotide repeat expansion disorders either do not involve the CAG triplet or the CAG triplet is not in the coding region of the gene and are, therefore, referred to as the non-polyglutamine disorders. The non-polyglutamine disorders comprise Fragile X Syndrome (FRAXA); Fragile XE Mental Retardation (FRAXE); Friedreich Ataxia (FRDA); Myotonic Dystrophy (DM); and Spinocerebellar Ataxias (SCA types 8, and 12).

The proteins associated with trinucleotide repeat expansion disorders are typically selected based on an experimental association of the protein associated with a trinucleotide repeat expansion disorder to a trinucleotide repeat expansion disorder. For example, the production rate or circulating concentration of a protein associated with a trinucleotide repeat expansion disorder may be elevated or depressed in a population having a trinucleotide repeat expansion disorder relative to a population lacking the trinucleotide repeat expansion disorder. Differences in protein levels may be assessed using proteomic techniques including but not limited to Western blot, immunohistochemical staining, enzyme linked immunosorbent assay (ELISA), and mass spectrometry. Alternatively, the proteins associated with trinucleotide repeat expansion disorders may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Non-limiting examples of proteins associated with trinucleotide repeat expansion disorders include AR (androgen receptor), FMR1 (fragile X mental retardation 1), HTT (huntingtin), DMPK (dystrophia myotonica-protein kinase), FXN (frataxin), ATXN2 (ataxin 2), ATN1 (atrophin 1), FEN1 (flap structure-specific endonuclease 1), TNRC6A (trinucleotide repeat containing 6A), PABPN1 (poly(A) binding protein, nuclear 1), JPH3 (junctophilin 3), MED15 (mediator complex subunit 15), ATXN1 (ataxin 1), ATXN3 (ataxin 3), TBP (TATA box binding protein), CACNA1A (calcium channel, voltage-dependent, P/Q type, alpha 1A subunit), ATXN80S (ATXN8 opposite strand (non-protein coding)), PPP2R2B (protein phosphatase 2, regulatory subunit B, beta), ATXN7 (ataxin 7), TNRC6B (trinucleotide repeat containing 6B), TNRC6C (trinucleotide repeat containing 6C), CELF3 (CUGBP, Elav-like family member 3), MAB21L1 (mab-21-like 1 (C. elegans)), MSH2 (mutS homolog 2, colon cancer, nonpolyposis type 1 (E. coli)), TMEM185A (transmembrane protein 185A), SIX5 (SIX homeobox 5), CNPY3 (canopy 3 homolog (zebrafish)), FRAXE (fragile site, folic acid type, rare, fra(X)(q28) E), GNB2 (guanine nucleotide binding protein (G protein), beta polypeptide 2), RPL14 (ribosomal protein L14), ATXN8 (ataxin 8), INSR (insulin receptor), TTR (transthyretin), EP400 (E1A binding protein p400), GIGYF2 (GRB10 interacting GYF protein 2), OGG1 (8-oxoguanine DNA glycosylase), STC1 (stanniocalcin 1), CNDP1 (carnosine dipeptidase 1 (metallopeptidase M20 family)), C10orf2 (chromosome 10 open reading frame 2), MAML3 (mastermind-like 3 (Drosophila), DKC1 (dyskeratosis congenita 1, dyskerin), PAXIP1 (PAX interacting (with transcription-activation domain) protein 1), CASK (calcium/calmodulin-dependent serine protein kinase (MAGUK family)), MAPT (microtubule-associated protein tau), SP1 (Sp1 transcription factor), POLG (polymerase (DNA directed), gamma), AFF2 (AF4/FMR2 family, member 2), THBS1 (thrombospondin 1), TP53 (tumor protein p53), ESR1 (estrogen receptor 1), CGGBP1 (CGG triplet repeat binding protein 1), ABT1 (activator of basal transcription 1), KLK3 (kallikrein-related peptidase 3), PRNP (prion protein), JUN (jun oncogene), KCNN3 (potassium intermediate/small conductance calcium-activated channel, subfamily N, member 3), BAX (BCL2-associated X protein), FRAXA (fragile site, folic acid type, rare, fra(X)(q27.3) A (macroorchidism, mental retardation)), KBTBD10 (kelch repeat and BTB (POZ) domain containing 10), MBNL1 (muscleblind-like (Drosophila)), RAD51 (RAD51 homolog (RecA homolog, E. coli) (S. cerevisiae)), NCOA3 (nuclear receptor coactivator 3), ERDA1 (expanded repeat domain, CAG/CTG 1), TSC1 (tuberous sclerosis 1), COMP (cartilage oligomeric matrix protein), GCLC (glutamate-cysteine ligase, catalytic subunit), RRAD (Ras-related associated with diabetes), MSH3 (mutS homolog 3 (E. coli)), DRD2 (dopamine receptor D2), CD44 (CD44 molecule (Indian blood group)), CTCF (CCCTC-binding factor (zinc finger protein)), CCND1 (cyclin D1), CLSPN (claspin homolog (Xenopus laevis)), MEF2A (myocyte enhancer factor 2A), PTPRU (protein tyrosine phosphatase, receptor type, U), GAPDH (glyceraldehyde-3-phosphate dehydrogenase), TRIM22 (tripartite motif-containing 22), WT1 (Wilms tumor 1), AHR (aryl hydrocarbon receptor), GPX1 (glutathione peroxidase 1), TPMT (thiopurine S-methyltransferase), NDP (Norrie disease (pseudoglioma)), ARX (aristaless related homeobox), MUS81 (MUS81 endonuclease homolog (S. cerevisiae)), TYR (tyrosinase (oculocutaneous albinism IA)), EGR1 (early growth response 1), UNG (uracil-DNA glycosylase), NUMBL (numb homolog (Drosophila)-like), FABP2 (fatty acid binding protein 2, intestinal), EN2 (engrailed homeobox 2), CRYGC (crystallin, gamma C), SRP14 (signal recognition particle 14 kDa (homologous Alu RNA binding protein)), CRYGB (crystallin, gamma B), PDCD1 (programmed cell death 1), HOXA1 (homeobox A1), ATXN2L (ataxin 2-like), PMS2 (PMS2 postmeiotic segregation increased 2 (*S. cerevisiae*)), GLA (galactosidase, alpha), CBL (Cas-Br-M (murine) ecotropic retroviral transforming sequence), FTH1 (ferritin, heavy polypeptide 1), IL12RB2 (interleukin 12 receptor, beta 2), OTX2 (orthodenticle homeobox 2), HOXA5 (homeobox A5), POLG2 (polymerase (DNA directed), gamma 2, accessory subunit), DLX2 (distal-less homeobox 2), SIRPA (signal-regulatory protein alpha), OTX1 (orthodenticle homeobox 1), AHRR (aryl-hydrocarbon receptor repressor), MANF (mesencephalic astrocyte-derived neurotrophic factor), TMEM158 (transmembrane protein 158 (gene/pseudogene)), and ENSG00000078687.

Preferred proteins associated with trinucleotide repeat expansion disorders include HTT (Huntingtin), AR (androgen receptor), FXN (frataxin), Atxn3 (ataxin), Atxn1 (ataxin), Atxn2 (ataxin), Atxn7 (ataxin), Atxn10 (ataxin), DMPK (dystrophia myotonica-protein kinase), Atn1 (atrophin 1), CBP (creb binding protein), VLDLR (very low density lipoprotein receptor), and any combination thereof.

Treating Hearing Diseases

The present invention also contemplates delivering the CRISPR-Cas system to one or both ears.

Researchers are looking into whether gene therapy could be used to aid current deafness treatments—namely, cochlear implants. Deafness is often caused by lost or damaged hair cells that cannot relay signals to auditory neurons. In such cases, cochlear implants may be used to respond to sound and transmit electrical signals to the nerve cells. But these neurons often degenerate and retract from the cochlea as fewer growth factors are released by impaired hair cells.

US patent application 20120328580 describes injection of a pharmaceutical composition into the ear (e.g., auricular administration), such as into the luminae of the cochlea (e.g., the Scala media, Sc vestibulae, and Sc tympani), e.g., using a syringe, e.g., a single-dose syringe. For example, one or more of the compounds described herein can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlear capsule. Other inner ear administration methods are known in the art (see, e.g., Salt and Plontke, Drug Discovery Today, 10:1299-1306, 2005).

In another mode of administration, the pharmaceutical composition can be administered in situ, via a catheter or pump. A catheter or pump can, for example, direct a pharmaceutical composition into the cochlear luminae or the round window of the ear and/or the lumen of the colon. Exemplary drug delivery apparatus and methods suitable for administering one or more of the compounds described herein into an ear, e.g., a human ear, are described by McKenna et al., (U.S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a patient during a surgical procedure. In some embodiments, a catheter or pump can be positioned, e.g., in the ear (e.g., the outer, middle, and/or inner ear) of a patient without the need for a surgical procedure.

Alternatively, or in addition, one or more of the compounds described herein can be administered in combination with a mechanical device such as a cochlear implant or a hearing aid, which is worn in the outer ear. An exemplary cochlear implant that is suitable for use with the present invention is described by Edge et al., (U.S. Publication No. 2007/0093878).

In some embodiments, the modes of administration described above may be combined in any order and can be simultaneous or interspersed.

Alternatively, or in addition, the present invention may be administered according to any of the Food and Drug Administration approved methods, for example, as described in CDER Data Standards Manual, version number 004 (which is available at fda.give/cder/dsm/DRG/drg00301.htm).

In general, the cell therapy methods described in US patent application 20120328580 can be used to promote complete or partial differentiation of a cell to or towards a mature cell type of the inner ear (e.g., a hair cell) in vitro. Cells resulting from such methods can then be transplanted or implanted into a patient in need of such treatment. The cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described below.

Cells suitable for use in the present invention include, but are not limited to, cells that are capable of differentiating completely or partially into a mature cell of the inner ear, e.g., a hair cell (e.g., an inner and/or outer hair cell), when contacted, e.g., in vitro, with one or more of the compounds described herein. Exemplary cells that are capable of differentiating into a hair cell include, but are not limited to stem cells (e.g., inner ear stem cells, adult stem cells, bone marrow derived stem cells, embryonic stem cells, mesenchymal stem cells, skin stem cells, iPS cells, and fat derived stem cells), progenitor cells (e.g., inner ear progenitor cells), support cells (e.g., Deiters' cells, pillar cells, inner phalangeal cells, tectal cells and Hensen's cells), and/or germ cells. The use of stem cells for the replacement of inner ear sensory cells is described in Li et al., (U.S. Publication No. 2005/0287127) and Li et al., (U.S. patent Ser. No. 11/953, 797). The use of bone marrow derived stem cells for the replacement of inner ear sensory cells is described in Edge et al., PCT/US2007/084654. iPS cells are described, e.g., at Takahashi et al., Cell, Volume 131, Issue 5, Pages 861-872 (2007); Takahashi and Yamanaka, Cell 126, 663-76 (2006); Okita et al., Nature 448, 260-262 (2007); Yu, J. et al., Science 318(5858):1917-1920 (2007); Nakagawa et al., Nat. Biotechnol. 26:101-106 (2008); and Zaehres and Scholer, Cell 131(5):834-835 (2007). Such suitable cells can be identified by analyzing (e.g., qualitatively or quantitatively) the presence of one or more tissue specific genes. For example, gene expression can be detected by detecting the protein product of one or more tissue-specific genes. Protein detection techniques involve staining proteins (e.g., using cell extracts or whole cells) using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized.

The CRISPR Cas molecules of the present invention may be delivered to the ear by direct application of pharmaceutical composition to the outer ear, with compositions modified from US Published application, 20110142917. In some embodiments the pharmaceutical composition is applied to the ear canal. Delivery to the ear may also be referred to as aural or otic delivery.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Qi et al. discloses methods for efficient siRNA transfection to the inner ear through the intact round window by a novel proteidic delivery technology which may be applied to the nucleic acid-targeting system of the present invention (see, e.g., Qi et al., Gene Therapy (2013), 1-9). In particular, a TAT double stranded RNA-binding domains (TAT-DRBDs), which can transfect Cy3-labeled siRNA into cells of the inner ear, including the inner and outer hair cells, *Crista ampullaris*, macula utriculi and macula sacculi, through intact round-window permeation was successful for delivering double stranded siRNAs in vivo for treating various inner ear ailments and preservation of hearing function. About 40 µl of 10 mM RNA may be contemplated as the dosage for administration to the ear.

According to Rejali et al. (Hear Res. 2007 June; 228(1-2):180-7), cochlear implant function can be improved by good preservation of the spiral ganglion neurons, which are the target of electrical stimulation by the implant and brain derived neurotrophic factor (BDNF) has previously been shown to enhance spiral ganglion survival in experimentally deafened ears. Rejali et al. tested a modified design of the cochlear implant electrode that includes a coating of fibroblast cells transduced by a viral vector with a BDNF gene insert. To accomplish this type of ex vivo gene transfer, Rejali et al. transduced guinea pig fibroblasts with an adenovirus with a BDNF gene cassette insert, and determined that these cells secreted BDNF and then attached BDNF-secreting cells to the cochlear implant electrode via an agarose gel, and implanted the electrode in the scala tympani. Rejali et al. determined that the BDNF expressing electrodes were able to preserve significantly more spiral ganglion neurons in the basal turns of the cochlea after 48 days of implantation when compared to control electrodes and demonstrated the feasibility of combining cochlear implant therapy with ex vivo gene transfer for enhancing spiral ganglion neuron survival. Such a system may be applied to the nucleic acid-targeting system of the present invention for delivery to the ear.

Mukherjea et al. (Antioxidants & Redox Signaling, Volume 13, Number 5, 2010) document that knockdown of NOX3 using short interfering (si) RNA abrogated cisplatin ototoxicity, as evidenced by protection of OHCs from damage and reduced threshold shifts in auditory brainstem responses (ABRs). Different doses of siNOX3 (0.3, 0.6, and 0.9 µg) were administered to rats and NOX3 expression was evaluated by real time RT-PCR. The lowest dose of NOX3 siRNA used (0.3 µg) did not show any inhibition of NOX3 mRNA when compared to transtympanic administration of scrambled siRNA or untreated *cochleae*. However, administration of the higher doses of NOX3 siRNA (0.6 and 0.9 µg) reduced NOX3 expression compared to control scrambled siRNA. Such a system may be applied to the CRISPR Cas system of the present invention for transtympanic administration with a dosage of about 2 mg to about 4 mg of CRISPR Cas for administration to a human.

Jung et al. (Molecular Therapy, vol. 21 no. 4, 834-841 April 2013) demonstrate that Hes5 levels in the utricle decreased after the application of siRNA and that the number of hair cells in these utricles was significantly larger than following control treatment. The data suggest that siRNA technology may be useful for inducing repair and regeneration in the inner ear and that the Notch signaling pathway is a potentially useful target for specific gene expression inhibition. Jung et al. injected 8 µg of Hes5 siRNA in 2 µl volume, prepared by adding sterile normal saline to the lyophilized siRNA to a vestibular epithelium of the ear. Such a system may be applied to the nucleic acid-targeting system of the present invention for administration to the vestibular epithelium of the ear with a dosage of about 1 to about 30 mg of CRISPR Cas for administration to a human.

Gene Targeting in Non-Dividing Cells (Neurons and Muscle)

Non-dividing (especially non-dividing, fully differentiated) cell types present issues for gene targeting or genome engineering, for example because homologous recombination (HR) is generally suppressed in the G1 cell-cycle phase. However, while studying the mechanisms by which cells control normal DNA repair systems, Durocher discovered a previously unknown switch that keeps HR "off" in non-dividing cells and devised a strategy to toggle this switch back on. Orthwein et al. (Daniel Durocher's lab at the Mount Sinai Hospital in Ottawa, Canada) recently reported (Nature 16142, published online 9 Dec. 2015) have shown that the suppression of HR can be lifted and gene targeting successfully concluded in both kidney (293T) and osteosarcoma (U20S) cells. Tumor suppressors, BRCA1, PALB2 and BRAC2 are known to promote DNA DSB repair by HR. They found that formation of a complex of BRCA1 with PALB2-BRAC2 is governed by a ubiquitin site on PALB2, such that action on the site by an E3 ubiquitin ligase. This E3 ubiquitin ligase is composed of KEAP1 (a PALB2-interacting protein) in complex with cullin-3 (CUL3)-RBX1. PALB2 ubiquitylation suppresses its interaction with BRCA1 and is counteracted by the deubiquitylase USP11, which is itself under cell cycle control. Restoration of the BRCA1-PALB2 interaction combined with the activation of DNA-end resection is sufficient to induce homologous recombination in G1, as measured by a number of methods including a CRISPR-Cas9-based gene-targeting assay directed at USP 11 or KEAP1 (expressed from a pX459 vector). However, when the BRCA1-PALB2 interaction was restored in resection-competent G1 cells using either KEAP1 depletion or expression of the PALB2-KR mutant, a robust increase in gene-targeting events was detected.

Thus, reactivation of HR in cells, especially non-dividing, fully differentiated cell types is preferred, in some embodiments. In some embodiments, promotion of the BRCA1-PALB2 interaction is preferred in some embodiments. In some embodiments, the target ell is a non-dividing cell. In some embodiments, the target cell is a neuron or muscle cell. In some embodiments, the target cell is targeted in vivo. In some embodiments, the cell is in G1 and HR is suppressed. In some embodiments, use of KEAP1 depletion, for example inhibition of expression of KEAP1 activity, is preferred. KEAP1 depletion may be achieved through siRNA, for example as shown in Orthwein et al. Alternatively, expression of the PALB2-KR mutant (lacking all eight Lys residues in the BRCA1-interaction domain is preferred, either in combination with KEAP1 depletion or alone. PALB2-KR interacts with BRCA1 irrespective of cell cycle position. Thus, promotion or restoration of the BRCA1-PALB2 interaction, especially in G1 cells, is preferred in some embodiments, especially where the target cells are non-dividing, or where removal and return (ex vivo gene targeting) is problematic, for example neurone or muscle cells. KEAP1 siRNA is available from ThermoFischer. In some embodiments, a BRCA1-PALB2 complex may be delivered to the G1 cell. In some embodiments, PALB2 deubiquitylation may be promoted for example by increased expression of the deubiquitylase USP 11, so it is envisaged that a construct may be provided to promote or up-regulate expression or activity of the deubiquitylase USP11.

Treating Diseases of the Eye

The present invention also contemplates delivering the CRISPR-Cas system to one or both eyes.

In particular embodiments of the invention, the CRISPR-Cas system may be used to correct ocular defects that arise from several genetic mutations further described in Genetic Diseases of the Eye, Second Edition, edited by Elias I. Traboulsi, Oxford University Press, 2012.

In some embodiments, the condition to be treated or targeted is an eye disorder. In some embodiments, the eye disorder may include glaucoma. In some embodiments, the eye disorder includes a retinal degenerative disease. In some embodiments, the retinal degenerative disease is selected from Stargardt disease, Bardet-Biedl Syndrome, Best disease, Blue Cone Monochromacy, Choroidermia, Cone-rod dystrophy, Congenital Stationary Night Blindness, Enhanced S-Cone Syndrome, Juvenile X-Linked Retinoschisis, Leber Congenital Amaurosis, Malattia Leventinesse, Norrie Disease or X-linked Familial Exudative Vitreoretinopathy, Pattern Dystrophy, Sorsby Dystrophy, Usher Syndrome, Retinitis Pigmentosa, Achromatopsia or Macular dystrophies or degeneration, Retinitis Pigmentosa, Achromatopsia, and age related macular degeneration. In some embodiments, the retinal degenerative disease is Leber Congenital Amaurosis (LCA) or Retinitis Pigmentosa. In some embodiments, the CRISPR system is delivered to the eye, optionally via intravitreal injection or subretinal injection.

For administration to the eye, lentiviral vectors, in particular equine infectious anemia viruses (EIAV) are particularly preferred.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285, Published online 21 Nov. 2005 in Wiley InterScience (www.interscience.wiley.com). DOI: 10.1002/jgm.845). The vectors are contemplated to have cytomegalovirus (CMV) promoter driving expression of the target gene. Intracameral, subretinal, intraocular and intravitreal injections are all contemplated (see, e.g., Balagaan, J Gene Med 2006; 8: 275-285, Published online 21 Nov. 2005 in Wiley InterScience (www.interscience.wiley.com). DOI: 10.1002/jgm.845). Intraocular injections may be performed with the aid of an operating microscope. For subretinal and intravitreal injections, eyes may be prolapsed by gentle digital pressure and fundi visualised using a contact lens system consisting of a drop of a coupling medium solution on the cornea covered with a glass microscope slide coverslip. For subretinal injections, the tip of a 10-mm 34-gauge needle, mounted on a 5-µl Hamilton syringe may be advanced under direct visualization through the superior equatorial sclera tangentially towards the posterior pole until the aperture of the needle was visible in the subretinal space. Then, 2 µl of vector suspension may be injected to produce a superior bullous retinal detachment, thus confirming subretinal vector administration. This approach creates a self-sealing sclerotomy allowing the vector suspension to be retained in the subretinal space until it is absorbed by the RPE, usually within 48 h of the procedure. This procedure may be repeated in the inferior hemisphere to produce an inferior retinal detachment. This technique results in the exposure of approximately 70% of neurosensory retina and RPE to the vector suspension. For intravitreal injections, the needle tip may be advanced through the sclera 1 mm posterior to the corneoscleral limbus and 2 µl of vector suspension injected into the vitreous cavity. For intracameral injections, the needle tip may be advanced through a corneoscleral limbal paracentesis, directed towards the central cornea, and 2 µl of vector suspension may be injected. For intracameral injections, the needle tip may be advanced through a corneoscleral limbal paracentesis, directed towards the central cornea, and 2 µl of vector suspension may be injected. These vectors may be injected at titres of either $1.0\text{-}1.4\times10^{10}$ or $1.0\text{-}1.4\times10^{9}$ transducing units (TU)/ml.

In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)). Such a vector may be modified for the CRISPR-Cas system of the present invention. Each eye may be treated with either RetinoStat® at a dose of $1.1\times10^5$ transducing units per eye (TU/eye) in a total volume of 100 µl.

In another embodiment, an E1-, partial E3-, E4-deleted adenoviral vector may be contemplated for delivery to the eye. Twenty-eight patients with advanced neovascular agerelated macular degeneration (AMD) were given a single intravitreous injection of an E1-, partial E3-, E4-deleted adenoviral vector expressing human pigment ep-ithelium-derived factor (AdPEDF.ll) (see, e.g., Campochiaro et al., Human Gene Therapy 17:167-176 (February 2006)). Doses ranging from 106 to 109.5 particle units (PU) were investigated and there were no serious adverse events related to AdPEDF.ll and no dose-limiting toxicities (see, e.g., Campochiaro et al., Human Gene Therapy 17:167-176 (February 2006)). Adenoviral vector-mediated ocular gene transfer appears to be a viable approach for the treatment of ocular disorders and could be applied to the CRISPR Cas system.

In another embodiment, the sd-rxRNA® system of RXi Pharmaceuticals may be used/and or adapted for delivering CRISPR Cas to the eye. In this system, a single intravitreal administration of 3 µg of sd-rxRNA results in sequence-specific reduction of PPIB mRNA levels for 14 days. The sd-rxRNA® system may be applied to the nucleic acid-targeting system of the present invention, contemplating a dose of about 3 to 20 mg of CRISPR administered to a human.

Millington-Ward et al. (Molecular Therapy, vol. 19 no. 4, 642-649 April 2011) describes adeno-associated virus (AAV) vectors to deliver an RNA interference (RNAi)-based rhodopsin suppressor and a codon-modified rhodopsin replacement gene resistant to suppression due to nucleotide alterations at degenerate positions over the RNAi target site. An injection of either $6.0 \times 10^8$ vp or $1.8 \times 10^{10}$ vp AAV were subretinally injected into the eyes by Millington-Ward et al. The AAV vectors of Millington-Ward et al. may be applied to the CRISPR Cas system of the present invention, contemplating a dose of about $2 \times 10^{11}$ to about $6 \times 10^{13}$ vp administered to a human.

Dalkara et al. (Sci Transl Med 5, 189ra76 (2013)) also relates to in vivo directed evolution to fashion an AAV vector that delivers wild-type versions of defective genes throughout the retina after noninjurious injection into the eyes' vitreous humor. Dalkara describes a 7mer peptide display library and an AAV library constructed by DNA shuffling of cap genes from AAV1, 2, 4, 5, 6, 8, and 9. The rcAAV libraries and rAAV vectors expressing GFP under a CAG or Rho promoter were packaged and deoxyribonuclease-resistant genomic titers were obtained through quantitative PCR. The libraries were pooled, and two rounds of evolution were performed, each consisting of initial library diversification followed by three in vivo selection steps. In each such step, P30 rho-GFP mice were intravitreally injected with 2 ml of iodixanol-purified, phosphate-buffered saline (PBS)-dialyzed library with a genomic titer of about $1 \times 1012$ vg/ml. The AAV vectors of Dalkara et al. may be applied to the nucleic acid-targeting system of the present invention, contemplating a dose of about $1 \times 10^{15}$ to about $1 \times 10^{16}$ vg/ml administered to a human.

In a particular embodiment, the rhodopsin gene may be targeted for the treatment of retinitis pigmentosa (RP), wherein the system of US Patent Publication No. 20120204282 assigned to Sangamo BioSciences, Inc. may be modified in accordance of the CRISPR Cas system of the present invention.

In another embodiment, the methods of US Patent Publication No. 20130183282 assigned to Cellectis, which is directed to methods of cleaving a target sequence from the human rhodopsin gene, may also be modified to the nucleic acid-targeting system of the present invention.

US Patent Publication No. 20130202678 assigned to Academia *Sinica* relates to methods for treating retinopathies and sight-threatening ophthalmologic disorders relating to delivering of the Puf-A gene (which is expressed in retinal ganglion and pigmented cells of eye tissues and displays a unique anti-apoptotic activity) to the sub-retinal or intravitreal space in the eye. In particular, desirable targets are zgc:193933, prdm1a, spata2, tex10, rbb4, ddx3, zp2.2, Blimp-1 and HtrA2, all of which may be targeted by the nucleic acid-targeting system of the present invention.

Wu (Cell Stem Cell, 13:659-62, 2013) designed a guide RNA that led Cas9 to a single base pair mutation that causes cataracts in mice, where it induced DNA cleavage. Then using either the other wild-type allele or oligos given to the zygotes repair mechanisms corrected the sequence of the broken allele and corrected the cataract-causing genetic defect in mutant mouse.

US Patent Publication No. 20120159653, describes use of zinc finger nucleases to genetically modify cells, animals and proteins associated with macular degeneration (MD). Macular degeneration (MD) is the primary cause of visual impairment in the elderly, but is also a hallmark symptom of childhood diseases such as Stargardt disease, Sorsby fundus, and fatal childhood neurodegenerative diseases, with an age of onset as young as infancy. Macular degeneration results in a loss of vision in the center of the visual field (the macula) because of damage to the retina. Currently existing animal models do not recapitulate major hallmarks of the disease as it is observed in humans. The available animal models comprising mutant genes encoding proteins associated with MD also produce highly variable phenotypes, making translations to human disease and therapy development problematic.

One aspect of US Patent Publication No. 20120159653 relates to editing of any chromosomal sequences that encode proteins associated with MD which may be applied to the nucleic acid-targeting system of the present invention. The proteins associated with MD are typically selected based on an experimental association of the protein associated with MD to an MD disorder. For example, the production rate or circulating concentration of a protein associated with MD may be elevated or depressed in a population having an MD disorder relative to a population lacking the MD disorder. Differences in protein levels may be assessed using proteomic techniques including but not limited to Western blot, immunohistochemical staining, enzyme linked immunosorbent assay (ELISA), and mass spectrometry. Alternatively, the proteins associated with MD may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with MD include but are not limited to the following proteins: (ABCA4) ATP-binding cassette, sub-family A (ABC1), member 4 ACHM1 achromatopsia (rod monochromacy) 1 ApoE Apolipoprotein E (ApoE) C1QTNF5 (CTRP5) Clq and tumor necrosis factor related protein 5 (ClQTNF5) C2 Complement component 2 (C2) C3 Complement components (C3) CCL2 Chemokine (C-C motif) Ligand 2 (CCL2) CCR2 Chemokine (C-C motif) receptor 2 (CCR2) CD36 Cluster of Differentiation 36 CFB Complement factor B CFH Complement factor CFH H CFHR1 complement factor H-related 1 CFHR3 complement factor H-related 3 CNGB3 cyclic nucleotide gated channel beta 3 CP ceruloplasmin (CP) CRP C reactive protein (CRP) CST3 cystatin C or cystatin 3 (CST3) CTSD Cathepsin D (CTSD) CX3CR1 chemokine (C-X3-C motif) receptor 1 ELOVL4 Elongation of very long chain fatty acids 4 ERCC6 excision repair cross-complementing rodent repair deficiency, complementation group 6 FBLN5 Fibulin-5 FBLN5 Fibulin 5 FBLN6 Fibulin 6 FSCN2 fascin (FSCN2) HMCN1 Hemicentrin 1 HMCN1 hemicentin 1 HTRA1 HtrA serine peptidase 1 (HTRA1) HTRA1 HtrA serine peptidase 1 IL-6 Interleukin 6 IL-8 Interleukin 8 LOC387715 Hypothetical protein PLEKHA1 Pleckstrin homology domain containing family A member 1 (PLEKHA1) PROM1 Prominin 1 (PROM1 or CD133) PRPH2 Peripherin-2 RPGR retinitis pigmentosa GTPase regulator SERPINGI serpin peptidase inhibitor, clade G, member 1 (C1-inhibitor) TCOF1 Treacle TIMP3 Metalloproteinase inhibitor 3 (TIMP3) TLR3 Toll-like receptor 3.

The identity of the protein associated with MD whose chromosomal sequence is edited can and will vary. In preferred embodiments, the proteins associated with MD whose chromosomal sequence is edited may be the ATP-binding cassette, sub-family A (ABC1) member 4 protein (ABCA4) encoded by the ABCR gene, the apolipoprotein E protein (APOE) encoded by the APOE gene, the chemokine (C-C motif) Ligand 2 protein (CCL2) encoded by the CCL2 gene, the chemokine (C-C motif) receptor 2 protein (CCR2) encoded by the CCR2 gene, the ceruloplasmin protein (CP) encoded by the CP gene, the cathepsin D protein (CTSD) encoded by the CTSD gene, or the metalloproteinase inhibitor 3 protein (TIMP3) encoded by the TIMP3 gene. In an exemplary embodiment, the genetically modified animal is a rat, and the edited chromosomal sequence encoding the protein associated with MD may be: (ABCA4) ATP-binding cassette, NM_000350 sub-family A (ABC1), member 4 APOE Apolipoprotein E NM_138828 (APOE) CCL2 Chemokine (C-C NM_031530 motif) Ligand 2 (CCL2) CCR2 Chemokine (C-C NM_021866 motif) receptor 2 (CCR2) CP ceruloplasmin (CP) NM_012532 CTSD Cathepsin D (CTSD) NM_134334 TIMP3 Metalloproteinase NM_012886 inhibitor 3 (TIMP3) The animal or cell may comprise 1, 2, 3, 4, 5, 6, 7 or more disrupted chromosomal sequences encoding a protein associated with MD and zero, 1, 2, 3, 4, 5, 6, 7 or more chromosomally integrated sequences encoding the disrupted protein associated with MD.

The edited or integrated chromosomal sequence may be modified to encode an altered protein associated with MD. Several mutations in MD-related chromosomal sequences have been associated with MD. Non-limiting examples of mutations in chromosomal sequences associated with MD include those that may cause MD including in the ABCR protein, E471K (i.e. glutamate at position 471 is changed to lysine), R1129L (i.e. arginine at position 1129 is changed to leucine), T1428M (i.e. threonine at position 1428 is changed to methionine), R1517S (i.e. arginine at position 1517 is changed to serine), I1562T (i.e. isoleucine at position 1562 is changed to threonine), and G1578R (i.e. glycine at position 1578 is changed to arginine); in the CCR2 protein, V64I (i.e. valine at position 192 is changed to isoleucine); in CP protein, G969B (i.e. glycine at position 969 is changed to asparagine or aspartate); in TIMP3 protein, S156C (i.e. serine at position 156 is changed to cysteine), G166C (i.e. glycine at position 166 is changed to cysteine), G167C (i.e. glycine at position 167 is changed to cysteine), Y168C (i.e. tyrosine at position 168 is changed to cysteine), S170C (i.e. serine at position 170 is changed to cysteine), Y172C (i.e. tyrosine at position 172 is changed to cysteine) and S181C (i.e. serine at position 181 is changed to cysteine). Other associations of genetic variants in MD-associated genes and disease are known in the art.

CRISPR systems are useful to correct diseases resulting from autosomal dominant genes. For example, CRISPR/Cas9 was used to remove an autosomal dominant gene that causes receptor loss in the eye. Bakondi, B. et al., *In Vivo CRISPR Cas9 Gene Editing Corrects Retinal Dystrophy in the S334ter-3 Rat Model of Autosomal Dominant Retinitis Pigmentosa. Molecular Therapy,* 2015; DOI: 10.1038/mt.2015.220.

Treating Circulatory and Muscular Diseases

The present invention also contemplates delivering the CRISPR-Cas system described herein, e.g. Cpf1 effector protein systems, to the heart. For the heart, a myocardium tropic adeno-associated virus (AAVM) is preferred, in particular AAVM41 which showed preferential gene transfer in the heart (see, e.g., Lin-Yanga et al., PNAS, Mar. 10, 2009, vol. 106, no. 10). Administration may be systemic or local. A dosage of about $1\text{-}10\times10^{14}$ vector genomes is contemplated for systemic administration. See also, e.g., Eulalio et al. (2012) Nature 492: 376 and Somasuntharam et al. (2013) Biomaterials 34: 7790.

For example, US Patent Publication No. 20110023139, describes use of zinc finger nucleases to genetically modify cells, animals and proteins associated with cardiovascular disease. Cardiovascular diseases generally include high blood pressure, heart attacks, heart failure, and stroke and TIA. Any chromosomal sequence involved in cardiovascular disease or the protein encoded by any chromosomal sequence involved in cardiovascular disease may be utilized in the methods described in this disclosure. The cardiovascular-related proteins are typically selected based on an experimental association of the cardiovascular-related protein to the development of cardiovascular disease. For example, the production rate or circulating concentration of a cardiovascular-related protein may be elevated or depressed in a population having a cardiovascular disorder relative to a population lacking the cardiovascular disorder. Differences in protein levels may be assessed using proteomic techniques including but not limited to Western blot, immunohistochemical staining, enzyme linked immunosorbent assay (ELISA), and mass spectrometry. Alternatively, the cardiovascular-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of example, the chromosomal sequence may comprise, but is not limited to, IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), CTSK (cathepsin K), PTGIR (prostaglandin 12 (prostacyclin) receptor (IP)), KCNJ11 (potassium inwardly-rectifying channel, subfamily J, member 11), INS (insulin), CRP (C-reactive protein, pentraxin-related), PDGFRB (platelet-derived growth factor receptor, beta polypeptide), CCNA2 (cyclin A2), PDGFB (platelet-derived growth factor beta polypeptide (simian sarcoma viral (v-sis) oncogene homolog)), KCNJ5 (potassium inwardly-rectifying channel, subfamily J, member 5), KCNN3 (potassium intermediate/small conductance calcium-activated channel, subfamily N, member 3), CAPN10 (calpain 10), PTGES (prostaglandin E synthase), ADRA2B (adrenergic, alpha-2B-, receptor), ABCG5 (ATP-binding cassette, sub-family G (WHITE), member 5), PRDX2 (peroxiredoxin 2), CAPN5 (calpain 5), PARP14 (poly (ADP-ribose) polymerase family, member 14), MEX3C (mex-3 homolog C (*C. elegans*)), ACE angiotensin I converting enzyme (peptidyl-dipeptidase A) 1), TNF (tumor necrosis factor (TNF superfamily, member 2)), IL6 (interleukin 6 (interferon, beta 2)), STN (statin), SERPINE1 (serpin peptidase inhibitor, clade E (nexin, plasminogen activator inhibitor type 1), member 1), ALB (albumin), ADIPOQ (adiponectin, C1Q and collagen domain containing), APOB (apolipoprotein B (including Ag(x) antigen)), APOE (apolipoprotein E), LEP (leptin), MTHFR (5,10-methylenetetrahydrofolate reductase (NADPH)), APOA1 (apolipoprotein A-I), EDN1 (endothelin 1), NPPB (natriuretic peptide precursor B), NOS3 (nitric oxide synthase 3 (endothelial cell)), PPARG (peroxisome proliferator-activated receptor gamma), PLAT (plasminogen activator, tissue), PTGS2 (prostaglandin-endoperoxide synthase 2 (prostaglandin G/H synthase and cyclooxygenase)), CETP (cholesteryl ester transfer protein, plasma), AGTR1 (angiotensin II receptor, type 1), HMGCR (3-hydroxy-3-methyl-glutaryl-Coenzyme A reductase), IGF1 (insulin-like growth factor 1 (somatomedin C)), SELE (selectin E), REN (renin), PPARA (peroxisome proliferator-activated receptor alpha), PON1 (paraoxonase 1), KNG1 (kininogen 1), CCL2 (chemokine (C-C motif) ligand 2), LPL (lipoprotein lipase), VWF (von Willebrand factor), F2 (coagulation factor II (thrombin)), ICAM1 (intercellular adhesion molecule 1), TGFB1 (transforming growth factor, beta 1), NPPA (natriuretic peptide precursor A), IL10 (interleukin 10), EPO (erythropoietin), SOD1 (superoxide dismutase 1, soluble), VCAM1 (vascular cell adhesion molecule 1), IFNG (interferon, gamma), LPA (lipoprotein, Lp(a)), MPO (myeloperoxidase), ESR1 (estrogen receptor 1), MAPK1 (mitogen-activated protein kinase 1), HP (haptoglobin), F3 (coagulation factor III (thromboplastin, tissue factor)), CST3 (cystatin C), COG2 (component of oligomeric golgi complex 2), MMP9 (matrix metallopeptidase 9 (gelatinase B, 92 kDa gelatinase, 92 kDa type IV collagenase)), SERPINC1 (serpin peptidase inhibitor, clade C (antithrombin), member 1), F8 (coagulation factor VIII, procoagulant component), HMOX1 (heme oxygenase (decycling) 1), APOC3 (apolipoprotein C-III), IL8 (interleukin 8), PROK1 (prokineticin 1), CBS (cystathionine-beta-synthase), NOS2 (nitric oxide synthase 2, inducible), TLR4 (toll-like receptor 4), SELP (selectin P (granule membrane protein 140 kDa, antigen CD62)), ABCA1 (ATP-binding cassette, sub-family A (ABC1), member 1), AGT (angiotensinogen (serpin peptidase inhibitor, clade A, member 8)), LDLR (low density lipoprotein receptor), GPT (glutamic-pyruvate transaminase (alanine aminotransferase)), VEGFA (vascular endothelial growth factor A), NR3C2 (nuclear receptor subfamily 3, group C, member 2), IL18 (interleukin 18 (interferon-gamma-inducing factor)), NOS1 (nitric oxide synthase 1 (neuronal)), NR3C1 (nuclear receptor subfamily 3, group C, member 1 (glucocorticoid receptor)), FGB (fibrinogen beta chain), HGF (hepatocyte growth factor (hepatopoietin A; scatter factor)), IL1A (interleukin 1, alpha), RETN (resistin), AKT1 (v-akt murine thymoma viral oncogene homolog 1), LIPC (lipase, hepatic), HSPD1 (heat shock 60 kDa protein 1 (chaperonin)), MAPK14 (mitogen-activated protein kinase 14), SPP1 (secreted phosphoprotein 1), ITGB3 (integrin, beta 3 (platelet glycoprotein 111a, antigen CD61)), CAT (catalase), UTS2 (urotensin 2), THBD (thrombomodulin), F10 (coagulation factor X), CP (ceruloplasmin (ferroxidase)), TNFRSF11B (tumor necrosis factor receptor superfamily, member 11b), EDNRA (endothelin receptor type A), EGFR (epidermal growth factor receptor (erythroblastic leukemia viral (v-erb-b) oncogene homolog, avian)), MMP2 (matrix metallopeptidase 2 (gelatinase A, 72 kDa gelatinase, 72 kDa type IV collagenase)), PLG (plasminogen), NPY (neuropeptide Y), RHOD (ras homolog gene family, member D), MAPK8 (mitogen-activated protein kinase 8), MYC (v-myc myelocytomatosis viral oncogene homolog (avian)), FN1 (fibronectin 1), CMA1 (chymase 1, mast cell), PLAU (plasminogen activator, urokinase), GNB3 (guanine nucleotide binding protein (G protein), beta polypeptide 3), ADRB2 (adrenergic, beta-2-, receptor, surface), APOA5 (apolipoprotein A-V), SOD2 (superoxide dismutase 2, mitochondrial), F5 (coagulation factor V (proaccelerin, labile factor)), VDR (vitamin D (1,25-dihydroxyvitamin D3) receptor), ALOX5 (arachidonate 5-lipoxygenase), HLA-DRB1 (major histocompatibility complex, class II, DR beta 1), PARP1 (poly (ADP-ribose) polymerase 1), CD40LG (CD40 ligand), PON2 (paraoxonase 2), AGER (advanced glycosylation end product-specific receptor), IRS1 (insulin receptor substrate 1), PTGS1 (prostaglandin-endoperoxide synthase 1 (prostaglandin G/H synthase and cyclooxygenase)), ECE1 (endothelin converting enzyme 1), F7 (coagulation factor VII (serum prothrombin conversion accelerator)), URN (interleukin 1 receptor antagonist), EPHX2 (epoxide hydrolase 2, cytoplasmic), IGFBP1 (insulin-like growth factor binding protein 1), MAPK10 (mitogen-activated protein kinase 10), FAS (Fas (TNF receptor superfamily, member 6)), ABCB1 (ATP-binding cassette, subfamily B (MDR/TAP), member 1), JUN (jun oncogene), IGFBP3 (insulin-like growth factor binding protein 3), CD14 (CD14 molecule), PDE5A (phosphodiesterase 5A, cGMP-specific), AGTR2 (angiotensin II receptor, type 2), CD40 (CD40 molecule, TNF receptor superfamily member 5), LCAT (lecithin-cholesterol acyltransferase), CCR5 (chemokine (C-C motif) receptor 5), MMP1 (matrix metallopeptidase 1 (interstitial collagenase)), TIMP1 (TIMP metallopeptidase inhibitor 1), ADM (adrenomedullin), DYT10 (dystonia 10), STAT3 (signal transducer and activator of transcription 3 (acute-phase response factor)), MMP3 (matrix metallopeptidase 3 (stromelysin 1, progelatinase)), ELN (elastin), USF1 (upstream transcription factor 1), CFH (complement factor H), HSPA4 (heat shock 70 kDa protein 4), MMP12 (matrix metallopeptidase 12 (macrophage elastase)), MME (membrane metallo-endopeptidase), F2R (coagulation factor II (thrombin) receptor), SELL (selectin L), CTSB (cathepsin B), ANXA5 (annexin A5), ADRB1 (adrenergic, beta-1-, receptor), CYBA (cytochrome b-245, alpha polypeptide), FGA (fibrinogen alpha chain), GGT1 (gamma-glutamyltransferase 1), LIPG (lipase, endothelial), HIF1A (hypoxia inducible factor 1, alpha subunit (basic helix-loop-helix transcription factor)), CXCR4 (chemokine (C—X-C motif) receptor 4), PROC (protein C (inactivator of coagulation factors Va and VIIIa)), SCARB1 (scavenger receptor class B, member 1), CD79A (CD79a molecule, immunoglobulin-associated alpha), PLTP (phospholipid transfer protein), ADD1 (adducin 1 (alpha)), FGG (fibrinogen gamma chain), SAA1 (serum amyloid A1), KCNH2 (potassium voltage-gated channel, subfamily H (eag-related), member 2), DPP4 (dipeptidyl-peptidase 4), G6PD (glucose-6-phosphate dehydrogenase), NPR1 (natriuretic peptide receptor A/guanylate cyclase A (atrionatriuretic peptide receptor A)), VTN (vitronectin), KIAA0101 (KIAA0101), FOS (FBJ murine osteosarcoma viral oncogene homolog), TLR2 (toll-like receptor 2), PPIG (peptidylprolyl isomerase G (cyclophilin G)), IL,1R1 (interleukin 1 receptor, type I), AR (androgen receptor), CYP1A1 (cytochrome P450, family 1, subfamily A, polypeptide 1), SERPINAl (serpin peptidase inhibitor, clade A (alpha-1 antiproteinase, antitrypsin), member 1), MTR (5-methyltetrahydrofolate-homocysteine methyltransferase), RBP4 (retinol binding protein 4, plasma), APOA4 (apolipoprotein A-IV), CDKN2A (cyclin-dependent kinase inhibitor 2A (melanoma, p16, inhibits CDK4)), FGF2 (fibroblast growth factor 2 (basic)), EDNRB (endothelin receptor type B), ITGA2 (integrin, alpha 2 (CD49B, alpha 2 subunit of VLA-2 receptor)), CABIN1 (calcineurin binding protein 1), SHBG (sex hormone-binding globulin), HMGB1 (high-mobility group box 1), HSP90B2P (heat shock protein 90 kDa beta (Grp94), member 2 (pseudogene)), CYP3A4 (cytochrome P450, family 3, subfamily A, polypeptide 4), GJA1 (gap junction protein, alpha 1, 43 kDa), CAV1 (caveolin 1, caveolae protein, 22 kDa), ESR2 (estrogen receptor 2 (ER beta)), LTA (lymphotoxin alpha (TNF superfamily, member 1)), GDF15 (growth differentiation factor 15), BDNF (brain-derived neurotrophic factor), CYP2D6 (cytochrome P450, family 2, subfamily D, polypeptide 6), NGF (nerve growth factor (beta polypeptide)), SP1 (Sp1 transcription factor), TGIF1 (TGFB-induced factor homeobox 1), SRC (v-src sarcoma (Schmidt-Ruppin A-2) viral oncogene homolog (avian)), EGF (epidermal growth factor (beta-urogastrone)), PIK3CG (phosphoinositide-3-kinase, catalytic, gamma polypeptide), HLA-A (major histocompatibility complex, class I, A), KCNQ1 (potassium voltage-gated channel, KQT-like subfamily, member 1), CNR1 (cannabinoid receptor 1 (brain)), FBN1 (fibrillin 1), CHKA (choline kinase alpha), BEST1 (bestrophin 1), APP (amyloid beta (A4) precursor protein), CTNNB1 (catenin (cadherin-associated protein), beta 1, 88 kDa), TL2 (interleukin 2), CD36 (CD36 molecule (thrombospondin receptor)), PRKAB1 (protein kinase, AMP-activated, beta 1 non-catalytic subunit), TPO (thyroid peroxidase), ALDH7A1 (aldehyde dehydrogenase 7 family, member A1), CX3CR1 (chemokine (C-X3-C motif) receptor 1), TH (tyrosine hydroxylase), F9 (coagulation factor IX), GH1 (growth hormone 1), TF (transferrin), HFE (hemochromatosis), IL17A (interleukin 17A), PTEN (phosphatase and tensin homolog), GSTM1 (glutathione S-transferase mu 1), DMD (dystrophin), GATA4 (GATA binding protein 4), F13A1 (coagulation factor XIII, A1 polypeptide), TTR (transthyretin), FABP4 (fatty acid binding protein 4, adipocyte), PON3 (paraoxonase 3), APOC1 (apolipoprotein C-I), INSR (insulin receptor), TNFRSF1B (tumor necrosis factor receptor superfamily, member 1B), HTR2A (5-hydroxytryptamine (serotonin) receptor 2A), CSF3 (colony stimulating factor 3 (granulocyte)), CYP2C9 (cytochrome P450, family 2, subfamily C, polypeptide 9), TXN (thioredoxin), CYP11B2 (cytochrome P450, family 11, subfamily B, polypeptide 2), PTH (parathyroid hormone), CSF2 (colony stimulating factor 2 (granulocyte-macrophage)), KDR (kinase insert domain receptor (a type III receptor tyrosine kinase)), PLA2G2A (phospholipase A2, group IIA (platelets, synovial fluid)), B2M (beta-2-microglobulin), THBS1 (thrombospondin 1), GCG (glucagon), RHOA (ras homolog gene family, member A), ALDH2 (aldehyde dehydrogenase 2 family (mitochondrial)), TCF7L2 (transcription factor 7-like 2 (T-cell specific, HMG-box)), BDKRB2 (bradykinin receptor B2), NFE2L2 (nuclear factor (erythroid-derived 2)-like 2), NOTCH1 (Notch homolog 1, translocation-associated (*Drosophila*)), UGT1A1 (UDP glucuronosyltransferase 1 family, polypeptide A1), IFNA1 (interferon, alpha 1), PPARD (peroxisome proliferator-activated receptor delta), SIRT1 (sirtuin (silent mating type information regulation 2 homolog) 1 (*S. cerevisiae*)), GNRH1 (gonadotropin-releasing hormone 1 (luteinizing-releasing hormone)), PAPPA (pregnancy-associated plasma protein A, pappalysin 1), ARR3 (arrestin 3, retinal (X-arrestin)), NPPC (natriuretic peptide precursor C), AHSP (alpha hemoglobin stabilizing protein), PTK2 (PTK2 protein tyrosine kinase 2), IL13 (interleukin 13), MTOR (mechanistic target of rapamycin (serine/threonine kinase)), ITGB2 (integrin, beta 2 (complement component 3 receptor 3 and 4 subunit)), GSTT1 (glutathione S-transferase theta 1), IL6ST (interleukin 6 signal transducer (gp130, oncostatin M receptor)), CPB2 (carboxypeptidase B2 (plasma)), CYP1A2 (cytochrome P450, family 1, subfamily A, polypeptide 2), HNF4A (hepatocyte nuclear factor 4, alpha), SLC6A4 (solute carrier family 6 (neurotransmitter transporter, serotonin), member 4), PLA2G6 (phospholipase A2, group VI (cytosolic, calcium-independent)), TNFSF11 (tumor necrosis factor (ligand) superfamily, member 11), SLC8A1 (solute carrier family 8 (sodium/calcium exchanger), member 1), F2RL1 (coagulation factor II (thrombin) receptor-like 1), AKR1A1 (aldo-keto reductase family 1, member A1 (aldehyde reductase)), ALDH9A1 (aldehyde dehydrogenase 9 family, member A1), BGLAP (bone gamma-carboxyglutamate (gla) protein), MTTP (microsomal triglyceride transfer protein), MTRR (5-methyltetrahydrofolate-homocysteine methyltransferase reductase), SULT1A3 (sulfotransferase family, cytosolic, 1A, phenol-preferring, member 3), RAGE (renal tumor antigen), C4B (complement component 4B (Chido blood group), P2RY12 (purinergic receptor P2Y, G-protein coupled, 12), RNLS (renalase, FAD-dependent amine oxidase), CREB1 (cAMP responsive element binding protein 1), POMC (proopiomelanocortin), RAC1 (ras-related C3 botulinum toxin substrate 1 (rho family, small GTP binding protein Rac1)), LMNA (lamin NC), CD59 (CD59 molecule, complement regulatory protein), SCN5A (sodium channel, voltage-gated, type V, alpha subunit), CYP1B1 (cytochrome P450, family 1, subfamily B, polypeptide 1), MIF (macrophage migration inhibitory factor (glycosylation-inhibiting factor)), MMP13 (matrix metallopeptidase 13 (collagenase 3)), TIMP2 (TIMP metallopeptidase inhibitor 2), CYP19A1 (cytochrome P450, family 19, subfamily A, polypeptide 1), CYP21A2 (cytochrome P450, family 21, subfamily A, polypeptide 2), PTPN22 (protein tyrosine phosphatase, non-receptor type 22 (lymphoid)), MYH14 (myosin, heavy chain 14, non-muscle), MBL2 (mannose-binding lectin (protein C) 2, soluble (opsonic defect)), SELPLG (selectin P ligand), AOC3 (amine oxidase, copper containing 3 (vascular adhesion protein 1)), CTSL1 (cathepsin L1), PCNA (proliferating cell nuclear antigen), IGF2 (insulin-like growth factor 2 (somatomedin A)), ITGB1 (integrin, beta 1 (fibronectin receptor, beta polypeptide, antigen CD29 includes MDF2, MSK12)), CAST (calpastatin), CXCL 12 (chemokine (C—X-C motif) ligand 12 (stromal cell-derived factor 1)), IGHE (immunoglobulin heavy constant epsilon), KCNE1 (potassium voltage-gated channel, Isk-related family, member 1), TFRC (transferrin receptor (p90, CD71)), COL1A1 (collagen, type I, alpha 1), COL1A2 (collagen, type I, alpha 2), IL2RB (interleukin 2 receptor, beta), PLA2G10 (phospholipase A2, group X), ANGPT2 (angiopoietin 2), PROCR (protein C receptor, endothelial (EPCR)), NOX4 (NADPH oxidase 4), HAMP (hepcidin antimicrobial peptide), PTPN11 (protein tyrosine phosphatase, non-receptor type 11), SLC2A1 (solute carrier family 2 (facilitated glucose transporter), member 1), IL2RA (interleukin 2 receptor, alpha), CCL5 (chemokine (C-C motif) ligand 5), IRF1 (interferon regulatory factor 1), CFLAR (CASP8 and FADD-like apoptosis regulator), CALCA (calcitonin-related polypeptide alpha), EIF4E (eukaryotic translation initiation factor 4E), GSTP1 (glutathione S-transferase pi 1), JAK2 (Janus kinase 2), CYP3A5 (cytochrome P450, family 3, subfamily A, polypeptide 5), HSPG2 (heparan sulfate proteoglycan 2), CCL3 (chemokine (C-C motif) ligand 3), MYD88 (myeloid differentiation primary response gene (88)), VIP (vasoactive intestinal peptide), SOAT1 (sterol O-acyltransferase 1), ADRBK1 (adrenergic, beta, receptor kinase 1), NR4A2 (nuclear receptor subfamily 4, group A, member 2), MMP8 (matrix metallopeptidase 8 (neutrophil collagenase)), NPR2 (natriuretic peptide receptor B/guanylate cyclase B (atrial natriuretic peptide receptor B)), GCH1 (GTP cyclohydrolase 1), EPRS (glutamyl-prolyl-tRNA synthetase), PPARGC1A (peroxisome proliferator-activated receptor gamma, coactivator 1 alpha), F12 (coagulation factor XII (Hageman factor)), PECAM1 (platelet/endothelial cell adhesion molecule), CCL4 (chemokine (C-C motif) ligand 4), SERPINA3 (serpin peptidase inhibitor, clade A (alpha-1 antiproteinase, antitrypsin), member 3), CASR (calcium-sensing receptor), GJA5 (gap junction protein, alpha 5, 40 kDa), FABP2 (fatty acid binding protein 2, intestinal), TTF2 (transcription termination factor, RNA polymerase II), PROS1 (protein S (alpha)), CTF1 (cardiotrophin 1), SGCB (sarcoglycan, beta (43 kDa dystrophin-associated glycoprotein)), YME1L1 (YME1-like 1 (*S. cerevisiae*)), CAMP (cathelicidin antimicrobial peptide), ZC3H12A (zinc finger CCCH-type containing 12A), AKR1B1 (aldo-keto reductase family 1, member B1 (aldose reductase)), DES (desmin), MMP7 (matrix metallopeptidase 7 (matrilysin, uterine)), AHR (aryl hydrocarbon receptor), CSF1 (colony stimulating factor 1 (macrophage)), HDAC9 (histone deacetylase 9), CTGF (connective tissue growth factor), KCNMA1 (potassium large conductance calcium-activated channel, subfamily M, alpha member 1), UGT1A (UDP glucuronosyltransferase 1 family, polypeptide A complex locus), PRKCA (protein kinase C, alpha), COMT (catechol-.beta.-methyltransferase), S100B (S100 calcium binding protein B), EGR1 (early growth response 1), PRL (prolactin), IL15 (interleukin 15), DRD4 (dopamine receptor D4), CAMK2G (calcium/calmodulin-dependent protein kinase II gamma), SLC22A2 (solute carrier family 22 (organic cation transporter), member 2), CCL11 (chemokine (C-C motif) ligand 11), PGF (B321 placental growth factor), THPO (thrombopoietin), GP6 (glycoprotein VI (platelet)), TACR1 (tachykinin receptor 1), NTS (neurotensin), HNF1A (HNF1 homeobox A), SST (somatostatin), KCND1 (potassium voltage-gated channel, Shal-related subfamily, member 1), LOC646627 (phospholipase inhibitor), TBXAS1 (thromboxane A synthase 1 (platelet)), CYP2J2 (cytochrome P450, family 2, subfamily J, polypeptide 2), TBXA2R (thromboxane A2 receptor), ADH1C (alcohol dehydrogenase 1C (class I), gamma polypeptide), ALOX12 (arachidonate 12-lipoxygenase), AHSG (alpha-2-HS-glycoprotein), BHMT (betaine-homocysteine methyltransferase), GJA4 (gap junction protein, alpha 4, 37 kDa), SLC25A4 (solute carrier family 25 (mitochondrial carrier; adenine nucleotide translocator), member 4), ACLY (ATP citrate lyase), ALOX5AP (arachidonate 5-lipoxygenase-activating protein), NUMA1 (nuclear mitotic apparatus protein 1), CYP27B1 (cytochrome P450, family 27, subfamily B, polypeptide 1), CYSLTR2 (cysteinyl leukotriene receptor 2), SOD3 (superoxide dismutase 3, extracellular), LTC4S (leukotriene $C_4$ synthase), UCN (urocortin), GHRL (ghrelin/obestatin prepropeptide), APOC2 (apolipoprotein C-II), CLEC4A (C-type lectin domain family 4, member A), KBTBD10 (kelch repeat and BTB (POZ) domain containing 10), TNC (tenascin C), TYMS (thymidylate synthetase), SHC1 (SHC (Src homology 2 domain containing) transforming protein 1), LRP1 (low density lipoprotein receptor-related protein 1), SOCS3 (suppressor of cytokine signaling 3), ADH1B (alcohol dehydrogenase 1B (class I), beta polypeptide), KLK3 (kallikrein-related peptidase 3), HSD11B1 (hydroxysteroid (11-beta) dehydrogenase 1), VKORC1 (vitamin K epoxide reductase complex, subunit 1), SERPINB2 (serpin peptidase inhibitor, clade B (ovalbumin), member 2), TNS1 (tensin 1), RNF19A (ring finger protein 19A), EPOR (erythropoietin receptor), ITGAM (integrin, alpha M (complement component 3 receptor 3 subunit)), PITX2 (paired-like homeodomain 2), MAPK7 (mitogen-activated protein kinase 7), FCGR3A (Fc fragment of IgG, low affinity 111a, receptor (CD16a)), LEPR (leptin receptor), ENG (endoglin), GPX1 (glutathione peroxidase 1), GOT2 (glutamic-oxaloacetic transaminase 2, mitochondrial (aspartate aminotransferase 2)), HRH1 (histamine receptor H1), NR112 (nuclear receptor subfamily 1, group I, member 2), CRH (corticotropin releasing hormone), HTR1A (5-hydroxytryptamine (serotonin) receptor 1A), VDAC1 (voltage-dependent anion channel 1), HPSE (heparanase), SFTPD (surfactant protein D), TAP2 (transporter 2, ATP-binding cassette, sub-family B (MDR/TAP)), RNF123 (ring finger protein 123), PTK2B (PTK2B protein tyrosine kinase 2 beta), NTRK2 (neurotrophic tyrosine kinase, receptor, type 2), IL6R (interleukin 6 receptor), ACHE (acetylcholinesterase (Yt blood group)), GLP1R (glucagon-like peptide 1 receptor), GHR (growth hormone receptor), GSR (glutathione reductase), NQO1 (NAD(P)H dehydrogenase, quinone 1), NR5A1 (nuclear receptor subfamily 5, group A, member 1), GJB2 (gap junction protein, beta 2, 26 kDa), SLC9A1 (solute carrier family 9 (sodium/hydrogen exchanger), member 1), MAOA (monoamine oxidase A), PCSK9 (proprotein convertase subtilisin/kexin type 9), FCGR2A (Fc fragment of IgG, low affinity IIa, receptor (CD32)), SERPINF1 (serpin peptidase inhibitor, clade F (alpha-2 antiplasmin, pigment epithelium derived factor), member 1), EDN3 (endothelin 3), DHFR (dihydrofolate reductase), GAS6 (growth arrest-specific 6), SMPD1 (sphingomyelin phosphodiesterase 1, acid lysosomal), UCP2 (uncoupling protein 2 (mitochondrial, proton carrier)), TFAP2A (transcription factor AP-2 alpha (activating enhancer binding protein 2 alpha)), C4BPA (complement component 4 binding protein, alpha), SERPINF2 (serpin peptidase inhibitor, clade F (alpha-2 antiplasmin, pigment epithelium derived factor), member 2), TYMP (thymidine phosphorylase), ALPP (alkaline phosphatase, placental (Regan isozyme)), CXCR2 (chemokine (C—X-C motif) receptor 2), SLC39A3 (solute carrier family 39 (zinc transporter), member 3), ABCG2 (ATP-binding cassette, sub-family G (WHITE), member 2), ADA (adenosine deaminase), JAK3 (Janus kinase 3), HSPA1A (heat shock 70 kDa protein 1A), FASN (fatty acid synthase), FGF1 (fibroblast growth factor 1 (acidic)), F11 (coagulation factor XI), ATP7A (ATPase, Cu++ transporting, alpha polypeptide), CR1 (complement component (3b/4b) receptor 1 (Knops blood group)), GFAP (glial fibrillary acidic protein), ROCK1 (Rho-associated, coiled-coil containing protein kinase 1), MECP2 (methyl CpG binding protein 2 (Rett syndrome)), MYLK (myosin light chain kinase), BCHE (butyrylcholinesterase), LIPE (lipase, hormone-sensitive), PRDX5 (peroxiredoxin 5), ADORA1 (adenosine A1 receptor), WRN (Werner syndrome, RecQ helicase-like), CXCR3 (chemokine (C—X-C motif) receptor 3), CD81 (CD81 molecule), SMAD7 (SMAD family member 7), LAMC2 (laminin, gamma 2), MAP3K5 (mitogen-activated protein kinase kinase kinase 5), CHGA (chromogranin A (parathyroid secretory protein 1)), IAPP (islet amyloid polypeptide), RHO (rhodopsin), ENPP1 (ectonucleotide pyrophosphatase/phosphodiesterase 1), PTHLH (parathyroid hormone-like hormone), NRG1 (neuregulin 1), VEGFC (vascular endothelial growth factor C), ENPEP (glutamyl aminopeptidase (aminopeptidase A)), CEBPB (CCAAT/enhancer binding protein (C/EBP), beta), NAGLU (N-acetylglucosaminidase, alpha-), F2RL3 (coagulation factor II (thrombin) receptor-like 3), CX3CL1 (chemokine (C-X3-C motif) ligand 1), BDKRB1 (bradykinin receptor B1), ADAMTS13 (ADAM metallopeptidase with thrombospondin type 1 motif, 13), ELANE (elastase, neutrophil expressed), ENPP2 (ectonucleotide pyrophosphatase/phosphodiesterase 2), CISH (cytokine inducible SH2-containing protein), GAST (gastrin), MYOC (myocilin, trabecular meshwork inducible glucocorticoid response), ATP1A2 (ATPase, Na+/K+ transporting, alpha 2 polypeptide), NF1 (neurofibromin 1), GJB1 (gap junction protein, beta 1, 32 kDa), MEF2A (myocyte enhancer factor 2A), VCL (vinculin), BMPR2 (bone morphogenetic protein receptor, type II (serine/threonine kinase)), TUBB (tubulin, beta), CDC42 (cell division cycle 42 (GTP binding protein, 25 kDa)), KRT18 (keratin 18), HSF1 (heat shock transcription factor 1), MYB (v-myb myeloblastosis viral oncogene homolog (avian)), PRKAA2 (protein kinase, AMP-activated, alpha 2 catalytic subunit), ROCK2 (Rho-associated, coiled-coil containing protein kinase 2), TFPI (tissue factor pathway inhibitor (lipoprotein-associated coagulation inhibitor)), PRKG1 (protein kinase, cGMP-dependent, type I), BMP2 (bone morphogenetic protein 2), CTNND1 (catenin (cadherin-associated protein), delta 1), CTH (cystathionase (cystathionine gamma-lyase)), CTSS (cathepsin S), VAV2 (vav 2 guanine nucleotide exchange factor), NPY2R (neuropeptide Y receptor Y2), IGFBP2 (insulin-like growth factor binding protein 2, 36 kDa), CD28 (CD28 molecule), GSTA1 (glutathione S-transferase alpha 1), PPIA (peptidylprolyl isomerase A (cyclophilin A)), APOH (apolipoprotein H (beta-2-glycoprotein I)), S100A8 (S100 calcium binding protein A8), IL11 (interleukin 11), ALOX15 (arachidonate 15-lipoxygenase), FBLN1 (fibulin 1), NR1H3 (nuclear receptor subfamily 1, group H, member 3), SCD (stearoyl-CoA desaturase (delta-9-desaturase)), GIP (gastric inhibitory polypeptide), CHGB (chromogranin B (secretogranin 1)), PRKCB (protein kinase C, beta), SRD5A1 (steroid-5-alpha-reductase, alpha polypeptide 1 (3-oxo-5 alpha-steroid delta 4-dehydrogenase alpha 1)), HSD11B2 (hydroxysteroid (11-beta) dehydrogenase 2), CALCRL (calcitonin receptor-like), GALNT2 (UDP-N-acetyl-alpha-D-galactosamine.polypeptide N-acetylgalactosaminyltransferase 2 (GalNAc-T2)), ANGPTL4 (angiopoietin-like 4), KCNN4 (potassium intermediate/small conductance calcium-activated channel, subfamily N, member 4), PIK3C$_2$A (phosphoinositide-3-kinase, class 2, alpha polypeptide), HBEGF (heparin-binding EGF-like growth factor), CYP7A1 (cytochrome P450, family 7, subfamily A, polypeptide 1), HLA-DRB5 (major histocompatibility complex, class II, DR beta 5), BNIP3 (BCL2/adenovirus E1B 19 kDa interacting protein 3), GCKR (glucokinase (hexokinase 4) regulator), S100A12 (S100 calcium binding protein A12), PADI4 (peptidyl arginine deiminase, type IV), HSPA14 (heat shock 70 kDa protein 14), CXCR1 (chemokine (C—X-C motif) receptor 1), H19 (H19, imprinted maternally expressed transcript (non-protein coding)), KRTAP19-3 (keratin associated protein 19-3), IDDM2 (insulin-dependent diabetes mellitus 2), RAC2 (ras-related C3 botulinum toxin substrate 2 (rho family, small GTP binding protein Rac2)), RYR1 (ryanodine receptor 1 (skeletal)), CLOCK (clock homolog (mouse)), NGFR (nerve growth factor receptor (TNFR superfamily, member 16)), DBH (dopamine beta-hydroxylase (dopamine beta-monooxygenase)), CHRNA4 (cholinergic receptor, nicotinic, alpha 4), CACNA1C (calcium channel, voltage-dependent, L type, alpha 1C subunit), PRKAG2 (protein kinase, AMP-activated, gamma 2 non-catalytic subunit), CHAT (choline acetyltransferase), PTGDS (prostaglandin D2 synthase 21 kDa (brain)), NR1H2 (nuclear receptor subfamily 1, group H, member 2), TEK (TEK tyrosine kinase, endothelial), VEGFB (vascular endothelial growth factor B), MEF2C (myocyte enhancer factor 2C), MAPKAPK2 (mitogen-activated protein kinase-activated protein kinase 2), TNFRSF11A (tumor necrosis factor receptor superfamily, member 11 a, NFKB activator), HSPA9 (heat shock 70 kDa protein 9 (mortalin)), CYSLTR1 (cysteinyl leukotriene receptor 1), MAT1A (methionine adenosyltransferase I, alpha), OPRL1 (opiate receptor-like 1), IMPA1 (inositol (myo)-1 (or 4)-monophosphatase 1), CLCN2 (chloride channel 2), DLD (dihydrolipoamide dehydrogenase), PSMA6 (proteasome (prosome, macropain) subunit, alpha type, 6), PSMB8 (proteasome (prosome, macropain) subunit, beta type, 8 (large multifunctional peptidase 7)), CHI3L 1 (chitinase 3-like 1 (cartilage glycoprotein-39)), ALDH1B1 (aldehyde dehydrogenase 1 family, member B1), PARP2 (poly (ADP-ribose) polymerase 2), STAR (steroidogenic acute regulatory protein), LBP (lipopolysaccharide binding protein), ABCC6 (ATP-binding cassette, sub-family C(CFTR/MRP), member 6), RGS2 (regulator of G-protein signaling 2, 24 kDa), EFNB2 (ephrin-B2), GJB6 (gap junction protein, beta 6, 30 kDa), APOA2 (apolipoprotein A-II), AMPD1 (adenosine monophosphate deaminase 1), DYSF (dysferlin, limb girdle muscular dystrophy 2B (autosomal recessive)), FDFT1 (farnesyl-diphosphate farnesyltransferase 1), EDN2 (endothelin 2), CCR6 (chemokine (C-C motif) receptor 6), GJB3 (gap junction protein, beta 3, 31 kDa), IL1RL1 (interleukin 1 receptor-like 1), ENTPD1 (ectonucleoside triphosphate diphosphohydrolase 1), BBS4 (Bardet-Biedl syndrome 4), CELSR2 (cadherin, EGF LAG seven-pass G-type receptor 2 (flamingo homolog, *Drosophila*)), F11R (F11 receptor), RAPGEF3 (Rap guanine nucleotide exchange factor (GEF) 3), HYAL1 (hyaluronoglucosaminidase 1), ZNF259 (zinc finger protein 259), ATOX1 (ATX1 antioxidant protein 1 homolog (yeast)), ATF6 (activating transcription factor 6), KHK (ketohexokinase (fructokinase)), SAT1 (spermidine/spermine N1-acetyltransferase 1), GGH (gamma-glutamyl hydrolase (conjugase, folylpolygammaglutamyl hydrolase)), TIMP4 (TIMP metallopeptidase inhibitor 4), SLC4A4 (solute carrier family 4, sodium bicarbonate cotransporter, member 4), PDE2A (phosphodiesterase 2A, cGMP-stimulated), PDE3B (phosphodiesterase 3B, cGMP-inhibited), FADS1 (fatty acid desaturase 1), FADS2 (fatty acid desaturase 2), TMSB4X (thymosin beta 4, X-linked), TXNIP (thioredoxin interacting protein), LIMS1 (LIM and senescent cell antigen-like domains 1), RHOB (ras homolog gene family, member B), LY96 (lymphocyte antigen 96), FOXO1 (forkhead box O1), PNPLA2 (patatin-like phospholipase domain containing 2), TRH (thyrotropin-releasing hormone), GJC1 (gap junction protein, gamma 1, 45 kDa), SLC17A5 (solute carrier family 17 (anion/sugar transporter), member 5), FTO (fat mass and obesity associated), GJD2 (gap junction protein, delta 2, 36 kDa), PSRC1 (proline/serine-rich coiled-coil 1), CASP12 (caspase 12 (gene/pseudogene)), GPBAR1 (G protein-coupled bile acid receptor 1), PXK (PX domain containing serine/threonine kinase), IL33 (interleukin 33), TRIB1 (tribbles homolog 1 (*Drosophila*)), PBX4 (pre-B-cell leukemia homeobox 4), NUPR1 (nuclear protein, transcriptional regulator, 1), 15-September(15 kDa selenoprotein), CILP2 (cartilage intermediate layer protein 2), TERC (telomerase RNA component), GGT2 (gamma-glutamyltransferase 2), MT-CO1 (mitochondrially encoded cytochrome c oxidase I), and UOX (urate oxidase, pseudogene). Any of these sequences, may be a target for the CRISPR-Cas system, e.g., to address mutation.

In an additional embodiment, the chromosomal sequence may further be selected from Pon1 (paraoxonase 1), LDLR (LDL receptor), ApoE (Apolipoprotein E), Apo B-100 (Apolipoprotein B-100), ApoA (Apolipoprotein(a)), ApoA1 (Apolipoprotein A1), CBS (Cystathione B-synthase), Glycoprotein IIb/IIb, MTHRF (5,10-methylenetetrahydrofolate reductase (NADPH), and combinations thereof. In one iteration, the chromosomal sequences and proteins encoded by chromosomal sequences involved in cardiovascular disease may be chosen from Cacna1C, Sod1, Pten, Ppar(alpha), Apo E, Leptin, and combinations thereof as target(s) for the CRISPR-Cas system.

Treating Diseases of the Liver and Kidney

The present invention also contemplates delivering the CRISPR-Cas system described herein, e.g. Cpf1 effector protein systems, to the liver and/or kidney. Delivery strategies to induce cellular uptake of the therapeutic nucleic acid include physical force or vector systems such as viral-, lipid- or complex-based delivery, or nanocarriers. From the initial applications with less possible clinical relevance, when nucleic acids were addressed to renal cells with hydrodynamic high-pressure injection systemically, a wide range of gene therapeutic viral and non-viral carriers have been applied already to target posttranscriptional events in different animal kidney disease models in vivo (Csaba Revesz and Peter Hamar (2011). Delivery Methods to Target RNAs in the Kidney, Gene Therapy Applications, Prof. Chunsheng Kang (Ed.), ISBN: 978-953-307-541-9, InTech, Available from: http://www.intechopen.com/books/gene-therapy-applications/delivery-methods-to-target-rnas-inthe-kidney).

Delivery methods to the kidney may include those in Yuan et al. (Am J Physiol Renal Physiol 295: F605-F617, 2008) investigated whether in vivo delivery of small interfering RNAs (siRNAs) targeting the 12/15-lipoxygenase (12/15-LO) pathway of arachidonate acid metabolism can ameliorate renal injury and diabetic nephropathy (DN) in a streptozotocin-injected mouse model of type 1 diabetes. To achieve greater in vivo access and siRNA expression in the kidney, Yuan et al. used double-stranded 12/15-LO siRNA oligonucleotides conjugated with cholesterol. About 400 µg of siRNA was injected subcutaneously into mice. The method of Yuang et al. may be applied to the CRISPR Cas system of the present invention contemplating a 1-2 g subcutaneous injection of CRISPR Cas conjugated with cholesterol to a human for delivery to the kidneys.

Molitoris et al. (J Am Soc Nephrol 20: 1754-1764, 2009) exploited proximal tubule cells (PTCs), as the site of oligonucleotide reabsorption within the kidney to test the efficacy of siRNA targeted to p53, a pivotal protein in the apoptotic pathway, to prevent kidney injury. Naked synthetic siRNA to p53 injected intravenously 4 h after ischemic injury maximally protected both PTCs and kidney function. Molitoris et al.'s data indicates that rapid delivery of siRNA to proximal tubule cells follows intravenous administration. For dose-response analysis, rats were injected with doses of siP53, 0.33; 1, 3, or 5 mg/kg, given at the same four time points, resulting in cumulative doses of 1.32; 4, 12, and 20 mg/kg, respectively. All siRNA doses tested produced a SCr reducing effect on day one with higher doses being effective over approximately five days compared with PBS-treated ischemic control rats. The 12 and 20 mg/kg cumulative doses provided the best protective effect. The method of Molitoris et al. may be applied to the nucleic acid-targeting system of the present invention contemplating 12 and 20 mg/kg cumulative doses to a human for delivery to the kidneys.

Thompson et al. (Nucleic Acid Therapeutics, Volume 22, Number 4, 2012) reports the toxicological and pharmacokinetic properties of the synthetic, small interfering RNA I5NP following intravenous administration in rodents and nonhuman primates. I5NP is designed to act via the RNA interference (RNAi) pathway to temporarily inhibit expression of the pro-apoptotic protein p53 and is being developed to protect cells from acute ischemia/reperfusion injuries such as acute kidney injury that can occur during major cardiac surgery and delayed graft function that can occur following renal transplantation. Doses of 800 mg/kg I5NP in rodents, and 1,000 mg/kg I5NP in nonhuman primates, were required to elicit adverse effects, which in the monkey were isolated to direct effects on the blood that included a sub-clinical activation of complement and slightly increased clotting times. In the rat, no additional adverse effects were observed with a rat analogue of I5NP, indicating that the effects likely represent class effects of synthetic RNA duplexes rather than toxicity related to the intended pharmacologic activity of I5NP. Taken together, these data support clinical testing of intravenous administration of I5NP for the preservation of renal function following acute ischemia/reperfusion injury. The no observed adverse effect level (NOAEL) in the monkey was 500 mg/kg. No effects on cardiovascular, respiratory, and neurologic parameters were observed in monkeys following i.v. administration at dose levels up to 25 mg/kg. Therefore, a similar dosage may be contemplated for intravenous administration of CRISPR Cas to the kidneys of a human.

Shimizu et al. (J Am Soc Nephrol 21: 622-633, 2010) developed a system to target delivery of siRNAs to glomeruli via poly(ethylene glycol)-poly(L-lysine)-based vehicles. The siRNA/nanocarrier complex was approximately 10 to 20 nm in diameter, a size that would allow it to move across the fenestrated endothelium to access to the mesangium. After intraperitoneal injection of fluorescence-labeled siRNA/nanocarrier complexes, Shimizu et al. detected siRNAs in the blood circulation for a prolonged time. Repeated intraperitoneal administration of a mitogen-activated protein kinase 1 (MAPK1) siRNA/nanocarrier complex suppressed glomerular MAPK1 mRNA and protein expression in a mouse model of glomerulonephritis. For the investigation of siRNA accumulation, Cy5-labeled siRNAs complexed with PIC nanocarriers (0.5 ml, 5 nmol of siRNA content), naked Cy5-labeled siRNAs (0.5 ml, 5 nmol), or Cy5-labeled siRNAs encapsulated in HVJ-E (0.5 ml, 5 nmol of siRNA content) were administered to BALBc mice. The method of Shimizu et al. may be applied to the nucleic acid-targeting system of the present invention contemplating a dose of about of 10-20 µmol CRISPR Cas complexed with nanocarriers in about 1-2 liters to a human for intraperitoneal administration and delivery to the kidneys.

Delivery methods to the kidney are summarized in Table 17:

TABLE 17

| Delivery method | Carrier | Target RNA | Disease | Model | Functional assays | Author |
|---|---|---|---|---|---|---|
| Hydrodynamic/ Lipid | TransIT In Vivo Gene Delivery System, DOTAP | p85α | Acute renal injury | Ischemia-reperfusion | Uptake, biodistribution | Larson et al., Surgery, (August 2007), Vol. 142, No. 2, pp. (262-269) |
| Hydrodynamic/ Lipid | Lipofectamine 2000 | Fas | Acute renal injury | Ischemia-reperfusion | Blood urea nitrogen, Fas Immunohistochemistry, apoptosis, histological scoring | Hamar et al., Proc Natl Acad Sci, (October 2004), Vol. 101, No. 41, pp. (14883-14888) |

TABLE 17-continued

| Delivery method | Carrier | Target RNA | Disease | Model | Functional assays | Author |
|---|---|---|---|---|---|---|
| Hydrodynamic | n.a. | Apoptosis cascade elements | Acute renal injury | Ischemia-reperfusion | n.a. | Zheng et al., Am J Pathol, (October 2008), Vol. 173, No. 4, pp. (973-980) |
| Hydrodynamic | n.a. | Nuclear factor kappa-b (NFkB) | Acute renal injury | Ischemia-reperfusion | n.a. | Feng et al., Transplantation, (May 2009), Vol. 87, No. 9, pp. (1283-1289) |
| Hydrodynamic/Viral | Lipofectamine 2000 | Apoptosis antagonizing transcription factor (AATF) | Acute renal injury | Ischemia-reperfusion | Apoptosis, oxidative stress, caspase activation, membrane lipid peroxidation | Xie & Guo, Am Soc Nephrol, (December 2006), Vol. 17, No. 12, pp. (3336-3346) |
| Hydrodynamic | pBAsi mU6 Neo/ TransIT-EE Hydrodynamic Delivery System | Gremlin | Diabetic nephropathy | Streptozotocin - induced diabetes | Proteinuria, serum creatinine, glomerular and tubular diameter, collagen type IV/BMP7 expression | Q. Zhang et al., PloS ONE, (July 2010), Vol. 5, No. 7, e11709, pp. (1-13) |
| Viral/Lipid | pSUPER vector/ Lipofectamine | TGF-β type II receptor | Interstitial renal fibrosis | Unilateral urethral obstruction | α-SMA expression, collagen content, | Kushibikia et al., J Controlled Release, (July 2005), Vol. 105, No. 3, pp. (318-331) |
| Viral | Adeno-associated virus-2 | Mineral corticoid receptor | Hyper-tension caused renal damage | Cold-induced hypertension | blood pressure, serum albumin, serum urea nitrogen, serum creatinine, kidney weight, urinary sodium uptake | Wang et al., Gene Therapy, (July 2006), Vol. 13, No. 14, pp. (1097-1103) |
| Hydrodynamic/Viral | pU6 vector | Luciferase | n.a. | n.a. | | Kobayashi et al., Journal of Pharmacology and Experimental Therapeutics, (February 2004), Vol. 308, No. 2, pp. (688-693) |
| Lipid | Lipoproteins, albumin | apoB1, apoM | n.a. | n.a. | Uptake, binding affinity to lipoproteins and albumin | Wolfrum et al., Nature Biotechnology, (September 2007), Vol. 25, No. 10, pp. (1149-1157) |
| Lipid | Lipofectamine2000 | p53 | Acute renal injury | Ischemic and cisplatin-induced acute injury | Histological scoring, apoptosis | Molitoris et al., J Am Soc Nephrol. (August 2009), Vol. 20, No. 8, pp. (1754-1764) |
| Lipid | DOTAP/DOPE, DOTAP/DOPE/ DOPE-PEG2000 | COX-2 | Breast adeno-carcinoma | MDA-MB-231 breast cancer xenograft-bearing mouse | Cell viability, uptake | Mikhaylova et al., Cancer Gene Therapy, (March 2011), Vol. 16, No. 3, pp. (217-226) |
| Lipid | Cholesterol | 12/15-lipoxygenase | Diabetic nephropathy | Streptozotocin - induced diabetes | Albuminuria, urinary creatinine, histology, type I and IV collagen, TGF-β, fibronectin, plasminogen activator inhibitor 1 | Yuan et al., Am J Physiol Renal Physiol, (June 2008), Vol. 295, pp. (F605-F617) |
| Lipid | Lipofectamine 2000 | Mitochondria 1 membrane 44 (TIM44) | Diabetic nephropathy | Streptozotocin - induced diabetes | Cell proliferation and apoptosis, histology, ROS, mitochondrial import of Mn-SOD and | Y. Zhang et al., J Am Soc Nephrol, (April 2006), Vol. 17, No. 4, pp. (1090-1101) |

TABLE 17-continued

| Delivery method | Carrier | Target RNA | Disease | Model | Functional assays | Author |
|---|---|---|---|---|---|---|
| Hydrodynamic/ Lipid | Proteoliposome | RLIP76 | Renal carcinoma | Caki-2 kidney cancer xenograft-bearing mouse | glutathione peroxidase, cellular membrane polarization uptake | Singhal et al., Cancer Res, (May 2009), Vol. 69, No. 10, pp. (4244-4251) |
| Polymer | PEGylated PEI | Luciferase pGL3 | n.a. | n.a. | Uptake, biodistribution, erythrocyte aggregation | Malek et al., Toxicology and Applied Pharmacology, (April 2009), Vol. 236, No. 1, pp. (97-108) |
| Polymer | PEGylated poly-L-lysine | MAPK1 | Lupus glomerulo-nephritis | Glomerulo-nephritis | Proteinuria, glomeruloscleros is, TGF- β, fibronectin, plasminogen activator inhibitor 1 | Shimizu et al., J Am Soc Nephrology, (April 2010), Vol. 21, No. 4, pp. (622-633) |
| Polymer/Nano particle | Hyaluronic acid/ Quantum dot/ PEI | VEGF | Kidney cancer/ melanoma | B16F1 melanoma tumor-bearing mouse | Biodistribution, citotoxicity, tumor volume, endocytosis | Jiang et al., Molecular Pharmaceutics, (May-June 2009), Vol. 6, No. 3, pp. (727-737) |
| Polymer/Nano particle | PEGylated polycapro-lactone nanofiber | GAPDH | n.a. | n.a. | cell viability, uptake | Cao et al, J Controlled Release, (June 2010), Vol. 144, No. 2, pp. (203-212) |
| Aptamer | Spiegelmer mNOX-E36 | CC chemokine ligand 2 | Glomerulo-sclerosis | Uninephrecto-mized mouse | urinary albumin, urinary creatinine, histopathology, glomerular filtration rate, macrophage count, serum Ccl2, Mac- 2+, Ki-67+ | Ninichuk et al., Am J Pathol, (March 2008), Vol. 172, No. 3, pp. (628-637) |
| Aptamer | Aptamer NOX-F37 | vasopressin (AVP) | Congestive heart failure | n.a. | Binding affinity to D-AVP, Inhibition of AVP Signaling, Urine osmolality and sodium concentration, | Purschke et al., Proc Natl Acad Sci, (March 2006), Vol. 103, No. 13, pp. (5173-5178) |

Targeting the Liver or Liver Cells

Targeting liver cells is provided. This may be in vitro or in vivo. Hepatocytes are preferred. Delivery of the CRISPR protein, such as Cpf1 herein may be via viral vectors, especially AAV (and in particular AAV2/6) vectors. These may be administered by intravenous injection.

A preferred target for liver, whether in vitro or in vivo, is the albumin gene. This is a so-called 'safe harbor" as albumin is expressed at very high levels and so some reduction in the production of albumin following successful gene editing is tolerated. It is also preferred as the high levels of expression seen from the albumin promoter/enhancer allows for useful levels of correct or transgene production (from the inserted donor template) to be achieved even if only a small fraction of hepatocytes are edited.

Intron 1 of albumin has been shown by Wechsler et al. (reported at the 57th Annual Meeting and Exposition of the American Society of Hematology—abstract available online at https://ash.confex.com/ash/2015/webprogram/Paper86495.html and presented on 6th December 2015) to be a suitable target site. Their work used Zn Fingers to cut the DNA at this target site, and suitable guide sequences can be generated to guide cleavage at the same site by a CRISPR protein.

The use of targets within highly-expressed genes (genes with highly active enhancers/promoters) such as albumin may also allow a promoterless donor template to be used, as reported by Wechsler et al. and this is also broadly applicable outside liver targeting. Other examples of highly-expressed genes are known.

In particular embodiments, the CRISPR proteins of the present invention are used in the treatment of liver disorders such as transthyretin amyloidosis (ATTR), alpha-1 antit-rypsin deficiency and other hepatic-based inborn errors of metabolism. FAP is caused by a mutation in the gene that encodes transthyretin (TTR). While it is an autosomal dominant disease, not all carriers develop the disease. There are over 100 mutations in the TTR gene known to be associated with the disease. Examples of common mutations include V30M. The principle of treatment of TTR based on gene silencing has been demonstrated by studies with iRNA (Ueda et al. 2014 Transl. Neurogener. 3:19). Wilson's Disease (WD) is caused by mutations in the gene encoding ATP7B, which is found exclusively in the hepatocyte. There are over 500 mutations associated with WD, with increased prevalence in specific regions such as East Asia. Other examples are A1ATD (an autosomal recessive disease caused by mutations in the SERPINA1 gene) and PKU (an autosomal recessive disease caused by mutations in the phenylalanine hydroxylase (PAH) gene).

Liver-Associated Blood Disorders, Especially Hemophilia and in Particular Hemophilia B Successful gene editing of hepatocytes has been achieved in mice (both in vitro and in vivo) and in non-human primates (in vivo), showing that treatment of blood disorders through gene editing/genome engineering in hepatocytes is feasible. In particular, expression of the human F9 (hF9) gene in hepatocytes has been shown in non-human primates indicating a treatment for Hemophillia B in humans.

Wechsler et al. reported at the 57th Annual Meeting and Exposition of the American Society of Hematology (abstract presented 6th December 2015 and available online at https.//ash.confex.com/ash/2015/webprogram/Paper86495.html) that they has successfully expressed human F9 (hF9) from hepatocytes in non-human primates through in vivo gene editing. This was achieved using 1) two zinc finger nucleases (ZFNs) targeting intron 1 of the albumin locus, and 2) a human F9 donor template construct. The ZFNs and donor template were encoded on separate hepatotropic adeno-associated virus serotype 2/6 (AAV2/6) vectors injected intravenously, resulting in targeted insertion of a corrected copy of the hF9 gene into the albumin locus in a proportion of liver hepatocytes.

The albumin locus was selected as a "safe harbor" as production of this most abundant plasma protein exceeds 10 g/day, and moderate reductions in those levels are well-tolerated. Genome edited hepatocytes produced normal hFIX (hF9) in therapeutic quantities, rather than albumin, driven by the highly active albumin enhancer/promoter. Targeted integration of the hF9 transgene at the albumin locus and splicing of this gene into the albumin transcript was shown.

Mice studies: C57BL/6 mice were administered vehicle (n=20) or AAV2/6 vectors (n=25) encoding mouse surrogate reagents at $1.0\times10^{13}$ vector genome (vg)/kg via tail vein injection. ELISA analysis of plasma hFIX in the treated mice showed peak levels of 50-1053 ng/mL that were sustained for the duration of the 6-month study. Analysis of FIX activity from mouse plasma confirmed bioactivity commensurate with expression levels.

Non-human primate (NHP) studies: a single intravenous co-infusion of AAV2/6 vectors encoding the NHP targeted albumin-specific ZFNs and a human F9 donor at $1.2\times10^{13}$ vg/kg (n=5/group) resulted in >50 ng/mL (>1% of normal) in this large animal model. The use of higher AAV2/6 doses (up to $1.5\times10^{14}$ vg/kg) yielded plasma hFIX levels up to 1000 ng/ml (or 20% of normal) in several animals and up to 2000 ng/ml (or 50% of normal) in a single animal, for the duration of the study (3 months).

The treatment was well tolerated in mice and NHPs, with no significant toxicological findings related to AAV2/6 ZFN+donor treatment in either species at therapeutic doses. Sangamo (CA, USA) has since applied to the FDA, and been granted, permission to conduct the world's first human clinical trial for an in vivo genome editing application. This follows on the back of the EMEA's approval of the Glybera gene therapy treatment of lipoprotein lipase deficiency.

Accordingly, it is preferred, in some embodiments, that any or all of the following are used: AAV (especially AAV2/6) vectors, preferably administered by intravenous injection; Albumin as target for gene editing/insertion of transgene/template-especially at intron 1 of albumin; human F9 donor template; and/or a promoterless donor template.

Hemophilia B

Accordingly, in some embodiments, it is preferred that the present invention is used to treat Hemophilia B. As such it is preferred that F9 (Factor IX) is targeted through provision of a suitable guide RNA. The enzyme and the guide may ideally be targeted to the liver where F9 is produced, although they can be delivered together or separately. A template is provided, in some embodiments, and that this is the human F9 gene. It will be appreciated that the hF9 template comprises the wt or 'correct' version of hF9 so that the treatment is effective. In some embodiments, a two-vector system may be used-one vector for the Cpf1 and one vector for the repair template(s). The repair template may include two or more repair templates, for example, two F9 sequences from different mammalian species. In some embodiments, both a mouse and human F9 sequence are provided. This is may be delivered to mice. Yang Yang, John White, McMenamin Deirdre, and Peter Bell, PhD, presenting at 58th Annual American Society of Hematology Meeting (November 2016), report that this increases potency and accuracy. The second vector inserted the human sequence of factor IX into the mouse genome. In some embodiments, the targeted insertion leads to the expression of a chimeric hyperactive factor IX protein. In some embodiments, this is under the control of the native mouse factor IX promoter. Injecting this two-component system (vector 1 and vector 2) into newborn and adult "knock-out" mice at increasing doses led to expression and activity of stable factor IX activity at normal (or even higher) levels for over four months. In the case of treating humans, a native human F9 promoter may be used instead. In some embodiments, the wild-type phenotype is restored.

In an alternative embodiment, the hemophilia B version of F9 may be delivered so as to create a model organism, cell or cell line (for example a murine or non-human primate model organism, cell or cell line), the model organism, cell or cell line having or carrying the Hemophilia B phenotype, i.e. an inability to produce wild-type F9.

Hemophilia A

In some embodiments, the F9 (factor IX) gene may be replaced by the F8 (factor VIII) gene described above, leading to treatment of Hemophilia A (through provision of a correct F8 gene) and/or creation of a Hemophilia A model organism, cell or cell line (through provision of an incorrect, Hemophilia A version of the F8 gene).

Hemophilia C

In some embodiments, the F9 (factor IX) gene may be replaced by the F11 (factor XI) gene described above, leading to treatment of Hemophilia C (through provision of a correct F11 gene) and/or creation of a Hemophilia C model organism, cell or cell line (through provision of an incorrect, Hemophilia C version of the F11 gene).

Transthyretin Amyloidosis

Transthyretin is a protein, mainly produced in the liver, present in the serum and CSF which carries thyroxin hormone and retinol binding protein bound to retinol (Vitamin A). Over 120 different mutations can cause Transthyretin amyloidosis (ATTR), a heritable genetic disorder wherein mutant forms of the protein aggregate in tissues, particularly the peripheral nervous system, causing polyneuropathy. Familial amyloid polyneuropathy (FAP) is the most common TTR disorder and, in 2014, was thought to affect 47 per 100,000 people in Europe. A mutation in the TTR gene of Val30Met is thought be the most common mutation, causing an estimated 50% of FAP cases. In the absence a liver transplant, the only known cure to date, the disease is usually fatal within a decade of diagnosis. The majority of cases are monogenic.

In mouse models of ATTR, the TTR gene may be edited in a dose dependent manner by the delivery of CRISPR/Cas9. In some embodiments, the Cpf1 is provided as mRNA. In some embodiments, Cpf1 mRNA and guide RNA are packaged in LNPs. A system comprising Cpf1 mRNA and guide RNA packaged in LNPs achieved up to 60% editing efficiency in the liver, with serum TTR levels being reduced by up to 80%. In some embodiments, therefore, Transthyretin is targeted, in particular correcting for the Val30Met mutation. In some embodiments, therefore, ATTR is treated.

Alpha-1 Antitrypsin Deficiency

Alpha-1 Antitrypsin (A1AT) is a protein produced in the liver which primarily functions to decrease the activity of neutrophil elastase, an enzyme which degrades connective tissue, in the lungs. Alpha-1 Antitrypsin Deficiency (ATTD) is a disease caused by mutation of the SERPINA1 gene, which encodes A1AT. Impaired production of A1AT leads to a gradual degradation of the connective tissue of the lung resulting in emphysema like symptoms.

Several mutations can cause ATTD, though the most common mutations are Glu342Lys (referred to as Z allele, wild-type is referred to as M) or Glu264Val (referred to as the S allele), and each allele contributes equally to the disease state, with two affected alleles resulting in more pronounced pathophysiology. These results not only resulted in degradation of the connective tissue of sensitive organs, such as the lung, but accumulation of the mutants in the liver can result in proteotoxicity. Current treatments focus on the replacement of A1AT by injection of protein retrieved from donated human plasma. In severe cases a lung and/or liver transplant may be considered.

The common variants of the disease are again monogenic. In some embodiments, the SERPINA1 gene is targeted. In some embodiments, the Glu342Lys mutation (referred to as Z allele, wild-type is referred to as M) or the Glu264Val mutation (referred to as the S allele) are corrected for. In some embodiments, therefore, the faulty gene would require replacement by the wild-type functioning gene. In some embodiments, a knockout and repair approach is required, so a repair template is provided. In the case of bi-allelic mutations, in some embodiments only one guide RNA would be required for homozygous mutations, but in the case of heterozygous mutations two guide RNAs may be required. Delivery is, in some embodiments, to the lung or liver.

Inborn Errors of Metabolism

Inborn errors of metabolism (IEMs) are an umbrella group of diseases which affect metabolic processes. In some embodiments, an IEM is to be treated. The majority of these diseases are monogenic in nature (e.g. phenylketonuria) and the pathophysiology results from either the abnormal accumulation of substances which are inherently toxic, or mutations which result in an inability to synthesize essential substances. Depending on the nature of the IEM, CRISPR/Cpf1 may be used to facilitate a knock-out alone, or in combination with replacement of a faulty gene via a repair template. Exemplary diseases that may benefit from CRISPR/Cpf1 technology are, in some embodiments: primary hyperoxaluria type 1 (PH1), argininosuccinic lyase deficiency, ornithine transcarbamylase deficiency, phenylketonuria, or PKU, and maple syrup urine disease.

Treating Epithelial and Lung Diseases

The present invention also contemplates delivering the CRISPR-Cas system described herein, e.g. Cpf1 effector protein systems, to one or both lungs.

Although AAV-2-based vectors were originally proposed for CFTR delivery to CF airways, other serotypes such as AAV-1, AAV-5, AAV-6, and AAV-9 exhibit improved gene transfer efficiency in a variety of models of the lung epithelium (see, e.g., Li et al., Molecular Therapy, vol. 17 no. 12, 2067-277 December 2009). AAV-1 was demonstrated to be ~100-fold more efficient than AAV-2 and AAV-5 at transducing human airway epithelial cells in vitro, 5 although AAV-1 transduced murine tracheal airway epithelia in vivo with an efficiency equal to that of AAV-5. Other studies have shown that AAV-5 is 50-fold more efficient than AAV-2 at gene delivery to human airway epithelium (HAE) in vitro and significantly more efficient in the mouse lung airway epithelium in vivo. AAV-6 has also been shown to be more efficient than AAV-2 in human airway epithelial cells in vitro and murine airways in vivo. 8 The more recent isolate, AAV-9, was shown to display greater gene transfer efficiency than AAV-5 in murine nasal and alveolar epithelia in vivo with gene expression detected for over 9 months suggesting AAV may enable long-term gene expression in vivo, a desirable property for a CFTR gene delivery vector. Furthermore, it was demonstrated that AAV-9 could be readministered to the murine lung with no loss of CFTR expression and minimal immune consequences. CF and non-CF HAE cultures may be inoculated on the apical surface with 100 µl of AAV vectors for hours (see, e.g., Li et al., Molecular Therapy, vol. 17 no. 12, 2067-277 December 2009). The MOI may vary from $1 \times 10^3$ to $4 \times 10^5$ vector genomes/cell, depending on virus concentration and purposes of the experiments. The above cited vectors are contemplated for the delivery and/or administration of the invention.

Zamora et al. (Am J Respir Crit Care Med Vol 183. pp 531-538, 2011) reported an example of the application of an RNA interference therapeutic to the treatment of human infectious disease and also a randomized trial of an antiviral drug in respiratory syncytial virus (RSV)-infected lung transplant recipients. Zamora et al. performed a randomized, double-blind, placebo-controlled trial in LTX recipients with RSV respiratory tract infection. Patients were permitted to receive standard of care for RSV. Aerosolized ALN-RSV01 (0.6 mg/kg) or placebo was administered daily for 3 days. This study demonstrates that an RNAi therapeutic targeting RSV can be safely administered to LTX recipients with RSV infection. Three daily doses of ALN-RSV01 did not result in any exacerbation of respiratory tract symptoms or impairment of lung function and did not exhibit any systemic proinflammatory effects, such as induction of cytokines or CRP. Pharmacokinetics showed only low, transient systemic exposure after inhalation, consistent with preclinical animal data showing that ALN-RSV01, administered intravenously or by inhalation, is rapidly cleared from the circulation through exonuclease-mediated digestion and renal excretion. The method of Zamora et al. may be applied to the nucleic acid-targeting system of the present invention and an aerosolized CRISPR Cas, for example with a dosage of 0.6 mg/kg, may be contemplated for the present invention.

Subjects treated for a lung disease may for example receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector. In this instance, the following constructs are provided as examples: Cbh or EF1a promoter for Cas (Cpf1), U6 or H1 promoter for guide RNA. A preferred arrangement is to use a CFTRdelta508 targeting guide, a repair template for deltaF508 mutation and a codon optimized Cpf1 enzyme, with optionally one or more nuclear localization signal or sequence(s) (NLS(s)), e.g., two (2) NLSs. Constructs without NLS are also envisaged.

Treating Diseases of the Muscular System

The present invention also contemplates delivering the CRISPR-Cas system described herein, e.g. Cpf1 effector protein systems, to muscle(s).

Bortolanza et al. (Molecular Therapy vol. 19 no. 11, 2055-264 November 2011) shows that systemic delivery of RNA interference expression cassettes in the FRG1 mouse, after the onset of facioscapulohumeral muscular dystrophy (FSHD), led to a dose-dependent long-term FRG1 knockdown without signs of toxicity. Bortolanza et al. found that a single intravenous injection of $5 \times 10^{12}$ vg of rAAV6-sh1FRG1 rescues muscle histopathology and muscle function of FRG1 mice. In detail, 200 μl containing $2 \times 10^{12}$ or $5 \times 10^{12}$ vg of vector in physiological solution were injected into the tail vein using a 25-gauge Terumo syringe. The method of Bortolanza et al. may be applied to an AAV expressing CRISPR Cas and injected into humans at a dosage of about $2 \times 1015$ or $2 \times 10^{16}$ vg of vector.

Dumonceaux et al. (Molecular Therapy vol. 18 no. 5, 881-887 May 2010) inhibit the myostatin pathway using the technique of RNA interference directed against the myostatin receptor AcvRIIb mRNA (sh-AcvRIIb). The restoration of a quasi-dystrophin was mediated by the vectorized U7 exon-skipping technique (U7-DYS). Adeno-associated vectors carrying either the sh-AcvrIIb construct alone, the U7-DYS construct alone, or a combination of both constructs were injected in the tibialis anterior (TA) muscle of dystrophic mdx mice. The injections were performed with $10^{11}$ AAV viral genomes. The method of Dumonceaux et al. may be applied to an AAV expressing CRISPR Cas and injected into humans, for example, at a dosage of about $10^{14}$ to about $10^{15}$ vg of vector.

Kinouchi et al. (Gene Therapy (2008) 15, 1126-1130) report the effectiveness of in vivo siRNA delivery into skeletal muscles of normal or diseased mice through nanoparticle formation of chemically unmodified siRNAs with atelocollagen (ATCOL). ATCOL-mediated local application of siRNA targeting myostatin, a negative regulator of skeletal muscle growth, in mouse skeletal muscles or intravenously, caused a marked increase in the muscle mass within a few weeks after application. These results imply that ATCOL-mediated application of siRNAs is a powerful tool for future therapeutic use for diseases including muscular atrophy. Mst-siRNAs (final concentration, 10 mM) were mixed with ATCOL (final concentration for local administration, 0.5%) (AteloGene, Kohken, Tokyo, Japan) according to the manufacturer's instructions. After anesthesia of mice (20-week-old male C57BL/6) by Nembutal (25 mg/kg, i.p.), the Mst-siRNA/ATCOL complex was injected into the masseter and biceps femoris muscles. The method of Kinouchi et al. may be applied to CRISPR Cas and injected into a human, for example, at a dosage of about 500 to 1000 ml of a 40 μM solution into the muscle. Hagstrom et al. (Molecular Therapy Vol. 10, No. 2, August 2004) describe an intravascular, nonviral methodology that enables efficient and repeatable delivery of nucleic acids to muscle cells (myofibers) throughout the limb muscles of mammals. The procedure involves the injection of naked plasmid DNA or siRNA into a distal vein of a limb that is transiently isolated by a tourniquet or blood pressure cuff. Nucleic acid delivery to myofibers is facilitated by its rapid injection in sufficient volume to enable extravasation of the nucleic acid solution into muscle tissue. High levels of transgene expression in skeletal muscle were achieved in both small and large animals with minimal toxicity. Evidence of siRNA delivery to limb muscle was also obtained. For plasmid DNA intravenous injection into a rhesus monkey, a three-way stopcock was connected to two syringe pumps (Model PHD 2000; Harvard Instruments), each loaded with a single syringe. Five minutes after a papaverine injection, pDNA (15.5 to 25.7 mg in 40-100 ml saline) was injected at a rate of 1.7 or 2.0 ml/s. This could be scaled up for plasmid DNA expressing CRISPR Cas of the present invention with an injection of about 300 to 500 mg in 800 to 2000 ml saline for a human. For adenoviral vector injections into a rat, $2 \times 10^9$ infectious particles were injected in 3 ml of normal saline solution (NSS). This could be scaled up for an adenoviral vector expressing CRISPR Cas of the present invention with an injection of about $1 \times 10^{13}$ infectious particles were injected in 10 liters of NSS for a human. For siRNA, a rat was injected into the great saphenous vein with 12.5 μg of a siRNA and a primate was injected into the great saphenous vein with 750 μg of a siRNA. This could be scaled up for a CRISPR Cas of the present invention, for example, with an injection of about 15 to about 50 mg into the great saphenous vein of a human.

See also, for example, WO2013163628 A2, Genetic Correction of Mutated Genes, published application of Duke University describes efforts to correct, for example, a frameshift mutation which causes a premature stop codon and a truncated gene product that can be corrected via nuclease mediated non-homologous end joining such as those responsible for Duchenne Muscular Dystrophy, ("DMD") a recessive, fatal, X-linked disorder that results in muscle degeneration due to mutations in the dystrophin gene. The majority of dystrophin mutations that cause DMD are deletions of exons that disrupt the reading frame and cause premature translation termination in the dystrophin gene. Dystrophin is a cytoplasmic protein that provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids. Exon 51 is frequently adjacent to frame-disrupting deletions in DMD patients and has been targeted in clinical trials for oligonucleotide-based exon skipping. A clinical trial for the exon 51 skipping compound Eteplirsen recently reported a significant functional benefit across 48 weeks, with an average of 47% dystrophin positive fibers compared to baseline. Mutations in exon 51 are ideally suited for permanent correction by NHEJ-based genome editing.

The methods of US Patent Publication No. 20130145487 assigned to Cellectis, which relates to meganuclease variants to cleave a target sequence from the human dystrophin gene (DMD), may also be modified to for the nucleic acid-targeting system of the present invention.

Treating Diseases of the Skin

The present invention also contemplates delivering the CRISPR-Cas system described herein, e.g. Cpf1 effector protein systems, to the skin.

Hickerson et al. (Molecular Therapy—Nucleic Acids (2013) 2, e129) relates to a motorized microneedle array skin delivery device for delivering self-delivery (sd)-siRNA to human and murine skin. The primary challenge to translating siRNA-based skin therapeutics to the clinic is the development of effective delivery systems. Substantial effort has been invested in a variety of skin delivery technologies with limited success. In a clinical study in which skin was treated with siRNA, the exquisite pain associated with the hypodermic needle injection precluded enrollment of additional patients in the trial, highlighting the need for improved, more "patient-friendly" (i.e., little or no pain) delivery approaches. Microneedles represent an efficient way to deliver large charged cargos including siRNAs across the primary barrier, the stratum corneum, and are generally regarded as less painful than conventional hypodermic needles. Motorized "stamp type" microneedle devices, including the motorized microneedle array (MMNA) device used by Hickerson et al., have been shown to be safe in hairless mice studies and cause little or no pain as evidenced by (i) widespread use in the cosmetic industry and (ii) limited testing in which nearly all volunteers found use of the device to be much less painful than a flu shot, suggesting siRNA delivery using this device will result in much less pain than was experienced in the previous clinical trial using hypodermic needle injections. The MMNA device (marketed as Triple-M or Tri-M by Bomtech Electronic Co, Seoul, South Korea) was adapted for delivery of siRNA to mouse and human skin. sd-siRNA solution (up to 300 μl of 0.1 mg/ml RNA) was introduced into the chamber of the disposable Tri-M needle cartridge (Bomtech), which was set to a depth of 0.1 mm. For treating human skin, deidentified skin (obtained immediately following surgical procedures) was manually stretched and pinned to a cork platform before treatment. All intradermal injections were performed using an insulin syringe with a 28-gauge 0.5-inch needle. The MMNA device and method of Hickerson et al. could be used and/or adapted to deliver the CRISPR Cas of the present invention, for example, at a dosage of up to 300 μl of 0.1 mg/ml CRISPR Cas to the skin.

Leachman et al. (Molecular Therapy, vol. 18 no. 2, 442-446 February 2010) relates to a phase Ib clinical trial for treatment of a rare skin disorder pachyonychia congenita (PC), an autosomal dominant syndrome that includes a disabling plantar keratoderma, utilizing the first short-interfering RNA (siRNA)-based therapeutic for skin. This siRNA, called TD101, specifically and potently targets the keratin 6a (K6a) N171K mutant mRNA without affecting wild-type K6a mRNA.

Zheng et al. (PNAS, Jul. 24, 2012, vol. 109, no. 30, 11975-11980) show that spherical nucleic acid nanoparticle conjugates (SNA-NCs), gold cores surrounded by a dense shell of highly oriented, covalently immobilized siRNA, freely penetrate almost 100% of keratinocytes in vitro, mouse skin, and human epidermis within hours after application. Zheng et al. demonstrated that a single application of 25 nM epidermal growth factor receptor (EGFR) SNA-NCs for 60 h demonstrate effective gene knockdown in human skin. A similar dosage may be contemplated for CRISPR Cas immobilized in SNA-NCs for administration to the skin.

Cancer and Neoplastic Disorders

In some embodiments, the treatment, prophylaxis or diagnosis of cancer is provided. The target is preferably one or more of the FAS, BID, CTLA4, PDCD1, CBLB, PTPN6, TRAC or TRBC genes. The cancer may be one or more of lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma. This may be implemented with engineered chimeric antigen receptor (CAR) T cell. This is described in WO2015161276, the disclosure of which is hereby incorporated by reference and described herein below.

Target genes suitable for the treatment or prophylaxis of cancer may include, in some embodiments, those described in WO2015048577 the disclosure of which is hereby incorporated by reference.

Usher Syndrome or Retinitis Pigmentosa

In some embodiments, the treatment, prophylaxis or diagnosis of Usher Syndrome or retinitis pigmentosa-39 is provided. The target is preferably the USH2A gene. In some embodiments, correction of a G deletion at position 2299 (2299delG) is provided. This is described in WO2015134812A1, the disclosure of which is hereby incorporated by reference.

Autoimmune and Inflammatory Disorders

In some embodiments, autoimmune and inflammatory disorders are treated. These include Multiple Sclerosis (MS) or Rheumatoid Arthritis (RA), for example.

Cystic Fibrosis (CF)

In some embodiments, the treatment, prophylaxis or diagnosis of cystic fibrosis is provided. The target is preferably the SCNN1A or the CFTR gene. This is described in WO2015157070, the disclosure of which is hereby incorporated by reference.

Schwank et al. (Cell Stem Cell, 13:653-58, 2013) used CRISPR-Cas9 to correct a defect associated with cystic fibrosis in human stem cells. The team's target was the gene for an ion channel, cystic fibrosis transmembrane conductor receptor (CFTR). A deletion in CFTR causes the protein to misfold in cystic fibrosis patients. Using cultured intestinal stem cells developed from cell samples from two children with cystic fibrosis, Schwank et al. were able to correct the defect using CRISPR along with a donor plasmid containing the reparative sequence to be inserted. The researchers then grew the cells into intestinal "organoids," or miniature guts, and showed that they functioned normally. In this case, about half of clonal organoids underwent the proper genetic correction.

In some embodiments, Cystic fibrosis is treated, for example. Delivery to the lungs is therefore preferred. The F508 mutation (delta-F508, full name CFTRΔF508 or F508del-CFTR) is preferably corrected. In some embodiments, the targets may be ABCC7, CF or MRP7.

Duchenne's Muscular Dystrophy

Duchenne's muscular dystrophy (DMD) is a recessive, sex-linked muscle wasting disease that affects approximately 1 in 5000 males at birth. Mutations of the dystrophin gene result in an absence of dystrophin in skeletal muscle, where it normally functions to connect the cytoskeleton of the muscle fiber to the basal lamina. The absence of dystrophin caused be these mutations results in excessive calcium entry into the soma which causes the mitochondria to rupture, destroying the cell. Current treatments are focused on easing the symptoms of DMD, and the average life expectancy is approximately 26 years.

CRISPR/Cas9 efficacy as a treatment for certain types of DMD has been demonstrated in mouse models. In one such study, the muscular dystrophy phenotype was partially corrected in the mouse by knocking-out a mutant exon resulting in a functional protein (see Nelson et al. (2016) Science, Long et al. (2016) Science, and Tabebordbar et al. (2016) Science).

In some embodiments, DMD is treated. In some embodiments, delivery is to the muscle by injection.

Glycogen Storage Diseases, including 1a

Glycogen Storage Disease 1a is a genetic disease resulting from deficiency of the enzyme glucose-6-phosphatase. The deficiency impairs the ability of the liver to produce free glucose from glycogen and from gluconeogenesis. In some embodiments, the gene encoding the glucose-6-phosphatase enzyme is targeted. In some embodiments, Glycogen Storage Disease 1a is treated. In some embodiments, delivery is to the liver by encapsulation of the Cpf1 (in protein or mRNA form) in a lipid particle, such as an LNP.

In some embodiments, Glycogen Storage Diseases, including 1a, are targeted and preferably treated, for example by targeting polynucleotides associated with the condition/disease/infection. The associated polynucleotides include DNA, which may include genes (where genes include any coding sequence and regulatory elements such as enhancers or promoters). In some embodiments, the associated polynucleotides may include the SLC2A2, GLUT2, G6PC, G6PT, G6PT1, GAA, LAMP2, LAMPB, AGL, GDE, GBE1, GYS2, PYGL, or PFKM genes.

Hurler Syndrome

Hurler syndrome, also known as mucopolysaccharidosis type I (MPS I), Hurler's disease, is a genetic disorder that results in the buildup of glycosaminoglycans (formerly known as mucopolysaccharides) due to a deficiency of alpha-L-iduronidase, an enzyme responsible for the degradation of mucopolysaccharides in lysosomes. Hurler syndrome is often classified as a lysosomal storage disease, and is clinically related to Hunter Syndrome. Hunter syndrome is X-linked while Hurler syndrome is autosomal recessive. MPS I is divided into three subtypes based on severity of symptoms. All three types result from an absence of, or insufficient levels of, the enzyme α-L-iduronidase. MPS I H or Hurler syndrome is the most severe of the MPS I subtypes. The other two types are MPS I S or Scheie syndrome and MPS I H-S or Hurler-Scheie syndrome. Children born to an MPS I parent carry a defective IDUA gene, which has been mapped to the 4p16.3 site on chromosome 4. The gene is named IDUA because of its iduronidase enzyme protein product. As of 2001, 52 different mutations in the IDUA gene have been shown to cause Hurler syndrome. Successful treatment of the mouse, dog, and cat models of MPS I by delivery of the iduronidase gene through retroviral, lentiviral, AAV, and even nonviral vectors.

In some embodiments, the α-L-iduronidase gene is targeted and a repair template preferably provided.

HIV and AIDS

In some embodiments, the treatment, prophylaxis or diagnosis of HIV and AIDS is provided. The target is preferably the CCR5 gene in HIV. This is described in WO2015148670A1, the disclosure of which is hereby incorporated by reference.

Beta Thalassaemia

In some embodiments, the treatment, prophylaxis or diagnosis of Beta Thalassemia is provided. The target is preferably the BCL11A gene. This is described in WO2015148860, the disclosure of which is hereby incorporated by reference.

Sickle Cell Disease (SCD)

In some embodiments, the treatment, prophylaxis or diagnosis of Sickle Cell Disease (SCD) is provided. The target is preferably the HBB or BCL11A gene. This is described in WO2015148863, the disclosure of which is hereby incorporated by reference.

Herpes Simplex Virus 1 and 2

Herpesviridae are a family of viruses composed of linear double-stranded DNA genomes with 75-200 genes. For the purposes of gene editing, the most commonly studied family member is Herpes Simplex Virus-1 (HSV-1), a virus which has a distinct number of advantages over other viral vectors (reviewed in Vannuci et al. (2003)). Thus, in some embodiments, the viral vector is an HSV viral vector. In some embodiments, the HSV viral vector is HSV-1.

HSV-1 has a large genome of approximately 152 kb of double stranded DNA. This genome comprises of more than 80 genes, many of which can be replaced or removed, allowing a gene insert of between 30-150 kb. The viral vectors derived from HSV-1 are generally separated into 3 groups: replication-competent attenuated vectors, replication-incompetent recombinant vectors, and defective helper-dependent vectors known as amplicons. Gene transfer using HSV-1 as a vector has been demonstrated previously, for instance for the treatment of neuropathic pain (see, e.g., Wolfe et al. (2009) Gene Ther) and rheumatoid arthritis (see e.g., Burton et al. (2001) Stem Cells).

Thus, in some embodiments, the viral vector is an HSV viral vector. In some embodiments, the HSV viral vector is HSV-1. In some embodiments, the vector is used for delivery of one or more CRISPR components. It may be particularly useful for delivery of the Cpf1 and one or more guide RNAs, for example 2 or more, 3 or more, or 4 or more guide RNAs. In some embodiments, the vector is therefore useful in a multiplex system. In some embodiments, this delivery is for the treatment of treatment of neuropathic pain or rheumatoid arthritis.

In some embodiments, the treatment, prophylaxis or diagnosis of HSV-1 (Herpes Simplex Virus 1) is provided. The target is preferably the UL19, UL30, UL48 or UL50 gene in HSV-1. This is described in WO2015153789, the disclosure of which is hereby incorporated by reference.

In other embodiments, the treatment, prophylaxis or diagnosis of HSV-2 (Herpes Simplex Virus 2) is provided. The target is preferably the UL19, UL30, UL48 or UL50 gene in HSV-2. This is described in WO2015153791, the disclosure of which is hereby incorporated by reference.

In some embodiments, the treatment, prophylaxis or diagnosis of Primary Open Angle Glaucoma (POAG) is provided. The target is preferably the MYOC gene. This is described in WO2015153780, the disclosure.

Adoptive Cell Therapies

The present invention also contemplates use of the CRISPR-Cas system described herein, e.g. Cpf1 effector protein systems, to modify cells for adoptive therapies. Aspects of the invention accordingly involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol.

348 no. 6230 pp. 62-68; and, Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144). Various strategies may for example be employed to genetically modify T cells by altering the specificity of the T cell receptor (TCR) for example by introducing new TCR a and R chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8a hinge domain and a CD8a transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI la-CD18, CD2, ICOS, CD27, CD154, CDS, OX40, 4-1BB, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-y). CAR T cells of this kind may for example be used in animal models, for example to threat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction). Dosing in CAR T cell therapies may for example involve administration of from 106 to 109 cells/kg, with or without a course of lymphodepletion, for example with cyclophosphamide.

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of 104-109 cells per kg body weight, preferably 105 to 106 cells/kg body weight including all integer values of cell numbers within those ranges. Dosing in CAR T cell therapies may for example involve administration of from 106 to 109 cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing with a CRISPR-Cas system as described herein may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853). For example, immunoresponsive cells may be edited to delete expression of some or all of the class of HLA type II and/or type I molecules, or to knockout selected genes that may inhibit the desired immune response, such as the PD1 gene.

Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T-cell receptors (TCR), disrupt the target of a chemotherapeutic agent, block an immune checkpoint, activate a T cell, and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene, it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, $\alpha$ and $\beta$, which assemble to form a heterodimer and associates with the CD3-transducing subunits to form the T cell receptor complex present on the cell surface. Each $\alpha$ and $\beta$ chain of the TCR consists of an immunoglobulin-like N-terminal variable (V) and constant (C) region, a hydrophobic transmembrane domain, and a short cytoplasmic region. As for immunoglobulin molecules, the variable region of the a and p chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCR$\alpha$ or TCR$\beta$ can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor $\alpha$-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, ILIORB, HMOX2, IL6R, IL6ST, EIF2AK4, CSK, PAG1, SIT1, FOXP3, PRDM1, BATF, VISTA, GUCY1A2, GUCY1A3, GUCY1B2, GUCYiB3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

The practice of the present invention employs, unless otherwise indicated, conventional techniques of immunology, biochemistry, chemistry, molecular biology, microbiology, cell biology, genomics and recombinant DNA, which are within the skill of the art. See MOLECULAR CLONING: A LABORATORY MANUAL, 2nd edition (1989) (Sambrook, Fritsch and Maniatis); MOLECULAR CLONING: A LABORATORY MANUAL, 4th edition (2012) (Green and Sambrook); CURRENT PROTOCOLS IN MOLECULAR BIOLOGY (1987) (F. M. Ausubel, et al. eds.); the series METHODS IN ENZYMOLOGY (Academic Press, Inc.); PCR 2: A PRACTICAL APPROACH (1995) (M. J. MacPherson, B. D. Hames and G. R. Taylor eds.); ANTIBODIES, A LABORATORY MANUAL (1988) (Harlow and Lane, eds.); ANTIBODIES A LABORATORY MANUAL, 2nd edition (2013) (E. A. Greenfield ed.); and ANIMAL CELL CULTURE (1987) (R.I. Freshney, ed.).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

In some embodiments, the invention described herein relates to a method for adoptive immunotherapy, in which T cells are edited ex vivo by CRISPR to modulate at least one gene and subsequently administered to a patient in need thereof. In some embodiments, the CRISPR editing comprising knocking-out or knocking-down the expression of at least one target gene in the edited T cells. In some embodiments, in addition to modulating the target gene, the T cells are also edited ex vivo by CRISPR to (1) knock-in an exogenous gene encoding a chimeric antigen receptor (CAR) or a T-cell receptor (TCR), (2) knock-out or knock-down expression of an immune checkpoint receptor, (3) knock-out or knock-down expression of an endogenous TCR, (4) knock-out or knock-down expression of a human leukocyte antigen class I (HLA-I) proteins, and/or (5) knock-out or knock-down expression of an endogenous gene encoding an antigen targeted by an exogenous CAR or TCR.

In some embodiments, the T cells are contacted ex vivo with an adeno-associated virus (AAV) vector encoding a CRISPR effector protein, and a guide molecule comprising a guide sequence hybridizable to a target sequence, a tracr mate sequence, and a tracr sequence hybridizable to the tracr mate sequence. In some embodiments, the T cells are contacted ex vivo (e.g., by electroporation) with a ribonucleoprotein (RNP) comprising a CRISPR effector protein complexed with a guide molecule, wherein the guide molecule comprising a guide sequence hybridizable to a target sequence, a tracr mate sequence, and a tracr sequence hybridizable to the tracr mate sequence. See Rupp et al., Scientific Reports 7:737 (2017); Liu et al., Cell Research 27:154-157 (2017). In some embodiments, the T cells are contacted ex vivo (e.g., by electroporation) with an mRNA encoding a CRISPR effector protein, and a guide molecule comprising a guide sequence hybridizable to a target sequence, a tracr mate sequence, and a tracr sequence hybridizable to the tracr mate sequence. See Eyquem et al.,

*Nature* 543:113-117 (2017). In some embodiments, the T cells are not contacted ex vivo with a lentivirus or retrovirus vector.

In some embodiments, the method comprises editing T cells ex vivo by CRISPR to knock-in an exogenous gene encoding a CAR, thereby allowing the edited T cells to recognize cancer cells based on the expression of specific proteins located on the cell surface. In some embodiments, T cells are edited ex vivo by CRISPR to knock-in an exogenous gene encoding a TCR, thereby allowing the edited T cells to recognize proteins derived from either the surface or inside of the cancer cells. In some embodiments, the method comprising providing an exogenous CAR-encoding or TCR-encoding sequence as a donor sequence, which can be integrated by homology-directed repair (HDR) into a genomic locus targeted by a CRISPR guide sequence. In some embodiments, targeting the exogenous CAR or TCR to an endogenous TCR a constant (TRAC) locus can reduce tonic CAR signaling and facilitate effective internalization and re-expression of the CAR following single or repeated exposure to antigen, thereby delaying effector T-cell differentiation and exhaustion. See Eyquem et al., *Nature* 543:113-117 (2017).

In some embodiments, the method comprises editing T cells ex vivo by CRISPR to block one or more immune checkpoint receptors to reduce immunosuppression by cancer cells. In some embodiments, T cells are edited ex vivo by CRISPR to knock-out or knock-down an endogenous gene involved in the programmed death-1 (PD-1) signaling pathway, such as PD-1 and PD-L1. In some embodiments, T cells are edited ex vivo by CRISPR to mutate the Pdcd1 locus or the CD274 locus. In some embodiments, T cells are edited ex vivo by CRISPR using one or more guide sequences targeting the first exon of PD-1. See Rupp et al., *Scientific Reports* 7:737 (2017); Liu et al., Cell Research 27:154-157 (2017).

In some embodiments, the method comprises editing T cells ex vivo by CRISPR to eliminate potential alloreactive TCRs to allow allogeneic adoptive transfer. In some embodiments, T cells are edited ex vivo by CRISPR to knock-out or knock-down an endogenous gene encoding a TCR (e.g., an αβ TCR) to avoid graft-versus-host-disease (GVHD). In some embodiments, T cells are edited ex vivo by CRISPR to mutate the TRAC locus. In some embodiments, T cells are edited ex vivo by CRISPR using one or more guide sequences targeting the first exon of TRAC. See Liu et al., *Cell Research* 27:154-157 (2017). In some embodiments, the method comprises use of CRISPR to knock-in an exogenous gene encoding a CAR or a TCR into the TRAC locus, while simultaneously knocking-out the endogenous TCR (e.g., with a donor sequence encoding a self-cleaving P2A peptide following the CAR cDNA). See Eyquem et al., *Nature* 543:113-117 (2017). In some embodiments, the exogenous gene comprises a promoter-less CAR-encoding or TCR-encoding sequence which is inserted operably downstream of an endogenous TCR promoter.

In some embodiments, the method comprises editing T cells ex vivo by CRISPR to knock-out or knock-down an endogenous gene encoding an HLA-I protein to minimize immunogenicity of the edited T cells. In some embodiments, T cells are edited ex vivo by CRISPR to mutate the beta-2 microglobulin (B2M) locus. In some embodiments, T cells are edited ex vivo by CRISPR using one or more guide sequences targeting the first exon of B2M. See Liu et al., *Cell Research* 27:154-157 (2017). In some embodiments, the method comprises use of CRISPR to knock-in an exogenous gene encoding a CAR or a TCR into the B2M locus, while simultaneously knocking-out the endogenous B2M (e.g., with a donor sequence encoding a self-cleaving P2A peptide following the CAR cDNA). See Eyquem et al., *Nature* 543:113-117 (2017). In some embodiments, the exogenous gene comprises a promoter-less CAR-encoding or TCR-encoding sequence which is inserted operably downstream of an endogenous B2M promoter.

In some embodiments, the method comprises editing T cells ex vivo by CRISPR to knock-out or knock-down an endogenous gene encoding an antigen targeted by an exogenous CAR or TCR. In some embodiments, the T cells are edited ex vivo by CRISPR to knock-out or knock-down the expression of a tumor antigen selected from human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (DI) (see WO2016/011210). In some embodiments, the T cells are edited ex vivo by CRISPR to knock-out or knock-down the expression of an antigen selected from B cell maturation antigen (BCMA), transmembrane activator and CAML Interactor (TACI), or B-cell activating factor receptor (BAFF-R), CD38, CD138, CS-1, CD33, CD26, CD30, CD53, CD92, CD100, CD148, CD150, CD200, CD261, CD262, or CD362 (see WO2017/011804).

Gene Drives

The present invention also contemplates use of the CRISPR-Cas system described herein, e.g. Cpf1 effector protein systems, to provide RNA-guided gene drives, for example in systems analogous to gene drives described in PCT Patent Publication WO 2015/105928. Systems of this kind may for example provide methods for altering eukaryotic germline cells, by introducing into the germline cell a nucleic acid sequence encoding an RNA-guided DNA nuclease and one or more guide RNAs. The guide RNAs may be designed to be complementary to one or more target locations on genomic DNA of the germline cell. The nucleic acid sequence encoding the RNA guided DNA nuclease and the nucleic acid sequence encoding the guide RNAs may be provided on constructs between flanking sequences, with promoters arranged such that the germline cell may express the RNA guided DNA nuclease and the guide RNAs, together with any desired cargo-encoding sequences that are also situated between the flanking sequences. The flanking sequences will typically include a sequence which is identical to a corresponding sequence on a selected target chromosome, so that the flanking sequences work with the components encoded by the construct to facilitate insertion of the foreign nucleic acid construct sequences into genomic DNA at a target cut site by mechanisms such as homologous recombination, to render the germline cell homozygous for the foreign nucleic acid sequence. In this way, gene-drive systems are capable of introgressing desired cargo genes throughout a breeding population (Gantz et al., 2015, Highly efficient Cas9-mediated gene drive for population modification of the malaria vector mosquito *Anopheles stephensi*, PNAS 2015, published ahead of print Nov. 23, 2015, doi: 10.1073/pnas.1521077112; Esvelt et al., 2014, Concerning RNA-guided gene drives for the alteration of wild populations eLife 2014; 3:e03401). In select embodiments, target sequences may be selected which have few potential off-target sites in a genome. Targeting multiple sites within a target locus, using multiple guide RNAs, may increase the cutting frequency and hinder the evolution of drive resistant alleles. Truncated guide RNAs may reduce off-target cutting. Paired nickases may be used instead of a single nuclease, to further increase specificity. Gene drive constructs may include cargo sequences encoding transcriptional regulators, for example to activate homologous recombination genes and/or repress non-homologous end-joining. Target sites may be chosen within an essential gene, so that non-homologous end-joining events may cause lethality rather than creating a drive-resistant allele. The gene drive constructs can be engineered to function in a range of hosts at a range of temperatures (Cho et al. 2013, Rapid and Tunable Control of Protein Stability in *Caenorhabditis elegans* Using a Small Molecule, PLoS ONE 8(8): e72393. doi:10.1371/journal.pone.0072393).

Xenotransplantation

The present invention also contemplates use of the CRISPR-Cas system described herein, e.g. Cpf1 effector protein systems, to provide RNA-guided DNA nucleases adapted to be used to provide modified tissues for transplantation. For example, RNA-guided DNA nucleases may be used to knockout, knockdown or disrupt selected genes in an animal, such as a transgenic pig (such as the human heme oxygenase-1 transgenic pig line), for example by disrupting expression of genes that encode epitopes recognized by the human immune system, i.e. xenoantigen genes. Candidate porcine genes for disruption may for example include a(1, 3)-galactosyltransferase and cytidine monophosphate-N-acetylneuraminic acid hydroxylase genes (see PCT Patent Publication WO 2014/066505). In addition, genes encoding endogenous retroviruses may be disrupted, for example the genes encoding all porcine endogenous retroviruses (see Yang et al., 2015, Genome-wide inactivation of porcine endogenous retroviruses (PERVs), Science 27 Nov. 2015: Vol. 350 no. 6264 pp. 1101-1104). In addition, RNA-guided DNA nucleases may be used to target a site for integration of additional genes in xenotransplant donor animals, such as a human CD55 gene to improve protection against hyperacute rejection.

General Gene Therapy Considerations

Examples of disease-associated genes and polynucleotides amd disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web.

Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex of the present invention. Examples of disease-associated genes and polynucleotides are listed in Tables 18 and 19. Examples of signaling biochemical pathway-associated genes and polynucleotides are listed in Table 20.

TABLE 18

| DISEASE/DISORDERS | GENE(S) |
|---|---|
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP - global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion - related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1; Uchl3; APP |

TABLE 18-continued

| DISEASE/DISORDERS | GENE(S) |
|---|---|
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE 19

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1. SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |

TABLE 19-continued

| | |
|---|---|
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, ADI, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado- Joseph's Dx), ATXN1 and ATXN2 (spinocerebellar ataxias), DMPK (myotonic dystrophy), Atrophin-1 and Atn1 (DRPLA Dx), CBP (Creb-BP - global instability), VLDLR (Alzheimer's), Atxn7, Atxn10). |
| Occular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE 20

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; |

TABLE 20-continued

| CELLULAR FUNCTION | GENES |
|---|---|
| | CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXO1; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1 |
| Axonal Guidance Signaling | PRKCE; ITGAM; ROCK1; ITGA5; CXCR4; ADAM12; IGF1; RAC1; RAP1A; EIF4E; PRKCZ; NRP1; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPH1; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |

TABLE 20-continued

| CELLULAR FUNCTION | GENES |
|---|---|
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RPS6KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BA$\chi$; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; |

TABLE 20-continued

| CELLULAR FUNCTION | GENES |
|---|---|
| | GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAFI; IKBKG; RELB; MAP3K7; CREBBP; MAP2K2; JAK2; CHUK; MAP2K1; NFKB1; TGFBR1; SMALM; JUN; IL1R1; PRKCA; IL6; HSP90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXO1; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RPS6KB1 |
| NRF2-mediated Oxidative Stress Response | PRKCE; EP300; SOD2; PRKCZ; MAPK1; SQSTM1; NQO1; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |

TABLE 20-continued

| CELLULAR FUNCTION | GENES |
|---|---|
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAχ; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |

TABLE 20-continued

| CELLULAR FUNCTION | GENES |
|---|---|
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NC0R2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |

TABLE 20-continued

| CELLULAR FUNCTION | GENES |
|---|---|
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; HK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | HK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CH KA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |

TABLE 20-continued

| CELLULAR FUNCTION | GENES |
|---|---|
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnr1; cnr2; Grk2; Trpa1; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4f1 or Brn3a); Numb; Reln |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA-DNA hybrids. McIvor E I, Polak U, Napierala M. RNA Biol. 2010 September-October; 7(5):551-8). The present effector protein systems may be harnessed to correct these defects of genomic instability.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

Combinational Gene Screening

As also may be described elsewhere herein, the engineered polynucleotides, vectors, and delivery systems thereof can be used in combinational (or multiplexed) genetic screen. In some aspects, the method can include modifying one or more targets in a cell by delivering an engineered polynucleotide as described herein, a vector as described herein, a Cas12 encoding polynucleotide or polypeptide, a Cas12 system, a delivery system described herein or a combination thereof to a cell; and determining an effect of modifying one or more targets in the cell. In some aspects the target(s) is/are a region(s) on a polynucleotide within the cell. In some aspects, modifying occurs in vitro, in vivo, or ex vivo. In some aspects, determining the effect of the one or more modification includes performing a suitable functional assay. The effect of the modification(s) can be qualitatively and/or quantitatively analyzed using the suitable functional assay. Suitable functional assays include, but are not limited to, genotypic assays, epigenetic assays, transcriptomic assays, proteomic assays, and phenotypic assays. In some aspects, the method further includes exposing the cell a test molecule, abiotic condition, or both before performing the functional assay. Other suitable assays will be appreciated by those of ordinary skill in the art in view of this description.

In some aspects, one or more of the engineered polynucleotides, Cas12 systems, Cas12 encoding polynucleotides or polypeptides, vectors, and/or delivery systems described elsewhere herein can be delivered to a cell such that the engineered polynucleotide(s) can complex or otherwise interact with one or more target regions on a target polynucleotide and a Cas12 polypeptide to modify one or more of the target regions. The effect of the modification(s) can be qualitatively and/or quantitatively analyzed using one or more suitable functional assays. Suitable functional assays include, but are not limited to, genotypic assays, epigenetic assays, transcriptomic assays, proteomic assays, and phenotypic assays. In some aspects, the target polynucleotide and/or one or more cells can be exposed to a test molecule or abiotic condition, before the functional assay can be performed. In this way the engineered polynucleotides, vectors, and delivery systems thereof can be used in drug screens, toxin screens, environmental screens and the like. In some embodiments, the systems described herein can be used in a synthetic-lethal screen. In some embodiments, the pairs of genes for a synthetic-lethal screen can be, but are not limited to, WSB2 and MCL1, WSB2 and MARCH5, MARCH5 and BCL2L1. Other pairs are described elsewhere herein.

Pharmaceutical Formulations

Also described herein are pharmaceutical formulations that can contain an amount, effective amount, and/or least effective amount, and/or therapeutically effective amount of one or more compounds, molecules, compositions, vectors, vector systems, cells, or a combination thereof (which are also referred to as the primary active agent or ingredient elsewhere herein) described in greater detail elsewhere herein a pharmaceutically acceptable carrier. When present, the compound can optionally be present in the pharmaceutical formulation as a pharmaceutically acceptable salt. In some embodiments, the pharmaceutical formulation can include, such as an active ingredient, a CRISPR-Cas system or a component thereof described in greater detail elsewhere herein. In some embodiments, the CRISPR-Cas system is a Cpf1-CRISPR system.

Where appropriate, compounds, molecules, compositions, vectors, vector systems, cells, or a combination thereof described in greater detail elsewhere herein can be provided to a subject in need thereof as an ingredient, such as an active ingredient, in a pharmaceutical formulation. As such, also described are pharmaceutical formulations containing one or more of the compounds and salts thereof, or pharmaceutically acceptable salts thereof described herein. Suitable salts include, hydrobromide, iodide, nitrate, bisulfate, phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, napthalenesulfonate, propionate, malonate, mandelate, malate, phthalate, and pamoate.

The pharmaceutical formulations described herein can be administered via any suitable method to a subject in need thereof. In some embodiments, the subject in need thereof has or is suspected of having a disease or a symptom thereof, such as any disease described and discussed in greater detail elsewhere herein.

Pharmaceutically Acceptable Carriers and Auxiliary Ingredients and Agents

The pharmaceutical formulation can include a pharmaceutically acceptable carrier. Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxy methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active compound.

In some embodiments, the pharmaceutical formulation can also include an effective amount of auxiliary active agents, including but not limited to, biologic agents or molecules (including but not limited to (e.g. polypeptides, polynucleotides, antibodies and fragments thereof, aptamers, and the like), chemotherapeutics, antineoplastic agents, hormones, antibiotics, antivirals, immunomodulating agents, antinausea, pain modifying compounds (such as opiates), anti-inflammatory agents, antipyretics, antibiotics, and combinations thereof.

Effective Amounts

In some embodiments, the amount of the primary active agent and/or optional auxiliary active agent can be an effective amount, least effective amount, and/or therapeutically effective amount. The effective amount, least effective amount, and/or therapeutically effective amount of the primary and optional auxiliary active agent described elsewhere herein contained in the pharmaceutical formulation can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pg, ng, µg, mg, or g or be any numerical value with any of these ranges. In some embodiments, the effective amount, least effective amount, and/or therapeutically effective amount can be an effective concentration, least effective concentration, and/or therapeutically effective concentration, which can each range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 pM, nM, µM, mM, or M or be any numerical value with any of these ranges.

In other embodiments, the effective amount, least effective amount, and/or therapeutically effective amount of the auxiliary active agent can range from about 0 to 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 IU or be any numerical value with any of these ranges.

In some embodiments, a primary active agent can be present in the pharmaceutical formulation can range from about 0 to 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.9, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the pharmaceutical formulation.

In some embodiments, the auxiliary active agent, when optionally present, can range from about 0 to 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.9, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the pharmaceutical formulation.

In embodiments where there is an auxiliary active agent contained in the pharmaceutical formulation, the effective amount of the auxiliary active agent will vary depending on the auxiliary active agent.

When optionally present in the pharmaceutical formulation, the auxiliary active agent can be included in the pharmaceutical formulation or can exist as a stand-alone compound or pharmaceutical formulation that can be administered contemporaneously or sequentially with the compound, derivative thereof, or pharmaceutical formulation thereof. In yet other embodiments, the effective amount of the auxiliary active agent can range from about, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total auxiliary active agent pharmaceutical formulation. In additional embodiments, the effective amount of the auxiliary active agent can range from about, to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.1, 99.2, 99.3, 99.4, 99.5, 99.6, 99.7, 99.8, 99.9% w/w, v/v, or w/v of the total pharmaceutical formulation.

Dosage Forms

In some embodiments, the pharmaceutical formulations described herein can be in a dosage form. The dosage form can be administered to a subject in need thereof. The dosage form can be effective generate specific concentration, such as an effective concentration, at a given site in the subject in need thereof. In some cases, the dosage form contains a greater amount of the active ingredient than the final intended amount needed to reach a specific region or location within the subject to account for loss of the active components such as via first and second pass metabolism.

The dosage forms can be adapted for administration by any appropriate route. Appropriate routes include, but are not limited to, oral (including buccal or sublingual), rectal, intraocular, inhaled, intranasal, topical (including buccal, sublingual, or transdermal), vaginal, parenteral, subcutaneous, intramuscular, intravenous, internasal, and intradermal. Other appropriate routes are described elsewhere herein. Such formulations can be prepared by any method known in the art.

Dosage forms adapted for oral administration can discrete dosage units such as capsules, pellets or tablets, powders or granules, solutions, or suspensions in aqueous or non-aqueous liquids; edible foams or whips, or in oil-in-water liquid emulsions or water-in-oil liquid emulsions. In some embodiments, the pharmaceutical formulations adapted for oral administration also include one or more agents which flavor, preserve, color, or help disperse the pharmaceutical formulation. Dosage forms prepared for oral administration can also be in the form of a liquid solution that can be delivered as a foam, spray, or liquid solution. The oral dosage form can be administered to a subject in need thereof. Where appropriate, the dosage forms described herein can be microencapsulated.

The dosage form can also be prepared to prolong or sustain the release of any ingredient. In some embodiments, compounds, molecules, compositions, vectors, vector systems, cells, or a combination thereof described herein can be the ingredient whose release is delayed. In some embodiments the primary active agent is the ingredient whose release is delayed. In some embodiments, an optional auxiliary agent can be the ingredient whose release is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, M D, 2000, and "Pharmaceutical dosage forms and drug delivery systems", 6th Edition, Ansel et al., (Media, PA: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings may be formed with a different ratio of water-soluble polymer, water insoluble polymers, and/or pH dependent polymers, with or without water insoluble/water soluble non-polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Where appropriate, the dosage forms described herein can be a liposome. In these embodiments, primary active ingredient(s), and/or optional auxiliary active ingredient(s), and/or pharmaceutically acceptable salt thereof where appropriate are incorporated into a liposome. In embodiments where the dosage form is a liposome, the pharmaceutical formulation is thus a liposomal formulation. The liposomal formulation can be administered to a subject in need thereof.

Dosage forms adapted for topical administration can be formulated as ointments, creams, suspensions, lotions, powders, solutions, pastes, gels, sprays, aerosols, or oils. In some embodiments for treatments of the eye or other external tissues, for example the mouth or the skin, the pharmaceutical formulations are applied as a topical ointment or cream. When formulated in an ointment, a primary active ingredient, optional auxiliary active ingredient, and/or pharmaceutically acceptable salt thereof where appropriate can be formulated with a paraffinic or water-miscible ointment base. In other embodiments, the primary and/or auxiliary active ingredient can be formulated in a cream with an oil-in-water cream base or a water-in-oil base. Dosage forms adapted for topical administration in the mouth include lozenges, pastilles, and mouth washes.

Dosage forms adapted for nasal or inhalation administration include aerosols, solutions, suspension drops, gels, or dry powders. In some embodiments, a primary active ingredient, optional auxiliary active ingredient, and/or pharmaceutically acceptable salt thereof where appropriate can be in a dosage form adapted for inhalation is in a particle-size-reduced form that is obtained or obtainable by micronization. In some embodiments, the particle size of the size reduced (e.g. micronized) compound or salt or solvate thereof, is defined by a $D_{50}$ value of about 0.5 to about 10 microns as measured by an appropriate method known in the art. Dosage forms adapted for administration by inhalation also include particle dusts or mists. Suitable dosage forms wherein the carrier or excipient is a liquid for administration as a nasal spray or drops include aqueous or oil solutions/suspensions of an active (primary and/or auxiliary) ingredient, which may be generated by various types of metered dose pressurized aerosols, nebulizers, or insufflators. The nasal/inhalation formulations can be administered to a subject in need thereof.

In some embodiments, the dosage forms are aerosol formulations suitable for administration by inhalation. In some of these embodiments, the aerosol formulation contains a solution or fine suspension of a primary active ingredient, auxiliary active ingredient, and/or pharmaceutically acceptable salt thereof where appropriate and a pharmaceutically acceptable aqueous or non-aqueous solvent. Aerosol formulations can be presented in single or multi-dose quantities in sterile form in a sealed container. For some of these embodiments, the sealed container is a single dose or multi-dose nasal or an aerosol dispenser fitted with a metering valve (e.g. metered dose inhaler), which is intended for disposal once the contents of the container have been exhausted.

Where the aerosol dosage form is contained in an aerosol dispenser, the dispenser contains a suitable propellant under pressure, such as compressed air, carbon dioxide, or an organic propellant, including but not limited to a hydrofluorocarbon. The aerosol formulation dosage forms in other embodiments are contained in a pump-atomizer. The pressurized aerosol formulation can also contain a solution or a suspension of a primary active ingredient, optional auxiliary active ingredient, and/or pharmaceutically acceptable salt thereof. In further embodiments, the aerosol formulation also contains co-solvents and/or modifiers incorporated to improve, for example, the stability and/or taste and/or fine particle mass characteristics (amount and/or profile) of the formulation. Administration of the aerosol formulation can be once daily or several times daily, for example 2, 3, 4, or 8 times daily, in which 1, 2, or 3 doses are delivered each time. The aerosol formulations can be administered to a subject in need thereof.

For some dosage forms suitable and/or adapted for inhaled administration, the pharmaceutical formulation is a dry powder inhalable formulations. In addition to a primary active agent, optional auxiliary active ingredient, and/or pharmaceutically acceptable salt thereof where appropriate, such a dosage form can contain a powder base such as lactose, glucose, trehalose, mannitol, and/or starch. In some of these embodiments, a primary active agent, auxiliary active ingredient, and/or pharmaceutically acceptable salt thereof where appropriate is in a particle-size reduced form. In further embodiments, a performance modifier, such as L-leucine or another amino acid, cellobiose octaacetate, and/or metals salts of stearic acid, such as magnesium or calcium stearate. In some embodiments, the aerosol formulations are arranged so that each metered dose of aerosol contains a predetermined amount of an active ingredient, such as the one or more of the compositions, compounds, vector(s), molecules, cells, and combinations thereof described herein.

Dosage forms adapted for vaginal administration can be presented as pessaries, tampons, creams, gels, pastes, foams, or spray formulations. Dosage forms adapted for rectal administration include suppositories or enemas. The vaginal formulations can be administered to a subject in need thereof.

Dosage forms adapted for parenteral administration and/or adapted for injection can include aqueous and/or non-aqueous sterile injection solutions, which can contain anti-oxidants, buffers, bacteriostats, solutes that render the composition isotonic with the blood of the subject, and aqueous and non-aqueous sterile suspensions, which can include suspending agents and thickening agents. The dosage forms adapted for parenteral administration can be presented in a single-unit dose or multi-unit dose containers, including but not limited to sealed ampoules or vials. The doses can be lyophilized and re-suspended in a sterile carrier to reconstitute the dose prior to administration. Extemporaneous injection solutions and suspensions can be prepared in some embodiments, from sterile powders, granules, and tablets. The parenteral formulations can be administered to a subject in need thereof.

For some embodiments, the dosage form contains a predetermined amount of a primary active agent, auxiliary active ingredient, and/or pharmaceutically acceptable salt thereof where appropriate per unit dose. In an embodiment, the predetermined amount of primary active agent, auxiliary active ingredient, and/or pharmaceutically acceptable salt thereof where appropriate can be an effective amount, a least effect amount, and/or a therapeutically effective amount. In some embodiments, the predetermined amount can be effective to treat or prevent a disease described elsewhere herein or a symptom thereof.

In other embodiments, the predetermined amount of a primary active agent, auxiliary active agent, and/or pharmaceutically acceptable salt thereof where appropriate, can be an appropriate fraction of the effective amount of the active ingredient. Such unit doses may therefore be administered once or more than once a day, month, or year (e.g. 1, 2, 3, 4, 5, 6, or more times per day, month, or year). Such pharmaceutical formulations may be prepared by any of the methods well known in the art.

Articles of Manufacture and Kits

Also provided are kits comprising one or more of the components described herein. In some embodiments, the kit comprises an engineered polynucleotide comprising 5' DR-G 3', 5' DR1-G1-DR2-G2 3'wherein DR1 is a first direct repeat, G1 is a first guide, DR2 is a second direct repeat, G2 is a second guide, G1 can be the same or different than G2, D1 and D2 are the same or different, wherein when different one of D1 and D2 is a wildtype direct repeat and the other comprises at least one mutation in comparison to the wildtype direct repeat, and when same each of D1 and D2 comprises at least one mutation in comparison to the wildtype direct repeat, wherein said at least one mutation may be the same or different when D1 and D2 both comprise at least one mutation. In an embodiment, the kit comprises a vector system and instructions for using the kit. In some embodiments, the vector system comprises (a) a first regulatory element operably linked to a direct repeat sequence and one or more insertion sites for inserting one or more guide sequences downstream of the DR sequence, wherein when expressed, the guide sequence directs sequence-specific binding of a CRISPR-Cas effector module complex to a target sequence in a eukaryotic cell, wherein the CRISPR-Cas effector module complex comprises a Cas effector module complexed with (1) the guide sequence that is hybridized to the target sequence, and (2) the DR sequence; and/or (b) a second regulatory element operably linked to an enzyme-coding sequence encoding said Cas effector module comprising a nuclear localization sequence and advantageously this includes a split Cas effector module. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a CRISPR-Cas effector module complex to a different target sequence in a eukaryotic cell.

Accordingly, packaged products (e.g., sterile containers containing one or more of the compositions described herein and packaged for storage, shipment, or sale at concentrated or ready-to-use concentrations) and kits, are also within the scope of the invention. A product can include a container (e.g., a vial, jar, bottle, bag, microplate, microchip, or beads) containing one or more compositions of the invention. In addition, an article of manufacture further may include, for example, packaging materials, instructions for use, syringes, delivery devices, buffers or other control reagents.

Each component of the kit can be enclosed within an individual container and all of the various containers can be within a single package, along with instructions for interpreting the results of the assays performed using the kit. The product may also include a legend (e.g., a printed label or insert or other medium describing the product's use (e.g., an audio- or videotape or computer readable medium)). The legend can be associated with the container (e.g., affixed to the container) and can describe the manner in which the reagents can be used. The reagents can be ready for use (e.g., present in appropriate units), and may include one or more additional adjuvants, carriers or other diluents. Alternatively, the reagents can be provided in a concentrated form with a diluent and instructions for dilution.

Further embodiments are illustrated in the following Examples which are given for illustrative purposes only and are not intended to limit the scope of the invention.

EXAMPLES

Example 1—Methods for Examples 2-9

Vectors

Lenti-AsCpf1-Blast: 1x-NLS-Cas12a lentiviral expression construct; also known as pRDA_113; Addgene 84750 pRDA_112: 2×-NLS-Cas12a lentiviral expression construct; also known as pTG_12; Addgene ##### pRDA_174: enCas12a lentiviral expression construct; modified version of pRDA_112 by introduction of point mutations; Addgene ##### pRDA_052: modified version of pLentiGuide for expression of AsCas12a guides; Addgene ##### pRosetta: lentiviral construct for expression of EGFP, puromycin resistance, and blasticidin resistance; Addgene 59700 pRosetta_v2: modification of pRosetta to include a hygromycin resistance cassette; Addgene ######

Lentiviral Vector Construction

Figure 10:
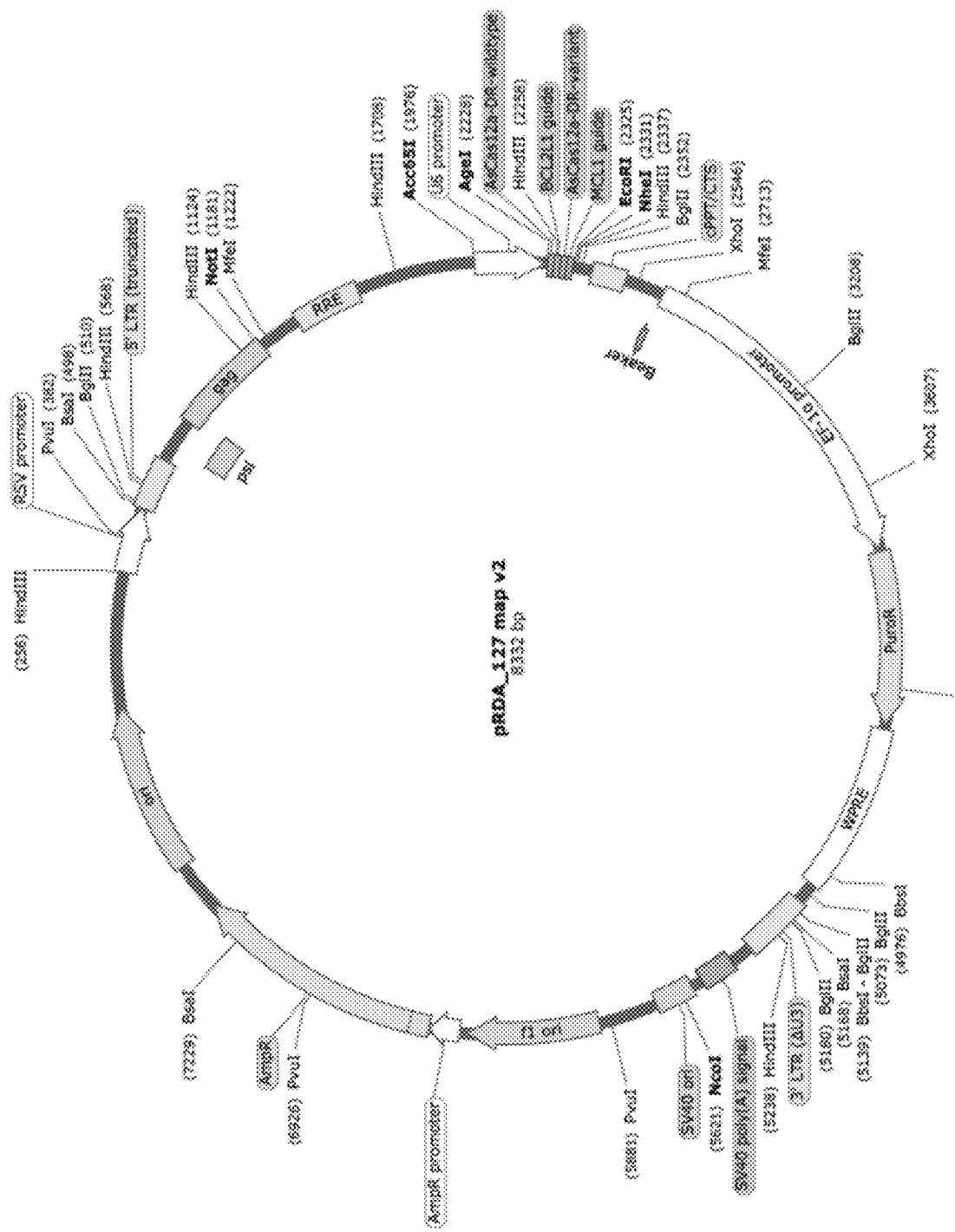
FIG. 10—Shows a map of the vector pRDA 127.
Figure 11:
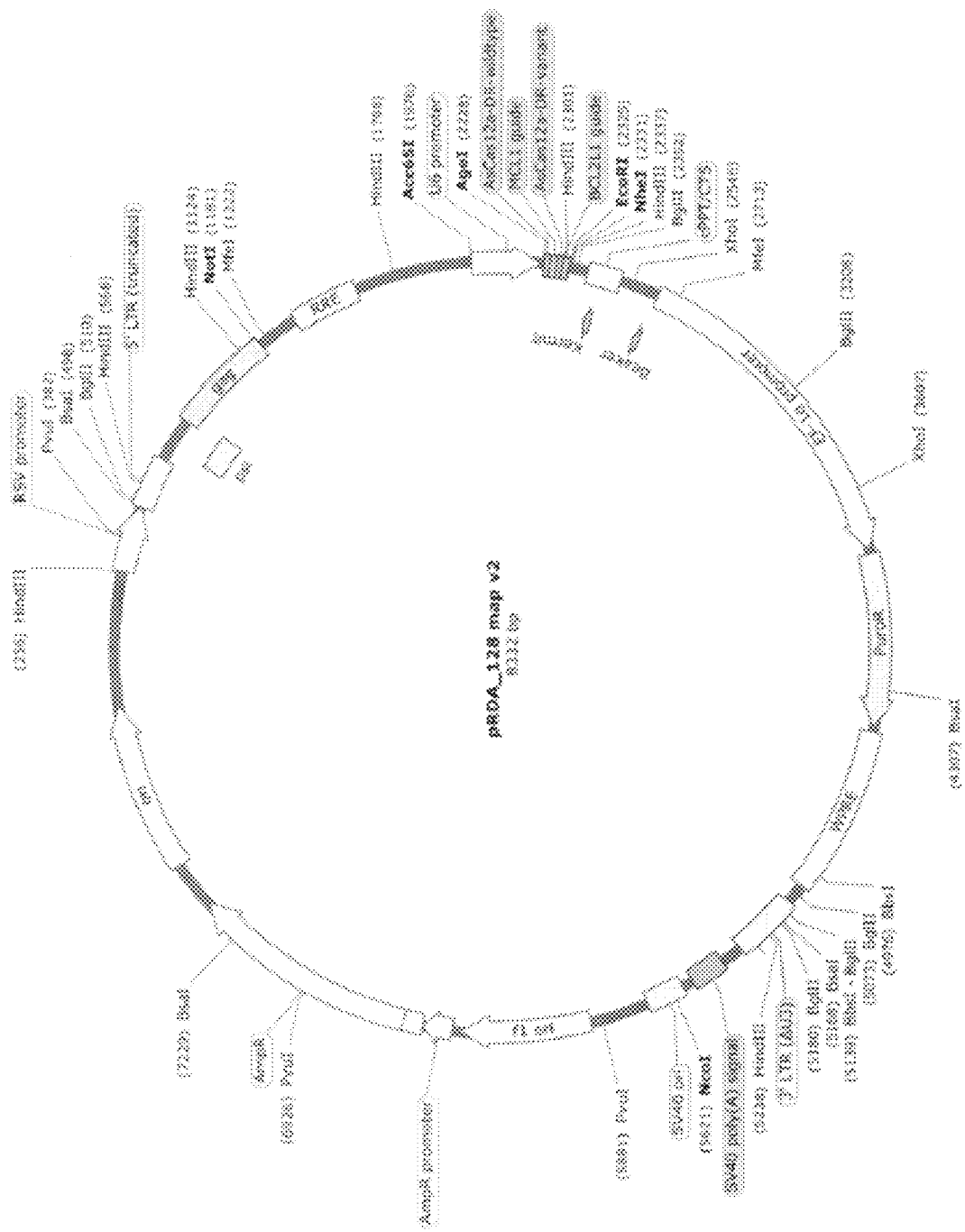
FIG. 11—Shows a map of the vector pRDA 128.
Figure 12:
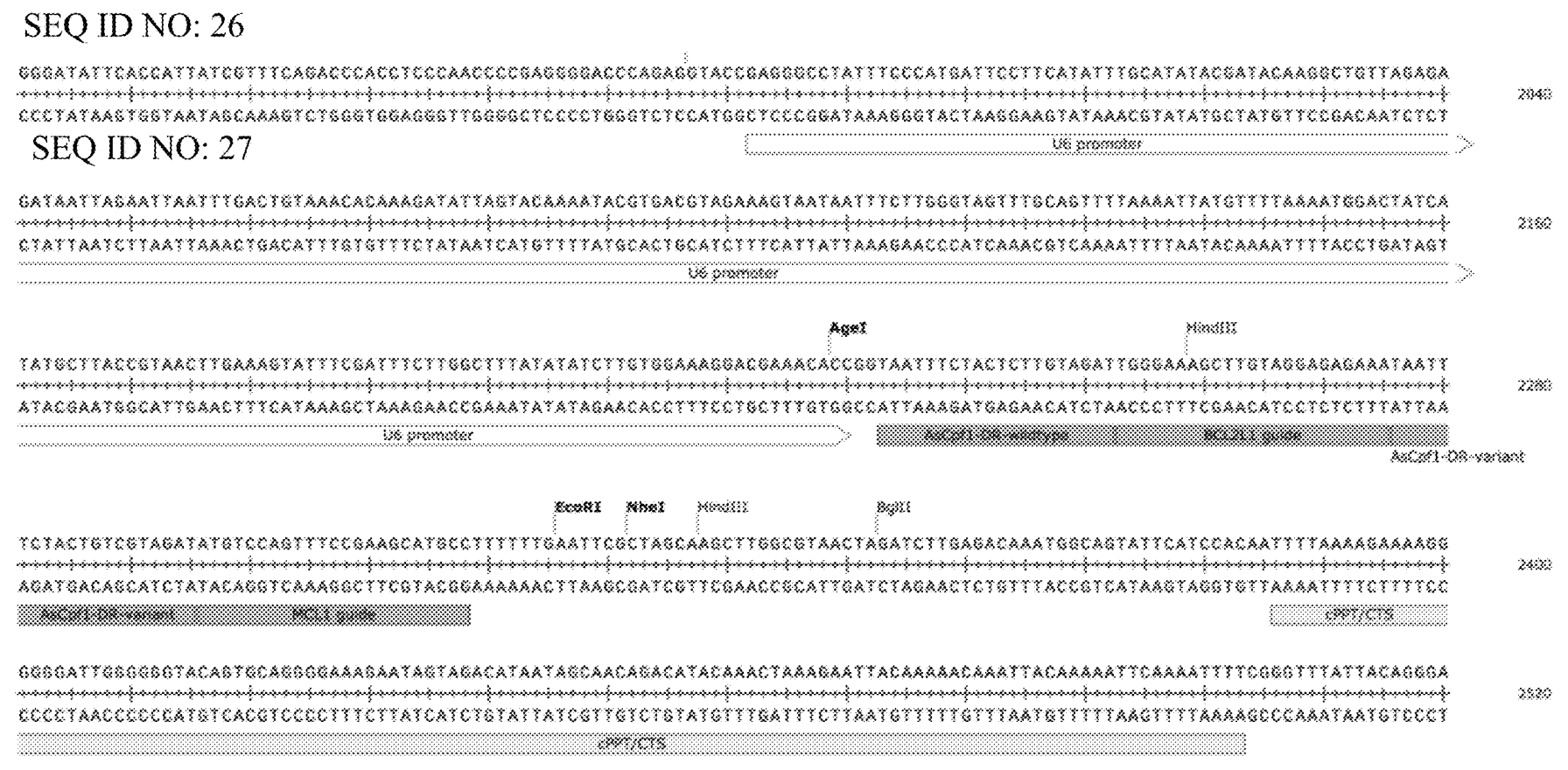

The lentiviral vector lentiGuide-puro was modified to remove the *Streptococcus pyogenes* tracrRNA sequence. The following elements were constructed by gene synthesis and cloned downstream of the U6 promoter: 5'-wildtype AsCas12a DR-BCL2L1 guide RNA—multicloning site—MCL1 guide RNA, to create the vector pRDA_128. Another version was made in which the position of the BCL2L1 and MCL1 guides were reversed (pRDA_127). Maps of the vectors pRDA 127 and pRDA 128 are shown in FIGS. 10 and 11, respectively. A detailed map of the DR expression cassette for pRDA 127 is shown in FIG. 12.

Library Production

Oligonucleotide pools were synthesized by CustomArray and Twist. BsmBI recognition sites were appended to each guide RNA sequence (whether single guides or tandem guides) along with the appropriate overhang sequences (bold italic) for cloning into the plasmid pRDA_052, as well as primer sites to allow differential amplification of subsets from the same synthesis pool. The final oligonucleotide sequence was thus: 5'-[Forward Primer]CGTCTCAAGAT (SEQ ID NO: 110) [guide RNA]TTTTTTGAATCGA-GACG (SEQ ID NO: 111) [Reverse Primer].

Primers were Used to Amplify Individual Subpools Using 25 μL 2×NEBnext PCR Master Mix (New England Biolabs), 2 μL of oligonucleotide pool (about 40 ng), 5 μL of primer mix at a final concentration of 0.5 μM, and 18 μL water. PCR cycling conditions: 30 seconds at 98° C., 30 seconds at 53° C., 30 seconds at 72° C., for 24 cycles. In cases where a library was divided into subsets unique primers could be used for amplification:

```
Primer Set; Forward Primer, 5'-3'; Reverse
Primer, 5'-3'
1;
                                        (SEQ ID NO: 112)
AGGCACTTGCTCGTACGACG;

(SEQ ID NO: 113)
ATGTGGGCCCGGCACCTTAA

2;
                                        (SEQ ID NO: 114)
GTGTAACCCGTAGGGCACCT;
```

-continued

GTCGAGAGCAGTCCTTCGAC     ((SEQ ID NO: 115)
3;
                         (SEQ ID NO: 116)
CAGCGCCAATGGGCTTTCGA;
                         (SEQ ID NO: 117)
AGCCGCTTAAGAGCCTGTCG
4;
                         (SEQ ID NO: 118)
CTACAGGTACCGGTCCTGAG;
                         (SEQ ID NO: 119)
GTACCTAGCGTGACGATCCG
5;
                         (SEQ ID NO: 120)
CATGTTGCCCTGAGGCACAG;
                         (SEQ ID NO: 121)
CCGTTAGGTCCCGAAAGGCT
6;
                         (SEQ ID NO: 122)
GGTCGTCGCATCACAATGCG;
                         (SEQ ID NO: 123)
TCTCGAGCGCCAATGTGACG

The resulting amplicons were PCR-purified (Qiagen) and cloned into the library vector via Golden Gate cloning with Esp3I (Fisher Scientific) and T7 ligase (Epizyme); the library vector was pre-digested with BsmBI (New England Biolabs). The ligation product was isopropanol precipitated and electroporated into Stbl4 electrocompetent cells (Life Technologies) and grown at 30° C. for 16 hours on agar with 100 ag mL$^{-1}$ carbenicillin. Colonies were scraped and plasmid DNA (pDNA) was prepared (HiSpeed Plasmid Maxi, Qiagen). To confirm library representation and distribution, the pDNA was sequenced.

Lentivirus Production

For small-scale virus production, the following procedure was used: 24 h before transfection, HEK293T cells were seeded in 6-well dishes at a density of 1.5×10$^6$ cells per well in 2 mL of DMEM+10% FBS. Transfection was performed using TransIT-LT1 (Mirus) transfection reagent according to the manufacturer's protocol. Briefly, one solution of Opti-MEM (Corning, 66.25 µL) and LT1 (8.75 µL) was combined with a DNA mixture of the packaging plasmid pCMV_VSVG (Addgene 8454, 250 ng), psPAX2 (Addgene 12260, 1,250 ng), and the transfer vector (e.g., pLentiGuide, 1,250 ng). The solutions were incubated at room temperature for 20-30 min, during which time media was changed on the HEK293T cells. After this incubation, the transfection mixture was added dropwise to the surface of the HEK293T cells, and the plates were centrifuged at 1,000 g for 30 min at room temperature. Following centrifugation, plates were transferred to a 37° C. incubator for 6-8 h, after which the media was removed and replaced with DMEM+10% FBS media supplemented with 1% BSA and 1% penicillin/streptomycin. Virus was harvested 36 h after this media change.

A larger-scale procedure was used for pooled library production. 20-24 h before transfection, 1.8×10$^7$ HEK293T cells were seeded in a 175 cm$^2$ tissue culture flask. The transfection was performed similarly to the small-scale production; 6 mL of Opti-MEM, 305 µL of LT1, and a DNA mixture of pCMV_VSVG (5 µg), psPAX2 (50 µg), and 40 µg of the transfer vector were used per reaction. Flasks were transferred to a 37° C. incubator for 6-8 h; after this, the media was aspirated and replaced with BSA-supplemented media. Virus was harvested 36 h after this media change.

Cell Culture

375, OVCAR8, MelJuSo, 7860, and A549 cells were obtained from the Cancer Cell Line Encyclopedia. HEK293 Ts were obtained from ATCC (CRL-3216).

All cell lines were routinely tested for *mycoplasma* contamination and were maintained without antibiotics except during screens, when the media was supplemented with 1% penicillin/streptomycin. Cell lines were kept in a 37° C. humidity-controlled incubator with 5.0% CO2 and were maintained in exponential phase growth by passaging every 2-4 days. The following media conditions and doses of polybrene, puromycin, and blasticidin, respectively, were used:

A375: RPMI+10% FBS; 1 µg mL$^{-1}$; 1 µg mL$^{-1}$; 5 µg mL$^{-1}$

HEK293T: DMEM+10% FBS; N/A; N/A; N/A

Meljuso: RPMI+10% FBS; 4 µg mL$^{-1}$; 1 µg mL$^{-1}$; 4 µg mL-1

OVCAR8: RPMI+10% FBS; 4 µg mL$^{-1}$; 1 µg mL$^{-1}$; 8 µg mL-1

A549: DMEM+10% FBS; 1 µg mL$^{-1}$; 1.5 µg mL$^{-1}$; 5 µg mL-1

7860: RPMI+10% FBS; 4 µg mL$^{-1}$; 1 µg mL$^{-1}$; 8 µg mL-1

Olaparib was obtained from Cayman Chemical Co (10621) and screened at a dose of 500 nM. Talazoparib was obtained from Selleckchem (BMN 673) and screened at a dose of 7.81 nM. S63845 was a gift from Guo Wei and was screened at 250 nM. A-1331852 was obtained from Active Biochem (A-6048) and was screened at a dose of 250 nM. Vemurafenib (S1267) was obtained from Selleckchem and screened at a dose of 2 µM. 6-thioguanine was obtained from Sigma-Aldrich and screened at a dose of 2 µg/mL.

Determiniation of an Abiotic Dose

In order to determine an appropriate antibiotic dose for each cell line, cells were transduced with the pRosetta or pRosetta_v2 lentivirus such that approximately 30% of cells were infected and therefore EGFP+. At least 1-day post-transduction, cells were seeded into 6-well dishes at a range of antibiotic doses (e.g. from 0 µg/mL to 8 µg/mL of puromycin). The rate of antibiotic selection at each dose was then monitored by performing flow cytometry for EGFP+ cells. For each cell line, the antibiotic dose was chosen to be the lowest dose that led to at least 95% EGFP+ cells after antibiotic treatment for 7 days (for puromycin) or 14 days (for blasticidin and hygromycin).

Determiniation of Lentiviral Titer

To determine lentiviral titer for transductions, cell lines were transduced in 12-well plates with a range of virus volumes (e.g. 0, 150, 300, 500, and 800 µL virus) with 3.0×10$^6$ cells per well in the presence of polybrene. The plates were centrifuged at 640×g for 2 h and were then transferred to a 37° C. incubator for 4-6 h. Each well was then trypsinized, and an equal number of cells seeded into each of two wells of a 6-well dish. Two days post-transduction, puromycin was added to one well out of the pair. After 5 days, both wells were counted for viability. A viral dose resulting in 30-50% transduction efficiency, corresponding to an MOI of ~0.35-0.70, was used for subsequent library screening.

Pooled Screens

Cell lines stably expressing Cas12a were transduced with guides cloned into the pRDA_052 vector in two biological replicates at a low MOI (~0.5). Transductions were performed with enough cells to achieve a representation of at least 500 cells per guide per replicate, taking into account a 30-50% transduction efficiency. Throughout the screen, cells were split at a density to maintain a representation of at least 500 cells per guide, and cell counts were taken at each passage to monitor growth. Puromycin selection was added 2 days post-transduction and was maintained for 5-7 days. After puromycin selection was complete, each replicate was divided into untreated (i.e. no drug/dropout arms) and small molecule treatment arms, each at a representation of at least 500 cells per guide. 14 days after the initiation of small molecule treatment, cells were pelleted by centrifugation, resuspended in PBS, and frozen promptly for genomic DNA isolation.

Genomic DNA Isolation and Sequencing

Genomic DNA (gDNA) was isolated using the Machery Nagel NucleoSpin Blood Maxi (2e7-1e8 cells), Midi (5e6-2e7 cells), or Mini (<5e6 cells) kits as per the manufacturer's instructions. The gDNA concentrations were quantitated by Qubit. For PCR amplification, gDNA was divided into 100 µL reactions such that each well had at most 10 µg of gDNA. Per 96 well plate, a master mix consisted of 150 µL ExTaq DNA Polymerase (Takara), 1 mL of 10×Ex Taq buffer, 800 µL of dNTP provided with the enzyme, 50 µL of P5 stagger primer mix (stock at 100 µM concentration), and 2 mL water. Each well consisted of 50 µL gDNA plus water, 40 µL PCR master mix, and 10 µL of a uniquely barcoded P7 primer (stock at 5 µM concentration). For future experiments, we recommend the use of Titanium Taq DNA Polymerase (Takara) and the addition of 5% DMSO per well, as we have found that these changes improve PCR efficiency.

PCR cycling conditions: an initial 1 min at 95° C.; followed by 30 s at 94° C., 30 s at 52.5° C., 30 s at 72° C., for 28 cycles; and a final 10 min extension at 72° C. PCR primers were synthesized at Integrated DNA Technologies (IDT). PCR products were purified with Agencourt AMPure XP SPRI beads according to manufacturer's instructions (Beckman Coulter, A63880). Samples were sequenced on a HiSeq2500 HighOutput (Illumina) with a custom primer of sequence: 5'-CTTGTGGAAAGGACGAAACACCGGTAATTTCTACTCTTGTAGAT (SEQ ID 124). The first nucleotide sequenced with the primer is the first nucleotide of the guide RNA, which will contain a mix of all four nucleotides, and thus staggered primers are not required to maintain diversity when using this approach. Reads were counted by alignment to a reference file of all possible guide RNAs present in the library. The read was then assigned to a condition (e.g. a well on the PCR plate) on the basis of the 8 nt index included in the P7 primer.

Screen Analysis

Following deconvolution, the resulting matrix of read counts was first normalized to reads per million within each condition by the following formula: read per guide RNA/total reads per condition×$10^6$. Reads per million was then log 2-transformed by first adding one to all values, which is necessary in order to take the log of guides with zero reads. For each guide, the $log_2$-fold-change from plasmid DNA (pDNA) was then calculated. All reported $log_2$-fold-changes for dropout screens are relative to pDNA; for positive selection screens with small molecules, the $log_2$-fold-change are calculated relative to the dropout arm (i.e. no small molecule treatment arm).

On-Target Modeling

To pick guides, genes were filtered for genes that had a significant spearman correlation across replicates and were more active than control genes (two-tailed Mann-Whitney test). Log 2-fold changes for all guides targeting the same loci in selected conditions were averaged.

Modeling was done as previously with Cas9 (Najm, F. J. et al. Orthologous CRISPR-Cas9 enzymes for combinatorial genetic screens. Nat. Biotechnol. 36, 179 (2017) and Doench, J. G. et al. Optimized sgRNA design to maximize activity and minimize off-target effects of CRISPR-Cas9. Nat. Biotechnol. 34, 184-191 (2016)) with a few additional features. Zipper (e.g. TNC) and tetramer (e.g. TTTT) features were added to extend the window for detecting nucleotide relationships. Physiochemical features were also added, which have been proven to be useful[18]. Model hyperparameters were chosen using a random grid search with the Python library scikit-learn.

In-Silico Mutagenesis

To understand the learned nucleotide features of the on-target models, we started with a random seed sequence, and then for each timestep one nucleotide was randomly changed from the previous step. Sequences were restricted to have a TTTN PAM and ensured each new sequence was unique. Sequences were iterated over 15,001 timesteps. Each sequence was then scored and the difference between its score and the score of the sequence from the previous step was obtained, which yielded 15,000 deltas. Then, for each position and nucleotide, an average difference for the substitution was calculated.

Calculating Expected LFCs

For a construct with the ordered elements guide1, DR, guide2, it can be said that the $$Avg.\ LFC \frac{expected}{guide1,\ DR,\ guide2} = m*(Avg.\ LFC_{guide1,DR,controls} + Avg.\ LFC_{controls,DR,guide2}) + \beta,$$

where m and $\beta$ are a fitted slope and intercept. The residual then is the difference between the observed and expected LFCs.

Filtering SynLet Libraries

Data from the Big Papi SynLet screen in A375 and OVCAR8 cells was used to compare with the multiplexed enCas12a system. Both libraries targeted the pairs MAPK1/MAPK3, PARP1/PARP2, BCL2L1/MCL1, BCL2L1/BCL2L2, MAP2K1/MAP2K2, and BRCA1/PARP1. Both data sets were filtered to account for the heterogeneity of the library designs. After filtering, there were 18 observations for each programmed pair (3 guides for each gene in both orientations), and each guide was paired with 15 cutting controls. In the enCas12a library we were left with fewer than 3 guides for MAP2K1, MAP2K2, and BCL2L2 so we removed these genes from the comparison.

To mitigate off-target effects in the enCas12a library guides that were predicted to cut in alternative protein-coding regions between 20% and 100% of the time (Tier I, Bins I and II in the GPP sgRNA design tool) were removed. On-target efficacy of enCas12a SynLet was maximized pairs by removing guides that cut in the first 5% or last 20% of the coding sequence of a gene. Then to match the number of guides in the Big Papi library we used Seq-DeepCpf1 to pick the 3 or 15 best remaining guides for SynLet or control genes respectively.

The Big Papi library was filtered for the same target pairs (3 guides per gene) as well as 15 control guides targeting the cell surface marker CD81 (10 guides) and intronic regions of HPRT1 (5 guides). Note that the original library design for Big Papi already included on and off-target filters.

Triple Knockout with Cas12a

A375 cells stably expressing enCas12a were transduced with 6 triple knockout arrays, 3 single knockout constructs, and one empty control vector. Two days after transduction, cells were selected with puromycin (1 g/mL), and passaged on puromycin for 7 days. Cells were visualized by flow cytometry on the BDAccuri C6 Sampler system 9, 18, and 25 days post infection. To prepare samples for visualization, cells were stained with FITC anti-human CD47 (Biolegend #323106), PE anti-human CD63 (Biolegend #353004) and APC anti-human β2-microglobulin (Biolegend #316312) antibodies, diluted 1:100 in flow buffer (PBS, 2% FBS, 5 µM EDTA), incubated for 30 min on ice, washed with flow buffer twice to remove residual antibody, and resuspended in flow buffer. Flow cytometry data were analyzed using FlowJo (v10). Compensation was applied using single stained empty vector control and triple stained empty vector control cell populations. Zero, single, double, and triple knockout populations were quantified using boolean gating in FlowJo.

Statistical Analysis

Correlation coefficients were calculated in base R or numpy in Python. Precision recall curves were generated using custom scripts in Python. Wilcoxon rank sum tests for filtering tiling data were performed in R.

Example 2—DR Variant Identification

A library of 35,783 DR variants was synthesized (CustomArray) and cloned into the MCS in both vectors between the MCL1 and BCL2L1 guide sequences. Exemplary DR sequences are shown in FIG. 13. The wild type DR is shown. An example oligonucleotide is: TNANTSC-TACTNTNGTAGST (SEQ ID NO: 134). Such a sequence can have 4 variants at each N position and 2 variants at each S position, resulting in $(4^4)*(2^2)=1,024$ combinations. As controls, the library included 100 random DRs (e.g. random 20mers) as well as 100 intend-6T DRs in which a run of 6 thymidines was inserted into the DR to terminate transcription. The wildtype DR was included.

Figure 4B:
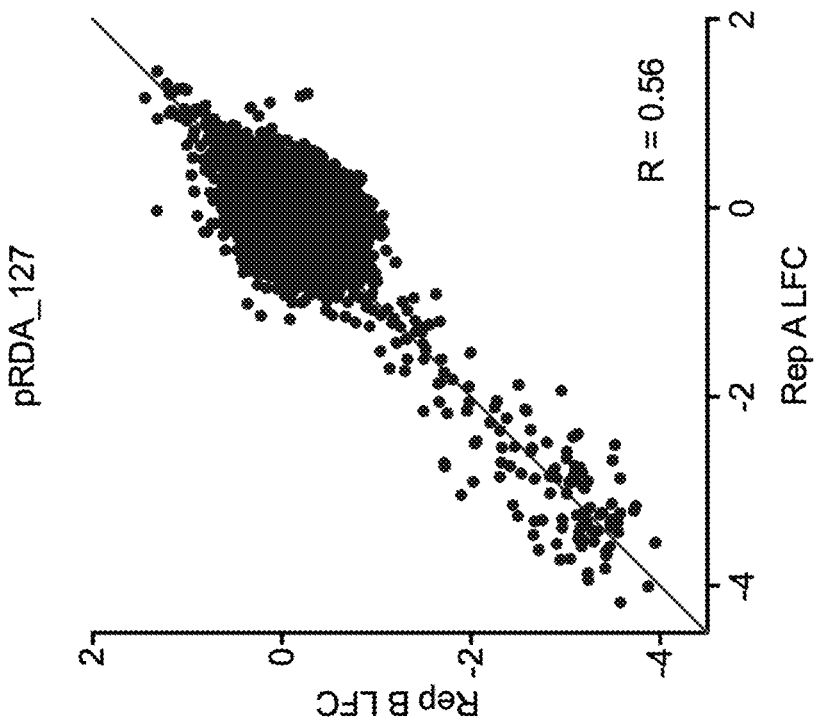
FIGS. 4A-4B—Depict (FIG. 4A) the correlation between replicate-log-fold-change (LFC) values obtained with the vector pRDA 127 and (FIG. 4B) the correlation between replicate-log-fold-change (LFC) values obtained with the vector pRDA 128.
Figure 4A:
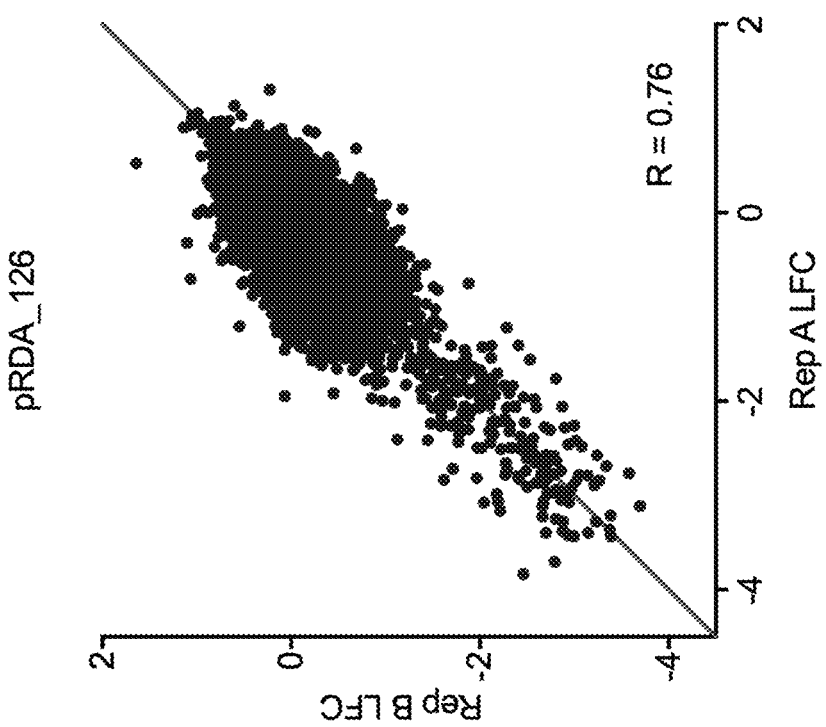
Figure 5:
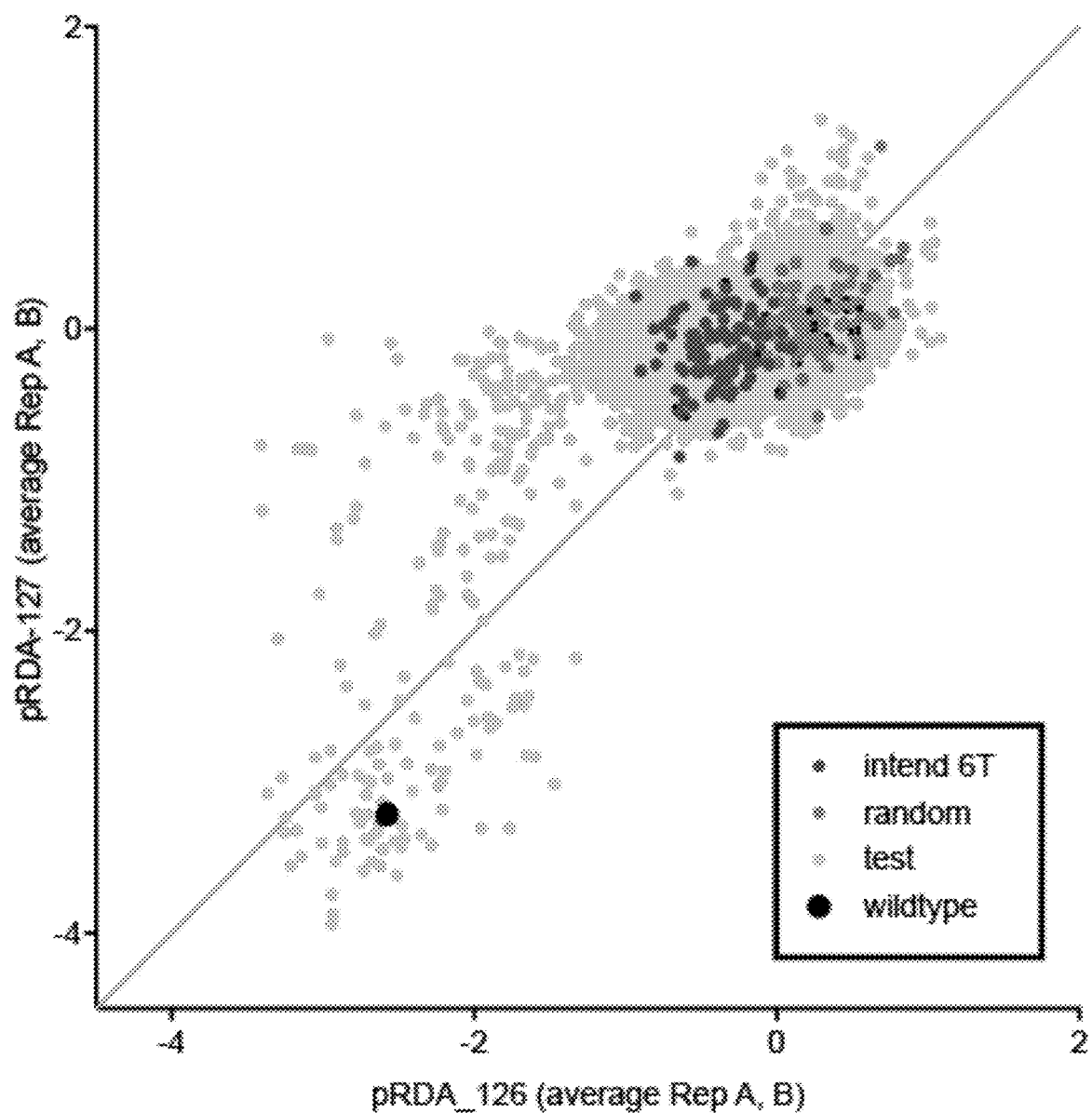
FIG. 5—Depicts the results of an analysis of DR variants obtained with the vectors pRDA 127 and pRDA 128.

Lentivirus was prepared and the two vectors were infected in duplicate into Meljuso cells (a melanoma cell line) previously engineered to express AsCas12a at a multiplicity of infection of about 0.5. Uninfected cells were removed with puromycin selection and the population cultured for 19 days to allow depletion of cells in which both BCL2L1 and MCL1 were eliminated. The cells were then harvested, genomic DNA was prepared, and PCR was used to retrieve the library of DR variants. The PCR products were sequenced (Illumina NextSeq) and the abundance of each variant was compared to the starting abundance, determined by sequencing the plasmid DNA of the library. As shown in FIGS. 4A and 4B, the log-fold-change values for the libraries in the two different vectors were well correlated. The DR variants that performed as well or better than the wildtype DR—i.e. depletion relative to their starting abundance—in both the pRDA_127 and pRDA_128 vector libraries were defined as hits. Most of the variants did not result in depletion, as shown in FIG. 5.

Nucleotide sequences of the DR variants that resulted in depletion are shown FIG. 6. Compensatory mutations were identified in the stem portion of the DR sequence. The stem loop portion of the DR sequence (positions 6-19) is indicated by shading at the bottom of the table shown in FIG. 7. The loop portion of the DR sequence (positions 9-16) is indicated by shading at the bottom of the table shown in FIG. 8. As shown in FIG. 9, certain positions in the loop tolerated changes (positions 12 and 14) while others (positions 11 and 13) did not.

Example 3—Characterization of Protospacer Adjacent Motif (PAM) for AsCas12s

Figure 2A:
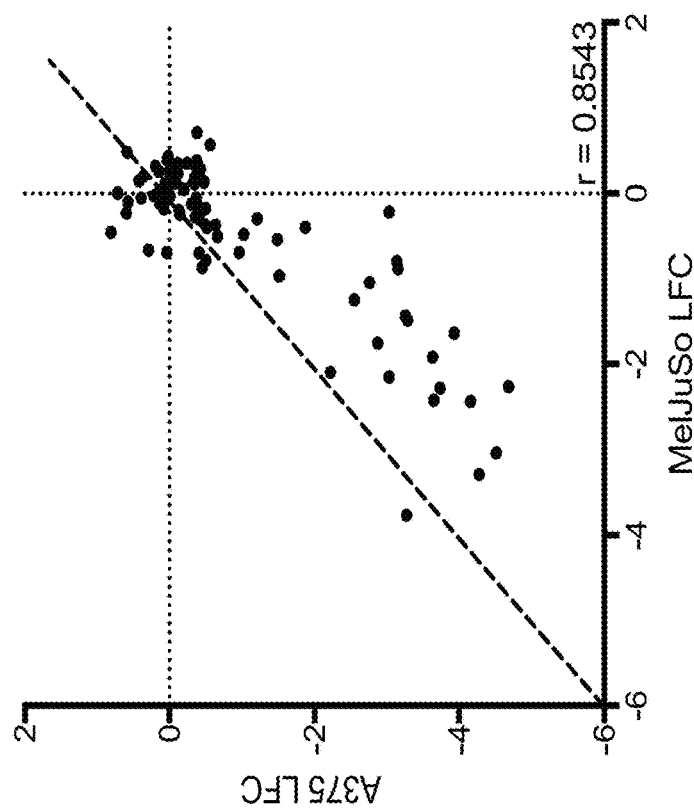
FIGS. 2A-2B—Depict (FIG. 2A) a comparison of protospacer adjacent motif (PAM) analysis of the lethal gene EEF2 in the cell lines A375 and MelJuSo and (FIG. 2B) a comparison of protospacer adjacent motif (PAM) analysis of the lethal gene SF3B1 in the cell lines A375 and MelJuSo.
Figure 2B:
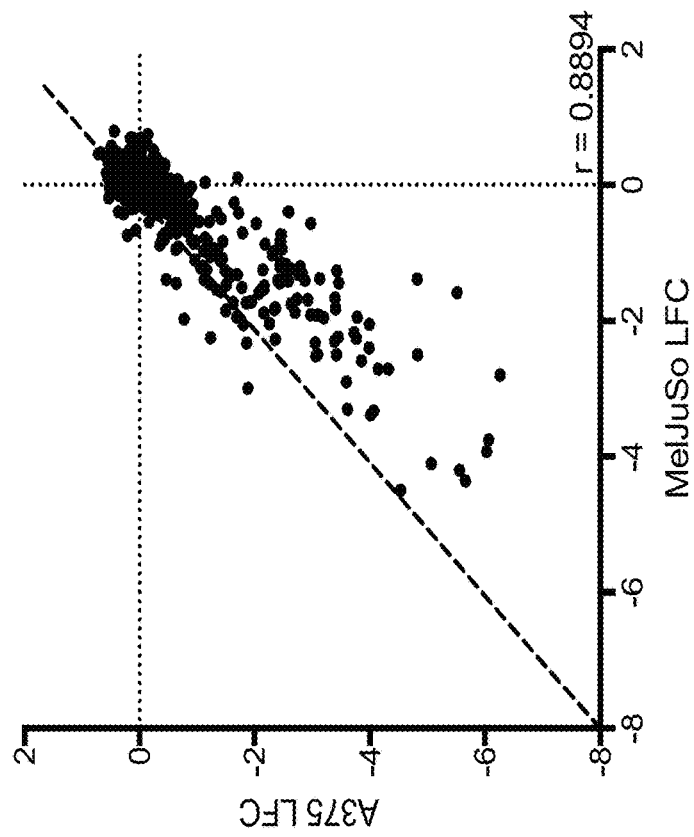
Figure 3A:
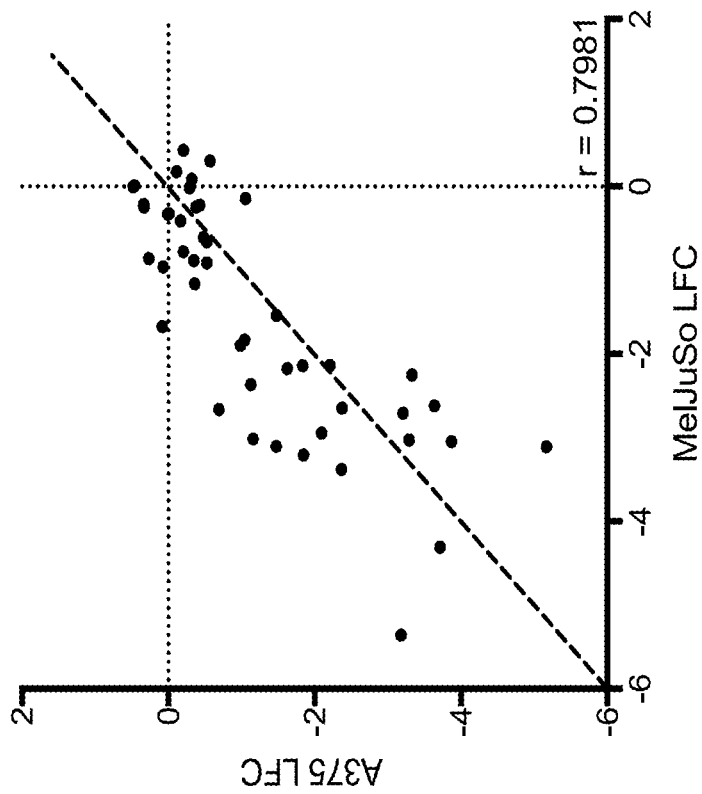
FIGS. 3A-3B—Depict (FIG. 3A) a comparison of protospacer adjacent motif (PAM) analysis of MCL1 in the cell lines A375 and MelJuSo following treatment with A1331852 and (FIG. 3B) a comparison of protospacer adjacent motif (PAM) analysis of BCL2L1 in the cell lines A375 and MelJuSo following treatment with the S63845.
Figure 3B:
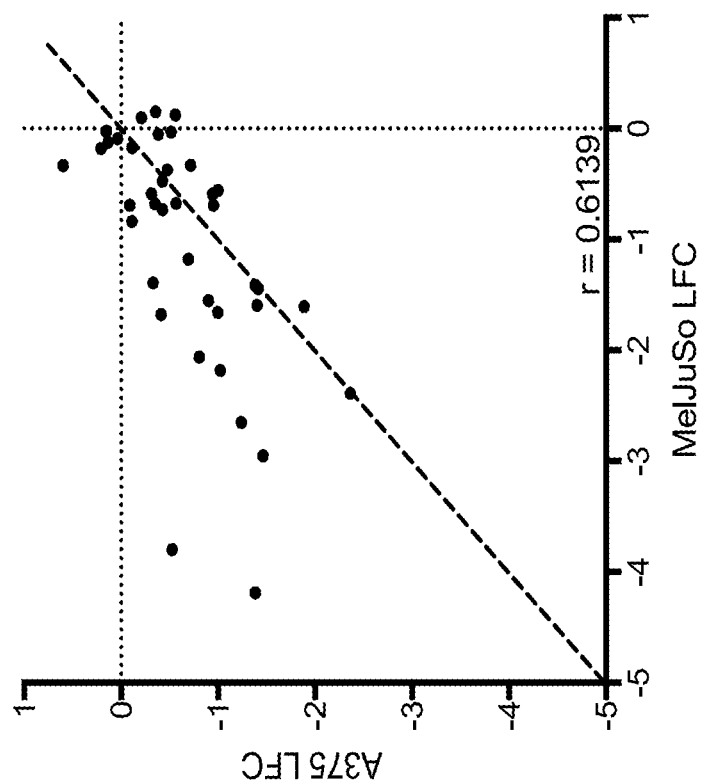

The protospacer adjacent motif (PAM) for AsCas12s was identified by analysis of essential genes in a dropout screen using cell lines A375, MelJuSo, A549, OVCAR8, and 7860. as shown in FIG. 1, the PAM for AsCas12s is TTTV, that is, TTTA, TTTC, TTTG, but not TTTT. These data were consistent across the cell lines A375 and MelJuSo for both the essential genes EEF2 and SF3B1, as shown in FIGS. 2A-2B, respectively. These data were also consistent across the cell lines A375 and MelJuSo for MCL1 following treatment with the selective BcL-2 inhibitor, A1331852, as shown in FIG. 3A. These data were also consistent across the cell lines A375 and MelJuSo for BCL2L1 following treatment with the selective MCL1 inhibitor, S63845, as shown in FIG. 3B.

Example 4—Optimization of the AsCas12a Protein

Figure 17A:
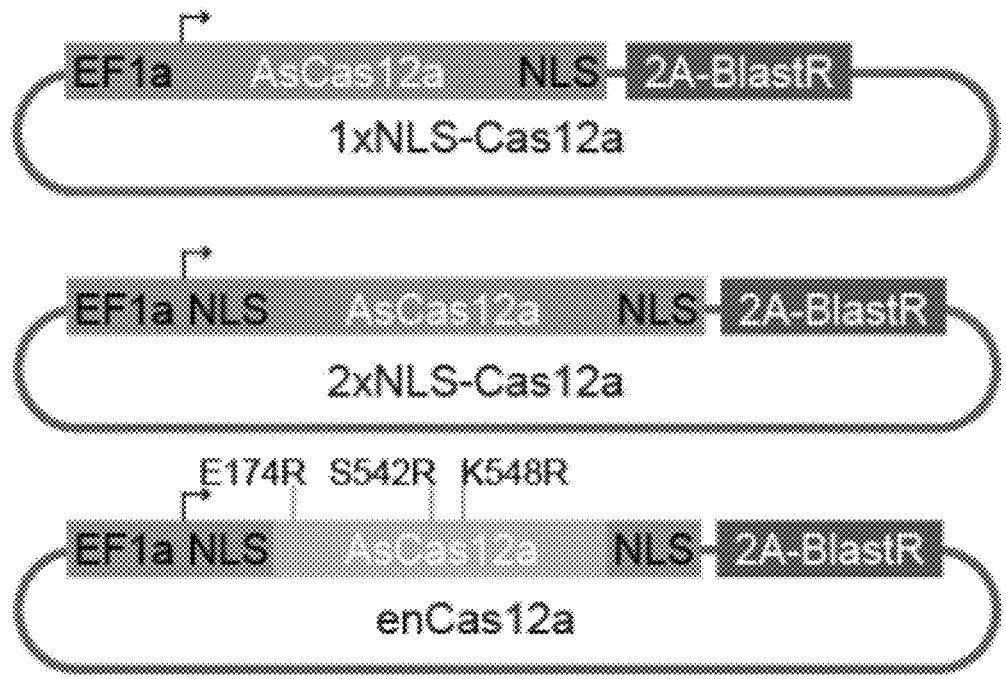

In order to assess the efficacy of Cas12a for screening purposes, a lentiviral vector from Kim et al. was obtained and used. See Kim, H. K. et al. In vivo high-throughput profiling of CRISPR-Cpf1 activity. Nat. Methods 14, 153-159 (2017), the disclosure of which is hereby incorporated by reference in its entirety. This served as a template for a third vector, into which the amino acid point mutations were introduced to generate enCas12a. See e.g. FIG. 17A. enCas12a is a recently-described variant of AsCas12a with increased activity and an expanded range of PAM sequences (See Kleinstiver, B. P. Nat. Biotechnol. 2019. Doi:10.1038/s41587-018-0011-0, which discloses enCas12a sequences (AsCas12a sequences comprising E174R/S542R/K548R mutations), the disclosure of which is hereby incorporated by reference in its entirety).

A tiling library for all possible guides ranging between 20 and 23 nucleotides in length targeting TTTN PAM sites across a set of 43 genes. The library included pan essential genes (Hart et al. Mol. Syst. Biol. 10:733 (2014)), cell-specific lethal genes, genes with well-characterized interactions with specific small-molecules, and cell surface genes, as well as all possible guides for the essential gene EEF2 regardless of PAM, for a total of 12,472 unique guides (FIG. 34).

Figure 17B:
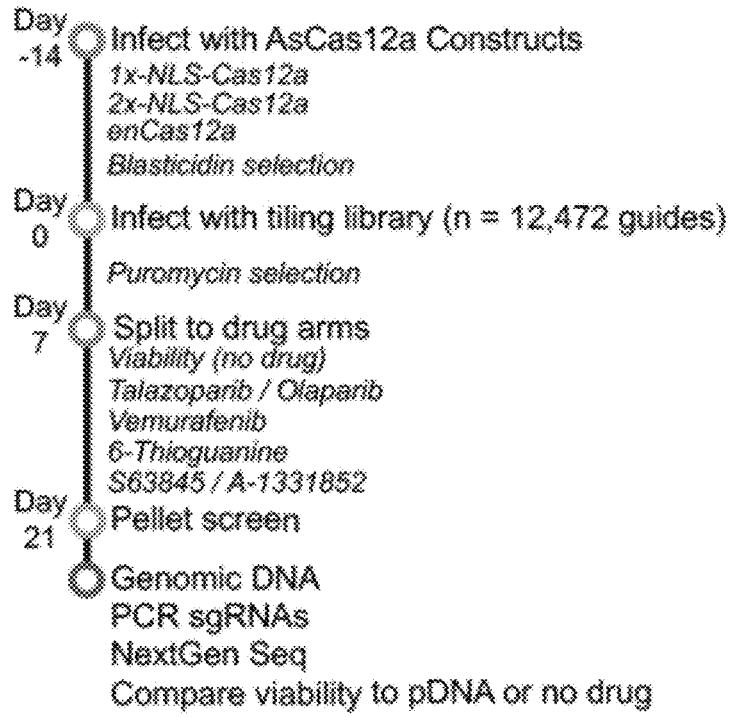
(FIG. 17B) Timeline for executing tiling screens.

An orthogonal version of this library targeting NGG PAMs for Cas9 was also synthesized for comparison. To assess protein performance, negative and positive selection screens were performed in duplicate across five cells lines stably expressing 1×NLS-Cas12a, 2×NLS-Cas12a, and enCas12a. The AsCas12a library was cloned into a modified version of lentiGuide, pRDA_052, which expresses the guide from a U6 promoter and confers puromycin resistance. Positive and negative selection screens were conducted over a three-week time course in duplicate (FIG. 17B), as has been done to assess activity of SaCas9 (Najm et al. Nat. Biotechnol. 36:179 (2017) and SpCas9 (Doench et al. Nat. Biotechnol. 34:184-191 (2016)) via growth assays. During the course of this study, the AsCas12a tiling library was screened across five different cell lines and six small molecule treatments (FIG. 35 and Supplementary Data 1 as set forth in Sanson et al. "Optimization of AsCas12a for combinatorial genetic screens in human cells" bioRxiv, Aug.

28, 2019 doi:http//dx.doi.org/10.1101/747170), which is incorporated herein by reference as if expressed in its entirety herein.

Figure 22C:
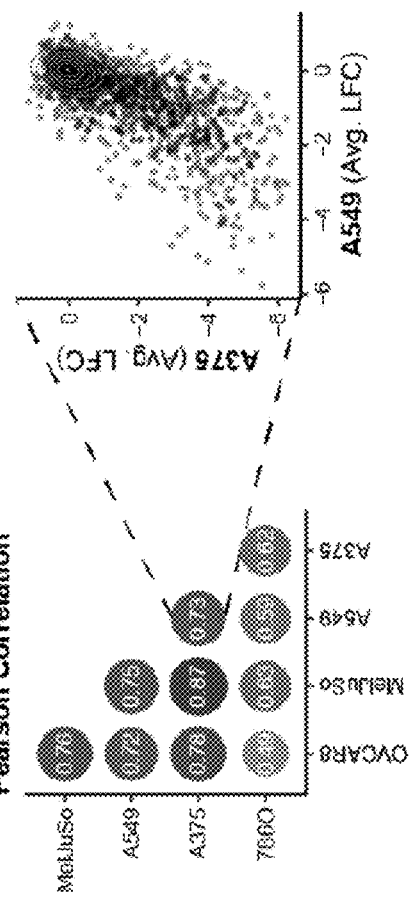

Across the five cell lines, 3 constructs and various positive and negative selection assays screened, a strong Pearson correlation was observed, indicating good reproducibility. The viability data from A375 cells was first examined, as this assay was conducted with all three AsCas12a constructs as well as SpCas9. For each of the AsCas12a variants, we observed similar performance across all lengths of guide RNAs (FIG. 22A). Further, the highest activity at TTTA PAM sites was observed followed closely by TTTC and TTTG, and the lowest activity levels was observed at TTTT sites for all variants (FIG. 22B), which has been observed (Kim et al. Nat. Methods. 14:153-159 (2107)). Defining the $5^{th}$ percentile of guides targeting control genes as a cutoff for activity, 57% of enCas12a guides targeting a TTTT site were observed to be active compared with 7% of 2×NLS-Cas12a and 7% of 1×NLS-Cas12a, demonstrating the ability of enCas12a to target previously inaccessible sites ((Kim et al. Nat. Methods. 14:153-159 (2107) and Kleinstiver et al., Nat. Biotechnol. 36:324-327 (2018)). Comparing across cell lines (FIG. 22C) we saw that guides that were effective in one tended to be effective in another.

Figure 17C:
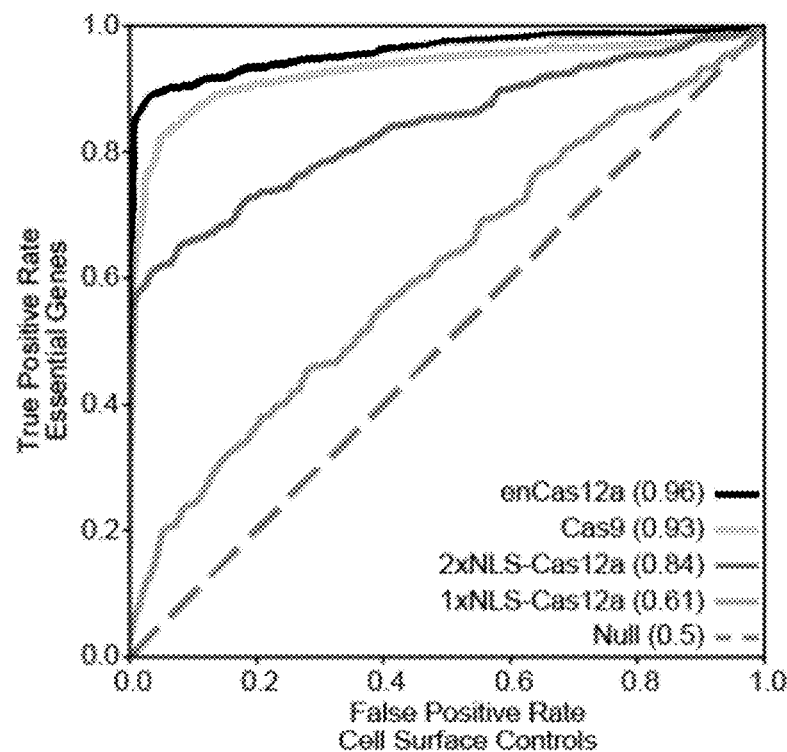
(FIG. 17C) Precision-recall curves for guides targeting essential and control genes for Cas12a and SpCas9, using viability data in A375 cells (n=1146 and 2468 for essential guides for Cas12a and Cas9, respectively, and 153 and 673 for control guides). The area under the curve for each enzyme is noted in parentheses.

To compare the efficacy of AsCas12a to SpCas9, we performed a precision recall analysis with the A375 viability data (excluding guides with TTTT PAMs for AsCas12a), defining guides targeting essential genes as true positives and guides targeting control genes as false positives, and calculating an area under curve (AUC) (FIG. 17C). SpCas9 performed well, with an AUC of 0.93, whereas the 1×NLS-Cas12a construct performed the worst with an AUC of 0.61. However, the additional NLS site improved performance, as the AUC with 2×NLS-Cas12a increased to 0.84, consistent with recent observations (Liu et al. 47:4169-4180 (2019). Finally, enCas12 showed the most robust performance, comparable to SpCas9, with an AUC 0.96. Thus, we chose to move forward with 2×-NLS-Cas12a and the enCas12a variant thereof for further experiments.

Example 5—Evaluation of On-Target Scoring Criteria

Figure 18A:
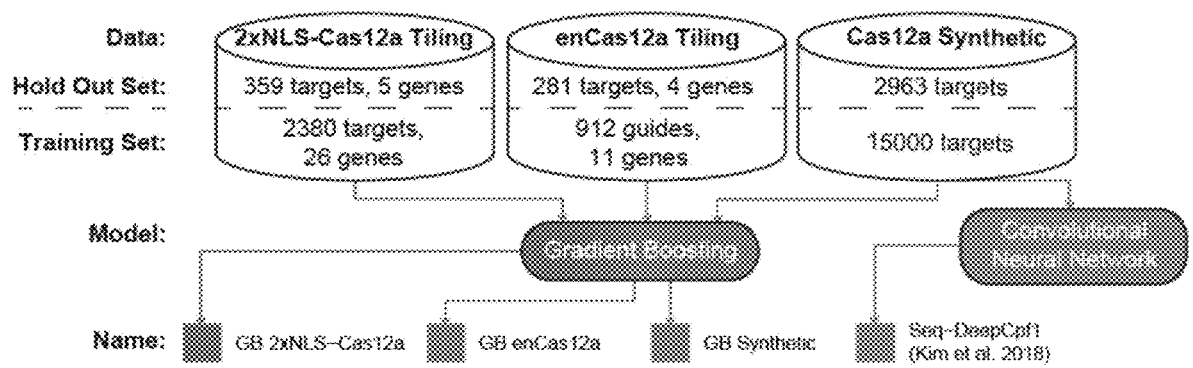
Figure 18B:
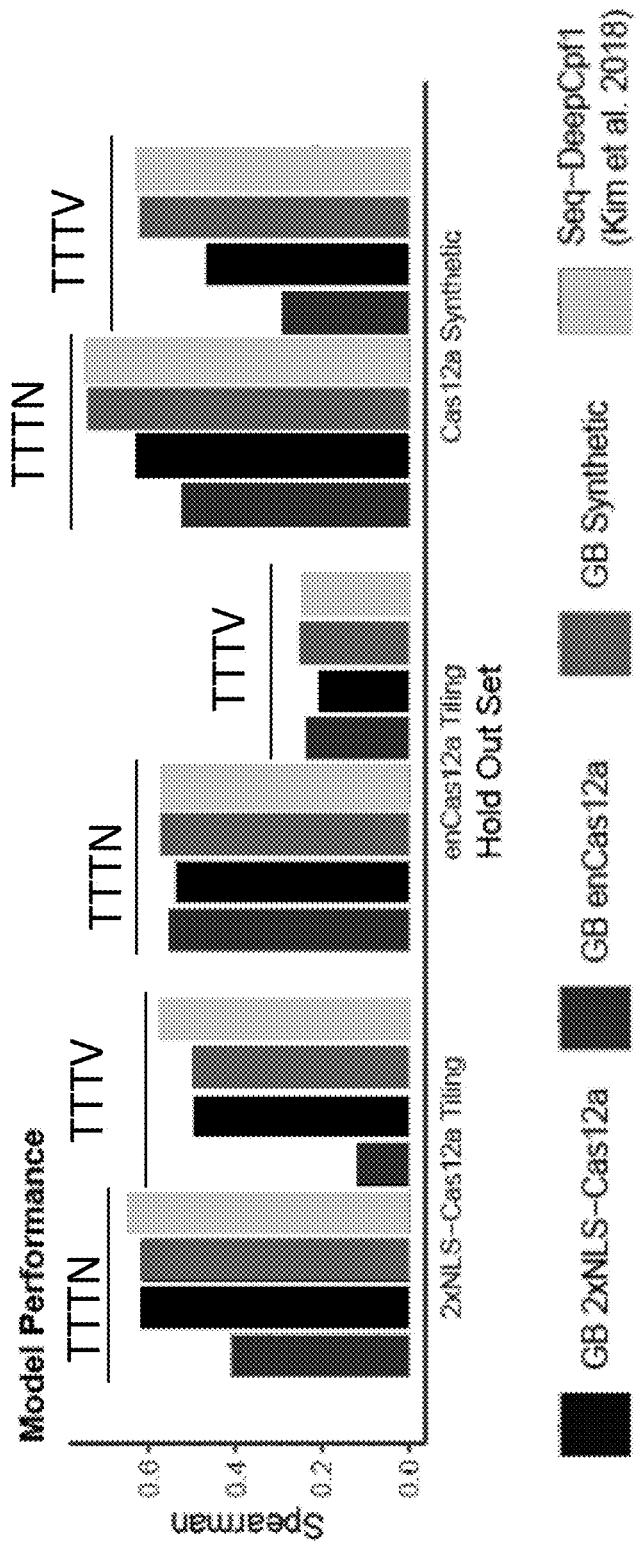
(FIG. 18B) Model performance on held out test sets. Spearman correlation shown for TTTN (dark) and TTTV only (light) target sites. Hold-out set sizes are noted in (FIG. 18A).
Figure 23A:
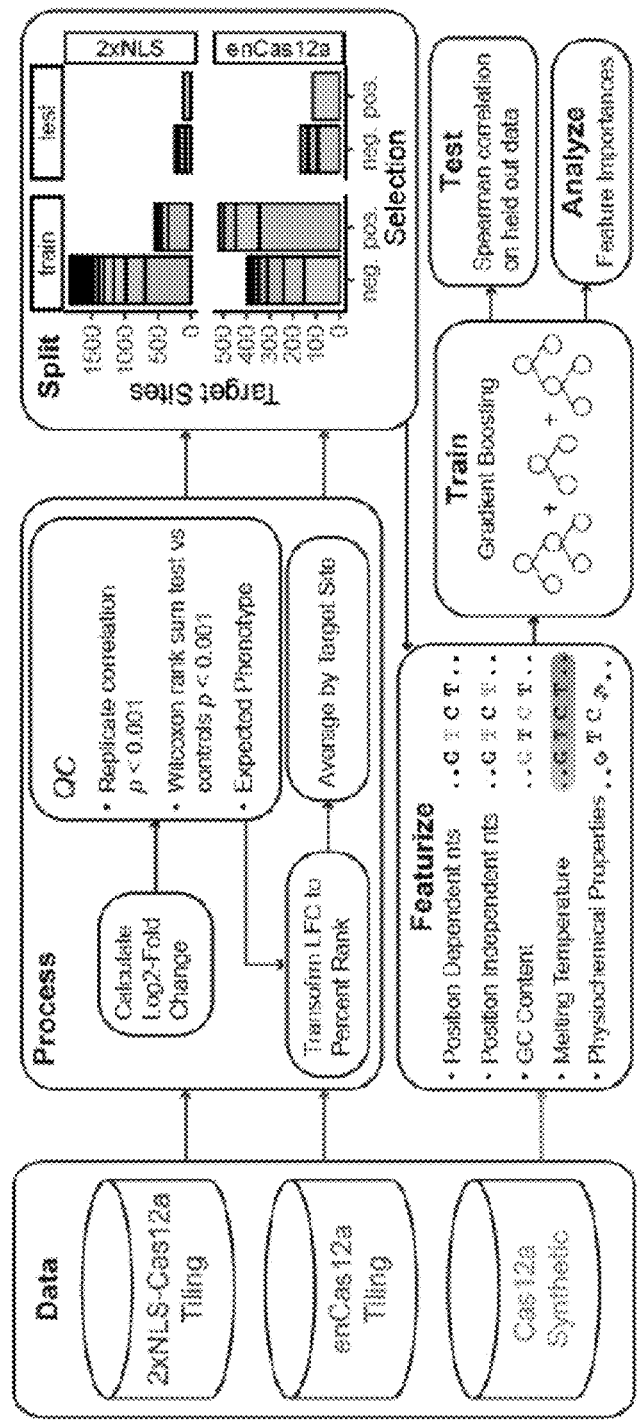

Data from the tiling screens (e.g. Example 4) were used to evaluate a published deep learning model, referred to as Seq-DeepCpf1 (Kim et al. Nat. Biotechnol. 36:239-241 (2018)). This model was trained using 15,000 insertion and deletion (indel) frequencies, generated by integrating guides and target sequences into the same cassette and read out with deep sequencing Kim et al. Nat. Methods. 14:153-159 (2107). This model was compared to a gradient boosted (GB) model trained on the same set of indel frequencies, as well as two GB models trained on 2×NLS-Cas12a and enCas12a tiling data (FIG. 18A). The GB models were fit using the same framework that we used for Cas9 ruleset development (Najm et al. Nat. Biotechnol. 36:179 (2017) and Doench et al. 34: 184-191), and held out a test set for all three sources of data (FIG. 23A). For each test set we evaluated guides targeting TTTN and TTTV PAMs separately, due to the relatively low activity of TTTT PAM targets. It was observed that Seq-DeepCpf1 performed well across test sets (FIG. 18B). Further, the GB model trained on the indel frequencies performed similarly to Seq-DeepCpf1, illustrating the high quality of this training dataset. It was observed that Seq-DeepCpf1 and the 2×NLS-Cas12a GB model made similar predictions on the 2×NLS-Cas12a test set (FIG. 18C), despite using orthogonal training data, suggesting that these models learned similar guide features. These results confirm the performance and generalizability of Seq-DeepCpf1.

Figure 23B:
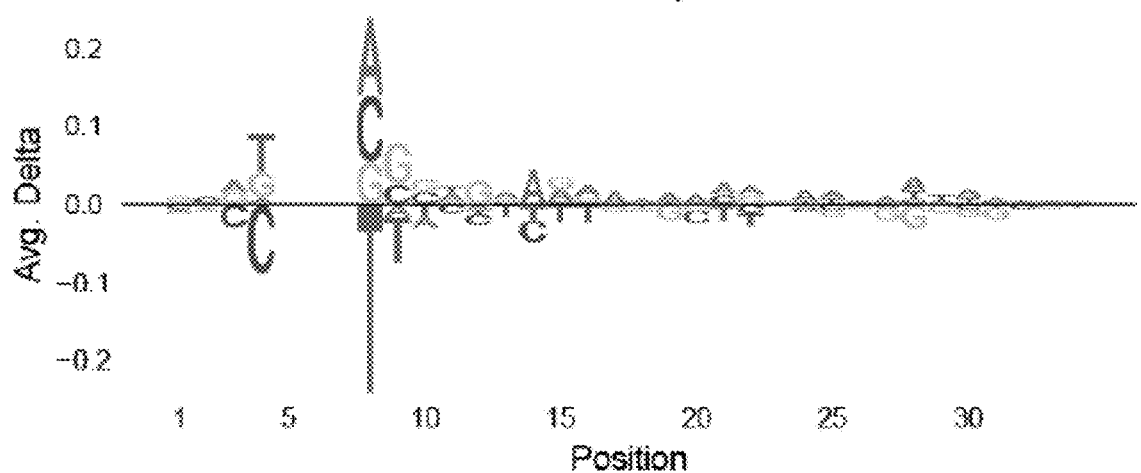
Figure 23C:
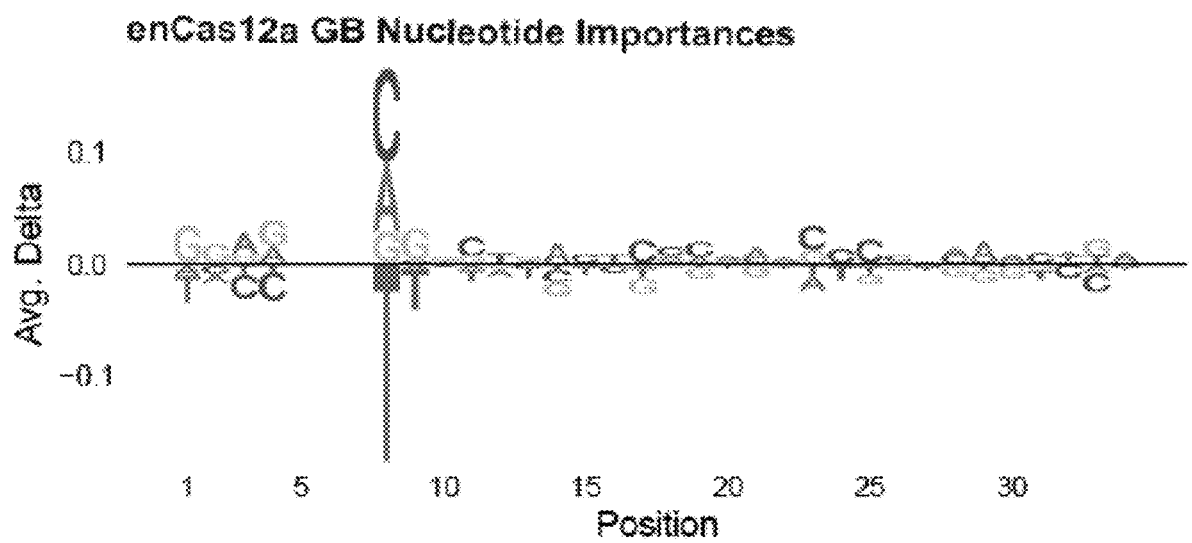
Figure 23D:
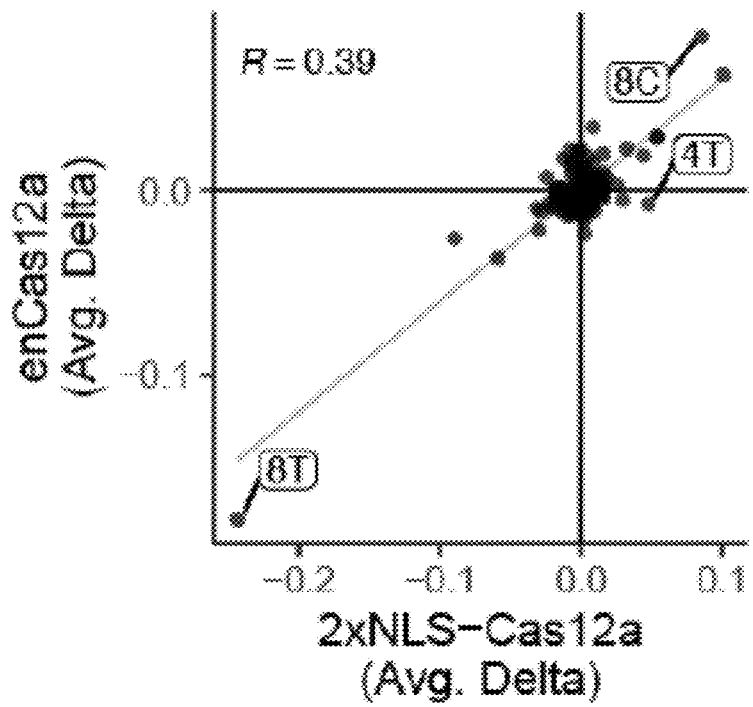

To determine if the underlying nucleotide preferences for 2×NLS-Cas12a and enCas12a were similar, the learned nucleotide importances of the two GB models were compared using in-silico saliency analysis (Koo and Eddy. Representation Learning of Genomic Sequence Motifs with Convolutional Neural Networks. BbioRxiv 362756 (2019). Doi:10.1101/362756) (see also methods for this Example). The models agreed on the most extreme features (FIG. 23B), but also showed some variation for smaller features (FIGS. 23C-23D) suggesting that the underlying affinities for the two AsCas12a variants are similar but not identical. This means that a model trained with wildtype AsCas12a data can reliably identify the most important nucleotide features for enCas12a as well. Thus, Seq-DeepCpf1 was used to generate on-target scores for 2×NLS-Cas12a and enCas12a moving forward.

Figure 24:
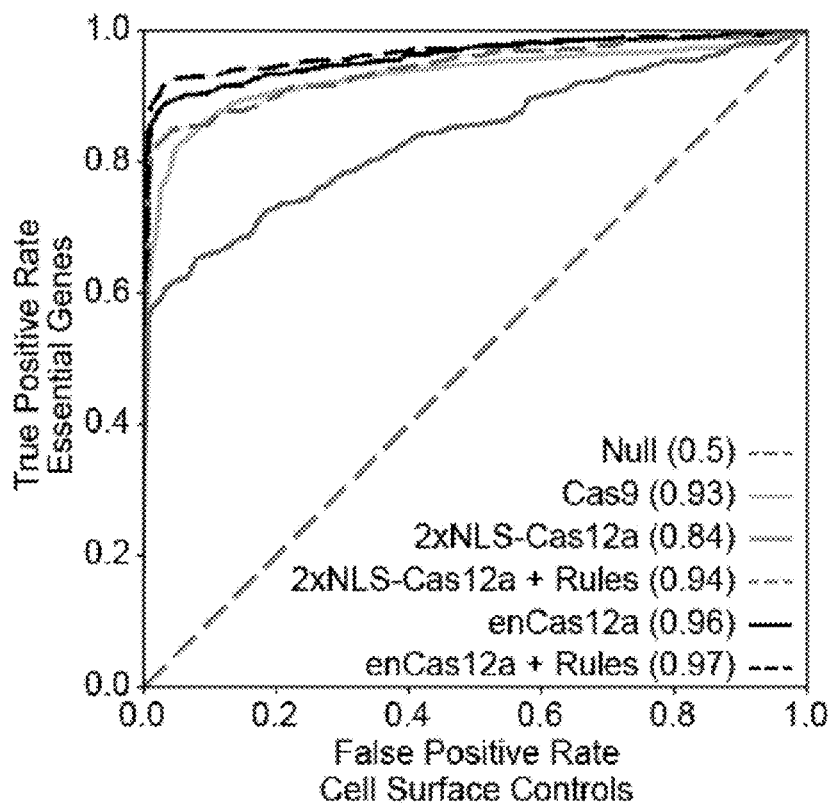
FIG. 24—Precision recall curves between essential and cell surface control guides for AsCas12a constructs and SpCas9. Solid lines are the same as in FIG. 17C; dashed lines indicate filtering the data for the top half of guides as scored by Seq-DeepCpf1. An area under the curve for each condition is noted in parentheses.

To understand how to best use Seq-DeepCpf1 scores to select active guides, we focused on guides targeting essential genes in the tiling library. As expected, when we binned guides by Seq-DeepCpf1 score we saw agreement between predicted quartiles and observed activity for both 2×NLS-Cas12a and enCas12a (FIG. 18D). Using the $5^{th}$ percentile of cell surface control guides as an activity cutoff, we saw 92% and 94% of guides were active for 2×NLS-Cas12a and enCas12a in the quartile with the highest prediction scores, compared with 47% and 80% for all guides, respectively. Furthermore, when we selected the top half of essential and non-essential guides by Seq-DeepCpf1 score from the 2×-NLS and enCas12a tiling screens we saw the AUC increase to 0.94 and 0.97, respectively (FIG. 24). Thus, applying Seq-DeepCpf1 scores increased the efficacy of guides for both constructs.

Figures 25A, 25B, 25C:
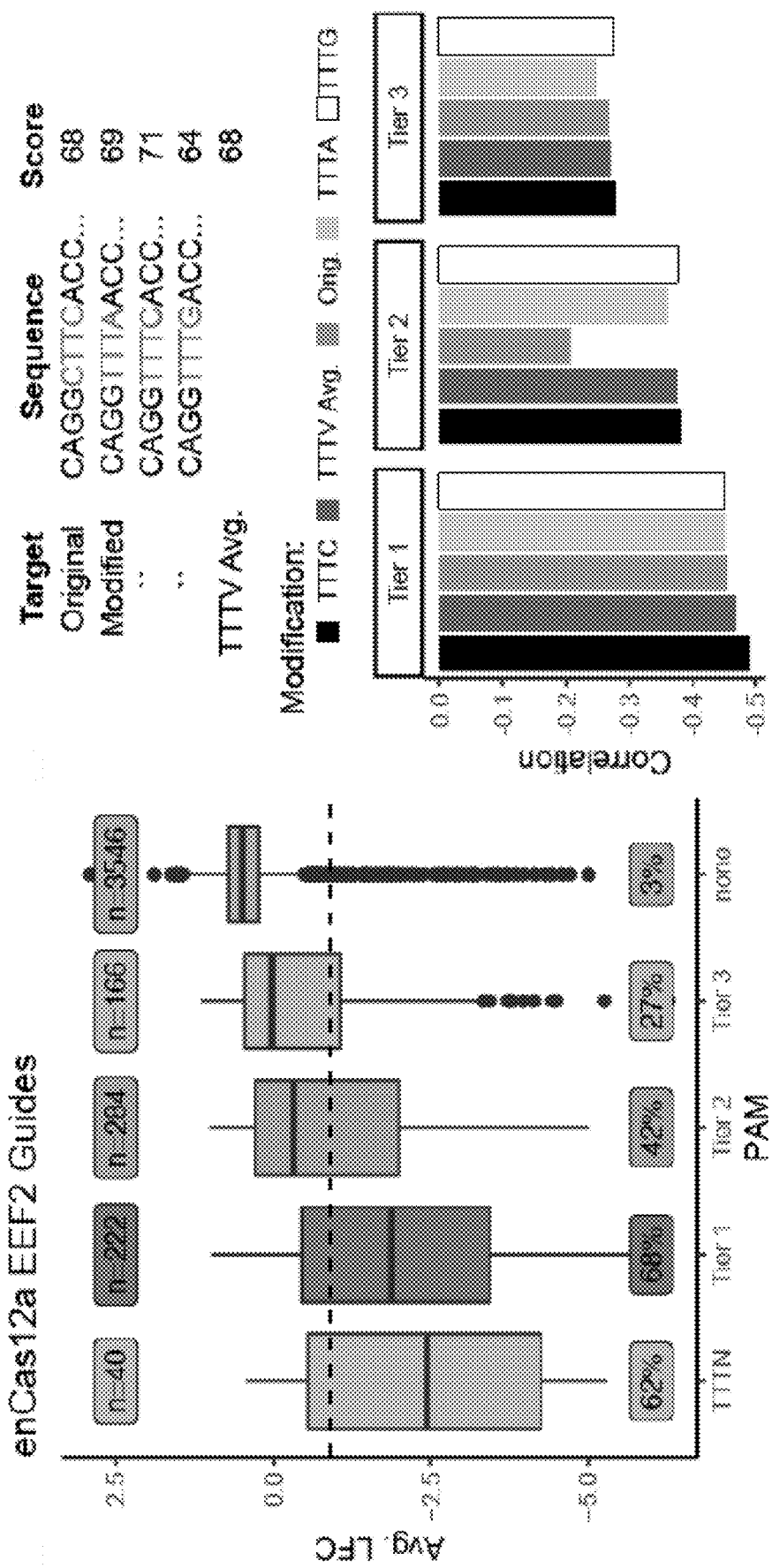

One major advantage of enCas12a is its ability to target a broader range of PAM sites, as the PAM for wildtype AsCas12a, TTTV, will occur only once every 96 nts on average, compared to NGG for SpCas9, which will occur once every 8 nts. The expanded PAMs of enCas12a were originally classified into three tiers (Kleinstiver et al. Nat. Biotechnol. (2019). Doi:10.1038/s41587-018-0011-0), with the first being the most active. To evaluate these alternative PAMs the set of EEF2 guides in the tiling library that targeted non-canonical PAMs (non-TTTN) were focused on. These controls covered 249 out of 264 possible PAMs with at least one guide. In agreement with previous results, we saw a relationship between the assigned tier and the measured activity (FIG. 25A). Notably, the guides targeting TTTN (62% active) showed similar efficacy to the other tier 1 PAMs (68% active).

Figure 25D:
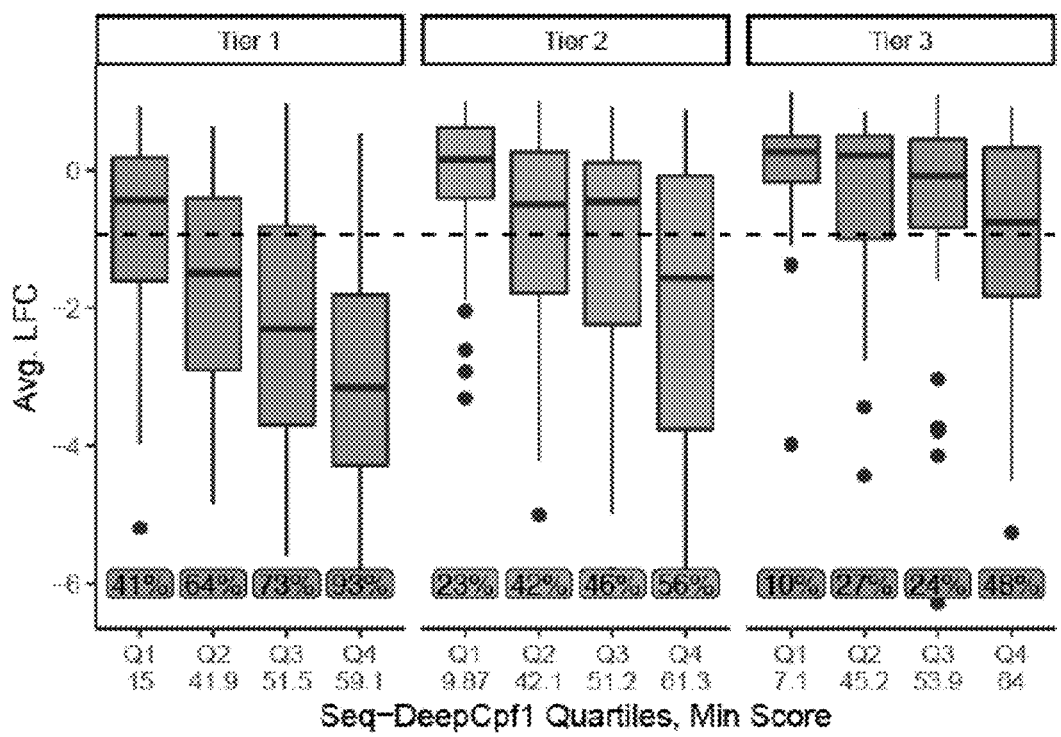
Figure 25E:
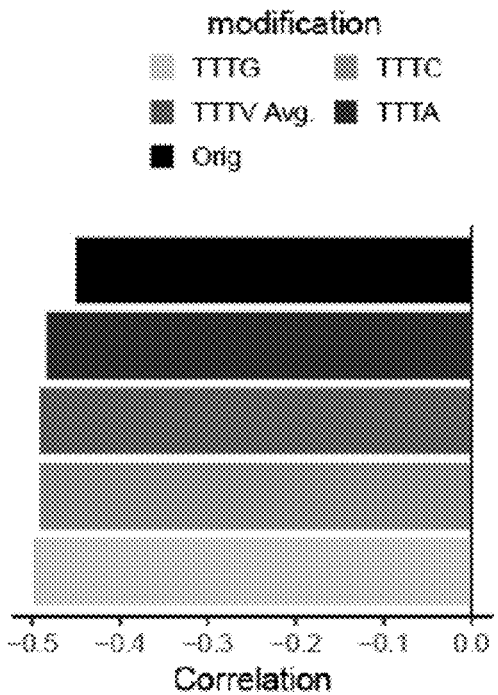

Because none of these alternative PAMs were included in the training set for Seq-DeepCpf1, it was reasoned that on-target activity predictions would be hindered if the model were provided with a non-TTTN PAM. Target sequences were modified in silico to include a canonical PAM to improve on-target prediction (FIG. 25B). It was observed that substituting TTTC for the actual, non-canonical PAM improved on-target predictions when compared to unaltered sequences for all three PAM tiers (FIG. 25C), identifying highly active guides targeting non-canonical PAMs (FIG. 25D). For the quartile of guides that had the highest Seq-DeepCpf1 scores, we saw that 93% of non-canonical tier 1 guides were active, which is comparable to the activity of guides targeting canonical PAMs. Since enCas12a also had increased activity at TTTT PAM sites, we performed a similar analysis focusing on essential guides targeting this PAM. We found that predictions also improved by in silico modification of the PAM (FIG. 25E). Thus, at least until more data can be acquired to properly train an activity model for enCas12a at non-canonical PAMs, modification of the input sequence to Seq-DeepCpf1 can be useful for selecting active guides. The ability to select active guides from the expanded set of Tier 1 PAMs increases the frequency of targetable sites to approximately once every 7 nts, an important criterion for broad utility of AsCas12a.

Example 6—Off-Target Predictions for Cas12a

Figure 19A:
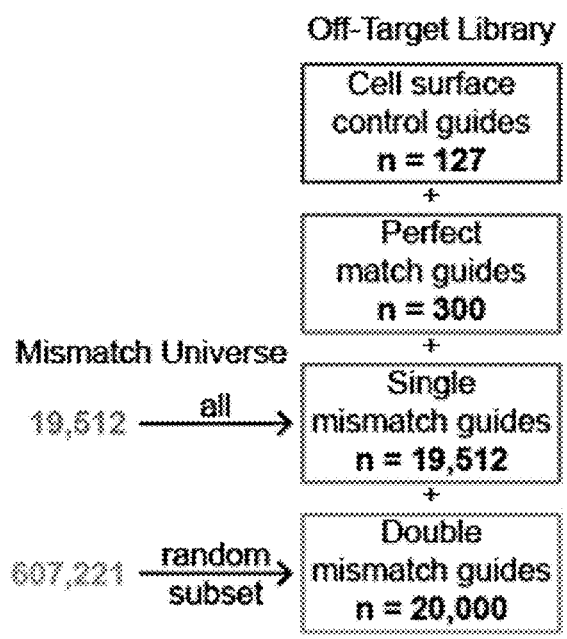
Figure 19B:
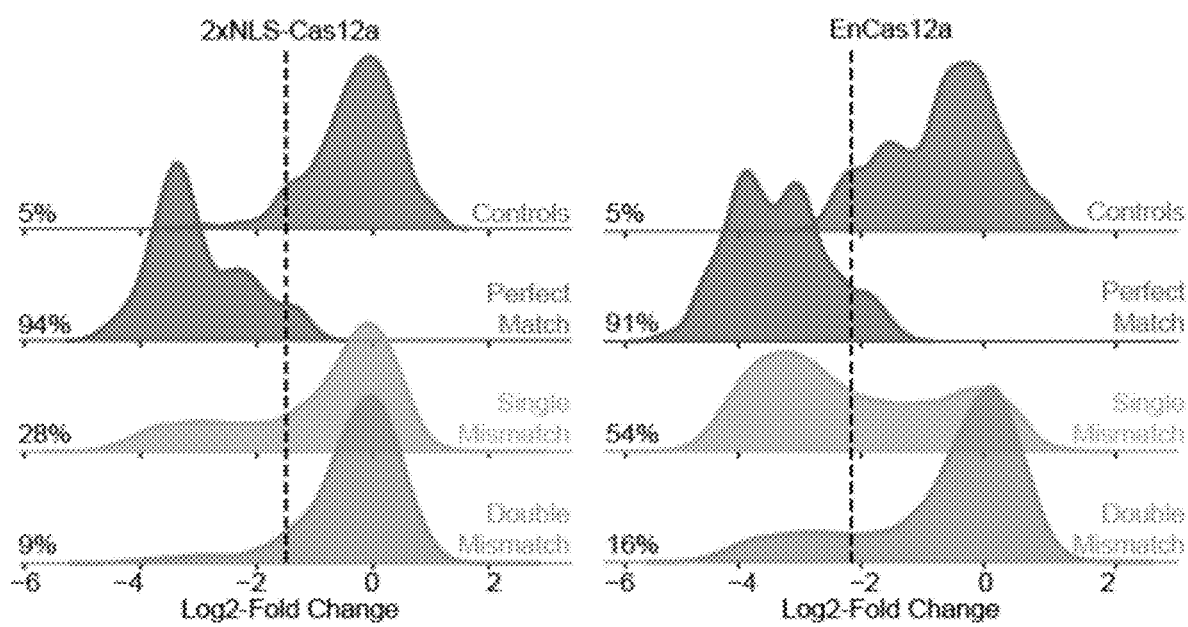

In order to assess the off-target tolerance of AsCas12a, a library of guides intentionally mismatched to their target was constructed. 300 of the most active guides were selected from the viability, vemurafenib, and 6-thioguanine screens with the tiling library (FIG. 34) in both A375 and Meljuso. Every possible single and double nucleotide mismatch for these guides were designed, and selected a random subset of the latter, resulting in a library with 300 perfect match guides, 19,512 single mismatch guides, 20,000 double mismatch guides, and finally 217 guides targeting cell surface genes as a set of negative controls (FIG. 19A). Screens were performed in duplicate in A375 cells with dropout, vemurafenib, and 6-thioguanine arms in cells stably expressing 2×NLS-Cas12a and enCas12a. In order to determine the fraction of guides that were active in this library we mapped the distribution of guides targeting essential genes in dropout assays and set an activity cutoff at the $5^{th}$ percentile of controls (FIG. 19B). The perfect match guides were observed to be highly active for both constructs, with 94% and 91% of guides scoring as active with 2×NLS-Cas12a and enCas12a, respectively. It was observed that enCas12a showed a higher tolerance for mismatches, with 54% and 16% of guides active for single and double mismatch guides respectively, compared with 28% and 9% for 2×NLS-Cas12a. Thus, enCas12a shows more propensity for off-target activity, as initially described (Kleinstiver et al. Nat. Biotechnol. 36:324-327 (2018)).

Figure 26A:
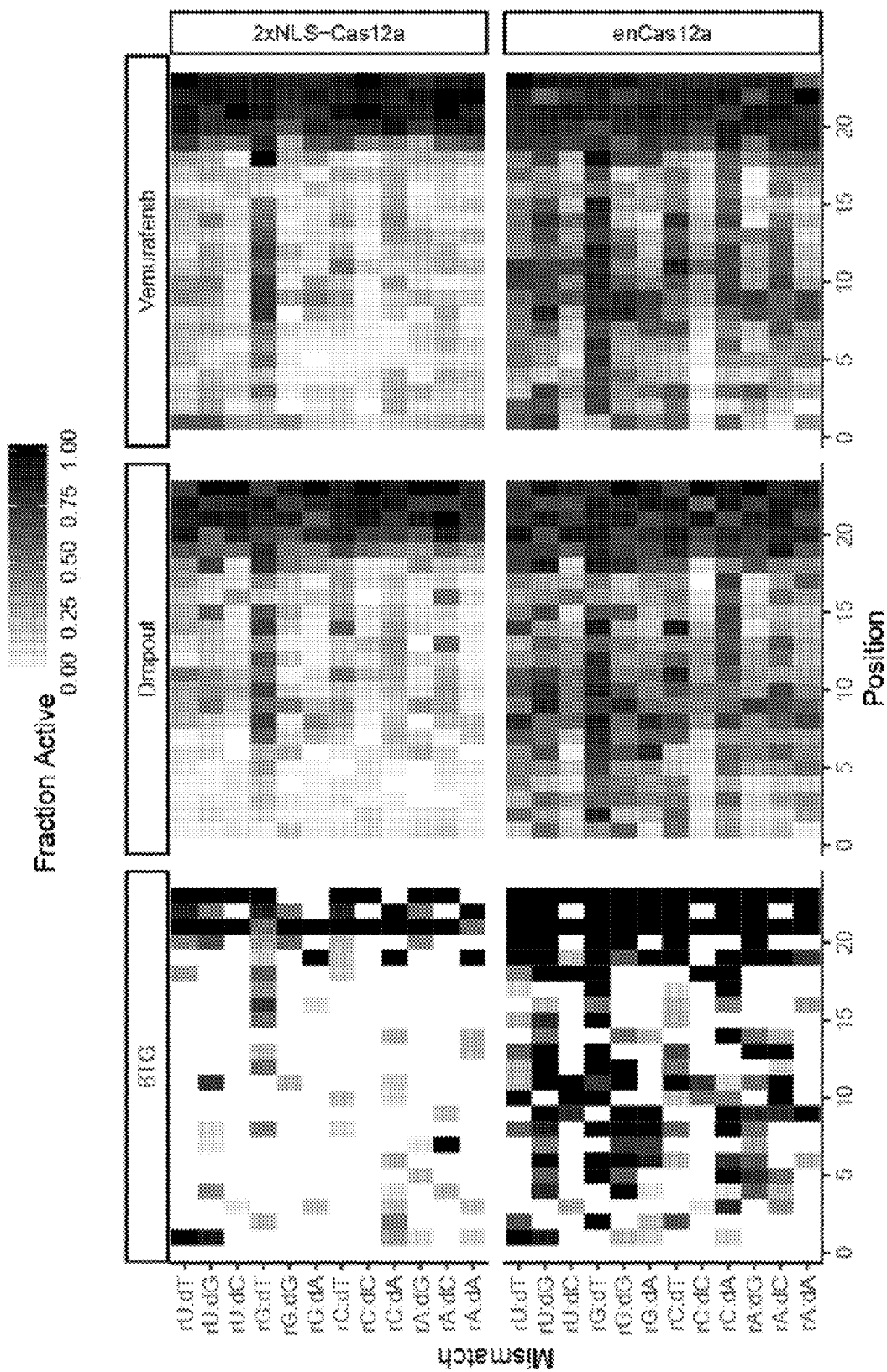

The single mismatch data was profiled to understand the off-target activity of each construct. Similar to the activity cutoff we set for essential genes, we used the $95^{th}$ percentile of controls as an activity cutoff for the positive selection assays. The fraction of active guides for each mismatch type and position were calculated to generate a cutting frequency determination (CFD) matrix, as was done previously with SpCas9 (Doench et al. Nat. Biotechnol. 34: 184-191 (2016)). These matrices were similar across experimental conditions (FIG. 26A), so the data was merged to create a single CFD matrix for each Cas12a (FIG. 19C). When the CFD values for 2×-NLS-Cas12a and enCas12a were compared, a monotonic relationship was observed (FIG. 26B), indicating similar specificity preferences. For both constructs a higher tolerance for mismatches at the PAM distal end of the guide was observed, as well as for rG:dT mismatches, which are two trends observed previously with other techniques to examine off-target activity of Cas12a enzyme (Kleinstiver et al. Nat. Biotechnol. 34: 869-874 (2016) and Kim et al. Nat. Biotechnol. 34: 863-868 (2016)) and that have also been seen with SpCas9 (Doench et al. Nat. Biotechnol. 34:184-191 (2016) and Hsu et al. Nat. Biotechnol. 31:827-832 (2013)). Reads from mismatch libraries for off target effects of 2×NLS-Cas12a and enCas12a are shown in Supplementary Data 2 as set forth in Sanson et al. "Optimization of AsCas12a for combinatorial genetic screens in human cells" bioRxiv, Aug. 28, 2019 doi:http//dx.doi.org/10.1101/747170, which is incorporated herein by reference as if expressed in its entirety herein.

To compare CFD matrices between the two AsCas12a constructs and SpCas9, we used data from our previously published SpCas9 CFD matrix (Doench et al. Nat. Biotechnol. 34:184-191 (2016)). Since SpCas9 guides are designed as 20mers, the 20 most PAM-proximal nucleotides of AsCas12a guides were focused on. Each mismatch and position was ranked by activity and it was observed that SpCas9 and enCas12a had similar activity levels across their profiles, whereas 2×NLS-Cas12a was the least promiscuous (FIG. 19D), consistent with previous examinations of the specificity of Cas12a enzymes by orthogonal techniques (Kleinstiver et al. Nat. Biotechnol. 36:324-327 (2018)). Thus, although enCas12a is more promiscuous than 2×NLS-Cas12a, its specificity is comparable to that of SpCas9, suggesting it is suitable for genetic screens.

Finally, the CFD matrix was used to predict the activity of double mismatch guides. To do this, a CFD score was calculated as the product of the activities of each individual mismatch, an approach that has also been used by others to identify problematic off-target sites with more than one mismatch for SpCas9 (Tycko et al. bioRxiv 520569 (2019) doi: 10.1101/520569 and Perez et al. Nat. Biotechnol. 35:347 (2017)). To evaluate this model, double mismatch guides targeting essential genes were binned into predicted quartiles and plotted the distribution of measured $\log_2$-fold-change values in the dropout screens (FIG. 19E). More activity from guides with a larger CFD score was observed, indicating that this model can help identify problematic multi-mismatch off-target sites when designing guides. Notably, the largest portion of double mismatch guides fell into the lowest quartile of CFD scores (FIG. 19E), which indicates that consideration of off-target activities does not overly restrict the set of guide RNAs available to target a gene of interest.

While the CFD score is an important tool, it is noted that the largest portion double mismatch guides fall into the lowest tier of CFD scores (n=x for 2×NLS-Cas12a and n=y for enCas12a) indicating that off-target activities do not prohibit effective guide design. The same trends were observed with guides targeting vemurafenib resistance genes and HPRT1 in positive selection assays.

Example 7—Testing Variants of the Direct Repeat to Enable Efficient Multiplexing Recombination of the constant regions has been a widely reported roadblock when delivering two guides for double knockout in Cas9 studies (Najm, F. J. et al. Orthologous CRISPR-Cas9 enzymes for combinatorial genetic screens. Nat. Biotechnol. 36, 179 (2017) and Adamson, B. et al. A Multiplexed Single-Cell CRISPR Screening Platform Enables Systematic Dissection of the Unfolded Protein Response. Cell 167, 1867-1882.e21 (2016)). In order to multiplex effectively with Cas12a one must deliver multiple constant regions, also known as direct repeats (DRs) within a single array, separated only by the 20-23 nucleotide guide sequence. When working with lentivirus, recombination of repetitive elements and shuffling of vectors at sites of homology can be a technical hurdle (Adamson et. al. Cell. 167:1867-1882.e21 (2016), Hill et al. Nat. Methods 15: 271-274 (2018), Najm et al. Nat. Biotechnol. 36: 179 (2017), and Hanna and Doench. Nat. Biotechnol. 36: 802-804 (2018)).

This Example can demonstrate the design and generation of variants of the DR sequence that can enable effective multiplexing, but that can also be less prone to potential recombination such as that undergone by lentivirus. Briefly, a library of 35,682 alternative DRs with up to 3 variable base pairs in the stem and 3 variable nucleotides in the single-stranded or loop regions. Two variations of control sequences were also included: random sequences of 20 nucleotides; and transcription termination sequences, with a run of 6 thymidines in the middle of the sequence that terminates transcription early.

To assay the efficacy of these DRs in a negative selection screen and to quantify multiplexing activity of direct repeats, guides targeting BCL2L1 and MCL1 were used, which are a known synthetically lethal pair (Najm, F. J. et al. Orthologous CRISPR-Cas9 enzymes for combinatorial genetic screens. Nat. Biotechnol. 36, 179 (2017), Han, K. et al. Synergistic drug combinations for cancer identified in a CRISPR screen for pairwise genetic interactions. Nat. Biotechnol. 35, 463-474 (2017), and van Delft, M. F. et al. Cancer Cell. 10: 389-399 (2006). This way the only effective use of both guide RNAs in the same cell should induce cell death. The BH3 mimetic ABT-737 targets selective Bcl-2 proteins and efficiently induces apoptosis via Bak/Bax if Mcl-1 is neutralized. van Delft, M. F. et al Cancer Cell 10, 389-399 (2006)).

Figure 14A:
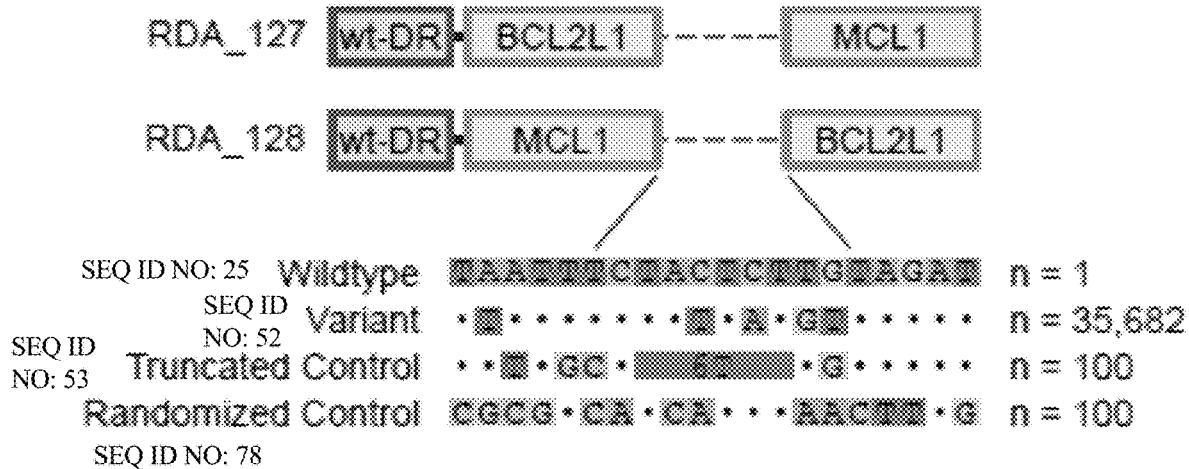
FIGS. 14A-14E—FIG. 14A depicts maps of vectors used to quantify multiplexing activity of exemplary direct repeats. (SEQ ID NOs: 52, 53 and 78)
Figure 14B:
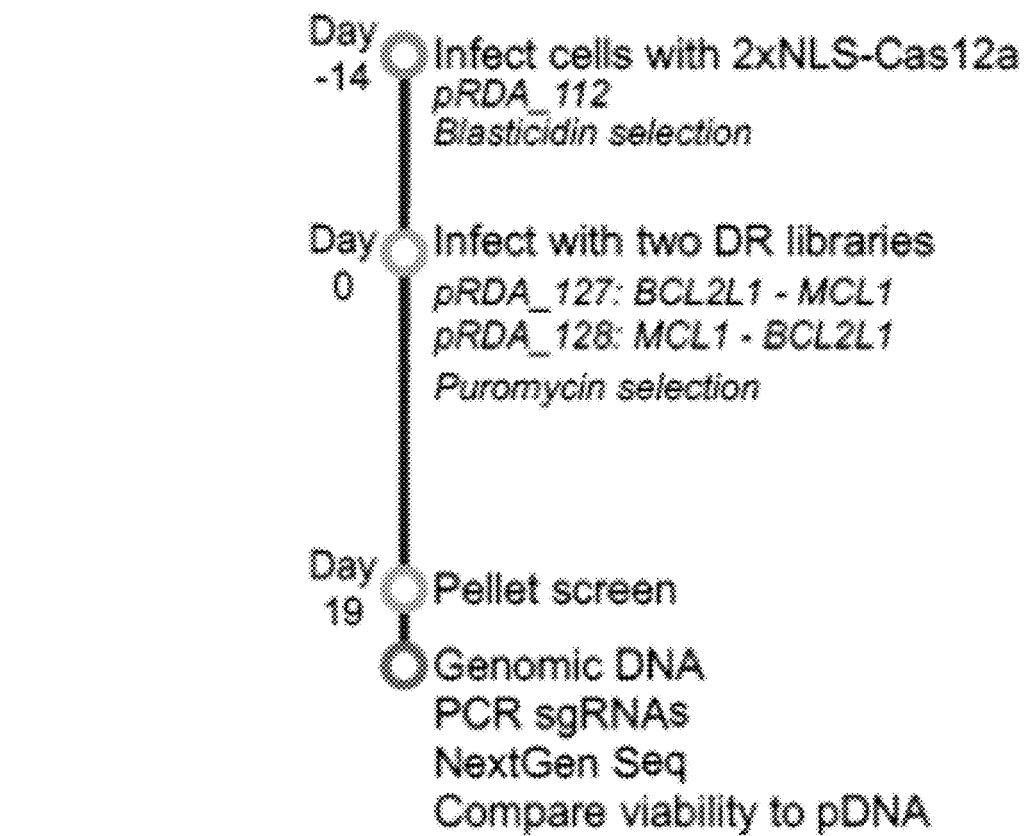
Figure 14C:
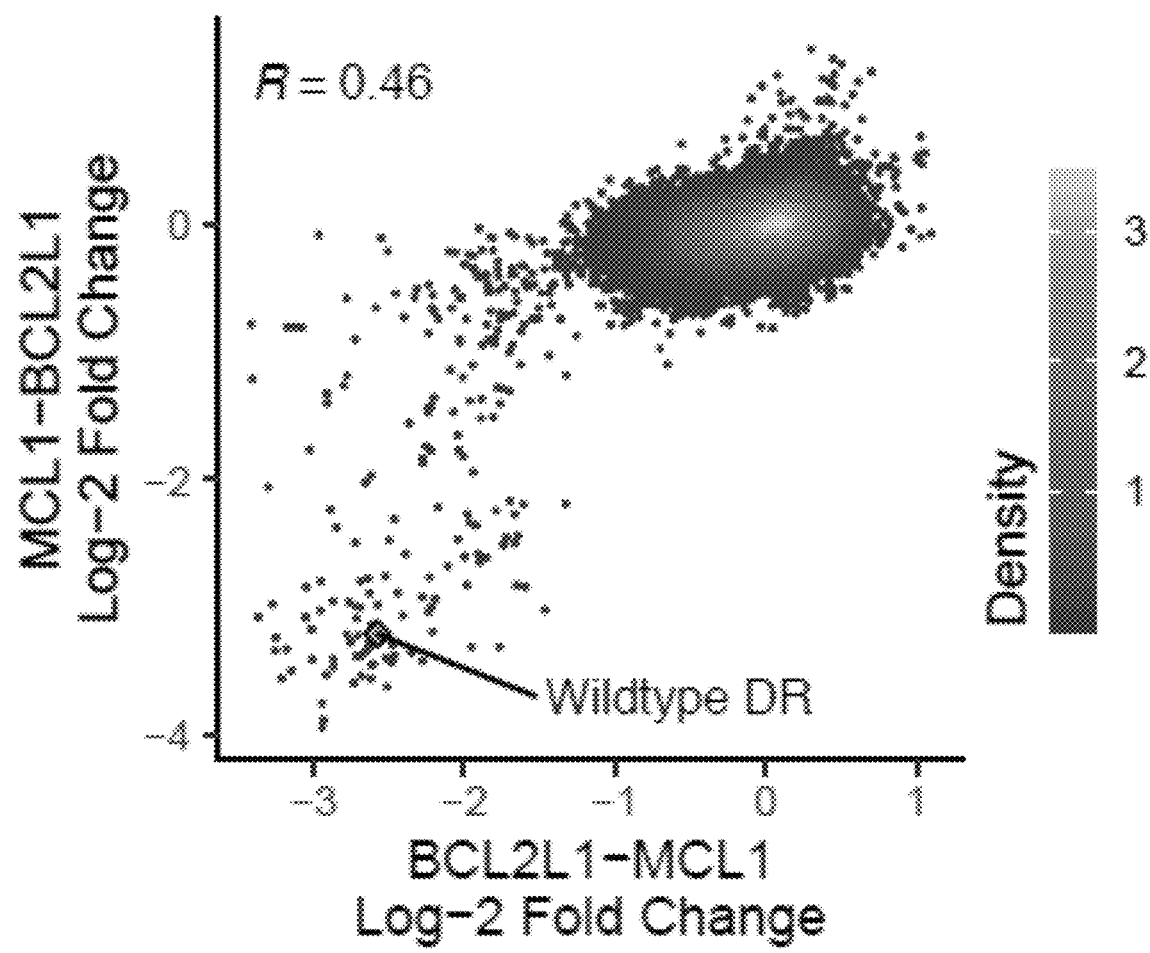
Figure 27D:
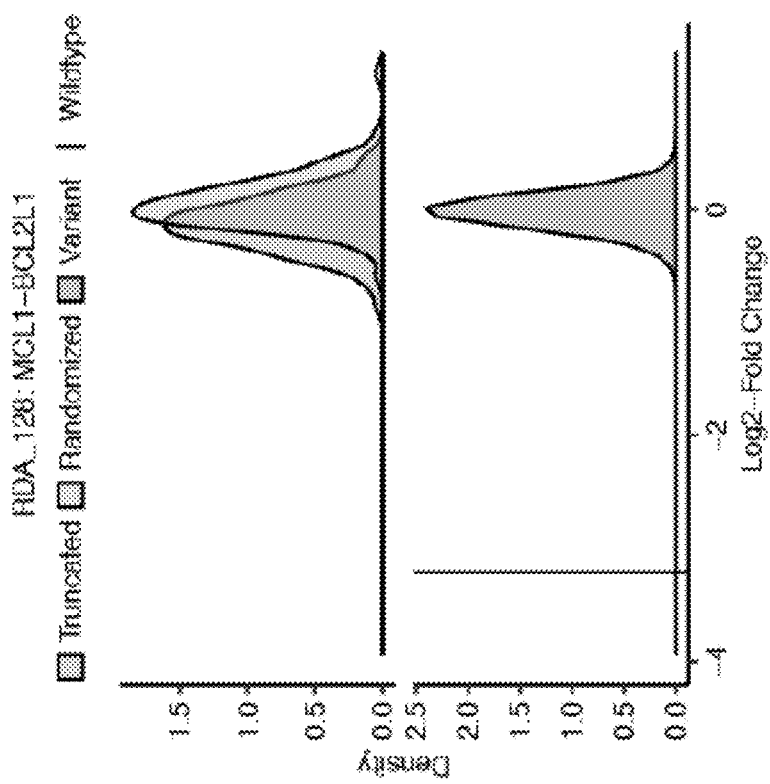
Figure 27C:
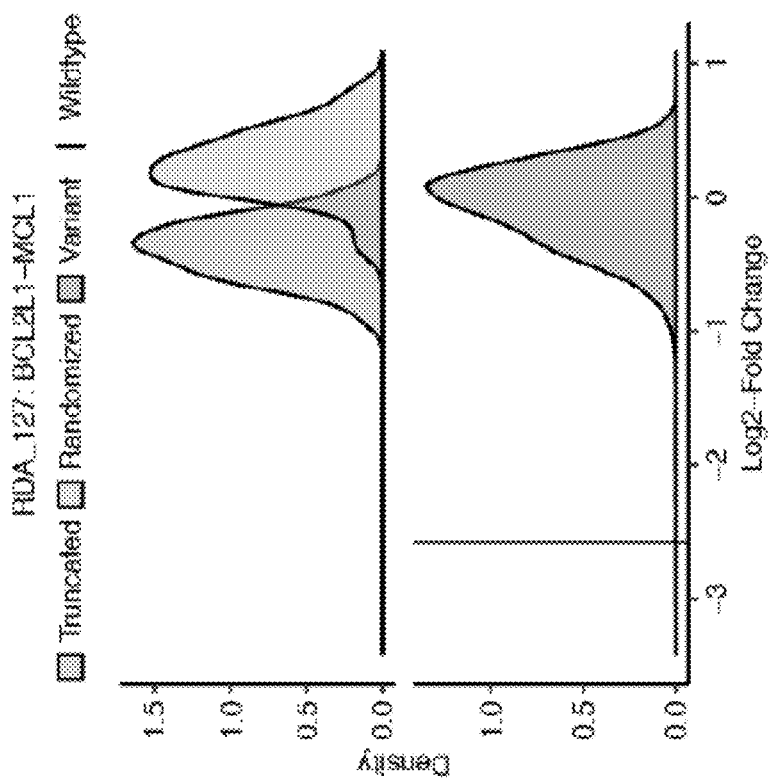

The library of DR sequences were cloned into two different vectors, pRDA_127, which has a BCL2L1 guide in position 1 and an MCL1 guide in position 2 and the reverse orientation for the other vector (FIG. 14A). The DR libraries were generated in 2×NLS-Cas12a expressing Melijuso cells using a blasticidin resistance cassette, and then transduced both sets of libraries were transduced and selected using puromycin, and kept in culture for 19 days (FIG. 14B). Genomic DNA was harvested, inserts were PCR-amplified, and the DR sequences were quantitated (FIG. 14B). Both RDA_127 and RDA_128 showed strong reproducibility across replicates (FIGS. 27A-27B) with Pearson correlations of 0.73 and 0.56, respectively between replicates HPRT1. Because loss of BCL2L1 has a slight growth effect on its own (Najm et al. Nat. Biotecnol. 36:1179 (2017)), a shift was observed in the control DR sequences that had a BCL2L1 guide in the first position followed by a truncated sequence, compared with an MCL1 guide in the first position (FIGS. 27C-27D). Arrays that had a BCL2L1 guide in the first position followed by a truncated sequence appeared to be more depleted than the same set of truncated sequences with an MCL1 guide in the first position. From the 35,682 variants tested, 73 sequences were identified that had a $\log_2$-fold change less than 3 standard deviations from the wildtype sequence with both guide orientations. Of the 73 hits, 38 outperformed the wildtype by Avg. LFC (FIG. 14C). Reads from the assays to identify DR sequences are shown in Supplementary Data 3 as set forth in Sanson et al. "Optimization of AsCas12a for combinatorial genetic screens in human cells" bioRxiv, Aug. 28, 2019 doi:http//dx.doi.org/10.1101/747170, which is incorporated herein by reference as if expressed in its entirety herein.

Figure 14D:
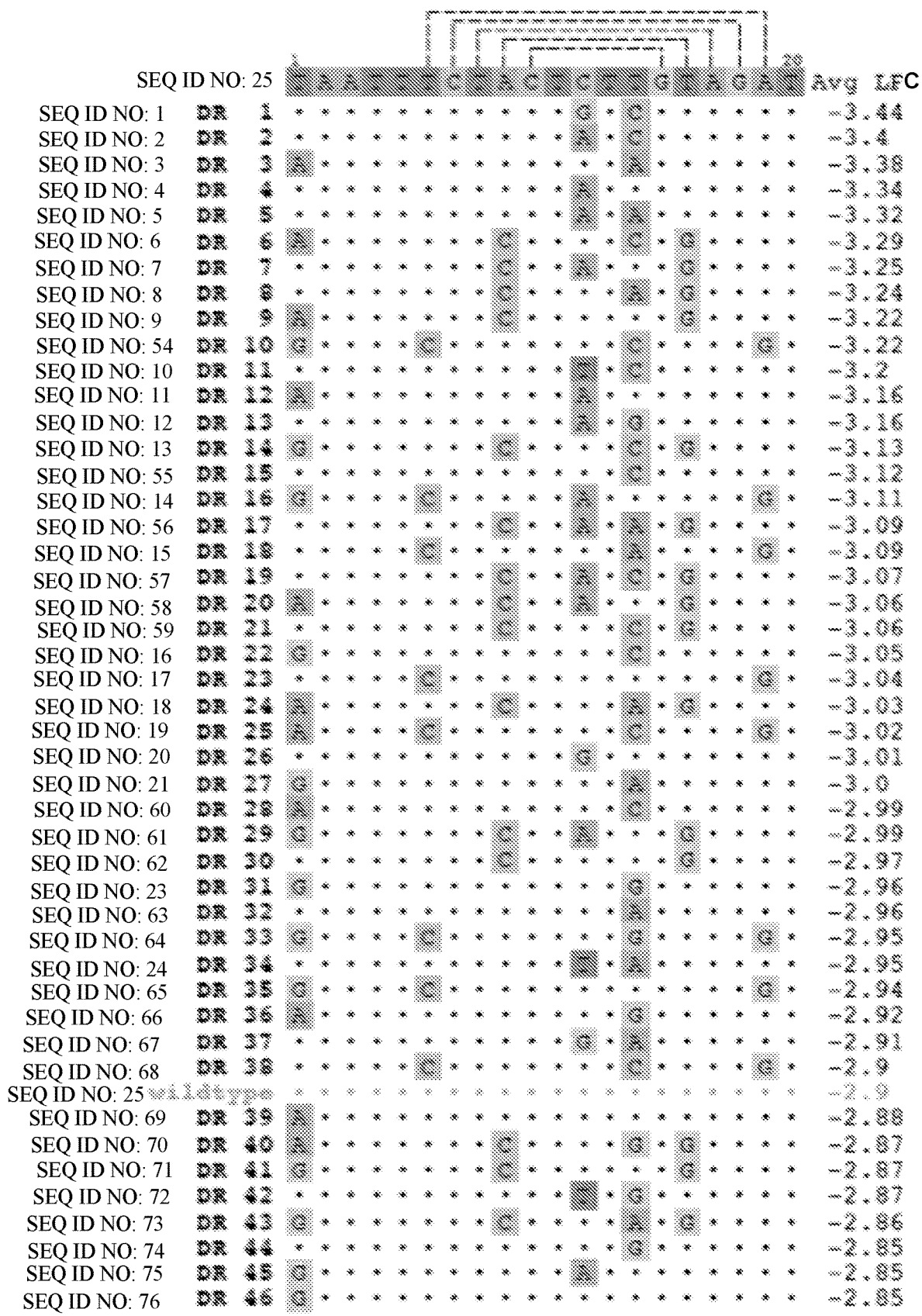
Figures 14E, 15A:
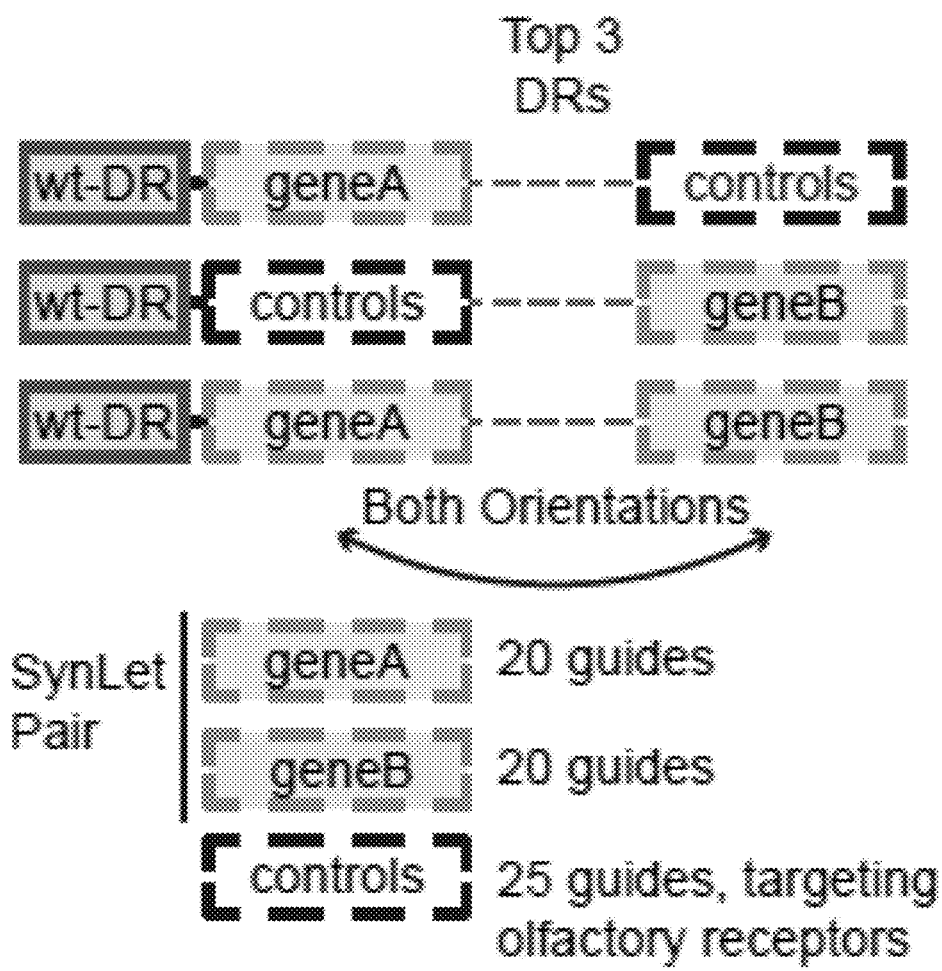
FIGS. 15A-15D—(FIG. 15A) a map of constructs used in a library targeting synthetically lethal (SynLet) gene pairs to assess the multiplexing activity of an exemplary Cas12a, (FIG. 15B) depicts exemplary LFC results in OVCAR8 cells, (FIG. 15C) depicts observed LFC results in OVCAR8s for all direct repeats, and (FIG. 15D) depicts residual results from A375 and OVCAR8 cells. (SEQ ID NOs: 54-76)

Examining these active DR variants, clear sequence preferences were observed (FIG. 14D). First, several single-stranded positions were intolerant of any changes, whereas others tolerated certain nucleotide substitutions. For example, position 1 tolerated A or G but not C, whereas active constructs were observed with all nucleotides at position 12 and 14 in the loop. (FIG. 14D). While the majority of nucleotides of this subset were consistent with the wildtype, some flexibility in the loop structure and, to a lesser extent in the stem, was observed (FIG. 14E). This observed tolerance in the $12^{th}$ position of the loop interestingly agrees with alignment of direct repeats of Cas12a orthologs (Teng, F. et al. Enhanced mammalian genome editing by new Cas12a orthologs with optimized crRNA scaffolds. Genome Biol. 20, 15 (2019)). All recovered active sequences maintained base pairing in the stem, but base pairing alone was insufficient for activity, as the nucleotide sequence proved important. At the base of the stem, a T-A base pair could be replaced with a C-G base pair, but no other orientations, indicating a preference for a pyrimidine on one side and a purine on the other. Likewise, in the 4th base pair of the stem, only A-T and C-G base pairs showed activity. Other stem positions, however, did not tolerate any substitutions. Thus, this Example can at least demonstrate an identified a consensus sequence for active variant DRs (FIG. 14E), and numerous examples thereof, which should assist in the creation of multiplexed arrays to minimize repetitive sequences.

Example 8—Multiplexing to Assay Synthetic Lethal Interactions

To assess the effectiveness of multiplexing across numerous endogenous genes, a library targeting synthetically lethal (SynLet) gene pairs was designed. In this Example, the design of AsCas12a arrays can at least be demonstrated to provide significant advantages when synthesizing and sequencing DNA compared to Cas9-based approaches. For As Cas12a, a second guide needed only 43 additional nucleotides. In comparison, a second Cas9 guide cassette requires at least 346 nucleotides (FIG. 20A). Furthermore, the proximity of guides in the enCas12a construct made sequencing and downstream analyses easier.

The screen was conducted in two cell lines targeting 12 gene pairs, which have been previously identified as synthetically lethal (Najm, F. J. et al. Orthologous CRISPR-Cas9 enzymes for combinatorial genetic screens. Nat. Biotechnol. 36, 179 (2017), Han, K. et al. Synergistic drug combinations for cancer identified in a CRISPR screen for pairwise genetic interactions. Nat. Biotechnol. 35, 463-474 (2017), and Shen, J. P. et al. Combinatorial CRISPR-Cas9 screens for de novo mapping of genetic interactions. Nat. Methods 14, 573-576 (2017)). For each gene in a given pair, up to 20 guides were picked at random, 15 and 5 of which targeted TTTV and TTTT PAMs respectively (FIG. 15A). Pairs were screened in both orientations and the top three direct repeats were used. Thus, each gene pair was assessed with up to 2,400 unique constructs (20 guides×20 guides×2 orientations×3 DRs). To account for single guide effects, each guide was also paired with 25 guides targeting olfactory receptor as controls. This library was screened in both A375 and OVCAR8 cells that were engineered to express enCas12a.

Figure 28A:
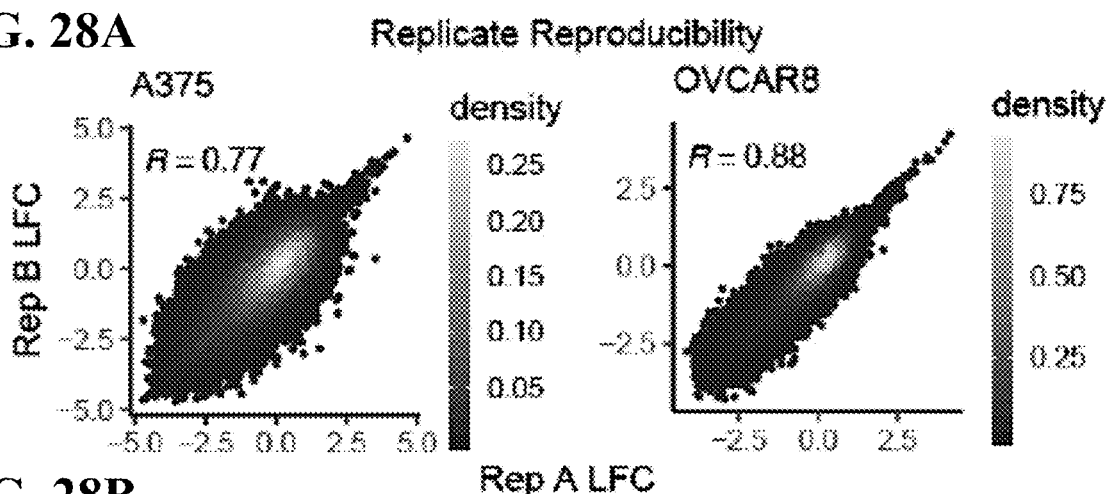
FIGS. 28A-28C—Quality control for synthetic lethality screen.
Figure 28B:
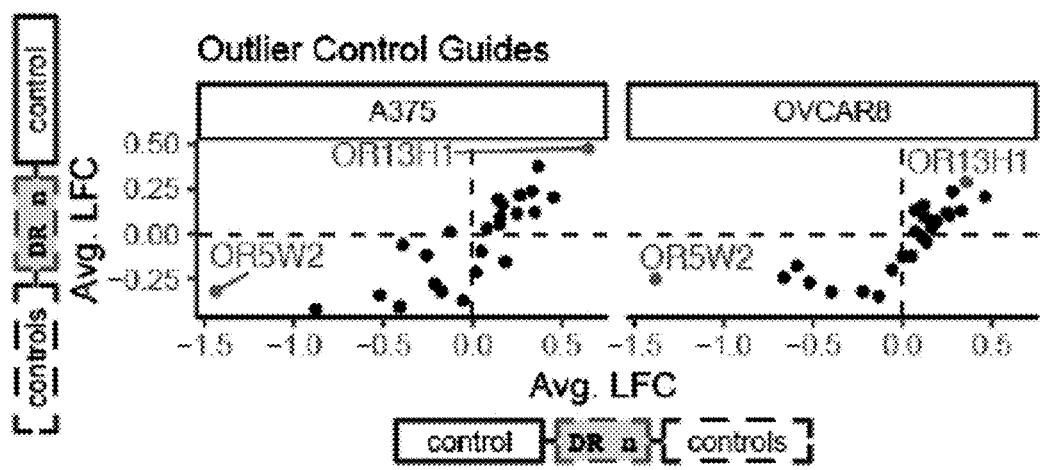
Figure 28C:
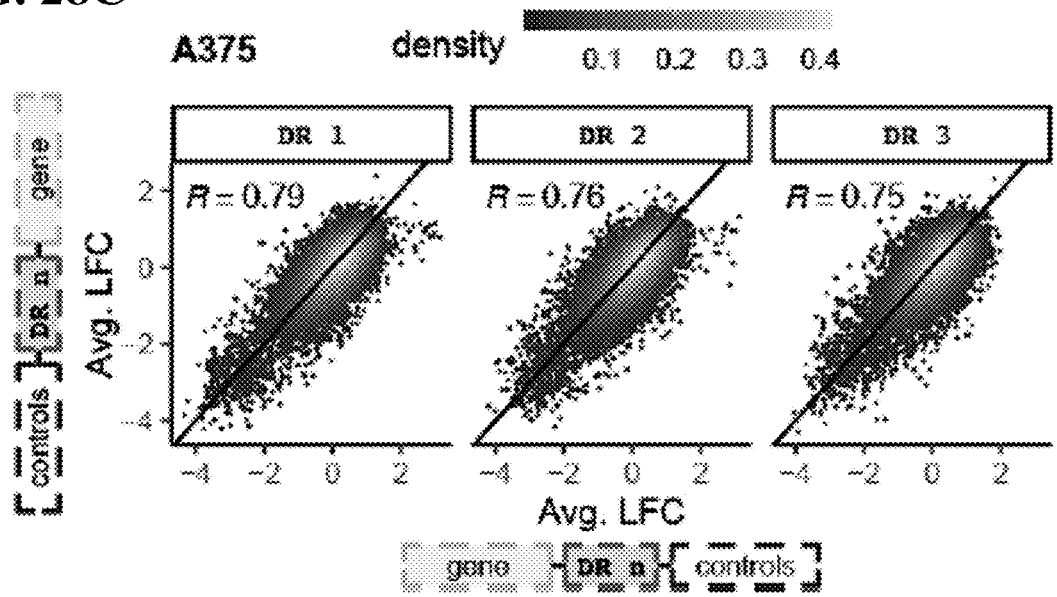

Following PCR and sequencing, the $\log_2$-fold-change (LFC) relative to pDNA was calculated. A good correlation between replicates in both cell lines was observed (FIG. 28A). For the olfactory controls, it was observed that two guides targeting OR5W2 and OR13H1 had a viability effect on their own, so these guides were removed for downstream analyses (FIG. 28B). To evaluate how position affects guide activity the average LFCs of the ordered target-control constructs was compared with the reverse orientation control-target constructs. It was observed that the LFCs of target guides in position 1 were well correlated with the LFCs in position 2 for all three DR variants in both OVCAR8 and A375 (FIGS. 20B-20C and 28C), suggesting that position has minimal effect on guide activity.

Figure 15B:
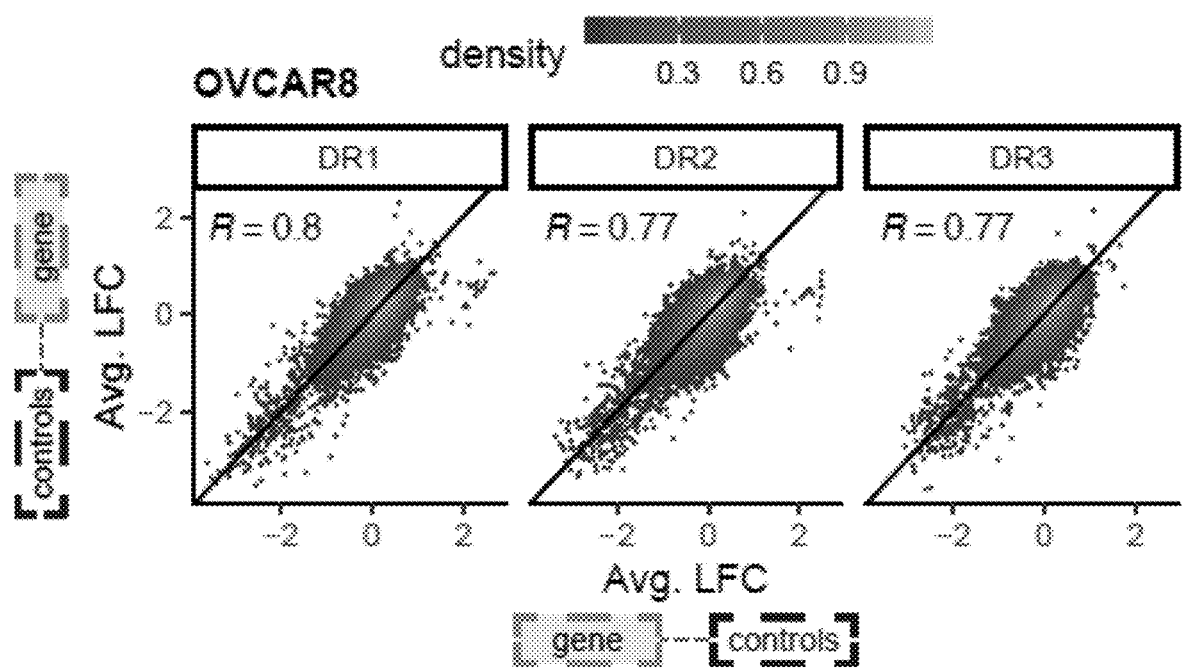
Figure 15C:
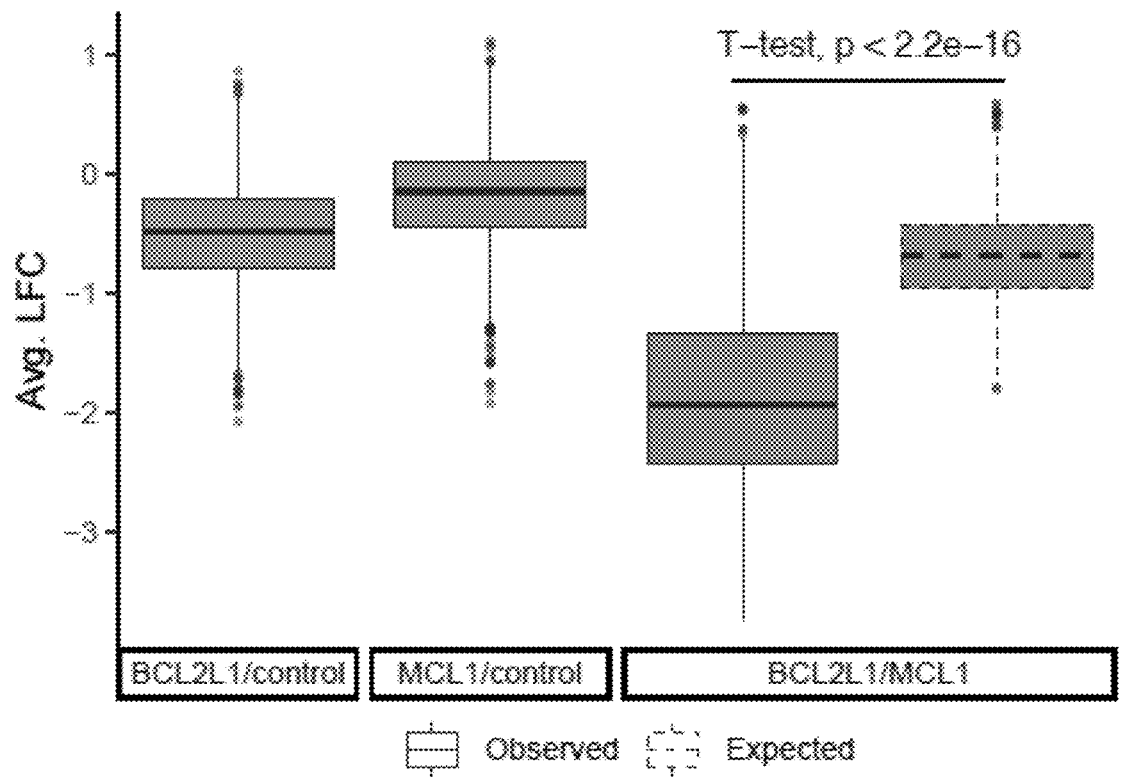
Figure 15D:
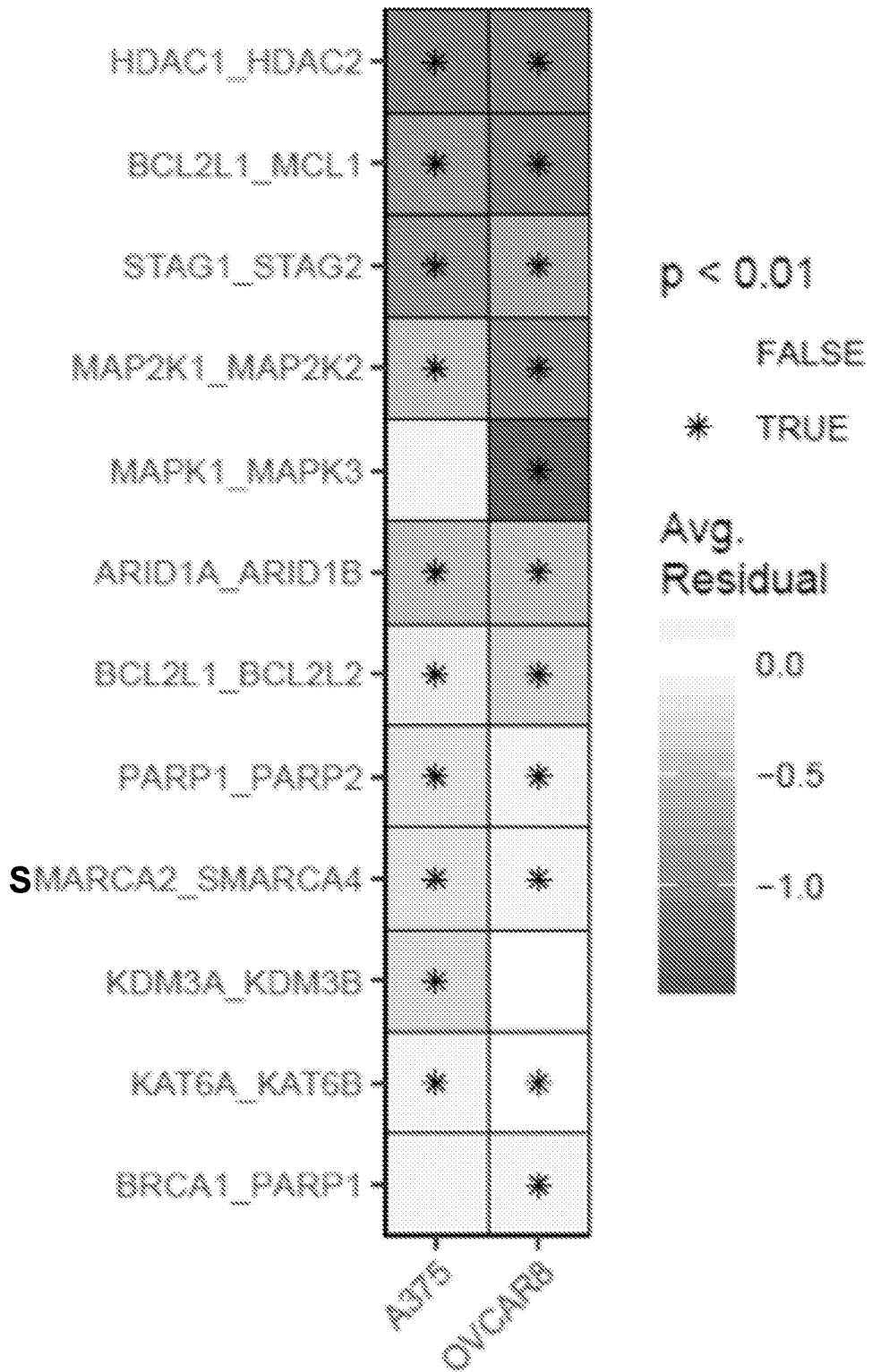
Figure 16:
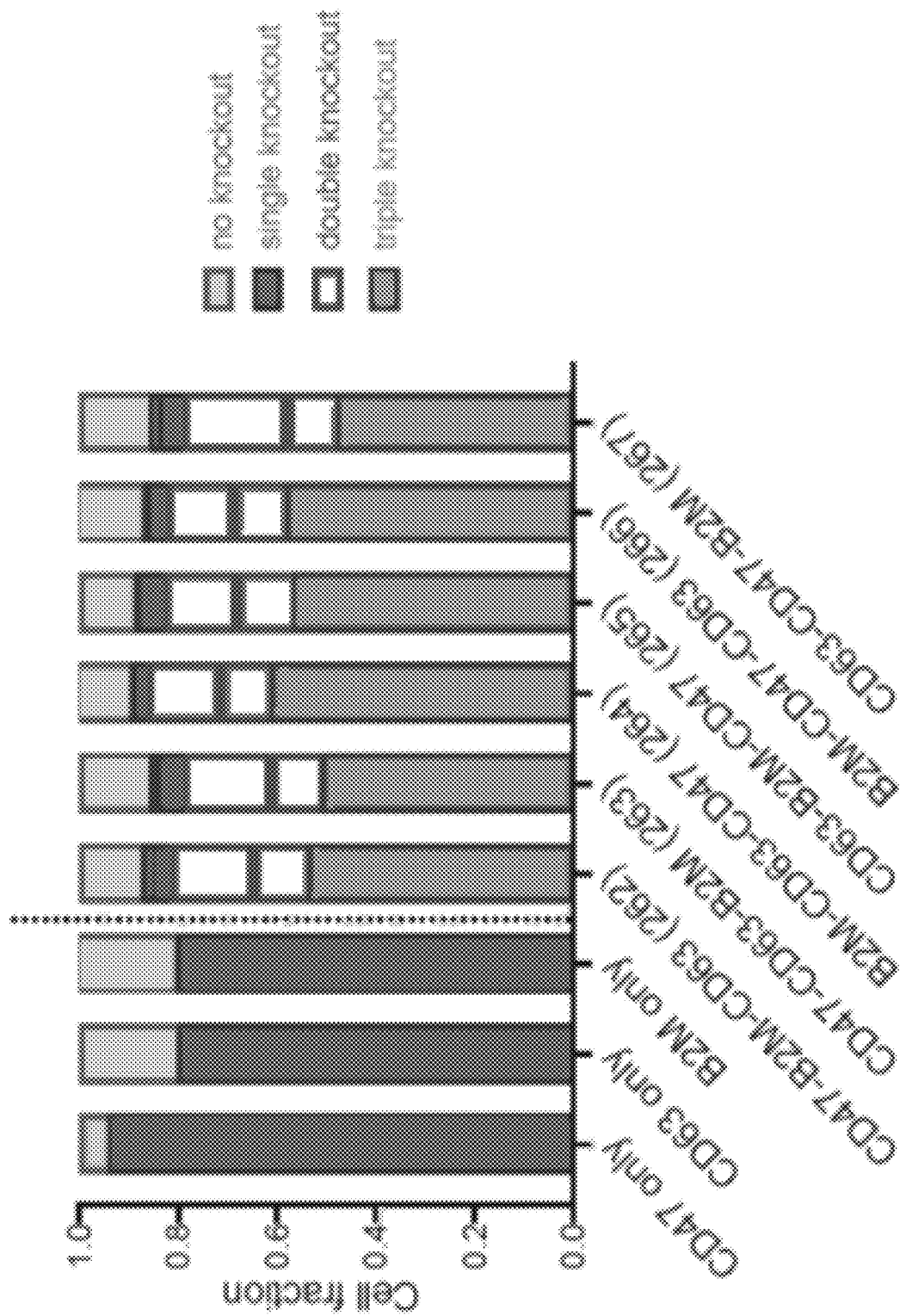

To determine the phenotypic effect of each construct, LFCs were taken relative to pDNA. Strong correlations between replicates were observed in both cell lines. Exemplary data from OVCAR8 cells is depicted in FIGS. 15B-15C. For the olfactory controls, two guides targeting OR5W2 and OR13H1 appeared to have a viability effect on their own. These guides were removed for downstream analyses. To evaluate the effect of position on activity, all SynLet guides paired with controls were considered. The LFCs of SynLet guides in position 1 were well correlated with the LFCs in position 2. Good correlations were observed across all three DR variants. To quantitate any difference in activity, the subset of guides defined as common essential in the Cancer Dependency Map—BRCA1, BCL2L1 and MCL1 (Tsherniak, A. et al. Defining a Cancer Dependency Map. Cell 170, 564-576.e16 (2017)) were considered. These guides had a LFC 0.060 and 0.039 less in the second position than in the first in A375 and OVCAR8 cells respectively, which was a small but significant difference.

Figure 20D:
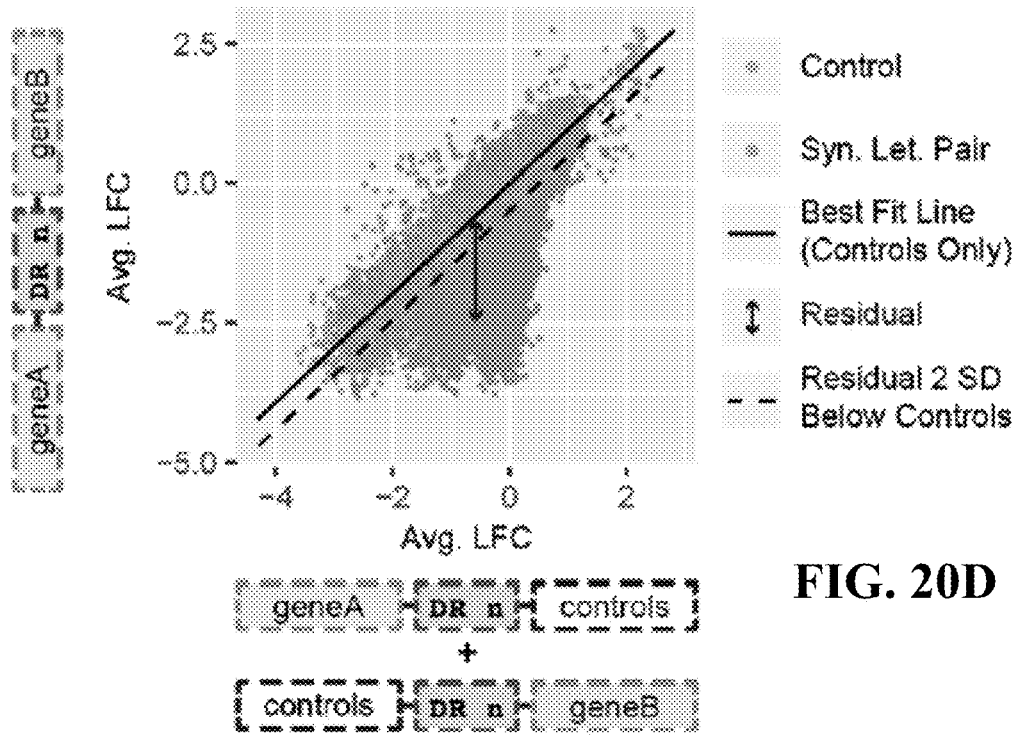
Figure 20E:
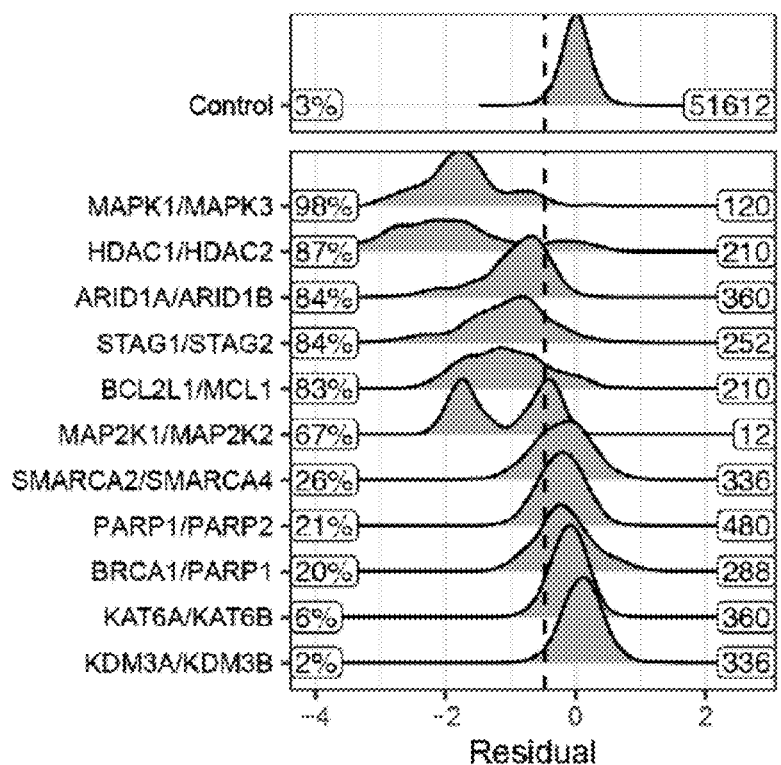
Figure 20F:
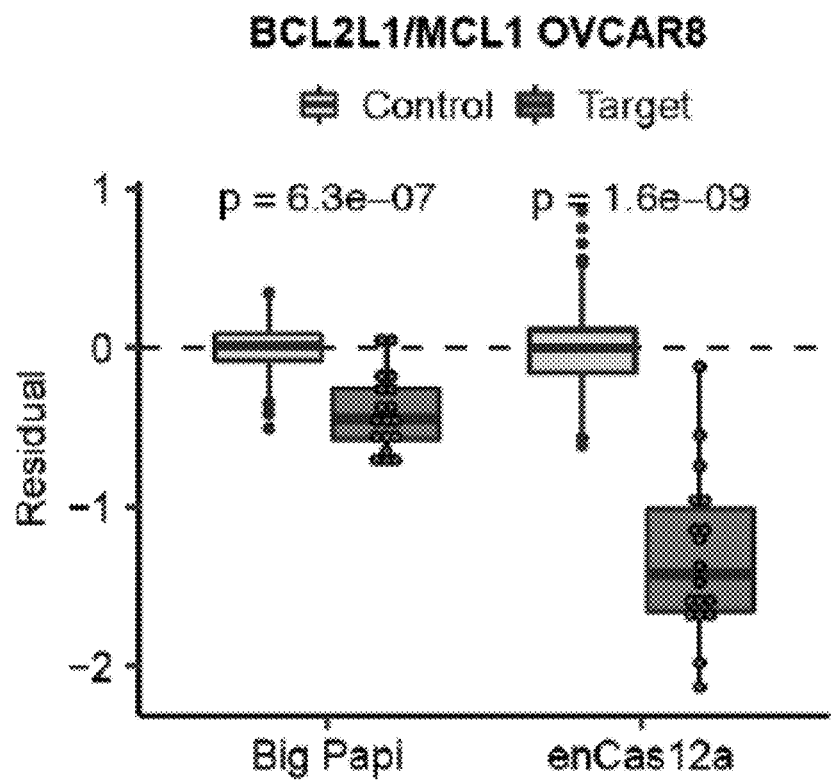
Figure 29A:
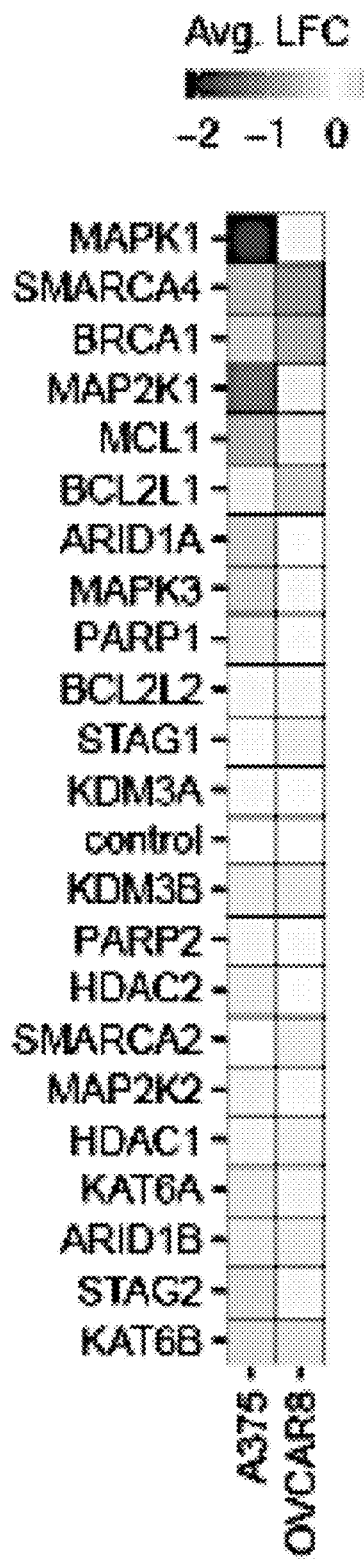
Figure 29B:
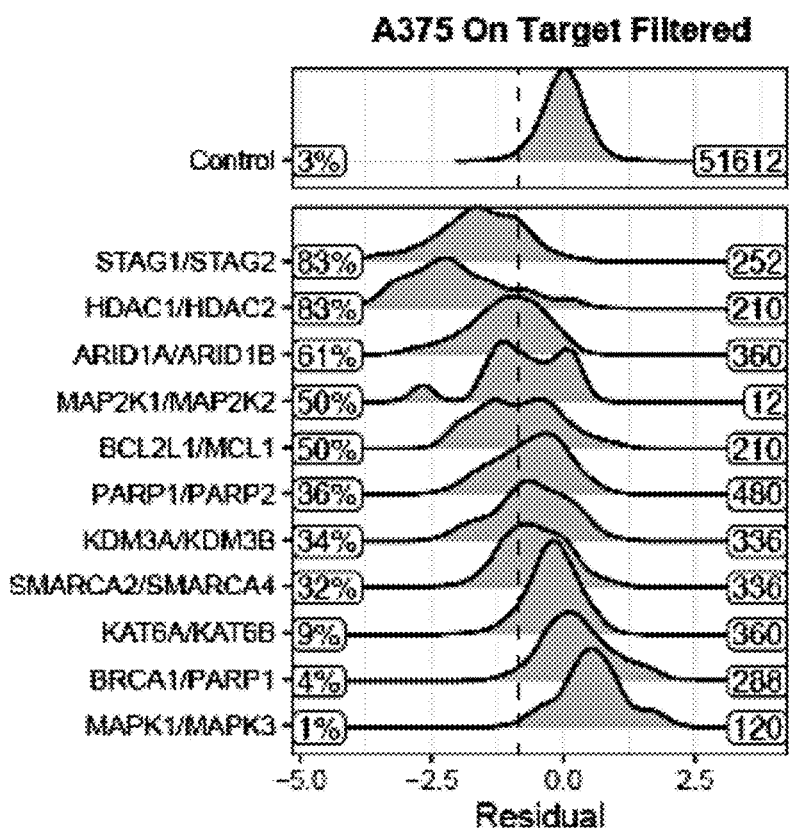
Figures 29C, 29D:
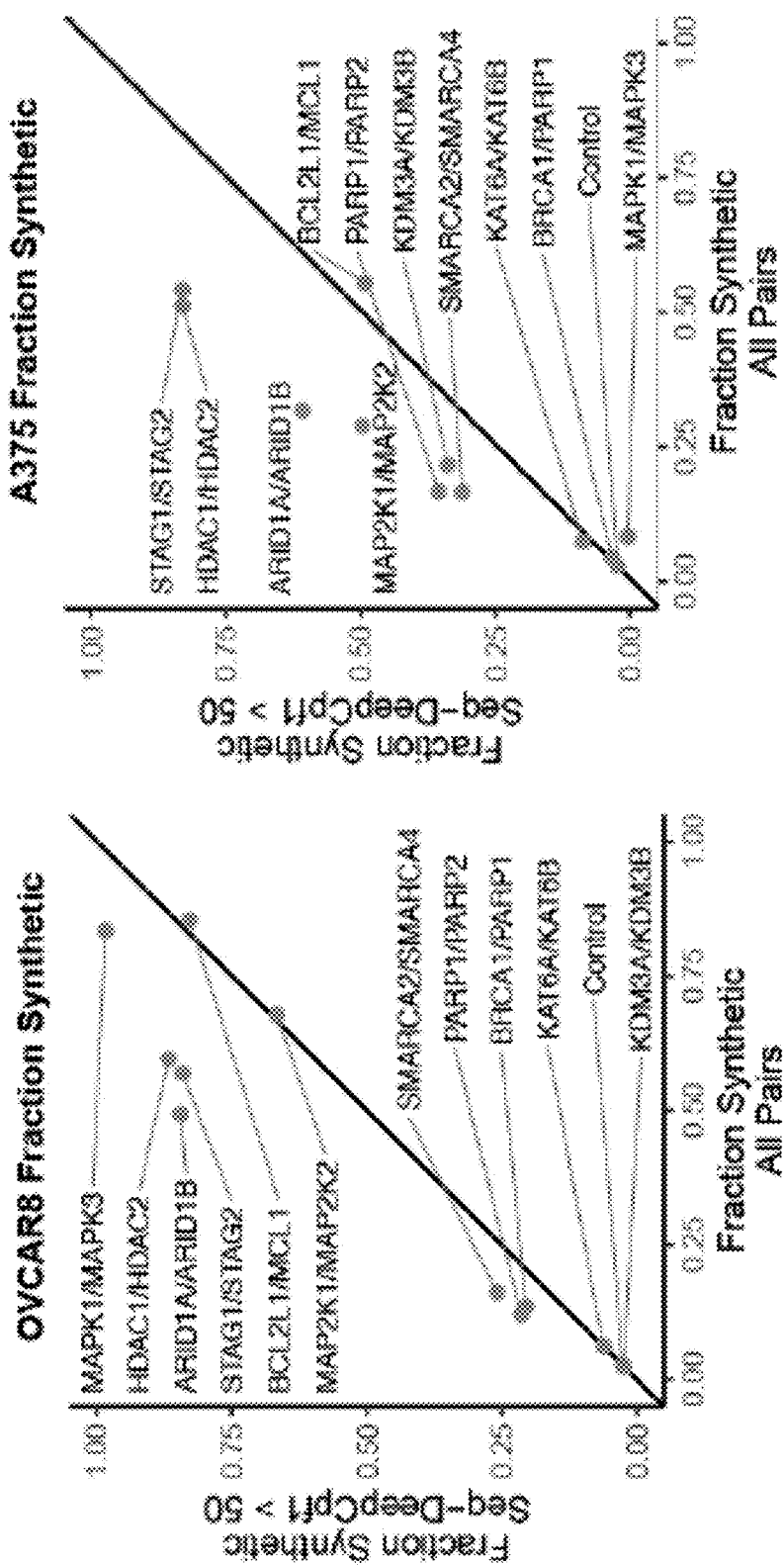

To quantitate synergies between guide pairs, an expected phenotype was first calculated by determining the average LFC of each targeting guide when it was coupled with controls (FIG. 29A), and then summing the average LFC for the two guides. A line was then fit between the expected and observed LFCs using constructs with one control and one target guide (FIG. 20D). Finally, the residual from the fit line for all constructs were calculated, where a negative residual indicates a synthetic lethal pair. A large fraction of constructs with residuals to standard deviations below the mean of the control-target pairs in both OVCAR8 and A375 cells was observed, which can indicate synthetic lethal interactions. To assess the efficacy of on-target rules in this experimental setting, data was filtered for guides with a Seq-DeepCpf1 score greater than 50. An increase in the fraction of synthetic lethal constructs for a majority of gene pairs (FIGS. 29B-29D). This confirmed the utility of this algorithm. Reads from the synthetic lethality library screened with en Cas12a are shown in Supplementary Data 4 as set forth in Sanson et al. "Optimization of AsCas12a for combinatorial genetic screens in human cells" bioRxiv, Aug. 28, 2019 doi:http// dx.doi.org/10.1101/747170, which is incorporated herein by reference as if expressed in its entirety herein.

For some gene pairs a very high fraction of gene pairs score as synthetic lethal was observed. For example, over 80% of guide pairs for STAG1-STAG2 and HDAC1-HDAC2 scored in both OVCAR8 (FIG. 20E) and A375 cells (FIG. 29B). ARID1A-ARID1B and MAP2K1-MAP2K2 also scored with the majority of guides in both cell lines. It was also observed cell line specific differences, such as KMD3A-KDM3B, which scored with 34% of guides in A375 cells, but only 2% in OVCAR8 cells (at a threshold at which 3% of control pairs score). Generally good correspondence between the activity of guides targeting essential genes across cell lines was observed (FIG. 22C). This can reflect a true biological difference.

Figure 30A:
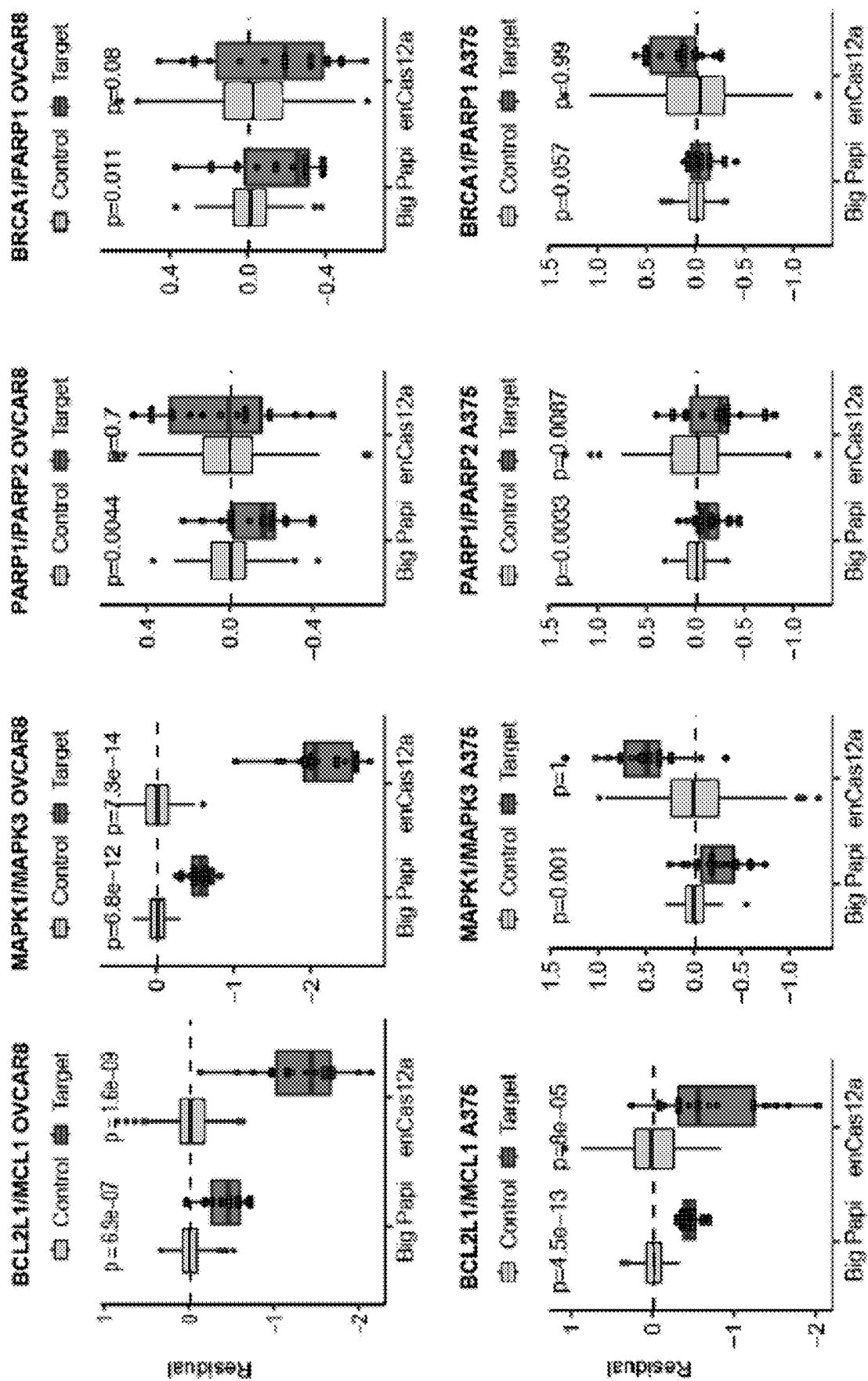
FIGS. 30A-30B—Comparison of synthetic lethality across Cas platforms.
Figure 30B:
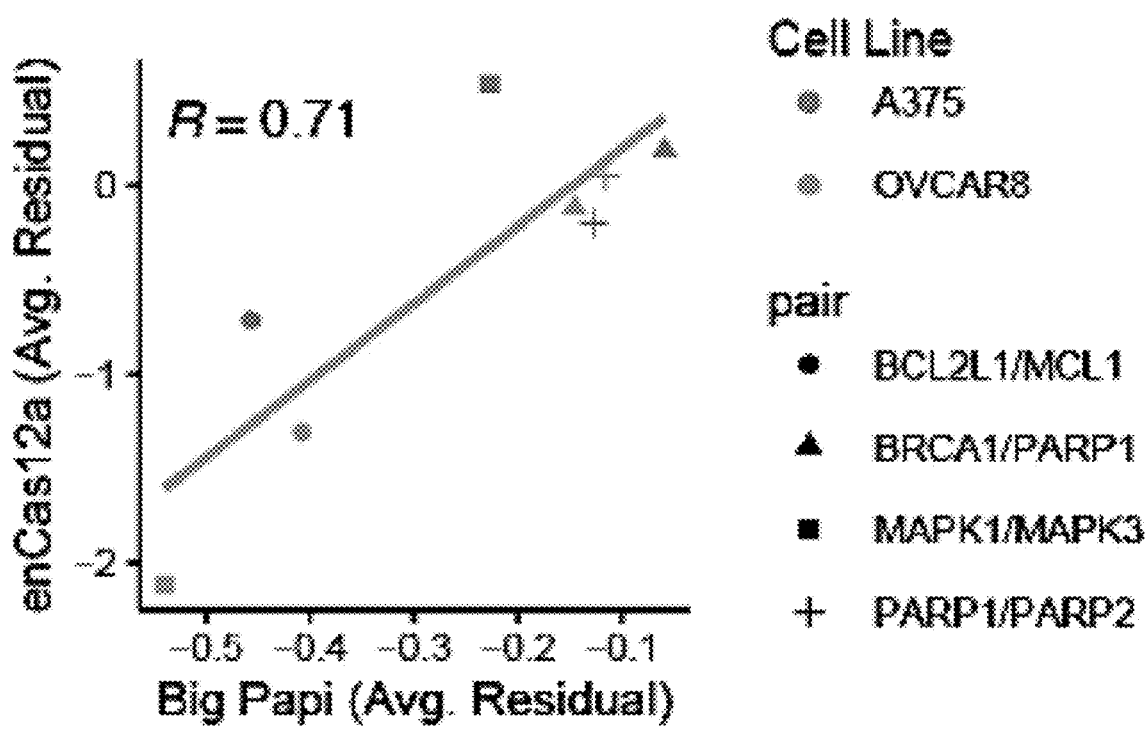
Figure 31A:
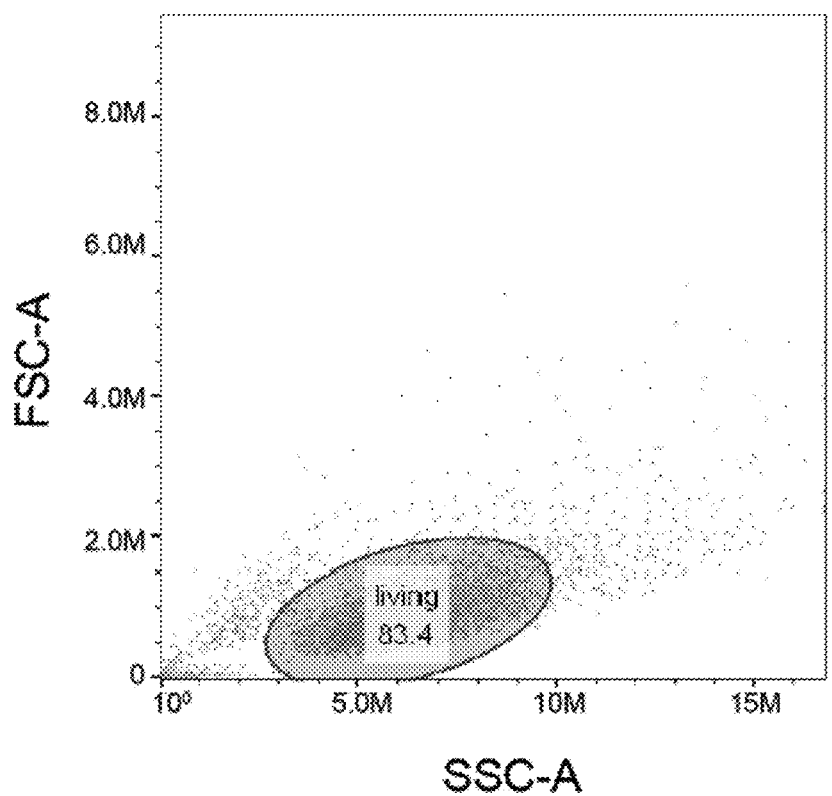
FIGS. 31A-31E—Gating strategy used in FIGS. 21A-21B.
Figure 31B:
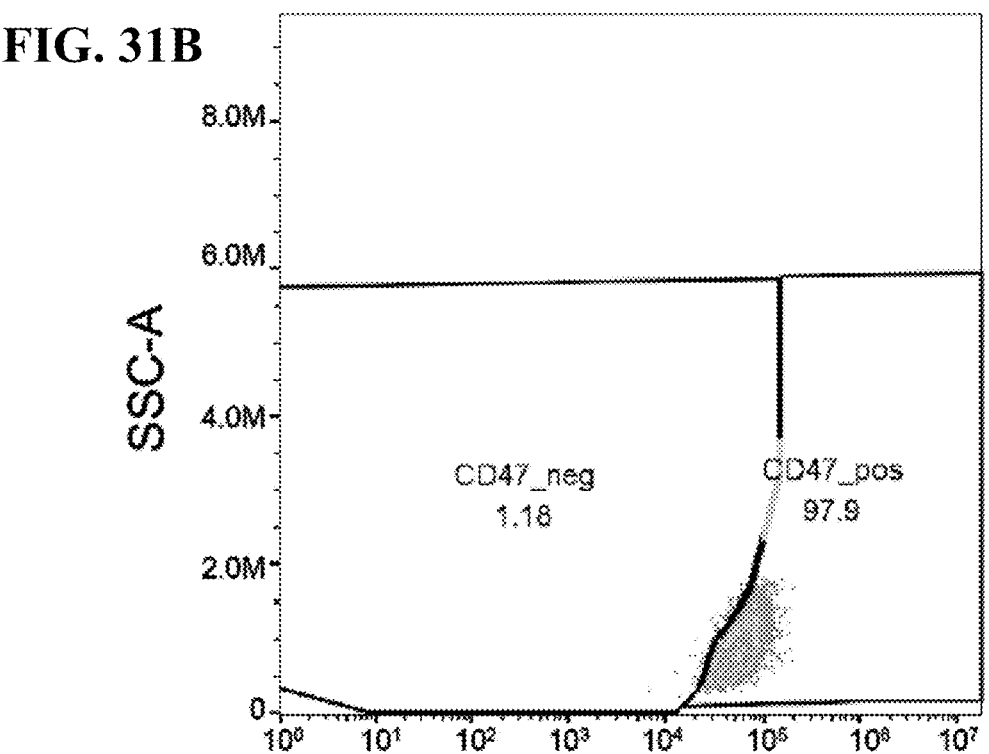
Figure 31C:
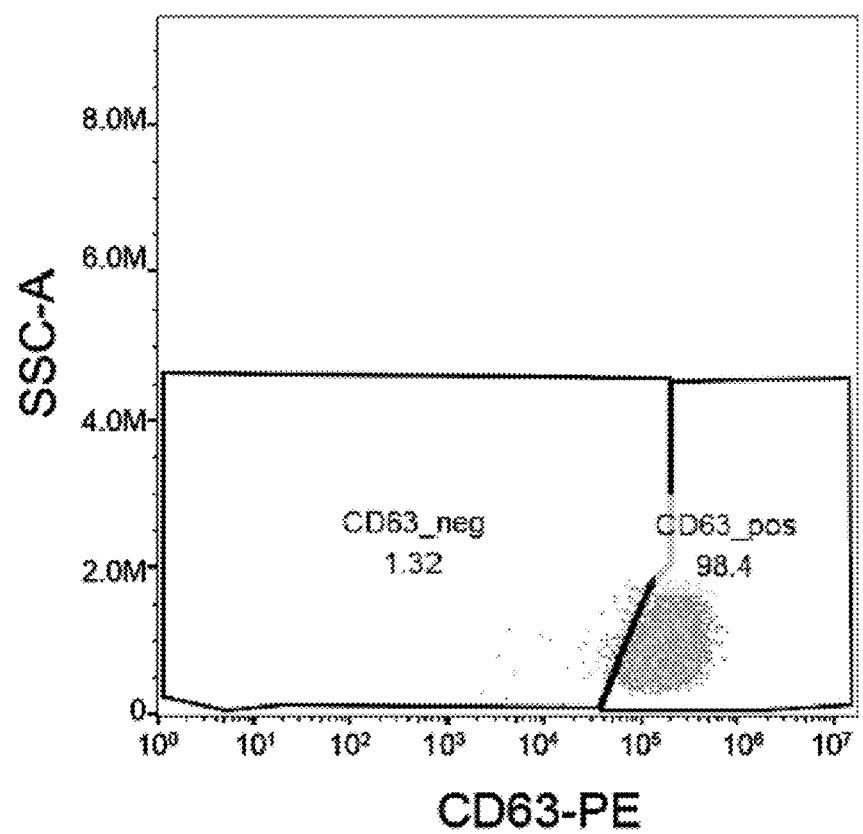
Figure 31D:
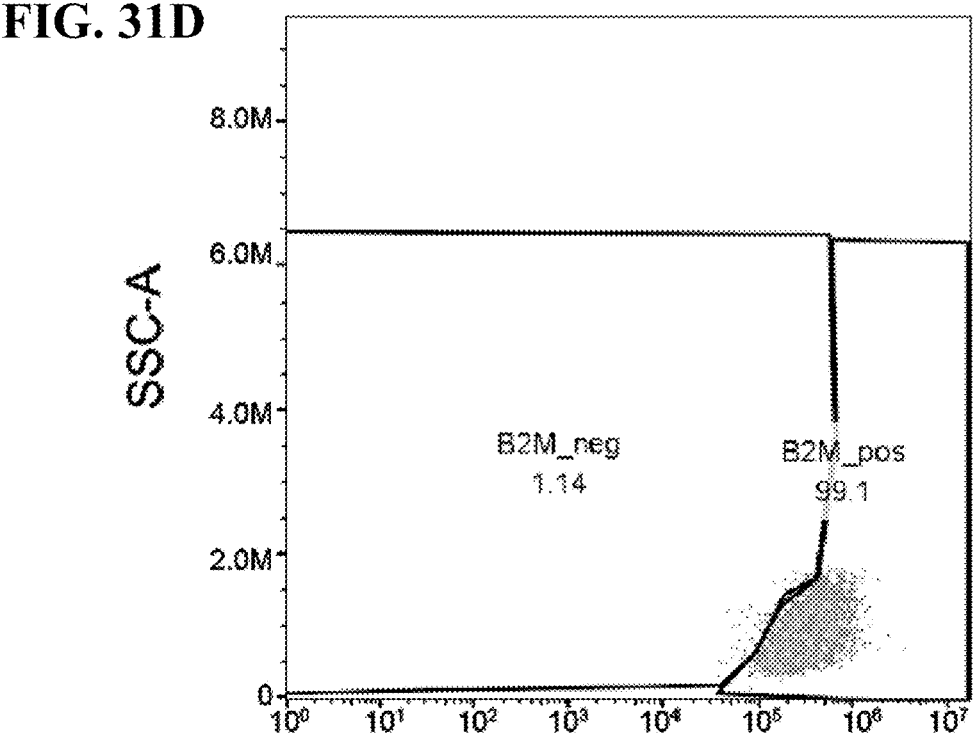
Figure 31E:
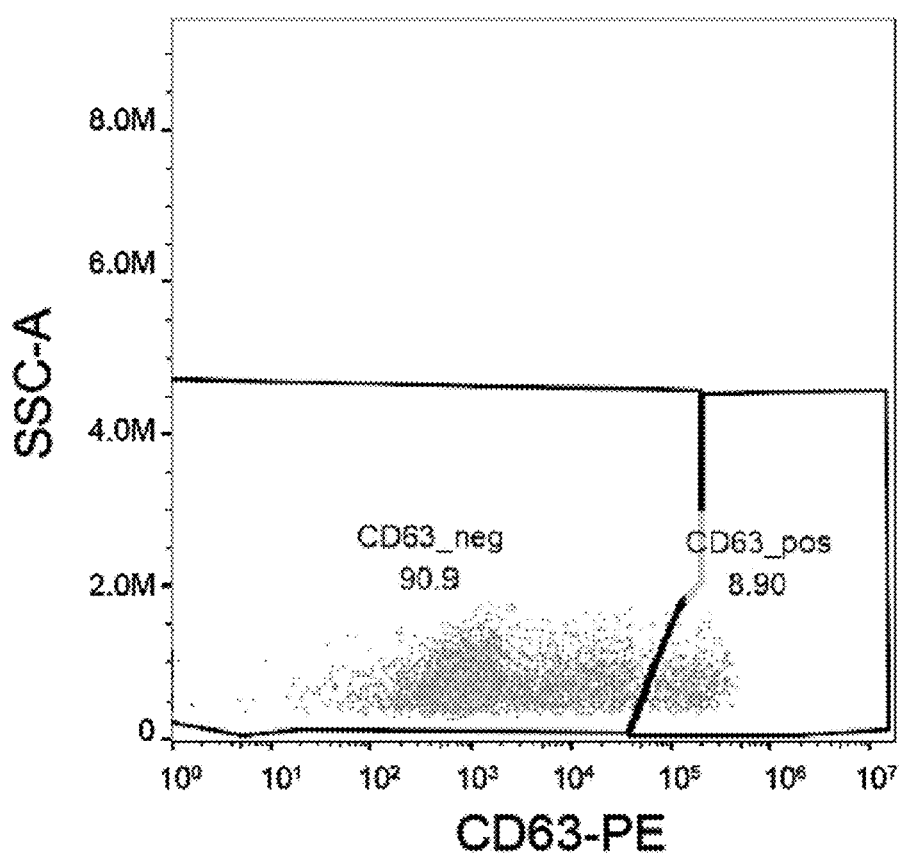
Figure 32A:
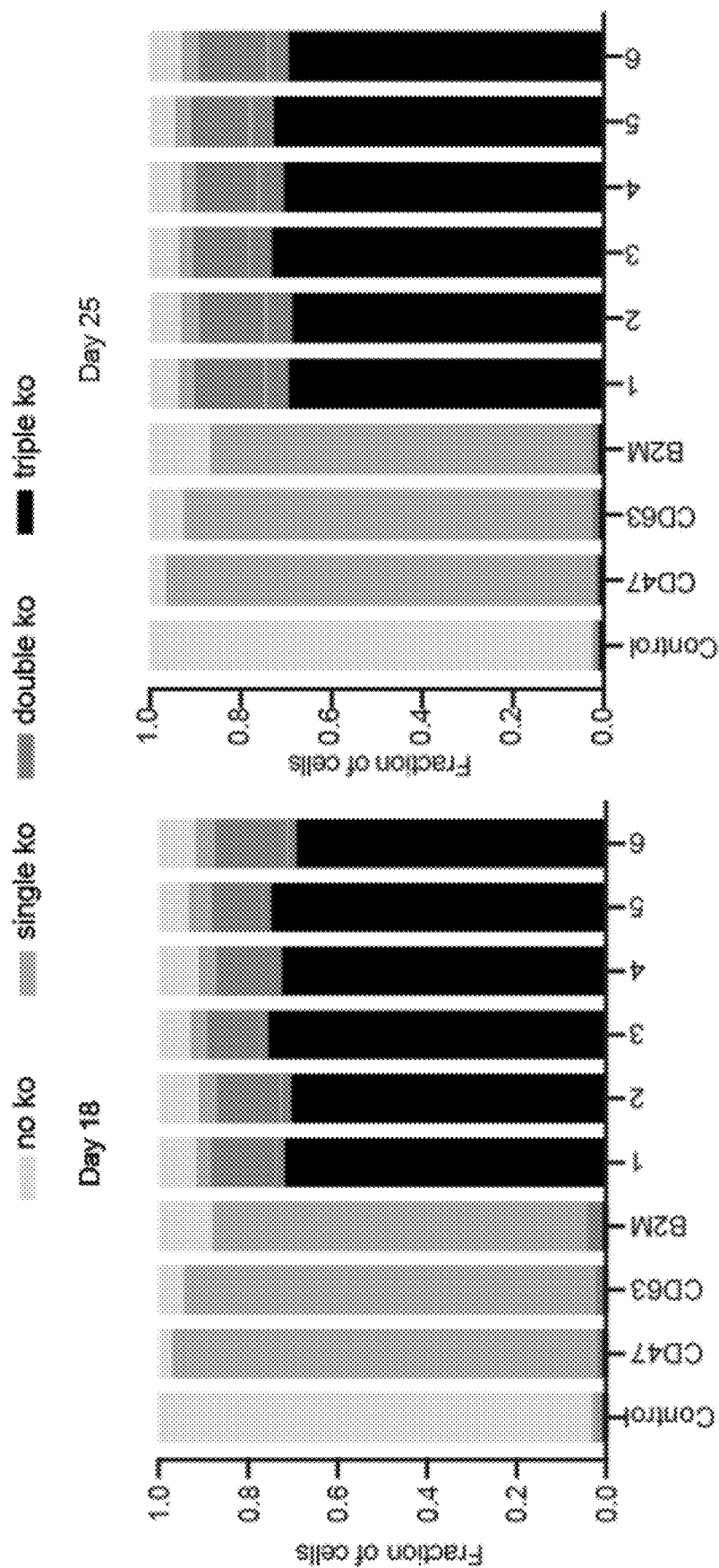
FIGS. 32A-32B—Fraction of edited cells at additional timepoints.
Figure 32B:
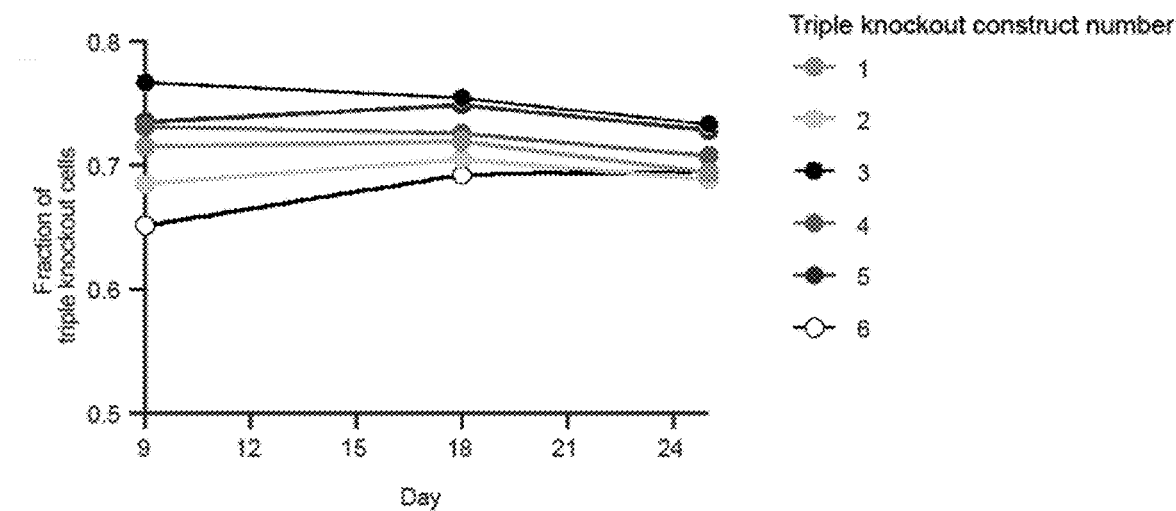

To compare this AsCAs12a system to previous synthetic lethal screens conducted with the "Big Papi" approach using SaCas9 and SpCas9 (Najm et al. Nat. Biotechnol. 36: 179 (2017)), the latter was first reanalyzed with the same analytical methodology to account for differences in library design strategy (see Methods). For BCL2L1-MCL1, a gene pair we previously validated with small molecule inhibitors, the magnitude of the residuals is substantially greater with AsCas12a in OVCAR8 cells (FIG. 20F) and comparable in A375 cells (FIG. 30A). For MAPK1-MAPK3, 98% of guide pairs scored as synthetic lethal in OVCAR8 cells with AsCas12a, with a greater magnitude of residuals than with the Cas9 approach (FIG. 30A). In contrast, synthetic lethality was not observed in A375 cells for this gene pair; this difference is likely due to the strong viability effect caused by loss of MAPK1 alone in A375 cells FIG. 29A), and thus combined targeting of MAPK1 and MAPK3 shows a buffering relationship. BRCA1-PARP1 and PARP1-PARP2 show milder phenotypes with both approaches. The correlation between the residuals from both approaches, albeit from a limited set of gene pairs, suggests the variability in synergies across cell lines largely reflects biological differences (FIG. 30B). Overall, these results can demonstrate that AsCas12a is at least comparable, and in some circumstances substantially more potent, than a Cas9-based approach. Given the considerable ease of generating and sequencing AsCas12a combinatorial libraries, we suspect that this will become the technology of choice for such screens.

Example 9—Triple Knockout with Cas12a

Figure 21A:
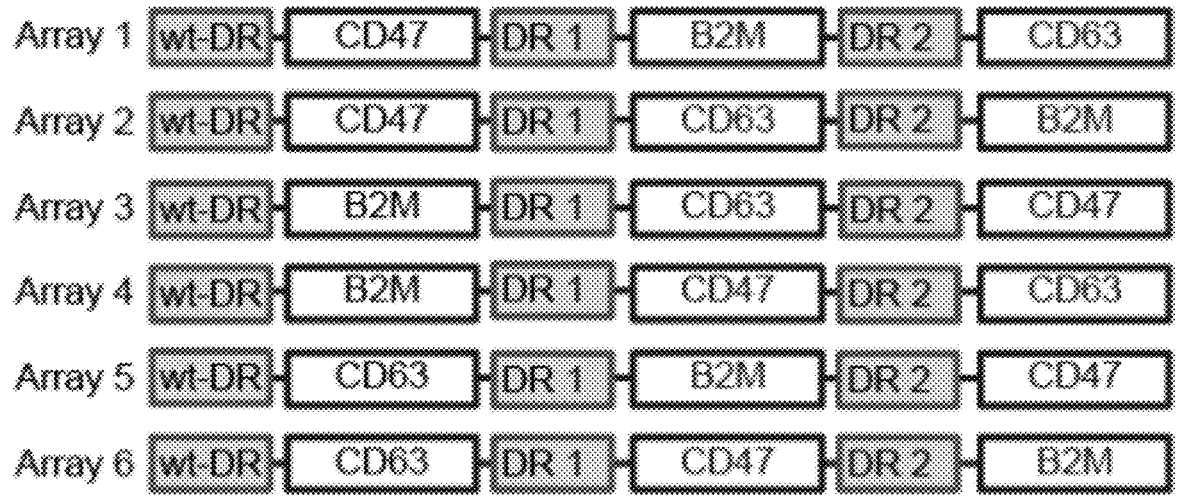
Figure 21B:
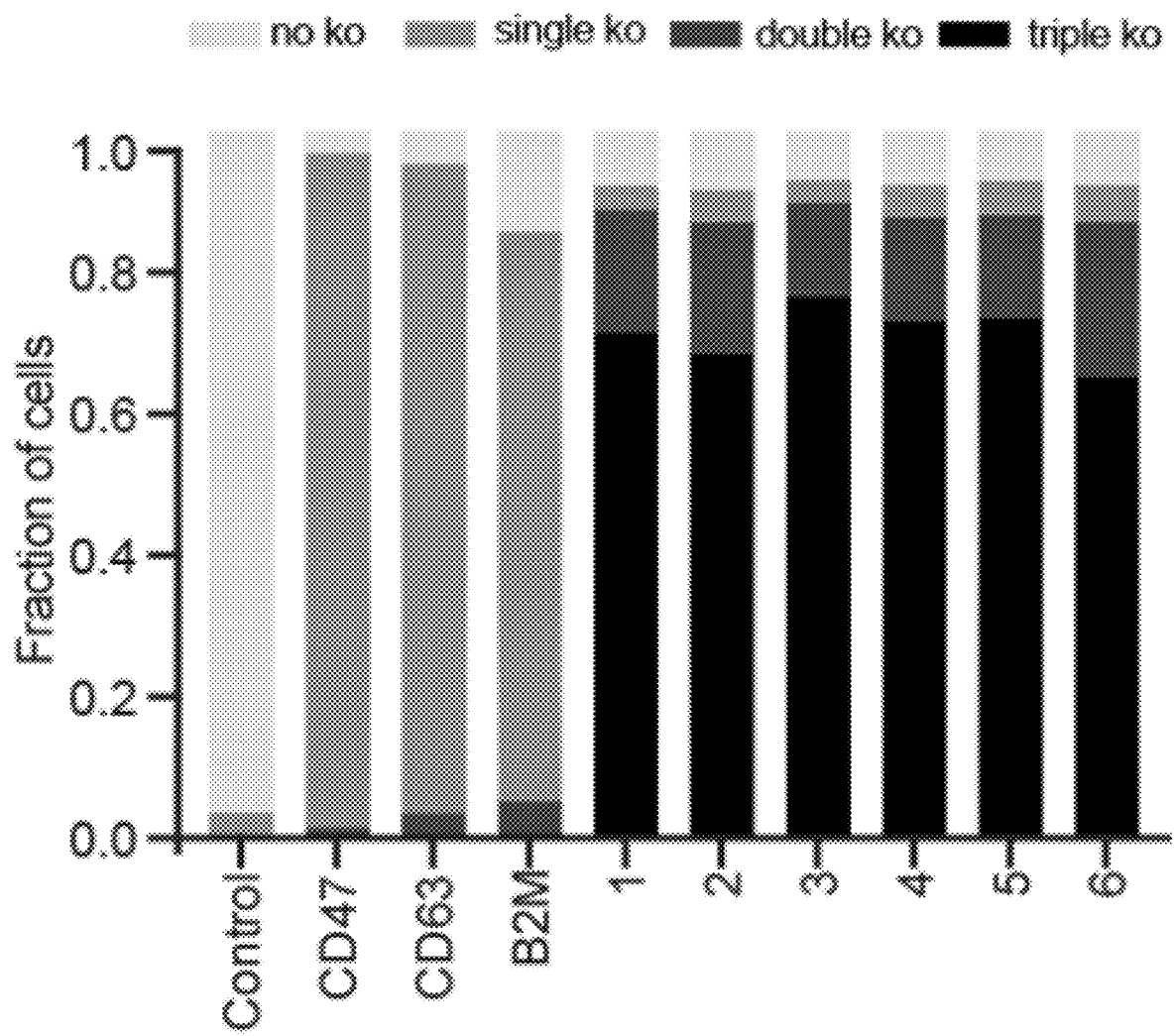
Figure 33A:
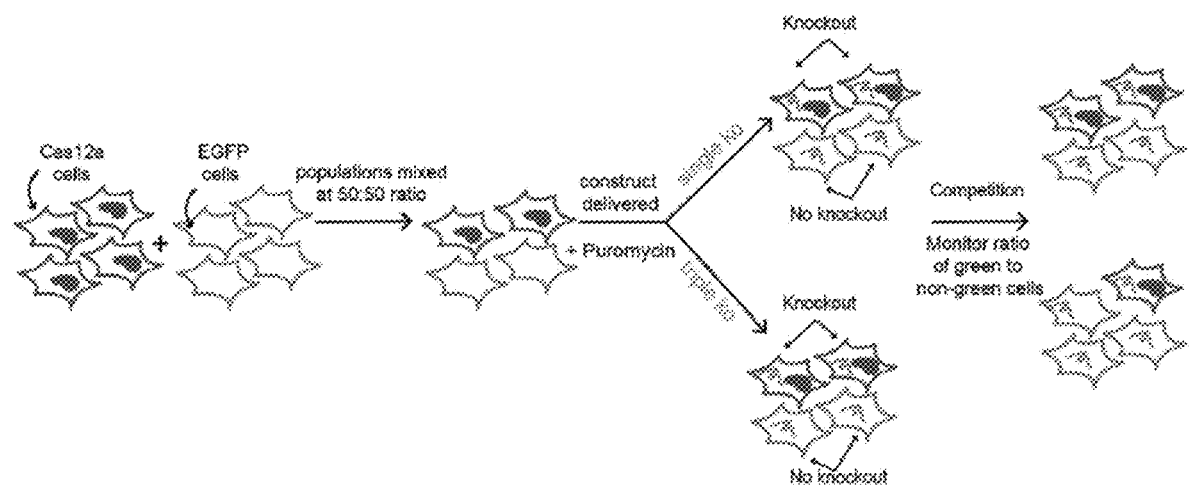
FIGS. 33A-33C—(FIG. 33A) Schematic of EGFP competition assay to compare viability of no knockout, single knockout and triple knockout of CD47, B2M and CD63. 2 populations of A375 cells, one expressing EnCas12a, the other expressing EGFP, were mixed together at a 50:50 ratio, and were then infected with 3 single knockout constructs, 3 triple knockout constructs, and an empty vector control. Knockout occurs only in EGFP- cells. The fraction of EGFP+ cells to EGFP- cells was assessed over time by flow cytometry (FIG. 33B) Fraction of EnCas12a+ cells monitored over time.
Figures 33B, 33C:
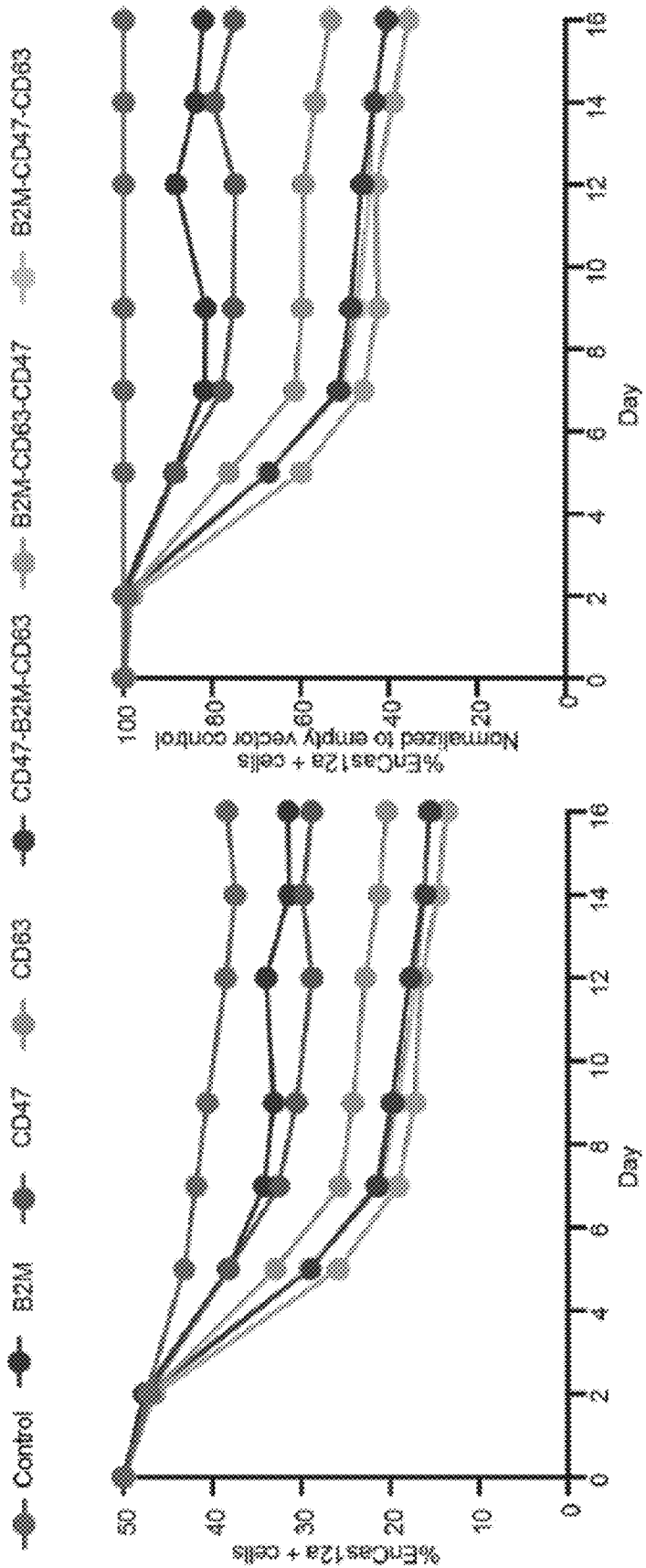

To assess the capacity of AsCas12a to target three genes, guides against the cell surface markers, CD47, CD63, and B2M, which are highly expressed in A375 cells and which do not show a viability effect upon knockout in the DepMap (Tsherniak et al. Cell. 170:564-576. E16 (2017)) were designed. Using these guides, 6 multiplexed arrays with all possible guide orientations were generated (FIG. 21A-21B). Three single guide constructs, and one empty vector control, and used flow cytometry were also included (FIGS. 31A-31E) to quantify the fraction of cells that were edited or not for all three markers. Irrespective of guide position, it was observed that approximately 70% of cells showed editing at all three loci at the three timepoints assayed (FIGS. 16, 21B, and 32A-32B). To assess the potential viability effect of simultaneously targeting three genes at once, we performed a competition assay with no guide, single guide, and triple guide constructs. In this internally-controlled assay, EGFP labels cells without enCas12a (and thus no dsDNA breaks) and the fraction of enCas12a-positive, EGFP-negative cells over time was measured by flow cytometry (FIG. 33A). It was observed that the fraction of EGFP-negative cells decreased by 20-40% over time with single guide constructs relative to an empty vector control (FIGS. 33B-33C), evidence of the cutting toxicity inherent to using wildtype Cas enzymes (Aguirre et al. Cancer Discov. 6: 914-929 (2016) and Munoz et al. Cancer Discov. 6:900-913 (2016)). With the triple knockout constructs an additional 10% decrease in viability was observed compared to single knockout, suggesting that the marginal impact of additional dsDNA breaks, at least in this cell type, is minor. Nuclease-deactivated versions of AsCas12a fused to KRAB have been described in mammalian cells (Liu et al. Nat. Commun. 8:2095 (2017)), as have transcriptional activators (Esther Tak et al. Nat. Methods. (2017) doi:10.10138/nmeth.4483; Kleinstiver et al. Nat. Biotechnol. (2019) doi:10.1038/ s41587-018-0011-0; Liu et al. Nat. Commun. 8:2095 (2017); and Campa et al. Nat. Methods (2019) doi:10.1038/s41592-019-0508-6) and such CRISPRa and CRISPRi based approaches can be useful in models where toxicity due to numerous dsDNA breaks is overly-confounding.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An engineered polynucleotide comprising:

a multiplexed guide sequence cassette comprising a nucleotide sequence encoding two or more Cas12a guide sequences and two or more Cas12a direct repeat (DR) sequences, wherein each guide sequence has a Cas12a DR sequence 5' of the guide sequence, wherein each Cas12a DR sequence is different, wherein at least one Cas12a DR sequence comprises a mutated Cas12a DR sequence relative to a wildtype Cas12a DR sequence, wherein the wildtype Cas12a DR sequence is TAATTTCTACTCTTGTAGAT (SEQ ID NO: 25), wherein the at least one mutated Cas12a DR sequence comprises a mutation at position 1, 6, 9, 12, 14, 16, 19, or any combination thereof, relative to SEQ ID NO: 25, wherein each mutated Cas12a DR sequence comprises at least one of:

(i) A or G at position 1;

(ii) A, G, or T at position 12;

(iii) A, G, or C at position 14;

(iv) C at position 6 and G at position 19; and (v) C at position 9 and G at position 16, and wherein the multiplexed guide sequence cassette is capable of directing equal or greater multiplexing activity of a Cas12a protein, a homologue thereof, or an orthologue thereof, to one or more target polynucleotides that the two or more Cas12a guide sequences target, as compared to a control multiplexed guide sequence cassette comprising only the wildtype Cas12a DR sequence.

2. The engineered polynucleotide of claim 1, wherein the two or more guide sequences are capable of hybridizing with different target sequences.

3. The engineered polynucleotide of claim 1, wherein the two or more guide sequences target a sequence in a eukaryotic cell.

4. The engineered polynucleotide of claim 1, wherein the Cas12a protein is an *Acidaminococcus* Cas12a (AsCas12a) protein comprising a polypeptide having a sequence that is 80-100% identical to SEQ ID NO: 34, or wherein the Cas12a protein is an enhanced AsCas12a (EnCas12a) protein comprising an AsCas12a polypeptide comprising E174R, S542R, and a K548R mutations or mutations homologous thereto relative to a wildtype AsCas12a having a polypeptide sequence that is 100% identical to SEQ ID NO: 34; or wherein the Cas12a protein is a Cas12a protein comprising a polypeptide that is 80% to 100% identical to any one of SEQ ID NOS: 28-33 and 35-51.

5. The engineered polynucleotide of claim 1, wherein the multiplexed guide sequence cassette comprises 5' ([Cas12a DR sequence]-[Cas12a guide sequence])$_n$ 3', wherein n=2-5 and wherein 1, 2, 3, 4, or 5 of the Cas12a DR sequences are independently selected from the mutated Cas12a DR sequences.

6. The engineered polynucleotide of claim 1, wherein the multiplexed guide sequence cassette comprises 5' [a first Cas 12a DR sequence]-[a first Cas12a guide sequence]-[a second Cas 12a DR sequence]-[a second Cas12a guide sequence] 3', wherein the first Cas12a DR sequence and the second Cas12a DR sequence are each independently selected from a Cas12a wildtype DR sequence and the mutated Cas12a DR sequences.

7. The engineered polynucleotide of claim 1, wherein the at least one mutation is in a loop of the Cas12a DR sequence, wherein the at least one mutation is in a stem loop of the Cas12a DR sequence, or both.

8. The engineered polynucleotide of claim 1, wherein the at least one mutated Cas12a DR sequence comprises one or more of SEQ ID NOs: 1-21, 23-24, 54-76.

9. The engineered polynucleotide of claim 1, wherein the at least one mutation comprises at least two, three, or four mutations.

10. The engineered polynucleotide of claim 6, wherein the first Cas12a guide sequence and the second Cas12a guide sequence each independently targets a target polynucleotide sequence independently selected from a target polynucleotide sequence in Myeloid Cell Leukemia-1 (MCL1) gene, B-Cell Lymphoma 2 (BCL2) Like 1 (BCL2L1) gene, BCL2 gene, BCL2L1-BCL2 gene, Membrane Associated Ring-CH-Type Finger 5 (MARCH5) gene, or WD Repeat and SOCS Box Containing 2 (WSB2) gene.

11. A vector system comprising: one or more vectors, wherein at least one of the one or more vectors comprises the engineered polynucleotide of claim 1, a polynucleotide encoding a Cas12a polypeptide, or both.

12. The vector system of claim 11, wherein the vector system comprises one or more plasmids, one or more Adeno-Associated Virus (AAV) vectors, one or more lentiviral vectors, or a combination thereof.

13. The vector system of claim 12, wherein the one or more AAV vectors is or comprises an AAV vector having a serotype or pseudotype of AAV1, AAV2, AAV3, AAV4, AAV5, AAV6, AAV8, AAV9, or any combination thereof.

14. An isolated host cell comprising:
(a) the engineered polynucleotide of claim 1;
(b) a vector system comprising one or more vectors, wherein at least of one of the one or more vectors comprises the engineered polynucleotide of claim 1, a polynucleotide encoding a Cas12a polypeptide, or both, wherein the vector system is capable of expressing the engineered polynucleotide, the Cas12a polypeptide, or both in the isolated host cell;
(c) a Cas12a polypeptide or a polynucleotide encoding a Cas12a polypeptide;
(d) a delivery system comprising any one of (a)-(c) or any combination of (a)-(c); or
(e) any combination of (a)-(d).

15. The cell of claim 14, wherein the isolated host cell is an isolated eukaryotic host cell.

16. The cell of claim 14, wherein the isolated host cell is an isolated prokaryotic host cell.

17. A kit comprising:
(a) the engineered polynucleotide of claim 1;
(b) a vector system comprising one or more vectors, wherein at least of one of the one or more vectors comprises the engineered polynucleotide of claim 1, a polynucleotide encoding a Cas12a polypeptide, or both, wherein the vector system is capable of expressing the engineered polynucleotide, the Cas12a polypeptide, or both in an isolated host cell;
(c) a Cas12a polypeptide or a polynucleotide encoding a Cas12a polypeptide;
(d) a delivery system comprising any one of (a)-(c) or any combination of (a)-(c);
(e) a cell comprising any one of (a)-(d) or any combination of (a)-(d); or
(f) any combination of (a)-(e).

18. A delivery system comprising:
(a) the engineered polynucleotide of claim 1;
(b) a vector system comprising one or more vectors, wherein at least of one of the one or more vectors comprises the engineered polynucleotide of claim 1, a polynucleotide encoding a Cas12a polypeptide, or both, wherein the vector system is capable of expressing the engineered polynucleotide, the Cas12a polypeptide, or both in an isolated host cell;
(c) a Cas12a polypeptide or a polynucleotide encoding a Cas12a polypeptide;
(d) one or more particles comprising any one of (a)-(c) or any combination thereof, or
(e) any combination of (a)-(d).

19. The delivery system of claim 18, wherein the vector system comprises one or more plasmids, one or more lentiviral vectors, one or more Adeno-Associated Virus (AAV) vectors, or a combination thereof.

20. The delivery system of claim 19, wherein the vector is or comprises an AAV vector, or wherein the vector is or comprises an AAV vector having a serotype or pseudotype of AAV1, AAV2, AAV3, AAV4, AAV5, AAV6, AAV8, AAV9, or any combination thereof.

21. The delivery system of claim 18, wherein the one or more particles is/are lipid-based, comprises a lipid, or is/are or comprises a liposome.

22. The delivery system of claim 18, wherein the Cas12a polypeptide, when present, is encoded by a single vector or by at least two vectors.

23. The delivery system of claim 22, wherein the single vector or the at least two vectors are contained in a particle or at least two particles.

24. The delivery system of claim 18, wherein the Cas12a polypeptide or polynucleotide encoding the Cas12a polypeptide, when present, is contained in one particle or at least two particles.

25. A method of modifying one or more targets in an isolated host cell comprising:
introducing into the isolated host cell
(a) the engineered polynucleotide of claim 1;
(b) a vector system comprising one or more vectors, wherein at least of one of the one or more vectors comprises the engineered polynucleotide of claim 1, a polynucleotide encoding a Cas12a polypeptide, or both, wherein the vector system is capable of expressing the engineered polynucleotide in the isolated host cell;

(c) a Cas12a polypeptide or a polynucleotide encoding a Cas12a polypeptide;
(d) a delivery system comprising any one of (a)-(c) or any combination thereof, or
(e) any combination of (a)-(d).

26. The method of claim 25, wherein the isolated host cell comprises an isolated eukaryotic host cell.

27. A gene therapy method comprising:
modifying one or more targets in an isolated host cell comprising:
introducing into the isolated host cell
(a) the engineered polynucleotide of claim 1;
(b) a vector system comprising one or more vectors, wherein at least of one of the one or more vectors comprises the engineered polynucleotide of claim 1, a polynucleotide encoding a Cas12a polypeptide, or both, wherein the vector system is capable of expressing the engineered polynucleotide in the isolated host cell;
(c) a Cas12 polypeptide or a polynucleotide encoding a Cas12 polypeptide;
(d) a delivery system comprising any one of (a)-(c) or any combination thereof; or
(e) any combination of (a)-(d).

28. The gene therapy method of claim 27, wherein the method includes expanding modified isolated host cells, introducing modified isolated host cells into a subject, or both.

29. A method comprising:
modifying a polynucleotide at one or more target regions by contacting the polynucleotide with
(a) the engineered polynucleotide of claim 1;
(b) a vector system comprising one or more vectors, wherein at least of one of the one or more vectors comprises the engineered polynucleotide of claim 1, a polynucleotide encoding a Cas12a polypeptide, or both, wherein the vector system is capable of expressing the engineered polynucleotide;
(c) a Cas12a polypeptide or a polynucleotide encoding a Cas12a polypeptide;
(d) a delivery system comprising any one of (a)-(c) or any combination thereof; or
(e) any combination of (a)-(d); and
performing a functional assay to determine an effect of modifying the polynucleotide.

30. The method of claim 29, wherein the functional assay is a genotypic assay, a transcriptomic assay, a proteomic assay, an epigenetic assay, a phenotypic assay, or a combination thereof.

31. The method of claim 29, further comprising exposing the modified polynucleotide to a test molecule, an abiotic condition, or both before performing the functional assay.

32. The method of claim 29, wherein the method comprises modifying two or more target regions.

33. The method of claim 32, wherein the two or more target regions are on a same gene.

* * * * *

```
                           SEQUENCE LISTING

<160> NUMBER OF SEQ ID NOS: 134

<210> SEQ ID NO 1
<211> LENGTH: 20
<212> TYPE: DNA
<213> ORGANISM: Artificial Sequence
<220> FEATURE:
<223> OTHER INFORMATION: Synthetic

<400> SEQUENCE: 1
taatttctac tgtcgtagat                                             20

<210> SEQ ID NO 2
<211> LENGTH: 20
<212> TYPE: DNA
<213> ORGANISM: Artificial Sequence
<220> FEATURE:
<223> OTHER INFORMATION: Synthetic

<400> SEQUENCE: 2
taatttctac tatcgtagat                                             20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
aaatttctac tctagtagat                                             20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
taatttctac tattgtagat                                             20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
taatttctac tatagtagat                                             20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
aaatttctcc tctcggagat                                             20
```

```
<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
taatttctcc tattggagat                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
taatttctcc tctaggagat                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
aaatttctcc tcttggagat                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
taatttctac tttcgtagat                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
aaatttctac tattgtagat                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
taatttctac tatggtagat                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic
```

<400> SEQUENCE: 13
gaatttctcc tctcggagat                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gaattcctac tattgtaggt                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic

<400> SEQUENCE: 15
taattcctac tctagtaggt                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
gaatttctac tctcgtagat                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
taattcctac tcttgtaggt                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
aaatttctcc tctaggagat                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
aaattcctac tctcgtaggt                                               20

<210> SEQ ID NO 20

```
<211> LENGTH: 20
<212> TYPE: DNA
<213> ORGANISM: Artificial Sequence
<220> FEATURE:
<223> OTHER INFORMATION: Synthetic

<400> SEQUENCE: 20
taatttctac tgttgtagat                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic

<400> SEQUENCE: 21
gaatttctac tctagtagat                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
taatttctcc tcttggagat                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gaatttctac tctggtagat                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
taatttctac tttagtagat                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
taatttctac tcttgtagat                                              20

<210> SEQ ID NO 26
<211> LENGTH: 601
<212> TYPE: DNA
<213> ORGANISM: Artificial Sequence
<220> FEATURE:
<223> OTHER INFORMATION: Synthetic

<400> SEQUENCE: 26
```

```
gggatattca ccattatcgt ttcagaccca cctcccaacc ccgaggggac ccagaggtac      60
cgagggccta tttcccatga ttccttcata tttgcatata cgatacaagg ctgttagaga    120
gataattaga attaatttga ctgtaaacac aaagatatta gtacaaaata cgtgacgtag    180
aaagtaataa tttcttgggt agtttgcagt tttaaaatta tgttttaaaa tggactatca    240
tatgcttacc gtaacttgaa agtatttcga tttcttggct ttatatatct tgtggaaagg    300
acgaaacacc ggtaatttct actcttgtag attgggaaag cttgtaggag agaaataatt    360
tctactgtcg ttagatatgt ccagtttccg aagcatgcct ttttttgaatt cgctagcaag    420
cttggcgtaa ctagatcttg agacaaatgg cagtattcat ccacaatttt aaaagaaaag    480
gggggattgg ggggtacagt gcaggggaaa gaatagtaga cataatagca acagacatac    540
aaactaaaga attacaaaaa caaattacaa aaattcaaaa ttttcgggtt tattacaggg    600
a                                                                    601
```

<210> SEQ ID NO 27
<211> LENGTH: 601
<212> TYPE: DNA
<213> ORGANISM: Artificial Sequence
<220> FEATURE:
<223> OTHER INFORMATION: Synthetic

<400> SEQUENCE: 27

```
ccctataagt ggtaatagca aagtctgggt ggagggttgg ggctcccctg ggtctccatg      60
gctcccggat aaagggtact aaggaagtat aaacgtatat gctatgttcc gacaatctct    120
ctattaatct taattaaact gacatttgtg tttctataat catgttttat gcactgcatc    180
tttcattatt aaagaaccca tcaaacgtca aatttttaat acaaaatttt acctgatagt    240
atacgaatgg cattgaactt tcataaagct aaagaaccga atatataga acacctttcc    300
tgctttgtgg ccattaaaga tgagaacatc taaccctttc gaacatcctc tctttattaa    360
agatgacagc aatctataca ggtcaaaggc ttcgtacgga aaaaacttaa gcgatcgttc    420
gaaccgcatt gatctagaac tctgtttacc gtcataagta ggtgttaaaa ttttcttttc    480
ccccctaacc ccccatgtca cgtccccttt cttatcatct gtattatcgt tgtctgtatg    540
tttgatttct taatgttttt gtttaatgtt tttaagtttt aaaagcccaa ataatgtccc    600
t                                                                    601
```

<210> SEQ ID NO 28
<211> LENGTH: 1345
<212> TYPE: PRT
<213> ORGANISM: Franscisella tularensis

<400> SEQUENCE: 28

```
Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asp Asn Leu Gln Lys
```

```
                    85                  90                  95
Asp Phe Lys Ser Ala Lys Asp Thr Ile Lys Lys Gln Ile Ser Glu Tyr
                100                 105                 110

Ile Lys Asp Ser Glu Lys Phe Lys Asn Leu Phe Asn Gln Asn Leu Ile
                115                 120                 125

Asp Ala Lys Lys Gly Gln Glu Ser Asp Leu Ile Leu Trp Leu Lys Gln
            130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Asn Val Tyr Ser Ser
                180                 185                 190

Asn Asp Ile Pro Thr Ser Ile Ile Tyr Arg Ile Val Asp Asp Asn Leu
                195                 200                 205

Pro Lys Phe Leu Glu Asn Lys Ala Lys Tyr Glu Ser Leu Lys Asp Lys
            210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255

Val Phe Ser Leu Asp Glu Val Phe Glu Ile Ala Asn Phe Asn Asn Tyr
                260                 265                 270

Leu Asn Gln Ser Gly Ile Thr Lys Phe Asn Thr Ile Ile Gly Gly Lys
            275                 280                 285

Phe Val Asn Gly Glu Asn Thr Lys Arg Lys Gly Ile Asn Glu Tyr Ile
            290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
                340                 345                 350

Gln Ser Phe Tyr Glu Gln Ile Ala Ala Phe Lys Thr Val Glu Glu Lys
            355                 360                 365

Ser Ile Lys Glu Thr Leu Ser Leu Leu Phe Asp Asp Leu Lys Ala Gln
            370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
                420                 425                 430

Pro Ser Lys Lys Glu Gln Glu Leu Ile Ala Lys Lys Thr Glu Lys Ala
            435                 440                 445

Lys Tyr Leu Ser Leu Glu Thr Ile Lys Leu Ala Leu Glu Glu Phe Asn
            450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510
```

```
Asp Leu Leu Gln Ala Ser Ala Glu Asp Val Lys Ala Ile Lys Asp
            515                 520                 525

Leu Leu Asp Gln Thr Asn Asn Leu Leu His Lys Leu Lys Ile Phe His
        530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

Ile Leu Ser Ile Asp Arg Gly Glu Arg His Leu Ala Tyr Tyr Thr Leu
        915                 920                 925
```

-continued

Val Asp Gly Lys Gly Asn Ile Ile Lys Gln Asp Thr Phe Asn Ile Ile
930                935                940

Gly Asn Asp Arg Met Lys Thr Asn Tyr His Asp Lys Leu Ala Ala Ile
945                950                955                960

Glu Lys Asp Arg Asp Ser Ala Arg Lys Asp Trp Lys Lys Ile Asn Asn
                965                970                975

Ile Lys Glu Met Lys Glu Gly Tyr Leu Ser Gln Val Val His Glu Ile
                980                985                990

Ala Lys Leu Val Ile Glu Tyr Asn Ala Ile Val Val Phe Glu Asp Leu
        995                1000                1005

Asn Phe Gly Phe Lys Arg Gly Arg Phe Lys Val Glu Lys Gln Val
   1010                1015                1020

Tyr Gln Lys Leu Glu Lys Met Leu Ile Glu Lys Leu Asn Tyr Leu
   1025                1030                1035

Val Phe Lys Asp Asn Glu Phe Asp Lys Thr Gly Gly Val Leu Arg
   1040                1045                1050

Ala Tyr Gln Leu Thr Ala Pro Phe Glu Thr Phe Lys Lys Met Gly
   1055                1060                1065

Lys Gln Thr Gly Ile Ile Tyr Tyr Val Pro Ala Gly Phe Thr Ser
   1070                1075                1080

Lys Ile Cys Pro Val Thr Gly Phe Val Asn Gln Leu Tyr Pro Lys
   1085                1090                1095

Tyr Glu Ser Val Ser Lys Ser Gln Glu Phe Phe Ser Lys Phe Asp
   1100                1105                1110

Lys Ile Cys Tyr Asn Leu Asp Lys Gly Tyr Phe Glu Phe Ser Phe
   1115                1120                1125

Asp Tyr Lys Asn Phe Gly Asp Lys Ala Ala Lys Gly Lys Trp Thr
   1130                1135                1140

Ile Ala Ser Phe Gly Ser Arg Leu Ile Asn Phe Arg Asn Ser Asp
   1145                1150                1155

Lys Asn His Asn Trp Asp Thr Arg Glu Val Tyr Pro Thr Lys Glu
   1160                1165                1170

Leu Glu Lys Leu Leu Lys Asp Tyr Ser Ile Glu Tyr Gly His Gly
   1175                1180                1185

Glu Cys Ile Lys Ala Ala Ile Cys Gly Glu Ser Asp Lys Lys Phe
   1190                1195                1200

Phe Ala Lys Leu Thr Ser Val Leu Asn Thr Ile Leu Gln Met Arg
   1205                1210                1215

Asn Ser Lys Thr Gly Thr Glu Leu Asp Tyr Leu Ile Ser Pro Val
   1220                1225                1230

Ala Asp Val Asn Gly Asn Phe Phe Asp Ser Arg Gln Ala Pro Lys
   1235                1240                1245

Asn Met Pro Gln Asp Ala Asp Ala Asn Gly Ala Tyr His Ile Gly
   1250                1255                1260

Leu Lys Gly Leu Met Leu Leu Gly Arg Ile Lys Asn Asn Gln Glu
   1265                1270                1275

Gly Lys Lys Leu Asn Leu Val Ile Lys Asn Glu Glu Tyr Phe Glu
   1280                1285                1290

Phe Val Gln Asn Arg Asn Asn Lys Arg Pro Ala Ala Thr Lys Lys
   1295                1300                1305

Ala Gly Gln Ala Lys Lys Lys Lys Gly Ser Tyr Pro Tyr Asp Val
   1310                1315                1320

Pro Asp Tyr Ala Tyr Pro Tyr Asp Val Pro Asp Tyr Ala Tyr Pro

Tyr Asp Val Pro Asp Tyr Ala
    1340               1345

<210> SEQ ID NO 29
<211> LENGTH: 1278
<212> TYPE: PRT
<213> ORGANISM: Lachnospiraceae bacterium

<400> SEQUENCE: 29

```
Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
            20                  25                  30

Arg Glu Gln Lys Leu Leu Glu Gln Asp Ala Ala Phe Arg Lys Leu Val
        35                  40                  45

Glu Thr Val Thr Pro Ile Val Asp Asp Cys Ile Arg Lys Ile Ala Asp
    50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
        115                 120                 125

Thr Leu Thr Ser Phe Val Gln Asp Asp Ala Asp Lys Arg Val Leu Ile
    130                 135                 140

Gln Glu Leu Lys Gly Lys Thr Val Leu Met Gln Arg Phe Leu Thr Thr
145                 150                 155                 160

Arg Ile Thr Ala Leu Thr Val Trp Leu Pro Asp Arg Val Phe Glu Asn
                165                 170                 175

Phe Asn Ile Phe Ile Glu Asn Ala Glu Lys Met Arg Ile Leu Leu Asp
            180                 185                 190

Ser Pro Leu Asn Glu Lys Ile Met Lys Phe Asp Pro Asp Ala Glu Gln
        195                 200                 205

Tyr Ala Ser Leu Glu Phe Tyr Gly Gln Cys Leu Ser Gln Lys Asp Ile
    210                 215                 220

Asp Ser Tyr Asn Leu Ile Ile Ser Gly Ile Tyr Ala Asp Asp Glu Val
225                 230                 235                 240

Lys Asn Pro Gly Ile Asn Glu Ile Val Lys Glu Tyr Asn Gln Gln Ile
                245                 250                 255

Arg Gly Asp Lys Asp Glu Ser Pro Leu Pro Lys Leu Lys Lys Leu His
            260                 265                 270

Lys Gln Ile Leu Met Pro Val Glu Lys Ala Phe Phe Val Arg Val Leu
        275                 280                 285

Ser Asn Asp Ser Asp Ala Arg Ser Ile Leu Glu Lys Ile Leu Lys Asp
    290                 295                 300

Thr Glu Met Leu Pro Ser Lys Ile Ile Glu Ala Met Lys Glu Ala Asp
305                 310                 315                 320

Ala Gly Asp Ile Ala Val Tyr Gly Ser Arg Leu His Glu Leu Ser His
                325                 330                 335

Val Ile Tyr Gly Asp His Gly Lys Leu Ser Gln Ile Ile Tyr Asp Lys
            340                 345                 350
```

```
Glu Ser Lys Arg Ile Ser Glu Leu Met Glu Thr Leu Ser Pro Lys Glu
            355                 360                 365

Arg Lys Glu Ser Lys Lys Arg Leu Glu Gly Leu Glu Glu His Ile Arg
    370                 375                 380

Lys Ser Thr Tyr Thr Phe Asp Glu Leu Asn Arg Tyr Ala Glu Lys Asn
385                 390                 395                 400

Val Met Ala Ala Tyr Ile Ala Ala Val Glu Glu Ser Cys Ala Glu Ile
                405                 410                 415

Met Arg Lys Glu Lys Asp Leu Arg Thr Leu Leu Ser Lys Glu Asp Val
            420                 425                 430

Lys Ile Arg Gly Asn Arg His Asn Thr Leu Ile Val Lys Asn Tyr Phe
        435                 440                 445

Asn Ala Trp Thr Val Phe Arg Asn Leu Ile Arg Ile Leu Arg Arg Lys
            450                 455                 460

Ser Glu Ala Glu Ile Asp Ser Asp Phe Tyr Asp Val Leu Asp Asp Ser
465                 470                 475                 480

Val Glu Val Leu Ser Leu Thr Tyr Lys Gly Glu Asn Leu Cys Arg Ser
                485                 490                 495

Tyr Ile Thr Lys Lys Ile Gly Ser Asp Leu Lys Pro Glu Ile Ala Thr
            500                 505                 510

Tyr Gly Ser Ala Leu Arg Pro Asn Ser Arg Trp Trp Ser Pro Gly Glu
        515                 520                 525

Lys Phe Asn Val Lys Phe His Thr Ile Val Arg Arg Asp Gly Arg Leu
            530                 535                 540

Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
                565                 570                 575

Thr Ile Phe Leu Pro Lys Leu Val Phe Lys Asp Pro Glu Ala Phe Phe
            580                 585                 590

Arg Asp Asn Pro Glu Ala Asp Glu Phe Val Phe Leu Ser Gly Met Lys
        595                 600                 605

Ala Pro Val Thr Ile Thr Arg Glu Thr Tyr Glu Ala Tyr Arg Tyr Lys
            610                 615                 620

Leu Tyr Thr Val Gly Lys Leu Arg Asp Gly Glu Val Ser Glu Glu Glu
625                 630                 635                 640

Tyr Lys Arg Ala Leu Leu Gln Val Leu Thr Ala Tyr Lys Glu Phe Leu
                645                 650                 655

Glu Asn Arg Met Ile Tyr Ala Asp Leu Asn Phe Gly Phe Lys Asp Leu
            660                 665                 670

Glu Glu Tyr Lys Asp Ser Ser Glu Phe Ile Lys Gln Val Glu Thr His
        675                 680                 685

Asn Thr Phe Met Cys Trp Ala Lys Val Ser Ser Gln Leu Asp Asp
            690                 695                 700

Leu Val Lys Ser Gly Asn Gly Leu Leu Phe Glu Ile Trp Ser Glu Arg
705                 710                 715                 720

Leu Glu Ser Tyr Tyr Lys Tyr Gly Asn Glu Lys Val Leu Arg Gly Tyr
                725                 730                 735

Glu Gly Val Leu Leu Ser Ile Leu Lys Asp Glu Asn Leu Val Ser Met
            740                 745                 750

Arg Thr Leu Leu Asn Ser Arg Pro Met Leu Val Tyr Arg Pro Lys Glu
        755                 760                 765

Ser Ser Lys Pro Met Val Val His Arg Asp Gly Ser Arg Val Val Asp
```

```
            770                 775                 780
Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
                805                 810                 815

Lys Ala Arg Lys Ile Leu Asp Asn Lys Val Lys Val Lys Val Leu
            820                 825                 830

Glu Ser Glu Arg Val Lys Trp Ser Lys Phe Tyr Asp Glu Gln Phe Ala
            835                 840                 845

Val Thr Phe Ser Val Lys Lys Asn Ala Asp Cys Leu Asp Thr Thr Lys
850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
                885                 890                 895

Lys Asn Gly Lys Val Leu Lys Gln Arg Ser Leu Asn Ile Ile Asn Asp
            900                 905                 910

Gly Ala Arg Asp Val Asp Trp Lys Glu Arg Phe Arg Gln Val Thr Lys
            915                 920                 925

Asp Arg Asn Glu Gly Tyr Asn Glu Trp Asp Tyr Ser Arg Thr Ser Asn
930                 935                 940

Asp Leu Lys Glu Val Tyr Leu Asn Tyr Ala Leu Lys Glu Ile Ala Glu
945                 950                 955                 960

Ala Val Ile Glu Tyr Asn Ala Ile Leu Ile Ile Glu Lys Met Ser Asn
                965                 970                 975

Ala Phe Lys Asp Lys Tyr Ser Phe Leu Asp Asp Val Thr Phe Lys Gly
            980                 985                 990

Phe Glu Thr Lys Leu Leu Ala Lys  Leu Ser Asp Leu His  Phe Arg Gly
            995                 1000                1005

Ile Lys  Asp Gly Glu Pro Cys  Ser Phe Thr Asn Pro  Leu Gln Leu
    1010                1015                1020

Cys Gln  Asn Asp Ser Asn Lys  Ile Leu Gln Asp Gly  Val Ile Phe
    1025                1030                1035

Met Val  Pro Asn Ser Met Thr  Arg Ser Leu Asp Pro  Asp Thr Gly
    1040                1045                1050

Phe Ile  Phe Ala Ile Asn Asp  His Asn Ile Arg Thr  Lys Lys Ala
    1055                1060                1065

Lys Leu  Asn Phe Leu Ser Lys  Phe Asp Gln Leu Lys  Val Ser Ser
    1070                1075                1080

Glu Gly  Cys Leu Ile Met Lys  Tyr Ser Gly Asp Ser  Leu Pro Thr
    1085                1090                1095

His Asn  Thr Asp Asn Arg Val  Trp Asn Cys Cys Cys  Asn His Pro
    1100                1105                1110

Ile Thr  Asn Tyr Asp Arg Glu  Thr Lys Lys Val Glu  Phe Ile Glu
    1115                1120                1125

Glu Pro  Val Glu Glu Leu Ser  Arg Val Leu Glu Glu  Asn Gly Ile
    1130                1135                1140

Glu Thr  Asp Thr Glu Leu Asn  Lys Leu Asn Glu Arg  Glu Asn Val
    1145                1150                1155

Pro Gly  Lys Val Val Asp Ala  Ile Tyr Ser Leu Val  Leu Asn Tyr
    1160                1165                1170

Leu Arg  Gly Thr Val Ser Gly  Val Ala Gly Gln Arg  Ala Val Tyr
    1175                1180                1185
```

```
Tyr Ser Pro Val Thr Gly Lys Lys Tyr Asp Ile Ser Phe Ile Gln
        1190            1195            1200

Ala Met Asn Leu Asn Arg Lys Cys Asp Tyr Tyr Arg Ile Gly Ser
        1205            1210            1215

Lys Glu Arg Gly Glu Trp Thr Asp Phe Val Ala Gln Leu Ile Asn
        1220            1225            1230

Lys Arg Pro Ala Ala Thr Lys Lys Ala Gly Gln Ala Lys Lys Lys
        1235            1240            1245

Lys Gly Ser Tyr Pro Tyr Asp Val Pro Asp Tyr Ala Tyr Pro Tyr
        1250            1255            1260

Asp Val Pro Asp Tyr Ala Tyr Pro Tyr Asp Val Pro Asp Tyr Ala
        1265            1270            1275

<210> SEQ ID NO 30
<211> LENGTH: 1286
<212> TYPE: PRT
<213> ORGANISM: Butyrivibrio proteoclasticus

<400> SEQUENCE: 30

Met Leu Leu Tyr Glu Asn Tyr Thr Lys Arg Asn Gln Ile Thr Lys Ser
1               5                   10                  15

Leu Arg Leu Glu Leu Arg Pro Gln Gly Lys Thr Leu Arg Asn Ile Lys
                20                  25                  30

Glu Leu Asn Leu Leu Glu Gln Asp Lys Ala Ile Tyr Ala Leu Leu Glu
            35                  40                  45

Arg Leu Lys Pro Val Ile Asp Glu Gly Ile Lys Asp Ile Ala Arg Asp
        50                  55                  60

Thr Leu Lys Asn Cys Glu Leu Ser Phe Glu Lys Leu Tyr Glu His Phe
65                  70                  75                  80

Leu Ser Gly Asp Lys Lys Ala Tyr Ala Lys Glu Ser Glu Arg Leu Lys
                85                  90                  95

Lys Glu Ile Val Lys Thr Leu Ile Lys Asn Leu Pro Glu Gly Ile Gly
                100                 105                 110

Lys Ile Ser Glu Ile Asn Ser Ala Lys Tyr Leu Asn Gly Val Leu Tyr
            115                 120                 125

Asp Phe Ile Asp Lys Thr His Lys Asp Ser Glu Glu Lys Gln Asn Ile
        130                 135                 140

Leu Ser Asp Ile Leu Glu Thr Lys Gly Tyr Leu Ala Leu Phe Ser Lys
145                 150                 155                 160

Phe Leu Thr Ser Arg Ile Thr Thr Leu Glu Gln Ser Met Pro Lys Arg
                165                 170                 175

Val Ile Glu Asn Phe Glu Ile Tyr Ala Ala Asn Ile Pro Lys Met Gln
                180                 185                 190

Asp Ala Leu Glu Arg Gly Ala Val Ser Phe Ala Ile Glu Tyr Glu Ser
            195                 200                 205

Ile Cys Ser Val Asp Tyr Tyr Asn Gln Ile Leu Ser Gln Glu Asp Ile
        210                 215                 220

Asp Ser Tyr Asn Arg Leu Ile Ser Gly Ile Met Asp Glu Asp Gly Ala
225                 230                 235                 240

Lys Glu Lys Gly Ile Asn Gln Thr Ile Ser Glu Lys Asn Ile Lys Ile
                245                 250                 255

Lys Ser Glu His Leu Glu Glu Lys Pro Phe Arg Ile Leu Lys Gln Leu
                260                 265                 270

His Lys Gln Ile Leu Glu Glu Arg Glu Lys Ala Phe Thr Ile Asp His
```

```
                275                 280                 285
Ile Asp Ser Asp Glu Glu Val Gln Val Thr Lys Glu Ala Phe Glu
290                 295                 300
Gln Thr Lys Glu Gln Trp Glu Asn Ile Lys Lys Ile Asn Gly Phe Tyr
305                 310                 315                 320
Ala Lys Asp Pro Gly Asp Ile Thr Leu Phe Ile Val Val Gly Pro Asn
                325                 330                 335
Gln Thr His Val Leu Ser Gln Leu Ile Tyr Gly Glu His Asp Arg Ile
                340                 345                 350
Arg Leu Leu Leu Glu Glu Tyr Glu Lys Asn Thr Leu Glu Val Leu Pro
                355                 360                 365
Arg Arg Thr Lys Ser Glu Lys Ala Arg Tyr Asp Lys Phe Val Asn Ala
                370                 375                 380
Val Pro Lys Lys Val Ala Lys Glu Ser His Thr Phe Asp Gly Leu Gln
385                 390                 395                 400
Lys Met Thr Gly Asp Asp Arg Leu Phe Ile Leu Tyr Arg Asp Glu Leu
                405                 410                 415
Ala Arg Asn Tyr Met Arg Ile Lys Glu Ala Tyr Gly Thr Phe Glu Arg
                420                 425                 430
Asp Ile Leu Lys Ser Arg Arg Gly Ile Lys Gly Asn Arg Asp Val Gln
                435                 440                 445
Glu Ser Leu Val Ser Phe Tyr Asp Glu Leu Thr Lys Phe Arg Ser Ala
450                 455                 460
Leu Arg Ile Ile Asn Ser Gly Asn Asp Glu Lys Ala Asp Pro Ile Phe
465                 470                 475                 480
Tyr Asn Thr Phe Asp Gly Ile Phe Glu Lys Ala Asn Arg Thr Tyr Lys
                485                 490                 495
Ala Glu Asn Leu Cys Arg Asn Tyr Val Thr Lys Ser Pro Ala Asp Asp
                500                 505                 510
Ala Arg Ile Met Ala Ser Cys Leu Gly Thr Pro Ala Arg Leu Arg Thr
                515                 520                 525
His Trp Trp Asn Gly Glu Glu Asn Phe Ala Ile Asn Asp Val Ala Met
                530                 535                 540
Ile Arg Arg Gly Asp Glu Tyr Tyr Tyr Phe Val Leu Thr Pro Asp Val
545                 550                 555                 560
Lys Pro Val Asp Leu Lys Thr Lys Asp Glu Thr Asp Ala Gln Ile Phe
                565                 570                 575
Val Gln Arg Lys Gly Ala Lys Ser Phe Leu Gly Leu Pro Lys Ala Leu
                580                 585                 590
Phe Lys Cys Ile Leu Glu Pro Tyr Phe Glu Ser Pro Glu His Lys Asn
                595                 600                 605
Asp Lys Asn Cys Val Ile Glu Glu Tyr Val Ser Lys Pro Leu Thr Ile
                610                 615                 620
Asp Arg Arg Ala Tyr Asp Ile Phe Lys Asn Gly Thr Phe Lys Lys Thr
625                 630                 635                 640
Asn Ile Gly Ile Asp Gly Leu Thr Glu Glu Lys Phe Lys Asp Asp Cys
                645                 650                 655
Arg Tyr Leu Ile Asp Val Tyr Lys Glu Phe Ile Ala Val Tyr Thr Arg
                660                 665                 670
Tyr Ser Cys Phe Asn Met Ser Gly Leu Lys Arg Ala Asp Glu Tyr Asn
                675                 680                 685
Asp Ile Gly Glu Phe Phe Ser Asp Val Asp Thr Arg Leu Cys Thr Met
                690                 695                 700
```

```
Glu Trp Ile Pro Val Ser Phe Glu Arg Ile Asn Asp Met Val Asp Lys
705                 710                 715                 720

Lys Glu Gly Leu Leu Phe Leu Val Arg Ser Met Phe Leu Tyr Asn Arg
                725                 730                 735

Pro Arg Lys Pro Tyr Glu Arg Thr Phe Ile Gln Leu Phe Ser Asp Ser
            740                 745                 750

Asn Met Glu His Thr Ser Met Leu Leu Asn Ser Arg Ala Met Ile Gln
                755                 760                 765

Tyr Arg Ala Ala Ser Leu Pro Arg Arg Val Thr His Lys Lys Gly Ser
770                 775                 780

Ile Leu Val Ala Leu Arg Asp Ser Asn Gly Glu His Ile Pro Met His
785                 790                 795                 800

Ile Arg Glu Ala Ile Tyr Lys Met Lys Asn Asn Phe Asp Ile Ser Ser
                805                 810                 815

Glu Asp Phe Ile Met Ala Lys Ala Tyr Leu Ala Glu His Asp Val Ala
                820                 825                 830

Ile Lys Lys Ala Asn Glu Asp Ile Ile Arg Asn Arg Tyr Thr Glu
                835                 840                 845

Asp Lys Phe Phe Leu Ser Leu Ser Tyr Thr Lys Asn Ala Asp Ile Ser
850                 855                 860

Ala Arg Thr Leu Asp Tyr Ile Asn Asp Lys Val Glu Glu Asp Thr Gln
865                 870                 875                 880

Asp Ser Arg Met Ala Val Ile Val Thr Arg Asn Leu Lys Asp Leu Thr
                885                 890                 895

Tyr Val Ala Val Val Asp Glu Lys Asn Asn Val Leu Glu Glu Lys Ser
                900                 905                 910

Leu Asn Glu Ile Asp Gly Val Asn Tyr Arg Glu Leu Leu Lys Glu Arg
                915                 920                 925

Thr Lys Ile Lys Tyr His Asp Lys Thr Arg Leu Trp Gln Tyr Asp Val
930                 935                 940

Ser Ser Lys Gly Leu Lys Glu Ala Tyr Val Glu Leu Ala Val Thr Gln
945                 950                 955                 960

Ile Ser Lys Leu Ala Thr Lys Tyr Asn Ala Val Val Val Glu Ser
                965                 970                 975

Met Ser Ser Thr Phe Lys Asp Lys Phe Ser Phe Leu Asp Glu Gln Ile
                980                 985                 990

Phe Lys Ala Phe Glu Ala Arg Leu Cys Ala Arg Met Ser Asp Leu Ser
            995                 1000                1005

Phe Asn Thr Ile Lys Glu Gly Glu Ala Gly Ser Ile Ser Asn Pro
            1010                1015                1020

Ile Gln Val Ser Asn Asn Gly Asn Ser Tyr Gln Asp Gly Val
        1025                1030                1035

Ile Tyr Phe Leu Asn Asn Ala Tyr Thr Arg Thr Leu Cys Pro Asp
        1040                1045                1050

Thr Gly Phe Val Asp Val Phe Asp Lys Thr Arg Leu Ile Thr Met
        1055                1060                1065

Gln Ser Lys Arg Gln Phe Phe Ala Lys Met Lys Asp Ile Arg Ile
        1070                1075                1080

Asp Asp Gly Glu Met Leu Phe Thr Phe Asn Leu Glu Glu Tyr Pro
        1085                1090                1095

Thr Lys Arg Leu Leu Asp Arg Lys Glu Trp Thr Val Lys Ile Ala
        1100                1105                1110
```

-continued

```
Gly Asp Gly Ser Tyr Phe Asp Lys Asp Lys Gly Glu Tyr Val Tyr
    1115                1120                1125

Val Asn Asp Ile Val Arg Glu Gln Ile Ile Pro Ala Leu Leu Glu
    1130                1135                1140

Asp Lys Ala Val Phe Asp Gly Asn Met Ala Glu Lys Phe Leu Asp
    1145                1150                1155

Lys Thr Ala Ile Ser Gly Lys Ser Val Glu Leu Ile Tyr Lys Trp
    1160                1165                1170

Phe Ala Asn Ala Leu Tyr Gly Ile Ile Thr Lys Lys Asp Gly Glu
    1175                1180                1185

Lys Ile Tyr Arg Ser Pro Ile Thr Gly Thr Glu Ile Asp Val Ser
    1190                1195                1200

Lys Asn Thr Thr Tyr Asn Phe Gly Lys Lys Phe Met Phe Lys Gln
    1205                1210                1215

Glu Tyr Arg Gly Asp Gly Asp Phe Leu Asp Ala Phe Leu Asn Tyr
    1220                1225                1230

Met Gln Ala Gln Asp Ile Ala Val Lys Arg Pro Ala Ala Thr Lys
    1235                1240                1245

Lys Ala Gly Gln Ala Lys Lys Lys Gly Ser Tyr Pro Tyr Asp
    1250                1255                1260

Val Pro Asp Tyr Ala Tyr Pro Tyr Asp Val Pro Asp Tyr Ala Tyr
    1265                1270                1275

Pro Tyr Asp Val Pro Asp Tyr Ala
    1280                1285

<210> SEQ ID NO 31
<211> LENGTH: 1522
<212> TYPE: PRT
<213> ORGANISM: Peregrinibacteria bacterium

<400> SEQUENCE: 31

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
            20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
    50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
                85                  90                  95

Leu Asn Asp Ser Glu Lys Lys Leu Arg Asn Lys Ile Gly Glu Thr Phe
            100                 105                 110

Asn Lys Ala Gly Glu Lys Trp Lys Lys Glu Lys Tyr Pro Gln Tyr Glu
        115                 120                 125

Trp Lys Lys Gly Ser Lys Ile Ala Asn Gly Ala Asp Ile Leu Ser Cys
    130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
                165                 170                 175

Gly Gly Phe Asn Gln Asn Arg Ala Asn Tyr Tyr Glu Thr Lys Lys Glu
            180                 185                 190
```

```
Ala Ser Thr Ala Val Ala Thr Arg Ile Val His Glu Asn Leu Pro Lys
        195                 200                 205

Phe Cys Asp Asn Val Ile Gln Phe Lys His Ile Ile Lys Arg Lys Lys
    210                 215                 220

Asp Gly Thr Val Glu Lys Thr Glu Arg Lys Thr Glu Tyr Leu Asn Ala
225                 230                 235                 240

Tyr Gln Tyr Leu Lys Asn Asn Lys Ile Thr Gln Ile Lys Asp Ala
                245                 250                 255

Glu Thr Glu Lys Met Ile Glu Ser Thr Pro Ile Ala Glu Lys Ile Phe
                260                 265                 270

Asp Val Tyr Tyr Phe Ser Ser Cys Leu Ser Gln Lys Gln Ile Glu Glu
                275                 280                 285

Tyr Asn Arg Ile Ile Gly His Tyr Asn Leu Leu Ile Asn Leu Tyr Asn
            290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
                340                 345                 350

Glu Ala Asn Lys Ser Arg Asn Glu Gly Lys Glu Ser His Ser Val Glu
                355                 360                 365

Glu Ile Ile Asn Lys Ala Gln Glu Ala Ile Asn Lys Tyr Phe Lys Ser
            370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                405                 410                 415

Met Asn Thr Ile Ser Asp Lys Tyr Phe Ala Asn Tyr His Asp Leu Gln
                420                 425                 430

Asp Arg Leu Lys Glu Ala Lys Val Phe Gln Lys Ala Asp Lys Lys Ser
            435                 440                 445

Glu Asp Asp Ile Lys Ile Pro Glu Ala Ile Glu Leu Ser Gly Leu Phe
450                 455                 460

Gly Val Leu Asp Ser Leu Ala Asp Trp Gln Thr Thr Leu Phe Lys Ser
465                 470                 475                 480

Ser Ile Leu Ser Asn Glu Asp Lys Leu Lys Ile Ile Thr Asp Ser Gln
                485                 490                 495

Thr Pro Ser Glu Ala Leu Leu Lys Met Ile Phe Asn Asp Ile Glu Lys
                500                 505                 510

Asn Met Glu Ser Phe Leu Lys Glu Thr Asn Asp Ile Ile Thr Leu Lys
            515                 520                 525

Lys Tyr Lys Gly Asn Lys Glu Gly Thr Glu Lys Ile Lys Gln Trp Phe
                530                 535                 540

Asp Tyr Thr Leu Ala Ile Asn Arg Met Leu Lys Tyr Phe Leu Val Lys
545                 550                 555                 560

Glu Asn Lys Ile Lys Gly Asn Ser Leu Asp Thr Asn Ile Ser Glu Ala
                565                 570                 575

Leu Lys Thr Leu Ile Tyr Ser Asp Asp Ala Glu Trp Phe Lys Trp Tyr
            580                 585                 590

Asp Ala Leu Arg Asn Tyr Leu Thr Gln Lys Pro Gln Asp Glu Ala Lys
                595                 600                 605
```

```
Glu Asn Lys Leu Lys Leu Asn Phe Asp Asn Pro Ser Leu Ala Gly Gly
    610                 615                 620

Trp Asp Val Asn Lys Glu Cys Ser Asn Phe Cys Val Ile Leu Lys Asp
625                 630                 635                 640

Lys Asn Glu Lys Lys Tyr Leu Ala Ile Met Lys Lys Gly Glu Asn Thr
                645                 650                 655

Leu Phe Gln Lys Glu Trp Thr Glu Gly Arg Gly Lys Asn Leu Thr Lys
            660                 665                 670

Lys Ser Asn Pro Leu Phe Glu Ile Asn Asn Cys Glu Ile Leu Ser Lys
        675                 680                 685

Met Glu Tyr Asp Phe Trp Ala Asp Val Ser Lys Met Ile Pro Lys Cys
    690                 695                 700

Ser Thr Gln Leu Lys Ala Val Val Asn His Phe Lys Gln Ser Asp Asn
705                 710                 715                 720

Glu Phe Ile Phe Pro Ile Gly Tyr Lys Val Thr Ser Gly Glu Lys Phe
                725                 730                 735

Arg Glu Glu Cys Lys Ile Ser Lys Gln Asp Phe Glu Leu Asn Asn Lys
            740                 745                 750

Val Phe Asn Lys Asn Glu Leu Ser Val Thr Ala Met Arg Tyr Asp Leu
        755                 760                 765

Ser Ser Thr Gln Glu Lys Gln Tyr Ile Lys Ala Phe Gln Lys Glu Tyr
770                 775                 780

Trp Glu Leu Leu Phe Lys Gln Glu Lys Arg Asp Thr Lys Leu Thr Asn
785                 790                 795                 800

Asn Glu Ile Phe Asn Glu Trp Ile Asn Phe Cys Asn Lys Lys Tyr Ser
                805                 810                 815

Glu Leu Leu Ser Trp Glu Arg Lys Tyr Lys Asp Ala Leu Thr Asn Trp
            820                 825                 830

Ile Asn Phe Cys Lys Tyr Phe Leu Ser Lys Tyr Pro Lys Thr Thr Leu
        835                 840                 845

Phe Asn Tyr Ser Phe Lys Glu Ser Glu Asn Tyr Asn Ser Leu Asp Glu
850                 855                 860

Phe Tyr Arg Asp Val Asp Ile Cys Ser Tyr Lys Leu Asn Ile Asn Thr
865                 870                 875                 880

Thr Ile Asn Lys Ser Ile Leu Asp Arg Leu Val Glu Glu Gly Lys Leu
                885                 890                 895

Tyr Leu Phe Glu Ile Lys Asn Gln Asp Ser Asn Asp Gly Lys Ser Ile
            900                 905                 910

Gly His Lys Asn Leu His Thr Ile Tyr Trp Asn Ala Ile Phe Glu
        915                 920                 925

Asn Phe Asp Asn Arg Pro Lys Leu Asn Gly Glu Ala Glu Ile Phe Tyr
930                 935                 940

Arg Lys Ala Ile Ser Lys Asp Lys Leu Gly Ile Val Lys Gly Lys Lys
945                 950                 955                 960

Thr Lys Asn Gly Thr Glu Ile Ile Lys Asn Tyr Arg Phe Ser Lys Glu
                965                 970                 975

Lys Phe Ile Leu His Val Pro Ile Thr Leu Asn Phe Cys Ser Asn Asn
            980                 985                 990

Glu Tyr Val Asn Asp Ile Val Asn  Thr Lys Phe Tyr Asn  Phe Ser Asn
        995                 1000                 1005

Leu His  Phe Leu Gly Ile Asp  Arg Gly Glu Lys His  Leu Ala Tyr
        1010                 1015                 1020

Tyr Ser  Leu Val Asn Lys Asn  Gly Glu Ile Val Asp  Gln Gly Thr
```

-continued

```
              1025                1030                1035
Leu Asn Leu Pro Phe Thr Asp Lys Asp Gly Asn Gln Arg Ser Ile
          1040                1045                1050
Lys Lys Glu Lys Tyr Phe Tyr Asn Lys Gln Glu Asp Lys Trp Glu
          1055                1060                1065
Ala Lys Glu Val Asp Cys Trp Asn Tyr Asn Asp Leu Leu Asp Ala
          1070                1075                1080
Met Ala Ser Asn Arg Asp Met Ala Arg Lys Asn Trp Gln Arg Ile
          1085                1090                1095
Gly Thr Ile Lys Glu Ala Lys Asn Gly Tyr Val Ser Leu Val Ile
          1100                1105                1110
Arg Lys Ile Ala Asp Leu Ala Val Asn Asn Glu Arg Pro Ala Phe
          1115                1120                1125
Ile Val Leu Glu Asp Leu Asn Thr Gly Phe Lys Arg Ser Arg Gln
          1130                1135                1140
Lys Ile Asp Lys Ser Val Tyr Gln Lys Phe Glu Leu Ala Leu Ala
          1145                1150                1155
Lys Lys Leu Asn Phe Leu Val Asp Lys Asn Ala Lys Arg Asp Glu
          1160                1165                1170
Ile Gly Ser Pro Thr Lys Ala Leu Gln Leu Thr Pro Pro Val Asn
          1175                1180                1185
Asn Tyr Gly Asp Ile Glu Asn Lys Lys Gln Ala Gly Ile Met Leu
          1190                1195                1200
Tyr Thr Arg Ala Asn Tyr Thr Ser Gln Thr Asp Pro Ala Thr Gly
          1205                1210                1215
Trp Arg Lys Thr Ile Tyr Leu Lys Ala Gly Pro Glu Glu Thr Thr
          1220                1225                1230
Tyr Lys Lys Asp Gly Lys Ile Lys Asn Lys Ser Val Lys Asp Gln
          1235                1240                1245
Ile Ile Glu Thr Phe Thr Asp Ile Gly Phe Asp Gly Lys Asp Tyr
          1250                1255                1260
Tyr Phe Glu Tyr Asp Lys Gly Glu Phe Val Asp Glu Lys Thr Gly
          1265                1270                1275
Glu Ile Lys Pro Lys Lys Trp Arg Leu Tyr Ser Gly Glu Asn Gly
          1280                1285                1290
Lys Ser Leu Asp Arg Phe Arg Gly Glu Arg Glu Lys Asp Lys Tyr
          1295                1300                1305
Glu Trp Lys Ile Asp Lys Ile Asp Ile Val Lys Ile Leu Asp Asp
          1310                1315                1320
Leu Phe Val Asn Phe Asp Lys Asn Ile Ser Leu Leu Lys Gln Leu
          1325                1330                1335
Lys Glu Gly Val Glu Leu Thr Arg Asn Asn Glu His Gly Thr Gly
          1340                1345                1350
Glu Ser Leu Arg Phe Ala Ile Asn Leu Ile Gln Gln Ile Arg Asn
          1355                1360                1365
Thr Gly Asn Asn Glu Arg Asp Asn Asp Phe Ile Leu Ser Pro Val
          1370                1375                1380
Arg Asp Glu Asn Gly Lys His Phe Asp Ser Arg Glu Tyr Trp Asp
          1385                1390                1395
Lys Glu Thr Lys Gly Glu Lys Ile Ser Met Pro Ser Ser Gly Asp
          1400                1405                1410
Ala Asn Gly Ala Phe Asn Ile Ala Arg Lys Gly Ile Ile Met Asn
          1415                1420                1425
```

```
Ala His Ile Leu Ala Asn Ser Asp Ser Lys Asp Leu Ser Leu Phe
    1430                1435                1440

Val Ser Asp Glu Glu Trp Asp Leu His Leu Asn Asn Lys Thr Glu
    1445                1450                1455

Trp Lys Lys Gln Leu Asn Ile Phe Ser Ser Arg Lys Ala Met Ala
    1460                1465                1470

Lys Arg Lys Lys Lys Arg Pro Ala Ala Thr Lys Lys Ala Gly Gln
    1475                1480                1485

Ala Lys Lys Lys Lys Gly Ser Tyr Pro Tyr Asp Val Pro Asp Tyr
    1490                1495                1500

Ala Tyr Pro Tyr Asp Val Pro Asp Tyr Ala Tyr Pro Tyr Asp Val
    1505                1510                1515

Pro Asp Tyr Ala
    1520

<210> SEQ ID NO 32
<211> LENGTH: 1397
<212> TYPE: PRT
<213> ORGANISM: Parcubacteria bacterium

<400> SEQUENCE: 32

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
                20                  25                  30

Lys Ile Asn Lys Val Phe Glu Lys Asp Gln Thr Ile Asp Asp Ser Tyr
            35                  40                  45

Asn Gln Ala Lys Phe Tyr Phe Asp Ser Leu His Gln Lys Phe Ile Asp
        50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
                100                 105                 110

Arg Leu Gln Lys Glu Ile Asn Asp Ala Glu Asp Ile Ile Gln Lys Glu
            115                 120                 125

Lys Glu Lys Ile Tyr Lys Asp Val Arg Thr Leu Phe Asp Asn Glu Ala
        130                 135                 140

Glu Ser Trp Lys Thr Tyr Tyr Gln Glu Arg Glu Val Asp Gly Lys Lys
145                 150                 155                 160

Ile Thr Phe Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
            180                 185                 190

Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
```

```
                260                 265                 270
Lys Asn Asn His Thr Asp Leu Gly Phe Asp Glu Glu Asn Ile Phe Glu
            275                 280                 285

Ile Glu Arg Tyr Lys Asn Cys Leu Leu Gln Arg Glu Ile Glu His Ile
        290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400

Glu Phe Glu Ser Glu Tyr Gly Ile Tyr Leu Lys Asn Lys Ala Ile
                405                 410                 415

Asn Thr Ile Ser Arg Arg Trp Phe Val Ser Asp Arg Asp Phe Glu Leu
            420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
    450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
            500                 505                 510

Lys Leu Leu Gly Tyr Asp Ser Cys Leu Lys Ile Ala Lys Gln Leu Gly
        515                 520                 525

Ile Phe Pro Gln Glu Lys Glu Ala Arg Glu Lys Ala Thr Ala Val Ile
    530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605

Asp Glu Asp Lys Ile Lys Leu Asn Phe Glu Asn Gly Ala Leu Leu Lys
    610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
            660                 665                 670

Gln Lys Met Ile Tyr Lys Gln Ile Ala Asp Ala Ser Lys Asp Val Pro
        675                 680                 685
```

-continued

Arg Leu Leu Leu Thr Ser Lys Lys Ala Met Glu Lys Phe Lys Pro Ser
690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
            725                 730                 735

Asn Cys Ile Pro Gln Tyr Ser Asn Trp Ser Phe Tyr Asp Phe Gln Phe
            740                 745                 750

Gln Asp Thr Gly Lys Tyr Gln Asn Ile Lys Glu Phe Thr Asp Asp Val
            755                 760                 765

Gln Lys Tyr Gly Tyr Lys Ile Ser Phe Arg Asp Ile Asp Glu Tyr
770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
            805                 810                 815

Leu Tyr Phe Glu His Ile Leu Ser Ala Glu Asn Leu Asn Asp Pro Val
            820                 825                 830

Phe Lys Leu Ser Gly Met Ala Glu Ile Phe Gln Arg Gln Pro Ser Val
            835                 840                 845

Asn Glu Arg Glu Lys Ile Thr Thr Gln Lys Asn Gln Cys Ile Leu Asp
850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
            885                 890                 895

Gln Val Gln Phe Asn Lys Ile Ile Asn Gln Arg Ile Ser Ser Ser Asp
            900                 905                 910

Asn Glu Met Arg Val Asn Val Ile Gly Ile Asp Arg Gly Glu Lys Asn
            915                 920                 925

Leu Leu Tyr Tyr Ser Val Val Lys Gln Asn Gly Glu Ile Ile Glu Gln
930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
            965                 970                 975

Val Lys Ile Lys Asp Leu Lys Lys Gly Tyr Ile Ser His Val Ile His
            980                 985                 990

Lys Ile Cys Gln Leu Ile Glu Lys Tyr Ser Ala Ile Val Val Leu Glu
            995                 1000                1005

Asp Leu Asn Met Arg Phe Lys Gln Ile Arg Gly Gly Ile Glu Arg
    1010                1015                1020

Ser Val Tyr Gln Gln Phe Glu Lys Ala Leu Ile Asp Lys Leu Gly
    1025                1030                1035

Tyr Leu Val Phe Lys Asp Asn Arg Asp Leu Arg Ala Pro Gly Gly
    1040                1045                1050

Val Leu Asn Gly Tyr Gln Leu Ser Ala Pro Phe Val Ser Phe Glu
    1055                1060                1065

Lys Met Arg Lys Gln Thr Gly Ile Leu Phe Tyr Thr Gln Ala Glu
    1070                1075                1080

Tyr Thr Ser Lys Thr Asp Pro Ile Thr Gly Phe Arg Lys Asn Val
    1085                1090                1095

Tyr Ile Ser Asn Ser Ala Ser Leu Asp Lys Ile Lys Glu Ala Val
    1100                1105                1110

Lys Lys Phe Asp Ala Ile Gly Trp Asp Gly Lys Glu Gln Ser Tyr
    1115                1120                1125

Phe Phe Lys Tyr Asn Pro Tyr Asn Leu Ala Asp Glu Lys Tyr Lys
    1130                1135                1140

Asn Ser Thr Val Ser Lys Glu Trp Ala Ile Phe Ala Ser Ala Pro
    1145                1150                1155

Arg Ile Arg Arg Gln Lys Gly Glu Asp Gly Tyr Trp Lys Tyr Asp
    1160                1165                1170

Arg Val Lys Val Asn Glu Glu Phe Glu Lys Leu Leu Lys Val Trp
    1175                1180                1185

Asn Phe Val Asn Pro Lys Ala Thr Asp Ile Lys Gln Glu Ile Ile
    1190                1195                1200

Lys Lys Glu Lys Ala Gly Asp Leu Gln Gly Glu Lys Glu Leu Asp
    1205                1210                1215

Gly Arg Leu Arg Asn Phe Trp His Ser Phe Ile Tyr Leu Phe Asn
    1220                1225                1230

Leu Val Leu Glu Leu Arg Asn Ser Phe Ser Leu Gln Ile Lys Ile
    1235                1240                1245

Lys Ala Gly Glu Val Ile Ala Val Asp Glu Gly Val Asp Phe Ile
    1250                1255                1260

Ala Ser Pro Val Lys Pro Phe Phe Thr Thr Pro Asn Pro Tyr Ile
    1265                1270                1275

Pro Ser Asn Leu Cys Trp Leu Ala Val Glu Asn Ala Asp Ala Asn
    1280                1285                1290

Gly Ala Tyr Asn Ile Ala Arg Lys Gly Val Met Ile Leu Lys Lys
    1295                1300                1305

Ile Arg Glu His Ala Lys Lys Asp Pro Glu Phe Lys Lys Leu Pro
    1310                1315                1320

Asn Leu Phe Ile Ser Asn Ala Glu Trp Asp Glu Ala Ala Arg Asp
    1325                1330                1335

Trp Gly Lys Tyr Ala Gly Thr Thr Ala Leu Asn Leu Asp His Lys
    1340                1345                1350

Arg Pro Ala Ala Thr Lys Lys Ala Gly Gln Ala Lys Lys Lys Lys
    1355                1360                1365

Gly Ser Tyr Pro Tyr Asp Val Pro Asp Tyr Ala Pro Tyr Asp
    1370                1375                1380

Val Pro Asp Tyr Ala Tyr Pro Tyr Asp Val Pro Asp Tyr Ala
    1385                1390                1395

<210> SEQ ID NO 33
<211> LENGTH: 1295
<212> TYPE: PRT
<213> ORGANISM: Smithella sp.

<400> SEQUENCE: 33

Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
                20                  25                  30

Glu Gln Lys Gly Leu Leu Lys Lys Asp Glu Asp Arg Ala Glu Lys Tyr
            35                  40                  45

Lys Lys Val Lys Asn Ile Ile Asp Glu Tyr His Lys Asp Phe Ile Glu
        50                  55                  60

```
Lys Ser Leu Asn Gly Leu Lys Leu Asp Gly Leu Glu Lys Tyr Lys Thr
65              70                  75                  80

Leu Tyr Leu Lys Gln Glu Lys Asp Asp Lys Asp Lys Lys Ala Phe Asp
                85                  90                  95

Lys Glu Lys Glu Asn Leu Arg Lys Gln Ile Ala Asn Ala Phe Arg Asn
                100                 105                 110

Asn Glu Lys Phe Lys Thr Leu Phe Ala Lys Glu Leu Ile Lys Asn Asp
                115                 120                 125

Leu Met Ser Phe Ala Cys Glu Glu Asp Lys Lys Asn Val Lys Glu Phe
130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

His Glu Asn Leu Pro Lys Phe Ile Asp Asn Ile Lys Ile Phe Glu Lys
                180                 185                 190

Met Lys Lys Glu Ala Pro Glu Leu Leu Ser Pro Phe Asn Gln Thr Leu
                195                 200                 205

Lys Asp Met Lys Asp Val Ile Lys Gly Thr Thr Leu Glu Glu Ile Phe
210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
                260                 265                 270

Thr Asp Lys Lys Arg Gln Pro Lys Phe Lys Gln Leu Tyr Lys Gln
                275                 280                 285

Ile Leu Ser Asp Arg Gln Ser Leu Ser Phe Ile Ala Glu Ala Phe Lys
                290                 295                 300

Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
                325                 330                 335

Ile Lys Asn Ala Val Ser Asn Leu Glu Ser Phe Asn Leu Thr Lys Met
                340                 345                 350

Tyr Phe Arg Ser Gly Ala Ser Leu Thr Asp Val Ser Arg Lys Val Phe
                355                 360                 365

Gly Glu Trp Ser Ile Ile Asn Arg Ala Leu Asp Asn Tyr Tyr Ala Thr
                370                 375                 380

Thr Tyr Pro Ile Lys Pro Arg Glu Lys Ser Glu Lys Tyr Glu Glu Arg
385                 390                 395                 400

Lys Glu Lys Trp Leu Lys Gln Asp Phe Asn Val Ser Leu Ile Gln Thr
                405                 410                 415

Ala Ile Asp Glu Tyr Asp Asn Glu Thr Val Lys Gly Lys Asn Ser Gly
                420                 425                 430

Lys Val Ile Ala Asp Tyr Phe Ala Lys Phe Cys Asp Asp Lys Glu Thr
                435                 440                 445

Asp Leu Ile Gln Lys Val Asn Glu Gly Tyr Ile Ala Val Lys Asp Leu
                450                 455                 460

Leu Asn Thr Pro Cys Pro Glu Asn Glu Lys Leu Gly Ser Asn Lys Asp
465                 470                 475                 480
```

```
Gln Val Lys Gln Ile Lys Ala Phe Met Asp Ser Ile Met Asp Ile Met
                485                 490                 495

His Phe Val Arg Pro Leu Ser Leu Lys Asp Thr Asp Lys Glu Lys Asp
            500                 505                 510

Glu Thr Phe Tyr Ser Leu Phe Thr Pro Leu Tyr Asp His Leu Thr Gln
            515                 520                 525

Thr Ile Ala Leu Tyr Asn Lys Val Arg Asn Tyr Leu Thr Gln Lys Pro
            530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
                565                 570                 575

Arg Lys Asp Asn Leu Tyr Tyr Leu Gly Ile Met Asp Lys Arg His Asn
                580                 585                 590

Arg Ile Phe Arg Asn Val Pro Lys Ala Asp Lys Lys Asp Phe Cys Tyr
            595                 600                 605

Glu Lys Met Val Tyr Lys Leu Leu Pro Gly Ala Asn Lys Met Leu Pro
            610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
                645                 650                 655

Phe Asn Leu Asn His Cys His Lys Leu Ile Asp Phe Phe Lys Asp Ser
                660                 665                 670

Ile Asn Lys His Glu Asp Trp Lys Asn Phe Asp Phe Arg Phe Ser Ala
            675                 680                 685

Thr Ser Thr Tyr Ala Asp Leu Ser Gly Phe Tyr His Glu Val Glu His
            690                 695                 700

Gln Gly Tyr Lys Ile Ser Phe Gln Ser Val Ala Asp Ser Phe Ile Asp
705                 710                 715                 720

Asp Leu Val Asn Glu Gly Lys Leu Tyr Leu Phe Gln Ile Tyr Asn Lys
                725                 730                 735

Asp Phe Ser Pro Phe Ser Lys Gly Lys Pro Asn Leu His Thr Leu Tyr
            740                 745                 750

Trp Lys Met Leu Phe Asp Glu Asn Asn Leu Lys Asp Val Val Tyr Lys
            755                 760                 765

Leu Asn Gly Glu Ala Glu Val Phe Tyr Arg Lys Lys Ser Ile Ala Glu
770                 775                 780

Lys Asn Thr Thr Ile His Lys Ala Asn Glu Ser Ile Ile Asn Lys Asn
785                 790                 795                 800

Pro Asp Asn Pro Lys Ala Thr Ser Thr Phe Asn Tyr Asp Ile Val Lys
                805                 810                 815

Asp Lys Arg Tyr Thr Ile Asp Lys Phe Gln Phe His Ile Pro Ile Thr
            820                 825                 830

Met Asn Phe Lys Ala Glu Gly Ile Phe Asn Met Asn Gln Arg Val Asn
            835                 840                 845

Gln Phe Leu Lys Ala Asn Pro Asp Ile Asn Ile Ile Gly Ile Asp Arg
            850                 855                 860

Gly Glu Arg His Leu Leu Tyr Tyr Ala Leu Ile Asn Gln Lys Gly Lys
865                 870                 875                 880

Ile Leu Lys Gln Asp Thr Leu Asn Val Ile Ala Asn Glu Lys Gln Lys
                885                 890                 895

Val Asp Tyr His Asn Leu Leu Asp Lys Lys Glu Gly Asp Arg Ala Thr
```

-continued

```
              900             905             910
Ala Arg Gln Glu Trp Gly Val Ile Glu Thr Ile Lys Glu Leu Lys Glu
        915             920             925
Gly Tyr Leu Ser Gln Val Ile His Lys Leu Thr Asp Leu Met Ile Glu
        930             935             940
Asn Asn Ala Ile Ile Val Met Glu Asp Leu Asn Phe Gly Phe Lys Arg
945             950             955             960
Gly Arg Gln Lys Val Glu Lys Gln Val Tyr Gln Lys Phe Glu Lys Met
            965             970             975
Leu Ile Asp Lys Leu Asn Tyr Leu Val Asp Lys Asn Lys Lys Ala Asn
            980             985             990
Glu Leu Gly Gly Leu Leu Asn Ala Phe Gln Leu Ala Asn Lys Phe Glu
        995             1000            1005
Ser Phe Gln Lys Met Gly Lys Gln Asn Gly Phe Ile Phe Tyr Val
    1010            1015            1020
Pro Ala Trp Asn Thr Ser Lys Thr Asp Pro Ala Thr Gly Phe Ile
    1025            1030            1035
Asp Phe Leu Lys Pro Arg Tyr Glu Asn Leu Asn Gln Ala Lys Asp
    1040            1045            1050
Phe Phe Glu Lys Phe Asp Ser Ile Arg Leu Asn Ser Lys Ala Asp
    1055            1060            1065
Tyr Phe Glu Phe Ala Phe Asp Phe Lys Asn Phe Thr Glu Lys Ala
    1070            1075            1080
Asp Gly Gly Arg Thr Lys Trp Thr Val Cys Thr Thr Asn Glu Asp
    1085            1090            1095
Arg Tyr Ala Trp Asn Arg Ala Leu Asn Asn Arg Gly Ser Gln
    1100            1105            1110
Glu Lys Tyr Asp Ile Thr Ala Glu Leu Lys Ser Leu Phe Asp Gly
    1115            1120            1125
Lys Val Asp Tyr Lys Ser Gly Lys Asp Leu Lys Gln Gln Ile Ala
    1130            1135            1140
Ser Gln Glu Ser Ala Asp Phe Phe Lys Ala Leu Met Lys Asn Leu
    1145            1150            1155
Ser Ile Thr Leu Ser Leu Arg His Asn Asn Gly Glu Lys Gly Asp
    1160            1165            1170
Asn Glu Gln Asp Tyr Ile Leu Ser Pro Val Ala Asp Ser Lys Gly
    1175            1180            1185
Arg Phe Phe Asp Ser Arg Lys Ala Asp Asp Met Pro Lys Asn
    1190            1195            1200
Ala Asp Ala Asn Gly Ala Tyr His Ile Ala Leu Lys Gly Leu Trp
    1205            1210            1215
Cys Leu Glu Gln Ile Ser Lys Thr Asp Asp Leu Lys Lys Val Lys
    1220            1225            1230
Leu Ala Ile Ser Asn Lys Glu Trp Leu Glu Phe Val Gln Thr Leu
    1235            1240            1245
Lys Gly Lys Arg Pro Ala Ala Thr Lys Lys Ala Gly Gln Ala Lys
    1250            1255            1260
Lys Lys Lys Gly Ser Tyr Pro Tyr Asp Val Pro Asp Tyr Ala Tyr
    1265            1270            1275
Pro Tyr Asp Val Pro Asp Tyr Ala Tyr Pro Tyr Asp Val Pro Asp
    1280            1285            1290
Tyr Ala
    1295
```

<210> SEQ ID NO 34
<211> LENGTH: 1352
<212> TYPE: PRT
<213> ORGANISM: Acidaminococcus sp.

<400> SEQUENCE: 34

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
```

```
              370                 375                 380
Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
                610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
                675                 680                 685

Lys Thr Thr Ser Ile Asp Leu Ser Ser Leu Arg Pro Ser Ser Gln Tyr
                690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750

Gly His His Gly Lys Pro Asn Leu His Thr Leu Tyr Trp Thr Gly Leu
                755                 760                 765

Phe Ser Pro Glu Asn Leu Ala Lys Thr Ser Ile Lys Leu Asn Gly Gln
                770                 775                 780

Ala Glu Leu Phe Tyr Arg Pro Lys Ser Arg Met Lys Arg Met Ala His
785                 790                 795                 800
```

-continued

```
Arg Leu Gly Glu Lys Met Leu Asn Lys Lys Leu Lys Asp Gln Lys Thr
                805                 810                 815
Pro Ile Pro Asp Thr Leu Tyr Gln Glu Leu Tyr Asp Tyr Val Asn His
                820                 825                 830
Arg Leu Ser His Asp Leu Ser Asp Glu Ala Arg Ala Leu Leu Pro Asn
                835                 840                 845
Val Ile Thr Lys Glu Val Ser His Glu Ile Ile Lys Asp Arg Arg Phe
            850                 855                 860
Thr Ser Asp Lys Phe Phe Phe His Val Pro Ile Thr Leu Asn Tyr Gln
865                 870                 875                 880
Ala Ala Asn Ser Pro Ser Lys Phe Asn Gln Arg Val Asn Ala Tyr Leu
                885                 890                 895
Lys Glu His Pro Glu Thr Pro Ile Ile Gly Ile Asp Arg Gly Glu Arg
                900                 905                 910
Asn Leu Ile Tyr Ile Thr Val Ile Asp Ser Thr Gly Lys Ile Leu Glu
                915                 920                 925
Gln Arg Ser Leu Asn Thr Ile Gln Gln Phe Asp Tyr Gln Lys Lys Leu
                930                 935                 940
Asp Asn Arg Glu Lys Glu Arg Val Ala Ala Arg Gln Ala Trp Ser Val
945                 950                 955                 960
Val Gly Thr Ile Lys Asp Leu Lys Gln Gly Tyr Leu Ser Gln Val Ile
                965                 970                 975
His Glu Ile Val Asp Leu Met Ile His Tyr Gln Ala Val Val Val Leu
                980                 985                 990
Glu Asn Leu Asn Phe Gly Phe Lys Ser Lys Arg Thr Gly Ile Ala Glu
                995                 1000                1005
Lys Ala Val Tyr Gln Gln Phe Glu Lys Met Leu Ile Asp Lys Leu
        1010                1015                1020
Asn Cys Leu Val Leu Lys Asp Tyr Pro Ala Glu Lys Val Gly Gly
        1025                1030                1035
Val Leu Asn Pro Tyr Gln Leu Thr Asp Gln Phe Thr Ser Phe Ala
        1040                1045                1050
Lys Met Gly Thr Gln Ser Gly Phe Leu Phe Tyr Val Pro Ala Pro
        1055                1060                1065
Tyr Thr Ser Lys Ile Asp Pro Leu Thr Gly Phe Val Asp Pro Phe
        1070                1075                1080
Val Trp Lys Thr Ile Lys Asn His Glu Ser Arg Lys His Phe Leu
        1085                1090                1095
Glu Gly Phe Asp Phe Leu His Tyr Asp Val Lys Thr Gly Asp Phe
        1100                1105                1110
Ile Leu His Phe Lys Met Asn Arg Asn Leu Ser Phe Gln Arg Gly
        1115                1120                1125
Leu Pro Gly Phe Met Pro Ala Trp Asp Ile Val Phe Glu Lys Asn
        1130                1135                1140
Glu Thr Gln Phe Asp Ala Lys Gly Thr Pro Phe Ile Ala Gly Lys
        1145                1150                1155
Arg Ile Val Pro Val Ile Glu Asn His Arg Phe Thr Gly Arg Tyr
        1160                1165                1170
Arg Asp Leu Tyr Pro Ala Asn Glu Leu Ile Ala Leu Leu Glu Glu
        1175                1180                1185
Lys Gly Ile Val Phe Arg Asp Gly Ser Asn Ile Leu Pro Lys Leu
        1190                1195                1200
```

-continued

```
Leu Glu Asn Asp Asp Ser His Ala Ile Asp Thr Met Val Ala Leu
1205                1210                1215

Ile Arg Ser Val Leu Gln Met Arg Asn Ser Asn Ala Ala Thr Gly
1220                1225                1230

Glu Asp Tyr Ile Asn Ser Pro Val Arg Asp Leu Asn Gly Val Cys
1235                1240                1245

Phe Asp Ser Arg Phe Gln Asn Pro Glu Trp Pro Met Asp Ala Asp
1250                1255                1260

Ala Asn Gly Ala Tyr His Ile Ala Leu Lys Gly Gln Leu Leu Leu
1265                1270                1275

Asn His Leu Lys Glu Ser Lys Asp Leu Lys Leu Gln Asn Gly Ile
1280                1285                1290

Ser Asn Gln Asp Trp Leu Ala Tyr Ile Gln Glu Leu Arg Asn Lys
1295                1300                1305

Arg Pro Ala Ala Thr Lys Lys Ala Gly Gln Ala Lys Lys Lys Lys
1310                1315                1320

Gly Ser Tyr Pro Tyr Asp Val Pro Asp Tyr Ala Tyr Pro Tyr Asp
1325                1330                1335

Val Pro Asp Tyr Ala Tyr Pro Tyr Asp Val Pro Asp Tyr Ala
1340                1345                1350

<210> SEQ ID NO 35
<211> LENGTH: 1251
<212> TYPE: PRT
<213> ORGANISM: Lachnospiraceae bacterium

<400> SEQUENCE: 35

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
                20                  25                  30

Asn Asn Ile Leu Glu Ser Asp Val Lys Arg Lys Gln Asn Tyr Glu His
            35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140

Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Glu Gln Asp
        195                 200                 205

Ser Leu Phe Ile Val Glu Thr Phe Asn Lys Thr Leu Thr Gln Asp Gly
    210                 215                 220
```

```
Ile Asp Thr Tyr Asn Ser Gln Val Gly Lys Ile Asn Ser Ser Ile Asn
225                 230                 235                 240

Leu Tyr Asn Gln Lys Asn Gln Lys Ala Asn Gly Phe Arg Lys Ile Pro
            245                 250                 255

Lys Met Lys Met Leu Tyr Lys Gln Ile Leu Ser Asp Arg Glu Glu Ser
            260                 265                 270

Phe Ile Asp Glu Phe Gln Ser Asp Glu Val Leu Ile Asp Asn Val Glu
            275                 280                 285

Ser Tyr Gly Ser Val Leu Ile Glu Ser Leu Lys Ser Ser Lys Val Ser
            290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Asn Ile Val Phe Glu Asn
            325                 330                 335

Trp Arg Thr Phe Asp Asp Leu Leu Asn Gln Glu Tyr Asp Leu Ala Asn
            340                 345                 350

Glu Asn Lys Lys Lys Asp Asp Lys Tyr Phe Glu Lys Arg Gln Lys Glu
            355                 360                 365

Leu Lys Lys Asn Lys Ser Tyr Ser Leu Glu His Leu Cys Asn Leu Ser
370                 375                 380

Glu Asp Ser Cys Asn Leu Ile Glu Asn Tyr Ile His Gln Ile Ser Asp
385                 390                 395                 400

Asp Ile Glu Asn Ile Ile Asn Asn Glu Thr Phe Leu Arg Ile Val
            405                 410                 415

Ile Asn Glu His Asp Arg Ser Arg Lys Leu Ala Lys Asn Arg Lys Ala
            420                 425                 430

Val Lys Ala Ile Lys Asp Phe Leu Asp Ser Ile Lys Val Leu Glu Arg
            435                 440                 445

Glu Leu Lys Leu Ile Asn Ser Ser Gly Gln Glu Leu Glu Lys Asp Leu
450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
            485                 490                 495

Ser Thr Glu Lys Val Lys Leu Asn Phe Asn Arg Ser Thr Leu Leu Asn
            500                 505                 510

Gly Trp Asp Arg Asn Lys Glu Thr Asp Asn Leu Gly Val Leu Leu Leu
            515                 520                 525

Lys Asp Gly Lys Tyr Tyr Leu Gly Ile Met Asn Thr Ser Ala Asn Lys
            530                 535                 540

Ala Phe Val Asn Pro Pro Val Ala Lys Thr Glu Lys Val Phe Lys Lys
545                 550                 555                 560

Val Asp Tyr Lys Leu Leu Pro Val Pro Asn Gln Met Leu Pro Lys Val
            565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
            595                 600                 605

Leu Glu Asp Cys His Asn Leu Ile Asp Phe Phe Lys Glu Ser Ile Ser
            610                 615                 620

Lys His Glu Asp Trp Ser Lys Phe Gly Phe Lys Phe Ser Asp Thr Ala
625                 630                 635                 640
```

```
Ser Tyr Asn Asp Ile Ser Glu Phe Tyr Arg Glu Val Glu Lys Gln Gly
                645                 650                 655
Tyr Lys Leu Thr Tyr Thr Asp Ile Asp Glu Thr Tyr Ile Asn Asp Leu
        660                 665                 670
Ile Glu Arg Asn Glu Leu Tyr Leu Phe Gln Ile Tyr Asn Lys Asp Phe
        675                 680                 685
Ser Met Tyr Ser Lys Gly Lys Leu Asn Leu His Thr Leu Tyr Phe Met
690                 695                 700
Met Leu Phe Asp Gln Arg Asn Ile Asp Asp Val Val Tyr Lys Leu Asn
705                 710                 715                 720
Gly Glu Ala Glu Val Phe Tyr Arg Pro Ala Ser Ile Ser Glu Asp Glu
                725                 730                 735
Leu Ile Ile His Lys Ala Gly Glu Glu Ile Lys Asn Lys Asn Pro Asn
                740                 745                 750
Arg Ala Arg Thr Lys Glu Thr Ser Thr Phe Ser Tyr Asp Ile Val Lys
                755                 760                 765
Asp Lys Arg Tyr Ser Lys Asp Lys Phe Thr Leu His Ile Pro Ile Thr
        770                 775                 780
Met Asn Phe Gly Val Asp Glu Val Lys Arg Phe Asn Asp Ala Val Asn
785                 790                 795                 800
Ser Ala Ile Arg Ile Asp Glu Asn Val Asn Val Ile Gly Ile Asp Arg
                805                 810                 815
Gly Glu Arg Asn Leu Leu Tyr Val Val Val Ile Asp Ser Lys Gly Asn
                820                 825                 830
Ile Leu Glu Gln Ile Ser Leu Asn Ser Ile Ile Asn Lys Glu Tyr Asp
        835                 840                 845
Ile Glu Thr Asp Tyr His Ala Leu Leu Asp Glu Arg Glu Gly Gly Arg
        850                 855                 860
Asp Lys Ala Arg Lys Asp Trp Asn Thr Val Glu Asn Ile Arg Asp Leu
865                 870                 875                 880
Lys Ala Gly Tyr Leu Ser Gln Val Val Asn Val Val Ala Lys Leu Val
                885                 890                 895
Leu Lys Tyr Asn Ala Ile Ile Cys Leu Glu Asp Leu Asn Phe Gly Phe
        900                 905                 910
Lys Arg Gly Arg Gln Lys Val Glu Lys Gln Val Tyr Gln Lys Phe Glu
        915                 920                 925
Lys Met Leu Ile Asp Lys Leu Asn Tyr Leu Val Ile Asp Lys Ser Arg
        930                 935                 940
Glu Gln Thr Ser Pro Lys Glu Leu Gly Gly Ala Leu Asn Ala Leu Gln
945                 950                 955                 960
Leu Thr Ser Lys Phe Lys Ser Phe Lys Glu Leu Gly Lys Gln Ser Gly
                965                 970                 975
Val Ile Tyr Tyr Val Pro Ala Tyr Leu Thr Ser Lys Ile Asp Pro Thr
                980                 985                 990
Thr Gly Phe Ala Asn Leu Phe Tyr Met Lys Cys Glu Asn Val Glu Lys
                995                1000                1005
Ser Lys Arg Phe Phe Asp Gly Phe Asp Phe Ile Arg Phe Asn Ala
        1010                1015                1020
Leu Glu Asn Val Phe Glu Phe Gly Phe Asp Tyr Arg Ser Phe Thr
        1025                1030                1035
Gln Arg Ala Cys Gly Ile Asn Ser Lys Trp Thr Val Cys Thr Asn
        1040                1045                1050
Gly Glu Arg Ile Ile Lys Tyr Arg Asn Pro Asp Lys Asn Asn Met
```

```
                1055                1060                1065
Phe Asp Glu Lys Val Val Val Thr Asp Glu Met Lys Asn Leu
        1070                1075                1080

Phe Glu Gln Tyr Lys Ile Pro Tyr Glu Asp Gly Arg Asn Val Lys
        1085                1090                1095

Asp Met Ile Ile Ser Asn Glu Glu Ala Glu Phe Tyr Arg Arg Leu
        1100                1105                1110

Tyr Arg Leu Leu Gln Gln Thr Leu Gln Met Arg Asn Ser Thr Ser
        1115                1120                1125

Asp Gly Thr Arg Asp Tyr Ile Ile Ser Pro Val Lys Asn Lys Arg
        1130                1135                1140

Glu Ala Tyr Phe Asn Ser Glu Leu Ser Asp Gly Ser Val Pro Lys
        1145                1150                1155

Asp Ala Asp Ala Asn Gly Ala Tyr Asn Ile Ala Arg Lys Gly Leu
        1160                1165                1170

Trp Val Leu Glu Gln Ile Arg Gln Lys Ser Glu Gly Glu Lys Ile
        1175                1180                1185

Asn Leu Ala Met Thr Asn Ala Glu Trp Leu Glu Tyr Ala Gln Thr
        1190                1195                1200

His Leu Leu Lys Arg Pro Ala Ala Thr Lys Lys Ala Gly Gln Ala
        1205                1210                1215

Lys Lys Lys Lys Gly Ser Tyr Pro Tyr Asp Val Pro Asp Tyr Ala
        1220                1225                1230

Tyr Pro Tyr Asp Val Pro Asp Tyr Ala Tyr Pro Tyr Asp Val Pro
        1235                1240                1245

Asp Tyr Ala
        1250

<210> SEQ ID NO 36
<211> LENGTH: 1283
<212> TYPE: PRT
<213> ORGANISM: Candidatus Methanoplasma termitum

<400> SEQUENCE: 36

Met Asn Asn Tyr Asp Glu Phe Thr Lys Leu Tyr Pro Ile Gln Lys Thr
1               5                   10                  15

Ile Arg Phe Glu Leu Lys Pro Gln Gly Arg Thr Met Glu His Leu Glu
                20                  25                  30

Thr Phe Asn Phe Phe Glu Glu Asp Arg Asp Arg Ala Glu Lys Tyr Lys
        35                  40                  45

Ile Leu Lys Glu Ala Ile Asp Glu Tyr His Lys Lys Phe Ile Asp Glu
    50                  55                  60

His Leu Thr Asn Met Ser Leu Asp Trp Asn Ser Leu Lys Gln Ile Ser
65                  70                  75                  80

Glu Lys Tyr Tyr Lys Ser Arg Glu Glu Lys Asp Lys Lys Val Phe Leu
                85                  90                  95

Ser Glu Gln Lys Arg Met Arg Gln Glu Ile Val Ser Glu Phe Lys Lys
                100                 105                 110

Asp Asp Arg Phe Lys Asp Leu Phe Ser Lys Lys Leu Phe Ser Glu Leu
        115                 120                 125

Leu Lys Glu Glu Ile Tyr Lys Lys Gly Asn His Gln Glu Ile Asp Ala
    130                 135                 140

Leu Lys Ser Phe Asp Lys Phe Ser Gly Tyr Phe Ile Gly Leu His Glu
145                 150                 155                 160
```

-continued

```
Asn Arg Lys Asn Met Tyr Ser Asp Gly Asp Glu Ile Thr Ala Ile Ser
            165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
        195                 200                 205

Glu Ser Ala Leu Val Ala His Asn Ile Lys Met Asp Glu Val Phe Ser
    210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
            245                 250                 255

Gly Leu Asn Asp Ala Leu Asn Leu Ala His Gln Ser Glu Lys Ser Ser
            260                 265                 270

Lys Gly Arg Ile His Met Thr Pro Leu Phe Lys Gln Ile Leu Ser Glu
        275                 280                 285

Lys Glu Ser Phe Ser Tyr Ile Pro Asp Val Phe Thr Glu Asp Ser Gln
    290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
            325                 330                 335

Glu Tyr Asp Thr Glu Arg Ile Tyr Ile Arg Gln Ala Asp Ile Asn Arg
            340                 345                 350

Val Ser Asn Val Ile Phe Gly Glu Trp Gly Thr Leu Gly Gly Leu Met
        355                 360                 365

Arg Glu Tyr Lys Ala Asp Ser Ile Asn Asp Ile Asn Leu Glu Arg Thr
    370                 375                 380

Cys Lys Lys Val Asp Lys Trp Leu Asp Ser Lys Glu Phe Ala Leu Ser
385                 390                 395                 400

Asp Val Leu Glu Ala Ile Lys Arg Thr Gly Asn Asn Asp Ala Phe Asn
            405                 410                 415

Glu Tyr Ile Ser Lys Met Arg Thr Ala Arg Glu Lys Ile Asp Ala Ala
            420                 425                 430

Arg Lys Glu Met Lys Phe Ile Ser Glu Lys Ile Ser Gly Asp Glu Glu
        435                 440                 445

Ser Ile His Ile Ile Lys Thr Leu Leu Asp Ser Val Gln Gln Phe Leu
    450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
            485                 490                 495

Val Pro Leu Tyr Asn Lys Val Arg Asn Tyr Leu Thr Lys Asn Asn Leu
            500                 505                 510

Asn Thr Lys Lys Ile Lys Leu Asn Phe Lys Asn Pro Thr Leu Ala Asn
        515                 520                 525

Gly Trp Asp Gln Asn Lys Val Tyr Asp Tyr Ala Ser Leu Ile Phe Leu
    530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
            565                 570                 575

Met Val Tyr Lys Gln Ile Pro Gly Pro Asn Lys Asn Leu Pro Arg Val
```

-continued

```
                580             585             590
Phe Leu Thr Ser Thr Lys Gly Lys Lys Glu Tyr Lys Pro Ser Lys Glu
            595             600             605

Ile Ile Glu Gly Tyr Glu Ala Asp Lys His Ile Arg Gly Asp Lys Phe
            610             615             620

Asp Leu Asp Phe Cys His Lys Leu Ile Asp Phe Phe Lys Glu Ser Ile
625             630             635             640

Glu Lys His Lys Asp Trp Ser Lys Phe Asn Phe Tyr Phe Ser Pro Thr
                645             650             655

Glu Ser Tyr Gly Asp Ile Ser Glu Phe Tyr Leu Asp Val Glu Lys Gln
                660             665             670

Gly Tyr Arg Met His Phe Glu Asn Ile Ser Ala Glu Thr Ile Asp Glu
                675             680             685

Tyr Val Glu Lys Gly Asp Leu Phe Leu Phe Gln Ile Tyr Asn Lys Asp
            690             695             700

Phe Val Lys Ala Ala Thr Gly Lys Lys Asp Met His Thr Ile Tyr Trp
705             710             715             720

Asn Ala Ala Phe Ser Pro Glu Asn Leu Gln Asp Val Val Lys Leu
                725             730             735

Asn Gly Glu Ala Glu Leu Phe Tyr Arg Asp Lys Ser Asp Ile Lys Glu
                740             745             750

Ile Val His Arg Glu Gly Glu Ile Leu Val Asn Arg Thr Tyr Asn Gly
            755             760             765

Arg Thr Pro Val Pro Asp Lys Ile His Lys Lys Leu Thr Asp Tyr His
            770             775             780

Asn Gly Arg Thr Lys Asp Leu Gly Glu Ala Lys Glu Tyr Leu Asp Lys
785             790             795             800

Val Arg Tyr Phe Lys Ala His Tyr Asp Ile Thr Lys Asp Arg Arg Tyr
                805             810             815

Leu Asn Asp Lys Ile Tyr Phe His Val Pro Leu Thr Leu Asn Phe Lys
                820             825             830

Ala Asn Gly Lys Lys Asn Leu Asn Lys Met Val Ile Glu Lys Phe Leu
            835             840             845

Ser Asp Glu Lys Ala His Ile Ile Gly Ile Asp Arg Gly Glu Arg Asn
850             855             860

Leu Leu Tyr Tyr Ser Ile Ile Asp Arg Ser Gly Lys Ile Ile Asp Gln
865             870             875             880

Gln Ser Leu Asn Val Ile Asp Gly Phe Asp Tyr Arg Glu Lys Leu Asn
                885             890             895

Gln Arg Glu Ile Glu Met Lys Asp Ala Arg Gln Ser Trp Asn Ala Ile
                900             905             910

Gly Lys Ile Lys Asp Leu Lys Glu Gly Tyr Leu Ser Lys Ala Val His
            915             920             925

Glu Ile Thr Lys Met Ala Ile Gln Tyr Asn Ala Ile Val Val Met Glu
            930             935             940

Glu Leu Asn Tyr Gly Phe Lys Arg Gly Arg Phe Lys Val Glu Lys Gln
945             950             955             960

Ile Tyr Gln Lys Phe Glu Asn Met Leu Ile Asp Lys Met Asn Tyr Leu
            965             970             975

Val Phe Lys Asp Ala Pro Asp Glu Ser Pro Gly Gly Val Leu Asn Ala
            980             985             990

Tyr Gln Leu Thr Asn Pro Leu Glu Ser Phe Ala Lys Leu Gly Lys Gln
            995             1000            1005
```

```
Thr Gly Ile Leu Phe Tyr Val Pro Ala Ala Tyr Thr Ser Lys Ile
    1010            1015            1020

Asp Pro Thr Thr Gly Phe Val Asn Leu Phe Asn Thr Ser Ser Lys
    1025            1030            1035

Thr Asn Ala Gln Glu Arg Lys Glu Phe Leu Gln Lys Phe Glu Ser
    1040            1045            1050

Ile Ser Tyr Ser Ala Lys Asp Gly Gly Ile Phe Ala Phe Ala Phe
    1055            1060            1065

Asp Tyr Arg Lys Phe Gly Thr Ser Lys Thr Asp His Lys Asn Val
    1070            1075            1080

Trp Thr Ala Tyr Thr Asn Gly Glu Arg Met Arg Tyr Ile Lys Glu
    1085            1090            1095

Lys Lys Arg Asn Glu Leu Phe Asp Pro Ser Lys Glu Ile Lys Glu
    1100            1105            1110

Ala Leu Thr Ser Ser Gly Ile Lys Tyr Asp Gly Gly Gln Asn Ile
    1115            1120            1125

Leu Pro Asp Ile Leu Arg Ser Asn Asn Asn Gly Leu Ile Tyr Thr
    1130            1135            1140

Met Tyr Ser Ser Phe Ile Ala Ala Ile Gln Met Arg Val Tyr Asp
    1145            1150            1155

Gly Lys Glu Asp Tyr Ile Ile Ser Pro Ile Lys Asn Ser Lys Gly
    1160            1165            1170

Glu Phe Phe Arg Thr Asp Pro Lys Arg Arg Glu Leu Pro Ile Asp
    1175            1180            1185

Ala Asp Ala Asn Gly Ala Tyr Asn Ile Ala Leu Arg Gly Glu Leu
    1190            1195            1200

Thr Met Arg Ala Ile Ala Glu Lys Phe Asp Pro Asp Ser Glu Lys
    1205            1210            1215

Met Ala Lys Leu Glu Leu Lys His Lys Asp Trp Phe Glu Phe Met
    1220            1225            1230

Gln Thr Arg Gly Asp Lys Arg Pro Ala Ala Thr Lys Lys Ala Gly
    1235            1240            1245

Gln Ala Lys Lys Lys Lys Gly Ser Tyr Pro Tyr Asp Val Pro Asp
    1250            1255            1260

Tyr Ala Tyr Pro Tyr Asp Val Pro Asp Tyr Ala Tyr Pro Tyr Asp
    1265            1270            1275

Val Pro Asp Tyr Ala
    1280

<210> SEQ ID NO 37
<211> LENGTH: 1327
<212> TYPE: PRT
<213> ORGANISM: Eubacterium eligens

<400> SEQUENCE: 37

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
                20                  25                  30

Gln Glu His Ile Ile Gln Asn Gly Leu Ile Gln Glu Asp Glu Leu Arg
            35                  40                  45

Gln Glu Lys Ser Thr Glu Leu Lys Asn Ile Met Asp Asp Tyr Tyr Arg
        50                  55                  60

Glu Tyr Ile Asp Lys Ser Leu Ser Gly Val Thr Asp Leu Asp Phe Thr
```

-continued

```
             65                  70                  75                  80
Leu Leu Phe Glu Leu Met Asn Leu Val Gln Ser Ser Pro Ser Lys Asp
                 85                  90                  95
Asn Lys Lys Ala Leu Glu Lys Glu Gln Ser Lys Met Arg Glu Gln Ile
                100                 105                 110
Cys Thr His Leu Gln Ser Asp Ser Asn Tyr Lys Asn Ile Phe Asn Ala
                115                 120                 125
Lys Leu Leu Lys Glu Ile Leu Pro Asp Phe Ile Lys Asn Tyr Asn Gln
                130                 135                 140
Tyr Asp Val Lys Asp Lys Ala Gly Lys Leu Glu Thr Leu Ala Leu Phe
145                 150                 155                 160
Asn Gly Phe Ser Thr Tyr Phe Thr Asp Phe Phe Glu Lys Arg Lys Asn
                165                 170                 175
Val Phe Thr Lys Glu Ala Val Ser Thr Ser Ile Ala Tyr Arg Ile Val
                180                 185                 190
His Glu Asn Ser Leu Ile Phe Leu Ala Asn Met Thr Ser Tyr Lys Lys
                195                 200                 205
Ile Ser Glu Lys Ala Leu Asp Glu Ile Glu Val Ile Glu Lys Asn Asn
210                 215                 220
Gln Asp Lys Met Gly Asp Trp Glu Leu Asn Gln Ile Phe Asn Pro Asp
225                 230                 235                 240
Phe Tyr Asn Met Val Leu Ile Gln Ser Gly Ile Asp Phe Tyr Asn Glu
                245                 250                 255
Ile Cys Gly Val Val Asn Ala His Met Asn Leu Tyr Cys Gln Gln Thr
                260                 265                 270
Lys Asn Asn Tyr Asn Leu Phe Lys Met Arg Lys Leu His Lys Gln Ile
                275                 280                 285
Leu Ala Tyr Thr Ser Thr Ser Phe Glu Val Pro Lys Met Phe Glu Asp
                290                 295                 300
Asp Met Ser Val Tyr Asn Ala Val Asn Ala Phe Ile Asp Glu Thr Glu
305                 310                 315                 320
Lys Gly Asn Ile Ile Gly Lys Leu Lys Asp Ile Val Asn Lys Tyr Asp
                325                 330                 335
Glu Leu Asp Glu Lys Arg Ile Tyr Ile Ser Lys Asp Phe Tyr Glu Thr
                340                 345                 350
Leu Ser Cys Phe Met Ser Gly Asn Trp Asn Leu Ile Thr Gly Cys Val
                355                 360                 365
Glu Asn Phe Tyr Asp Glu Asn Ile His Ala Lys Gly Lys Ser Lys Glu
                370                 375                 380
Glu Lys Val Lys Lys Ala Val Lys Glu Asp Lys Tyr Lys Ser Ile Asn
385                 390                 395                 400
Asp Val Asn Asp Leu Val Glu Lys Tyr Ile Asp Glu Lys Glu Arg Asn
                405                 410                 415
Glu Phe Lys Asn Ser Asn Ala Lys Gln Tyr Ile Arg Glu Ile Ser Asn
                420                 425                 430
Ile Ile Thr Asp Thr Glu Thr Ala His Leu Glu Tyr Asp Asp His Ile
                435                 440                 445
Ser Leu Ile Glu Ser Glu Glu Lys Ala Asp Glu Met Lys Lys Arg Leu
                450                 455                 460
Asp Met Tyr Met Asn Met Tyr His Trp Ala Lys Ala Phe Ile Val Asp
465                 470                 475                 480
Glu Val Leu Asp Arg Asp Glu Met Phe Tyr Ser Asp Ile Asp Asp Ile
                485                 490                 495
```

-continued

```
Tyr Asn Ile Leu Glu Asn Ile Val Pro Leu Tyr Asn Arg Val Arg Asn
            500                 505                 510
Tyr Val Thr Gln Lys Pro Tyr Asn Ser Lys Lys Ile Lys Leu Asn Phe
        515                 520                 525
Gln Ser Pro Thr Leu Ala Asn Gly Trp Ser Gln Ser Lys Glu Phe Asp
    530                 535                 540
Asn Asn Ala Ile Ile Leu Ile Arg Asp Asn Lys Tyr Tyr Leu Ala Ile
545                 550                 555                 560
Phe Asn Ala Lys Asn Lys Pro Asp Lys Lys Ile Ile Gln Gly Asn Ser
                565                 570                 575
Asp Lys Lys Asn Asp Asn Asp Tyr Lys Lys Met Val Tyr Asn Leu Leu
            580                 585                 590
Pro Gly Ala Asn Lys Met Leu Pro Lys Val Phe Leu Ser Lys Lys Gly
        595                 600                 605
Ile Glu Thr Phe Lys Pro Ser Asp Tyr Ile Ile Ser Gly Tyr Asn Ala
    610                 615                 620
His Lys His Ile Lys Thr Ser Glu Asn Phe Asp Ile Ser Phe Cys Arg
625                 630                 635                 640
Asp Leu Ile Asp Tyr Phe Lys Asn Ser Ile Glu Lys His Ala Glu Trp
                645                 650                 655
Arg Lys Tyr Glu Phe Lys Phe Ser Ala Thr Asp Ser Tyr Ser Asp Ile
            660                 665                 670
Ser Glu Phe Tyr Arg Glu Val Glu Met Gln Gly Tyr Arg Ile Asp Trp
        675                 680                 685
Thr Tyr Ile Ser Glu Ala Asp Ile Asn Lys Leu Asp Glu Glu Gly Lys
    690                 695                 700
Ile Tyr Leu Phe Gln Ile Tyr Asn Lys Asp Phe Ala Glu Asn Ser Thr
705                 710                 715                 720
Gly Lys Glu Asn Leu His Thr Met Tyr Phe Lys Asn Ile Phe Ser Glu
                725                 730                 735
Glu Asn Leu Lys Asp Ile Ile Ile Lys Leu Asn Gly Gln Ala Glu Leu
            740                 745                 750
Phe Tyr Arg Arg Ala Ser Val Lys Asn Pro Val Lys His Lys Lys Asp
        755                 760                 765
Ser Val Leu Val Asn Lys Thr Tyr Lys Asn Gln Leu Asp Asn Gly Asp
    770                 775                 780
Val Val Arg Ile Pro Ile Pro Asp Asp Ile Tyr Asn Glu Ile Tyr Lys
785                 790                 795                 800
Met Tyr Asn Gly Tyr Ile Lys Glu Ser Asp Leu Ser Glu Ala Ala Lys
                805                 810                 815
Glu Tyr Leu Asp Lys Val Glu Val Arg Thr Ala Gln Lys Asp Ile Val
            820                 825                 830
Lys Asp Tyr Arg Tyr Thr Val Asp Lys Tyr Phe Ile His Thr Pro Ile
        835                 840                 845
Thr Ile Asn Tyr Lys Val Thr Ala Arg Asn Asn Val Asn Asp Met Val
    850                 855                 860
Val Lys Tyr Ile Ala Gln Asn Asp Asp Ile His Val Ile Gly Ile Asp
865                 870                 875                 880
Arg Gly Glu Arg Asn Leu Ile Tyr Ile Ser Val Ile Asp Ser His Gly
                885                 890                 895
Asn Ile Val Lys Gln Lys Ser Tyr Asn Ile Leu Asn Asn Tyr Asp Tyr
            900                 905                 910
```

```
Lys Lys Lys Leu Val Glu Lys Glu Lys Thr Arg Glu Tyr Ala Arg Lys
            915                 920                 925

Asn Trp Lys Ser Ile Gly Asn Ile Lys Glu Leu Lys Glu Gly Tyr Ile
        930                 935                 940

Ser Gly Val Val His Glu Ile Ala Met Leu Ile Val Glu Tyr Asn Ala
945                 950                 955                 960

Ile Ile Ala Met Glu Asp Leu Asn Tyr Gly Phe Lys Arg Gly Arg Phe
                965                 970                 975

Lys Val Glu Arg Gln Val Tyr Gln Lys Phe Glu Ser Met Leu Ile Asn
            980                 985                 990

Lys Leu Asn Tyr Phe Ala Ser Lys Glu Lys Ser Val Asp Glu Pro Gly
        995                 1000                1005

Gly Leu Leu Lys Gly Tyr Gln Leu Thr Tyr Val Pro Asp Asn Ile
    1010                1015                1020

Lys Asn Leu Gly Lys Gln Cys Gly Val Ile Phe Tyr Val Pro Ala
    1025                1030                1035

Ala Phe Thr Ser Lys Ile Asp Pro Ser Thr Gly Phe Ile Ser Ala
    1040                1045                1050

Phe Asn Phe Lys Ser Ile Ser Thr Asn Ala Ser Arg Lys Gln Phe
    1055                1060                1065

Phe Met Gln Phe Asp Glu Ile Arg Tyr Cys Ala Glu Lys Asp Met
    1070                1075                1080

Phe Ser Phe Gly Phe Asp Tyr Asn Asn Phe Asp Thr Tyr Asn Ile
    1085                1090                1095

Thr Met Gly Lys Thr Gln Trp Thr Val Tyr Thr Asn Gly Glu Arg
    1100                1105                1110

Leu Gln Ser Glu Phe Asn Asn Ala Arg Arg Thr Gly Lys Thr Lys
    1115                1120                1125

Ser Ile Asn Leu Thr Glu Thr Ile Lys Leu Leu Leu Glu Asp Asn
    1130                1135                1140

Glu Ile Asn Tyr Ala Asp Gly His Asp Ile Arg Ile Asp Met Glu
    1145                1150                1155

Lys Met Asp Glu Asp Lys Lys Ser Glu Phe Phe Ala Gln Leu Leu
    1160                1165                1170

Ser Leu Tyr Lys Leu Thr Val Gln Met Arg Asn Ser Tyr Thr Glu
    1175                1180                1185

Ala Glu Glu Gln Glu Asn Gly Ile Ser Tyr Asp Lys Ile Ile Ser
    1190                1195                1200

Pro Val Ile Asn Asp Glu Gly Glu Phe Phe Asp Ser Asp Asn Tyr
    1205                1210                1215

Lys Glu Ser Asp Asp Lys Glu Cys Lys Met Pro Lys Asp Ala Asp
    1220                1225                1230

Ala Asn Gly Ala Tyr Cys Ile Ala Leu Lys Gly Leu Tyr Glu Val
    1235                1240                1245

Leu Lys Ile Lys Ser Glu Trp Thr Glu Asp Gly Phe Asp Arg Asn
    1250                1255                1260

Cys Leu Lys Leu Pro His Ala Glu Trp Leu Asp Phe Ile Gln Asn
    1265                1270                1275

Lys Arg Tyr Glu Lys Arg Pro Ala Ala Thr Lys Lys Ala Gly Gln
    1280                1285                1290

Ala Lys Lys Lys Lys Gly Ser Tyr Pro Tyr Asp Val Pro Asp Tyr
    1295                1300                1305

Ala Tyr Pro Tyr Asp Val Pro Asp Tyr Ala Tyr Pro Tyr Asp Val
```

Pro Asp Tyr Ala
    1325

<210> SEQ ID NO 38
<211> LENGTH: 1418
<212> TYPE: PRT
<213> ORGANISM: Moraxella bovoculi

<400> SEQUENCE: 38

Met Leu Phe Gln Asp Phe Thr His Leu Tyr Pro Leu Ser Lys Thr Val
1               5                   10                  15

Arg Phe Glu Leu Lys Pro Ile Asp Arg Thr Leu Glu His Ile His Ala
            20                  25                  30

Lys Asn Phe Leu Ser Gln Asp Glu Thr Met Ala Asp Met His Gln Lys
        35                  40                  45

Val Lys Val Ile Leu Asp Asp Tyr His Arg Asp Phe Ile Ala Asp Met
    50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Glu Leu Gln Lys Gln Leu
            85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
            115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
                165                 170                 175

Met Tyr Ser Asp Glu Asp Lys His Thr Ala Ile Ala Tyr Arg Leu Ile
            180                 185                 190

His Glu Asn Leu Pro Arg Phe Ile Asp Asn Leu Gln Ile Leu Thr Thr
            195                 200                 205

Ile Lys Gln Lys His Ser Ala Leu Tyr Asp Gln Ile Ile Asn Glu Leu
    210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Thr Leu Leu
                245                 250                 255

Gly Gly Ile Ser Gly Glu Ala Gly Ser Pro Lys Ile Gln Gly Ile Asn
            260                 265                 270

Glu Leu Ile Asn Ser His His Asn Gln His Cys His Lys Ser Glu Arg
    275                 280                 285

Ile Ala Lys Leu Arg Pro Leu His Lys Gln Ile Leu Ser Asp Gly Met
    290                 295                 300

Ser Val Ser Phe Leu Pro Ser Lys Phe Ala Asp Asp Ser Glu Met Cys
305                 310                 315                 320

Gln Ala Val Asn Glu Phe Tyr Arg His Tyr Ala Asp Val Phe Ala Lys
                325                 330                 335

Val Gln Ser Leu Phe Asp Gly Phe Asp Asp His Gln Lys Asp Gly Ile
            340                 345                 350

```
Tyr Val Glu His Lys Asn Leu Asn Glu Leu Ser Lys Gln Ala Phe Gly
        355                 360                 365

Asp Phe Ala Leu Leu Gly Arg Val Leu Asp Gly Tyr Tyr Val Asp Val
370                 375                 380

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
                405                 410                 415

His Ser Leu Ala Ser Leu Glu Gln Ala Ile Glu His Tyr Thr Ala Arg
            420                 425                 430

His Asp Asp Glu Ser Val Gln Ala Gly Lys Leu Gly Gln Tyr Phe Lys
            435                 440                 445

His Gly Leu Ala Gly Val Asp Asn Pro Ile Gln Lys Ile His Asn Asn
        450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
                485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
        515                 520                 525

Asn Phe Tyr Gly Glu Phe Gly Val Leu Tyr Asp Glu Leu Ala Lys Ile
    530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
                565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
        595                 600                 605

Val Phe Asp Asn Ala Pro Asn Thr Gly Lys Ser Ile Tyr Gln Lys Met
    610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
                645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
        675                 680                 685

Lys Lys Phe Glu Gly Ala Ile Gly Asp Ile Gln Leu Phe Lys Lys Asp
    690                 695                 700

Lys Lys Gly Arg Glu Val Pro Ile Ser Glu Lys Asp Leu Phe Asp Lys
705                 710                 715                 720

Ile Asn Gly Ile Phe Ser Ser Lys Pro Lys Leu Glu Met Glu Asp Phe
                725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
        755                 760                 765

Glu Asn Phe Tyr Asn Asn His Pro Lys Phe Lys Lys Asp Leu Val Arg
```

```
            770             775             780
Tyr Tyr Tyr Glu Ser Met Cys Lys His Glu Glu Trp Glu Glu Ser Phe
785             790             795             800

Glu Phe Ser Lys Lys Leu Gln Asp Ile Gly Cys Tyr Val Asp Val Asn
            805             810             815

Glu Leu Phe Thr Glu Ile Glu Thr Arg Arg Leu Asn Tyr Lys Ile Ser
            820             825             830

Phe Cys Asn Ile Asn Ala Asp Tyr Ile Asp Glu Leu Val Glu Gln Gly
            835             840             845

Gln Leu Tyr Leu Phe Gln Ile Tyr Asn Lys Asp Phe Ser Pro Lys Ala
            850             855             860

His Gly Lys Pro Asn Leu His Thr Leu Tyr Phe Lys Ala Leu Phe Ser
865             870             875             880

Glu Asp Asn Leu Ala Asp Pro Ile Tyr Lys Leu Asn Gly Glu Ala Gln
            885             890             895

Ile Phe Tyr Arg Lys Ala Ser Leu Asp Met Asn Glu Thr Thr Ile His
            900             905             910

Arg Ala Gly Glu Val Leu Glu Asn Lys Asn Pro Asp Asn Pro Lys Lys
            915             920             925

Arg Gln Phe Val Tyr Asp Ile Ile Lys Asp Lys Arg Tyr Thr Gln Asp
            930             935             940

Lys Phe Met Leu His Val Pro Ile Thr Met Asn Phe Gly Val Gln Gly
945             950             955             960

Met Thr Ile Lys Glu Phe Asn Lys Lys Val Asn Gln Ser Ile Gln Gln
            965             970             975

Tyr Asp Glu Val Asn Val Ile Gly Ile Asp Arg Gly Glu Arg His Leu
            980             985             990

Leu Tyr Leu Thr Val Ile Asn Ser  Lys Gly Glu Ile Leu  Glu Gln Cys
            995              1000              1005

Ser Leu Asn Asp Ile Thr Thr  Ala Ser Ala Asn Gly  Thr Gln Met
    1010             1015              1020

Thr Thr Pro Tyr His Lys Ile  Leu Asp Lys Arg Glu  Ile Glu Arg
    1025             1030              1035

Leu Asn Ala Arg Val Gly Trp  Gly Glu Ile Glu Thr  Ile Lys Glu
    1040             1045              1050

Leu Lys Ser Gly Tyr Leu Ser  His Val Val His Gln  Ile Ser Gln
    1055             1060              1065

Leu Met Leu Lys Tyr Asn Ala  Ile Val Val Leu Glu  Asp Leu Asn
    1070             1075              1080

Phe Gly Phe Lys Arg Gly Arg  Phe Lys Val Glu Lys  Gln Ile Tyr
    1085             1090              1095

Gln Asn Phe Glu Asn Ala Leu  Ile Lys Lys Leu Asn  His Leu Val
    1100             1105              1110

Leu Lys Asp Lys Ala Asp Asp  Glu Ile Gly Ser Tyr  Lys Asn Ala
    1115             1120              1125

Leu Gln Leu Thr Asn Asn Phe  Thr Asp Leu Lys Ser  Ile Gly Lys
    1130             1135              1140

Gln Thr Gly Phe Leu Phe Tyr  Val Pro Ala Trp Asn  Thr Ser Lys
    1145             1150              1155

Ile Asp Pro Glu Thr Gly Phe  Val Asp Leu Leu Lys  Pro Arg Tyr
    1160             1165              1170

Glu Asn Ile Ala Gln Ser Gln  Ala Phe Phe Gly Lys  Phe Asp Lys
    1175             1180              1185
```

```
Ile Cys Tyr Asn Ala Asp Lys Asp Tyr Phe Glu Phe His Ile Asp
    1190                1195                1200

Tyr Ala Lys Phe Thr Asp Lys Ala Lys Asn Ser Arg Gln Ile Trp
    1205                1210                1215

Thr Ile Cys Ser His Gly Asp Lys Arg Tyr Val Tyr Asp Lys Thr
    1220                1225                1230

Ala Asn Gln Asn Lys Gly Ala Ala Lys Gly Ile Asn Val Asn Asp
    1235                1240                1245

Glu Leu Lys Ser Leu Phe Ala Arg His His Ile Asn Glu Lys Gln
    1250                1255                1260

Pro Asn Leu Val Met Asp Ile Cys Gln Asn Asn Asp Lys Glu Phe
    1265                1270                1275

His Lys Ser Leu Met Tyr Leu Leu Lys Thr Leu Leu Ala Leu Arg
    1280                1285                1290

Tyr Ser Asn Ala Ser Ser Asp Glu Asp Phe Ile Leu Ser Pro Val
    1295                1300                1305

Ala Asn Asp Glu Gly Val Phe Phe Asn Ser Ala Leu Ala Asp Asp
    1310                1315                1320

Thr Gln Pro Gln Asn Ala Asp Ala Asn Gly Ala Tyr His Ile Ala
    1325                1330                1335

Leu Lys Gly Leu Trp Leu Leu Asn Glu Leu Lys Asn Ser Asp Asp
    1340                1345                1350

Leu Asn Lys Val Lys Leu Ala Ile Asp Asn Gln Thr Trp Leu Asn
    1355                1360                1365

Phe Ala Gln Asn Arg Lys Arg Pro Ala Ala Thr Lys Lys Ala Gly
    1370                1375                1380

Gln Ala Lys Lys Lys Lys Gly Ser Tyr Pro Tyr Asp Val Pro Asp
    1385                1390                1395

Tyr Ala Tyr Pro Tyr Asp Val Pro Asp Tyr Ala Tyr Pro Tyr Asp
    1400                1405                1410

Val Pro Asp Tyr Ala
    1415

<210> SEQ ID NO 39
<211> LENGTH: 1308
<212> TYPE: PRT
<213> ORGANISM: Leptospira inadai

<400> SEQUENCE: 39

Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
                20                  25                  30

Lys Lys Gly Phe Leu Lys Lys Asp Lys Ile Arg Ala Glu Asp Tyr Lys
            35                  40                  45

Ala Val Lys Lys Ile Ile Asp Lys Tyr His Arg Ala Tyr Ile Glu Glu
        50                  55                  60

Val Phe Asp Ser Val Leu His Gln Lys Lys Lys Lys Asp Lys Thr Arg
65                  70                  75                  80

Phe Ser Thr Gln Phe Ile Lys Glu Ile Lys Glu Phe Ser Glu Leu Tyr
                85                  90                  95

Tyr Lys Thr Glu Lys Asn Ile Pro Asp Lys Glu Arg Leu Glu Ala Leu
                100                 105                 110

Ser Glu Lys Leu Arg Lys Met Leu Val Gly Ala Phe Lys Gly Glu Phe
```

-continued

```
            115                 120                 125
Ser Glu Glu Val Ala Glu Lys Tyr Lys Asn Leu Phe Ser Lys Glu Leu
130                 135                 140

Ile Arg Asn Glu Ile Glu Lys Phe Cys Glu Thr Asp Glu Glu Arg Lys
145                 150                 155                 160

Gln Val Ser Asn Phe Lys Ser Phe Thr Thr Tyr Phe Thr Gly Phe His
                    165                 170                 175

Ser Asn Arg Gln Asn Ile Tyr Ser Asp Glu Lys Lys Ser Thr Ala Ile
                    180                 185                 190

Gly Tyr Arg Ile Ile His Gln Asn Leu Pro Lys Phe Leu Asp Asn Leu
                    195                 200                 205

Lys Ile Ile Glu Ser Ile Gln Arg Arg Phe Lys Asp Phe Pro Trp Ser
210                 215                 220

Asp Leu Lys Lys Asn Leu Lys Lys Ile Asp Lys Asn Ile Lys Leu Thr
225                 230                 235                 240

Glu Tyr Phe Ser Ile Asp Gly Phe Val Asn Val Leu Asn Gln Lys Gly
                    245                 250                 255

Ile Asp Ala Tyr Asn Thr Ile Leu Gly Gly Lys Ser Glu Glu Ser Gly
                    260                 265                 270

Glu Lys Ile Gln Gly Leu Asn Glu Tyr Ile Asn Leu Tyr Arg Gln Lys
                    275                 280                 285

Asn Asn Ile Asp Arg Lys Asn Leu Pro Asn Val Lys Ile Leu Phe Lys
290                 295                 300

Gln Ile Leu Gly Asp Arg Glu Thr Lys Ser Phe Ile Pro Glu Ala Phe
305                 310                 315                 320

Pro Asp Asp Gln Ser Val Leu Asn Ser Ile Thr Glu Phe Ala Lys Tyr
                    325                 330                 335

Leu Lys Leu Asp Lys Lys Lys Ser Ile Ile Ala Glu Leu Lys Lys
                    340                 345                 350

Phe Leu Ser Ser Phe Asn Arg Tyr Glu Leu Asp Gly Ile Tyr Leu Ala
                    355                 360                 365

Asn Asp Asn Ser Leu Ala Ser Ile Ser Thr Phe Leu Phe Asp Asp Trp
370                 375                 380

Ser Phe Ile Lys Lys Ser Val Ser Phe Lys Tyr Asp Glu Ser Val Gly
385                 390                 395                 400

Asp Pro Lys Lys Ile Lys Ser Pro Leu Lys Tyr Glu Lys Glu Lys
                    405                 410                 415

Glu Lys Trp Leu Lys Gln Lys Tyr Tyr Thr Ile Ser Phe Leu Asn Asp
                    420                 425                 430

Ala Ile Glu Ser Tyr Ser Lys Ser Gln Asp Glu Lys Arg Val Lys Ile
                    435                 440                 445

Arg Leu Glu Ala Tyr Phe Ala Glu Phe Lys Ser Lys Asp Asp Ala Lys
                    450                 455                 460

Lys Gln Phe Asp Leu Leu Glu Arg Ile Glu Glu Ala Tyr Ala Ile Val
465                 470                 475                 480

Glu Pro Leu Leu Gly Ala Glu Tyr Pro Arg Asp Arg Asn Leu Lys Ala
                    485                 490                 495

Asp Lys Lys Glu Val Gly Lys Ile Lys Asp Phe Leu Asp Ser Ile Lys
                    500                 505                 510

Ser Leu Gln Phe Phe Leu Lys Pro Leu Leu Ser Ala Glu Ile Phe Asp
                    515                 520                 525

Glu Lys Asp Leu Gly Phe Tyr Asn Gln Leu Glu Gly Tyr Tyr Glu Glu
                    530                 535                 540
```

-continued

```
Ile Asp Ser Ile Gly His Leu Tyr Asn Lys Val Arg Asn Tyr Leu Thr
545                 550                 555                 560

Gly Lys Ile Tyr Ser Lys Glu Lys Phe Lys Leu Asn Phe Glu Asn Ser
                565                 570                 575

Thr Leu Leu Lys Gly Trp Asp Glu Asn Arg Glu Val Ala Asn Leu Cys
            580                 585                 590

Val Ile Phe Arg Glu Asp Gln Lys Tyr Tyr Leu Gly Val Met Asp Lys
        595                 600                 605

Glu Asn Asn Thr Ile Leu Ser Asp Ile Pro Lys Val Lys Pro Asn Glu
610                 615                 620

Leu Phe Tyr Glu Lys Met Val Tyr Lys Leu Ile Pro Thr Pro His Met
625                 630                 635                 640

Gln Leu Pro Arg Ile Ile Phe Ser Ser Asp Asn Leu Ser Ile Tyr Asn
                645                 650                 655

Pro Ser Lys Ser Ile Leu Lys Ile Arg Glu Ala Lys Ser Phe Lys Glu
            660                 665                 670

Gly Lys Asn Phe Lys Leu Lys Asp Cys His Lys Phe Ile Asp Phe Tyr
        675                 680                 685

Lys Glu Ser Ile Ser Lys Asn Glu Asp Trp Ser Arg Phe Asp Phe Lys
690                 695                 700

Phe Ser Lys Thr Ser Ser Tyr Glu Asn Ile Ser Glu Phe Tyr Arg Glu
705                 710                 715                 720

Val Glu Arg Gln Gly Tyr Asn Leu Asp Phe Lys Lys Val Ser Lys Phe
                725                 730                 735

Tyr Ile Asp Ser Leu Val Glu Asp Gly Lys Leu Tyr Leu Phe Gln Ile
            740                 745                 750

Tyr Asn Lys Asp Phe Ser Ile Phe Ser Lys Gly Lys Pro Asn Leu His
        755                 760                 765

Thr Ile Tyr Phe Arg Ser Leu Phe Ser Lys Glu Asn Leu Lys Asp Val
770                 775                 780

Cys Leu Lys Leu Asn Gly Glu Ala Glu Met Phe Phe Arg Lys Lys Ser
785                 790                 795                 800

Ile Asn Tyr Asp Glu Lys Lys Lys Arg Glu Gly His His Pro Glu Leu
                805                 810                 815

Phe Glu Lys Leu Lys Tyr Pro Ile Leu Lys Asp Lys Arg Tyr Ser Glu
            820                 825                 830

Asp Lys Phe Gln Phe His Leu Pro Ile Ser Leu Asn Phe Lys Ser Lys
        835                 840                 845

Glu Arg Leu Asn Phe Asn Leu Lys Val Asn Glu Phe Leu Lys Arg Asn
850                 855                 860

Lys Asp Ile Asn Ile Ile Gly Ile Asp Arg Gly Glu Arg Asn Leu Leu
865                 870                 875                 880

Tyr Leu Val Met Ile Asn Gln Lys Gly Glu Ile Leu Lys Gln Thr Leu
                885                 890                 895

Leu Asp Ser Met Gln Ser Gly Lys Gly Arg Pro Glu Ile Asn Tyr Lys
            900                 905                 910

Glu Lys Leu Gln Glu Lys Glu Ile Glu Arg Asp Lys Ala Arg Lys Ser
        915                 920                 925

Trp Gly Thr Val Glu Asn Ile Lys Glu Leu Lys Glu Gly Tyr Leu Ser
930                 935                 940

Ile Val Ile His Gln Ile Ser Lys Leu Met Val Glu Asn Asn Ala Ile
945                 950                 955                 960
```

```
Val Val Leu Glu Asp Leu Asn Ile Gly Phe Lys Arg Gly Arg Gln Lys
            965                 970                 975

Val Glu Arg Gln Val Tyr Gln Lys Phe Glu Lys Met Leu Ile Asp Lys
            980                 985                 990

Leu Asn Phe Leu Val Phe Lys Glu Asn Lys Pro Thr Glu Pro Gly Gly
            995                 1000                1005

Val Leu Lys Ala Tyr Gln Leu Thr Asp Glu Phe Gln Ser Phe Glu
        1010                1015                1020

Lys Leu Ser Lys Gln Thr Gly Phe Leu Phe Tyr Val Pro Ser Trp
        1025                1030                1035

Asn Thr Ser Lys Ile Asp Pro Arg Thr Gly Phe Ile Asp Phe Leu
        1040                1045                1050

His Pro Ala Tyr Glu Asn Ile Glu Lys Ala Lys Gln Trp Ile Asn
        1055                1060                1065

Lys Phe Asp Ser Ile Arg Phe Asn Ser Lys Met Asp Trp Phe Glu
        1070                1075                1080

Phe Thr Ala Asp Thr Arg Lys Phe Ser Glu Asn Leu Met Leu Gly
        1085                1090                1095

Lys Asn Arg Val Trp Val Ile Cys Thr Thr Asn Val Glu Arg Tyr
        1100                1105                1110

Phe Thr Ser Lys Thr Ala Asn Ser Ser Ile Gln Tyr Asn Ser Ile
        1115                1120                1125

Gln Ile Thr Glu Lys Leu Lys Glu Leu Phe Val Asp Ile Pro Phe
        1130                1135                1140

Ser Asn Gly Gln Asp Leu Lys Pro Glu Ile Leu Arg Lys Asn Asp
        1145                1150                1155

Ala Val Phe Phe Lys Ser Leu Leu Phe Tyr Ile Lys Thr Thr Leu
        1160                1165                1170

Ser Leu Arg Gln Asn Asn Gly Lys Lys Gly Glu Glu Glu Lys Asp
        1175                1180                1185

Phe Ile Leu Ser Pro Val Val Asp Ser Lys Gly Arg Phe Phe Asn
        1190                1195                1200

Ser Leu Glu Ala Ser Asp Asp Glu Pro Lys Asp Ala Asp Ala Asn
        1205                1210                1215

Gly Ala Tyr His Ile Ala Leu Lys Gly Leu Met Asn Leu Leu Val
        1220                1225                1230

Leu Asn Glu Thr Lys Glu Glu Asn Leu Ser Arg Pro Lys Trp Lys
        1235                1240                1245

Ile Lys Asn Lys Asp Trp Leu Glu Phe Val Trp Glu Arg Asn Arg
        1250                1255                1260

Lys Arg Pro Ala Ala Thr Lys Lys Ala Gly Gln Ala Lys Lys Lys
        1265                1270                1275

Lys Gly Ser Tyr Pro Tyr Asp Val Pro Asp Tyr Ala Tyr Pro Tyr
        1280                1285                1290

Asp Val Pro Asp Tyr Ala Tyr Pro Tyr Asp Val Pro Asp Tyr Ala
        1295                1300                1305

<210> SEQ ID NO 40
<211> LENGTH: 1273
<212> TYPE: PRT
<213> ORGANISM: Lachnospiraceae bacterium

<400> SEQUENCE: 40

Met Ser Lys Leu Glu Lys Phe Thr Asn Cys Tyr Ser Leu Ser Lys Thr
1               5                   10                  15
```

```
Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430
```

-continued

```
Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
            595                 600                 605

Ser Glu Asp Ile Gln Lys Ile Tyr Lys Asn Gly Thr Phe Lys Lys Gly
            610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
            675                 680                 685

Glu Val Asp Lys Leu Val Glu Glu Gly Lys Leu Tyr Met Phe Gln Ile
            690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
            755                 760                 765

Asn Pro Asp Asn Pro Lys Lys Thr Thr Thr Leu Ser Tyr Asp Val Tyr
770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
                820                 825                 830

Arg Gly Glu Arg Asn Leu Leu Tyr Ile Val Val Val Asp Gly Lys Gly
            835                 840                 845

Asn Ile Val Glu Gln Tyr Ser Leu Asn Glu Ile Ile Asn Asn Phe Asn
```

```
                850             855             860
Gly Ile Arg Ile Lys Thr Asp Tyr His Ser Leu Leu Asp Lys Glu
865             870             875             880

Lys Glu Arg Phe Glu Ala Arg Gln Asn Trp Thr Ser Ile Glu Asn Ile
                885             890             895

Lys Glu Leu Lys Ala Gly Tyr Ile Ser Gln Val Val His Lys Ile Cys
                900             905             910

Glu Leu Val Glu Lys Tyr Asp Ala Val Ile Ala Leu Glu Asp Leu Asn
            915             920             925

Ser Gly Phe Lys Asn Ser Arg Val Lys Val Glu Lys Gln Val Tyr Gln
        930             935             940

Lys Phe Glu Lys Met Leu Ile Asp Lys Leu Asn Tyr Met Val Asp Lys
945             950             955             960

Lys Ser Asn Pro Cys Ala Thr Gly Gly Ala Leu Lys Gly Tyr Gln Ile
                965             970             975

Thr Asn Lys Phe Glu Ser Phe Lys Ser Met Ser Thr Gln Asn Gly Phe
            980             985             990

Ile Phe Tyr Ile Pro Ala Trp Leu Thr Ser Lys Ile Asp Pro Ser Thr
            995             1000            1005

Gly Phe Val Asn Leu Leu Lys Thr Lys Tyr Thr Ser Ile Ala Asp
    1010            1015            1020

Ser Lys Lys Phe Ile Ser Ser Phe Asp Arg Ile Met Tyr Val Pro
    1025            1030            1035

Glu Glu Asp Leu Phe Glu Phe Ala Leu Asp Tyr Lys Asn Phe Ser
    1040            1045            1050

Arg Thr Asp Ala Asp Tyr Ile Lys Lys Trp Lys Leu Tyr Ser Tyr
    1055            1060            1065

Gly Asn Arg Ile Arg Ile Phe Arg Asn Pro Lys Lys Asn Asn Val
    1070            1075            1080

Phe Asp Trp Glu Glu Val Cys Leu Thr Ser Ala Tyr Lys Glu Leu
    1085            1090            1095

Phe Asn Lys Tyr Gly Ile Asn Tyr Gln Gln Gly Asp Ile Arg Ala
    1100            1105            1110

Leu Leu Cys Glu Gln Ser Asp Lys Ala Phe Tyr Ser Ser Phe Met
    1115            1120            1125

Ala Leu Met Ser Leu Met Leu Gln Met Arg Asn Ser Ile Thr Gly
    1130            1135            1140

Arg Thr Asp Val Asp Phe Leu Ile Ser Pro Val Lys Asn Ser Asp
    1145            1150            1155

Gly Ile Phe Tyr Asp Ser Arg Asn Tyr Glu Ala Gln Glu Asn Ala
    1160            1165            1170

Ile Leu Pro Lys Asn Ala Asp Ala Asn Gly Ala Tyr Asn Ile Ala
    1175            1180            1185

Arg Lys Val Leu Trp Ala Ile Gly Gln Phe Lys Lys Ala Glu Asp
    1190            1195            1200

Glu Lys Leu Asp Lys Val Lys Ile Ala Ile Ser Asn Lys Glu Trp
    1205            1210            1215

Leu Glu Tyr Ala Gln Thr Ser Val Lys His Lys Arg Pro Ala Ala
    1220            1225            1230

Thr Lys Lys Ala Gly Gln Ala Lys Lys Lys Lys Gly Ser Tyr Pro
    1235            1240            1245

Tyr Asp Val Pro Asp Tyr Ala Tyr Pro Tyr Asp Val Pro Asp Tyr
    1250            1255            1260
```

```
Ala Tyr Pro Tyr Asp Val Pro Asp Tyr Ala
    1265            1270
```

<210> SEQ ID NO 41
<211> LENGTH: 1305
<212> TYPE: PRT
<213> ORGANISM: Porphyromonas crevioricanis

<400> SEQUENCE: 41

```
Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
                20                  25                  30

Lys Ala Gly Ile Leu Lys Glu Asp Glu His Arg Ala Glu Ser Tyr Arg
            35                  40                  45

Arg Val Lys Lys Ile Ile Asp Thr Tyr His Lys Val Phe Ile Asp Ser
        50                  55                  60

Ser Leu Glu Asn Met Ala Lys Met Gly Ile Glu Asn Glu Ile Lys Ala
65                  70                  75                  80

Met Leu Gln Ser Phe Cys Glu Leu Tyr Lys Lys Asp His Arg Thr Glu
                85                  90                  95

Gly Glu Asp Lys Ala Leu Asp Lys Ile Arg Ala Val Leu Arg Gly Leu
                100                 105                 110

Ile Val Gly Ala Phe Thr Gly Val Cys Gly Arg Arg Glu Asn Thr Val
            115                 120                 125

Gln Asn Glu Lys Tyr Glu Ser Leu Phe Lys Glu Lys Leu Ile Lys Glu
130                 135                 140

Ile Leu Pro Asp Phe Val Leu Ser Thr Glu Ala Glu Ser Leu Pro Phe
145                 150                 155                 160

Ser Val Glu Glu Ala Thr Arg Ser Leu Lys Glu Phe Asp Ser Phe Thr
                165                 170                 175

Ser Tyr Phe Ala Gly Phe Tyr Glu Asn Arg Lys Asn Ile Tyr Ser Thr
            180                 185                 190

Lys Pro Gln Ser Thr Ala Ile Ala Tyr Arg Leu Ile His Glu Asn Leu
        195                 200                 205

Pro Lys Phe Ile Asp Asn Ile Leu Val Phe Gln Lys Ile Lys Glu Pro
    210                 215                 220

Ile Ala Lys Glu Leu Glu His Ile Arg Ala Asp Phe Ser Ala Gly Gly
225                 230                 235                 240

Tyr Ile Lys Lys Asp Glu Arg Leu Glu Asp Ile Phe Ser Leu Asn Tyr
                245                 250                 255

Tyr Ile His Val Leu Ser Gln Ala Gly Ile Glu Lys Tyr Asn Ala Leu
            260                 265                 270

Ile Gly Lys Ile Val Thr Glu Gly Asp Gly Glu Met Lys Gly Leu Asn
        275                 280                 285

Glu His Ile Asn Leu Tyr Asn Gln Gln Arg Gly Arg Glu Asp Arg Leu
    290                 295                 300

Pro Leu Phe Arg Pro Leu Tyr Lys Gln Ile Leu Ser Asp Arg Glu Gln
305                 310                 315                 320

Leu Ser Tyr Leu Pro Glu Ser Phe Glu Lys Asp Glu Glu Leu Leu Arg
                325                 330                 335

Ala Leu Lys Glu Phe Tyr Asp His Ile Ala Glu Asp Ile Leu Gly Arg
            340                 345                 350

Thr Gln Gln Leu Met Thr Ser Ile Ser Glu Tyr Asp Leu Ser Arg Ile
```

```
                355                 360                 365
Tyr Val Arg Asn Asp Ser Gln Leu Thr Asp Ile Ser Lys Lys Met Leu
370                 375                 380
Gly Asp Trp Asn Ala Ile Tyr Met Ala Arg Glu Arg Ala Tyr Asp His
385                 390                 395                 400
Glu Gln Ala Pro Lys Arg Ile Thr Ala Lys Tyr Glu Arg Asp Arg Ile
                405                 410                 415
Lys Ala Leu Lys Gly Glu Glu Ser Ile Ser Leu Ala Asn Leu Asn Ser
                420                 425                 430
Cys Ile Ala Phe Leu Asp Asn Val Arg Asp Cys Arg Val Asp Thr Tyr
                435                 440                 445
Leu Ser Thr Leu Gly Gln Lys Glu Gly Pro His Gly Leu Ser Asn Leu
                450                 455                 460
Val Glu Asn Val Phe Ala Ser Tyr His Glu Ala Glu Gln Leu Leu Ser
465                 470                 475                 480
Phe Pro Tyr Pro Glu Glu Asn Asn Leu Ile Gln Asp Lys Asp Asn Val
                485                 490                 495
Val Leu Ile Lys Asn Leu Leu Asp Asn Ile Ser Asp Leu Gln Arg Phe
                500                 505                 510
Leu Lys Pro Leu Trp Gly Met Gly Asp Glu Pro Asp Lys Asp Glu Arg
                515                 520                 525
Phe Tyr Gly Glu Tyr Asn Tyr Ile Arg Gly Ala Leu Asp Gln Val Ile
                530                 535                 540
Pro Leu Tyr Asn Lys Val Arg Asn Tyr Leu Thr Arg Lys Pro Tyr Ser
545                 550                 555                 560
Thr Arg Lys Val Lys Leu Asn Phe Gly Asn Ser Gln Leu Leu Ser Gly
                565                 570                 575
Trp Asp Arg Asn Lys Glu Lys Asp Asn Ser Cys Val Ile Leu Arg Lys
                580                 585                 590
Gly Gln Asn Phe Tyr Leu Ala Ile Met Asn Asn Arg His Lys Arg Ser
                595                 600                 605
Phe Glu Asn Lys Met Leu Pro Glu Tyr Lys Glu Gly Glu Pro Tyr Phe
                610                 615                 620
Glu Lys Met Asp Tyr Lys Phe Leu Pro Asp Pro Asn Lys Met Leu Pro
625                 630                 635                 640
Lys Val Phe Leu Ser Lys Lys Gly Ile Glu Ile Tyr Lys Pro Ser Pro
                645                 650                 655
Lys Leu Leu Glu Gln Tyr Gly His Gly Thr His Lys Lys Gly Asp Thr
                660                 665                 670
Phe Ser Met Asp Asp Leu His Glu Leu Ile Asp Phe Phe Lys His Ser
                675                 680                 685
Ile Glu Ala His Glu Asp Trp Lys Gln Phe Gly Phe Lys Phe Ser Asp
                690                 695                 700
Thr Ala Thr Tyr Glu Asn Val Ser Ser Phe Tyr Arg Glu Val Glu Asp
705                 710                 715                 720
Gln Gly Tyr Lys Leu Ser Phe Arg Lys Val Ser Glu Ser Tyr Val Tyr
                725                 730                 735
Ser Leu Ile Asp Gln Gly Lys Leu Tyr Leu Phe Gln Ile Tyr Asn Lys
                740                 745                 750
Asp Phe Ser Pro Cys Ser Lys Gly Thr Pro Asn Leu His Thr Leu Tyr
                755                 760                 765
Trp Arg Met Leu Phe Asp Glu Arg Asn Leu Ala Asp Val Ile Tyr Lys
                770                 775                 780
```

-continued

Leu Asp Gly Lys Ala Glu Ile Phe Phe Arg Glu Lys Ser Leu Lys Asn
785             790             795             800

Asp His Pro Thr His Pro Ala Gly Lys Pro Ile Lys Lys Ser Arg
        805             810             815

Gln Lys Lys Gly Glu Glu Ser Leu Phe Glu Tyr Asp Leu Val Lys Asp
        820             825             830

Arg Arg Tyr Thr Met Asp Lys Phe Gln Phe His Val Pro Ile Thr Met
        835             840             845

Asn Phe Lys Cys Ser Ala Gly Ser Lys Val Asn Asp Met Val Asn Ala
850             855             860

His Ile Arg Glu Ala Lys Asp Met His Val Ile Gly Ile Asp Arg Gly
865             870             875             880

Glu Arg Asn Leu Leu Tyr Ile Cys Val Ile Asp Ser Arg Gly Thr Ile
                885             890             895

Leu Asp Gln Ile Ser Leu Asn Thr Ile Asn Asp Ile Asp Tyr His Asp
            900             905             910

Leu Leu Glu Ser Arg Asp Lys Asp Arg Gln Gln Glu His Arg Asn Trp
        915             920             925

Gln Thr Ile Glu Gly Ile Lys Glu Leu Lys Gln Gly Tyr Leu Ser Gln
        930             935             940

Ala Val His Arg Ile Ala Glu Leu Met Val Ala Tyr Lys Ala Val Val
945             950             955             960

Ala Leu Glu Asp Leu Asn Met Gly Phe Lys Arg Gly Arg Gln Lys Val
            965             970             975

Glu Ser Ser Val Tyr Gln Gln Phe Glu Lys Gln Leu Ile Asp Lys Leu
            980             985             990

Asn Tyr Leu Val Asp Lys Lys Lys Arg Pro Glu Asp Ile Gly Gly Leu
        995             1000            1005

Leu Arg Ala Tyr Gln Phe Thr Ala Pro Phe Lys Ser Phe Lys Glu
    1010            1015            1020

Met Gly Lys Gln Asn Gly Phe Leu Phe Tyr Ile Pro Ala Trp Asn
    1025            1030            1035

Thr Ser Asn Ile Asp Pro Thr Thr Gly Phe Val Asn Leu Phe His
    1040            1045            1050

Val Gln Tyr Glu Asn Val Asp Lys Ala Lys Ser Phe Phe Gln Lys
    1055            1060            1065

Phe Asp Ser Ile Ser Tyr Asn Pro Lys Lys Asp Trp Phe Glu Phe
    1070            1075            1080

Ala Phe Asp Tyr Lys Asn Phe Thr Lys Lys Ala Glu Gly Ser Arg
    1085            1090            1095

Ser Met Trp Ile Leu Cys Thr His Gly Ser Arg Ile Lys Asn Phe
    1100            1105            1110

Arg Asn Ser Gln Lys Asn Gly Gln Trp Asp Ser Glu Glu Phe Ala
    1115            1120            1125

Leu Thr Glu Ala Phe Lys Ser Leu Phe Val Arg Tyr Glu Ile Asp
    1130            1135            1140

Tyr Thr Ala Asp Leu Lys Thr Ala Ile Val Asp Glu Lys Gln Lys
    1145            1150            1155

Asp Phe Phe Val Asp Leu Leu Lys Leu Phe Lys Leu Thr Val Gln
    1160            1165            1170

Met Arg Asn Ser Trp Lys Glu Lys Asp Leu Asp Tyr Leu Ile Ser
    1175            1180            1185

-continued

```
Pro Val Ala Gly Ala Asp Gly Arg Phe Phe Asp Thr Arg Glu Gly
    1190                1195                1200

Asn Lys Ser Leu Pro Lys Asp Ala Asp Ala Asn Gly Ala Tyr Asn
    1205                1210                1215

Ile Ala Leu Lys Gly Leu Trp Ala Leu Arg Gln Ile Arg Gln Thr
    1220                1225                1230

Ser Glu Gly Gly Lys Leu Lys Leu Ala Ile Ser Asn Lys Glu Trp
    1235                1240                1245

Leu Gln Phe Val Gln Glu Arg Ser Tyr Glu Lys Asp Lys Arg Pro
    1250                1255                1260

Ala Ala Thr Lys Lys Ala Gly Gln Ala Lys Lys Lys Lys Gly Ser
    1265                1270                1275

Tyr Pro Tyr Asp Val Pro Asp Tyr Ala Tyr Pro Tyr Asp Val Pro
    1280                1285                1290

Asp Tyr Ala Tyr Pro Tyr Asp Val Pro Asp Tyr Ala
    1295                1300                1305
```

<210> SEQ ID NO 42
<211> LENGTH: 1368
<212> TYPE: PRT
<213> ORGANISM: Prevotella disiens

<400> SEQUENCE: 42

```
Met Glu Asn Tyr Gln Glu Phe Thr Asn Leu Phe Gln Leu Asn Lys Thr
1                5                  10                  15

Leu Arg Phe Glu Leu Lys Pro Ile Gly Lys Thr Cys Glu Leu Leu Glu
                20                  25                  30

Glu Gly Lys Ile Phe Ala Ser Gly Ser Phe Leu Glu Lys Asp Lys Val
            35                  40                  45

Arg Ala Asp Asn Val Ser Tyr Val Lys Lys Glu Ile Asp Lys Lys His
        50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Val Lys Lys Thr Ala Leu Arg
                100                 105                 110

Asn Lys Cys Thr Ser Ile Gln Arg Ala Met Arg Glu Ala Ile Ser Gln
            115                 120                 125

Ala Phe Leu Lys Ser Pro Gln Lys Lys Leu Leu Ala Ile Lys Asn Leu
        130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255
```

-continued

```
Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
            275                 280                 285

Phe Phe Ile Ser Leu Lys Lys Gln Ile Leu Ser Asp Arg Glu Ala Leu
290                 295                 300

Ser Trp Leu Pro Asp Met Phe Lys Asn Asp Ser Glu Val Ile Lys Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
            355                 360                 365

Tyr Arg Asn Phe Ser Ile Asp Glu Ala Ile Asp Ala Asn Ala Glu Leu
370                 375                 380

Gln Thr Phe Asn Asn Tyr Glu Leu Ile Ala Asn Ala Leu Arg Ala Lys
385                 390                 395                 400

Ile Lys Lys Glu Thr Lys Gln Gly Arg Lys Ser Phe Glu Lys Tyr Glu
                405                 410                 415

Glu Tyr Ile Asp Lys Lys Val Lys Ala Ile Asp Ser Leu Ser Ile Gln
            420                 425                 430

Glu Ile Asn Glu Leu Val Glu Asn Tyr Val Ser Glu Phe Asn Ser Asn
            435                 440                 445

Ser Gly Asn Met Pro Arg Lys Val Glu Asp Tyr Phe Ser Leu Met Arg
450                 455                 460

Lys Gly Asp Phe Gly Ser Asn Asp Leu Ile Glu Asn Ile Lys Thr Lys
465                 470                 475                 480

Leu Ser Ala Ala Glu Lys Leu Leu Gly Thr Lys Tyr Gln Glu Thr Ala
                485                 490                 495

Lys Asp Ile Phe Lys Lys Asp Glu Asn Ser Lys Leu Ile Lys Glu Leu
            500                 505                 510

Leu Asp Ala Thr Lys Gln Phe Gln His Phe Ile Lys Pro Leu Leu Gly
            515                 520                 525

Thr Gly Glu Glu Ala Asp Arg Asp Leu Val Phe Tyr Gly Asp Phe Leu
530                 535                 540

Pro Leu Tyr Glu Lys Phe Glu Glu Leu Thr Leu Leu Tyr Asn Lys Val
545                 550                 555                 560

Arg Asn Arg Leu Thr Gln Lys Pro Tyr Ser Lys Asp Lys Ile Arg Leu
                565                 570                 575

Cys Phe Asn Lys Pro Lys Leu Met Thr Gly Trp Val Asp Ser Lys Thr
            580                 585                 590

Glu Lys Ser Asp Asn Gly Thr Gln Tyr Gly Gly Tyr Leu Phe Arg Lys
            595                 600                 605

Lys Asn Glu Ile Gly Glu Tyr Asp Tyr Phe Leu Gly Ile Ser Ser Lys
610                 615                 620

Ala Gln Leu Phe Arg Lys Asn Glu Ala Val Ile Gly Asp Tyr Glu Arg
625                 630                 635                 640

Leu Asp Tyr Tyr Gln Pro Lys Ala Asn Thr Ile Tyr Gly Ser Ala Tyr
                645                 650                 655

Glu Gly Glu Asn Ser Tyr Lys Glu Asp Lys Lys Arg Leu Asn Lys Val
            660                 665                 670
```

-continued

```
Ile Ile Ala Tyr Ile Glu Gln Ile Lys Gln Thr Asn Ile Lys Lys Ser
            675                 680                 685

Ile Ile Glu Ser Ile Ser Lys Tyr Pro Asn Ile Ser Asp Asp Lys
690                 695                 700

Val Thr Pro Ser Ser Leu Leu Glu Lys Ile Lys Lys Val Ser Ile Asp
705                 710                 715                 720

Ser Tyr Asn Gly Ile Leu Ser Phe Lys Ser Phe Gln Ser Val Asn Lys
                725                 730                 735

Glu Val Ile Asp Asn Leu Leu Lys Thr Ile Ser Pro Leu Lys Asn Lys
            740                 745                 750

Ala Glu Phe Leu Asp Leu Ile Asn Lys Asp Tyr Gln Ile Phe Thr Glu
        755                 760                 765

Val Gln Ala Val Ile Asp Glu Ile Cys Lys Gln Lys Thr Phe Ile Tyr
770                 775                 780

Phe Pro Ile Ser Asn Val Glu Leu Glu Lys Glu Met Gly Asp Lys Asp
785                 790                 795                 800

Lys Pro Leu Cys Leu Phe Gln Ile Ser Asn Lys Asp Leu Ser Phe Ala
                805                 810                 815

Lys Thr Phe Ser Ala Asn Leu Arg Lys Lys Arg Gly Ala Glu Asn Leu
            820                 825                 830

His Thr Met Leu Phe Lys Ala Leu Met Glu Gly Asn Gln Asp Asn Leu
        835                 840                 845

Asp Leu Gly Ser Gly Ala Ile Phe Tyr Arg Ala Lys Ser Leu Asp Gly
    850                 855                 860

Asn Lys Pro Thr His Pro Ala Asn Glu Ala Ile Lys Cys Arg Asn Val
865                 870                 875                 880

Ala Asn Lys Asp Lys Val Ser Leu Phe Thr Tyr Asp Ile Tyr Lys Asn
                885                 890                 895

Arg Arg Tyr Met Glu Asn Lys Phe Leu Phe His Leu Ser Ile Val Gln
            900                 905                 910

Asn Tyr Lys Ala Ala Asn Asp Ser Ala Gln Leu Asn Ser Ser Ala Thr
        915                 920                 925

Glu Tyr Ile Arg Lys Ala Asp Asp Leu His Ile Gly Ile Asp Arg
    930                 935                 940

Gly Glu Arg Asn Leu Leu Tyr Tyr Ser Val Ile Asp Met Lys Gly Asn
945                 950                 955                 960

Ile Val Glu Gln Asp Ser Leu Asn Ile Ile Arg Asn Asn Asp Leu Glu
                965                 970                 975

Thr Asp Tyr His Asp Leu Leu Asp Lys Arg Glu Lys Gly Arg Lys Ala
            980                 985                 990

Asn Arg Gln Asn Trp Glu Ala Val  Glu Gly Ile Lys Asp  Leu Lys Lys
        995                 1000                 1005

Gly Tyr Leu Ser Gln Ala Val  His Gln Ile Ala Gln  Leu Met Leu
    1010                1015                 1020

Lys Tyr Asn Ala Ile Ile Ala  Leu Glu Asp Leu Gly  Gln Met Phe
    1025                1030                 1035

Val Thr Arg Gly Gln Lys Ile  Glu Lys Ala Val Tyr  Gln Gln Phe
    1040                1045                 1050

Glu Lys Ser Leu Val Asp Lys  Leu Ser Tyr Leu Val  Asp Lys Lys
    1055                1060                 1065

Arg Pro Tyr Asn Glu Leu Gly  Gly Ile Leu Lys Ala  Tyr Gln Leu
    1070                1075                 1080

Ala Ser Ser Ile Thr Lys Asn  Asn Ser Asp Lys Gln  Asn Gly Phe
```

```
                   1085                1090                1095
Leu Phe Tyr Val Pro Ala Trp Asn Thr Ser Lys Ile Asp Pro Val
                   1100                1105                1110

Thr Gly Phe Thr Asp Leu Leu Arg Pro Lys Ala Met Thr Ile Lys
                   1115                1120                1125

Glu Ala Gln Asp Phe Phe Gly Ala Phe Asp Asn Ile Ser Tyr Asn
                   1130                1135                1140

Asp Lys Gly Tyr Phe Glu Phe Glu Thr Asn Tyr Asp Lys Phe Lys
                   1145                1150                1155

Ile Arg Met Lys Ser Ala Gln Thr Arg Trp Thr Ile Cys Thr Phe
                   1160                1165                1170

Gly Asn Arg Ile Lys Arg Lys Lys Asp Lys Asn Tyr Trp Asn Tyr
                   1175                1180                1185

Glu Glu Val Glu Leu Thr Glu Glu Phe Lys Lys Leu Phe Lys Asp
                   1190                1195                1200

Ser Asn Ile Asp Tyr Glu Asn Cys Asn Leu Lys Glu Glu Ile Gln
                   1205                1210                1215

Asn Lys Asp Asn Arg Lys Phe Phe Asp Asp Leu Ile Lys Leu Leu
                   1220                1225                1230

Gln Leu Thr Leu Gln Met Arg Asn Ser Asp Asp Lys Gly Asn Asp
                   1235                1240                1245

Tyr Ile Ile Ser Pro Val Ala Asn Ala Glu Gly Gln Phe Phe Asp
                   1250                1255                1260

Ser Arg Asn Gly Asp Lys Lys Leu Pro Leu Asp Ala Asp Ala Asn
                   1265                1270                1275

Gly Ala Tyr Asn Ile Ala Arg Lys Gly Leu Trp Asn Ile Arg Gln
                   1280                1285                1290

Ile Lys Gln Thr Lys Asn Asp Lys Lys Leu Asn Leu Ser Ile Ser
                   1295                1300                1305

Ser Thr Glu Trp Leu Asp Phe Val Arg Glu Lys Pro Tyr Leu Lys
                   1310                1315                1320

Lys Arg Pro Ala Ala Thr Lys Lys Ala Gly Gln Ala Lys Lys Lys
                   1325                1330                1335

Lys Gly Ser Tyr Pro Tyr Asp Val Pro Asp Tyr Ala Tyr Pro Tyr
                   1340                1345                1350

Asp Val Pro Asp Tyr Ala Tyr Pro Tyr Asp Val Pro Asp Tyr Ala
                   1355                1360                1365

<210> SEQ ID NO 43
<211> LENGTH: 1291
<212> TYPE: PRT
<213> ORGANISM: Porphyromonas macacae

<400> SEQUENCE: 43

Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
                20                  25                  30

Asn Ile Lys Lys Asn Gly Leu Ile Arg Arg Asp Glu Gln Arg Leu Asp
            35                  40                  45

Asp Tyr Glu Lys Leu Lys Lys Val Ile Asp Glu Tyr His Glu Asp Phe
        50                  55                  60

Ile Ala Asn Ile Leu Ser Ser Phe Ser Phe Ser Glu Glu Ile Leu Gln
65                  70                  75                  80
```

```
Ser Tyr Ile Gln Asn Leu Ser Glu Ser Glu Ala Arg Ala Lys Ile Glu
                85                  90                  95
Lys Thr Met Arg Asp Thr Leu Ala Lys Ala Phe Ser Glu Asp Glu Arg
            100                 105                 110
Tyr Lys Ser Ile Phe Lys Lys Glu Leu Val Lys Lys Asp Ile Pro Val
        115                 120                 125
Trp Cys Pro Ala Tyr Lys Ser Leu Cys Lys Lys Phe Asp Asn Phe Thr
    130                 135                 140
Thr Ser Leu Val Pro Phe His Glu Asn Arg Lys Asn Leu Tyr Thr Ser
145                 150                 155                 160
Asn Glu Ile Thr Ala Ser Ile Pro Tyr Arg Ile Val His Val Asn Leu
                165                 170                 175
Pro Lys Phe Ile Gln Asn Ile Glu Ala Leu Cys Glu Leu Gln Lys Lys
            180                 185                 190
Met Gly Ala Asp Leu Tyr Leu Glu Met Met Glu Asn Leu Arg Asn Val
        195                 200                 205
Trp Pro Ser Phe Val Lys Thr Pro Asp Leu Cys Asn Leu Lys Thr
    210                 215                 220
Tyr Asn His Leu Met Val Gln Ser Ser Ile Ser Glu Tyr Asn Arg Phe
225                 230                 235                 240
Val Gly Gly Tyr Ser Thr Glu Asp Gly Thr Lys His Gln Gly Ile Asn
                245                 250                 255
Glu Trp Ile Asn Ile Tyr Arg Gln Arg Asn Lys Glu Met Arg Leu Pro
            260                 265                 270
Gly Leu Val Phe Leu His Lys Gln Ile Leu Ala Lys Val Asp Ser Ser
        275                 280                 285
Ser Phe Ile Ser Asp Thr Leu Glu Asn Asp Asp Gln Val Phe Cys Val
    290                 295                 300
Leu Arg Gln Phe Arg Lys Leu Phe Trp Asn Thr Val Ser Ser Lys Glu
305                 310                 315                 320
Asp Asp Ala Ala Ser Leu Lys Asp Leu Phe Cys Gly Leu Ser Gly Tyr
                325                 330                 335
Asp Pro Glu Ala Ile Tyr Val Ser Asp Ala His Leu Ala Thr Ile Ser
            340                 345                 350
Lys Asn Ile Phe Asp Arg Trp Asn Tyr Ile Ser Asp Ala Ile Arg Arg
        355                 360                 365
Lys Thr Glu Val Leu Met Pro Arg Lys Lys Glu Ser Val Glu Arg Tyr
    370                 375                 380
Ala Glu Lys Ile Ser Lys Gln Ile Lys Lys Arg Gln Ser Tyr Ser Leu
385                 390                 395                 400
Ala Glu Leu Asp Asp Leu Leu Ala His Tyr Ser Glu Glu Ser Leu Pro
                405                 410                 415
Ala Gly Phe Ser Leu Leu Ser Tyr Phe Thr Ser Leu Gly Gly Gln Lys
            420                 425                 430
Tyr Leu Val Ser Asp Gly Glu Val Ile Leu Tyr Glu Glu Gly Ser Asn
        435                 440                 445
Ile Trp Asp Glu Val Leu Ile Ala Phe Arg Asp Leu Gln Val Ile Leu
    450                 455                 460
Asp Lys Asp Phe Thr Glu Lys Lys Leu Gly Lys Asp Glu Glu Ala Val
465                 470                 475                 480
Ser Val Ile Lys Lys Ala Leu Asp Ser Ala Leu Arg Leu Arg Lys Phe
                485                 490                 495
Phe Asp Leu Leu Ser Gly Thr Gly Ala Glu Ile Arg Arg Asp Ser Ser
```

```
            500                 505                 510
Phe Tyr Ala Leu Tyr Thr Asp Arg Met Asp Lys Leu Lys Gly Leu Leu
            515                 520                 525

Lys Met Tyr Asp Lys Val Arg Asn Tyr Leu Thr Lys Lys Pro Tyr Ser
            530                 535                 540

Ile Glu Lys Phe Lys Leu His Phe Asp Asn Pro Ser Leu Leu Ser Gly
545                 550                 555                 560

Trp Asp Lys Asn Lys Glu Leu Asn Asn Leu Ser Val Ile Phe Arg Gln
                565                 570                 575

Asn Gly Tyr Tyr Tyr Leu Gly Ile Met Thr Pro Lys Gly Lys Asn Leu
            580                 585                 590

Phe Lys Thr Leu Pro Lys Leu Gly Ala Glu Glu Met Phe Tyr Glu Lys
            595                 600                 605

Met Glu Tyr Lys Gln Ile Ala Glu Pro Met Leu Met Leu Pro Lys Val
            610                 615                 620

Phe Phe Pro Lys Lys Thr Lys Pro Ala Phe Ala Pro Asp Gln Ser Val
625                 630                 635                 640

Val Asp Ile Tyr Asn Lys Lys Thr Phe Lys Thr Gly Gln Lys Gly Phe
                645                 650                 655

Asn Lys Lys Asp Leu Tyr Arg Leu Ile Asp Phe Tyr Lys Glu Ala Leu
            660                 665                 670

Thr Val His Glu Trp Lys Leu Phe Asn Phe Ser Phe Ser Pro Thr Glu
            675                 680                 685

Gln Tyr Arg Asn Ile Gly Glu Phe Phe Asp Glu Val Arg Glu Gln Ala
            690                 695                 700

Tyr Lys Val Ser Met Val Asn Val Pro Ala Ser Tyr Ile Asp Glu Ala
705                 710                 715                 720

Val Glu Asn Gly Lys Leu Tyr Leu Phe Gln Ile Tyr Asn Lys Asp Phe
                725                 730                 735

Ser Pro Tyr Ser Lys Gly Ile Pro Asn Leu His Thr Leu Tyr Trp Lys
            740                 745                 750

Ala Leu Phe Ser Glu Gln Asn Gln Ser Arg Val Tyr Lys Leu Cys Gly
            755                 760                 765

Gly Gly Glu Leu Phe Tyr Arg Lys Ala Ser Leu His Met Gln Asp Thr
            770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
                805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
            835                 840                 845

Ala Gln Asn Asp Asp Leu Gln Ile Ile Gly Ile Asp Arg Gly Glu Arg
            850                 855                 860

Asn Leu Leu Tyr Ile Ser Arg Ile Asp Thr Arg Gly Asn Leu Leu Glu
865                 870                 875                 880

Gln Phe Ser Leu Asn Val Ile Glu Ser Asp Lys Gly Asp Leu Arg Thr
                885                 890                 895

Asp Tyr Gln Lys Ile Leu Gly Asp Arg Glu Gln Glu Arg Leu Arg Arg
            900                 905                 910

Arg Gln Glu Trp Lys Ser Ile Glu Ser Ile Lys Asp Leu Lys Asp Gly
            915                 920                 925
```

```
Tyr Met Ser Gln Val Val His Lys Ile Cys Asn Met Val Val Glu His
            930                 935                 940

Lys Ala Ile Val Val Leu Glu Asn Leu Asn Leu Ser Phe Met Lys Gly
945                 950                 955                 960

Arg Lys Lys Val Glu Lys Ser Val Tyr Glu Lys Phe Glu Arg Met Leu
                965                 970                 975

Val Asp Lys Leu Asn Tyr Leu Val Val Asp Lys Lys Asn Leu Ser Asn
            980                 985                 990

Glu Pro Gly Gly Leu Tyr Ala Ala Tyr Gln Leu Thr Asn Pro Leu Phe
        995                 1000                1005

Ser Phe Glu Glu Leu His Arg Tyr Pro Gln Ser Gly Ile Leu Phe
    1010                1015                1020

Phe Val Asp Pro Trp Asn Thr Ser Leu Thr Asp Pro Ser Thr Gly
    1025                1030                1035

Phe Val Asn Leu Leu Gly Arg Ile Asn Tyr Thr Asn Val Gly Asp
    1040                1045                1050

Ala Arg Lys Phe Phe Asp Arg Phe Asn Ala Ile Arg Tyr Asp Gly
    1055                1060                1065

Lys Gly Asn Ile Leu Phe Asp Leu Asp Leu Ser Arg Phe Asp Val
    1070                1075                1080

Arg Val Glu Thr Gln Arg Lys Leu Trp Thr Leu Thr Thr Phe Gly
    1085                1090                1095

Ser Arg Ile Ala Lys Ser Lys Ser Gly Lys Trp Met Val Glu
    1100                1105                1110

Arg Ile Glu Asn Leu Ser Leu Cys Phe Leu Glu Leu Phe Glu Gln
    1115                1120                1125

Phe Asn Ile Gly Tyr Arg Val Glu Lys Asp Leu Lys Lys Ala Ile
    1130                1135                1140

Leu Ser Gln Asp Arg Lys Glu Phe Tyr Val Arg Leu Ile Tyr Leu
    1145                1150                1155

Phe Asn Leu Met Met Gln Ile Arg Asn Ser Asp Gly Glu Glu Asp
    1160                1165                1170

Tyr Ile Leu Ser Pro Ala Leu Asn Glu Lys Asn Leu Gln Phe Asp
    1175                1180                1185

Ser Arg Leu Ile Glu Ala Lys Asp Leu Pro Val Asp Ala Asp Ala
    1190                1195                1200

Asn Gly Ala Tyr Asn Val Ala Arg Lys Gly Leu Met Val Val Gln
    1205                1210                1215

Arg Ile Lys Arg Gly Asp His Glu Ser Ile His Arg Ile Gly Arg
    1220                1225                1230

Ala Gln Trp Leu Arg Tyr Val Gln Glu Gly Ile Val Glu Lys Arg
    1235                1240                1245

Pro Ala Ala Thr Lys Lys Ala Gly Gln Ala Lys Lys Lys Lys Gly
    1250                1255                1260

Ser Tyr Pro Tyr Asp Val Pro Asp Tyr Ala Tyr Pro Tyr Asp Val
    1265                1270                1275

Pro Asp Tyr Ala Tyr Pro Tyr Asp Val Pro Asp Tyr Ala
    1280                1285                1290

<210> SEQ ID NO 44
<211> LENGTH: 1343
<212> TYPE: PRT
<213> ORGANISM: Thiomicrospira sp.
```

```
<400> SEQUENCE: 44

Met Thr Lys Thr Phe Asp Ser Glu Phe Phe Asn Leu Tyr Ser Leu Gln
1               5                   10                  15

Lys Thr Val Arg Phe Glu Leu Lys Pro Val Gly Glu Thr Ala Ser Phe
            20                  25                  30

Val Glu Asp Phe Lys Asn Glu Gly Leu Lys Arg Val Val Ser Glu Asp
            35                  40                  45

Glu Arg Arg Ala Val Asp Tyr Gln Lys Val Lys Glu Ile Ile Asp Asp
        50                  55                  60

Tyr His Arg Asp Phe Ile Glu Glu Ser Leu Asn Tyr Phe Pro Glu Gln
65                  70                  75                  80

Val Ser Lys Asp Ala Leu Glu Gln Ala Phe His Leu Tyr Gln Lys Leu
            85                  90                  95

Lys Ala Ala Lys Val Glu Glu Arg Glu Lys Ala Leu Lys Glu Trp Glu
            100                 105                 110

Ala Leu Gln Lys Lys Leu Arg Glu Lys Val Val Lys Cys Phe Ser Asp
        115                 120                 125

Ser Asn Lys Ala Arg Phe Ser Arg Ile Asp Lys Lys Glu Leu Ile Lys
    130                 135                 140

Glu Asp Leu Ile Asn Trp Leu Val Ala Gln Asn Arg Glu Asp Asp Ile
145                 150                 155                 160

Pro Thr Val Glu Thr Phe Asn Asn Phe Thr Thr Tyr Phe Thr Gly Phe
            165                 170                 175

His Glu Asn Arg Lys Asn Ile Tyr Ser Lys Asp Asp His Ala Thr Ala
            180                 185                 190

Ile Ser Phe Arg Leu Ile His Glu Asn Leu Pro Lys Phe Phe Asp Asn
        195                 200                 205

Val Ile Ser Phe Asn Lys Leu Lys Glu Gly Phe Pro Glu Leu Lys Phe
    210                 215                 220

Asp Lys Val Lys Glu Asp Leu Glu Val Asp Tyr Asp Leu Lys His Ala
225                 230                 235                 240

Phe Glu Ile Glu Tyr Phe Val Asn Phe Val Thr Gln Ala Gly Ile Asp
            245                 250                 255

Gln Tyr Asn Tyr Leu Leu Gly Gly Lys Thr Leu Glu Asp Gly Thr Lys
            260                 265                 270

Lys Gln Gly Met Asn Glu Gln Ile Asn Leu Phe Lys Gln Gln Gln Thr
        275                 280                 285

Arg Asp Lys Ala Arg Gln Ile Pro Lys Leu Ile Pro Leu Phe Lys Gln
    290                 295                 300

Ile Leu Ser Glu Arg Thr Glu Ser Gln Ser Phe Ile Pro Lys Gln Phe
305                 310                 315                 320

Glu Ser Asp Gln Glu Leu Phe Ser Leu Gln Lys Leu His Asn Asn
            325                 330                 335

Cys Gln Asp Lys Phe Thr Val Leu Gln Gln Ala Ile Leu Gly Leu Ala
            340                 345                 350

Glu Ala Asp Leu Lys Lys Val Phe Ile Lys Thr Ser Asp Leu Asn Ala
        355                 360                 365

Leu Ser Asn Thr Ile Phe Gly Asn Tyr Ser Val Phe Ser Asp Ala Leu
    370                 375                 380

Asn Leu Tyr Lys Glu Ser Leu Lys Thr Lys Lys Ala Gln Glu Ala Phe
385                 390                 395                 400

Glu Lys Leu Pro Ala His Ser Ile His Asp Leu Ile Gln Tyr Leu Glu
            405                 410                 415
```

```
Gln Phe Asn Ser Ser Leu Asp Ala Glu Lys Gln Gln Ser Thr Asp Thr
            420                 425                 430

Val Leu Asn Tyr Phe Ile Lys Thr Asp Glu Leu Tyr Ser Arg Phe Ile
            435                 440                 445

Lys Ser Thr Ser Glu Ala Phe Thr Gln Val Gln Pro Leu Phe Glu Leu
            450                 455                 460

Glu Ala Leu Ser Ser Lys Arg Arg Pro Glu Ser Glu Asp Glu Gly
465                 470                 475                 480

Ala Lys Gly Gln Glu Gly Phe Glu Gln Ile Lys Arg Ile Lys Ala Tyr
                485                 490                 495

Leu Asp Thr Leu Met Glu Ala Val His Phe Ala Lys Pro Leu Tyr Leu
            500                 505                 510

Val Lys Gly Arg Lys Met Ile Glu Gly Leu Asp Lys Asp Gln Ser Phe
            515                 520                 525

Tyr Glu Ala Phe Glu Met Ala Tyr Gln Glu Leu Glu Ser Leu Ile Ile
            530                 535                 540

Pro Ile Tyr Asn Lys Ala Arg Ser Tyr Leu Ser Arg Lys Pro Phe Lys
545                 550                 555                 560

Ala Asp Lys Phe Lys Ile Asn Phe Asp Asn Asn Thr Leu Leu Ser Gly
            565                 570                 575

Trp Asp Ala Asn Lys Glu Thr Ala Asn Ala Ser Ile Leu Phe Lys Lys
            580                 585                 590

Asp Gly Leu Tyr Tyr Leu Gly Ile Met Pro Lys Gly Lys Thr Phe Leu
            595                 600                 605

Phe Asp Tyr Phe Val Ser Ser Glu Asp Ser Glu Lys Leu Lys Gln Arg
            610                 615                 620

Arg Gln Lys Thr Ala Glu Glu Ala Leu Ala Gln Asp Gly Glu Ser Tyr
625                 630                 635                 640

Phe Glu Lys Ile Arg Tyr Lys Leu Leu Pro Gly Ala Ser Lys Met Leu
            645                 650                 655

Pro Lys Val Phe Phe Ser Asn Lys Asn Ile Gly Phe Tyr Asn Pro Ser
            660                 665                 670

Asp Asp Ile Leu Arg Ile Arg Asn Thr Ala Ser His Thr Lys Asn Gly
            675                 680                 685

Thr Pro Gln Lys Gly His Ser Lys Val Glu Phe Asn Leu Asn Asp Cys
690                 695                 700

His Lys Met Ile Asp Phe Phe Lys Ser Ser Ile Gln Lys His Pro Glu
705                 710                 715                 720

Trp Gly Ser Phe Gly Phe Thr Phe Ser Asp Thr Ser Asp Phe Glu Asp
                725                 730                 735

Met Ser Ala Phe Tyr Arg Glu Val Glu Asn Gln Gly Tyr Val Ile Ser
            740                 745                 750

Phe Asp Lys Ile Lys Glu Thr Tyr Ile Gln Ser Gln Val Glu Gln Gly
            755                 760                 765

Asn Leu Tyr Leu Phe Gln Ile Tyr Asn Lys Asp Phe Ser Pro Tyr Ser
            770                 775                 780

Lys Gly Lys Pro Asn Leu His Thr Leu Tyr Trp Lys Ala Leu Phe Glu
785                 790                 795                 800

Glu Ala Asn Leu Asn Asn Val Val Ala Lys Leu Asn Gly Glu Ala Glu
            805                 810                 815

Ile Phe Phe Arg Arg His Ser Ile Lys Ala Ser Asp Lys Val Val His
            820                 825                 830
```

-continued

```
Pro Ala Asn Gln Ala Ile Asp Asn Lys Asn Pro His Thr Glu Lys Thr
            835                 840                 845

Gln Ser Thr Phe Glu Tyr Asp Leu Val Lys Asp Lys Arg Tyr Thr Gln
850                 855                 860

Asp Lys Phe Phe Phe His Val Pro Ile Ser Leu Asn Phe Lys Ala Gln
865                 870                 875                 880

Gly Val Ser Lys Phe Asn Asp Lys Val Asn Gly Phe Leu Lys Gly Asn
                885                 890                 895

Pro Asp Val Asn Ile Ile Gly Ile Asp Arg Gly Glu Arg His Leu Leu
            900                 905                 910

Tyr Phe Thr Val Val Asn Gln Lys Gly Glu Ile Leu Val Gln Glu Ser
        915                 920                 925

Leu Asn Thr Leu Met Ser Asp Lys Gly His Val Asn Asp Tyr Gln Gln
    930                 935                 940

Lys Leu Asp Lys Lys Glu Gln Glu Arg Asp Ala Ala Arg Lys Ser Trp
945                 950                 955                 960

Thr Thr Val Glu Asn Ile Lys Glu Leu Lys Glu Gly Tyr Leu Ser His
                965                 970                 975

Val Val His Lys Leu Ala His Leu Ile Ile Lys Tyr Asn Ala Ile Val
            980                 985                 990

Cys Leu Glu Asp Leu Asn Phe Gly Phe Lys Arg Gly Arg Phe Lys Val
        995                 1000                1005

Glu Lys Gln Val Tyr Gln Lys Phe Glu Lys Ala Leu Ile Asp Lys
    1010                1015                1020

Leu Asn Tyr Leu Val Phe Lys Glu Lys Glu Leu Gly Glu Val Gly
    1025                1030                1035

His Tyr Leu Thr Ala Tyr Gln Leu Thr Ala Pro Phe Glu Ser Phe
    1040                1045                1050

Lys Lys Leu Gly Lys Gln Ser Gly Ile Leu Phe Tyr Val Pro Ala
    1055                1060                1065

Asp Tyr Thr Ser Lys Ile Asp Pro Thr Thr Gly Phe Val Asn Phe
    1070                1075                1080

Leu Asp Leu Arg Tyr Gln Ser Val Glu Lys Ala Lys Gln Leu Leu
    1085                1090                1095

Ser Asp Phe Asn Ala Ile Arg Phe Asn Ser Val Gln Asn Tyr Phe
    1100                1105                1110

Glu Phe Glu Ile Asp Tyr Lys Lys Leu Thr Pro Lys Arg Lys Val
    1115                1120                1125

Gly Thr Gln Ser Lys Trp Val Ile Cys Thr Tyr Gly Asp Val Arg
    1130                1135                1140

Tyr Gln Asn Arg Arg Asn Gln Lys Gly His Trp Glu Thr Glu Glu
    1145                1150                1155

Val Asn Val Thr Glu Lys Leu Lys Ala Leu Phe Ala Ser Asp Ser
    1160                1165                1170

Lys Thr Thr Thr Val Ile Asp Tyr Ala Asn Asp Asp Asn Leu Ile
    1175                1180                1185

Asp Val Ile Leu Glu Gln Asp Lys Ala Ser Phe Phe Lys Glu Leu
    1190                1195                1200

Leu Trp Leu Leu Lys Leu Thr Met Thr Leu Arg His Ser Lys Ile
    1205                1210                1215

Lys Ser Glu Asp Asp Phe Ile Leu Ser Pro Val Lys Asn Glu Gln
    1220                1225                1230

Gly Glu Phe Tyr Asp Ser Arg Lys Ala Gly Glu Val Trp Pro Lys
```

-continued

```
                1235                1240                1245

Asp Ala Asp Ala Asn Gly Ala Tyr His Ile Ala Leu Lys Gly Leu
        1250                1255                1260

Trp Asn Leu Gln Gln Ile Asn Gln Trp Glu Lys Gly Lys Thr Leu
1265                1270                1275

Asn Leu Ala Ile Lys Asn Gln Asp Trp Phe Ser Phe Ile Gln Glu
        1280                1285                1290

Lys Pro Tyr Gln Glu Lys Arg Pro Ala Ala Thr Lys Lys Ala Gly
1295                1300                1305

Gln Ala Lys Lys Lys Gly Ser Tyr Pro Tyr Asp Val Pro Asp
        1310                1315                1320

Tyr Ala Tyr Pro Tyr Asp Val Pro Asp Tyr Ala Tyr Pro Tyr Asp
1325                1330                1335

Val Pro Asp Tyr Ala
        1340

<210> SEQ ID NO 45
<211> LENGTH: 1296
<212> TYPE: PRT
<213> ORGANISM: Moraxella bovoculi

<400> SEQUENCE: 45

Met Leu Phe Gln Asp Phe Thr His Leu Tyr Pro Leu Ser Lys Thr Val
1               5                   10                  15

Arg Phe Glu Leu Lys Pro Ile Gly Arg Thr Leu Glu His Ile His Ala
            20                  25                  30

Lys Asn Phe Leu Ser Gln Asp Glu Thr Met Ala Asp Met Tyr Gln Lys
        35                  40                  45

Val Lys Val Ile Leu Asp Asp Tyr His Arg Asp Phe Ile Ala Asp Met
50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Gly Leu Gln Lys Gln Leu
            85                  90                  95

Lys Asp Leu Gln Ala Val Leu Arg Lys Glu Ser Val Lys Pro Ile Gly
        100                 105                 110

Ser Gly Gly Lys Tyr Lys Thr Gly Tyr Asp Arg Leu Phe Gly Ala Lys
    115                 120                 125

Leu Phe Lys Asp Gly Lys Glu Leu Gly Asp Leu Ala Lys Phe Val Ile
130                 135                 140

Ala Gln Glu Gly Glu Ser Ser Pro Lys Leu Ala His Leu Ala His Phe
145                 150                 155                 160

Glu Lys Phe Ser Thr Tyr Phe Thr Gly Phe His Asp Asn Arg Lys Asn
            165                 170                 175

Met Tyr Ser Asp Glu Asp Lys His Thr Ala Ile Ala Tyr Arg Leu Ile
        180                 185                 190

His Glu Asn Leu Pro Arg Phe Ile Asp Asn Leu Gln Ile Leu Thr Thr
    195                 200                 205

Ile Lys Gln Lys His Ser Ala Leu Tyr Asp Gln Ile Ile Asn Glu Leu
210                 215                 220

Thr Ala Ser Gly Leu Asp Val Ser Leu Ala Ser His Leu Asp Gly Tyr
225                 230                 235                 240

His Lys Leu Leu Thr Gln Glu Gly Ile Thr Ala Tyr Asn Arg Ile Ile
            245                 250                 255
```

```
Gly Glu Val Asn Gly Tyr Thr Asn Lys His Asn Gln Ile Cys His Lys
            260                 265                 270

Ser Glu Arg Ile Ala Lys Leu Arg Pro Leu His Lys Gln Ile Leu Ser
    275                 280                 285

Asp Gly Met Gly Val Ser Phe Leu Pro Ser Lys Phe Ala Asp Asp Ser
290                 295                 300

Glu Met Cys Gln Ala Val Asn Glu Phe Tyr Arg His Tyr Thr Asp Val
305                 310                 315                 320

Phe Ala Lys Val Gln Ser Leu Phe Asp Gly Phe Asp His Gln Lys
                325                 330                 335

Asp Gly Ile Tyr Val Glu His Lys Asn Leu Asn Glu Leu Ser Lys Gln
            340                 345                 350

Ala Phe Gly Asp Phe Ala Leu Leu Gly Arg Val Leu Asp Gly Tyr Tyr
            355                 360                 365

Val Asp Val Val Asn Pro Glu Phe Asn Glu Arg Phe Ala Lys Ala Lys
        370                 375                 380

Thr Asp Asn Ala Lys Ala Lys Leu Thr Lys Glu Lys Asp Lys Phe Ile
385                 390                 395                 400

Lys Gly Val His Ser Leu Ala Ser Leu Glu Gln Ala Ile Glu His His
                405                 410                 415

Thr Ala Arg His Asp Asp Glu Ser Val Gln Ala Gly Lys Leu Gly Gln
            420                 425                 430

Tyr Phe Lys His Gly Leu Ala Gly Val Asp Asn Pro Ile Gln Lys Ile
            435                 440                 445

His Asn Asn His Ser Thr Ile Lys Gly Phe Leu Glu Arg Glu Arg Pro
450                 455                 460

Ala Gly Glu Arg Ala Leu Pro Lys Ile Lys Ser Gly Lys Asn Pro Glu
465                 470                 475                 480

Met Thr Gln Leu Arg Gln Leu Lys Glu Leu Leu Asp Asn Ala Leu Asn
                485                 490                 495

Val Ala His Phe Ala Lys Leu Leu Thr Thr Lys Thr Thr Leu Asp Asn
                500                 505                 510

Gln Asp Gly Asn Phe Tyr Gly Glu Phe Gly Val Leu Tyr Asp Glu Leu
        515                 520                 525

Ala Lys Ile Pro Thr Leu Tyr Asn Lys Val Arg Asp Tyr Leu Ser Gln
530                 535                 540

Lys Pro Phe Ser Thr Glu Lys Tyr Lys Leu Asn Phe Gly Asn Pro Thr
545                 550                 555                 560

Leu Leu Asn Gly Trp Asp Leu Asn Lys Glu Lys Asp Asn Phe Gly Val
                565                 570                 575

Ile Leu Gln Lys Asp Gly Cys Tyr Tyr Leu Ala Leu Leu Asp Lys Ala
            580                 585                 590

His Lys Lys Val Phe Asp Asn Ala Pro Asn Thr Gly Lys Asn Val Tyr
            595                 600                 605

Gln Lys Met Val Tyr Lys Leu Leu Pro Gly Pro Asn Lys Met Leu Pro
        610                 615                 620

Lys Val Phe Phe Ala Lys Ser Asn Leu Asp Tyr Tyr Asn Pro Ser Ala
625                 630                 635                 640

Glu Leu Leu Asp Lys Tyr Ala Lys Gly Thr His Lys Lys Gly Asp Asn
                645                 650                 655

Phe Asn Leu Lys Asp Cys His Ala Leu Ile Asp Phe Phe Lys Ala Gly
            660                 665                 670

Ile Asn Lys His Pro Glu Trp Gln His Phe Gly Phe Lys Phe Ser Pro
```

```
                    675                 680                 685
Thr Ser Ser Tyr Arg Asp Leu Ser Asp Phe Tyr Arg Glu Val Glu Pro
            690                 695                 700
Gln Gly Tyr Gln Val Lys Phe Val Asp Ile Asn Ala Asp Tyr Ile Asp
705                 710                 715                 720
Glu Leu Val Glu Gln Gly Lys Leu Tyr Leu Phe Gln Ile Tyr Asn Lys
                    725                 730                 735
Asp Phe Ser Pro Lys Ala His Gly Lys Pro Asn Leu His Thr Leu Tyr
            740                 745                 750
Phe Lys Ala Leu Phe Ser Glu Asp Asn Leu Ala Asp Pro Ile Tyr Lys
            755                 760                 765
Leu Asn Gly Glu Ala Gln Ile Phe Tyr Arg Lys Ala Ser Leu Asp Met
    770                 775                 780
Asn Glu Thr Thr Ile His Arg Ala Gly Glu Val Leu Glu Asn Lys Asn
785                 790                 795                 800
Pro Asp Asn Pro Lys Lys Arg Gln Phe Val Tyr Asp Ile Ile Lys Asp
                    805                 810                 815
Lys Arg Tyr Thr Gln Asp Lys Phe Met Leu His Val Pro Ile Thr Met
            820                 825                 830
Asn Phe Gly Val Gln Gly Met Thr Ile Lys Glu Phe Asn Lys Lys Val
            835                 840                 845
Asn Gln Ser Ile Gln Gln Tyr Asp Glu Val Asn Val Ile Gly Ile Asp
    850                 855                 860
Arg Gly Glu Arg His Leu Leu Tyr Leu Thr Val Ile Asn Ser Lys Gly
865                 870                 875                 880
Glu Ile Leu Glu Gln Arg Ser Leu Asn Asp Ile Thr Thr Ala Ser Ala
                    885                 890                 895
Asn Gly Thr Gln Val Thr Thr Pro Tyr His Lys Ile Leu Asp Lys Arg
            900                 905                 910
Glu Ile Glu Arg Leu Asn Ala Arg Val Gly Trp Gly Glu Ile Glu Thr
            915                 920                 925
Ile Lys Glu Leu Lys Ser Gly Tyr Leu Ser His Val Val His Gln Ile
    930                 935                 940
Asn Gln Leu Met Leu Lys Tyr Asn Ala Ile Val Val Leu Glu Asp Leu
945                 950                 955                 960
Asn Phe Gly Phe Lys Arg Gly Arg Phe Lys Val Glu Lys Gln Ile Tyr
                    965                 970                 975
Gln Asn Phe Glu Asn Ala Leu Ile Lys Lys Leu Asn His Leu Val Leu
            980                 985                 990
Lys Asp Lys Ala Asp Asp Glu Ile Gly Ser Tyr Lys Asn Ala Leu Gln
            995                 1000                1005
Leu Thr Asn Asn Phe Thr Asp Leu Lys Ser Ile Gly Lys Gln Thr
    1010                1015                1020
Gly Phe Leu Phe Tyr Val Pro Ala Trp Asn Thr Ser Lys Ile Asp
    1025                1030                1035
Pro Glu Thr Gly Phe Val Asp Leu Leu Lys Pro Arg Tyr Glu Asn
    1040                1045                1050
Ile Ala Gln Ser Gln Ala Phe Phe Gly Lys Phe Asp Lys Ile Cys
    1055                1060                1065
Tyr Asn Thr Asp Lys Gly Tyr Phe Glu Phe His Ile Asp Tyr Ala
    1070                1075                1080
Lys Phe Thr Asp Lys Ala Lys Asn Ser Arg Gln Lys Trp Ala Ile
    1085                1090                1095
```

-continued

```
Cys Ser His Gly Asp Lys Arg Tyr Val Tyr Asp Lys Thr Ala Asn
    1100                1105                1110

Gln Asn Lys Gly Ala Ala Lys Gly Ile Asn Val Asn Asp Glu Leu
    1115                1120                1125

Lys Ser Leu Phe Ala Arg Tyr His Ile Asn Asp Lys Gln Pro Asn
    1130                1135                1140

Leu Val Met Asp Ile Cys Gln Asn Asp Lys Glu Phe His Lys
    1145                1150                1155

Ser Leu Met Cys Leu Leu Lys Thr Leu Leu Ala Leu Arg Tyr Ser
    1160                1165                1170

Asn Ala Ser Ser Asp Glu Asp Phe Ile Leu Ser Pro Val Ala Asn
    1175                1180                1185

Asp Glu Gly Val Phe Phe Asn Ser Ala Leu Ala Asp Asp Thr Gln
    1190                1195                1200

Pro Gln Asn Ala Asp Ala Asn Gly Ala Tyr His Ile Ala Leu Lys
    1205                1210                1215

Gly Leu Trp Leu Leu Asn Glu Leu Lys Asn Ser Asp Asp Leu Asn
    1220                1225                1230

Lys Val Lys Leu Ala Ile Asp Asn Gln Thr Trp Leu Asn Phe Ala
    1235                1240                1245

Gln Asn Arg Lys Arg Pro Ala Ala Thr Lys Lys Ala Gly Gln Ala
    1250                1255                1260

Lys Lys Lys Lys Gly Ser Tyr Pro Tyr Asp Val Pro Asp Tyr Ala
    1265                1270                1275

Tyr Pro Tyr Asp Val Pro Asp Tyr Ala Tyr Pro Tyr Asp Val Pro
    1280                1285                1290

Asp Tyr Ala
    1295

<210> SEQ ID NO 46
<211> LENGTH: 1306
<212> TYPE: PRT
<213> ORGANISM: Moraxella bovoculi

<400> SEQUENCE: 46

Met Leu Phe Gln Asp Phe Thr His Leu Tyr Pro Leu Ser Lys Thr Val
1               5                   10                  15

Arg Phe Glu Leu Lys Pro Ile Gly Lys Thr Leu Glu His Ile His Ala
                20                  25                  30

Lys Asn Phe Leu Asn Gln Asp Glu Thr Met Ala Asp Met Tyr Gln Lys
            35                  40                  45

Val Lys Ala Ile Leu Asp Asp Tyr His Arg Asp Phe Ile Ala Asp Met
        50                  55                  60

Met Gly Glu Val Lys Leu Thr Lys Leu Ala Glu Phe Tyr Asp Val Tyr
65                  70                  75                  80

Leu Lys Phe Arg Lys Asn Pro Lys Asp Asp Gly Leu Gln Lys Gln Leu
                85                  90                  95

Lys Asp Leu Gln Ala Val Leu Arg Lys Glu Ile Val Lys Pro Ile Gly
            100                 105                 110

Asn Gly Gly Lys Tyr Lys Ala Gly Tyr Asp Arg Leu Phe Gly Ala Lys
        115                 120                 125

Leu Phe Lys Asp Gly Lys Glu Leu Gly Asp Leu Ala Lys Phe Val Ile
    130                 135                 140

Ala Gln Glu Gly Glu Ser Ser Pro Lys Leu Ala His Leu Ala His Phe
```

```
145                 150                 155                 160
Glu Lys Phe Ser Thr Tyr Phe Thr Gly Phe His Asp Asn Arg Lys Asn
                165                 170                 175
Met Tyr Ser Asp Glu Asp Lys His Thr Ala Ile Ala Tyr Arg Leu Ile
            180                 185                 190
His Glu Asn Leu Pro Arg Phe Ile Asp Asn Leu Gln Ile Leu Ala Thr
                195                 200                 205
Ile Lys Gln Lys His Ser Ala Leu Tyr Asp Gln Ile Ile Asn Glu Leu
        210                 215                 220
Thr Ala Ser Gly Leu Asp Val Ser Leu Ala Ser His Leu Asp Gly Tyr
225                 230                 235                 240
His Lys Leu Leu Thr Gln Glu Gly Ile Thr Ala Tyr Asn Thr Leu Leu
                245                 250                 255
Gly Gly Ile Ser Gly Glu Ala Gly Ser Arg Lys Ile Gln Gly Ile Asn
                260                 265                 270
Glu Leu Ile Asn Ser His His Asn Gln His Cys His Lys Ser Glu Arg
            275                 280                 285
Ile Ala Lys Leu Arg Pro Leu His Lys Gln Ile Leu Ser Asp Gly Met
        290                 295                 300
Gly Val Ser Phe Leu Pro Ser Lys Phe Ala Asp Asp Ser Glu Val Cys
305                 310                 315                 320
Gln Ala Val Asn Glu Phe Tyr Arg His Tyr Ala Asp Val Phe Ala Lys
                325                 330                 335
Val Gln Ser Leu Phe Asp Gly Phe Asp Asp Tyr Gln Lys Asp Gly Ile
            340                 345                 350
Tyr Val Glu Tyr Lys Asn Leu Asn Glu Leu Ser Lys Gln Ala Phe Gly
        355                 360                 365
Asp Phe Ala Leu Leu Gly Arg Val Leu Asp Gly Tyr Tyr Val Asp Val
        370                 375                 380
Val Asn Pro Glu Phe Asn Glu Arg Phe Ala Lys Ala Lys Thr Asp Asn
385                 390                 395                 400
Ala Lys Ala Lys Leu Thr Lys Glu Lys Asp Lys Phe Ile Lys Gly Val
                405                 410                 415
His Ser Leu Ala Ser Leu Glu Gln Ala Ile Glu His Tyr Thr Ala Arg
            420                 425                 430
His Asp Asp Glu Ser Val Gln Ala Gly Lys Leu Gly Gln Tyr Phe Lys
        435                 440                 445
His Gly Leu Ala Gly Val Asp Asn Pro Ile Gln Lys Ile His Asn Asn
450                 455                 460
His Ser Thr Ile Lys Gly Phe Leu Glu Arg Glu Arg Pro Ala Gly Glu
465                 470                 475                 480
Arg Ala Leu Pro Lys Ile Lys Ser Asp Lys Ser Pro Glu Ile Arg Gln
                485                 490                 495
Leu Lys Glu Leu Leu Asp Asn Ala Leu Asn Val Ala His Phe Ala Lys
            500                 505                 510
Leu Leu Thr Thr Lys Thr Thr Leu His Asn Gln Asp Gly Asn Phe Tyr
        515                 520                 525
Gly Glu Phe Gly Ala Leu Tyr Asp Glu Leu Ala Lys Ile Ala Thr Leu
        530                 535                 540
Tyr Asn Lys Val Arg Asp Tyr Leu Ser Gln Lys Pro Phe Ser Thr Glu
545                 550                 555                 560
Lys Tyr Lys Leu Asn Phe Gly Asn Pro Thr Leu Leu Asn Gly Trp Asp
                565                 570                 575
```

-continued

```
Leu Asn Lys Glu Lys Asp Asn Phe Gly Val Ile Leu Gln Lys Asp Gly
            580                 585                 590

Cys Tyr Tyr Leu Ala Leu Leu Asp Lys Ala His Lys Lys Val Phe Asp
        595                 600                 605

Asn Ala Pro Asn Thr Gly Lys Ser Val Tyr Gln Lys Met Ile Tyr Lys
610                 615                 620

Leu Leu Pro Gly Pro Asn Lys Met Leu Pro Lys Val Phe Phe Ala Lys
625                 630                 635                 640

Ser Asn Leu Asp Tyr Tyr Asn Pro Ser Ala Glu Leu Leu Asp Lys Tyr
                645                 650                 655

Ala Gln Gly Thr His Lys Lys Gly Asp Asn Phe Asn Leu Lys Asp Cys
            660                 665                 670

His Ala Leu Ile Asp Phe Phe Lys Ala Gly Ile Asn Lys His Pro Glu
        675                 680                 685

Trp Gln His Phe Gly Phe Lys Phe Ser Pro Thr Ser Ser Tyr Gln Asp
    690                 695                 700

Leu Ser Asp Phe Tyr Arg Glu Val Glu Pro Gln Gly Tyr Gln Val Lys
705                 710                 715                 720

Phe Val Asp Ile Asn Ala Asp Tyr Ile Asn Glu Leu Val Glu Gln Gly
                725                 730                 735

Gln Leu Tyr Leu Phe Gln Ile Tyr Asn Lys Asp Phe Ser Pro Lys Ala
            740                 745                 750

His Gly Lys Pro Asn Leu His Thr Leu Tyr Phe Lys Ala Leu Phe Ser
        755                 760                 765

Glu Asp Asn Leu Val Asn Pro Ile Tyr Lys Leu Asn Gly Glu Ala Glu
    770                 775                 780

Ile Phe Tyr Arg Lys Ala Ser Leu Asp Met Asn Glu Thr Thr Ile His
785                 790                 795                 800

Arg Ala Gly Glu Val Leu Glu Asn Lys Asn Pro Asp Asn Pro Lys Lys
                805                 810                 815

Arg Gln Phe Val Tyr Asp Ile Ile Lys Asp Lys Arg Tyr Thr Gln Asp
            820                 825                 830

Lys Phe Met Leu His Val Pro Ile Thr Met Asn Phe Gly Val Gln Gly
        835                 840                 845

Met Thr Ile Lys Glu Phe Asn Lys Lys Val Asn Gln Ser Ile Gln Gln
    850                 855                 860

Tyr Asp Glu Val Asn Val Ile Gly Ile Asp Arg Gly Glu Arg His Leu
865                 870                 875                 880

Leu Tyr Leu Thr Val Ile Asn Ser Lys Gly Glu Ile Leu Glu Gln Arg
                885                 890                 895

Ser Leu Asn Asp Ile Thr Thr Ala Ser Ala Asn Gly Thr Gln Met Thr
            900                 905                 910

Thr Pro Tyr His Lys Ile Leu Asp Lys Arg Glu Ile Glu Arg Leu Asn
        915                 920                 925

Ala Arg Val Gly Trp Gly Glu Ile Glu Thr Ile Lys Glu Leu Lys Ser
    930                 935                 940

Gly Tyr Leu Ser His Val Val His Gln Ile Ser Gln Leu Met Leu Lys
945                 950                 955                 960

Tyr Asn Ala Ile Val Val Leu Glu Asp Leu Asn Phe Gly Phe Lys Arg
                965                 970                 975

Gly Arg Phe Lys Val Glu Lys Gln Ile Tyr Gln Asn Phe Glu Asn Ala
            980                 985                 990
```

-continued

```
Leu Ile Lys Lys Leu Asn His Leu  Val Leu Lys Asp Lys  Ala Asp Asp
        995              1000              1005

Glu Ile Gly Ser Tyr Lys Asn  Ala Leu Gln Leu Thr  Asn Asn Phe
   1010              1015              1020

Thr Asp Leu Lys Ser Ile Gly  Lys Gln Thr Gly Phe  Leu Phe Tyr
   1025              1030              1035

Val Pro Ala Trp Asn Thr Ser  Lys Ile Asp Pro Glu  Thr Gly Phe
   1040              1045              1050

Val Asp Leu Leu Lys Pro Arg  Tyr Glu Asn Ile Ala  Gln Ser Gln
   1055              1060              1065

Ala Phe Phe Gly Lys Phe Asp  Lys Ile Cys Tyr Asn  Ala Asp Arg
   1070              1075              1080

Gly Tyr Phe Glu Phe His Ile  Asp Tyr Ala Lys Phe  Asn Asp Lys
   1085              1090              1095

Ala Lys Asn Ser Arg Gln Ile  Trp Lys Ile Cys Ser  His Gly Asp
   1100              1105              1110

Lys Arg Tyr Val Tyr Asp Lys  Thr Ala Asn Gln Asn  Lys Gly Ala
   1115              1120              1125

Thr Ile Gly Val Asn Val Asn  Asp Glu Leu Lys Ser  Leu Phe Thr
   1130              1135              1140

Arg Tyr His Ile Asn Asp Lys  Gln Pro Asn Leu Val  Met Asp Ile
   1145              1150              1155

Cys Gln Asn Asn Asp Lys Glu  Phe His Lys Ser Leu  Met Tyr Leu
   1160              1165              1170

Leu Lys Thr Leu Leu Ala Leu  Arg Tyr Ser Asn Ala  Ser Ser Asp
   1175              1180              1185

Glu Asp Phe Ile Leu Ser Pro  Val Ala Asn Asp Glu  Gly Val Phe
   1190              1195              1200

Phe Asn Ser Ala Leu Ala Asp  Asp Thr Gln Pro Gln  Asn Ala Asp
   1205              1210              1215

Ala Asn Gly Ala Tyr His Ile  Ala Leu Lys Gly Leu  Trp Leu Leu
   1220              1225              1230

Asn Glu Leu Lys Asn Ser Asp  Asp Leu Asn Lys Val  Lys Leu Ala
   1235              1240              1245

Ile Asp Asn Gln Thr Trp Leu  Asn Phe Ala Gln Asn  Arg Lys Arg
   1250              1255              1260

Pro Ala Ala Thr Lys Lys Ala  Gly Gln Ala Lys Lys  Lys Lys Gly
   1265              1270              1275

Ser Tyr Pro Tyr Asp Val Pro  Asp Tyr Ala Tyr Pro  Tyr Asp Val
   1280              1285              1290

Pro Asp Tyr Ala Tyr Pro Tyr  Asp Val Pro Asp Tyr  Ala
   1295              1300              1305

<210> SEQ ID NO 47
<211> LENGTH: 1251
<212> TYPE: PRT
<213> ORGANISM: Butyrivibrio sp.

<400> SEQUENCE: 47

Met Tyr Tyr Gln Asn Leu Thr Lys Lys Tyr Pro Val Ser Lys Thr Ile
1               5                   10                  15

Arg Asn Glu Leu Ile Pro Ile Gly Lys Thr Leu Glu Asn Ile Arg Lys
            20                  25                  30

Asn Asn Ile Leu Glu Ser Asp Val Lys Arg Lys Gln Asp Tyr Glu His
        35                  40                  45
```

```
Val Lys Gly Ile Met Asp Glu Tyr His Lys Gln Leu Ile Asn Glu Ala
 50                  55                  60

Leu Asp Asn Tyr Met Leu Pro Ser Leu Asn Gln Ala Ala Glu Ile Tyr
 65                  70                  75                  80

Leu Lys Lys His Val Asp Val Glu Asp Arg Glu Glu Phe Lys Lys Thr
                 85                  90                  95

Gln Asp Leu Leu Arg Arg Glu Val Thr Gly Arg Leu Lys Glu His Glu
                100                 105                 110

Asn Tyr Thr Lys Ile Gly Lys Lys Asp Ile Leu Asp Leu Leu Glu Lys
                115                 120                 125

Leu Pro Ser Ile Ser Glu Glu Asp Tyr Asn Ala Leu Glu Ser Phe Arg
130                 135                 140

Asn Phe Tyr Thr Tyr Phe Thr Ser Tyr Asn Lys Val Arg Glu Asn Leu
145                 150                 155                 160

Tyr Ser Asp Glu Glu Lys Ser Ser Thr Val Ala Tyr Arg Leu Ile Asn
                165                 170                 175

Glu Asn Leu Pro Lys Phe Leu Asp Asn Ile Lys Ser Tyr Ala Phe Val
                180                 185                 190

Lys Ala Ala Gly Val Leu Ala Asp Cys Ile Glu Glu Glu Gln Asp
                195                 200                 205

Ala Leu Phe Met Val Glu Thr Phe Asn Met Thr Leu Thr Gln Glu Gly
210                 215                 220

Ile Asp Met Tyr Asn Tyr Gln Ile Gly Lys Val Asn Ser Ala Ile Asn
225                 230                 235                 240

Leu Tyr Asn Gln Lys Asn His Lys Val Glu Phe Lys Lys Ile Pro
                245                 250                 255

Lys Met Lys Val Leu Tyr Lys Gln Ile Leu Ser Asp Arg Glu Glu Val
                260                 265                 270

Phe Ile Gly Glu Phe Lys Asp Asp Glu Thr Leu Leu Ser Ser Ile Gly
                275                 280                 285

Ala Tyr Gly Asn Val Leu Met Thr Tyr Leu Lys Ser Glu Lys Ile Asn
290                 295                 300

Ile Phe Phe Asp Ala Leu Arg Glu Ser Glu Gly Lys Asn Val Tyr Val
305                 310                 315                 320

Lys Asn Asp Leu Ser Lys Thr Thr Met Ser Asn Ile Val Phe Gly Ser
                325                 330                 335

Trp Ser Ala Phe Asp Glu Leu Leu Asn Gln Glu Tyr Asp Leu Ala Asn
                340                 345                 350

Glu Asn Lys Lys Lys Asp Asp Lys Tyr Phe Glu Lys Arg Gln Lys Glu
                355                 360                 365

Leu Lys Lys Asn Lys Ser Tyr Thr Leu Glu Gln Met Ser Asn Leu Ser
                370                 375                 380

Lys Glu Asp Ile Ser Pro Ile Glu Asn Tyr Ile Glu Arg Ile Ser Glu
385                 390                 395                 400

Asp Ile Glu Lys Ile Cys Ile Tyr Asn Gly Glu Phe Glu Lys Ile Val
                405                 410                 415

Val Asn Glu His Asp Ser Ser Arg Lys Leu Ser Lys Asn Ile Lys Ala
                420                 425                 430

Val Lys Val Ile Lys Asp Tyr Leu Asp Ser Ile Lys Glu Leu Glu His
                435                 440                 445

Asp Ile Lys Leu Ile Asn Gly Ser Gly Gln Glu Leu Glu Lys Asn Leu
450                 455                 460
```

```
Val Val Tyr Val Gly Gln Glu Glu Ala Leu Glu Gln Leu Arg Pro Val
465                 470                 475                 480

Asp Ser Leu Tyr Asn Leu Thr Arg Asn Tyr Leu Thr Lys Lys Pro Phe
            485                 490                 495

Ser Thr Glu Lys Val Lys Leu Asn Phe Asn Lys Ser Thr Leu Leu Asn
        500                 505                 510

Gly Trp Asp Lys Asn Lys Glu Thr Asp Asn Leu Gly Ile Leu Phe Phe
        515                 520                 525

Lys Asp Gly Lys Tyr Tyr Leu Gly Ile Met Asn Thr Thr Ala Asn Lys
    530                 535                 540

Ala Phe Val Asn Pro Pro Ala Ala Lys Thr Glu Asn Val Phe Lys Lys
545                 550                 555                 560

Val Asp Tyr Lys Leu Leu Pro Gly Ser Asn Lys Met Leu Pro Lys Val
            565                 570                 575

Phe Phe Ala Lys Ser Asn Ile Gly Tyr Tyr Asn Pro Ser Thr Glu Leu
            580                 585                 590

Tyr Ser Asn Tyr Lys Lys Gly Thr His Lys Lys Gly Pro Ser Phe Ser
    595                 600                 605

Ile Asp Asp Cys His Asn Leu Ile Asp Phe Phe Lys Glu Ser Ile Lys
    610                 615                 620

Lys His Glu Asp Trp Ser Lys Phe Gly Phe Glu Phe Ser Asp Thr Ala
625                 630                 635                 640

Asp Tyr Arg Asp Ile Ser Glu Phe Tyr Arg Glu Val Glu Lys Gln Gly
            645                 650                 655

Tyr Lys Leu Thr Phe Thr Asp Ile Asp Glu Ser Tyr Ile Asn Asp Leu
            660                 665                 670

Ile Glu Lys Asn Glu Leu Tyr Leu Phe Gln Ile Tyr Asn Lys Asp Phe
    675                 680                 685

Ser Glu Tyr Ser Lys Gly Lys Leu Asn Leu His Thr Leu Tyr Phe Met
    690                 695                 700

Met Leu Phe Asp Gln Arg Asn Leu Asp Asn Val Val Tyr Lys Leu Asn
705                 710                 715                 720

Gly Glu Ala Glu Val Phe Tyr Arg Pro Ala Ser Ile Ala Glu Asn Glu
            725                 730                 735

Leu Val Ile His Lys Ala Gly Glu Gly Ile Lys Asn Lys Asn Pro Asn
            740                 745                 750

Arg Ala Lys Val Lys Glu Thr Ser Thr Phe Ser Tyr Asp Ile Val Lys
    755                 760                 765

Asp Lys Arg Tyr Ser Lys Tyr Lys Phe Thr Leu His Ile Pro Ile Thr
    770                 775                 780

Met Asn Phe Gly Val Asp Glu Val Arg Arg Phe Asn Asp Val Ile Asn
785                 790                 795                 800

Asn Ala Leu Arg Thr Asp Asp Asn Val Asn Val Ile Gly Ile Asp Arg
            805                 810                 815

Gly Glu Arg Asn Leu Leu Tyr Val Val Ile Asn Ser Glu Gly Lys
            820                 825                 830

Ile Leu Glu Gln Ile Ser Leu Asn Ser Ile Asn Lys Glu Tyr Asp
    835                 840                 845

Ile Glu Thr Asn Tyr His Ala Leu Leu Asp Glu Arg Glu Asp Asp Arg
    850                 855                 860

Asn Lys Ala Arg Lys Asp Trp Asn Thr Ile Glu Asn Ile Lys Glu Leu
865                 870                 875                 880

Lys Thr Gly Tyr Leu Ser Gln Val Val Asn Val Val Ala Lys Leu Val
```

|     |     |     |     | 885 |     |     |     | 890 |     |     |     | 895 |     |     |
| --- | --- | --- | --- | --- | --- | --- | --- | --- | --- | --- | --- | --- | --- | --- |

Leu Lys Tyr Asn Ala Ile Ile Cys Leu Glu Asp Leu Asn Phe Gly Phe
                900                 905                 910

Lys Arg Gly Arg Gln Lys Val Glu Lys Gln Val Tyr Gln Lys Phe Glu
            915                 920                 925

Lys Met Leu Ile Glu Lys Leu Asn Tyr Leu Val Ile Asp Lys Ser Arg
        930                 935                 940

Glu Gln Val Ser Pro Glu Lys Met Gly Gly Ala Leu Asn Ala Leu Gln
945                 950                 955                 960

Leu Thr Ser Lys Phe Lys Ser Phe Ala Glu Leu Gly Lys Gln Ser Gly
                965                 970                 975

Ile Ile Tyr Tyr Val Pro Ala Tyr Leu Thr Ser Lys Ile Asp Pro Thr
            980                 985                 990

Thr Gly Phe Val Asn Leu Phe Tyr Ile Lys Tyr Glu Asn Ile Glu Lys
        995                 1000                1005

Ala Lys Gln Phe Phe Asp Gly Phe Asp Phe Ile Arg Phe Asn Lys
    1010                1015                1020

Lys Asp Asp Met Phe Glu Phe Ser Phe Asp Tyr Lys Ser Phe Thr
    1025                1030                1035

Gln Lys Ala Cys Gly Ile Arg Ser Lys Trp Ile Val Tyr Thr Asn
    1040                1045                1050

Gly Glu Arg Ile Ile Lys Tyr Pro Asn Pro Glu Lys Asn Asn Leu
    1055                1060                1065

Phe Asp Glu Lys Val Ile Asn Val Thr Asp Glu Ile Lys Gly Leu
    1070                1075                1080

Phe Lys Gln Tyr Arg Ile Pro Tyr Glu Asn Gly Glu Asp Ile Lys
    1085                1090                1095

Glu Ile Ile Ile Ser Lys Ala Glu Ala Asp Phe Tyr Lys Arg Leu
    1100                1105                1110

Phe Arg Leu Leu His Gln Thr Leu Gln Met Arg Asn Ser Thr Ser
    1115                1120                1125

Asp Gly Thr Arg Asp Tyr Ile Ile Ser Pro Val Lys Asn Asp Arg
    1130                1135                1140

Gly Glu Phe Phe Cys Ser Glu Phe Ser Glu Gly Thr Met Pro Lys
    1145                1150                1155

Asp Ala Asp Ala Asn Gly Ala Tyr Asn Ile Ala Arg Lys Gly Leu
    1160                1165                1170

Trp Val Leu Glu Gln Ile Arg Gln Lys Asp Glu Gly Glu Lys Val
    1175                1180                1185

Asn Leu Ser Met Thr Asn Ala Glu Trp Leu Lys Tyr Ala Gln Leu
    1190                1195                1200

His Leu Leu Lys Arg Pro Ala Ala Thr Lys Lys Ala Gly Gln Ala
    1205                1210                1215

Lys Lys Lys Lys Gly Ser Tyr Pro Tyr Asp Val Pro Asp Tyr Ala
    1220                1225                1230

Tyr Pro Tyr Asp Val Pro Asp Tyr Ala Tyr Pro Tyr Asp Val Pro
    1235                1240                1245

Asp Tyr Ala
    1250

<210> SEQ ID NO 48
<211> LENGTH: 1262
<212> TYPE: PRT
<213> ORGANISM: Eubacterium rectale -continued

```
<400> SEQUENCE: 48

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Thr Glu Tyr Arg Lys Ala Ile His Lys Lys
            100                 105                 110

Phe Ala Asn Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Ser Leu Ser Asn Asp Asp Ile Asn Lys Ile Ser Gly Asp Met Lys Asp
210                 215                 220

Ser Leu Lys Glu Met Ser Leu Glu Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Gln Lys Leu His Lys Gln Ile Leu Cys
        275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
            340                 345                 350

Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Ser Asp Asp Asn Ile Lys
```

-continued

```
                405                 410                 415
Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
                435                 440                 445

Leu Lys Ala Ser Glu Leu Lys Asn Val Leu Asp Val Ile Met Asn Ala
            450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
            515                 520                 525

Asp Gly Trp Ser Lys Ser Lys Glu Tyr Ser Asn Asn Ala Ile Ile Leu
        530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Ile Lys Ser
    610                 615                 620

Ser Lys Asp Phe Asp Ile Thr Phe Cys His Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765

Thr Tyr Glu Ala Glu Glu Lys Asp Gln Phe Gly Asn Gln Ile Val Arg
    770                 775                 780

Lys Asn Ile Pro Glu Asn Ile Tyr Gln Glu Leu Tyr Lys Tyr Phe Asn
785                 790                 795                 800

Asp Lys Ser Asp Lys Glu Leu Ser Asp Glu Ala Ala Lys Leu Lys Asn
                805                 810                 815

Val Val Gly His His Glu Ala Ala Thr Asn Ile Val Lys Asp Tyr Arg
            820                 825                 830
```

```
Tyr Thr Tyr Asp Lys Tyr Phe Leu His Met Pro Ile Thr Ile Asn Phe
        835                 840                 845

Lys Ala Asn Lys Thr Gly Phe Ile Asn Asp Arg Ile Leu Gln Tyr Ile
    850                 855                 860

Ala Lys Glu Lys Asp Leu His Val Ile Gly Ile Asp Arg Gly Glu Arg
865                 870                 875                 880

Asn Leu Ile Tyr Val Ser Val Ile Asp Thr Cys Gly Asn Ile Val Glu
            885                 890                 895

Gln Lys Ser Phe Asn Ile Val Asn Gly Tyr Asp Tyr Gln Ile Lys Leu
                900                 905                 910

Lys Gln Gln Glu Gly Ala Arg Gln Ile Ala Arg Lys Glu Trp Lys Glu
            915                 920                 925

Ile Gly Lys Ile Lys Glu Ile Lys Glu Gly Tyr Leu Ser Leu Val Ile
    930                 935                 940

His Glu Ile Ser Lys Met Val Ile Lys Tyr Asn Ala Ile Ile Ala Met
945                 950                 955                 960

Glu Asp Leu Ser Tyr Gly Phe Lys Lys Gly Arg Phe Lys Val Glu Arg
                965                 970                 975

Gln Val Tyr Gln Lys Phe Glu Thr Met Leu Ile Asn Lys Leu Asn Tyr
            980                 985                 990

Leu Val Phe Lys Asp Ile Ser Ile Thr Glu Asn Gly Gly Leu Leu Lys
            995                 1000                1005

Gly Tyr Gln Leu Thr Tyr Ile Pro Asp Lys Leu Lys Asn Val Gly
    1010                1015                1020

His Gln Cys Gly Cys Ile Phe Tyr Val Pro Ala Ala Tyr Thr Ser
    1025                1030                1035

Lys Ile Asp Pro Thr Thr Gly Phe Val Asn Ile Phe Lys Phe Lys
    1040                1045                1050

Asp Leu Thr Val Asp Ala Lys Arg Glu Phe Ile Lys Lys Phe Asp
    1055                1060                1065

Ser Ile Arg Tyr Asp Ser Glu Lys Asn Leu Phe Cys Phe Thr Phe
    1070                1075                1080

Asp Tyr Asn Asn Phe Ile Thr Gln Asn Thr Val Met Ser Lys Ser
    1085                1090                1095

Ser Trp Ser Val Tyr Thr Tyr Gly Val Arg Ile Lys Arg Arg Phe
    1100                1105                1110

Val Asn Gly Arg Phe Ser Asn Glu Ser Asp Thr Ile Asp Ile Thr
    1115                1120                1125

Lys Asp Met Glu Lys Thr Leu Glu Met Thr Asp Ile Asn Trp Arg
    1130                1135                1140

Asp Gly His Asp Leu Arg Gln Asp Ile Ile Asp Tyr Glu Ile Val
    1145                1150                1155

Gln His Ile Phe Glu Ile Phe Arg Leu Thr Val Gln Met Arg Asn
    1160                1165                1170

Ser Leu Ser Glu Leu Glu Asp Arg Asp Tyr Asp Arg Leu Ile Ser
    1175                1180                1185

Pro Val Leu Asn Glu Asn Asn Ile Phe Tyr Asp Ser Ala Lys Ala
    1190                1195                1200

Gly Asp Ala Leu Pro Lys Asp Ala Asp Ala Asn Gly Ala Tyr Cys
    1205                1210                1215

Ile Ala Leu Lys Gly Leu Tyr Glu Ile Lys Gln Ile Thr Glu Asn
    1220                1225                1230
```

```
Trp Lys Glu Asp Gly Lys Phe Ser Arg Asp Lys Leu Lys Ile Ser
    1235                1240                1245

Asn Lys Asp Trp Phe Asp Phe Ile Gln Asn Lys Arg Tyr Leu
    1250                1255                1260

<210> SEQ ID NO 49
<211> LENGTH: 1263
<212> TYPE: PRT
<213> ORGANISM: Eubacterium rectale

<400> SEQUENCE: 49

Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
                20                  25                  30

Gln Phe Ile Val Lys Asn Gly Ile Ile Lys Glu Asp Glu Leu Arg Gly
            35                  40                  45

Glu Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Ala Gly Lys Arg Lys Ala Ile Tyr Lys Lys
            100                 105                 110

Phe Ala Asp Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
130                 135                 140

Ser Glu Lys Glu Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Asn Leu Ser Asn Asp Asp Ile Asn Lys Ile Ser Gly Asp Met Lys Asp
210                 215                 220

Ser Leu Lys Glu Met Ser Leu Asp Glu Ile Tyr Ser Tyr Glu Lys Tyr
225                 230                 235                 240

Gly Glu Phe Ile Thr Gln Glu Gly Ile Ser Phe Tyr Asn Asp Ile Cys
                245                 250                 255

Gly Lys Val Asn Ser Phe Met Asn Leu Tyr Cys Gln Lys Asn Lys Glu
            260                 265                 270

Asn Lys Asn Leu Tyr Lys Leu Arg Lys Leu His Lys Gln Ile Leu Cys
        275                 280                 285

Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Arg Phe Tyr Glu Ser Val Ser
            340                 345                 350
```

```
Gln Lys Thr Tyr Arg Asp Trp Glu Thr Ile Asn Thr Ala Leu Glu Ile
        355                 360                 365

His Tyr Asn Asn Ile Leu Pro Gly Asn Gly Lys Ser Lys Ala Asp Lys
    370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Pro Asp Asp Asn Ile Lys
                405                 410                 415

Ala Glu Thr Tyr Ile His Glu Ile Ser His Ile Leu Asn Asn Phe Glu
            420                 425                 430

Ala Gln Glu Leu Lys Tyr Asn Pro Glu Ile His Leu Val Glu Ser Glu
        435                 440                 445

Leu Lys Ala Ser Glu Leu Lys Asn Val Leu Asp Val Ile Met Asn Ala
    450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
            500                 505                 510

Tyr Ser Thr Lys Lys Ile Lys Leu Asn Phe Gly Ile Pro Thr Leu Ala
        515                 520                 525

Asp Gly Trp Ser Lys Ser Lys Glu Tyr Ser Asn Asn Ala Ile Ile Leu
    530                 535                 540

Met Arg Asp Asn Leu Tyr Tyr Leu Gly Ile Phe Asn Ala Lys Asn Lys
545                 550                 555                 560

Pro Asp Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
            580                 585                 590

Pro Lys Val Phe Leu Ser Ser Lys Thr Gly Val Glu Thr Tyr Lys Pro
        595                 600                 605

Ser Ala Tyr Ile Leu Glu Gly Tyr Lys Gln Asn Lys His Leu Lys Ser
    610                 615                 620

Ser Lys Asp Phe Asp Ile Thr Phe Cys Arg Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
        675                 680                 685

Asp Ile Asp Leu Leu Gln Glu Lys Gly Gln Leu Tyr Leu Phe Gln Ile
    690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
        755                 760                 765
```

```
Thr Tyr Glu Ala Glu Lys Asp Gln Phe Gly Asn Ile Gln Ile Val
770                 775                 780

Arg Lys Thr Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
                820                 825                 830

Arg Tyr Thr Tyr Asp Lys Tyr Phe Leu His Met Pro Ile Thr Ile Asn
                835                 840                 845

Phe Lys Ala Asn Lys Thr Ser Phe Ile Asn Asp Arg Ile Leu Gln Tyr
850                 855                 860

Ile Ala Lys Glu Asn Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
                900                 905                 910

Leu Lys Gln Gln Glu Gly Ala Arg Gln Ile Ala Arg Lys Glu Trp Lys
                915                 920                 925

Glu Ile Gly Lys Ile Lys Glu Ile Lys Glu Gly Tyr Leu Ser Leu Val
930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
                980                 985                 990

Tyr Leu Val Phe Lys Asp Ile Ser Ile Thr Glu Asn Gly Gly Leu Leu
                995                 1000                1005

Lys Gly Tyr Gln Leu Thr Tyr Ile Pro Glu Lys Leu Lys Asn Val
1010                1015                1020

Gly His Gln Cys Gly Cys Ile Phe Tyr Val Pro Ala Ala Tyr Thr
1025                1030                1035

Ser Lys Ile Asp Pro Thr Thr Gly Phe Ala Asn Ile Phe Lys Phe
1040                1045                1050

Lys Asp Leu Thr Val Asp Ala Lys Arg Glu Phe Ile Lys Lys Phe
1055                1060                1065

Asp Ser Ile Arg Tyr Asp Ser Glu Lys Asn Leu Phe Cys Phe Thr
1070                1075                1080

Phe Asp Tyr Asn Asn Phe Ile Thr Gln Asn Thr Val Met Ser Lys
1085                1090                1095

Ser Ser Trp Ser Val Tyr Thr Tyr Gly Val Arg Ile Lys Arg Arg
1100                1105                1110

Phe Val Asn Gly Arg Phe Ser Asn Glu Ser Asp Thr Ile Asp Ile
1115                1120                1125

Thr Lys Asp Met Glu Lys Thr Leu Glu Met Thr Asp Ile Asn Trp
1130                1135                1140

Arg Asp Gly His Asp Leu Arg Gln Asp Ile Ile Asp Tyr Glu Ile
1145                1150                1155

Val Gln His Ile Phe Glu Ile Phe Lys Leu Thr Val Gln Met Arg
1160                1165                1170

Asn Ser Leu Ser Glu Leu Glu Asp Arg Asp Tyr Asp Arg Leu Ile
```

```
                   1175                1180                1185

Ser  Pro  Val  Leu  Asn  Glu  Asn  Asn  Ile  Phe  Tyr  Asp  Ser  Ala  Lys
          1190                1195                1200

Ala  Gly  Asp  Ala  Leu  Pro  Lys  Asp  Ala  Asp  Ala  Asn  Gly  Ala  Tyr
          1205                1210                1215

Cys  Ile  Ala  Leu  Lys  Gly  Leu  Tyr  Glu  Ile  Lys  Gln  Ile  Thr  Glu
          1220                1225                1230

Asn  Trp  Lys  Glu  Asp  Gly  Lys  Phe  Ser  Arg  Asp  Lys  Leu  Lys  Ile
          1235                1240                1245

Ser  Asn  Lys  Asp  Trp  Phe  Asp  Phe  Ile  Gln  Asn  Lys  Arg  Tyr  Leu
          1250                1255                1260

<210> SEQ ID NO 50
<211> LENGTH: 1263
<212> TYPE: PRT
<213> ORGANISM: Eubacterium rectale

<400> SEQUENCE: 50

Met  Asn  Asn  Gly  Thr  Asn  Asn  Phe  Gln  Asn  Phe  Ile  Gly  Ile  Ser  Ser
1                   5                   10                  15

Leu  Gln  Lys  Thr  Leu  Arg  Asn  Ala  Leu  Thr  Pro  Thr  Glu  Thr  Thr  Gln
          20                  25                  30

Gln  Phe  Ile  Val  Lys  Asn  Gly  Ile  Ile  Lys  Glu  Asp  Glu  Leu  Arg  Gly
          35                  40                  45

Glu  Asn  Arg  Gln  Ile  Leu  Lys  Asp  Ile  Met  Asp  Asp  Tyr  Tyr  Arg  Gly
          50                  55                  60

Phe  Ile  Ser  Glu  Thr  Leu  Ser  Ser  Ile  Asp  Asp  Ile  Asp  Trp  Thr  Ser
65                  70                  75                  80

Leu  Phe  Glu  Lys  Met  Glu  Ile  Gln  Leu  Lys  Asn  Gly  Asp  Asn  Lys  Asp
                    85                  90                  95

Thr  Leu  Ile  Lys  Glu  Gln  Ala  Glu  Lys  Arg  Lys  Ala  Ile  Tyr  Lys  Lys
          100                 105                 110

Phe  Ala  Asp  Asp  Asp  Arg  Phe  Lys  Asn  Met  Phe  Ser  Ala  Lys  Leu  Ile
          115                 120                 125

Ser  Asp  Ile  Leu  Pro  Glu  Phe  Val  Ile  His  Asn  Asn  Tyr  Ser  Ala
          130                 135                 140

Ser  Glu  Lys  Glu  Glu  Lys  Thr  Gln  Val  Ile  Lys  Leu  Phe  Ser  Arg  Phe
145                 150                 155                 160

Ala  Thr  Ser  Phe  Lys  Asp  Tyr  Phe  Lys  Asn  Arg  Ala  Asn  Cys  Phe  Ser
                    165                 170                 175

Ala  Asp  Asp  Ile  Ser  Ser  Ser  Cys  His  Arg  Ile  Val  Asn  Asp  Asn
          180                 185                 190

Ala  Glu  Ile  Phe  Phe  Ser  Asn  Ala  Leu  Val  Tyr  Arg  Arg  Ile  Val  Lys
          195                 200                 205

Asn  Leu  Ser  Asn  Asp  Asp  Ile  Asn  Lys  Ile  Ser  Gly  Asp  Met  Lys  Asp
          210                 215                 220

Ser  Leu  Lys  Lys  Met  Ser  Leu  Glu  Lys  Ile  Tyr  Ser  Tyr  Glu  Lys  Tyr
225                 230                 235                 240

Gly  Glu  Phe  Ile  Thr  Gln  Glu  Gly  Ile  Ser  Phe  Tyr  Asn  Asp  Ile  Cys
                    245                 250                 255

Gly  Lys  Val  Asn  Ser  Phe  Met  Asn  Leu  Tyr  Cys  Gln  Lys  Asn  Lys  Glu
          260                 265                 270

Asn  Lys  Asn  Leu  Tyr  Lys  Leu  Arg  Lys  Leu  His  Lys  Gln  Ile  Leu  Cys
          275                 280                 285
```

```
Ile Ala Asp Thr Ser Tyr Glu Val Pro Tyr Lys Phe Glu Ser Asp Glu
290                 295                 300

Glu Val Tyr Gln Ser Val Asn Gly Phe Leu Asp Asn Ile Ser Ser Lys
305                 310                 315                 320

His Ile Val Glu Arg Leu Arg Lys Ile Gly Asp Asn Tyr Asn Gly Tyr
                325                 330                 335

Asn Leu Asp Lys Ile Tyr Ile Val Ser Lys Phe Tyr Glu Ser Val Ser
                340                 345                 350

Gln Lys Thr Tyr Arg Asp Trp Glu Thr Ile Asn Thr Ala Leu Glu Ile
                355                 360                 365

His Tyr Asn Asn Ile Leu Pro Gly Asn Gly Lys Ser Lys Ala Asp Lys
370                 375                 380

Val Lys Lys Ala Val Lys Asn Asp Leu Gln Lys Ser Ile Thr Glu Ile
385                 390                 395                 400

Asn Glu Leu Val Ser Asn Tyr Lys Leu Cys Pro Asp Asp Asn Ile Lys
                405                 410                 415

Ala Glu Thr Tyr Ile His Glu Ile Ser His Ile Leu Asn Asn Phe Glu
                420                 425                 430

Ala Gln Glu Leu Lys Tyr Asn Pro Glu Ile His Leu Val Glu Ser Glu
                435                 440                 445

Leu Lys Ala Ser Glu Leu Lys Asn Val Leu Asp Val Ile Met Asn Ala
450                 455                 460

Phe His Trp Cys Ser Val Phe Met Thr Glu Glu Leu Val Asp Lys Asp
465                 470                 475                 480

Asn Asn Phe Tyr Ala Glu Leu Glu Glu Ile Tyr Asp Glu Ile Tyr Pro
                485                 490                 495

Val Ile Ser Leu Tyr Asn Leu Val Arg Asn Tyr Val Thr Gln Lys Pro
                500                 505                 510

Tyr Ser Thr Lys Lys Ile Lys Leu Asn Phe Gly Ile Pro Thr Leu Ala
                515                 520                 525

Asp Gly Trp Ser Lys Ser Lys Glu Tyr Ser Asn Asn Ala Ile Ile Leu
530                 535                 540

Met Arg Asp Asn Leu Tyr Tyr Leu Gly Ile Phe Asn Ala Lys Asn Lys
545                 550                 555                 560

Pro Glu Lys Lys Ile Ile Glu Gly Asn Thr Ser Glu Asn Lys Gly Asp
                565                 570                 575

Tyr Lys Lys Met Ile Tyr Asn Leu Leu Pro Gly Pro Asn Lys Met Ile
                580                 585                 590

Pro Lys Val Phe Leu Ser Ser Lys Thr Gly Val Glu Thr Tyr Lys Pro
                595                 600                 605

Ser Ala Tyr Ile Leu Glu Gly Tyr Lys Gln Asn Lys His Leu Lys Ser
610                 615                 620

Ser Lys Asp Phe Asp Ile Thr Phe Cys Arg Asp Leu Ile Asp Tyr Phe
625                 630                 635                 640

Lys Asn Cys Ile Ala Ile His Pro Glu Trp Lys Asn Phe Gly Phe Asp
                645                 650                 655

Phe Ser Asp Thr Ser Thr Tyr Glu Asp Ile Ser Gly Phe Tyr Arg Glu
                660                 665                 670

Val Glu Leu Gln Gly Tyr Lys Ile Asp Trp Thr Ile Ser Glu Lys
                675                 680                 685

Asp Ile Asp Leu Leu Gln Glu Lys Gly Gln Leu Tyr Leu Phe Gln Ile
690                 695                 700

Tyr Asn Lys Asp Phe Ser Lys Lys Ser Thr Gly Asn Asp Asn Leu His
```

```
                705                 710                 715                 720
            Thr Met Tyr Leu Lys Asn Leu Phe Ser Glu Glu Asn Leu Lys Asp Val
                            725                 730                 735

Val Leu Lys Leu Asn Gly Glu Ala Glu Ile Phe Phe Arg Lys Ser Ser
                            740                 745                 750

Ile Lys Asn Pro Ile Ile His Lys Gly Ser Ile Leu Val Asn Arg
                            755                 760                 765

Thr Tyr Glu Ala Glu Lys Asp Gln Phe Gly Asn Ile Gln Ile Val
                            770                 775                 780

Arg Lys Thr Ile Pro Glu Asn Ile Tyr Gln Glu Leu Tyr Lys Tyr Phe
            785                 790                 795                 800

Asn Asp Lys Ser Asp Lys Glu Leu Ser Asp Glu Ala Ala Lys Leu Lys
                            805                 810                 815

Asn Ala Val Gly His His Glu Ala Ala Thr Asn Ile Val Lys Asp Tyr
                            820                 825                 830

Arg Tyr Thr Tyr Asp Lys Tyr Phe Leu His Met Pro Ile Thr Ile Asn
                            835                 840                 845

Phe Lys Ala Asn Lys Thr Ser Phe Ile Asn Asp Arg Ile Leu Gln Tyr
                            850                 855                 860

Ile Ala Lys Glu Lys Asp Leu His Val Ile Gly Ile Asp Arg Gly Glu
            865                 870                 875                 880

Arg Asn Leu Ile Tyr Val Ser Val Ile Asp Thr Cys Gly Asn Ile Val
                            885                 890                 895

Glu Gln Lys Ser Phe Asn Ile Val Asn Gly Tyr Asp Tyr Gln Ile Lys
                            900                 905                 910

Leu Lys Gln Gln Glu Gly Ala Arg Gln Ile Ala Arg Lys Glu Trp Lys
                            915                 920                 925

Glu Ile Gly Lys Ile Lys Glu Ile Lys Glu Gly Tyr Leu Ser Leu Val
                            930                 935                 940

Ile His Glu Ile Ser Lys Met Val Ile Lys Tyr Asn Ala Ile Ile Ala
            945                 950                 955                 960

Met Glu Asp Leu Ser Tyr Gly Phe Lys Lys Gly Arg Phe Lys Val Glu
                            965                 970                 975

Arg Gln Val Tyr Gln Lys Phe Glu Thr Met Leu Ile Asn Lys Leu Asn
                            980                 985                 990

Tyr Leu Val Phe Lys Asp Ile Ser Ile Thr Glu Asn Gly Gly Leu Leu
                            995                 1000                1005

Lys Gly Tyr Gln Leu Thr Tyr Ile Pro Glu Lys Leu Lys Asn Val
                1010                1015                1020

Gly His Gln Cys Gly Cys Ile Phe Tyr Val Pro Ala Ala Tyr Thr
                1025                1030                1035

Ser Lys Ile Asp Pro Thr Thr Gly Phe Val Asn Ile Phe Lys Phe
                1040                1045                1050

Lys Asp Leu Thr Val Asp Ala Lys Arg Glu Phe Ile Lys Lys Phe
                1055                1060                1065

Asp Ser Ile Arg Tyr Asp Ser Asp Lys Asn Leu Phe Cys Phe Thr
                1070                1075                1080

Phe Asp Tyr Asn Asn Phe Ile Thr Gln Asn Thr Val Met Ser Lys
                1085                1090                1095

Ser Ser Trp Ser Val Tyr Thr Tyr Gly Val Arg Ile Lys Arg Arg
                1100                1105                1110

Phe Val Asn Gly Arg Phe Ser Asn Glu Ser Asp Thr Ile Asp Ile
                1115                1120                1125
```

```
Thr Lys Asp Met Glu Lys Thr Leu Glu Met Thr Asp Ile Asn Trp
    1130                1135                1140

Arg Asp Gly His Asp Leu Arg Gln Asp Ile Ile Asp Tyr Glu Ile
    1145                1150                1155

Val Gln His Ile Phe Glu Ile Phe Lys Leu Thr Val Gln Met Arg
    1160                1165                1170

Asn Ser Leu Ser Glu Leu Glu Asp Arg Asn Tyr Asp Arg Leu Ile
    1175                1180                1185

Ser Pro Val Leu Asn Glu Asn Asn Ile Phe Tyr Asp Ser Ala Lys
    1190                1195                1200

Ala Gly Asp Ala Leu Pro Lys Asp Ala Asp Ala Asn Gly Ala Tyr
    1205                1210                1215

Cys Ile Ala Leu Lys Gly Leu Tyr Glu Ile Lys Gln Ile Thr Glu
    1220                1225                1230

Asn Trp Lys Glu Asp Gly Lys Phe Ser Arg Asp Lys Leu Lys Ile
    1235                1240                1245

Ser Asn Lys Asp Trp Phe Asp Phe Ile Gln Asn Lys Arg Tyr Leu
    1250                1255                1260
```

<210> SEQ ID NO 51
<211> LENGTH: 1263
<212> TYPE: PRT
<213> ORGANISM: Eubacterium sp.

<400> SEQUENCE: 51

```
Met Asn Asn Gly Thr Asn Asn Phe Gln Asn Phe Ile Gly Ile Ser Ser
1               5                   10                  15

Leu Gln Lys Thr Leu Arg Asn Ala Leu Ile Pro Thr Glu Thr Thr Gln
            20                  25                  30

Gln Phe Ile Val Lys Asn Gly Ile Ile Lys Glu Asp Glu Leu Arg Gly
        35                  40                  45

Lys Asn Arg Gln Ile Leu Lys Asp Ile Met Asp Tyr Tyr Arg Gly
    50                  55                  60

Phe Ile Ser Glu Thr Leu Ser Ser Ile Asp Asp Ile Asp Trp Thr Ser
65                  70                  75                  80

Leu Phe Glu Lys Met Glu Ile Gln Leu Lys Asn Gly Asp Asn Lys Asp
                85                  90                  95

Thr Leu Ile Lys Glu Gln Ala Glu Lys Arg Lys Ala Ile Tyr Lys Lys
            100                 105                 110

Phe Ala Asp Asp Asp Arg Phe Lys Asn Met Phe Ser Ala Lys Leu Ile
        115                 120                 125

Ser Asp Ile Leu Pro Glu Phe Val Ile His Asn Asn Asn Tyr Ser Ala
    130                 135                 140

Ser Glu Lys Lys Glu Lys Thr Gln Val Ile Lys Leu Phe Ser Arg Phe
145                 150                 155                 160

Ala Thr Ser Phe Lys Asp Tyr Phe Lys Asn Arg Ala Asn Cys Phe Ser
                165                 170                 175

Ala Asp Asp Ile Ser Ser Ser Cys His Arg Ile Val Asn Asp Asn
            180                 185                 190

Ala Glu Ile Phe Phe Ser Asn Ala Leu Val Tyr Arg Arg Ile Val Lys
        195                 200                 205

Asn Leu Ser Asn Asp Asp Ile Asn Lys Ile Ser Gly Asp Met Lys Asp
    210                 215                 220

Ser Leu Lys Glu Met Ser Leu Glu Glu Ile Tyr Ser Tyr Glu Lys Tyr
```

```
            225                 230                 235                 240
Gly Glu Phe Ile Thr Gln Glu Gly Ile Ser Phe Tyr Asn Asp Ile Cys
                245                 250                 255
Gly Lys Val Asn Ser Phe Met Asn Leu Tyr Cys Gln Lys Asn Lys Glu
                260                 265                 270
Asn Lys Asn Leu Tyr Lys Leu Arg Lys Leu His Lys Gln Ile Leu Cys
                275                 280                 285
Ile Ala Asp Thr Ser Tyr Glu Val Pro Tyr Lys Phe Glu Ser Asp Glu
            290                 295                 300
Glu Val Tyr Gln Ser Val Asn Gly Phe Leu Asp Asn Ile Ser Ser Lys
305                 310                 315                 320
His Ile Val Glu Arg Leu Arg Lys Ile Gly Asp Asn Tyr Asn Asp Tyr
                325                 330                 335
Asn Leu Asp Lys Ile Tyr Ile Val Ser Lys Phe Tyr Glu Ser Val Ser
                340                 345                 350
Gln Lys Thr Tyr Arg Asp Trp Glu Thr Ile Asn Thr Ala Leu Glu Ile
                355                 360                 365
His Tyr Asn Asn Ile Leu Pro Gly Asn Gly Lys Ser Lys Ala Asp Lys
                370                 375                 380
Val Lys Lys Ala Val Lys Asn Asp Leu Gln Lys Ser Ile Thr Glu Ile
385                 390                 395                 400
Asn Glu Leu Val Ser Asn Tyr Lys Leu Cys Ser Asp Asp Asn Ile Lys
                405                 410                 415
Ala Glu Thr Tyr Ile His Glu Ile Ser His Ile Leu Asn Asn Phe Glu
                420                 425                 430
Ala His Glu Leu Lys Tyr Asn Pro Glu Ile His Leu Val Glu Ser Glu
                435                 440                 445
Leu Lys Ala Ser Glu Leu Lys Asn Val Leu Asp Ile Ile Met Asn Ala
                450                 455                 460
Phe His Trp Cys Ser Val Phe Met Thr Glu Glu Leu Val Asp Lys Asp
465                 470                 475                 480
Asn Asn Phe Tyr Ala Glu Leu Glu Glu Ile Tyr Asp Glu Ile Tyr Pro
                485                 490                 495
Val Ile Ser Leu Tyr Asn Leu Val Arg Asn Tyr Val Thr Gln Lys Pro
                500                 505                 510
Tyr Ser Thr Lys Lys Ile Lys Leu Asn Phe Gly Ile Pro Thr Leu Ala
                515                 520                 525
Asp Gly Trp Ser Lys Ser Lys Glu Tyr Ser Asn Asn Ala Ile Ile Leu
            530                 535                 540
Met Arg Asp Asn Leu Tyr Tyr Leu Gly Ile Phe Asn Ala Lys Asn Lys
545                 550                 555                 560
Pro Asp Lys Lys Ile Ile Glu Gly Asn Thr Ser Glu Asn Lys Gly Asp
                565                 570                 575
Tyr Lys Lys Met Ile Tyr Asn Leu Leu Pro Gly Pro Asn Lys Met Ile
                580                 585                 590
Pro Lys Val Phe Leu Ser Ser Lys Thr Gly Val Glu Thr Tyr Lys Pro
                595                 600                 605
Ser Ala Tyr Ile Leu Glu Gly Tyr Lys Gln Asn Lys His Leu Lys Ser
            610                 615                 620
Ser Lys Asp Phe Asp Ile Thr Phe Cys His Asp Leu Ile Asp Tyr Phe
625                 630                 635                 640
Lys Asn Cys Ile Ala Ile His Pro Glu Trp Lys Asn Phe Gly Phe Asp
                645                 650                 655
```

-continued

```
Phe Ser Asp Thr Ser Ala Tyr Glu Asp Ile Ser Gly Phe Tyr Arg Glu
            660                 665                 670

Val Glu Leu Gln Gly Tyr Lys Ile Asp Trp Thr Tyr Ile Ser Glu Lys
            675                 680                 685

Asp Ile Asp Leu Leu Gln Glu Lys Gly Gln Leu Tyr Leu Phe Gln Ile
            690                 695                 700

Tyr Asn Lys Asp Phe Ser Lys Lys Ser Thr Gly Asn Asp Asn Leu His
705                 710                 715                 720

Thr Met Tyr Leu Lys Asn Leu Phe Ser Glu Glu Asn Leu Lys Asp Ile
                725                 730                 735

Val Leu Lys Leu Asn Gly Glu Ala Glu Ile Phe Phe Arg Lys Ser Ser
            740                 745                 750

Ile Lys Asn Pro Ile Ile His Lys Lys Gly Ser Ile Leu Val Asn Arg
            755                 760                 765

Thr Tyr Glu Ala Glu Lys Asp Gln Phe Gly Asn Ile Gln Ile Val
            770                 775                 780

Arg Lys Thr Ile Pro Glu Asn Ile Tyr Gln Glu Leu Tyr Lys Tyr Phe
785                 790                 795                 800

Asn Asp Lys Ser Asp Lys Glu Leu Ser Asp Glu Ala Ala Lys Leu Lys
                805                 810                 815

Asn Val Val Gly His His Glu Ala Ala Thr Asn Ile Val Lys Asp Tyr
            820                 825                 830

Arg Tyr Thr Tyr Asp Lys Tyr Phe Leu His Met Pro Ile Thr Ile Asn
            835                 840                 845

Phe Lys Ala Asn Lys Thr Ser Phe Ile Asn Asp Arg Ile Leu Gln Tyr
            850                 855                 860

Ile Ala Lys Glu Lys Asp Leu His Val Ile Gly Ile Asp Arg Gly Glu
865                 870                 875                 880

Arg Asn Leu Ile Tyr Val Ser Val Ile Asp Thr Cys Gly Asn Ile Val
                885                 890                 895

Glu Gln Lys Ser Phe Asn Ile Val Asn Gly Tyr Asp Tyr Gln Ile Lys
            900                 905                 910

Leu Lys Gln Gln Glu Gly Ala Arg Gln Ile Ala Arg Lys Glu Trp Lys
            915                 920                 925

Glu Ile Gly Lys Ile Lys Glu Ile Lys Glu Gly Tyr Leu Ser Leu Val
            930                 935                 940

Ile His Glu Ile Ser Lys Met Val Ile Lys Tyr Asn Ala Ile Ile Ala
945                 950                 955                 960

Met Glu Asp Leu Ser Tyr Gly Phe Lys Lys Gly Arg Phe Lys Val Glu
                965                 970                 975

Arg Gln Val Tyr Gln Lys Phe Glu Thr Met Leu Ile Asn Lys Leu Asn
            980                 985                 990

Tyr Leu Val Phe Lys Asp Ile Ser Ile Thr Glu Asn Gly Gly Leu Leu
            995                 1000                1005

Lys Gly Tyr Gln Leu Thr Tyr Ile Pro Asp Lys Leu Lys Asn Val
            1010                1015                1020

Gly His Gln Cys Gly Cys Ile Phe Tyr Val Pro Ala Ala Tyr Thr
            1025                1030                1035

Ser Lys Ile Asp Pro Thr Thr Gly Phe Val Asn Ile Phe Lys Phe
            1040                1045                1050

Lys Asp Leu Thr Val Asp Ala Lys Arg Glu Phe Ile Lys Lys Phe
            1055                1060                1065
```

Asp Ser Ile Arg Tyr Asp Ser Glu Lys Asn Leu Phe Cys Phe Thr
    1070            1075                1080

Phe Asp Tyr Asn Asn Phe Ile Thr Gln Asn Thr Val Met Ser Lys
    1085            1090                1095

Ser Ser Trp Ser Val Tyr Thr Tyr Gly Val Arg Ile Lys Arg Arg
    1100            1105                1110

Phe Val Asn Gly Arg Phe Ser Asn Glu Ser Asp Thr Ile Asp Ile
    1115            1120                1125

Thr Lys Asp Met Glu Lys Thr Leu Glu Met Thr Asp Ile Asn Trp
    1130            1135                1140

Arg Asp Gly His Asp Leu Arg Gln Asp Ile Ile Asp Tyr Glu Ile
    1145            1150                1155

Val Gln His Ile Phe Glu Ile Phe Lys Leu Thr Val Gln Met Arg
    1160            1165                1170

Asn Ser Leu Ser Glu Leu Glu Asp Arg Asp Tyr Asp Arg Leu Ile
    1175            1180                1185

Ser Pro Val Leu Asn Glu Asn Asn Ile Phe Tyr Asp Ser Ala Lys
    1190            1195                1200

Ala Gly Tyr Ala Leu Pro Lys Asp Ala Asp Ala Asn Gly Ala Tyr
    1205            1210                1215

Cys Ile Ala Leu Lys Gly Leu Tyr Glu Ile Lys Gln Ile Thr Glu
    1220            1225                1230

Asn Trp Lys Glu Asp Gly Lys Phe Ser Arg Asp Lys Leu Lys Ile
    1235            1240                1245

Ser Asn Lys Asp Trp Phe Asp Phe Ile Gln Asn Lys Arg Tyr Leu
    1250            1255                1260

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
ttatttctat tatgttagat                                              20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
tattgccttt ttttgtagat                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
gaattcctac tctcgtaggt                                              20

<210> SEQ ID NO 55
<211> LENGTH: 20
<212> TYPE: DNA

```
<213> ORGANISM: Artificial Sequence
<220> FEATURE:
<223> OTHER INFORMATION: Synthetic

<400> SEQUENCE: 55
taatttctac tctcgtagat                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
taatttctcc tataggagat                                               20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
taatttctcc tatcggagat                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
aaatttctac tattggagat                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
taatttctcc tctcggagat                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
aaatttctac tctcgtagat                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
gaatttctcc tattggagat                                               20
```

<210> SEQ ID NO 62
<211> LENGTH: 19
<212> TYPE: DNA
<213> ORGANISM: Artificial Sequence
<220> FEATURE:
<223> OTHER INFORMATION: Synthetic

<400> SEQUENCE: 62
taatttctct cttggagat                                                   19

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
taatttctac tctagtagat                                                  20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
gaattcctac tctggtaggt                                                  20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
gaattcctac tcttgtaggt                                                  20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
aaatttctac tctggtagat                                                  20

<210> SEQ ID NO 67
<211> LENGTH: 20
<212> TYPE: DNA
<213> ORGANISM: Artificial Sequence
<220> FEATURE:
<223> OTHER INFORMATION: Synthetic

<400> SEQUENCE: 67
taatttctac tgtagtagat                                                  20

<210> SEQ ID NO 68
<211> LENGTH: 20
<212> TYPE: DNA
<213> ORGANISM: Artificial Sequence
<220> FEATURE:

```
<223> OTHER INFORMATION: Synthetic

<400> SEQUENCE: 68
taattcctac tctcgtaggt                                               20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
aaatttctac tcttgtagat                                               20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
aaatttctcc tctgggagat                                               20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
gaatttctcc tcttggagat                                               20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
taatttctac tttggtagat                                               20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
gaatttctcc tctaggagat                                               20

<210> SEQ ID NO 74
<211> LENGTH: 20
<212> TYPE: DNA
<213> ORGANISM: Artificial Sequence
<220> FEATURE:
<223> OTHER INFORMATION: Synthetic

<400> SEQUENCE: 74
taatttctac tctggtagat                                               20
```

```
<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
gaatttctac tattgtagat                                              20

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
gaatttctac tcttgtagat                                              20

<210> SEQ ID NO 77
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (14)..(14)
<223> OTHER INFORMATION: n is a, c, g, or t

<400> SEQUENCE: 77
daattyctmc tntngkagrt                                              20

<210> SEQ ID NO 78
<211> LENGTH: 21
<212> TYPE: DNA
<213> ORGANISM: Artificial Sequence
<220> FEATURE:
<223> OTHER INFORMATION: Synthetic

<400> SEQUENCE: 78
cgcgtcatca tctaacttta g                                            21

<210> SEQ ID NO 79
<211> LENGTH: 11
<212> TYPE: DNA
<213> ORGANISM: Artificial Sequence
<220> FEATURE:
<223> OTHER INFORMATION: Synthetic

<400> SEQUENCE: 79
caggcttcac c                                                       11

<210> SEQ ID NO 80
<211> LENGTH: 11
<212> TYPE: DNA
<213> ORGANISM: Artificial Sequence
<220> FEATURE:
<223> OTHER INFORMATION: Synthetic

<400> SEQUENCE: 80
caggtttaac c                                                       11
```

<210> SEQ ID NO 81
<211> LENGTH: 11
<212> TYPE: DNA
<213> ORGANISM: Artificial Sequence
<220> FEATURE:
<223> OTHER INFORMATION: Synthetic

<400> SEQUENCE: 81
caggtttcac c                                                            11

<210> SEQ ID NO 82
<211> LENGTH: 11
<212> TYPE: DNA
<213> ORGANISM: Artificial Sequence
<220> FEATURE:
<223> OTHER INFORMATION: Synthetic

<400> SEQUENCE: 82
caggtttgac c                                                            11

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
taatttctac tcttgtagat                                                   20

<210> SEQ ID NO 84
<211> LENGTH: 17
<212> TYPE: DNA
<213> ORGANISM: Artificial Sequence
<220> FEATURE:
<223> OTHER INFORMATION: Synthetic

<400> SEQUENCE: 84
tttctactct tgtagat                                                      17

<210> SEQ ID NO 85
<211> LENGTH: 17
<212> TYPE: DNA
<213> ORGANISM: Artificial Sequence
<220> FEATURE:
<223> OTHER INFORMATION: Synthetic

<400> SEQUENCE: 85
tttctactct tgtagat                                                      17

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
gagtccgagc agaagaagaa                                                   20

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
gagtcctagc aggagaagaa                                               20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
gagtctaagc agaagaagaa                                               20

<210> SEQ ID NO 89
<211> LENGTH: 5
<212> TYPE: PRT
<213> ORGANISM: Artificial Sequence
<220> FEATURE:
<223> OTHER INFORMATION: Synthetic

<400> SEQUENCE: 89

Gly Gly Gly Gly Ser
1               5

<210> SEQ ID NO 90
<211> LENGTH: 10
<212> TYPE: PRT
<213> ORGANISM: Artificial Sequence
<220> FEATURE:
<223> OTHER INFORMATION: Synthetic

<400> SEQUENCE: 90

Gly Gly Gly Gly Ser Gly Gly Gly Gly Ser
1               5                   10

<210> SEQ ID NO 91
<211> LENGTH: 15
<212> TYPE: PRT
<213> ORGANISM: Artificial Sequence
<220> FEATURE:
<223> OTHER INFORMATION: Synthetic

<400> SEQUENCE: 91

Gly Gly Gly Gly Ser Gly Gly Gly Gly Ser Gly Gly Gly Gly Ser
1               5                   10                  15

<210> SEQ ID NO 92
<211> LENGTH: 7
<212> TYPE: PRT
<213> ORGANISM: Artificial Sequence
<220> FEATURE:
<223> OTHER INFORMATION: Synthetic

<400> SEQUENCE: 92

Glu Asn Leu Tyr Phe Gln Gly
1               5

<210> SEQ ID NO 93
<211> LENGTH: 12
<212> TYPE: PRT
<213> ORGANISM: Artificial Sequence
<220> FEATURE:
<223> OTHER INFORMATION: Synthetic

<400> SEQUENCE: 93

```
Phe Trp Tyr His Lys Met Ile Leu Val Ala Gly Cys
1               5                   10
```

<210> SEQ ID NO 94
<211> LENGTH: 12
<212> TYPE: PRT
<213> ORGANISM: Artificial Sequence
<220> FEATURE:
<223> OTHER INFORMATION: Synthetic

<400> SEQUENCE: 94

```
Trp Tyr His Lys Arg Glu Asp Cys Ser Thr Asn Gln
1               5                   10
```

<210> SEQ ID NO 95
<211> LENGTH: 9
<212> TYPE: PRT
<213> ORGANISM: Artificial Sequence
<220> FEATURE:
<223> OTHER INFORMATION: Synthetic

<400> SEQUENCE: 95

```
Val Cys Ala Gly Ser Pro Thr Asn Asp
1               5
```

<210> SEQ ID NO 96
<211> LENGTH: 4
<212> TYPE: PRT
<213> ORGANISM: Artificial Sequence
<220> FEATURE:
<223> OTHER INFORMATION: Synthetic

<400> SEQUENCE: 96

```
Phe Trp Tyr His
1
```

<210> SEQ ID NO 97
<211> LENGTH: 5
<212> TYPE: PRT
<213> ORGANISM: Artificial Sequence
<220> FEATURE:
<223> OTHER INFORMATION: Synthetic

<400> SEQUENCE: 97

```
His Lys Arg Glu Asp
1               5
```

<210> SEQ ID NO 98
<211> LENGTH: 4
<212> TYPE: PRT
<213> ORGANISM: Artificial Sequence
<220> FEATURE:
<223> OTHER INFORMATION: Synthetic

<400> SEQUENCE: 98

```
Gly Gly Gly Ser
1
```

<210> SEQ ID NO 99
<211> LENGTH: 12
<212> TYPE: PRT
<213> ORGANISM: Artificial Sequence
<220> FEATURE:
<223> OTHER INFORMATION: Synthetic

<400> SEQUENCE: 99

```
Gly Gly Gly Ser Gly Gly Gly Ser Gly Gly Gly Ser
```

<210> SEQ ID NO 100
<211> LENGTH: 7
<212> TYPE: PRT
<213> ORGANISM: Artificial Sequence
<220> FEATURE:
<223> OTHER INFORMATION: Synthetic

<400> SEQUENCE: 100

Ala Glu Ala Ala Ala Lys Ala
1               5

<210> SEQ ID NO 101
<211> LENGTH: 30
<212> TYPE: PRT
<213> ORGANISM: Artificial Sequence
<220> FEATURE:
<223> OTHER INFORMATION: Synthetic

<400> SEQUENCE: 101

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 102
<211> LENGTH: 45
<212> TYPE: PRT
<213> ORGANISM: Artificial Sequence
<220> FEATURE:
<223> OTHER INFORMATION: Synthetic

<400> SEQUENCE: 102

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 103
<211> LENGTH: 60
<212> TYPE: PRT
<213> ORGANISM: Artificial Sequence
<220> FEATURE:
<223> OTHER INFORMATION: Synthetic

<400> SEQUENCE: 103

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60

<210> SEQ ID NO 104
<211> LENGTH: 20
<212> TYPE: PRT
<213> ORGANISM: Artificial Sequence
<220> FEATURE:
<223> OTHER INFORMATION: Synthetic

```
<400> SEQUENCE: 104

Gly Gly Gly Gly Ser Gly Gly Gly Ser Gly Gly Gly Ser Gly
1               5                   10                  15

Gly Gly Gly Ser
            20

<210> SEQ ID NO 105
<211> LENGTH: 25
<212> TYPE: PRT
<213> ORGANISM: Artificial Sequence
<220> FEATURE:
<223> OTHER INFORMATION: Synthetic

<400> SEQUENCE: 105

Gly Gly Gly Gly Ser Gly Gly Gly Ser Gly Gly Gly Ser Gly
1               5                   10                  15

Gly Gly Gly Ser Gly Gly Gly Gly Ser
            20                  25

<210> SEQ ID NO 106
<211> LENGTH: 35
<212> TYPE: PRT
<213> ORGANISM: Artificial Sequence
<220> FEATURE:
<223> OTHER INFORMATION: Synthetic

<400> SEQUENCE: 106

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly
            20                  25                  30

Gly Gly Ser
        35

<210> SEQ ID NO 107
<211> LENGTH: 40
<212> TYPE: PRT
<213> ORGANISM: Artificial Sequence
<220> FEATURE:
<223> OTHER INFORMATION: Synthetic

<400> SEQUENCE: 107

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly
            20                  25                  30

Gly Gly Ser Gly Gly Gly Gly Ser
        35                  40

<210> SEQ ID NO 108
<211> LENGTH: 50
<212> TYPE: PRT
<213> ORGANISM: Artificial Sequence
<220> FEATURE:
<223> OTHER INFORMATION: Synthetic

<400> SEQUENCE: 108

Gly Gly Gly Gly Ser Gly Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30
```

Gly Gly Ser Gly Gly Gly Ser Gly Gly Gly Ser Gly Gly
        35                  40                  45

Gly Ser
    50

<210> SEQ ID NO 109
<211> LENGTH: 55
<212> TYPE: PRT
<213> ORGANISM: Artificial Sequence
<220> FEATURE:
<223> OTHER INFORMATION: Synthetic

<400> SEQUENCE: 109

Gly Gly Gly Gly Ser Gly Gly Gly Ser Gly Gly Gly Ser Gly
1               5                  10                  15

Gly Gly Gly Ser Gly Gly Gly Ser Gly Gly Gly Ser Gly Gly
            20                  25                  30

Gly Gly Ser Gly Gly Gly Ser Gly Gly Gly Ser Gly Gly Gly
        35                  40                  45

Gly Ser Gly Gly Gly Gly Ser
    50                  55

<210> SEQ ID NO 110
<211> LENGTH: 11
<212> TYPE: DNA
<213> ORGANISM: Artificial Sequence
<220> FEATURE:
<223> OTHER INFORMATION: Synthetic

<400> SEQUENCE: 110
cgtctcaaga t                                                          11

<210> SEQ ID NO 111
<211> LENGTH: 17
<212> TYPE: DNA
<213> ORGANISM: Artificial Sequence
<220> FEATURE:
<223> OTHER INFORMATION: Synthetic

<400> SEQUENCE: 111 tttttttgaat cgagacg                                                   17

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
aggcacttgc tcgtacgacg                                                 20

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
atgtgggccc ggcaccttaa                                                 20

<210> SEQ ID NO 114
<211> LENGTH: 20

```
<212> TYPE: DNA
<213> ORGANISM: Artificial Sequence
<220> FEATURE:
<223> OTHER INFORMATION: Synthetic

<400> SEQUENCE: 114
gtgtaacccg tagggcacct                                            20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
gtcgagagca gtccttcgac                                            20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
cagcgccaat gggctttcga                                            20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
agccgcttaa gagcctgtcg                                            20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
ctacaggtac cggtcctgag                                            20

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
gtacctagcg tgacgatccg                                            20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
```

```
catgttgccc tgaggcacag                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
ccgttaggtc ccgaaaggct                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
ggtcgtcgca tcacaatgcg                                               20

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
tctcgagcgc caatgtgacg                                               20

<210> SEQ ID NO 124
<211> LENGTH: 44
<212> TYPE: DNA
<213> ORGANISM: Artificial Sequence
<220> FEATURE:
<223> OTHER INFORMATION: Synthetic

<400> SEQUENCE: 124
cttgtggaaa ggacgaaaca ccggtaattt ctactcttgt agat                    44

<210> SEQ ID NO 125

<400> SEQUENCE: 125

000

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
taatttctcc tcttgtagat                                               20

<210> SEQ ID NO 127
<211> LENGTH: 9
<212> TYPE: PRT
<213> ORGANISM: Artificial Sequence
<220> FEATURE:
<223> OTHER INFORMATION: Synthetic

<400> SEQUENCE: 127
```

```
Leu Ala Gly Leu Ile Asp Ala Asp Gly
1               5
```

<210> SEQ ID NO 128
<211> LENGTH: 5
<212> TYPE: PRT
<213> ORGANISM: Artificial Sequence
<220> FEATURE:
<223> OTHER INFORMATION: Synthetic peptide
<220> FEATURE:
<221> NAME/KEY: SITE
<222> LOCATION: (3)..(3)
<223> OTHER INFORMATION: Xaa = Asp or Glu
<220> FEATURE:
<221> NAME/KEY: misc_feature
<222> LOCATION: (4)..(4)
<223> OTHER INFORMATION: Xaa can be any naturally occurring amino acid

<400> SEQUENCE: 128

```
Pro Asp Xaa Xaa Lys
1               5
```

<210> SEQ ID NO 129
<211> LENGTH: 8
<212> TYPE: PRT
<213> ORGANISM: Artificial Sequence
<220> FEATURE:
<223> OTHER INFORMATION: Synthetic octapeptide

<400> SEQUENCE: 129

```
Gly Pro Leu Gly Ile Ala Gly Gln
1               5
```

<210> SEQ ID NO 130
<211> LENGTH: 5
<212> TYPE: PRT
<213> ORGANISM: Artificial Sequence
<220> FEATURE:
<223> OTHER INFORMATION: Synthetic peptide

<400> SEQUENCE: 130

```
Arg Gly Asp Tyr Cys
1               5
```

<210> SEQ ID NO 131
<211> LENGTH: 5
<212> TYPE: PRT
<213> ORGANISM: Artificial Sequence
<220> FEATURE:
<223> OTHER INFORMATION: Synthetic peptide

<400> SEQUENCE: 131

```
Ala Ser Ser His Asn
1               5
```

<210> SEQ ID NO 132
<211> LENGTH: 6
<212> TYPE: PRT
<213> ORGANISM: Artificial Sequence
<220> FEATURE:
<223> OTHER INFORMATION: Synthetic peptide

<400> SEQUENCE: 132

```
Lys Cys Cys Tyr Ser Leu
1               5
```

<210> SEQ ID NO 133
<211> LENGTH: 7

```
<212> TYPE: PRT
<213> ORGANISM: Artificial Sequence
<220> FEATURE:
<223> OTHER INFORMATION: Synthetic peptide

<400> SEQUENCE: 133

Tyr Glu Val Gly His Arg Cys
1               5

<210> SEQ ID NO 134
<211> LENGTH: 20
<212> TYPE: DNA
<213> ORGANISM: Artificial Sequence
<220> FEATURE:
<223> OTHER INFORMATION: Synthetic oligonucleotide sequence
<220> FEATURE:
<221> NAME/KEY: MISC_FEATURE
<222> LOCATION: (2)..(2)
<223> OTHER INFORMATION: n is a, c, g, or t and may have 4 variants at
      the n position
<220> FEATURE:
<221> NAME/KEY: MISC_FEATURE
<222> LOCATION: (4)..(4)
<223> OTHER INFORMATION: n is a, c, g, or t and may have 4 variants at
      the n position
<220> FEATURE:
<221> NAME/KEY: MISC_FEATURE
<222> LOCATION: (6)..(6)
<223> OTHER INFORMATION: n is a, c, g, or t and may have 2 variants at
      the n position
<220> FEATURE:
<221> NAME/KEY: MISC_FEATURE
<222> LOCATION: (12)..(12)
<223> OTHER INFORMATION: n is a, c, g, or t and may have 4 variants at
      the n position
<220> FEATURE:
<221> NAME/KEY: MISC_FEATURE
<222> LOCATION: (14)..(14)
<223> OTHER INFORMATION: n is a, c, g, or t and may have 4 variants at
      the n position
<220> FEATURE:
<221> NAME/KEY: MISC_FEATURE
<222> LOCATION: (19)..(19)
<223> OTHER INFORMATION: n is a, c, g, or t and may have 2 variants at
      the n position

<400> SEQUENCE: 134
tnantnctac tntngtagnt                                               20
```